US010407730B2

(12) United States Patent
Modlin et al.

(10) Patent No.: US 10,407,730 B2
(45) Date of Patent: Sep. 10, 2019

(54) COMPOSITIONS, METHODS AND KITS FOR DIAGNOSIS OF A GASTROENTEROPANCREATIC NEUROENDOCRINE NEOPLASM

(71) Applicant: Clifton Life Sciences LLC, Charlestown, Saint Kitts and Nevis (KN)

(72) Inventors: Irvin Mark Modlin, Woodbridge, CT (US); Mark Kidd, New Haven, CT (US); Ignat Drozdov, Warwick (GB)

(73) Assignee: Clifton Life Sciences LLC, Charlestown (KN)

( * ) Notice: Subject to any disclaimer, the term of this patent is extended or adjusted under 35 U.S.C. 154(b) by 99 days.

(21) Appl. No.: 14/855,229

(22) Filed: Sep. 15, 2015

(65) Prior Publication Data

US 2016/0076106 A1 Mar. 17, 2016

Related U.S. Application Data

(60) Provisional application No. 62/050,465, filed on Sep. 15, 2014.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

| | | |
|---|---|---|
| WO | WO2005/020795 | 3/2005 |
| WO | WO2012/119013 A1 | 9/2012 |

OTHER PUBLICATIONS

Simon et al. Journal of Clinical Oncology. 2005. 23(29):7332-7341.*
Whitehead et al. Genome Biology. 2005. 6(2): Article R13.*
Hoshikawa et al. Physical Genomics. 2003. 12: 209-219.*
Wong et al. BioTechniques. 2005. 39(1):1-11.*
Supplementary Methods for Modlin et al. PloS ONE. 2013. 8(5):e63364.*
International Search Report and Written Opinion corresponding to International Application No. PCT/US2015/050274, dated Dec. 2, 2015.
Schimmack et al., "The Clinical Implications and Biologic Relevance of Neurofilament Expression in Gastroenteropancreatic Neuroendocrine Neoplasms", May 15, 2012, Cancer, vol. 118, No. 10, pp. 2763-2775.
Kinross et al., "Metabonomic profiling: A Novel Approach in Neuroendocrine Neoplasias" Surgery, Dec. 1, 2013, vol. 154, No. 6, pp. 1185-1193.
Banck M. et al., "The genomic landscape of small intestine neuroendocrine tumors," *J Clin Invest* 2013; 123(6):2502-2508.
Cai YC, et al., "Cytokeratin 7 and 20 and thyroid transcription factor 1 can help distinguish pulmonary from gastrointestinal carcinoid and pancreatic endocrine tumors," *Hum Pathol* 2001;32(10): 1087-1093.
Cohen SJ et al. "Isolation and characterization of circulating tumor cells in patients with metastatic colorectal cancer", *Clin Colorectal Cancer* 2006; 6(2): 125-132.
Cristofanilli M. et al., "Circulating tumor cells, disease progression, and survival in metastatic breast cancer", *N Engl J Med* 2004, 351(8):781-791.
Danila D. et al. "Circulating tumor cell number and prognosis in progressive castration-resistant prostate cancer", *Clin Cancer Res* 2007; 13(23):7053-7058.
Kahan L., "Medical devices; immunology and microbiology devices; classification of the immunomagnetic circulating cancer cell selection and enumeration system", Final rule, *Fed Regist* 2004; 69:26036-26038.
Kidd M. et al. Microsatellite instability and gene mutations in transforming growth factor-beta type II receptor are absent in small bowel carcinoid tumors, *Cancer* 2005; 103(2):229-236.
Kidd M, et al., "Isolation, Functional Characterization and transcriptome of the Mastomys ileal enterochromaffin cells," *Am J Physiol* Gastrointest Liver Physiol 2006; 291:G778-791.
Mimori K, et al, "A large-scale study of MT1-MMP as a marker for isolated tumor cells in peripheral blood and bone marrow in gastric cancer cases," *Ann Surg Oncol* 2008; 15(10):2934-2942.
Modlin I. et al. "The Identification of gut neuroendocrine tumor disease by multiple synchronous transcript analysis in blood", *Plos One* 2013, vol. 8, Issue 5, e63364 (12 pages).
Modlin I. et al., "The functional characterization of normal and neoplastic human enterochromaffin cells", *Clin Endocrinol Metab* 2006; 91(6):2340-2348.
Ross AA, et al. "Detection and viability of tumor cells in peripheral blood stem cell collections from breast cancer patients using immunocytochemical and clonogenic assay techniques," *Blood* 1993; 82(9):2605-2610.
Sieuwerts AM, et al., "Molecular characterization of circulating tumor cells in large quantities of contaminating leukocytes by a multiplex real-time PCR," *Breast Cancer Res Treat* 2009; 118(3):455-468.

(Continued)

*Primary Examiner* — Joseph G. Dauner
(74) *Attorney, Agent, or Firm* — Cooley LLP; Ivor R. Elrifi; Matthew Pavao

(57) ABSTRACT

Methods are provided for diagnosing, detecting, or prognosticating a GEP-NEN based on the expression level score of biomarkers exhibiting differential expression in subjects having a GEP-NEN relative to a reference or control sample. The invention also provides compositions and kits comprising these biomarkers and methods of using these biomarkers in subsets or panels thereof to diagnose, classify, and monitor GEP-NEN and types of GEP-NEN. The methods and compositions provided herein may be used to diagnose or classify a subject as having a GEP-NEN, to distinguish between different stages of GEP-NENs, e.g., stable or progressive, to provide a measure of risk of developing a progressive GEP-NEN, and to gauge the completeness of treatments for GEP-NEN including, but not limited to surgery and somatostatin therapy.

9 Claims, 47 Drawing Sheets

Specification includes a Sequence Listing.

(56) References Cited

OTHER PUBLICATIONS

Tannapfel A. et al., "BRAF gene mutations are rare events in gastroenteropancreatic neuroendocrine tumors," *Am J Clin Pathol* 2005; 123(2):256-260.
Van Feden S. et al. "Classification of low-grade neuroendocrine tumors of midgut and unknown origin," *Hum Pathol* 2002; 33(11): 1126-1132.
Zikusoka MN et al., "Molecular genetics of gastroenteropancreatic neuroendocrine tumors", *Cancer* 2005; 104:2292-2309.
Boom, R. et al. (1990) "Rapid and Simple Method for Purification of Nucleic Acids" *J Clin Microbiol*, 28(3):495-503.
Chomczynski, P. (2006). "The single-step method of RNA isolation by acid guanidinium thiocyanate-phenol-chloroform extraction: twenty-something years on" *Nat Protoc*, 1(2):581-585.
Dhawan, M. et al. (2010) "Application of committee κNN classifiers for gene expression profile classification" *Int J Bioinform Res Appl*, 6(4):344-352.
Drozdov, I. et al. (2010) "Genome-wide expression patterns in physiological cardiac hypertrophy" *BMC Genomics*, 11:557, 13 pages.
Evgeniou, T. et al. (1999) "Regularization Networks and Support Vector Machines" *Advances in Computational Math*, 13(1):1-53.
Freeman, T.C. et al. (Oct. 2007) "Construction, visualization, and clustering of transcription networks from microarray expression data" *PLoS Comput Biol*, 3(10):2032-2042.
Gabriel, K.R. (Dec. 1971) "The Biplot Graphic Display of Matrices with Application to Principal Component Analysis" *Biometrika*, 58(3):453-467.
Gallant, S.I. (Jun. 1990) "Perceptron-Based Learning Algorithms" *IEEE Transactions on Neural Networks*, 1(2):179-191.
Glotsos, D. et al. (2005) "Automated diagnosis of brain tumours astrocytomas using probabilistic neural network clustering and support vector machines" *Int J Neural Syst*, 15(1-2):1-11.
Godfrey, T.E. et al. (May 2000) "Quantitative mRNA Expression Analysis from Formalin-Fixed, Paraffin-Embedded Tissues Using 5' Nuclease Quantitative Reverse Transcription-Polymerase Chain Reaction" *Molec Diagnostics*, 2(2):84-91.
Hanahan, D and R.A. Weinberg (Mar. 4, 2011) "Hallmarks of cancer: The next generation" *Cell*, 144(5):646-674.
Hod, Y. (1992) "A Simplified Ribonuclease Protection Assay" *Biotechniques*, 13(6):852-853.
Ji, S. and J. Ye (Oct. 2008) "Kernel Uncorrelated and Regularized Discriminant Analysis: A Theoretical and Computational Study" *IEEE Transactions on Knowledge and Data Engineering*, 20(10):1311-1321.
Kawarazaki, S. et al. (2010) "Conversion of a molecular classifier obtained by gene expression profiling into a classifier based on real-time PCR: a prognosis predictor for gliomas" *BMC Med Genomics*, 3:52, 8 pages.
Kidd, M. et al. (2006) "The Role of Genetic Markers—*Nap1L1*, *MAGE-D2*, and *MTA1*—in Defining Small-Intestinal Carcinoid Neoplasia" *Ann Surg Oncol*, 13(2):253-262.
Kidd, M. et al. (2007) "GeneChip, geNorm, and Gastrointestinal tumors: novel reference genes for real-time PCR" *Physiol Genomics*, 30:363-370.
Kohavi, R. (1995) "A Sudy of Cross-Validation and Bootstrap for Accuracy Estimation and Model Selection" *Proceedings of the Fourteenth International Joint Conference on Artificial Intelligence*, 2(12): 1137-1143.
Lawlor, G, et al. (2011) "Increased Peripheral Blood GATA-3 Expression in Asymptomatic Patients With Active Ulcerative Colitis at Colonoscopy" *Gastroenterology*, 140(Suppl 1):S-842, Abstract Tu1827.
Lilien, R.H. et al. (2003) "Probabilistic Disease Classification of Expression-Dependent Proteomic Data from Mass Spectrometry of Human Serum" *J Comput Biol*, 10(6):925-946.
Markey, M.K. et al. (2002) "Perceptron error surface analysis: a case study in breast cancer diagnosis" *Comput Biol Med*, 32(2):99-109.
Mattfeldt, T. et al. (2003) "Classification of Prostatic Carcinoma with Artificial Neural Networks Using Comparative Genomic Hybridization and Quantitative Stereological Data" *Pathol Res Pract*, 199(12):773-784.
Mazzaglia, P.J. et al. (2007) "Laparoscopic radiofrequency ablation of neuroendocrine liver metastases: a 10-year experience evaluating predictors of survival" *Surgery*, 142(1):10-19.
Michiels, et al. (2007) "Interpretation of microarray data in cancer" *Br J Cancer*, 96(8):1155-1158.
Noble, W.S. (Dec. 2006) "What is a support vector machine?" *Nat Biotechnol*, 24(12):1565-1567.
Parker, R.M.C. and N.M. Barnes (1999) "mRNA: Detection by In Situ and Northern Hypridization" *Methods in Molecular Biology*, 106:247-283.
Peng, H. et al. (Aug. 2005) "Feature Selection Based on Mutual Information: Criteria of Max-Dependency, Max-Relevance, and Min-Redundancy" *IEEE Transactions on Pattern Analysis and Machine Intelligence*, 27(8):1226-1238.
Picon, A. et al. (1998) "A subset of metastatic human colon cancers expresses elevated levels of transforming growth factor beta 1" *Cancer Epidemiol Biomarkers Prev*, 7(6):497-504.
Pima, I. and M. Aladjem (2004) "Regularized discriminant analysis for face recognition" *Pattern Recognition*, 37(9):1945-1948.
Pimentel, M. et al. (2011) "Validating a New Genomic Test for Irritable Bowel Syndrome" *Gastroenterology*, 140(Suppl 1):S-798, Abstract Tu1329.
Pirooznia, M. et al. (2008) "A comparative study of different machine learning methods on microarray gene expression data" *BMC Genomics*, 9(Suppl 1):S13, 13 pages.
Specht, K. et al. (Feb. 2001) "Quantitative Gene Expression Analysis in Microdissected Archival Formalin-Fixed and Paraffin-Embedded Tumor Tissue" *Am J Pathol*, 158:419-429.
Urgard, E. et al. (2011) "Metagenes Associated with Survival in Non-Small Cell Lung Cancer" *Cancer Inform*, 10:175-183.
Vandebriel, R.J. et al. (1998) "Altered cytokine (receptor) mRNA expression as a tool in immunotoxicology" *Toxicology*, 130(1): 43-67.
Vandesompele, J. et al. (2002) "Accurate normalization of real-time quantitative RT-PCR data by geometric averaging of multiple internal control genes" *Genome Biol*, 3(7):research0034.1-0031.11.
Weis, J.H. et al. (Aug. 1992) "Detection of rare mRNAs via quantitative RT-PCT" *Trends in Genetics*, 8:263-264.
Yu, L. et al (2002) "TGF-beta receptor-activated p38 MAP kinase mediates Smad-independent TGF-beta responses" *EMBO J*, 21(14):3749-3759.
Zampetaki, A. et al. (2010) "Plasma MicroRNA Profiling Reveals Loss of Endothelial MiR-126 and Other MicroRNAs in Type 2 Diabetes" *Circ Res*, 107(6): 810-817.
Zhang, H. et al (2001) "Recursive Partitioning for Tumor Classification with Gene Expression Microarray Data" *Proc Natl Acad Sci USA*, 98(12):6730-6735.

* cited by examiner

NETest 4

Group 1

Group 2

COMPOSITIONS, METHODS AND KITS FOR DIAGNOSIS OF A GASTROENTEROPANCREATIC NEUROENDOCRINE NEOPLASM

CROSS REFERENCE TO RELATED APPLICATIONS

The present invention claims the benefit of, and priority to, U.S. Ser. No. 62/050,465, filed on Sep. 15, 2014, the contents of which are herein incorporated in its entirety.

SEQUENCE LISTING

The Sequence Listing associated with this application is provided in text format in lieu of a paper copy, and is hereby incorporated by reference into the specification. The name of the text file containing the Sequence Listing is CLSL-001-001US-SEQ.txt. The text file is 291 KB, was created on Nov. 18, 2015, and is being submitted electronically via EFS-Web.

BACKGROUND OF THE INVENTION

Gastroenteropancreatic (GEP) neuroendocrine neoplasm (GEP-NEN), also referred to as Gastroenteropancreatic Neuroendocrine Tumor and Neuroendocrine Tumor (NET), is the second most prevalent malignant tumor in the gastrointestinal (GI) tract in the U.S. Incidence and prevalence have increased between 100 and 600 percent in the U.S. over the last thirty years, with no significant increase in survival.

Heterogeneity and complexity of GEP-NENs has made diagnosis, treatment, and classification difficult. These neoplasms lack several mutations commonly associated with other cancers and microsatellite instability is largely absent. See Tannapfel A, Vomschloss S, Karhoff D, et al., "BRAF gene mutations are rare events in gastroenteropancreatic neuroendocrine tumors," *Am J Clin Pathol* 2005; 123(2): 256-60; Banck M, Kanwar R, Kulkarni A A, et al., "The genomic landscape of small intestine neuroendocrine tumors," *J Clin Invest* 2013; 123(6):2502-8; Zikusoka M N, Kidd M, Eick G, et al., Molecular genetics of gastroenteropancreatic neuroendocrine tumors. *Cancer* 2005; 104:2292-309; Kidd M, Eick G, Shapiro M D, et al. Microsatellite instability and gene mutations in transforming growth factor-beta type II receptor are absent in small bowel carcinoid tumors," *Cancer* 2005; 103(2):229-36.

Individual histopathologic subtypes as determined from tissue resources e.g., biopsy, associate with distinct clinical behavior, yet there is no definitive, generally accepted pathologic classification or prediction scheme, hindering treatment assessment and follow-up.

Existing diagnostic and prognostic approaches for GEP-NENs include imaging (e.g., CT or MRI), histology, measurements of circulating hormones and proteins associated with NENs e.g., chromogranin A and detection of some gene products. Available methods are limited, for example, by low sensitivity and/or specificity, inability to detect early-stage disease, or exposure to radiation risk. GEP-NENs often go undiagnosed until they are metastatic and often untreatable. In addition, follow-up is difficult, particularly in patients with residual disease burden.

There is a need for specific and sensitive methods and agents for the detection of GEP-NEN, including stable and progressive GEP-NEN, for example, for use in diagnosis, prognosis, prediction, staging, classification, treatment, monitoring, and risk assessment, and for investigating and understanding molecular factors of pathogenesis, malignancy, and aggressiveness of this disease. For example, such methods and agents are needed that can be repeatedly and directly collected with low risk exposure e.g., non-invasive peripheral blood test, be performed simply, rapidly, and at relatively low cost.

The present application overcomes the above-noted problems by providing novel compositions, methods, and kits for accurately diagnosing, detecting, and monitoring the presence of GEP-NENs and/or the types or stage of GEP-NEN in circulating peripheral blood samples. The described embodiments furthermore may be used to identify a level of risk for a patient to develop a progressive GEP-NEN, and/or to determine the risk of residual or reoccurring progressive GEP-NEN in a post-surgery or post-somatostatin treated human patient. In addition, it can be used as a prognostic for predicting response to therapy e.g., peptide receptor radiotherapy (PRRT).

SUMMARY OF THE INVENTION

In one aspect, the present invention relates to gastroenteropancreatic neuroendocrine neoplasm (GEP-NEN) biomarkers measured in circulating blood, the detection of which may be used in diagnostic, prognostic and predictive methods. Among the provided objects are GEP-NEN biomarkers, feature subsets and panels of the biomarkers, agents for binding and detecting the biomarkers, kits and systems containing such agents, and methods and compositions for detecting the biomarkers, for example, in biological samples e.g., blood, as well as prognostic, predictive, diagnostic, and therapeutic uses thereof.

Provided are agents, sets of agents, and systems containing the agents for GEP-NEN prognosis, detection and diagnosis. Typically, the systems include a plurality of agents (e.g., set of agents), where the plurality specifically binds to and/or detects a plurality of GEP-NEN biomarkers in a panel of GEP-NEN biomarkers. The agents may be isolated polypeptides or polynucleotides which specifically bind to one or more GEP-NEN biomarkers. For example, provided are sets of isolated polynucleotides and polypeptides that bind to a panel of GEP-NEN biomarkers, and methods and uses of the same.

Also provided are prognostic, diagnostic, and predictive methods and uses of the agents, compositions, systems, and kits for GEP-NEN and associated conditions, syndromes and symptoms. For example, provided are methods and uses for detection, diagnosis, classification, prediction, therapeutic monitoring, prognosis, or other evaluation of GEP-NEN or an outcome, stage or level of aggressiveness or risk thereof, or associated condition. In some embodiments, the methods are performed by determining the presence, absence, expression levels, or expression profile of a GEP-NEN biomarker, more typically a plurality of GEP-NEN biomarkers, such as a feature subset chosen from a panel of biomarkers, and/or comparing such information with normal or reference expression levels or profiles or standards. Thus, in some embodiments, the methods are carried out by obtaining a biological test sample and detecting the presence, absence, expression level score, or expression profile of a GEP-NEN biomarker as described herein. For example, the methods can be performed with any of the systems of agents, e.g., polynucleotides or polypeptides, provided herein. For example, the methods generally are carried out using one or more of the provided systems.

Provided are methods, agents and compositions for detection of and distinguishing between a number of different GEP-NEN types or stages. Exemplary GEP-NEN types and stages include stable disease (SD) and progressive (highly active) disease (PD).

In one aspect, the provided methods and compositions may be used to specifically and sensitively detect different stages of GEP-NENs, such as GEP-NENs in a stable disease (SD) or progressive disease (PD) states; in some aspects, the methods and compositions may be used to predict disease progression, treatment response, and metastasis. Methods and compositions provided herein are useful for diagnosis, prognosis, prediction, staging, classification, treatment, monitoring, assessing risk, and investigating molecular factors associated with GEP-NEN disease.

Provided are such methods capable of being carried out quickly, simply, and at relatively low cost, as compared to other diagnostic and prognostic methods.

Provided are methods and compositions that are useful for defining gene expression-based classification of GEP-NENs, and thus are useful for allowing the prediction of malignancy and metastasis, such as in early stage disease or using histologically negative samples, providing accurate staging, facilitating rational therapy, and in developing large validated clinical datasets for GEP-NEN-specific therapeutics.

The GEP-NEN biomarkers may include a subset of biomarkers, the expression of which is different in or is associated with the presence or absence of GEP-NEN, or is different in or is associated with a particular classification, stage, aggressiveness, severity, degree, metastasis, symptom, risk, treatment responsiveness or efficacy, or associated syndrome. The subset of GEP-NEN biomarkers typically includes at least 22 GEP-NEN biomarkers. In some embodiments, the subset of biomarkers includes at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers, or includes at or about 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers.

For example, in some aspects, the subset of biomarkers includes at least 22, or at least 38, or at least 51 biomarkers. In a particular example, the subset contains at least 22 biomarkers, or about 22 biomarkers, or 22 biomarkers, chosen from a panel of 38 biomarkers. In some embodiments, the subset of biomarkers includes at least 22, 23, 24, 25, 26, 27, 28, 29, 30, 31, 32, 33, 34, 35, 36, 37, or 38 biomarkers chosen from a panel of 38 biomarkers.

Because the systems, methods, and kits contain a plurality of agents that specifically bind to or hybridize to the biomarkers in the panel, the number of biomarkers generally relates to the number of agents in a particular system. For example, among the provided methods is a method that contains at least 22 binding agents, which specifically hybridizes to or binds to a subset of at least 22 GEP-NEN biomarkers, respectively.

In some aspects, the subset of biomarkers includes at least 22, 23, 24, 25, 26, 27, 28, 29, 30, 31, 32, 33, 34, 35, 36, 37, and/or all of the following group of gene products, including polynucleotides (e.g. 38 transcripts) and polypeptides: PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/K67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and/or GLT8D1 gene products.

In a particular example, the subset of 22 biomarkers includes PNMA2, NAP1L1, FZD7, SLC18A2, NOL3, SSTR5, TPH1, RAF1, RSF1, SSTR3, SSTR1, CD59, ARAF, APLP2, KRAS, MORF4L2, TRMT112, MKI67, SSTR4, CTGF, SPATA7, and ZFHX3 gene products.

Among the provided methods, agents, and systems are those that are able to classify or detect a GEP-NEN in a human blood sample. In some embodiments, the provided systems and methods can identify or classify a GEP-NEN in a human blood sample. In some examples, the systems can provide such information with a specificity, sensitivity, and/or accuracy of at least 75%, 80%, 85%, 90%, 91%, 92%, 93%, 94%, 95%, 96%, 97%, 98%, 99% or 100%, e.g., at least 80%.

In some embodiments, the system can predict treatment responsiveness to, or determine whether a patient has become clinically stable following, or is responsive or non-responsive to, a GEP-NEN treatment, such as a surgical intervention or drug therapy (for example, somatostatin analog therapy). In some cases, the methods and systems do so with a specificity, sensitivity, and/or accuracy of at least 75%, 80%, 85%, 90%, 91%, 92%, 93%, 94%, 95%, 96%, 97%, 98%, 99% or 100%, e.g., with at least 90% accuracy. In some cases, it can differentiate between treated and untreated GEP-NEN with a specificity, sensitivity, and/or accuracy of at least 75%, 80%, 85%, 90%, 91%, 92%, 93%, 94%, 95%, 96%, 97%, 98%, 99% or 100%, e.g., with a sensitivity and specificity of at least 85%.

In some cases, the system can determine diagnostic or prognostic information regarding a subject previously diagnosed with GEP-NEN, for example, whether the subject has a stable disease (SD) or progressive disease (PD) state of GEP-NEN, or is in complete remission, for example, would be clinically categorized as having stable disease, progressive disease, or being in complete remission.

In some embodiments, the agents for detecting the biomarkers, e.g., the sets of polynucleotide or polypeptide agents, and uses thereof, are capable of distinguishing between the presence and absence of GEP-NEN in a biological sample, between GEP-NEN and mucosal samples and GEP-NEN samples, and/or between specific classes or subtypes of GEP-NENs, for example, between aggressive (high activity) and benign (low activity) GEP-NEN samples.

In one aspect, the system is able to classify or detect a GEP-NEN in a human blood sample or human saliva sample. In one aspect, the human sample is whole blood or nucleic acid or protein prepared from whole blood, without first sorting or enriching for any particular population of cells. In one aspect, the system includes agents that bind to biomarkers in a subset of at least 22 GEP-NEN biomarkers.

In some embodiments, in addition to the agents that bind the GEP-NEN biomarkers, the provided systems contain one or more agents that bind to gene products for use in normalization or as controls, for example, housekeeping gene products include ALG9 gene products;

In some embodiments, the methods include selecting a subset of at least 22 biomarkers chosen from a panel of 38 biomarkers useful in generating a classifier for GEP-NEN and different stages of GEP-NEN.

In some embodiments, the methods further include contacting a test sample from the human patient with a plurality of agents specific to the biomarkers in the subset.

The biological test sample used with the methods can be any biological sample, such as tissue, biological fluid, or other sample, including blood samples, such as plasma, serum, whole blood, buffy coat, or other blood sample, tissue, saliva, serum, urine, or semen sample. In some aspects, the sample is obtained from blood. Often, the test sample is taken from a GEP-NEN patient.

The agents can be any agents for detection of biomarkers, and typically are isolated polynucleotides or isolated polypeptides or proteins, such as antibodies, for example, those that specifically hybridize to or bind to a subset or panel of GEP-NEN biomarkers including at least 22 GEP-NEN biomarkers.

In some embodiments, the methods are performed by contacting the test sample with one of the provided agents, more typically with a plurality of the provided agents, for example, one of the provided systems, such as a set of polynucleotides that specifically bind to the subset of GEP-NEN biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the GEP-NEN biomarkers, such as expression levels thereof, includes detecting the presence, absence, or amount of RNA. In one example, the RNA is detected by PCR or by hybridization.

In one aspect, the polynucleotides include sense and antisense primers, such as a pair of primers that is specific to each of the GEP-NEN biomarkers in the subset of biomarkers. In one aspect of this embodiment, the detection of the GEP-NEN biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of GEP-NEN biomarkers, and detecting products of the amplification. In some embodiments, the GEP-NEN biomarkers include mRNA, cDNA, or protein.

In some embodiments, the methods further include determining a mathematically-derived expression level score of biomarkers selected in the subset in the test sample. This is the MAARC-NET score (Multi-Analyte Risk Classification for NETs). It has two scales 0-8 and the percentage-derivatives scaled to 100% i.e., 0-100%.

The mathematically-derived MAARC-NET score is the product of a classifier built from predictive classification algorithms, e.g. support vector machines (SVM), linear discriminant analysis (LDA), K-nearest neighbor (KNN) and/or naive Bayes (NB). In some examples, the classifier is generated from a combination of SVM, LDA, KNN, and NB classification algorithms and a 10-fold cross-validation design.

In some embodiments, the methods further include a step of determining a mathematically-derived expression level score of biomarkers in the subset in a normal or reference sample, typically carried out prior to the normalization and comparing steps.

The normal or reference sample may be from a healthy patient or a patient who has GEP-NEN. Where the test sample is from a patient with GEP-NEN, the normal or reference sample or level may be from the same or a different patient. For example, the normal or reference sample may be from the GEP-NEN patient from a tissue, fluid or cell not expected to contain GEP-NEN or GEP-NEN cells. On another aspect, the normal or control sample is from the GEP-NEN patient before or after therapeutic intervention, such as after surgery or chemical intervention. In another aspect, the reference or normal sample is from a tissue or fluid that corresponds to the GEP-NEN or metastasis of the test sample, from a healthy individual, such as normal enterochromaffin cell (EC) preparation or small intestinal (SI) sample, or normal liver, lung, bone, blood, saliva, or other bodily fluid, tissue, or biological sample. In another embodiment, the test sample is from a metastasis, plasma, or whole blood or other fluid of a GEP-NEN patient and the reference sample is from primary tumor or fluorescent activated cell (FAC)-sorted tumor cells.

In other aspects, the test sample is from blood and the test biological sample is from the GEP-NEN patient after treatment and the reference sample is from the same GEP-NEN patient as the test biological sample, prior to treatment; the reference sample is from a tissue or fluid not containing GEP-NEN cells; the reference sample is from a healthy individual; the reference sample is from a cancer other than GEP-NEN; the reference sample is from an EC cell or SI tissue; the test biological sample is from a metastatic GEP-NEN and the reference sample is from a non-metastatic GEP-NEN; or the reference sample is from a GEP-NEN of a different classification compared to the GEP-NEN patient from which the test biological sample is obtained.

In one aspect, the test biological sample is from a GEP-NEN patient prior to treatment and the normal or reference sample is from the GEP-NEN patient after treatment. In another aspect, the normal or reference sample is from a non-metastatic tissue of the GEP-NEN patient.

In some cases, a normalization step is performed to normalize the level of expression score of the biomarkers in the subset in the test sample to the level of expression score of the biomarkers in the subset in the reference sample.

In some cases, a comparison step is performed to determine whether there is a difference, such as a significant difference, between the normalized expression level score and a predetermined cut-off value or score threshold. Certain predetermined cut-off values or score thresholds are indicative of different stages of GEP-NEN, while others are indicative of different levels of risk, i.e. low, intermediate, or high, for developing a progressive GEP-NEN.

In one aspect, the methods include comparing the normalized expression level score with a predetermined cutoff value chosen to exclude a control or reference sample, wherein a normalized expression level above the predetermined cutoff value is indicative of a GEP-NEN, wherein the cutoff value is about 2 (on a scale of 0-8, or 13.4% on a scale of 0-100%).

In another aspect, the methods include comparing the normalized expression level score with a predetermined cutoff value chosen to exclude a non-progressive GEP-NEN, wherein a normalized expression level above the predetermined cutoff value of 5 (on a scale of 0-8, or 43.4% on a scale of 0-100%) is indicative of progressive GEP-NEN.

In another aspect, the methods further include identifying the level of risk for a human patient to develop progressive GEP-NEN, wherein a normalized expression level score below about 5 (or 43.4%) is indicative of a low level of risk for developing a progressive GEP-NEN, a normalized expression level score between about 5 and 7 (43.4%-63.4%) is indicative of an intermediate level of risk for developing progressive GEP-NEN, and a normalized expression level score between about 7 and 8 (>63.4%) is indicative of a high level of risk for developing progressive GEP-NEN.

In some cases, a subsequent determination is performed for the actual expression level (not mathematically-derived expression level score) of individual genes, where identifying the intermediate level of risk for developing progressive GEP-NEN further includes determining a first state of intermediate risk, wherein the normalized expression level score between a non-progressive reference sample and the test sample is about 5 (43.4%), the normalized expression level of SMARCD3 is below a first threshold value, and the expression level of TPH1 is below a second threshold value.

In other cases, identifying the intermediate level of risk for developing progressive GEP-NEN further includes determining a second state of intermediate risk, wherein the normalized expression level score between a non-progressive reference sample and the test sample is about 6 (52.7%), the normalized expression level of VMAT1 is equal to or above 0, and the expression level of PHF21A is equal to or above a first threshold value.

In some cases, identifying the intermediate level of risk for developing progressive GEP-NEN further includes determining a third state of intermediate risk, wherein the normalized expression level score between a non-progressive reference sample and the test sample is about 7 (63.4%), the expression level of VMAT1 is equal to or above 0, and the expression level of PHF21A is equal to or below a first threshold value.

In other cases, identifying the high level of risk for developing progressive GEP-NEN further includes determining the normalized expression level score of ZZZ3, wherein the expression level score of ZZZ3 is equal to or less than 14.

Also provided are methods and uses of the provided biomarkers, agents, systems and detection methods for use in determining the risk of residual or reoccurring progressive GEP-NEN in a post-surgery human patient. In such cases, the level of risk for residual or reoccurring progressive GEP-NEN in the post-surgical test sample is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8>63.4%) is indicative of a high level of risk.

In some cases, identifying the level of risk for residual or reoccurring progressive GEP-NEN further includes determining an elevated expression level score of gene products in at least one gene cluster as determined between a pre-surgical test sample from the patient and the post-surgical test sample.

In some embodiments, the at least one gene cluster includes the proliferome, signalome, secretome I and II, plurome, epigenome, plurome, SSTRome, and combinations thereof.

In other embodiments, the at least one gene cluster includes the PD cluster, the ND cluster, the TD cluster, and the ID cluster. The PD cluster includes the proliferome, signalome, secretome II, plurome, and epigenome. The ND cluster includes the ARAF1, BRAF, KRAS, RAF1, Ki67, NAP1L1, NOL3, GLT8D1, PLD3, PNMA2, VMAT2, TPH1, FZD7, MORF4L2, and ZFHX3. The TD cluster includes the Secretome (I), the Plurome, and the SSTRome. The ID cluster includes the Proliferome, secretome (II), plurome, and epigenome.

In other embodiments, determining the elevated expression of gene products in at least one gene cluster includes evaluating a plurality of gene cluster algorithms including the PDA, NDA, TDA, and IDA algorithms.

In some embodiments, the methods further include treating the patient based on the indication of intermediate or high level of risk for residual or recurring progressive GEP-NEN by one of surgery or therapy.

Also provided are methods and uses of the provided biomarkers, agents, systems and detection methods for use in determining the risk of residual or reoccurring progressive GEP-NEN in a post-somatostatin analog treated patient. In such cases, the level of risk for somatostatin treatment failure is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8 (>63.4%) is indicative of a high level of risk.

The methods may further include determining the difference in expression level score in at least one of the SSTRome and Proliferome gene clusters between a pre-therapy test sample from the human patient and the post-therapy test sample, wherein an increased level of expression score is indicative of increased risk for residual or reoccurring progressive GEP-NEN.

In some cases, a somatostatin analog is administered to the human patient-based on the indication of intermediate or high level of risk for residual or recurring progressive GEP-NEN and an increased level of expression in at least one of the SSTRome and Proliferome gene clusters.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

(FIG. 4A) Frequency distribution for the 0-4 score in the controls, SD and PD; (FIG. 4B) Frequency distribution using a 0-8 score in the same sample set; (FIG. 4C) Correlation assessment for each of the two scores in (FIG. 4A) and (FIG. 4B).

(FIG. 6B) a frequency distribution graph for the 0-8 score in SD and PD. #p<0.0001 vs. SD (2-tailed Mann-Whitney U-test).

FIG. 14A shows a delineation of tumor (adenocarcinoma) derived hallmarks from Hanahan D, Weinberg R A: Hallmarks of cancer: the next generation. Cell 2011, 144(5): 646-674. FIG. 14B shows NET hallmark based on the Hanahan and Weinberg classification.

(FIG. 40A) and (FIG. 40C)) and all genes (Group II: (FIG. 40B) and (FIG. 40D)).

(FIG. 44C) change in CgA level versus clinical status at 6M FuP.

DETAILED DESCRIPTION OF THE INVENTION

Figures 1A, 1B, 1C, 1D, 1E:
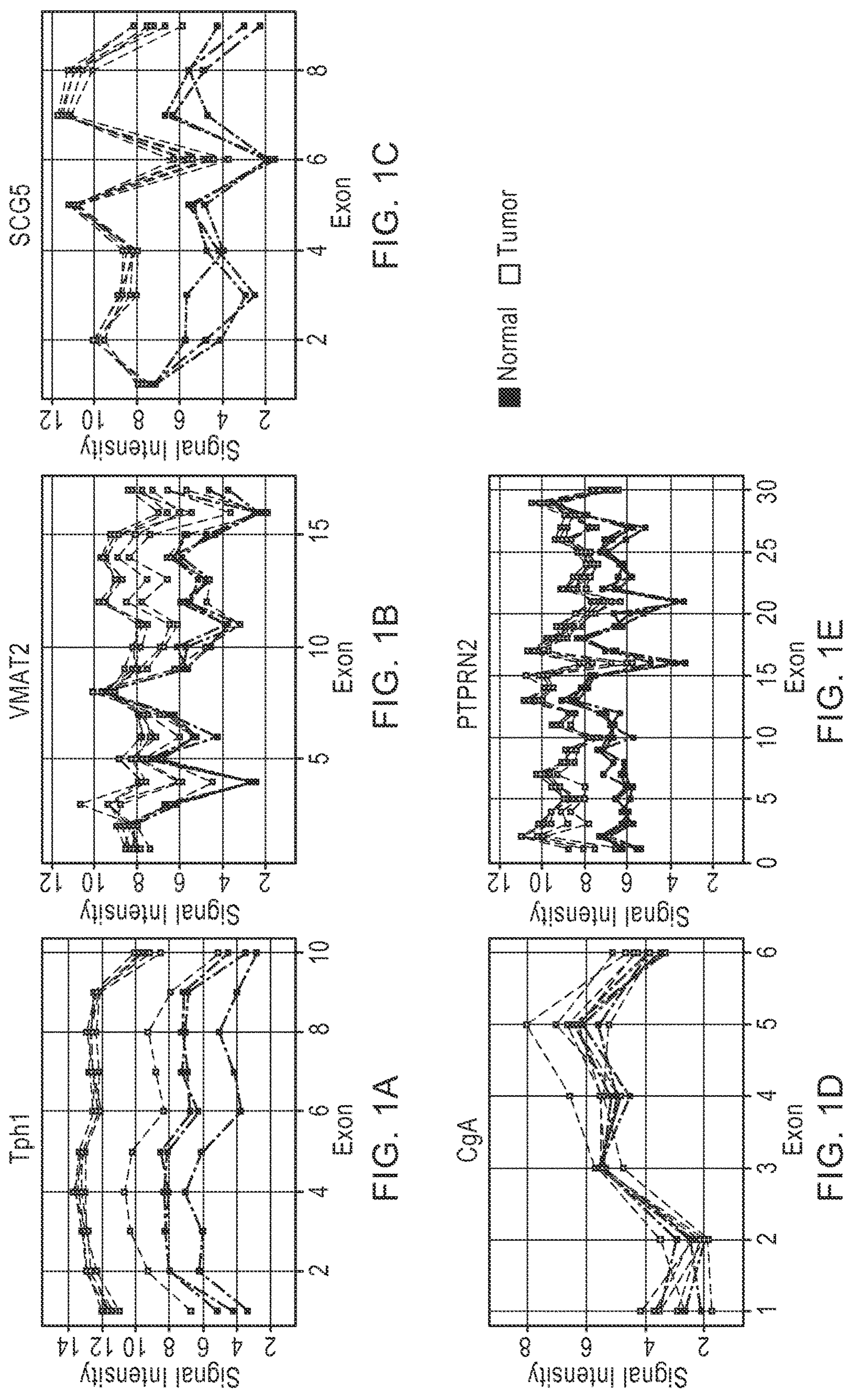
FIGS. 1A-1E are graphs showing differential exon expression in a marker gene panel inferred from an Affymetrix Human Exon 1.0 ST array in neuroendocrine tumor (NET) tissue relative to normal intestinal mucosa controls. RMA-normalized exon expressions of (FIG. 1A) Tph1, (FIG. 1B) VMAT2, (FIG. 1C) SCG5, (FIG. 1D) CgA, and (FIG. 1E) PTPRN2 were visualized in normal (green) and tumor (samples).
Figures 2A, 2B, 2C, 2D, 2E:
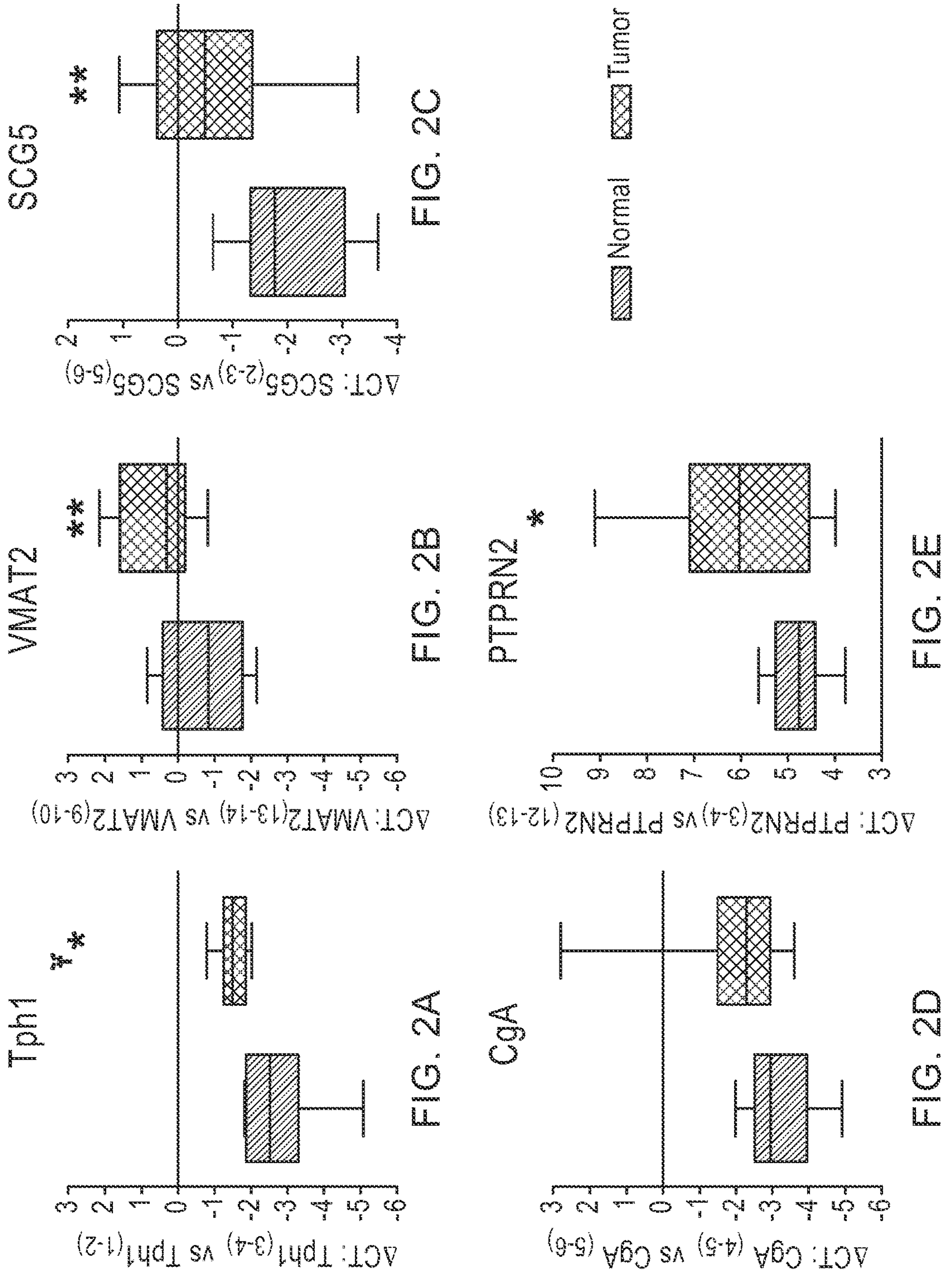
FIGS. 2A-2E are graphs showing the validation of alternative splicing in marker genes by Reverse transcriptase polymerase chain reaction (RT-PCR). Marker genes (FIG. 2A) Tph1, (FIG. 2B) VMAT2, (FIG. 2C) SCG5, (FIG. 2D) CgA, and (FIG. 2E) PTPRN2 were differentially expressed in NET samples relative to normal mucosa controls.

Three-quarters of all human genes undergo alternative splicing. Identifying and defining cancer-specific splice variants is therefore advantageous for the development of biomarker assays. The described embodiments derive from the surprising discovery that particular cancer-specific splice variants of NET marker genes can be used to maximize the difference between neoplasia and normal samples in biomarker diagnostic methods.

The present invention provides a method for detecting a gastroenteropancreatic neuroendocrine neoplasm (GEP-NEN) in a subject in need thereof, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%.

The score is based on a "majority vote" strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naive Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN.

The at least 22 biomarkers can include APLP2, ARAF, CD59, CTGF, FZD7, KRAS, MKI67/KI67, MORF4L2, NAP1L1, NOL3, PNMA2, RAF1, RSF1, SLC18A2/VMAT2, SMARCD3, SPATA7, SSTR1, SSTR3, SSTR4, SSTR5, TPH1, TRMT112, and ZFHX3.

The methods can further include determining the presence of a progressive GEP-NEN in the subject when the normalized expression level is equal to or higher than the predetermined cutoff value, wherein the predetermined cutoff value is 5 on a scale of 0-8, or less than 55% on a scale of 0-100%.

The methods can further include identifying a level of risk for the subject to develop a progressive GEP-NEN the method further including identifying a low level of risk for developing a progressive GEP-NEN when the normalized expression level is less than a predetermined cutoff value of 5 on a scale of 0-8, or less than 55% on a scale of 0-100%; identifying an intermediate level of risk for developing a progressive GEP-NEN when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk for developing a progressive GEP-NEN when the normalized expression level is equal to or greater than a predetermined cutoff value of 7 on a scale of 0-8, or equal to or greater than 75% on a scale of 0-100%.

The biomarker can be RNA, cDNA, or protein. When the biomarker is RNA, the RNA can be reverse transcribed to produce cDNA (such as by RT-PCR, and the produced cDNA expression level is detected. The expression level of the biomarker can be detected by forming a complex between the biomarker and a labeled probe or primer. When the biomarker is RNA or cDNA, the RNA or cDNA detected by forming a complex between the RNA or cDNA and a labeled nucleic acid probe or primer. The complex between the RNA or cDNA and the labeled nucleic acid probe or primer can be a hybridization complex. When the biomarker is protein, the protein can be detected by forming a complex between the protein and a labeled antibody. The label can be any label for example a fluorescent label, chemiluminescence label, radioactive label, etc.

The test sample can be any biological fluid obtained from the subject. Preferably, the test sample is blood, serum, plasma or neoplastic tissue. The reference sample can be any biological fluid obtained from a subject not having, showing symptoms of or diagnosed with a neoplastic disease. Preferably, the reference sample is blood, serum, plasma or non-neoplastic tissue.

The subject in need thereof can be a subject diagnosed with a GEP-NEN, a subject having at least one GEP-NEN symptom or a subject having a predisposition or familial history for developing a GEP-NEN. The subject can be any mammal. Preferably, the subject is human. The terms subject and patient are used interchangeably herein.

The methods can further include treating a subject identified as having an intermediate level or high level of risk for developing a progressive GEP-NEN with surgery or drug therapy. The drug therapy can be somatostatin analog treatment or peptide receptor radiotherapy therapy (PRRT). The methods can further include treating a subject identified as having a low level of risk for developing a progressive GEP-NEN with regular or periodic monitoring over at least a six month period, a twelve month period, an eighteen month period or twenty four month period.

The present invention also provides a method for differentiating stable and progressive GEP-NEN in a subject comprising determining that the normalized expression level of the at least 22 biomarkers from the test sample from the subject is equal to or greater than a predetermined cutoff value of 5 and less than a predetermined cutoff value of 6, according to the methods of the present invention; detecting an expression level of SMARCD3 and TPH1 from the test sample and from a reference sample by contacting the test sample and the reference sample with a plurality of agents specific to detect the expression of SMARCD3 and the expression of TPH1; normalizing the expression level of SMARCD3 and TPH1 in the test sample to the expression level of SMARCD3 and TPH1 in the reference sample; comparing the normalized expression level of SMARCD3 and TPH1 in the test sample with a first and a second predetermined cutoff value, respectively; and determining the presence of stable GEP-NEN in the subject when the normalized expression level of SMARCD3 is greater than the first predetermined cutoff value and the expression level of TPH1 is equal to or greater than the second predetermined cutoff value, or determining the presence of progressive GEP-NEN in the subject when the normalized expression level of SMARCD3 is equal to or less than the first predetermined cutoff value and the expression level of TPH1 is less than the second predetermined cutoff value wherein the first predetermined cutoff value is 1.3 on a scale of 0-8 and wherein the second predetermined cutoff value is 4 on a scale of 0-8.

The first predetermined cutoff value of 1.3 corresponds to 12% on a scale of 0-100% and wherein the second predetermined cutoff value of 4 corresponds to 41% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 6 and less than a predetermined cutoff value of 7, according to the methods of the present invention; detecting an expression level of VMAT1 and PHF21A from the test sample and from a reference sample by contacting the test sample and reference sample with a plurality of agents specific to detect the expression of VMAT1 and the expression of PHF21A, normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is less than the second predetermined cutoff value, or determining the presence of progressive GEP-NEN in the subject when the normalized expression level of VMAT1 is equal to or greater than the first predetermined cutoff value and the expression level of PHF21A is equal to or greater than the second predetermined cutoff value wherein the first predetermined cutoff value is 0 on a scale of 0-8 and wherein the second predetermined cutoff value is 1.2 on a scale of 0-8.

The first predetermined cutoff value of 0 corresponds to 0% on a scale of 0-100% and wherein the second predetermined cutoff value of 1.2 corresponds to 8% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 7 and less than a predetermined cutoff value of 8, according to the methods of the present invention; detecting an expression level of VMAT1 and PHF21A from the test sample and a reference sample by contacting the test sample and the reference sample with a plurality of agents specific to detect the expression of VMAT1 and the expression of PHF21A; normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is greater than the second predetermined cutoff value, or determining the presence of progressive GEP-NEN in the subject when the normalized expression level of VMAT1 is equal to or greater than the first predetermined cutoff value and the expression level of PHF21A is equal to or less than the second predetermined cutoff value wherein the first predetermined cutoff value is 0 on a scale of 0-8 and wherein the second predetermined cutoff value is 1 on a scale of 0-8.

The first predetermined cutoff value of 0 corresponds to 0% on a scale of 0-100% and wherein the second predetermined cutoff value of 1 corresponds to 7% on a scale of 0-100%.

The present invention also provides a method for differentiating stable and progressive GEP-NEN in a subject comprising determining that the normalized expression level of the at least 22 biomarkers from the test sample from the subject is equal to a predetermined cutoff value of 8, according to the methods of the present invention; detecting an expression level of ZZZ3 from the test sample and a reference sample by contacting the test sample and the reference sample with at least one agent specific to detect the expression of ZZZ3; normalizing the expression level of ZZZ3 in the test sample to the expression level of ZZZ3 in the reference sample; comparing the normalized expression level of ZZZ3 in the test sample with a predetermined cutoff value; and determining the presence of progressive GEP-NEN in the subject when the normalized expression level of ZZZ3 is equal to or less than the predetermined cutoff value, wherein the predetermined cutoff value is 1 on a scale of 0-8.

The predetermined cutoff value of 1 corresponds to 18% on a scale of 0-100%.

The methods of the present invention further include determining the expression level of each of 16 biomarkers from a test sample from the subject and a reference sample by contacting the test sample and the reference sample with a plurality of agents specific to detect the expression of each of the 16 biomarkers, wherein the 16 biomarkers comprise Ki67, NAP1L1, NOL3, TECPR2, ARAF1, BRAF, KRAS, RAF1, PQBP1, TPH1, COMMD9, MORF4L2, RNF41, RSF1, SMARCD3, and ZFHX3; summing the expression level of each of the 16 biomarkers of the test sample to generate a progressive diagnostic I total test value and summing the expression level of each of the 16 biomarkers of the reference sample to generate a progressive diagnostic I total reference value, wherein an increased value of the progressive diagnostic I total test value compared to the progressive diagnostic I total reference value indicates the presence of progressive GEP-NEN in the subject.

The methods of the present invention further include determining the expression level of each of 15 biomarkers from a test sample from the subject and a reference sample by contacting the test sample and the reference sample with a plurality of agents specific to detect the amount of each of the 15 biomarkers, wherein the 15 biomarkers comprise ARAF1, BRAF, KRAS, RAF1, Ki67, NAP1L1, NOL3, GLT8D1, PLD3, PNMA2, VMAT2, TPH1, FZD7, MORF4L2 and ZFHX3; averaging the expression level of each of the 15 biomarkers of the test sample to generate a progressive diagnostic II test value and averaging the expression level of each of the 15 biomarkers of the reference sample to generate a progressive diagnostic II reference value, wherein an increased value of the progressive diagnostic II test value compared to the progressive diagnostic II reference value indicates the presence of progressive GEP-NEN in the subject.

The methods of the present invention further include determining the expression level of each of 7 biomarkers from a test sample from the subject and a reference sample by contacting the test sample and the reference sample with a plurality of agents specific to detect the amount of each of the 7 biomarkers, wherein the 7 biomarkers comprise PNMA2, VMAT2, COMMD9, SSTR1, SSTR3, SSTR4, and SSTR5; summing the expression level of each of the 7 biomarkers of the test sample to generate a progressive diagnostic III total test value and summing the expression level of each of the 7 biomarkers of the reference sample to generate a progressive diagnostic III total reference value, wherein an increased value of the progressive diagnostic III total test value compared to the progressive diagnostic III total reference value indicates the presence of progressive GEP-NEN in the subject.

The methods of the present invention further include determining the expression level of each of 11 biomarkers from a test sample from the subject and a reference sample by contacting the test sample and the reference sample with a plurality of agents specific to detect the amount of each of the 11 biomarkers, wherein the 11 biomarkers comprise Ki67, NAP1L1, NOL3, TECPR2, PQBP1, TPH1, MORF4L2, RNF41, RSF1, SMARCD3, and ZFHX3; summing the expression level of each of the 11 biomarkers of the test sample to generate a progressive diagnostic IV total test value and summing the expression level of each of the 11 biomarkers of the reference sample to generate a progressive diagnostic IV total reference value, wherein an increased value of the progressive diagnostic IV total test value compared to the progressive diagnostic IV total reference value indicates the presence of progressive GEP-NEN in the subject.

The present invention also provides a method for determining the risk of relapsing or reoccurring progressive GEP-NEN in a post-surgery subject, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; identifying an absence of risk of relapsing or reoccurring progressive GEP-NEN post-surgery when the normalized expression level is less than a predetermined cutoff value of 2 on a scale of 0-8, or less than 0% on a scale of 0-100%; identifying a low level of risk of relapsing or reoccurring progressive GEP-NEN post-surgery when the normalized expression level is less than a predetermined cutoff value of 5 on a scale of 0-8, or less than 55% on a scale of 0-100%; identifying an intermediate level of risk of relapsing or reoccurring progressive GEP-NEN post-surgery when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk of relapsing or reoccurring progressive GEP-NEN post-surgery when the normalized expression level is equal to or greater than a predetermined cutoff value of 7 on a scale of 0-8, or equal to or greater than 75% on a scale of 0-100%.

The present invention also provides a method for determining the risk of relapsing or reoccurring progressive GEP-NEN in a subject treated with somatostatin, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; when a GEP-NEN is present, determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise Ki67, NAP1L1, NOL3, TECPR2, SSTR1, SSTR2, SSTR4, and SSTR5; summing the expression level of each of the 8 biomarkers of the test sample to generate a progressive diagnostic V total test value and summing the expression level of each of the 8 biomarkers of the reference sample to generate a progressive diagnostic V total reference value, wherein an increased value of the progressive diagnostic V total test value compared to the progressive diagnostic V total reference value indicates the presence of relapsing or reoccurring progressive GEP-NEN in the subject.

The present invention also provides a method for determining a response of a peptide receptor radionucleotide therapy (PRRT) of a GEP-NEN in a subject in need thereof, including determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise ARAF1, BRAF, KRAS, RAF1, ATP6V1H, OAZ2, PANK2, PLD3; normalizing the expression level of the 8 biomarkers in the test sample to the expression level of the 8 biomarkers in the reference sample; comparing the normalized expression level of the 8 biomarkers in the test sample with a predetermined cutoff value; determining the presence of a PRRT-responsive GEP-NEN in the subject when the normalized expression level of the 8 biomarkers is greater than a predetermined cutoff value, wherein the predetermined cutoff value is 5.9 on a scale of 0-8.

The present invention also provides a method for determining a response of a peptide receptor radionucleotide therapy (PRRT) of a GEP-NEN in a subject in need thereof, including (a) following a first cycle of PRRT therapy: determining the expression level of at least 22 biomarkers from a first cycle test sample from the subject by contacting the first cycle test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the first cycle test sample to the expression level of the at least 22 biomarkers in the reference sample; (b) following a second cycle of PRRT therapy, determining the expression level of at least 22 biomarkers from a second cycle test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the second cycle test sample to the expression level of the at least 22 biomarkers in the reference sample; (c) determining a ratio of change of the normalized expression levels from (a) to the normalized expression levels from (b); (d) determining the presence of a PRRT-responsive GEP-NEN when the ratio of change is greater than a pre-PRRT therapy cutoff value, wherein the pre-PRRT therapy cutoff value is 1 on a scale of 0-8.

The present invention also provides a method for determining a progression of a GEP-NEN in a subject in need thereof, including determining the expression level of ZFHX3 from a test sample from the subject by contacting the test sample with an agent specific to detect the expression of ZFHX3; determining the expression level of ZFHX3 from a reference sample by contacting the reference sample with an agent specific to detect the expression of ZFHX3; normalizing the expression level of ZFHX3 in the test sample to the expression level of ZFHX3 in the reference sample; comparing the normalized expression level of ZFHX3 in the test sample with a predetermined cutoff value; determining the progression of a GEP-NEN in the subject when the normalized expression level is equal to or greater than the predetermined cutoff value, wherein the predetermined cutoff value is 0.5 on a scale of 0-8.

The present invention also provides a method for predicting tumor proliferation of a GEP-NEN in a subject in need thereof, including (a) determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; (b) when a GEP-NEN is present, determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise KRAS, SSTR4 and VPS13C; summing the expression level of each of the 3 biomarkers of the test sample to generate a progressive diagnostic VI total test value and summing the expression level of each of the 3 biomarkers of the reference sample to generate a progressive diagnostic VI total reference value, wherein an increased value of the progressive diagnostic VI total test value compared to the progressive diagnostic VI total reference value indicates the presence of tumor proliferation of a GEP-NEN in the subject.

The method wherein (b) further includes determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise SSTR1, SSTR2 and SSTR5; summing the expression level of each of the 3 biomarkers of the test sample to generate a progressive diagnostic VII total test value and summing the expression level of each of the 3 biomarkers of the reference sample to generate a progressive diagnostic VII total reference value, wherein an increased value of the progressive diagnostic VII total test value compared to the progressive diagnostic VII total reference value indicates the presence of tumor proliferation of a GEP-NEN in the subject.

As used herein, the term "GEP-NEN biomarker" and "NET biomarker" refer synonymously to a biological molecule, such as a gene product, the expression or presence of which (e.g., the expression level or expression profile) on its own or as compared to one or more other biomarkers (e.g., relative expression) differs (i.e., is increased or decreased) depending on the presence, absence, type, class, severity, metastasis, location, stage, prognosis, associated symptom, outcome, risk, likelihood or treatment responsiveness, or prognosis of GEP-NEN disease, or is associated positively or negatively with such factors of the prediction thereof.

As used herein, the term "polynucleotide" or nucleic acid molecule means a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees and temperatures for washing in 0.1×SSC/0.1% SDS are above 55 degrees C., and most preferably to stringent hybridization conditions.

The term "blood biopsy" refers to a diagnostic study of the blood to determine whether a patient presenting with symptoms has a condition that may be classified as either benign (low activity) or malignant (high activity/metastatic).

The term "classifying" as used herein with regard to different types or stages of GEP-NEN refers to the act of compiling and analyzing expression data for using statistical techniques to provide a classification to aid in diagnosis of a stage or type of GEP-NEN.

The term "classifier" as used herein refers to an algorithm that discriminates between disease states with a predetermined level of statistical significance. A two-class classifier is an algorithm that uses data points from measurements from a sample and classifies the data into one of two groups. A multi-class classifier is an algorithm that uses data points from measurements from a sample and classifies the data into one of multiple groups. The "classifier" maximizes the probability of distinguishing a randomly selected cancer sample from a randomly selected benign sample, i.e., the area under a curve (AUC) of receiver operating characteristic (ROC) curve.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression.

The term "condition" as used herein refers generally to a disease, event, or change in health status.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

The term "disease prevalence" refers to the number of all new and old cases of a disease or occurrences of an event during a particular period. Prevalence is expressed as a ratio in which the number of events is the numerator and the population at risk is the denominator.

The term "disease incidence" refers to a measure of the risk of developing some new condition within a specified period of time; the number of new cases during some time period, it is better expressed as a proportion or a rate with a denominator.

The term "stable disease" refers to a diagnosis for the presence of GEP-NEN, however GEP-NEN has been treated and remains in a stable condition, i.e. one that that is not progressive, as determined by imaging data and/or best clinical judgment.

The term "progressive disease" refers to a diagnosis for the presence of a highly active state of GEP-NEN, i.e. one has not been treated and is not stable or has been treated and has not responded to therapy, or has been treated and active disease remains, as determined by imaging data and/or best clinical judgment.

The term "expression level score" or "NETest score" refers to the output of a mathematically-derived classifier algorithm generated from the combination of classification algorithms, i.e. SVM, LDA, KNN, and Bayes. This score ranges between 0 and 100%. The expression level score from a test sample, once compared to the expression level score for a reference or control sample, may be used to diagnose the presence of GEP-NEN, the different stages of GEP-NEN, predict the risk of contracting a stage of GEP-NEN, or determines the risk of recurrence of GEP-NEN in post-therapy human patients. Distinctions between GEP-NEN disease states are based on pre-determined expression level score thresholds and/or ranges as further defined in the present application.

Diagnosis and prognosis of GEP-NEN has been difficult, in part due to the prosaic symptoms and syndromes of the disease, such as carcinoid syndrome, diarrhea, flushing, sweating, bronchoconstriction, gastrointestinal bleeding, cardiac disease, intermittent abdominal pain, which often remain silent for years. Available diagnostic methods include anatomical localization, such as by imaging, e.g., X-ray, gastrointestinal endoscopy, abdominal computed tomography (CT), combined stereotactic radiosurgery (SRS)/CT, and MRI, and detection of some gene products e.g., chromogranin A. Known methods are limited, for example by low specificity and/or sensitivity and/or in the ability to detect early-stage disease.

Detection of single biomarkers has not been entirely satisfactory, for example, to identify malignancy in human blood samples and to predict complex outcomes like fibrosis and metastasis. See Michiels S, Koscielny S, Hill C, "Interpretation of microarray data in cancer," Br J Cancer 2007; 96(8): 1155-8. Limitations in available methods have contributed to difficulties in pathological classification, staging, and prediction, treatment developing and monitoring therapeutic effects. Among the embodiments provided herein are methods and compositions that address these limitations.

In one aspect, the present application relates to the detection and identification of GEP-NEN biomarkers and panels of such biomarkers, for example, in biological samples. Provided are methods and compositions (e.g., agents, such as polynucleotides), for detecting, determining expression levels of, and recognizing or binding to the biomarkers, in biological samples, typically blood samples.

Also provided are models and biomathematical algorithms, e.g., supervised learning algorithms, and methods using the same, for prediction, classification, and evaluation of GEP-NEN and associated outcomes, for example, predicting degree of risk, responsiveness to treatment, metastasis or aggressiveness, and for determining GEP-NEN subtype.

Detection of the biomarkers using the provided embodiments is useful for improving GEP-NEN diagnostics and prognostics, and to inform treatment protocols. In some aspects, detection of the biomarkers and/or expression levels by the provided embodiments confirms or indicates the presence, absence, stage, class, location, sub-type, aggressiveness, malignancy, metastasis, prognosis, or other outcome of GEP-NEN, or a GEP-NEN cell, such as a circulating GEP-NEN cell (CNC). The provided methods and compositions may be used for tumor localization, and for predicting or detecting metastases, micrometastases, and small lesions, and/or for determining degree of risk, likelihood of recurrence, treatment responsiveness or remission, and informing appropriate courses of treatment. For example, detecting the biomarkers, e.g., in circulation may be used to detect early-stage and primary GEP-NENs (e.g., to identify GEP-NEN disease or metastases in a patient previously deemed "negative" by another approach, such as anatomic localization).

The provided methods and compositions may be used for designing, implementing, and monitoring treatment strategies, including patient-specific treatment strategies. In one example, detected expression levels of the GEP-NEN biomarkers serve as surrogate markers for treatment efficacy, e.g., to monitor the effects of surgical therapy, e.g., removal of tumors, targeted medical therapy, e.g., inhibition of tumor secretion/proliferation, and other therapeutic approaches, by detecting remission or recurrence of tumors, even in the form of small micrometastases. The methods also may be used in evaluating clinical symptoms and outcomes, and for histological grading and molecular characterization of GEP-NENs.

The provided biomarkers including GEP-NEN biomarkers, and subsets and panels of the same. Among the provided GEP-NEN biomarkers are gene products, such as DNA, RNA, e.g., transcripts, and protein, which are differentially expressed in GEP-NEN disease, and/or in different stages or sub-types of GEP-NEN, or in different GEP-NEN tumors, such as gene products differentially expressed in metastatic versus non-metastatic tumors, tumors with different degrees of aggressiveness, high versus low-risk tumors, responsive versus non-responsive tumors, tumors exhibiting different pathological classifications and/or likelihood of response to particular courses of treatment, as well as those associated with features of GEP-NEN disease, stage, or type, or with neuroendocrine cells or related cell-types.

For example, the biomarkers include gene products whose expression is associated with or implicated in tumorogenicity, metastasis, or hormone production, or a phenotype of primary or metastatic GEP-NEN, such as adhesion, migration, proliferation, apoptosis, metastasis, and hormone secretion, and those associated with neoplasia or malignancy in general.

Among the biomarkers are GEP-NEN cell secretion products, including hormones and amines, e.g., gastrin, ghrelin, pancreatic polypeptide, substance P, histamine, and serotonin, and growth factors such as tumor growth factor-beta (TGF-β) and connective tissue growth factor (CTGF), which are detectable in the circulation. Secretion products can vary with tumor sub-type and origin.

In one example, the biomarkers are gene products associated with regulatory genotypes (i.e., adhesion, migration, proliferation, apoptosis, metastasis, and/or hormone secretion) that underlay various GEP-NEN subtypes, stages, degrees of aggressiveness, or treatment responsiveness.

A total of 51 differentially expressed biomarker genes have been discovered for the diagnosis, prognosis, and/or monitoring of GEP-NENs. Further details regarding the 51 differentially expressed GEP-NEN biomarkers as well as the housekeeping gene, ALG9, are found in TABLE 1.

TABLE 1

GEP-NEN Biomarker/Houskeeper Sequence Information

| Gene Name | RefSeq Accession | Sequence | SEQ ID NO: |
|---|---|---|---|
| ALG9 | NM_024740.2 | GTCTTTTGTCCCTCGGCGGACACCGTTTGCCAGCCAAAGC<br>TATGTCTGCGCGCTCACCGACTTCATAGGGTGCCGAATTC<br>TTTTTTCCCCAGGCTTGCCATGGCTAGTCGAGGGGCTCGG<br>CAGCGCCTGAAGGGCAGCGGGGCCAGCAGTGGGGATACGG<br>CCCCGGCTGCGGACAAGCTGCGGGAGCTGCTGGGCAGCCG<br>AGAGGCGGGCGGCGCGGAGCACCGGACCGAGTTATCTGGG<br>AACAAAGCAGGACAAGTCTGGGCACCTGAAGGATCTACTG<br>CTTTCAAGTGTCTGCTTTCAGCAAGGTTATGTGCTGCTCT<br>CCTGAGCAACATCTCTGACTGTGATGAAACATTCAACTAC<br>TGGGAGCCAACACACTACCTCATCTATGGGGAAGGGTTTC<br>AGACTTGGGAATATTCCCCAGCATATGCCATTCGCTCCTA<br>TGCTTACCTGTTGCTTCATGCCTGGCCAGCTGCATTTCAT<br>GCAAGAATTCTACAAACTAATAAGATTCTTGTGTTTTACT<br>TTTTGCGATGTCTTCTGGCTTTTGTGAGCTGTATTTGTGA<br>ACTTTACTTTTACAAGGCTGTGTGCAAGAAGTTTGGGTTG<br>CACGTGAGTCGAATGATGCTAGCCTTCTTGGTTCTCAGCA<br>CTGGCATGTTTTGCTCATCATCAGCATTCCTTCCTAGTAG<br>CTTCTGTATGTACACTACGTTGATAGCCATGACTGGATGG<br>TATATGGACAAGACTTCCATTGCTGTGCTGGGAGTAGCAG<br>CTGGGGCTATCTTAGGCTGGCCATTCAGTGCAGCTCTTGG<br>TTTACCCATTGCCTTTGATTTGCTGGTCATGAAACACAGG<br>TGGAAGAGTTTCTTTCATTGGTCGCTGATGGCCCTCATAC<br>TATTTCTGGTGCCTGTGGTGGTCATTGACAGCTACTATTA<br>TGGGAAGTTGGTGATTGCACCACTCAACATTGTTTTGTAT<br>AATGTCTTTACTCCTCATGGACCTGATCTTTATGGTACAG<br>AACCCTGGTATTTCTATTTAATTAATGGATTTCTGAATTT<br>CAATGTAGCCTTTGCTTTGGCTCTCCTAGTCCTACCACTG<br>ACTTCTCTTATGGAATACCTGCTGCAGAGATTTCATGTTC<br>AGAATTTAGGCCACCCGTATTGGCTTACCTTGGCTCCAAT<br>GTATATTTGGTTTATAATTTTCTTCATCCAGCCTCACAAA<br>GAGGAGAGATTTCTTTTCCCTGTGTATCCACTTATATGTC<br>TCTGTGGCGCTGTGGCTCTCTCTGCACTTCAGCACAGTTT<br>TCTGTACTTCCAGAAATGTTACCACTTTGTGTTTCAACGA | 1 |

TABLE 1-continued

GEP-NEN Biomarker/Houskeeper Sequence Information

| Gene Name | RefSeq Accession | Sequence | SEQ ID NO: |
|---|---|---|---|
| | | TATCGCCTGGAGCACTATACTGTGACATCGAATTGGCTGG<br>CATTAGGAACTGTCTTCCTGTTTGGGCTCTTGTCATTTTC<br>TCGCTCTGTGGCACTGTTCAGAGGATATCACGGGCCCCTT<br>GATTTGTATCCAGAATTTTACCGAATTGCTACAGACCCAA<br>CCATCCACACTGTCCCAGAAGGCAGACCTGTGAATGTCTG<br>TGTGGGAAAAGAGTGGTATCGATTTCCCAGCAGCTTCCTT<br>CTTCCTGACAATTGGCAGCTTCAGTTCATTCCATCAGAGT<br>TCAGAGGTCAGTTACCAAAACCTTTTGCAGAAGGACCTCT<br>GGCCACCCGGATTGTTCCTACTGACATGAATGACCAGAAT<br>CTAGAAGAGCCATCCAGATATATTGATATCAGTAAATGCC<br>ATTATTTAGTGGATTTGGACACCATGAGAGAAACACCCCG<br>GGAGCCAAAATATTCATCCAATAAAGAAGAATGGATCAGC<br>TTGGCCTATAGACCATTCCTTGATGCTTCTAGATCTTCAA<br>AGCTGCTGCGGGCATTCTATGTCCCCTTCCTGTCAGATCA<br>GTATACAGTGTACGTAAACTACACCATCCTCAAACCCCGG<br>AAAGCAAAGCAAATCAGGAAGAAAAGTGGAGGTTAGCAAC<br>ACACCTGTGGCCCCAAAGGACAACCATCTTGTTAACTATT<br>GATTCCAGTGACCTGACTCCCTGCAAGTCATCGCCTGTAA<br>CATTTGTAATAAAGGTCTTCTGACATGAATACTGGAATCT<br>GGGTGCTCTGGGCTAGTCAAAGTCTATTTCAAAGTCTAAT<br>CAAAGTCACATTTGCTCCCTGTGTGTGTCTCTGTTCTGCA<br>TGTAAACTTTTTGCAGCTAGGCAGAGAAAGGCCCTAAAGC<br>ACAGATAGATATATTGCTCCACATCTCATTGTTTTTCCTC<br>TGTTCAATTATTTACTAGACCGGAGAAGAGCAGAACCAAC<br>TTACAGGAAGAATTGAAAATCCTGGTACTGGATGGCTGTG<br>ATAAGCTGTTCTCCACACTCTGGCCTGGCATCTGAGAACT<br>AGCAAGCCTCTCTTAGGCCATATGGGCTTCTCCACCAAAG<br>CTGTTTGGCAGCTCCTAGCAGACCTTCTTATTGAAATCCT<br>CATGCTGAAAATGAACACAGCCTAGTTGCCAACCCACATG<br>TCCTTTTCACCTCCAGCAAGACTAAGCTTCTTTAAAGCAC<br>TTCACAGGACTAGGACCCTGTCCTGGAGCTATCTCAGGAA<br>AAAGGTGACCATTTGAGGAACTGTGACCTAATTTTATTAT<br>AATGATGCCTCTAATTTTCATTTCCTTTACAACCAACTGT<br>AACTATAAGGTTGTATTGCTTTTTTGTTCAGTTTTAGCAT<br>GCTATTTTTTGAATTCTAGACTCCTCCATGTGAAGATATC<br>AACAGACAAAACTACAACTGTATAGGACATATTTGGAGAA<br>AATTCTATCAATTGATACATTTGGATGACATCACATTTTT<br>AAGTAATGTAATCTGAGGCCATTGCTGAGGAAATTAAGAA<br>TTTTCCTTTTTTTTTAACCACCCCCAGTGAAAAGGATCAG<br>TGTATATTTATAGCACCTATTTTTTAGTTCTGTCTGTTGT<br>GAGGCACATCCTGCATGGGGCACTTCTAGTCAAATAGGCA<br>ATGATAAGGACCTAATTAAAATGTGATAAGTGTATACTAT<br>TACTTTAAAAGCCTTTACAGTCAGTACTTCAGTTTACAAG<br>GCACTTTCACAGCATCTCGTTTGATCCTCACAGTCACAAC<br>ATGTGGTAGACAAGGCAGGTGATTTTTATCCCCATTTTAC<br>AGATAAGGAAACAGGCTGCGGGTGGGGAGTGAGGGGAGGT<br>AAAGATAGTTAGTTGCCTAAGGTCACACAGCCAGTAAGTA<br>ATAGAGCTGGGACTGGAACCCAGGTTTCCTTACTCTCATC<br>TATTGCTCCTCCATATTCCTCACTCAACCATGAAAACATT<br>ACTTGAAAGGACTGATGAGGTTAACCAGAGACCTAACTGA<br>TATTGTAACTTTCTATTTTAAGGAAGAATTGTGTCTGTAT<br>TTGAGTTCTTTGGAGCCTCCAGTCTGCCTGTGTGTTAGAC<br>CAGCACAGCAGTGCTGTGTGATGCAGCCTGACCTGTGGCA<br>GGAAAGTAGTGCTTCTGTTTGGAAGTCATGTTCTTTTGCA<br>GCCACACAGGATCCAAATATCAGTACTATTCCTGTAGTCA<br>ATCTGGGGTCACATTATAGGTGCCTTATTTCCCTAAGGGT<br>AACTGATCTGAATATCTGCAAATAGGATGAATCTATTTTT<br>CAGAAGTTCCATCTTTCATTTTTCTTTTTTTTTTTGAGAC<br>AGAGTCTCATTCTGTCGCCCATGCTGGAGTGCAGTGGCGC<br>GATCTCGGCTCGCTGCAACCTCTGCCTCCCAGGTTGAAGC<br>AATTCTCATGCCTCAGCCACCCGAGTAGCTGGGATTACAG<br>GCATGCGCCATCATGCCCAGCTAATTTATGTATTTTTAGT<br>AGAGTTGGAGTTTCACCATGTTGGCCAGGCTGGTCTTGGA<br>CTCCTGACCTCAGGTCATCCACCCGCCTCAGCCTCCCAAA<br>GTGCTGGTATTACAGGCGTGAGCCACCGCACCCAGCCCCA<br>TCTTTCATTTTCAAAGAGAAGGGCATTCTAATAGGAACTG<br>GTGCCAAGAGAGAAGAAAAGAAGTGATAACAGAAGAAATG<br>GCTAGTTACAATATTAAAAAGCTCCTCTTTGAGATCTCCT<br>CTGCAGGAATATCAGAGACGGAGTTGAAGCGCTGGAGAGG<br>TAATAGGTCTAGACAGTACAGAACAATAACTGGGGAGTGT<br>GTGAGGATAGACTGGGCTCCCCCTTGCTTGAAAGATCTCT<br>GGCATTTAATTCTCAATTCTTGATTACTATTTTCCAGTGT<br>AAAACTAGCACATATGATCTGACTACAGGACAGAGAATTT<br>TAAGTGAAACATTTGCCTTACTTGCAGTAATAATGTGCTG<br>TTCTTCACAGTAGCTAAGGCCCTCTATGTTTCCCAGAGGT | |

TABLE 1-continued

GEP-NEN Biomarker/Houskeeper Sequence Information

| Gene Name | RefSeq Accession | Sequence | SEQ ID NO: |
|---|---|---|---|
| | | AAATAAGAATCCAGGAATGGAGGTCCATCTGTGATGAATG<br>GCTTTTTTCTAATCAAAGTAGTATAATGCTGTTTTATCTG<br>TTTTGTCATCTTGTTTTTTTTTTTTTTTAAAAAAACAAAA<br>CCTTAATTATAATATAGCGCAAAGAAAGGCCAGGACTGAT<br>GCAGGGATTCCTTGGAAATATCAGTTCCTATCACTTTTAA<br>AACCTGATTTTGGATCTCTCTGTTCTATGTATGTCTTTAG<br>TGAGAGCACAATACATGGCAGAACGCTGTGCCAAATGTTA<br>TAGGTAAGGAATATAGAAATGAATGTTTTTTGTTGTGAAG<br>GTGTTTTCATGTGATATTTTATAAACACATTTTAAAAAAT<br>CTCCATCACTTTTTAGTATAGGAAGGATAGCTTTGCCTGG<br>GAAAAACAGTTTCAACACACCTGCTCAGAGTAGCAGTTCT<br>CCCTCAAAAAAGCAGTGTTCAGCCTGCACTGACTGTTCTG<br>CTTGCCAAAAGGAGGAAGCATGCAAGATACTTATTTCTCC<br>ATAGATTGTGGAGTATAGAGGGATGTGGGACTACAGATTA<br>TTATTTTTTTTCCCCGAGACAGAGTCTTGCTCTGTCGCCC<br>AGGTTGGAACACAATGGCACGACCTCAGCTCACTGCAACC<br>TCTGTCTCCCGGGTTCAAGCAATTCTCCTGCTTCAGCCTC<br>CTGAGTAGCTGGGATTACAGGCACACACCACCACCGCACT<br>CAGCTAATTTTTGTATTTTTAGTAGAGGTGGGGTTTTACC<br>ATGTTGGCCAGGCTGGTCTTAAACTCCTGACCTTGTAATC<br>ATCCCGCCTCGGCCTCCTAAAGTGCTAGGATTACAGGCAT<br>GAGCCACCGCACCCGGCCCAGATAATTTTTAATAGCCTTT<br>GATCATGGGGTGAGTGAGGGAGTAGGTATACTTGGCAAAT<br>GCATGGTTCTCTGATTTCTAGCTCTAAAGCAGCCTTATCT<br>GAATCCCCAAATCTTGTGATGCTGAGTACCATTACTGAAC<br>CAGTCTGCACGGTAGGCATCTGCTACCAAAATTTACCTCC<br>TACCTGGTAGGTGTCATCTGATAAGAAAGAAGACAGGTTA<br>TTTTAATTTTTTGAGATAATCACAGAAAATTGCAGCCCAT<br>ACTCTTTATTACCGAATTCAAGTTTGGAAATAGACCCTTT<br>GTTTTAAATCATGATGGGTCTTTATCCCAATCATTTATCT<br>GGGTCATTTTTCCAACTTTGGAGTTCTAGGAAAGAACCTT<br>GAAAACCTGATATGATTCTGCAGCATGAGGTCTACGGTGA<br>CCATTTGGGCAAAGCTCCAGTGGCAATCATTTATTGTGTT<br>TTGCATTTCCTGGGATTTATTGAAATAAGAATTCACTGTG<br>ATTATGTAGTCTTCTGGCTAGTATCAGGCAGCTCTGCTTT<br>TAATTTGGTTAATTTTATTTTCTCTGAAGAGGGAGAAGAG<br>GTACAATTTAATCTTGGCCTCCACAAGCATATTAAAGCTC<br>ACGTGTTAATCAGTGCATTCTTATGCTCCTACATTAAATG<br>CCTTGGGTAAATGGATAAATGGACATGTGCCCAGCTTTAA<br>TTTTTTTTGCAACAGAAAGATCAGACTTCCGTATGGCATC<br>GTTGGATTTCAGAGGCTTTCTGGTGTATCTGTAAATCTGA<br>ATGTTGCCTTCTGCCAGTCTGTATAACCAGGTGATTCATG<br>CTGCAAATGAAATCAGGAAGCAGTAAAGTGTTAAAGCAAG<br>AGTATTGTCCAATTCACTTGTCTTCCTGATCCTTGTACTT<br>TATTTCACGTGTCGGTGTTTACATTACATACTTATATTTC<br>CTGTGAAAGAAAGAGTTAAATAAATTGTAGCAGTTTGA | |
| AKAP8L | NM_014371.3 | ACTGATATGAGGAGGCATAGAGATAGACAGCGGTTCCTTC<br>CAATAGACGTGAAGCCGAGGCCGGTATGAGCCAATGCGGT<br>CGGGAGGCGGGGCTCGGGTGTGTGTGGAGGGGACCCTGTG<br>GTTAGCAGCAGCTATCGCAGCGTCGGATGTTCAGAGCAGC<br>AGAAGCCGGCGTCGTCGGATGTTGTGTTGCCCGCCACCAT<br>GAGCTACACAGGCTTTGTCCAGGGATCTGAAACCACTTTG<br>CAGTCGACATACTCGGATACCAGCGCTCAGCCCACCTGTG<br>ATTATGGATATGGAACTTGGAACTCTGGGACAAATAGAGG<br>CTACGAGGGCTATGGCTATGGCTATGGCTATGGCCAGGAT<br>AACACCACCAACTATGGGTATGGTATGGCCACTTCACACT<br>CTTGGGAAATGCCTAGCTCTGACACAAATGCAAACACTAG<br>TGCCTCGGGTAGCGCCAGTGCCGATTCCGTTTTATCCAGA<br>ATTAACCAGCGCTTAGATATGGTGCCGCATTTGGAGACAG<br>ACATGATGCAAGGAGGCGTGTACGGCTCAGGTGGAGAAAG<br>GTATGACTCTTATGAGTCCTGCGACTCGAGGGCCGTCCTG<br>AGTGAGCGCGACCTGTACCGGTCAGGCTATGACTACAGCG<br>AGCTTGACCCTGAGATGGAAATGGCCTATGAGGGCCAATA<br>CGATGCCTACCGCGACCAGTTCCGCATGCGTGGCAACGAC<br>ACCTTCGGTCCCAGGGCACAGGGCTGGGCCCGGGATGCCC<br>GGAGCGGCCGGCCAATGGCCTCAGGCTATGGGCGCATGTG<br>GGAAGACCCCATGGGGGCCCGGGGCCAGTGCATGTCTGGT<br>GCCTCTCGGCTGCCCTCCCTCTTCTCCCAGAACATCATCC<br>CCGAGTACGGCATGTTCCAGGGCATGCGAGGTGGGGGCGC<br>CTTCCCGGGCGGCTCCCGCTTTGGTTTCGGGTTTGGCAAT<br>GGCATGAAGCAGATGAGGCGGACCTGGAAGACCTGGACCA<br>CAGCCGACTTCCGAACCAAGAAGAAGAAGAGAAAGCAGGG<br>CGGCAGTCCTGATGAGCCAGATAGCAAAGCCACCCGCACG<br>GACTGCTCGGACAACAGCGACTCAGACAATGATGAGGGCA | 2 |

TABLE 1-continued

GEP-NEN Biomarker/Houskeeper Sequence Information

| Gene Name | RefSeq Accession | Sequence | SEQ ID NO: |
|---|---|---|---|
| | | CCGAGGGGGAAGCCACAGAGGGCCTTGAAGGCACCGAGGC<br>TGTGGAGAAGGGCTCCAGAGTGGACGGAGAGGATGAGGAG<br>GGAAAAGAGGATGGGAGAGAAGAAGGCAAAGAGGATCCAG<br>AGAAGGGGGCCCTAACCACCCAGGATGAAAATGGCCAGAC<br>CAAGCGCAAGTTGCAGGCAGGCAAGAAGAGTCAGGACAAG<br>CAGAAAAAGCGGCAGCGAGACCGCATGGTGGAAAGGATCC<br>AGTTTGTGTGTTCTCTGTGCAAATACCGGACCTTCTATGA<br>GGACGAGATGGCCAGCCATCTTGACAGCAAGTTCCACAAG<br>GAACACTTTAAGTACGTAGGCACCAAGCTCCCTAAGCAGA<br>CGGCTGACTTTCTGCAGGAGTACGTCACTAACAAGACCAA<br>GAAGACAGAGGAGCTCCGAAAAACCGTGGAGGACCTTGAT<br>GGCCTCATCCAGCAAATCTACAGAGACCAGGATCTGACCC<br>AGGAAATTGCCATGGAGCATTTTGTGAAGAAGGTGGAGGC<br>AGCCCATTGTGCAGCCTGCGACCTCTTCATTCCCATGCAG<br>TTTGGGATCATCCAGAAGCATCTGAAGACCATGGATCACA<br>ACCGGAACCGCAGGCTCATGATGGAGCAGTCCAAGAAGTC<br>CTCCCTCATGGTGGCCCGCAGTATTCTCAACAACAAGCTC<br>ATCAGCAAGAAGCTGGAGCGCTACCTGAAGGGCGAGAACC<br>CTTTCACCGACAGCCCCGAGGAGGAGAAGGAGCAGGAGGA<br>GGCTGAGGGCGGTGCCCTGGACGAGGGGGCGCAGGGCGAA<br>GCGGCAGGGATCTCGGAGGGCGCAGAGGGCGTGCCGGCGC<br>AGCCTCCCGTGCCCCCAGAGCCAGCCCCCGGGGCCGTGTC<br>GCCGCCACCGCCGCCGCCCCCAGAGGAGGAGGAGGAGGGC<br>GCCGTGCCCTTGCTGGGAGGGGCGCTGCAACGCCAGATCC<br>GCGGCATCCCGGGCCTCGACGTGGAGGACGACGAGGAGGG<br>CGGCGGGGGCGCCCCGTGACCCGAGCTCGGGGCGGGCGGA<br>GCCCGCGTGGCCGAAGCTGGAAACCAAACCTAATAAAGTT<br>TTCCCATCCCACCAAAAAAAAAAAAAAAAAA | |
| APLP2 | NM_001142276.1 | AGAAGGAGGGCGTGGTAATATGAAGTCAGTTCCGGTTGGT<br>GTAAAACCCCCGGGGCGGCGGCGAACTGGCTTTAGATGCT<br>TCTGGGTCGCGGTGTGCTAAGCGAGGAGTCCGAGTGTGTG<br>AGCTTGAGAGCCGCGCGCTAGAGCGACCCGGCGAGGGATG<br>GCGGCCACCGGGACCGCGGCCGCCGCAGCCACGGGCAGGC<br>TCCTGCTTCTGCTGCTGGTGGGGCTCACGGCGCCTGCCTT<br>GGCGCTGGCCGGCTACATCGAGGCTCTTGCAGCCAATGCC<br>GGAACAGGATTTGCTGTTGCTGAGCCTCAAATCGCAATGT<br>TTTGTGGGAAGTTAAATATGCATGTGAACATTCAGACTGG<br>GAAATGGGAACCTGATCCAACAGGCACCAAGAGCTGCTTT<br>GAAACAAAAGAAGAAGTTCTTCAGTACTGTCAGGAGATGT<br>ATCCAGAGCTACAGATCACAAATGTGATGGAGGCAAACCA<br>GCGGGTTAGTATTGACAACTGGTGCCGGAGGGACAAAAAG<br>CAATGCAAGAGTCGCTTTGTTACACCTTTCAAGTGTCTCG<br>TGGGTGAATTTGTAAGTGATGTCCTGCTAGTTCCAGAAAA<br>GTGCCAGTTTTTCCACAAAGAGCGGATGGAGGTGTGTGAG<br>AATCACCAGCACTGGCACACGGTAGTCAAAGAGGCATGTC<br>TGACTCAGGGAATGACCTTATATAGCTACGGCATGCTGCT<br>CCCATGTGGGGTAGACCAGTTCCATGGCACTGAATATGTG<br>TGCTGCCCTCAGACAAAGATTATTGGATCTGTGTCAAAAG<br>AAGAGGAAGAGGAAGATGAAGAGGAAGAGGAAGAGGAAGA<br>TGAAGAGGAAGACTATGATGTTTATAAAAGTGAATTTCCT<br>ACTGAAGCAGATCTGGAAGACTTCACAGAAGCAGCTGTGG<br>ATGAGGATGATGAGGATGAGGAAGAAGGGGAGGAAGTGGT<br>GGAGGACCGAGATTACTACTATGACACCTTCAAAGGAGAT<br>GACTACAATGAGGAGAATCCTACTGAACCCGGCAGCGACG<br>GCACCATGTCAGACAAGGAAATTACTCATGATGTCAAAGC<br>TGTCTGCTCCCAGGAGGCGATGACGGGGCCCTGCCGGGCC<br>GTGATGCCTCGTTGGTACTTCGACCTCTCCAAGGGAAAGT<br>GCGTGCGCTTTATATATGGTGGCTGCGGCGGCAACAGGAA<br>CAATTTTGAGTCTGAGGATTATTGTATGGCTGTGTGTAAA<br>GCGATGATTCCTCCAACTCCTCTGCCAACCAATGATGTTG<br>ATGTGTATTTCGAGACCTCTGCAGATGATAATGAGCATGC<br>TCGCTTCCAGAAGGCTAAGGAGCAGCTGGAGATTCGGCAC<br>CGCAACCGAATGGACAGGGTAAAGAAGGAATGGGAAGAGG<br>CAGAGCTTCAAGCTAAGAACCTCCCCAAAGCAGAGAGGCA<br>GACTCTGATTCAGCACTTCCAAGCCATGGTTAAAGCTTTA<br>GAGAAGGAAGCAGCCAGTGAGAAGCAGCAGCTGGTGGAGA<br>CCCACCTGGCCCGAGTGGAAGCTATGCTGAATGACCGCCG<br>TCGGATGGCTCTGGAGAACTACCTGGCTGCCTTGCAGTCT<br>GACCCGCCACGGCCTCATCGCATTCTCCAGGCCTTACGGC<br>GTTATGTCCGTGCTGAGAACAAAGATCGCTTACATACCAT<br>CCGTCATTACCAGCATGTGTTGGCTGTTGACCCAGAAAAG<br>GCGGCCCAGATGAAATCCCAGGTGATGACACATCTCCACG<br>TGATTGAAGAAAGGAGGAACCAAAGCCTCTCTCTGCTCTA<br>CAAAGTACCTTATGTAGCCCAAGAAATTCAAGAGGAAATT | 3 |

TABLE 1-continued

| GEP-NEN Biomarker/Houskeeper Sequence Information | | | |
|---|---|---|---|
| Gene Name | RefSeq Accession | Sequence | SEQ ID NO: |
| | | GATGAGCTCCTTCAGGAGCAGCGTGCAGATATGGACCAGT<br>TCACTGCCTCAATCTCAGAGACCCCTGTGGACGTCCGGGT<br>GAGCTCTGAGGAGAGTGAGGAGATCCCACCGTTCCACCCC<br>TTCCACCCCTTCCCAGCCCTACCTGAGAACGAAGGATCTG<br>GAGTGGGAGAGCAGGATGGGGGACTGATCGGTGCCGAAGA<br>GAAAGTGATTAACAGTAAGAATAAAGTGGATGAAAACATG<br>GTCATTGACGAGACTCTGGATGTTAAGGAAATGATTTTCA<br>ATGCCGAGAGAGTTGGAGGCCTCGAGGAAGAGCGGGAATC<br>CGTGGGCCCACTGCGGGAGGACTTCAGTCTGAGTAGCAGT<br>GCTCTCATTGGCCTGCTGGTCATCGCAGTGGCCATTGCCA<br>CGGTCATCGTCATCAGCCTGGTGATGCTGAGGAAGAGGCA<br>GTATGGCACCATCAGCCACGGGATCGTGGAGGTTGATCCA<br>ATGCTCACCCCAGAAGAGCGTCACCTGAACAAGATGCAGA<br>ACCATGGCTATGAGAACCCCACCTACAAATACCTGGAGCA<br>GATGCAGATTTAGGTGGCAGGGAGCGCGGCAGCCCTGGCG<br>GAGGGATGCAGGTGGGCCGGAAGATCCCACGATTCCGATC<br>GACTGCCAAGCAGCAGCCGCTGCCAGGGGCTGCGTCTGAC<br>ATCCTGACCTCCTGGACTGTAGGACTATATAAAGTACTAC<br>TGTAGAACTGCAATTTCCATTCTTTTAAATGGGTGAAAAA<br>TGGTAATATAACAATATATGATATATAAACCTTAAATGAA<br>AAAAATGATCTATTGCAGATATTTGATGTAGTTTTCTTTT<br>TTAAATTAATCAGAAACCCCACTTCCATTGTATTGTCTGA<br>CACATGCTCTCAATATATAATAAATGGGAAATGTCGATTT<br>TCAATAATAGACTTATATGCAGGCTGTCGTTCCGGTTATG<br>TTGTGTAAGTCAACTCTTCAGCCTCATTCACTGTCCTGGC<br>TTTTATTTAAAGAAAAAAAAGGCAGTATTCCCTTTTTAAA<br>TGAGCTTTCAGGAAGTTGCTGAGAAATGGGGTGGAATAGG<br>GAACTGTAATGGCCACTGAAGCACGTGAGAGACCCTCGCA<br>AAATGATGTGAAAGGACCAGTTTCTTGAAGTCCAGTGTTT<br>CCACGGCTGGATACCTGTGTGTCTCCATAAAAGTCCTGTC<br>ACCAAGGACGTTAAAGGCATTTTATTCCAGCGTCTTCTAG<br>AGAGCTTAGTGTATACAGATGAGGGTGTCCGCTGCTGCTT<br>TCCTTCGGAATCCAGTGCTTCCACAGAGATTAGCCTGTAG<br>CTTATATTTGACATTCTTCACTGTCTGTTGTTTACCTACC<br>GTAGCTTTTTACCGTTCACTTCCCCTTCCAACTATGTCCA<br>GATGTGCAGGCTCCTCCTCTCTGGACTTTCTCCAAAGGCA<br>CTGACCCTCGGCCTCTACTTTGTCCCCTCACCTCCACCCC<br>CTCCTGTCACCGGCCTTGTGACATTCACTCAGAGAAGACC<br>ACACCAAGGAGGCGGCCGCTGGCCCAGGAGAGAACACGGG<br>GAGGTTTGTTTGTGTGAAAGGAAAGTAGTCCAGGCTGTCC<br>CTGAAACTGAGTCTGTGGACACTGTGGAAAGCTTTGAACA<br>ATTGTGTTTTCGTCACAGGAGTCTTTGTAATGCTTGTACA<br>GTTGATGTCGATGCTCACTGCTTCTGCTTTTTCTTTCTTT<br>TTATTTTAAATCTGAAGGTTCTGGTAACCTGTGGTGTATT<br>TTTATTTTCCTGTGACTGTTTTTGTTTTGTTTTTTTCCTT<br>TTTCCTCCCCTTTGACCCTATTCATGTCTCTACCCACTAT<br>GCACAGATTAAACTTCACCTACAAACTCCTTAATATGATC<br>TGTGGAGAATGTACACAGTTTAAACACATCAATAAATACT<br>TTAACTTCCACCGAGAAAAAAAAAAAAAAAAA | |
| ARAF1 | NM_001654.4 | CTTGACAGACGTGACCCTGACCCAATAAGGGTGGAAGGCT<br>GAGTCCCGCAGAGCCAATAACGAGAGTCCGAGAGGCGACG<br>GAGGCGGACTCTGTGAGGAAACAAGAAGAGAGGCCCAAGA<br>TGGAGACGGCGGCGGCTGTAGCGGCGTGACAGGAGCCCCA<br>TGGCACCTGCCCAGCCCCACCTCAGCCCATCTTGACAAAA<br>TCTAAGGCTCCATGGAGCCACCACGGGGCCCCCCTGCCAA<br>TGGGGCCGAGCCATCCCGGGCAGTGGGCACCGTCAAAGTA<br>TACCTGCCCAACAAGCAACGCACGGTGGTGACTGTCCGGG<br>ATGGCATGAGTGTCTACGACTCTCTAGACAAGGCCCTGAA<br>GGTGCGGGGTCTAAATCAGGACTGCTGTGTGGTCTACCGA<br>CTCATCAAGGGACGAAAGACGGTCACTGCCTGGGACACAG<br>CCATTGCTCCCCTGGATGGCGAGGAGCTCATTGTCGAGGT<br>CCTTGAAGATGTCCCGCTGACCATGCACAATTTTGTACGG<br>AAGACCTTCTTCAGCCTGGCGTTCTGTGACTTCTGCCTTA<br>AGTTTCTGTTCCATGGCTTCCGTTGCCAAACCTGTGGCTA<br>CAAGTTCCACCAGCATTGTTCCTCCAAGGTCCCCACAGTC<br>TGTGTTGACATGAGTACCAACCGCCAACAGTTCTACCACA<br>GTGTCCAGGATTTGTCCGGAGGCTCCAGACAGCATGAGGC<br>TCCCTCGAACCGCCCCCTGAATGAGTTGCTAACCCCCCAG<br>GGTCCCAGCCCCCGCACCCAGCACTGTGACCCGGAGCACT<br>TCCCCTTCCCTGCCCCAGCCAATGCCCCCCTACAGCGCAT<br>CCGCTCCACGTCCACTCCCAACGTCCATATGGTCAGCACC<br>ACGGCCCCCATGGACTCCAACCTCATCCAGCTCACTGGCC<br>AGAGTTTCAGCACTGATGCTGCCGGTAGTAGAGGAGGTAG<br>TGATGGAACCCCCCGGGGGAGCCCCAGCCCAGCCAGCGTG | 4 |

TABLE 1-continued

GEP-NEN Biomarker/Houskeeper Sequence Information

| Gene Name | RefSeq Accession | Sequence | SEQ ID NO: |
|---|---|---|---|
| | | TCCTCGGGGAGGAAGTCCCCACATTCCAAGTCACCAGCAG<br>AGCAGCGCGAGCGGAAGTCCTTGGCCGATGACAAGAAGAA<br>AGTGAAGAACCTGGGGTACCGGGACTCAGGCTATTACTGG<br>GAGGTACCACCCAGTGAGGTGCAGCTGCTGAAGAGGATCG<br>GGACGGGCTCGTTTGGCACCGTGTTTCGAGGGCGGTGGCA<br>TGGCGATGTGGCCGTGAAGGTGCTCAAGGTGTCCCAGCCC<br>ACAGCTGAGCAGGCCCAGGCTTTCAAGAATGAGATGCAGG<br>TGCTCAGGAAGACGCGACATGTCAACATCTTGCTGTTTAT<br>GGGCTTCATGACCCGGCCGGGATTTGCCATCATCACACAG<br>TGGTGTGAGGGCTCCAGCCTCTACCATCACCTGCATGTGG<br>CCGACACACGCTTCGACATGGTCCAGCTCATCGACGTGGC<br>CCGGCAGACTGCCCAGGGCATGGACTACCTCCATGCCAAG<br>AACATCATCCACCGAGATCTCAAGTCTAACAACATCTTCC<br>TACATGAGGGGCTCACGGTGAAGATCGGTGACTTTGGCTT<br>GGCCACAGTGAAGACTCGATGGAGCGGGGCCCAGCCCTTG<br>GAGCAGCCCTCAGGATCTGTGCTGTGGATGGCAGCTGAGG<br>TGATCCGTATGCAGGACCCGAACCCCTACAGCTTCCAGTC<br>AGACGTCTATGCCTACGGGGTTGTGCTCTACGAGCTTATG<br>ACTGGCTCACTGCCTTACAGCCACATTGGCTGCCGTGACC<br>AGATTATCTTTATGGTGGGCCGTGGCTATCTGTCCCCGGA<br>CCTCAGCAAAATCTCCAGCAACTGCCCCAAGGCCATGCGG<br>CGCCTGCTGTCTGACTGCCTCAAGTTCCAGCGGGAGGAGC<br>GGCCCCTCTTCCCCCAGATCCTGGCCACAATTGAGCTGCT<br>GCAACGGTCACTCCCCAAGATTGAGCGGAGTGCCTCGGAA<br>CCCTCCTTGCACCGCACCCAGGCCGATGAGTTGCCTGCCT<br>GCCTACTCAGCGCAGCCCGCCTTGTGCCTTAGGCCCCGCC<br>CAAGCCACCAGGGAGCCAATCTCAGCCCTCCACGCCAAGG<br>AGCCTTGCCCACCAGCCAATCAATGTTCGTCTCTGCCCTG<br>ATGCTGCCTCAGGATCCCCCATTCCCCACCCTGGGAGATG<br>AGGGGGTCCCCATGTGCTTTTCCAGTTCTTCTGGAATTGG<br>GGGACCCCCGCCAAAGACTGAGCCCCCTGTCTCCTCCATC<br>ATTTGGTTTCCTCTTGGCTTTGGGGATACTTCTAAATTTT<br>GGGAGCTCCTCCATCTCCAATGGCTGGGATTTGTGGCAGG<br>GATTCCACTCAGAACCTCTCTGGAATTTGTGCCTGATGTG<br>CCTTCCACTGGATTTTGGGGTTCCCAGCACCCCATGTGGA<br>TTTTGGGGGGTCCCTTTTGTGTCTCCCCCGCCATTCAAGG<br>ACTCCTCTCTTTCTTCACCAAGAAGCACAGAATTCTGCTG<br>GGCCTTTGCTTGTTTAAAAAAAAAAAAAAAAAAAAAAAAA<br>AAAAAAAAAAAAAAAAAAAAAAAAAAAAAAAAAAAAAAAA<br>AA | |
| ATP6V1H | NM_015941.3 | AGCAGTCACGTGCCTCCGATCACGTGACCGGCGCCTCTGT<br>CATTCTACTGCGGCCGCCCTGGCTTCCTTCTACCTGTGCG<br>GCCCTCAACGTCTCCTTGGTGCGGGACCCGCTTCACTTTC<br>GGCTCCCGGAGTCTCCCTCCACTGCTCAGACCTCTGGACC<br>TGACAGGAGACGCCTACTTGGCTCTGACGCGGCGCCCCAG<br>CCCGGCTGTGTCCCCGGCGCCCCGGACCACCCTCCCTGCC<br>GGCTTTGGGTGCGTTGTGGGGTCCCGAGGATTCGCGAGAT<br>TTGTTGAAAGACATTCAAGATTACGAAGTTTAGATGACCA<br>AAATGGATATCCGAGGTGCTGTGGATGCTGCTGTCCCCAC<br>CAATATTATTGCTGCCAAGGCTGCAGAAGTTCGTGCAAAC<br>AAAGTCAACTGGCAATCCTATCTTCAGGGACAGATGATTT<br>CTGCTGAAGATTGTGAGTTTATTCAGAGGTTTGAAATGAA<br>ACGAAGCCCTGAAGAGAAGCAAGAGATGCTTCAAACTGAA<br>GGCAGCCAGTGTGCTAAAACATTTATAAATCTGATGACTC<br>ATATCTGCAAAGAACAGACCGTTCAGTATATACTAACTAT<br>GGTGGATGATATGCTGCAGGAAAATCATCAGCGTGTTAGC<br>ATTTTCTTTGACTATGCAAGATGTAGCAAGAACACTGCGT<br>GGCCCTACTTTCTGCCAATGTTGAATCGCCAGGATCCCTT<br>CACTGTTCATATGGCAGCAAGAATTATTGCCAAGTTAGCA<br>GCTTGGGGAAAAGAACTGATGGAAGGCAGTGACTTAAATT<br>ACTATTTCAATTGGATAAAAACTCAGCTGAGTTCACAGAA<br>ACTGCGTGGTAGCGGTGTTGCTGTTGAAACAGGAACAGTC<br>TCTTCAAGTGATAGTTCGCAGTATGTGCAGTGCGTGGCCG<br>GGTGTTTGCAGCTGATGCTCCGGGTCAATGAGTACCGCTT<br>TGCTTGGGTGGAAGCAGATGGGGTAAATTGCATAATGGGA<br>GTGTTGAGTAACAAGTGTGGCTTTCAGCTCCAGTATCAAA<br>TGATTTTTTCAATATGGCTCCTGGCATTCAGTCCTCAAAT<br>GTGTGAACACCTGCGGCGCTATAATATCATTCCAGTTCTG<br>TCTGATATCCTTCAGGAGTCTGTCAAAGAGAAAGTAACAA<br>GAATCATTCTTGCAGCATTTCGTAACTTTTTAGAAAAATC<br>AACTGAAAGAGAAACTCGCCAAGAATATGCCCTGGCTATG<br>ATTCAGTGCAAAGTTCTGAAACAGTTGGAGAACTTGGAAC<br>AGCAGAAGTACGATGATGAAGATATCAGCGAAGATATCAA<br>ATTTCTTTTGGAAAAACTTGGAGAGAGTGTCCAGGACCTT | 5 |

TABLE 1-continued

| GEP-NEN Biomarker/Houskeeper Sequence Information | | | |
|---|---|---|---|
| Gene Name | RefSeq Accession | Sequence | SEQ ID NO: |
| | | AGTTCATTTGATGAATACAGTTCAGAACTTAAATCTGGAA<br>GGTTGGAATGGAGTCCTGTGCACAAATCTGAGAAATTTTG<br>GAGAGAGAATGCTGTGAGGTTAAATGAGAAGAATTATGAA<br>CTCTTGAAAATCTTGACAAAACTTTTGGAAGTGTCAGATG<br>ATCCCCAAGTCTTAGCTGTTGCTGCTCACGATGTTGGAGA<br>ATATGTGCGGCATTATCCACGAGGCAAACGGGTCATCGAG<br>CAGCTCGGTGGGAAGCAGCTGGTCATGAACCACATGCATC<br>ATGAAGACCAGCAGGTCCGCTATAATGCTCTGCTGGCCGT<br>GCAGAAGCTCATGGTGCACAACTGGGAATACCTTGGCAAG<br>CAGCTCCAGTCCGAGCAGCCCCAGACCGCTGCCGCCCGAA<br>GCTAAGCCTGCCTCTGGCCTTCCCCTCCGCCTCAATGCAG<br>AACCAGTAGTGGGAGCACTGTGTTTAGAGTTAAGAGTGAA<br>CACTGTTTGATTTTACTTGGAATTTCCTCTGTTATATAGC<br>TTTTCCCAATGCTAATTTCCAAACAACAACAACAAAATAA<br>CATGTTTGCCTGTTAAGTTGTATAAAAGTAGGTGATTCTG<br>TATTTAAAGAAAATATTACTGTTACATATACTGCTTGCAA<br>TTTCTGTATTTATTGTTCTCTGGAAATAAATATAGTTATT<br>AAAGGATTCTCACTCCAAACATGGCCTCTCTCTTTACTTG<br>GACTTTGAACAAAAGTCAACTGTTGTCTCTTTTCAAACCA<br>AATTGGGAGAATTGTTGCAAAGTAGTGAATGGCAAATAAA<br>TGTTTTAAAATCTATCGCTCTATCAA | |
| BNIP3L | NM_004331.2 | CGTCAGGGGCAGGGGAGGGACGGCGCAGGCGCAGAAAAGG<br>GGGCGGCGGACTCGGCTTGTTGTGTTGCTGCCTGAGTGCC<br>GGAGACGGTCCTGCTGCTGCCGCAGTCCTGCCAGCTGTCC<br>GACAATGTCGTCCCACCTAGTCGAGCCGCCGCCGCCCCTG<br>CACAACAACAACAACAACTGCGAGGAAAATGAGCAGTCTC<br>TGCCCCCGCCGGCCGGCCTCAACAGTTCCTGGGTGGAGCT<br>ACCCATGAACAGCAGCAATGGCAATGATAATGGCAATGGG<br>AAAAATGGGGGGCTGGAACACGTACCATCCTCATCCTCCA<br>TCCACAATGGAGACATGGAGAAGATTCTTTTGGATGCACA<br>ACATGAATCAGGACAGAGTAGTTCCAGAGGCAGTTCTCAC<br>TGTGACAGCCCTTCGCCACAAGAAGATGGGCAGATCATGT<br>TTGATGTGGAAATGCACACCAGCAGGGACCATAGCTCTCA<br>GTCAGAAGAAGAAGTTGTAGAAGGAGAGAAGGAAGTCGAG<br>GCTTTGAAGAAAAGTGCGGACTGGGTATCAGACTGGTCCA<br>GTAGACCCGAAAACATTCCACCCAAGGAGTTCCACTTCAG<br>ACACCCTAAACGTTCTGTGTCTTTAAGCATGAGGAAAAGT<br>GGAGCCATGAAGAAAGGGGGTATTTTCTCCGCAGAATTTC<br>TGAAGGTGTTCATTCCATCTCTCTTCCTTTCTCATGTTTT<br>GGCTTTGGGGCTAGGCATCTATATTGGAAAGCGACTGAGC<br>ACACCCTCTGCCAGCACCTACTGAGGGAAAGGAAAAGCCC<br>CTGGAAATGCGTGTGACCTGTGAAGTGGTGTATTGTCACA<br>GTAGCTTATTTGAACTTGAGACCATTGTAAGCATGACCCA<br>ACCTACCACCCTGTTTTTACATATCCAATTCCAGTAACTC<br>TCAAATTCAATATTTTATTCAAACTCTGTTGAGGCATTTT<br>ACTAACCTTATACCCTTTTTGGCCTGAAGACATTTTAGAA<br>TTTCCTAACAGAGTTTACTGTTGTTTAGAAATTTGCAAGG<br>GCTTCTTTTCCGCAAATGCCACCAGCAGATTATAATTTTG<br>TCAGCAATGCTATTATCTCTAATTAGTGCCACCAGACTAG<br>ACCTGTATCATTCATGGTATAAATTTTACTCTTGCAACAT<br>AACTACCATCTCTCTCTTAAAACGAGATCAGGTTAGCAAA<br>TGATGTAAAAGAAGCTTTATTGTCTAGTTGTTTTTTTTCC<br>CCCAAGACAAAGGCAAGTTTCCCTAAGTTTGAGTTGATAG<br>TTATTAAAAAGAAAACAAAACAAAAAAAAAAGGCAAGGCA<br>CAACAAAAAAATATCCTGGGCAATAAAAAAAATATTTTAA<br>ACCAGCTTTGGAGCCACTTTTTTGTCTAAGCCTCCTAATA<br>GCGTCTTTTAATTTATAGGAGGCAAACTGTATAAATGATA<br>GGTATGAAATAGAATAAGAAGTAAAATACATCAGCAGATT<br>TTCATACTAGTATGTTGTAATGCTGTCTTTTCTATGGTGT<br>AGAATCTTTCTTTCTGATAAGGAACGTCTCAGGCTTAGAA<br>ATATATGAAATTGCTTTTTGAGATTTTTGCGTGTGTGTTT<br>GATATTTTTTACGATAATTAGCTGCATGTGAATTTTTCAT<br>GACCTTCTTTACATTTTTTATTTTTTATTTCTTTATTTTT<br>TTTTCTCTAAGAAGAGGCTTTGGAATGAGTTCCAATTTGT<br>GATGTTAATACAGGCTTCTTGTTTTAGGAAGCATCACCTA<br>TACTCTGAAGCCTTTAAACTCTGAAGAGAATTGTTTCAGA<br>GTTATTCCAAGCACTTGTGCAACTTGGAAAAACAGACTTG<br>GGTTGTGGGAACAGTTGACAGCGTTCTGAAAAGATGCCAT<br>TTGTTTCCTTCTGATCTCTCACTGAATAATGTTTACTGTA<br>CAGTCTTCCCAAGGTGATTCCTGCGACTGCAGGCACTGGT<br>CATTTTCTCATGTAGCTGTCTTTTCAGTTATGGTAAACTC<br>TTAAAGTTCAGAACACTCAACAGATTCCTTCAGTGATATA<br>CTTGTTCGTTCATTTCTAAAATGTGAAGCTTTAGGACCAA<br>ATTGTTAGAAAGCATCAGGATGACCAGTTATCTCGAGTAG | 6 |

TABLE 1-continued

GEP-NEN Biomarker/Houskeeper Sequence Information

| Gene Name | RefSeq Accession | Sequence | SEQ ID NO: |
|---|---|---|---|
| | | ATTTTCTTGGATTTCAGAACATCTAGCATGACTCTGAAGG<br>ATACCACATGTTTTATATATAAATAATTACTGTTTATGAT<br>ATAGACATTGATATTGACTATTTAGAGAACCGTTGTTAAT<br>TTTAAAACTAGCAATCTATAAAGTGCACCAGGTCAACTTG<br>AATAAAAACACTATGACAGACAGGTTTGCCAGTTTGCAGA<br>AACTAACTCTTTTCTCACATCAACATTTGTAAAATTGATG<br>TGTTATAGTGGAAAATAACATATAGATTAAACAAAATTTT<br>TATCTTTTTTCAAGAATATAGCTGGCTATCTTTAAGAAAG<br>ATGATATATCCTAGTTTTGAAAGTAATTTTCTTTTTTCTT<br>TCTAGCATTTGATGTCTAAATAATTTTGGACATCTTTTTC<br>CTAGACCATGTTTCTGTCTTACTCTTAAACCTGGTAACAC<br>TTGATTTGCCTTCTATAACCTATTTATTTCAAGTGTTCAT<br>ATTTGAATTTCTTTGGGAAGAAAGTAAATCTGATGGCTCA<br>CTGATTTTTGAAAAGCCTGAATAAAATTGGAAAGACTGGA<br>AAGTTAGGAGAACTGACTAGCTAAACTGCTACAGTATGCA<br>ATTTCTATTACAATTGGTATTACAGGGGGGAAAAGTAAAA<br>TTACACTTTACCTGAAAGTGACTTCTTACAGCTAGTGCAT<br>TGTGCTCTTTCCAAGTTCAGCAGCAGTTCTATCAGTGGTG<br>CCACTGAAACTGGGTATATTTATGATTTCTTTCAGCGTTA<br>AAAAGAAACATAGTGTTGCCCTTTTTCTTAAAGCATCAGT<br>GAAATTATGGAAAATTACTTAAAACGTGAATACATCATCA<br>CAGTAGAATTTATTATGAGAGCATGTAGTATGTATCTGTA<br>GCCCTAACACATGGGATGAACGTTTTACTGCTACACCCAG<br>ATTTGTGTTGAACGAAAACATTGTGGTTTGGAAAGGAGAA<br>TTCAACAATTAATAGTTGAAATTGTGAGGTTAATGTTTAA<br>AAAGCTTTACACCTGTTTACAATTTGGGGACAAAAAGGCA<br>GGCTTCATTTTTCATATGTTTGATGAAAACTGGCTCAAGA<br>TGTTTGTAAATAGAATCAAGAGCAAAACTGCACAAACTTG<br>CACATTGGAAAGTGCAACAAGTTCCCGTGATTGCAGTAAA<br>AATATTTACTATTCTAAAAAAATGAGAATTGAAGACTTAG<br>CCAGTCAGATAAGTTTTTTCATGAACCCGTTGTGGAAATT<br>ATTGGAATTAACTGAGCCAAAGTGATTATGCATTCTTCAT<br>CTATTTTAGTTAGCACTTTGTATCGTTATATACAGTTTAC<br>AATACATGTATAACTTGTAGCTATAAACATTTTGTGCCAT<br>TAAAGCTCTCACAAAACTTTAAAAA | |
| BRAF | NM_004333.4 | CGCCTCCCTTCCCCCTCCCCGCCCGACAGCGGCCGCTCGG<br>GCCCCGGCTCTCGGTTATAAGATGGCGGCGCTGAGCGGTG<br>GCGGTGGTGGCGGCGCGGAGCCGGGCCAGGCTCTGTTCAA<br>CGGGGACATGGAGCCCGAGGCCGGCGCCGGCGCCGGCGCC<br>GCGGCCTCTTCGGCTGCGGACCCTGCCATTCCGGAGGAGG<br>TGTGGAATATCAAACAAATGATTAAGTTGACACAGGAACA<br>TATAGAGGCCCTATTGGACAAATTTGGTGGGGAGCATAAT<br>CCACCATCAATATATCTGGAGGCCTATGAAGAATACACCA<br>GCAAGCTAGATGCACTCCAACAAAGAGAACAACAGTTATT<br>GGAATCTCTGGGGAACGGAACTGATTTTTCTGTTTCTAGC<br>TCTGCATCAATGGATACCGTTACATCTTCTTCCTCTTCTA<br>GCCTTTCAGTGCTACCTTCATCTCTTTCAGTTTTTCAAAA<br>TCCCACAGATGTGGCACGGAGCAACCCCAAGTCACCACAA<br>AAACCTATCGTTAGAGTCTTCCTGCCCAACAAACAGAGGA<br>CAGTGGTACCTGCAAGGTGTGGAGTTACAGTCCGAGACAG<br>TCTAAAGAAAGCACTGATGATGAGAGGTCTAATCCCAGAG<br>TGCTGTGCTGTTTACAGAATTCAGGATGGAGAGAAGAAAC<br>CAATTGGTTGGGACACTGATATTTCCTGGCTTACTGGAGA<br>AGAATTGCATGTGGAAGTGTTGGAGAATGTTCCACTTACA<br>ACACACAACTTTGTACGAAAAACGTTTTTCACCTTAGCAT<br>TTTGTGACTTTTGTCGAAAGCTGCTTTTCCAGGGTTTCCG<br>CTGTCAAACATGTGGTTATAAATTTCACCAGCGTTGTAGT<br>ACAGAAGTTCCACTGATGTGTGTTAATTATGACCAACTTG<br>ATTTGCTGTTTGTCTCCAAGTTCTTTGAACACCACCCAAT<br>ACCACAGGAAGAGGCGTCCTTAGCAGAGACTGCCCTAACA<br>TCTGGATCATCCCCTTCCGCACCCGCCTCGGACTCTATTG<br>GGCCCCAAATTCTCACCAGTCCGTCTCCTTCAAAATCCAT<br>TCCAATTCCACAGCCCTTCCGACCAGCAGATGAAGATCAT<br>CGAAATCAATTTGGGCAACGAGACCGATCCTCATCAGCTC<br>CCAATGTGCATATAAACACAATAGAACCTGTCAATATTGA<br>TGACTTGATTAGAGACCAAGGATTTCGTGGTGATGGAGGA<br>TCAACCACAGGTTTGTCTGCTACCCCCCCTGCCTCATTAC<br>CTGGCTCACTAACTAACGTGAAAGCCTTACAGAAATCTCC<br>AGGACCTCAGCGAGAAAGGAAGTCATCTTCATCCTCAGAA<br>GACAGGAATCGAATGAAAACACTTGGTAGACGGGACTCGA<br>GTGATGATTGGGAGATTCCTGATGGGCAGATTACAGTGGG<br>ACAAAGAATTGGATCTGGATCATTTGGAACAGTCTACAAG<br>GGAAAGTGGCATGGTGATGTGGCAGTGAAAATGTTGAATG<br>TGACAGCACCTACACCTCAGCAGTTACAAGCCTTCAAAAA | 7 |

TABLE 1-continued

GEP-NEN Biomarker/Houskeeper Sequence Information

| Gene Name | RefSeq Accession | Sequence | SEQ ID NO: |
|---|---|---|---|
| | | TGAAGTAGGAGTACTCAGGAAAACACGACATGTGAATATC<br>CTACTCTTCATGGGCTATTCCACAAAGCCACAACTGGCTA<br>TTGTTACCCAGTGGTGTGAGGGCTCCAGCTTGTATCACCA<br>TCTCCATATCATTGAGACCAAATTTGAGATGATCAAACTT<br>ATAGATATTGCACGACAGACTGCACAGGGCATGGATTACT<br>TACACGCCAAGTCAATCATCCACAGAGACCTCAAGAGTAA<br>TAATATATTTCTTCATGAAGACCTCACAGTAAAAATAGGT<br>GATTTTGGTCTAGCTACAGTGAAATCTCGATGGAGTGGGT<br>CCCATCAGTTTGAACAGTTGTCTGGATCCATTTTGTGGAT<br>GGCACCAGAAGTCATCAGAATGCAAGATAAAAATCCATAC<br>AGCTTTCAGTCAGATGTATATGCATTTGGAATTGTTCTGT<br>ATGAATTGATGACTGGACAGTTACCTTATTCAAACATCAA<br>CAACAGGGACCAGATAATTTTTATGGTGGGACGAGGATAC<br>CTGTCTCCAGATCTCAGTAAGGTACGGAGTAACTGTCCAA<br>AAGCCATGAAGAGATTAATGGCAGAGTGCCTCAAAAAGAA<br>AAGAGATGAGAGACCACTCTTTCCCCAAATTCTCGCCTCT<br>ATTGAGCTGCTGGCCCGCTCATTGCCAAAAATTCACCGCA<br>GTGCATCAGAACCCTCCTTGAATCGGGCTGGTTTCCAAAC<br>AGAGGATTTTAGTCTATATGCTTGTGCTTCTCCAAAAACA<br>CCCATCCAGGCAGGGGGATATGGTGCGTTTCCTGTCCACT<br>GAAACAAATGAGTGAGAGAGTTCAGGAGAGTAGCAACAAA<br>AGGAAAATAAATGAACATATGTTTGCTTATATGTTAAATT<br>GAATAAAATACTCTCTTTTTTTTTAAGGTGAACCAAAGAA<br>CACTTGTGTGGTTAAAGACTAGATATAATTTTTCCCCAAA<br>CTAAAATTTATACTTAACATTGGATTTTTAACATCCAAGG<br>GTTAAAATACATAGACATTGCTAAAAATTGGCAGAGCCTC<br>TTCTAGAGGCTTTACTTTCTGTTCCGGGTTTGTATCATTC<br>ACTTGGTTATTTTAAGTAGTAAACTTCAGTTTCTCATGCA<br>ACTTTTGTTGCCAGCTATCACATGTCCACTAGGGACTCCA<br>GAAGAAGACCCTACCTATGCCTGTGTTTGCAGGTGAGAAG<br>TTGGCAGTCGGTTAGCCTGGGTTAGATAAGGCAAACTGAA<br>CAGATCTAATTTAGGAAGTCAGTAGAATTTAATAATTCTA<br>TTATTATTCTTAATAATTTTTCTATAACTATTTCTTTTTA<br>TAACAATTTGGAAAATGTGGATGTCTTTTATTTCCTTGAA<br>GCAATAAACTAAGTTTCTTTTTATAAAAA | |
| C21ORF7 | NM_020152.3 | CGCAGCCCCGGTTCCTGCCCGCACCTCTCCCTCCACACCT<br>CCCCGCAAGCTGAGGGAGCCGGCTCCGGCCTCGGCCAGCC<br>CAGGAAGGCGCTCCCACAGCGCAGTGGTGGGCTGAAGGGC<br>TCCTCAAGTGCCGCCAAAGTGGGAGCCCAGGCAGAGGAGG<br>CGCCGAGAGCGAGGGAGGGCTGTGAGGACTGCCAGCACGC<br>TGTCACCTCTCAATAGCAGCCCAAACAGATTAAGACATGG<br>GAGATGTACAAGGGCAGCCGTGGGGCTGGCAACAGCTTCG<br>TAATCCTGGCTTCCTGCTTTCTGGGTCAAAGCCCTGGTGG<br>TGTGTTCTTGATATCGGTCCATCTAGTGGCGTTGTTTGAT<br>TCCTCCCACCTTGCTGATCATTCGTAGTGTAGCCCCCAAG<br>GTGTGGAATAACCCTTAAGCCCTTACCGGGGTCCTTCTGG<br>ACTGAGAATTGTTGTAAAGTAATACTGCTCAGGTGAAAGA<br>CAACTTGAGTGGTTAAATTACTGTCATGCAAAGCGACTAG<br>ATGGTTCAGCTGATTGCACCTTTAGAAGTTATGTGGAACG<br>AGGCAGCAGATCTTAAGCCCCTTGCTCTGTCACGCAGGCT<br>GGAATGCAGTGGTGGAATCATGGCTCACTACAGCCCTGAC<br>CTCCTGGGCCCAGAGATGGAGTCTCGCTATTTTGCCCAGG<br>TTGGTCTTGAACACCTGGCTTCAAGCAGTCCTCCTGCTTT<br>TGGCTTCTTGAAGTGCTTGGATTACAGTATTTCAGTTTTA<br>TGCTCTGCAACAAGTTTGGCCATGTTGGAGGACAATCCAA<br>AGGTCAGCAAGTTGGCTACTGGCGATTGGATGCTCACTCT<br>GAAGCCAAAGTCTATTACTGTGCCCGTGGAAATCCCCAGC<br>TCCCCTCTGGATGATACACCCCCTGAAGACTCCATTCCTT<br>TGGTCTTTCCAGAATTAGACCAGCAGCTACAGCCCCTGCC<br>GCCTTGTCATGACTCCGAGGAATCCATGGAGGTGTTCAAA<br>CAGCACTGCCAAATAGCAGAAGAATACCATGAGGTCAAAA<br>AGGAAATCACCCTGCTTGAGCAAAGGAAGAAGGAGCTCAT<br>TGCCAAGTTAGATCAGGCAGAAAAGGAGAAGGTGGATGCT<br>GCTGAGCTGGTTCGGGAATTCGAGGCTCTGACGGAGGAGA<br>ATCGGACGTTGAGGTTGGCCCAGTCTCAATGTGTGGAACA<br>ACTGGAGAAACTTCGAATACAGTATCAGAAGAGGCAGGGC<br>TCGTCCTAACTTTAAATTTTTCAGTGTGAGCATACGAGGC<br>TGATGACTGCCCTGTGCTGGCCAAAAGATTTTTATTTTAA<br>ATGAATAGTGAGTCAGATCTATTGCTTCTCTGTATTACCC<br>ACATGACAACTGTCTATAATGAGTTTACTGCTTGCCAGCT<br>TCTAGCTTGAGAGAAGGGATATTTTAAATGAGATCATTAA<br>CGTGAAACTATTACTAGTATATGTTTTTGGAGATCAGAAT<br>TCTTTTCCAAAGATATATGTTTTTTTCTTTTTTAGGAAGA<br>TATGATCATGCTGTACAACAGGGTAGAAAATGATAAAAAT | 8 |

TABLE 1-continued

GEP-NEN Biomarker/Houskeeper Sequence Information

| Gene Name | RefSeq Accession | Sequence | SEQ ID NO: |
|---|---|---|---|
| | | AGACTATTGACTGACCCAGCTAAGAATCGTGGGCTGAGCA<br>GAGTTAAACCATGGGACAAACCCATAACATGTTCACCATA<br>GTTTCACGTATGTGTATTTTTAAATTTCATGCCTTTAATA<br>TTTCAAATATGCTCAAATTTAAACTGTCAGAAACTTCTGT<br>GCATGTATTTATATTTGCCAGAGTATAAACTTTTATACTC<br>TGATTTTTATCCTTCAATGATTGATTATACTAAGAATAAA<br>TGGTCACATATCCTAAAAGCTTCTTCATGAAATTATTAGC<br>AGAAACCATGTTTGTAACCAAAGCACATTTGCCAATGCTA<br>ACTGGCTGTTGTAATAATAAACAGATAAGGCTGCATTTGC<br>TTCATGCCATGTGACCTCACAGTAAACATCTCTGCCTTTG<br>CCTGTGTGTGTTCTGGGGGAGGGGGGACATGGAAAAATAT<br>TGTTTGGACATTACTTGGGTGAGTGCCCATGAAAACATCA<br>GTGAACTTGTAACTATTGTTTTGTTTTGGATTTAAGGAGA<br>TGTTTTAGATCAGTAACAGCTAATAGGAATATGCGAGTAA<br>ATTCAGAATTGAAACAATTTCTCCTTGTTCTACCTATCAC<br>CACATTTTCTCAAATTGAACTCTTTGTTATATGTCCATTT<br>CTATTCATGTAACTTCTTTTTCATTAAACATGGATCAAAA<br>CTGACAAAAAAAAAAAAAAA | |
| CD59 | NM_203331.2 | GGGGCCGGGGGGCGGAGCCTTGCGGGCTGGAGCGAAAGAA<br>TGCGGGGGCTGAGCGCAGAAGCGGCTCGAGGCTGGAAGAG<br>GATCTTGGGCGCCGCCAGTCTTTAGCACCAGTTGGTGTAG<br>GAGTTGAGACCTACTTCACAGTAGTTCTGTGGACAATCAC<br>AATGGGAATCCAAGGAGGGTCTGTCCTGTTCGGGCTGCTG<br>CTCGTCCTGGCTGTCTTCTGCCATTCAGGTCATAGCCTGC<br>AGTGCTACAACTGTCCTAACCCAACTGCTGACTGCAAAAC<br>AGCCGTCAATTGTTCATCTGATTTTGATGCGTGTCTCATT<br>ACCAAAGCTGGGTTACAAGTGTATAACAAGTGTTGGAAGT<br>TTGAGCATTGCAATTTCAACGACGTCACAACCCGCTTGAG<br>GGAAAATGAGCTAACGTACTACTGCTGCAAGAAGGACCTG<br>TGTAACTTTAACGAACAGCTTGAAAATGGTGGGACATCCT<br>TATCAGAGAAAACAGTTCTTCTGCTGGTGACTCCATTTCT<br>GGCAGCAGCCTGGAGCCTTCATCCCTAAGTCAACACCAGG<br>AGAGCTTCTCCCAAACTCCCCGTTCCTGCGTAGTCCGCTT<br>TCTCTTGCTGCCACATTCTAAAGGCTTGATATTTTCCAAA<br>TGGATCCTGTTGGGAAAGAATAAAATTAGCTTGAGCAACC<br>TGGCTAAGATAGAGGGGCTCTGGGAGACTTTGAAGACCAG<br>TCCTGTTTGCAGGGAAGCCCCACTTGAAGGAAGAAGTCTA<br>AGAGTGAAGTAGGTGTGACTTGAACTAGATTGCATGCTTC<br>CTCCTTTGCTCTTGGGAAGACCAGCTTTGCAGTGACAGCT<br>TGAGTGGGTTCTCTGCAGCCCTCAGATTATTTTTCCTCTG<br>GCTCCTTGGATGTAGTCAGTTAGCATCATTAGTACATCTT<br>TGGAGGGTGGGGCAGGAGTATATGAGCATCCTCTCTCACA<br>TGGAACGCTTTCATAAACTTCAGGGATCCCGTGTTGCCAT<br>GGAGGCATGCCAAATGTTCCATATGTGGGTGTCAGTCAGG<br>GACAACAAGATCCTTAATGCAGAGCTAGAGGACTTCTGGC<br>AGGGAAGTGGGGAAGTGTTCCAGATAGCAGGGCATGAAAA<br>CTTAGAGAGGTACAAGTGGCTGAAAATCGAGTTTTTCCTC<br>TGTCTTTAAATTTTATATGGGCTTTGTTATCTTCCACTGG<br>AAAAGTGTAATAGCATACATCAATGGTGTGTTAAAGCTAT<br>TTCCTTGCCTTTTTTTTATTGGAATGGTAGGATATCTTGG<br>CTTTGCCACACACAGTTACAGAGTGAACACTCTACTACAT<br>GTGACTGGCAGTATTAAGTGTGCTTATTTTAAATGTTACT<br>GGTAGAAAGGCAGTTCAGGTATGTGTGTATATAGTATGAA<br>TGCAGTGGGGACACCCTTTGTGGTTACAGTTTGAGACTTC<br>CAAAGGTCATCCTTAATAACAACAGATCTGCAGGGGTATG<br>TTTTACCATCTGCATCCAGCCTCCTGCTAACTCCTAGCTG<br>ACTCAGCATAGATTGTATAAAATACCTTTGTAACGGCTCT<br>TAGCACACTCACAGATGTTTGAGGCTTTCAGAAGCTCTTC<br>TAAAAAATGATACACACCTTTCACAAGGGCAAACTTTTTC<br>CTTTTCCCTGTGTATTCTAGTGAATGAATCTCAAGATTCA<br>GTAGACCTAATGACATTTGTATTTTATGATCTTGGCTGTA<br>TTTAATGGCATAGGCTGACTTTTGCAGATGGAGGAATTTC<br>TTGATTAATGTTGAAAAAAAACCCTTGATTATACTCTGTT<br>GGACAAACCGAGTGCAATGAATGATGCTTTTCTGAAAATG<br>AAATATAACAAGTGGGTGAATGTGGTTATGGCCGAAAAGG<br>ATATGCAGTATGCTTAATGGTAGCAACTGAAAGAAGACAT<br>CCTGAGCAGTGCCAGCTTTCTTCTGTTGATGCCGTTCCCT<br>GAACATAGGAAAATAGAAACTTGCTTATCAAAACTTAGCA<br>TTACCTTGGTGCTCTGTGTTCTCTGTTAGCTCAGTGTCTT<br>TCCTTACATCAATAGGTTTTTTTTTTTTTTTTTGGCCTGA<br>GGAAGTACTGACCATGCCCACAGCCACCGGCTGAGCAAAG<br>AAGCTCATTTCATGTGAGTTCTAAGGAATGAGAAACAATT<br>TTGATGAATTTAAGCAGAAAATGAATTTCTGGGAACTTTT<br>TTGGGGGCGGGGGGGTGGGGAATTCAGCCACACTCCAGAA | 9 |

TABLE 1-continued

GEP-NEN Biomarker/Houskeeper Sequence Information

| Gene Name | RefSeq Accession | Sequence | SEQ ID NO: |
|---|---|---|---|
| | | AGCCAGGAGTCGACAGTTTTGGAAGCCTCTCTCAGGATTG | |
| | | AGATTCTAGGATGAGATTGGCTTACTGCTATCTTGTGTCA | |
| | | TGTACCCACTTTTTGGCCAGACTACACTGGGAAGAAGGTA | |
| | | GTCCTCTAAAGCAAAATCTGAGTGCCACTAAATGGGGAGA | |
| | | TGGGGCTGTTAAGCTGTCCAAATCAACAAGGGTCATATAA | |
| | | ATGGCCTTAAACTTTGGGGTTGCTTTCTGCAAAAAGTTGC | |
| | | TGTGACTCATGCCATAGACAAGGTTGAGTGCCTGGACCCA | |
| | | AAGGCAATACTGTAATGTAAAGACATTTATAGTACTAGGC | |
| | | AAACAGCACCCCAGGTACTCCAGGCCCTCCTGGCTGGAGA | |
| | | GGGCTGTGGCAATAGAAAATTAGTGCCAACTGCAGTGAGT | |
| | | CAGCCTAGGTTAAATAGAGAGTGTAAGAGTGCTGGACAGG | |
| | | AACCTCCACCCTCATGTCACATTTCTTCAATGTGACCCTT | |
| | | CTGGCCCCTCTCCTCCTGACAGCGGAACAATGACTGCCCC | |
| | | GATAGGTGAGGCTGGAGGAAGAATCAGTCCTGTCCTTGGC | |
| | | AAGCTCTTCACTATGACAGTAAAGGCTCTCTGCCTGCTGC | |
| | | CAAGGCCTGTGACTTTCTAACCTGGCCTCACGCTGGGTAA | |
| | | GCTTAAGGTAGAGGTGCAGGATTAGCAAGCCCACCTGGCT | |
| | | ACCAGGCCGACAGCTACATCCTCCAACTGACCCTGATCAA | |
| | | CGAAGAGGGATTCATGTGTCTGTCTCAGTTGGTTCCAAAT | |
| | | GAAACCAGGGAGCAGGGGAGTTAGGAATCGAACACCAGTC | |
| | | ATGCCTACTGGCTCTCTGCTCGAGAGCCAATACCCTGTGC | |
| | | CCTCCACTCATCTGGATTTACAGGAACTGTCATAGTGTTC | |
| | | AGTATTGGGTGGTGATAAGCCCATTGGATTGTCCCCTTGG | |
| | | GGGGATGAGCTAGGGGTGCAAGGAACACCTGATGAGTAGA | |
| | | TAAGTGGAGCTCATGGTATTTCCTGAAAGATGCTAATCTA | |
| | | TTTGCCAAACTTGGTCTTGAATGTACTGGGGGCTTCAAGG | |
| | | TATGGGTATATTTTTCTTGTGTCCTTGCAGTTAGCCCCCA | |
| | | TGTCTTATGTGTGTCCTGAAAAAATAAGAGCCTGCCCAAG | |
| | | ACTTTGGGCCTCTTGACAGAATTAACCACTTTTATACATC | |
| | | TGAGTTCTCTTGGTAAGTTCTTTAGCAGTGTTCAAAGTCT | |
| | | ACTAGCTCGCATTAGTTTCTGTTGCTGCCAACAGATCTGA | |
| | | ACTAATGCTAACAGATCCCCCTGAGGGATTCTTGATGGGC | |
| | | TGAGCAGCTGGCTGGAGCTAGTACTGACTGACATTCATTG | |
| | | TGATGAGGGCAGCTTTCTGGTACAGGATTCTAAGCTCTAT | |
| | | GTTTTATATACATTTTCATCTGTACTTGCACCTCACTTTA | |
| | | CACAAGAGGAAACTATGCAAAGTTAGCTGGATCGCTCAAG | |
| | | GTCACTTAGGTAAGTTGGCAAGTCCATGCTTCCCACTCAG | |
| | | CTCCTCAGGTCAGCAAGTCTACTTCTCTGCCTATTTTGTA | |
| | | TACTCTCTTTAATATGTGCCTAGCTTTGGAAAGTCTAGAA | |
| | | TGGGTCCCTGGTGCCTTTTTACTTTGAAGAAATCAGTTTC | |
| | | TGCCTCTTTTTGGAAAAGAAAACAAAGTGCAATTGTTTTT | |
| | | TACTGGAAAGTTACCCAATAGCATGAGGTGAACAGGACGT | |
| | | AGTTAGGCCTTCCTGTAAACAGAAAATCATATCAAAACAC | |
| | | TATCTTCCCATCTGTTTCTCAATGCCTGCTACTTCTTGTA | |
| | | GATATTTCATTTCAGGAGAGCAGCAGTTAAACCCGTGGAT | |
| | | TTTGTAGTTAGGAACCTGGGTTCAAACCCTCTTCCACTAA | |
| | | TTGGCTATGTCTCTGGACAAGTTTTTTTTTTTTTTTTTTT | |
| | | TTAAACCCTTTCTGAACTTTCACTTTCTATGTCTACCTCA | |
| | | AAGAATTGTTGTGAGGCTTGAGATAATGCATTTGTAAAGG | |
| | | GTCTGCCAGATAGGAAGATGCTAGTTATGGATTTACAAGG | |
| | | TTGTTAAGGCTGTAAGAGTCTAAAACCTACAGTGAATCAC | |
| | | AATGCATTTACCCCCACTGACTTGGACATAAGTGAAAACT | |
| | | AGCCAGAAGTCTCTTTTTCAAATTACTTACAGGTTATTCA | |
| | | ATATAAAATTTTTGTAATGGATAATCTTATTTATCTAAAC | |
| | | TAAAGCTTCCTGTTTATACACACTCCTGTTATTCTGGGAT | |
| | | AAGATAAATGACCACAGTACCTTAATTTCTAGGTGGGTGC | |
| | | CTGTGATGGTTCATTGTAGGTAAGGACATTTTCTCTTTTT | |
| | | CAGCAGCTGTGTAGGTCCAGAGCCTCTGGGAGAGGAGGGG | |
| | | GGTAGCATGCACCCAGCAGGGGACTGAACTGGGAAACTCA | |
| | | AGGTTCTTTTTACTGTGGGGTAGTGAGCTGCCTTTCTGTG | |
| | | ATCGGTTTCCCTAGGGATGTTGCTGTTCCCCTCCTTGCTA | |
| | | TTCGCAGCTACATACAACGTGGCCAACCCCAGTAGGCTGA | |
| | | TCCTATATATGATCAGTGCTGGTGCTGACTCTCAATAGCC | |
| | | CCACCCAAGCTGGCTATAGGTTTACAGATACATTAATTAG | |
| | | GCAACCTAAAATATTGATGCTGGTGTTGGTGTGACATAAT | |
| | | GCTATGGCCAGAACTGAAACTTAGAGTTATAATTCATGTA | |
| | | TTAGGGTTCTCCAGAGGGACAGAATTAGTAGGATATATGT | |
| | | ATATATGAAAGGGAGGTTATTAGGGAGAACTGGCTCCCAC | |
| | | AGTTAGAAGGCGAAGTCGCACAATAGGCCGTCTGCAAGCT | |
| | | GGGTTAGAGAGAAGCCAGTAGTGGCTCAGCCTGAGTTCAA | |
| | | AAACCTCAAAACTGGGGAAGCTGACAGTGCAGCCAGCCTT | |
| | | CAGTCTGTGGCCAAAGGCCCAAGAGCCCCTGGCAACCAAC | |
| | | CCACTGGTGCAAGTCCTAGATTCCAAAGGCTGAAGAACCT | |
| | | GGAGTCTGATGTCCAAGAGCAGGAAGAGTGGAAGAAAGCC | |
| | | AGAAGACTCAGCAAACAAGGTAGACAGTGTCTACCACCAT | |

TABLE 1-continued

GEP-NEN Biomarker/Houskeeper Sequence Information

| Gene Name | RefSeq Accession | Sequence | SEQ ID NO: |
|---|---|---|---|
| | | AGTGGCCATACCAAAGAGGCTACCGATTCCTTCCTGCTAC<br>CTGGATCCCTGAAGTTGCCCTGGTCTCTGCACCTTCTAAA<br>CCTAGTTCTTAAGAGCTTTCCATTACATGAGCTGTCTCAA<br>AGCCCTCCAATAAATTCTCAGTGTAAGCTTCTGTTGCTTG<br>TGGACAGAAAATTCTGACAGACCTACCCTATAAGTGTTAC<br>TGTCAGGATAACATGAGAACGCACAACAGTAAGTGGTCAC<br>TAAGTGTTAGCTACGGTTATTTTGCCCAAGGTAGCATGGC<br>TAGTTGATGCCGGTTGATGGGGCTTAAACCCAGCTCCCTC<br>ATCTTCCAGGCCTCTGTACTCCCTATTCCACTAAACTACC<br>TCTCAGGTTTATTTTTTTAAATTCTTACTCTGCAAGTACA<br>TAGGACCACATTTACCTGGGAAAACAAGAATAAAGGCTGC<br>TCTGCATTTTTTAGAAACTTTTTTGAAAGGGAGATGGGAA<br>TGCCTGCACCCCCAAGTCCAGACCAACACAATGGTTAATT<br>GAGATGAATAATAAAGGAAAGACTGTTCTGGGCTTCCCAG<br>AATAGCTTGGTCCTTAAATTGTGGCACAAACAACCTCCTG<br>TCAGAGCCAGCCTCCTGCCAGGAAGAGGGGTAGGAGACTA<br>GAGGCCGTGTGTGCAGCCTTGCCCTGAAGGCTAGGGTGAC<br>AATTTGGAGGCTGTCCAAACACCCTGGCCTCTAGAGCTGG<br>CCTGTCTATTTGAAATGCCGGCTCTGATGCTAATCGGCGA<br>CCCTCAGGCAAGTTACTTAACCTTACATGCCTCAGTTTTC<br>TCATCTGGAAAATGAGAACCCTAGGTTTAGGGTTGTTAGA<br>AAAGTTAAATGAGTTAAGACAAGTGCCTGGGACACAGTAG<br>CCTCTTGTGTGTGTTTATCATTATGTCCTCAGCAGGTCGT<br>AGAAGCAGCTTCTCAGGTGTGAGGCTGGCGCGATTATCTG<br>GAGTGGGTTGGGTTTTCTAGGATGGACCCCCTGCTGCATT<br>TTCCTCATTCATCCACCAGGGCTTAATGGGGAATCAAGGA<br>ATCCATGTGTAACTGTATAATAACTGTAGCCACACTCCAA<br>TGACCACCTACTAGTTGTCCCTGGCACTGCTTATACATAT<br>GTCCATCAAATCAATCCTATGAAGTAGATACTGTCTTCAT<br>TTTATAGATCAGAGACAATTGGGGTTCAGAGAGCTGATGT<br>GATTTTCCCAGGGTCACAGAGAGTCCCAGATTCAGGCACA<br>ACTCTTGTATTCCAAGACACAACCACTACATGTCCAAAGG<br>CTGCCCAGAGCCACCGGGCACGGCAAATTGTGACATATCC<br>CTAAAGAGGCTGAGCACCTGGTCAGGATCTGATGGCTGAC<br>AGTGTGTCCAGATGCAGAGCTGGAGTGGGGGAGGGGAAGG<br>GGGGCTCCTTGGGACAGAGAAGGCTTTCTGTGCTTTCTCT<br>GAAGGGAGCAGTCTGAGGACCAAGGGAACCCGGCAAACAG<br>CACCTCAGGTACTCCAGGCCCTCCTGGCTGGAGAGGGCTG<br>TGGCAATGGAAAATTAGTGCCAACTGCAATGAGTCAGCCT<br>CGGTTAAATAGAGAGTGAAGAATGCTGGACAGGAACCTCC<br>ACCCTCATGTCACATTTCTTCAGTGTGACCCTTCTGGCCC<br>CTCTCCTCCTGACAGCGGAACAATGACTGCCCCGATAGGT<br>GAGGCTGGAGGAAGAATCAGTCCTGTCCTTGGCAAGCTCT<br>TCACTATGACAGTAAAGGCTCTCTGCCTGCTGCCAAGGCC<br>TGTGACTTTCTAACCTGGCCTCACGCTGGGTAAGCTTAAG<br>GTAGAGGTGCAGGATTAGCAAGCCCACCTGGCTACCAGGC<br>CGACAGCTACATCTTTCAACTGACCCTGATCAACGAAGAG<br>GGACTTGTGTCTCTCAGTTGGTTCCAAATGAAACCAGGGA<br>GCAGGGGCGTTAGGAAGCTCCAACAGGATGGTACTTAATG<br>GGGCATTTGAGTGGAGAGGTAGGTGACATAGTGCTTTGGA<br>GCCCAGGGAGGGAAAGGTTCTGCTGAAGTTGAATTCAAGA<br>CTGTTCTTTCATCACAAACTTGAGTTTCCTGGACATTTGT<br>TTGCAGAAACAACCGTAGGGTTTTGCCTTAACCTCGTGGG<br>TTTATTATTACCTCATAGGGACTTTGCCTCCTGACAGCAG<br>TTTATGGGTGTTCATTGTGGCACTTGAGTTTTCTTGCATA<br>CTTGTTAGAGAAACCAAGTTTGTCATCAACTTCTTATTTA<br>ACCCCCTGGCTATAACTTCATGGATTATGTTATAATTAAG<br>CCATCCAGAGTAAAATCTGTTTAGATTATCTTGGAGTAAG<br>GGGGAAAAAATCTGTAATTTTTTCTCCTCAACTAGATATA<br>TACATAAAAAATGATTGTATTGCTTCATTTAAAAAATATA<br>ACGCAAAATCTCTTTTCCTTCTAAAAAAAAAAAAAAAAAA | |
| COMMD9 | NM_001101653.1 | GCTTCCCTGGGTGCCACGGTCATGTGACTTCGGCAAGATG<br>GCTGCCCTGACAGCGGAGCATTTTGCAGCACTCCAGAGCC<br>TGCTCAAGCTGCTCCAGGCTCTGCACCGCCTCACTAGGCT<br>GGTGGCATTCCGTGACCTGTCCTCTGCCGAGGCAATTCTG<br>GCTCTCTTTCCAGAAAATTTCCACCAAAACCTCAAAAACC<br>TGCTGACAAAGATCATCCTAGAACATGTGTCTACTTGGAG<br>AACCGAAGCCCAGGCAAATCAGATCTCTCTGCCACGCCTG<br>GTCGATCTGGACTGGAGAGTGGATATCAAAACCTCCTCAG<br>ACAGCATCAGCCGCATGGCCGTCCCCACCTGCCTGCTCCA<br>GATGAAGATCCAAGAAGATCCCAGCCTATGCGGAGACAAA<br>CCCTCCATCTCAGCTGTCACCGTGGAGCTGAGCAAAGAAA<br>CACTGGACACCATGTTAGATGGCCTGGGCCGCATCCGAGA<br>CCAACTCTCTGCCGTGGCCAGTAAATGATCCAGCCAGCTG | 10 |

TABLE 1-continued

GEP-NEN Biomarker/Houskeeper Sequence Information

| Gene Name | RefSeq Accession | Sequence | SEQ ID NO: |
|---|---|---|---|
| | | CCAGGGCCACTGCCATGACCCAGCTGCTCATGAGTGATAA | |
| | | ATGTCTCCCCATATGCAGGCTGCCCTTGCAGCTGCAGCTG | |
| | | ACAACAGGCAGGATGGTGGGGACAGCAGGGGGCTACTGCC | |
| | | ATCCAGAAGTTACAGTTGGATTGGGAAGAAGCAGCCAGAT | |
| | | CCCCCGCTGTTCTCACTCATCTTCTTTCTCTTTCTGAAGC | |
| | | TGGAGAGCAGAAGCCCCCATCTTTGAAAAGCTCCTGAGTG | |
| | | CAACTTAATTACCACCATGGCAGGGTGAGGGAACATTTGC | |
| | | ATCGTCAGCTGCCTCTGCATAGCTGTTTGAGAAATTCAGG | |
| | | CCCAAATCATGCAGCCTATCCAATAAGTAAGTTTATTTCC | |
| | | AACATTAGCTCTAATTAGTTCATTTCCAATCCCAGAACAC | |
| | | ATGGAGGGAATCGGACAGGTGATGCCAGCAGTTCCTGCTC | |
| | | CTCTGTCAGGGAAGCCAGGCAGAGCCCACAGAGCATGGTC | |
| | | CATCCAGAGTGTTCCCTGAGCCCCCTCCACCATACTGGAA | |
| | | CCCCTCTTCAGTGTAGGAAGTCTGAAATGGGTGCTAATTC | |
| | | CCTTCTTCATGAAACCAGGGCCCTCTTCCTTCATCTAATG | |
| | | CAGCCACTCCTAGGTGAAGAAGTGGGAATAATTGGAAATA | |
| | | AACAACAGTTCTAAAACTTCCATGATTTTTGTAGCTTCTT | |
| | | TTGTCCCCAAGTTGAAGCTTTTGGCCAGTACCTTCTCTAG | |
| | | TTTTTAAAGATGATCCCAACTTCCTAATTCCCAGCTAAGC | |
| | | CCTTGACCCATGGTGTGACATGAAATCAGGCAATTGAATC | |
| | | GCACCACTTTCTGTGTTTTCACCTGTTACGTAGAACAAAA | |
| | | GGAAGCAAGGTGGCCAGGCGCAATGGCTCACGCCTGTAAT | |
| | | CCCAGCACTTTGGGAGGCCGAGGCAGGCAGATCATGAGGT | |
| | | CAGGAGATCGAGACCATGGTGAAACCCCATCTCTACTAAA | |
| | | AATACAAAAAATTAGCTGGGCGCGGTGGCGGGCATCTGTA | |
| | | GTCCCAGCTCCTCGGGAGGCTGAGGCAGGAGAATGGCGTG | |
| | | AACCTGGGAGGCAGAGCTTGCAGTGAGCCGAGATCGTGCC | |
| | | ACTGCACTCCAGTCTGGGTGACAGAGAAGGACTCGTCTCA | |
| | | AAAAATAAAAATAAATAAAAAGGAAGCAAGGCTAATCATC | |
| | | AGTATGTGCTTGTTACAAGAGCTATGATGAAGGCACTCCT | |
| | | TCGAGTTTAACCAAATGAGATCATCTCTGTCATGTGCCTC | |
| | | ACGCCTCACAGGGACTCCATGTGTGAAGATTCCCCCTTCA | |
| | | CTCACCAGATCATCTCCATGGCAACAGCTTGCAGCCTGCT | |
| | | CTTGGAGTGCTTTGTTTTGGCAGCTTCTCTGCTAGTTTGT | |
| | | GTATGGAGTGAATGGAGGAGGTAAATCCACAGATTAAGAA | |
| | | TATGCTGTCAGGAGTCAGGCAGCCAAGGTCAGAAGCCAGC | |
| | | TCTGCTTCTCAGTGGTAAGGTGCTTGACTTCTACATCTCA | |
| | | ATTTTCACCCACTTTGTACTTTTTTCCTAAATTAAATGAG | |
| | | TATAATAGTAGTACCTACTTGATAGGACTTTTGTGAAAAT | |
| | | TAAATGATATAATGCACCTAAAAACAGTACTGTTACAACT | |
| | | AATAGGAAAGGCTTTGATTATTAATGGATGAGAGTAGAAA | |
| | | GCTTGGTGCATTTATTGTCTCATCTACTATAACAGAGTTG | |
| | | GTGTGAGAATTAGTATTATCATCCTCCCTTTATTGACCAG | |
| | | GAAACCAGCTCATTGAGATTGAGTCATCTGCTGGTAAATG | |
| | | GTCTCATTAAGAGGTGGACCCATATTTCTCTAGCTTTCTC | |
| | | TTTACAACACAGGACTTTGCAAGGAACATATAATTCTGTG | |
| | | ACTAGCGCCATTTGGAAAATGTTGAAACTGAAGTAGAGAT | |
| | | GAGAGATCTTACGTCTGCCTACCCAGTGAGATACGAGGAA | |
| | | GGTCAAGGGAAAAAAAATTCCAAGCTCTTCTTTATCTGCT | |
| | | ATAGGAAATGAACATTCAATTTTTTGCATGCAACGACAAG | |
| | | AGGTCAAGGACCCCAGAAGCCAGCCCGCTACTTCCAAGTT | |
| | | GAGAGCCCCTGGTCATACCCTCCAGTTGAGCTCAGATTTG | |
| | | TCACAAATTTACCCCTCTCCTTTCCTTCCATTCCCCATGA | |
| | | CCTGCAGAGAGAGATGTCAGATACCTTCCTCTTGGCCTCC | |
| | | CATGGGCATCCATAAGAAACTTACTTGAAGCAAGAAGCCC | |
| | | AGTATAGGTGTCTGGGCAGTTGGACATTTCCTCTAGCCAG | |
| | | ATCTGTCCGAATAGAGCCATCTGGGTACATGACGCAGAGG | |
| | | GCATTTGATAAATAACTGGAAAAGTCAATAAATCTTTGCT | |
| | | ACCCTTCAAAAAAAAAAAAAAAAAAAAAAAAAAAAAAAAA | |
| CTGF | NM_001901.2 | AAACTCACACAACAACTCTTCCCCGCTGAGAGGAGACAGC | 11 |
| | | CAGTGCGACTCCACCCTCCAGCTCGACGGCAGCCGCCCCG | |
| | | GCCGACAGCCCCGAGACGACAGCCCGGCGCGTCCCGGTCC | |
| | | CCACCTCCGACCACCGCCAGCGCTCCAGGCCCCGCCGCTC | |
| | | CCCGCTCGCCGCCACCGCGCCCTCCGCTCCGCCCGCAGTG | |
| | | CCAACCATGACCGCCGCCAGTATGGGCCCCGTCCGCGTCG | |
| | | CCTTCGTGGTCCTCCTCGCCCTCTGCAGCCGGCCGGCCGT | |
| | | CGGCCAGAACTGCAGCGGGCCGTGCCGGTGCCCGGACGAG | |
| | | CCGGCGCCGCGCTGCCCGGCGGGCGTGAGCCTCGTGCTGG | |
| | | ACGGCTGCGGCTGCTGCCGCGTCTGCGCCAAGCAGCTGGG | |
| | | CGAGCTGTGCACCGAGCGCGACCCCTGCGACCCGCACAAG | |
| | | GGCCTCTTCTGTGACTTCGGCTCCCCGGCCAACCGCAAGA | |
| | | TCGGCGTGTGCACCGCCAAAGATGGTGCTCCCTGCATCTT | |
| | | CGGTGGTACGGTGTACCGCAGCGGAGAGTCCTTCCAGAGC | |
| | | AGCTGCAAGTACCAGTGCACGTGCCTGGACGGGGCGGTGG | |

TABLE 1-continued

GEP-NEN Biomarker/Houskeeper Sequence Information

| Gene Name | RefSeq Accession | Sequence | SEQ ID NO: |
|---|---|---|---|
| | | GCTGCATGCCCCTGTGCAGCATGGACGTTCGTCTGCCCAG<br>CCCTGACTGCCCCTTCCCGAGGAGGGTCAAGCTGCCCGGG<br>AAATGCTGCGAGGAGTGGGTGTGTGACGAGCCCAAGGACC<br>AAACCGTGGTTGGGCCTGCCCTCGCGGCTTACCGACTGGA<br>AGACACGTTTGGCCCAGACCCAACTATGATTAGAGCCAAC<br>TGCCTGGTCCAGACCACAGAGTGGAGCGCCTGTTCCAAGA<br>CCTGTGGGATGGGCATCTCCACCCGGGTTACCAATGACAA<br>CGCCTCCTGCAGGCTAGAGAAGCAGAGCCGCCTGTGCATG<br>GTCAGGCCTTGCGAAGCTGACCTGGAAGAGAACATTAAGA<br>AGGGCAAAAAGTGCATCCGTACTCCCAAAATCTCCAAGCC<br>TATCAAGTTTGAGCTTTCTGGCTGCACCAGCATGAAGACA<br>TACCGAGCTAAATTCTGTGGAGTATGTACCGACGGCCGAT<br>GCTGCACCCCCCACAGAACCACCACCCTGCCGGTGGAGTT<br>CAAGTGCCCTGACGGCGAGGTCATGAAGAAGAACATGATG<br>TTCATCAAGACCTGTGCCTGCCATTACAACTGTCCCGGAG<br>ACAATGACATCTTTGAATCGCTGTACTACAGGAAGATGTA<br>CGGAGACATGGCATGAAGCCAGAGAGTGAGAGACATTAAC<br>TCATTAGACTGGAACTTGAACTGATTCACATCTCATTTTT<br>CCGTAAAAATGATTTCAGTAGCACAAGTTATTTAAATCTG<br>TTTTTCTAACTGGGGGAAAAGATTCCCACCCAATTCAAAA<br>CATTGTGCCATGTCAAACAAATAGTCTATCAACCCCAGAC<br>ACTGGTTTGAAGAATGTTAAGACTTGACAGTGGAACTACA<br>TTAGTACACAGCACCAGAATGTATATTAAGGTGTGGCTTT<br>AGGAGCAGTGGGAGGGTACCAGCAGAAAGGTTAGTATCAT<br>CAGATAGCATCTTATACGAGTAATATGCCTGCTATTTGAA<br>GTGTAATTGAGAAGGAAAATTTTAGCGTGCTCACTGACCT<br>GCCTGTAGCCCCAGTGACAGCTAGGATGTGCATTCTCCAG<br>CCATCAAGAGACTGAGTCAAGTTGTTCCTTAAGTCAGAAC<br>AGCAGACTCAGCTCTGACATTCTGATTCGAATGACACTGT<br>TCAGGAATCGGAATCCTGTCGATTAGACTGGACAGCTTGT<br>GGCAAGTGAATTTGCCTGTAACAAGCCAGATTTTTTAAAA<br>TTTATATTGTAAATATTGTGTGTGTGTGTGTGTGTGTATA<br>TATATATATATGTACAGTTATCTAAGTTAATTTAAAGTTG<br>TTTGTGCCTTTTTATTTTTGTTTTTAATGCTTTGATATTT<br>CAATGTTAGCCTCAATTTCTGAACACCATAGGTAGAATGT<br>AAAGCTTGTCTGATCGTTCAAAGCATGAAATGGATACTTA<br>TATGGAAATTCTGCTCAGATAGAATGACAGTCCGTCAAAA<br>CAGATTGTTTGCAAAGGGGAGGCATCAGTGTCCTTGGCAG<br>GCTGATTTCTAGGTAGGAAATGTGGTAGCCTCACTTTTAA<br>TGAACAAATGGCCTTTATTAAAAACTGAGTGACTCTATAT<br>AGCTGATCAGTTTTTTCACCTGGAAGCATTTGTTTCTACT<br>TTGATATGACTGTTTTTCGGACAGTTTATTTGTTGAGAGT<br>GTGACCAAAAGTTACATGTTTGCACCTTTCTAGTTGAAAA<br>TAAAGTGTATATTTTTTCTATAAAAAAAAAAAAAAAAA | |
| ENPP4 | NM_014936.4 | AGACGCTCGCCTGGCAGCTGCGCACACTCGGAGCGCCCCG<br>AGCGGCGCAGATAGGGACGTTGGGGCTGTGCCCCGCGGCG<br>CGGCGCCTGCCACTGCGCAGGCGCCTCAGGAAGAGCTCGG<br>CATCGCCCCTCTTCCTCCAGGTCCCCCTTCCCCGCAACTT<br>CCCACGAGTGCCAGGTGCCGCGAGCGCCGAGTTCCGCGCA<br>TTGGAAAGAAGCGACCGCGGCGGCTGGAACCCTGATTGCT<br>GTCCTTCAACGTGTTCATTATGAAGTTATTAGTAATACTT<br>TTGTTTTCTGGACTTATAACTGGTTTTAGAAGTGACTCTT<br>CCTCTAGTTTGCCACCTAAGTTACTACTAGTATCCTTTGA<br>TGGCTTCAGAGCTGATTATCTGAAGAACTATGAATTTCCT<br>CATCTCCAGAATTTTATCAAAGAAGGTGTTTTGGTAGAGC<br>ATGTTAAAAATGTTTTTATCACAAAAACATTTCCAAACCA<br>CTACAGTATTGTGACAGGCTTGTATGAAGAAAGCCATGGC<br>ATTGTGGCTAATTCCATGTATGATGCAGTCACAAAGAAAC<br>ACTTTTCTGACTCTAATGACAAGGATCCTTTTTGGTGGAA<br>TGAGGCAGTACCTATTTGGGTGACCAATCAGCTTCAGGAA<br>AACAGATCAAGTGCTGCTGCTATGTGGCCTGGTACTGATG<br>TACCCATTCACGATACCATCTCTTCCTATTTTATGAATTA<br>CAACTCCTCAGTGTCATTTGAGGAAAGACTAAATAATATT<br>ACTATGTGGCTAAACAATTCGAACCCACCAGTCACCTTTG<br>CAACACTATATTGGGAAGAACCAGATGCAAGTGGCCACAA<br>ATACGGACCTGAAGATAAAGAAAACATGAGCAGAGTGTTG<br>AAAAAAATAGATGATCTTATCGGTGACTTAGTCCAAAGAC<br>TCAAGATGTTAGGGCTATGGGAAAATCTTAATGTGATCAT<br>TACAAGTGATCATGGGATGACCCAGTGTTCTCAGGACAGA<br>CTGATAAACCTGGATTCCTGCATCGATCATTCATACTACA<br>CTCTTATAGATTTGAGCCCAGTTGCTGCAATACTTCCCAA<br>AATAAATAGAACAGAGGTTTATAACAAACTGAAAAACTGT<br>AGCCCTCATATGAATGTTTATCTCAAAGAAGACATTCCTA<br>ACAGATTTTATTACCAACATAATGATCGAATTCAGCCCAT | 12 |

TABLE 1-continued

GEP-NEN Biomarker/Houskeeper Sequence Information

| Gene Name | RefSeq Accession | Sequence | SEQ ID NO: |
|---|---|---|---|
| | | TATTTTGGTTGCCGATGAAGGCTGGACAATTGTGCTAAAT<br>GAATCATCACAAAAATTAGGTGACCATGGTTATGATAATT<br>CTTTGCCTAGTATGCATCCATTTCTAGCTGCCCACGGACC<br>TGCATTTCACAAAGGCTACAAGCATAGCACAATTAACATT<br>GTGGATATTTATCCAATGATGTGCCACATCCTGGGATTAA<br>AACCACATCCCAATAATGGGACCTTTGGTCATACTAAGTG<br>CTTGTTAGTTGACCAGTGGTGCATTAATCTCCCAGAAGCC<br>ATCGCGATTGTTATCGGTTCACTCTTGGTGTTAACCATGC<br>TAACATGCCTCATAATAATCATGCAGAATAGACTTTCTGT<br>ACCTCGTCCATTTTCTCGACTTCAGCTACAAGAAGATGAT<br>GATGATCCTTTAATTGGGTGACATGTGCTAGGGCTTATAC<br>AAAGTGTCTTTGATTAATCACAAAACTAAGAATACATCCA<br>AAGAATAGTGTTGTAACTATGAAAAAGAATACTTTGAAAG<br>ACAAAGAACTTAGACTAAGCATGTTAAAATTATTACTTTG<br>TTTTCCTTGTGTTTTGTTTCGGTGCATTTGCTAATAAGAT<br>AACGCTGACCATAGTAAAATTGTTAGTAAATCATTAGGTA<br>ACATCTTGTGGTAGGAAATCATTAGGTAACATCAATCCTA<br>ACTAGAAATACTAAAAATGGCTTTTGAGAAAAATACTTCC<br>TCTGCTTGTATTTTGCGATGAAGATGTGATACATCTTTAA<br>ATGAAAATATACCAAAATTTAGTAGGCATGTTTTTCTAAT<br>AAATTTATATATTTGTAAAGAAAACAACAGAAATCTTTAT<br>GCAATTTGTGAATTTTGTATATTAGGGAGGAAAAGCTTCC<br>TATATTTTTATATTTACCTTTAATTAGTTTGTATCTCAAG<br>TACCCTCTTGAGGTAGGAAATGCTCTGTGATGGTAAATAA<br>AATTGGAGCAGACAGAAAAGATATAGCAAATGAAGAAATA<br>TTTTAAGGAAACCTATTTGAAAAAAAAAGCAAAGACCATT<br>TGATAAAAGCCTGAGTTGTCACCATTATGTCTTAAGCTGT<br>TAGTCTTAAAGATTATTGTTAAAAAATTCAGAAGAAAAGA<br>GAGACAAGTGCTCTTCTCTCTATCTATGCTTAATGCCTTT<br>ATGTAAGTTACTTAGTTGTTTGCGTGTGCCTGTGCAAGTG<br>TGTTTGTGTGTGGTTGTGTGGACATTATGTGATTTACTAT<br>ATAAGGAGGTCAGAGATGGACTGTGGCCAGGCTTCCACAT<br>TCCTGAAGCACACAGATCTCAGGAAAGGTTATTTTTGCAC<br>TTCATATTTGTTTACTTTCTCCTAACTCACAAGTTAAAAT<br>CATAACTTAATTTCATTAACTTTTATCATTTAACTCTCTC<br>ATGTTTGTTGTAACCTGAGGTATCCAAATGCTACAGAAAA<br>ATTTATGACCCAAATACAAATCTCAATTTGACTGGGACAG<br>AATGAGGAATGGAGATTTTTGTATTTATCTTTGGGACTTT<br>ATGCCTTACTTTTTAGGCTATAGAATAGTTAAGAAATTTT<br>AAACAAAATTTAGTATCTTTTGGTCTTTCACACCATTCAT<br>ATGTTAAGTGGCAGAATAGCCTTAGTGCTACCTCCACTTT<br>TTTCTCCAGTATTTGCATCACAGAAATAATCCCTCTGTTT<br>AACATGTTTGTTCAGAGCCAAGGGTTTATTGTGAAGAACT<br>GTCATCCTGCCTTTGCTAGCTGGTACCTTCTAGTAATCAA<br>AATTAATATGAAGAAACTAGGTTGTGACAGACTAGATTAT<br>ATTTAGTAGGGGAAAAATTGGGCTCAAGAACCATTCATCA<br>GTACGTGAGACAAGCAGTTAATAGTATGATCTTTAAAGTT<br>TTGACAATATAAAATAAACTTGGTAACTGTTTTACAAATA<br>TAAAAGTATAATAAATATGCAGCCCAGTTAAATATTGATT<br>ATCTGTGATGGTAAAGAACAACAGTGGTGCCAGTCATCAA<br>ACATACAGTGCGTCCTATTGAGTCACTGCTAATTTCTTGA<br>GCCTGGTATTTGCTGCCTATTGTATTTGTGGTTGTTGAGA<br>GGCATTTTCAAACCCTGTATAAATAATCCATGCTGTTGGT<br>CATAAGTTAACTGTATTAAGAACAGTAAAATAAATAAAAA<br>CCAATAGTACTAATTTTGCTTTAAAAAAATTTCTAATTTT<br>TTTCACATAAAACAATTATCCTAAAGGTTAATAGTTGATC<br>GAAACAGAATAATAGAAAAATTCTACTTTAATTTCCATTA<br>AAAAGCAAATAGCATTGACACATTTAAAGCTTTTCATTTA<br>AAGTAGTGGATGTTTTTGAAGTATCTAAAATAGTAGCAGA<br>ATATTTTATACTTGGTCCTTGCAATGGTGTGAGTTTTAAT<br>GATTGCATTATCGTGATTGGTGGTTATGAGTTTCAGAAAT<br>CTATACTTGGCATCCAACTCATGAGTGGATTTTATATAGG<br>ATGGAACAGGAAGGTATGTCCTGTCAGTATCTTAACCCTT<br>TCAACAAGACATTTACCTATTTGTCTTTCCTTACGTTCTC<br>AAAATATTAACTCGAATTGTAAATTAAGCAAAAATTTAAA<br>AAGTATATGTTGATGGGACAAGAAGAATAGTATTTATTTA<br>ATAAAACATATATTATATTGAACTATGTGTTAATTCATTT<br>GTATCTTTTAAAAAATTATCACTGTTAAAGCCATTGACTC<br>CTTTAGTACACTGAGAAAAATCTTATAGTAAAACTAGCCT<br>TTCACATTAAGGTTTTGGTGTGTATTTTGTTAAATAACTA<br>ACATGCTGCTCTATTTTCTGGGTGTAGAAAGTATTTGGCT<br>CTAGGAAACATTTACTTGTTTGTGAAAACAATACCCCAAG<br>GTAATAGGAAAAGTTTGAGTTAAGTGTTTTTAATTCAGTC<br>AGTGAATTCAGAATAAGTACATTCATGTATAACATAGGGA<br>CAGTTCTGCTGCTGTTATTTATATGCAATTCTTCTGGTAA | |

TABLE 1-continued

| GEP-NEN Biomarker/Houskeeper Sequence Information | | | |
|---|---|---|---|
| Gene Name | RefSeq Accession | Sequence | SEQ ID NO: |
| | | ATAGCAATAGAATAAAACATATTTCAATGTTTGTGTATAG | |
| | | GTTTTATATTATTATTCCACTAGGAATGGCATAAGAATTT | |
| | | ATAGATAAATTCTTGTAACATTAAAGGATTAAAATGTTTT | |
| | | TACATTGTTTTTGGGTGTCTCCTTCTTGTGCCCATATCTG | |
| | | ATAAGCTTTATGGATTATTGCATTTAATTCCTTTTATTTG | |
| | | GAGGGTTTTACTTCCTTGTTAACATATAAAGTTATAAATG | |
| | | AAGGACAAGGAGGAGATGGAAAATGTGTATTTATTGTTAA | |
| | | TTCTTAAAATAGTGTGTAAATAAAATAACATCAGTGTGCT | |
| | | TTAAAGAAATGTGTATGTAGTGCCTTAATTTAAATTAAAA | |
| | | TATTTTTGACTGTTACTTGAGTTCAGAATTAATGACTTTG | |
| | | TTCATGATTTTTAAAATGTGTGTGAATAAAATCTACCAAA | |
| | | AAATTCTTACTGTAATTATTAAATATAAAGTTCAGTGTCA | |
| | | AAAAAAAAAAAAAAAAA | |
| FAM131A | NM_001171093.1 | ACCGGCCCGGTTCCCTCTCCGGGGAGCGGCGGCGGACGCG | 13 |
| | | CGGCTCCCACCCCTCCCCTCTCACGGGCTCTCCCCTCCCC | |
| | | AGTGTGGCCGCGACCCTACCCTCTGCAAGGCGATGGCCCG | |
| | | CGCCCCGAGCGCAGGCTAGCGTGCCTGGGTGCCCGGCCAT | |
| | | GGGCTGTATCGGCTCTCGGAGCCCGGCGGGTCAGGCATTT | |
| | | CTGGGGACCAACAGCTGGCCGAGGCTCAGGGATAGAGACG | |
| | | GCTGCTCCAGCTAAAGGTGAATGTTGGAGACACAGTCGCG | |
| | | ATGCTGCCCAAGTCCCGGCGAGCCCTAACTATCCAGGAGA | |
| | | TCGCTGCGCTGGCCAGGTCCTCCCTGCATGGTATTTCCCA | |
| | | GGTGGTGAAGGACCACGTGACCAAGCCTACCGCCATGGCC | |
| | | CAGGGCCGAGTGGCTCACCTCATTGAGTGGAAGGGCTGGA | |
| | | GCAAGCCGAGTGACTCACCTGCTGCCCTGGAATCAGCCTT | |
| | | TTCCTCCTATTCAGACCTCAGCGAGGGCGAACAAGAGGCT | |
| | | CGCTTTGCAGCAGGAGTGGCTGAGCAGTTTGCCATCGCGG | |
| | | AAGCCAAGCTCCGAGCATGGTCTTCGGTGGATGGCGAGGA | |
| | | CTCCACTGATGACTCCTATGATGAGGACTTTGCTGGGGGA | |
| | | ATGGACACAGACATGGCTGGGCAGCTGCCCCTGGGGCCGC | |
| | | ACCTCCAGGACCTGTTCACCGGCCACCGGTTCTCCCGGCC | |
| | | TGTGCGCCAGGGCTCCGTGGAGCCTGAGAGCGACTGCTCA | |
| | | CAGACCGTGTCCCCAGACACCCTGTGCTCTAGTCTGTGCA | |
| | | GCCTGGAGGATGGGTTGTTGGGCTCCCCGGCCCGGCTGGC | |
| | | CTCCCAGCTGCTGGGCGATGAGCTGCTTCTCGCCAAACTG | |
| | | CCCCCCAGCCGGGAAAGTGCCTTCCGCAGCCTGGGCCCAC | |
| | | TGGAGGCCCAGGACTCACTCTACAACTCGCCCCTCACAGA | |
| | | GTCCTGCCTTTCCCCCGCGGAGGAGGAGCCAGCCCCCTGC | |
| | | AAGGACTGCCAGCCACTCTGCCCACCACTAACGGGCAGCT | |
| | | GGGAACGGCAGCGGCAAGCCTCTGACCTGGCCTCTTCTGG | |
| | | GGTGGTGTCCTTAGATGAGGATGAGGCAGAGCCAGAGGAA | |
| | | CAGTGACCCACATCATGCCTGGCAGTGGCATGCATCCCCC | |
| | | GGCTGCTGCCAGGGGCAGAGCCTCTGTGCCCAAGTGTGGG | |
| | | CTCAAGGCTCCCAGCAGAGCTCCACAGCCTAGAGGGCTCC | |
| | | TGGGAGCGCTCGCTTCTCCGTTGTGTGTTTTGCATGAAAG | |
| | | TGTTTGGAGAGGAGGCAGGGGCTGGGCTGGGGGCGCATGT | |
| | | CCTGCCCCCACTCCCGGGGCTTGCCGGGGGTTGCCCGGGG | |
| | | CCTCTGGGGCATGGCTACAGCTGTGGCAGACAGTGATGTT | |
| | | CATGTTCTTAAAATGCCACACACACATTTCCTCCTCGGAT | |
| | | AATGTGAACCACTAAGGGGGTTGTGACTGGGCTGTGTGAG | |
| | | GGTGGGGTGGGAGGGGGCCCAGCAACCCCCCACCCTCCCC | |
| | | ATGCCTCTCTCTTCTCTGCTTTTCTTCTCACTTCCGAGTC | |
| | | CATGTGCAGTGCTTGATAGAATCACCCCCACCTGGAGGGG | |
| | | CTGGCTCCTGCCCTCCCGGAGCCTATGGGTTGAGCCGTCC | |
| | | CTCAAGGGCCCCTGCCCAGCTGGGCTCGTGCTGTGCTTCA | |
| | | TTCACCTCTCCATCGTCTCTAAATCTTCCTCTTTTTTCCT | |
| | | AAAGACAGAAGGTTTTTGGTCTGTTTTTTCAGTCGGATCT | |
| | | TCTCTTCTCTGGGAGGCTTTGGAATGATGAAAGCATGTAC | |
| | | CCTCCACCCTTTTCCTGGCCCCCTAATGGGGCCTGGGCCC | |
| | | TTTCCCAACCCCTCCTAGGATGTGCGGGCAGTGTGCTGGC | |
| | | GCCTCACAGCCAGCCGGGCTGCCCATTCACGCAGAGCTCT | |
| | | CTGAGCGGGAGGTGGAAGAAAGGATGGCTCTGGTTGCCAC | |
| | | AGAGCTGGGACTTCATGTTCTTCTAGAGAGGGCCACAAGA | |
| | | GGGCCACAGGGGTGGCCGGGAGTTGTCAGCTGATGCCTGC | |
| | | TGAGAGGCAGGAATTGTGCCAGTGAGTGACAGTCATGAGG | |
| | | GAGTGTCTCTTCTTGGGGAGGAAAGAAGGTAGAGCCTTTC | |
| | | TGTCTGAATGAAAGGCCAAGGCTACAGTACAGGGCCCCAC | |
| | | CCCAGCCAGGGTGTTAATGCCCACGTAGTGGAGGCCTCTG | |
| | | GCAGATCCTGCATTCCAAGGTCACTGGACTGTACGTTTTT | |
| | | ATGGTTGTGGGAAGGGTGGGTGGCTTTAGAATTAAGGGCC | |
| | | TTGTAGGCTTTGGCAGGTAAGAGGGCCCAAGGTAAGAACG | |

TABLE 1-continued

GEP-NEN Biomarker/Houskeeper Sequence Information

| Gene Name | RefSeq Accession | Sequence | SEQ ID NO: |
|---|---|---|---|
| | | AGAGCCAACGGGCACAAGCATTCTATATATAAGTGGCTCA | |
| | | TTAGGTGTTTATTTTGTTCTATTTAAGAATTTGTTTTATT | |
| | | AAATTAATATAAAAATCTTTGTAAATCTCTAAAAAAAAAA | |
| | | AAAAAAAA | |
| FLJ10357 | NM_018071.4 | GGAGCGGGCCGAGCCGCCACCGCGGCCGGAGCTGTCCCTT | 14 |
| | | AGCCAGACCCGGCGAGACACGAGCGGCGGGAGGGAGGCGG | |
| | | TGGCGCGCCCGGCCCCGCCCGCCCGACCAAGCGTCGGACG | |
| | | CGGCCCGGCGCCGAGCCATGGAGCCTGAGCCAGTGGAGGA | |
| | | CTGTGTGCAGAGCACTCTCGCCGCCCTGTATCCACCCTTT | |
| | | GAGGCAACAGCCCCCACCCTGTTGGGCCAGGTGTTCCAGG | |
| | | TGGTGGAGAGGACTTATCGGGAGGACGCACTGAGGTACAC | |
| | | GCTGGACTTCCTGGTACCAGCCAAGCACCTGCTTGCCAAG | |
| | | GTCCAGCAGGAAGCCTGTGCCCAATACAGTGGATTCCTCT | |
| | | TCTTCCATGAGGGGTGGCCGCTCTGCCTGCATGAACAGGT | |
| | | GGTGGTGCAGCTAGCAGCCCTACCCTGGCAACTGCTGCGC | |
| | | CCAGGAGACTTCTATCTGCAGGTGGTGCCCTCAGCTGCCC | |
| | | AAGCACCCCGACTAGCACTCAAGTGTCTGGCCCCTGGGGG | |
| | | TGGGCGGGTGCAGGAGGTTCCTGTGCCCAATGAGGCTTGT | |
| | | GCCTACCTATTCACACCTGAGTGGCTACAAGGCATCAACA | |
| | | AGGACCGGCCAACAGGTCGCCTCAGTACCTGCCTACTGTC | |
| | | TGCGCCCTCTGGGATTCAGCGGCTGCCCTGGGCTGAGCTC | |
| | | ATCTGTCCACGATTTGTGCACAAAGAGGGCCTCATGGTTG | |
| | | GACATCAGCCAAGTACACTGCCCCCAGAACTGCCCTCTGG | |
| | | ACCTCCAGGGCTTCCCAGCCCTCCACTTCCTGAGGAGGCG | |
| | | CTGGGTACCCGGAGTCCTGGGGATGGGCACAATGCCCCTG | |
| | | TGGAAGGACCTGAGGGCGAGTATGTGGAGCTGTTAGAGGT | |
| | | GACGCTGCCCGTGAGGGGGAGCCCAACAGATGCTGAAGGC | |
| | | TCCCCAGGCCTCTCCAGAGTCCGGACGGTACCCACCCGCA | |
| | | AGGGCGCTGGAGGGAAGGGCCGCCACCGGAGACACCGGGC | |
| | | GTGGATGCACCAGAAGGGCCTGGGGCCTCGGGGCCAGGAT | |
| | | GGAGCACGCCCACCCGGCGAGGGGAGCAGCACCGGAGCCT | |
| | | CCCCTGAGTCTCCCCCAGGAGCTGAGGCTGTCCCAGAGGC | |
| | | AGCAGTCTTGGAGGTGTCTGAGCCCCCAGCAGAGGCTGTG | |
| | | GGAGAAGCCTCCGGATCTTGCCCCCTGAGGCCAGGGGAGC | |
| | | TTAGAGGAGGAGGAGGAGGAGGCCAGGGGGCTGAAGGACC | |
| | | ACCTGGTACCCCTCGGAGAACAGGCAAAGGAAACAGAAGA | |
| | | AAGAAGCGAGCTGCAGGTCGAGGGGCTCTTAGCCGAGGAG | |
| | | GGGACAGTGCCCCACTGAGCCCTGGGGACAAGGAAGATGC | |
| | | CAGCCACCAAGAAGCCCTTGGCAATCTGCCCTCACCAAGT | |
| | | GAGCACAAGCTTCCAGAATGCCACCTGGTTAAGGAGGAAT | |
| | | ATGAAGGCTCAGGGAAGCCAGAATCTGAGCCAAAAGAGCT | |
| | | CAAAACAGCAGGCGAGAAAGAGCCTCAGCTCTCTGAAGCC | |
| | | TGTGGGCCTACAGAAGAGGGGGCCGGAGAGAGAGAGCTGG | |
| | | AGGGGCCAGGCCTGCTGTGTATGGCAGGACACACAGGCCC | |
| | | AGAAGGCCCCCTGTCTGACACTCCAACACCTCCGCTGGAG | |
| | | ACTGTGCAGGAAGGAAAAGGGGACAACATTCCAGAAGAGG | |
| | | CCCTTGCAGTCTCCGTCTCTGATCACCCTGATGTAGCTTG | |
| | | GGACTTGATGGCATCTGGATTCCTCATCCTGACGGGAGGG | |
| | | GTGGACCAGAGTGGGCGAGCTCTGCTGACCATTACCCCAC | |
| | | CGTGCCCTCCTGAGGAGCCCCCACCCTCCCGAGACACGCT | |
| | | GAACACAACTCTTCATTACCTCCACTCACTGCTCAGGCCT | |
| | | GATCTACAGACACTGGGGCTGTCCGTCCTGCTGGACCTTC | |
| | | GTCAGGCACCTCCACTGCCTCCAGCACTCATTCCTGCCTT | |
| | | GAGCCAACTTCAGGACTCAGGAGATCCTCCCCTTGTTCAG | |
| | | CGGCTGCTGATTCTCATTCATGATGACCTTCCAACTGAAC | |
| | | TCTGTGGATTTCAGGGTGCTGAGGTGCTGTCAGAGAATGA | |
| | | TCTGAAAAGAGTGGCCAAGCCAGAGGAGCTGCAGTGGGAG | |
| | | TTAGGAGGTCACAGGGACCCCTCTCCCAGTCACTGGGTAG | |
| | | AGATACACCAGGAAGTGGTAAGGCTATGTCGCCTGTGCCA | |
| | | AGGTGTGCTGGGCTCGGTACGGCAGGCCATTGAGGAGCTG | |
| | | GAGGGAGCAGCAGAGCCAGAGGAAGAGGAGGCAGTGGGAA | |
| | | TGCCCAAGCCACTGCAGAAGGTGCTGGCAGATCCCCGGCT | |
| | | GACGGCACTGCAGAGGGATGGGGGGCCATCCTGATGAGG | |
| | | CTGCGCTCCACTCCCAGCAGCAAGCTGGAGGGCCAAGGCC | |
| | | CAGCTACACTGTATCAGGAAGTGGACGAGGCCATTCACCA | |
| | | GCTTGTGCGCCTCTCCAACCTGCACGTGCAGCAGCAAGAG | |
| | | CAGCGGCAGTGCCTGCGGCGACTCCAGCAGGTGTTGCAGT | |
| | | GGCTCTCGGGCCCAGGGGAGGAGCAGCTGGCAAGCTTTGC | |
| | | TATGCCTGGGGACACCTTGTCTGCCCTGCAGGAGACAGAG | |
| | | CTGCGATTCCGTGCTTTCAGCGCTGAGGTCCAGGAGCGCC | |
| | | TGGCCCAGGCACGGGAGGCCCTGGCTCTGGAGGAGAATGC | |
| | | CACCTCCCAGAAGGTGCTGGATATCTTTGAACAGCGGCTG | |
| | | GAGCAGGTTGAGAGTGGCCTCCATCGGGCCCTGCGGCTAC | |
| | | AGCGCTTCTTCCAGCAGGCACATGAATGGGTGGATGAGGG | |

TABLE 1-continued

GEP-NEN Biomarker/Houskeeper Sequence Information

| Gene Name | RefSeq Accession | Sequence | SEQ ID NO: |
|---|---|---|---|
| | | CTTTGCTCGGCTGGCAGGAGCTGGGCCGGGTCGGGAGGCT<br>GTGCTGGCTGCACTGGCCCTGCGGCGGGCCCCAGAGCCCA<br>GTGCCGGCACCTTCCAGGAGATGCGGGCCCTGGCCCTGGA<br>CCTGGGCAGCCCAGCAGCCCTGCGAGAATGGGGCCGCTGC<br>CAGGCCCGCTGCCAAGAGCTAGAGAGGAGGATCCAGCAAC<br>ACGTGGGAGAGGAGGCGAGCCCACGGGGCTACCGACGACG<br>GCGGGCAGACGGTGCCAGCAGTGGAGGGGCCCAGTGGGGG<br>CCCCGCAGCCCCTCGCCCAGCCTCAGCTCCTTGCTGCTCC<br>CCAGCAGCCCTGGGCCACGGCCAGCCCCATCCCATTGCTC<br>CCTGGCCCCATGTGGAGAGGACTATGAGGAAGAGGGCCCT<br>GAGCTGGCTCCAGAAGCAGAGGGCAGGCCCCCAAGAGCTG<br>TGCTGATCCGAGGCCTGGAGGTCACCAGCACTGAGGTGGT<br>AGACAGGACGTGCTCACCACGGGAACACGTGCTGCTGGGC<br>CGGGCTAGGGGGCCAGACGGACCCTGGGGAGTAGGCACCC<br>CCCGGATGGAGCGCAAGCGAAGCATCAGTGCCCAGCAGCG<br>GCTGGTGTCTGAGCTGATTGCCTGTGAACAAGATTACGTG<br>GCCACCTTGAGTGAGCCAGTGCCACCCCCTGGGCCTGAGC<br>TGACGCCTGAACTTCGGGGCACCTGGGCTGCTGCCCTGAG<br>TGCCCGGGAAAGGCTTCGCAGCTTCCACCGGACACACTTT<br>CTGCGGGAGCTTCAGGGCTGCGCCACCCACCCCCTACGCA<br>TTGGGGCCTGCTTCCTTCGCCACGGGGACCAGTTCAGCCT<br>TTATGCACAGTACGTGAAGCACCGACACAAACTGGAGAAT<br>GGTCTGGCTGCGCTCAGTCCCTTAAGCAAGGGCTCCATGG<br>AGGCTGGCCCTTACCTGCCCCGAGCCCTGCAGCAGCCTCT<br>GGAACAGCTGACTCGGTATGGGCGGCTCCTGGAGGAGCTC<br>CTGAGGGAAGCTGGGCCTGAGCTCAGTTCTGAGTGCCGGG<br>CCCTTGGGGCTGCTGTACAGCTGCTCCGGGAACAAGAGGC<br>CCGTGGCAGAGACCTGCTGGCCGTGGAGGCGGTGCGTGGC<br>TGTGAGATAGATCTGAAGGAGCAGGGACAGCTCTTGCATC<br>GAGACCCCTTCACTGTCATCTGTGGCCGAAAGAAGTGCCT<br>TCGCCATGTCTTTCTCTTCGAGCATCTCCTCCTGTTCAGC<br>AAGCTCAAGGGCCCTGAAGGGGGGTCAGAGATGTTTGTTT<br>ACAAGCAGGCCTTTAAGACTGCTGATATGGGGCTGACAGA<br>AAACATCGGGGACAGCGGACTCTGCTTTGAGTTGTGGTTT<br>CGGCGGCGGCGTGCACGAGAGGCATACACTCTGCAGGCAA<br>CCTCACCAGAGATCAAACTCAAGTGGACAAGTTCTATTGC<br>CCAGCTGCTGTGGAGACAGGCAGCCCACAACAAGGAGCTC<br>CGAGTGCAGCAGATGGTGTCCATGGGCATTGGGAATAAAC<br>CCTTCCTGGACATCAAAGCCCTTGGGGAGCGGACGCTGAG<br>TGCCCTGCTCACTGGAAGAGCCGCCCGCACCCGGGCCTCC<br>GTGGCCGTGTCATCCTTTGAGCATGCCGGCCCCTCCCTTC<br>CCGGCCTTTCGCCGGGAGCCTGCTCCCTGCCTGCCCGCGT<br>CGAGGAGGAGGCCTGGGATCTGGACGTCAAGCAAATTTCC<br>CTGGCCCCAGAAACACTTGACTCTTCTGGAGATGTGTCCC<br>CAGGACCAAGAAACAGCCCCAGCCTGCAACCCCCCCACCC<br>TGGGAGCAGCACTCCCACCCTGGCCAGTCGAGGGATCTTA<br>GGGCTATCCCGACAGAGTCATGCTCGAGCCCTGAGTGACC<br>CCACCACGCCTCTGTGACCTGGAGAAGATCCAGAACTTGC<br>GTGCAGCTTCTCCTCTCAGCACACTTTGGGCTGGGATGGC<br>AGTGGGGCATAATGGAGCCCTGGGCGATCGCTGAATTTCT<br>TCCCTCTGCTTCCTGGACACAGAGGAGGTCTAACGACCAG<br>AGTATTGCCCTGCCACCACTATCTCTAGTCTCCCTAGCTT<br>GGTGCCTTCTCCTGCAGGAGTCAGAGCAGCCACATTGCTT<br>GCCTTCATACCCTGGAGGTGGGGAAGTTATCCCTCTTCCG<br>GTGCTTTCCCATCCTGGGCCACTGTATCCAGGACATCACT<br>CCCATGCCAGCCCTCCCTGGCAGCCCATGTTCTCCTCTTT<br>TCTCACCCCCTGACTTTCCCTGAGAAGAATCATCTCTGCC<br>AGGTCAACTGGAGTCCCTGGTGACTCCATTCTGAGGTGTC<br>ACAAGCAATGAAGCTATGCAAACAATAGGAGGGTGTGACA<br>GGGGAACCGTAGACTTTATATATGTAATTACTGTTATTAT<br>AATACTATTGTTATATTAAATGTATTTACTCACACTTTGC<br>CTCTAAGGAGCTAGAGTAGTCCTCTGGATTAAGGTGATAA<br>ATAACTTGAGCACTTTCCCTCAACCAGCCCTTAACTAGAA<br>CACAGAAAATAAAACCAAGACTGGAAGGTCCCCTCTACCC<br>CTCCCAGGCCCAGAGCTAGCTGACTGTGTATGAGCCTGGG<br>AGAATGTGTCTCCTCCACAGTGGCTCCCAGAGGTTCCACA<br>CACTCTCTGAAGCTCCTTCTCCCACACTGCACCTACTCCT<br>TGAGGCTGAACTGGTCACAGACAAACTGGGATCCAGCACA<br>GTCCAGCAGTTCTCAAAATGAGGTCCTCAGGCCACAGTGC<br>GTGAGAACTTGCTTGGCTGTTTGTTAAATGCTAATTCTTG<br>GGCCCCATCAGAGCTACTGCATCGAAACCTGGGGGTAAAA<br>CCCAATATTCTGCATTTCTTATCAAACTCTTTGGGTGATA<br>ACTAAGTGTCTGAAGAGGTGACTATTTCCTGACAGAAGGA<br>CCCAAAGAGGGAAGCAGGACATAGGTAGGCAGACAGACAC<br>AGGGCCCTGTGCCTCAAGACACCTGTTTATTGGGGACACG | |

TABLE 1-continued

GEP-NEN Biomarker/Houskeeper Sequence Information

| Gene Name | RefSeq Accession | Sequence | SEQ ID NO: |
|---|---|---|---|
| | | ACTCTGCAATAGGGATGACAGGAATCGTACCAAAAATAGC | |
| | | GACGTCTACAGGGCCCCTGATGGGGCTAGAAGGGTACAGT | |
| | | GCCCCCCACCCTCACCCCTTGTACAAAAATAAACTCTCAC | |
| | | GCCTATGGACCAGCAAAAAAAAAAAAAA | |
| FZD7 | NM_003507.1 | CTCTCCCAACCGCCTCGTCGCACTCCTCAGGCTGAGAGCA | 15 |
| | | CCGCTGCACTCGCGGCCGGCGATGCGGGACCCCGGCGCGG | |
| | | CCGCTCCGCTTTCGTCCCTGGGCCTCTGTGCCCTGGTGCT | |
| | | GGCGCTGCTGGGCGCACTGTCCGCGGGCGCCGGGGCGCAG | |
| | | CCGTACCACGGAGAGAAGGGCATCTCCGTGCCGGACCACG | |
| | | GCTTCTGCCAGCCCATCTCCATCCCGCTGTGCACGGACAT | |
| | | CGCCTACAACCAGACCATCCTGCCCAACCTGCTGGGCCAC | |
| | | ACGAACCAAGAGGACGCGGGCCTCGAGGTGCACCAGTTCT | |
| | | ACCCGCTGGTGAAGGTGCAGTGTTCTCCCGAACTCCGCTT | |
| | | TTTCTTATGCTCCATGTATGCGCCCGTGTGCACCGTGCTC | |
| | | GATCAGGCCATCCCGCCGTGTCGTTCTCTGTGCGAGCGCG | |
| | | CCCGCCAGGGCTGCGAGGCGCTCATGAACAAGTTCGGCTT | |
| | | CCAGTGGCCCGAGCGGCTGCGCTGCGAGAACTTCCCGGTG | |
| | | CACGGTGCGGGCGAGATCTGCGTGGGCCAGAACACGTCGG | |
| | | ACGGCTCCGGGGGCCCAGGCGGCGGCCCCACTGCCTACCC | |
| | | TACCGCGCCCTACCTGCCGGACCTGCCCTTCACCGCGCTG | |
| | | CCCCCGGGGGCCTCAGATGGCAGGGGGCGTCCCGCCTTCC | |
| | | CCTTCTCATGCCCCCGTCAGCTCAAGGTGCCCCCGTACCT | |
| | | GGGCTACCGCTTCCTGGGTGAGCGCGATTGTGGCGCCCCG | |
| | | TGCGAACCGGGCCGTGCCAACGGCCTGATGTACTTTAAGG | |
| | | AGGAGGAGAGGCGCTTCGCCCGCCTCTGGGTGGGCGTGTG | |
| | | GTCCGTGCTGTGCTGCGCCTCGACGCTCTTTACCGTTCTC | |
| | | ACCTACCTGGTGGACATGCGGCGCTTCAGCTACCCAGAGC | |
| | | GGCCCATCATCTTCCTGTCGGGCTGCTACTTCATGGTGGC | |
| | | CGTGGCGCACGTGGCCGGCTTCCTTCTAGAGGACCGCGCC | |
| | | GTGTGCGTGGAGCGCTTCTCGGACGATGGCTACCGCACGG | |
| | | TGGCGCAGGGCACCAAGAAGGAGGGCTGCACCATCCTCTT | |
| | | CATGGTGCTCTACTTCTTCGGCATGGCCAGCTCCATCTGG | |
| | | TGGGTCATTCTGTCTCTCACTTGGTTCCTGGCGGCCGGCA | |
| | | TGAAGTGGGGCCACGAGGCCATCGAGGCCAACTCGCAGTA | |
| | | CTTCCACCTGGCCGCGTGGGCCGTGCCCGCCGTCAAGACC | |
| | | ATCACTATCCTGGCCATGGGCCAGGTAGACGGGGACCTGC | |
| | | TGAGCGGGGTGTGCTACGTTGGCCTCTCCAGTGTGGACGC | |
| | | GCTGCGGGGCTTCGTGCTGGCGCCTCTGTTCGTCTACCTC | |
| | | TTCATAGGCACGTCCTTCTTGCTGGCCGGCTTCGTGTCCC | |
| | | TCTTCCGTATCCGCACCATCATGAAACACGACGGCACCAA | |
| | | GACCGAGAAGCTGGAGAAGCTCATGGTGCGCATCGGCGTC | |
| | | TTCAGCGTGCTCTACACAGTGCCCGCCACCATCGTCCTGG | |
| | | CCTGCTACTTCTACGAGCAGGCCTTCCGCGAGCACTGGGA | |
| | | GCGCACCTGGCTCCTGCAGACGTGCAAGAGCTATGCCGTG | |
| | | CCCTGCCCGCCCGGCCACTTCCCGCCCATGAGCCCCGACT | |
| | | TCACCGTCTTCATGATCAAGTACCTGATGACCATGATCGT | |
| | | CGGCATCACCACTGGCTTCTGGATCTGGTCGGGCAAGACC | |
| | | CTGCAGTCGTGGCGCCGCTTCTACCACAGACTTAGCCACA | |
| | | GCAGCAAGGGGGAGACTGCGGTATGAGCCCCGGCCCCTCC | |
| | | CCACCTTTCCCACCCCAGCCCTCTTGCAAGAGGAGAGGCA | |
| | | CGGTAGGGAAAAGAACTGCTGGGTGGGGGCCTGTTTCTGT | |
| | | AACTTTCTCCCCCTCTACTGAGAAGTGACCTGGAAGTGAG | |
| | | AAGTTCTTTGCAGATTTGGGGCGAGGGGTGATTTGGAAAA | |
| | | GAAGACCTGGGTGGAAAGCGGTTTGGATGAAAAGATTTCA | |
| | | GGCAAAGACTTGCAGGAAGATGATGATAACGGCGATGTGA | |
| | | ATCGTCAAAGGTACGGGCCAGCTTGTGCCTAATAGAAGGT | |
| | | TGAGACCAGCAGAGACTGCTGTGAGTTTCTCCCGGCTCCG | |
| | | AGGCTGAACGGGGACTGTGAGCGATCCCCCTGCTGCAGGG | |
| | | CGAGTGGCCTGTCCAGACCCCTGTGAGGCCCCGGGAAAGG | |
| | | TACAGCCCTGTCTGCGGTGGCTGCTTTGTTGGAAAGAGGG | |
| | | AGGGCCTCCTGCGGTGTGCTTGTCAAGCAGTGGTCAAACC | |
| | | ATAATCTCTTTTCACTGGGGCCAAACTGGAGCCCAGATGG | |
| | | GTTAATTTCCAGGGTCAGACATTACGGTCTCTCCTCCCCT | |
| | | GCCCCCTCCCGCCTGTTTTTCCTCCCGTACTGCTTTCAGG | |
| | | TCTTGTAAAATAAGCATTTGGAAGTCTTGGGAGGCCTGCC | |
| | | TGCTAGAATCCTAATGTGAGGATGCAAAAGAAATGATGAT | |
| | | AACATTTTGAGATAAGGCCAAGGAGACGTGGAGTAGGTAT | |
| | | TTTTGCTACTTTTTCATTTTCTGGGGAAGGCAGGAGGCAG | |
| | | AAAGACGGGTGTTTTATTTGGTCTAATACCCTGAAAAGAA | |
| | | GTGATGACTTGTTGCTTTTCAAAACAGGAATGCATTTTTC | |
| | | CCCTTGTCTTTGTTGTAAGAGACAAAAGAGGAAACAAAAG | |
| | | TGTCTCCCTGTGGAAAGGCATAACTGTGACGAAAGCAACT | |
| | | TTTATAGGCAAAGCAGCGCAAATCTGAGGTTTCCCGTTGG | |
| | | TTGTTAATTTGGTTGAGATAAACATTCCTTTTTAAGGAAA | |

TABLE 1-continued

GEP-NEN Biomarker/Houskeeper Sequence Information

| Gene Name | RefSeq Accession | Sequence | SEQ ID NO: |
|---|---|---|---|
| | | AGTGAAGAGCAGTGTGCTGTCACACACCGTTAAGCCAGAG<br>GTTCTGACTTCGCTAAAGGAAATGTAAGAGGTTTTGTTGT<br>CTGTTTTAAATAAATTTAATTCGGAACACATGATCCAACA<br>GACTATGTTAAAATATTCAGGGAAATCTCTCCCTTCATTT<br>ACTTTTTCTTGCTATAAGCCTATATTTAGGTTTCTTTTCT<br>ATTTTTTTCTCCCATTTGGATCCTTTGAGGTAAAAAAACA<br>TAATGTCTTCAGCCTCATAATAAAGGAAAGTTAATTAAAA<br>AAAAAAAGCAAAGAGCCATTTTGTCCTGTTTTCTTGGTTC<br>CATCAATCTGTTTATTAAACATCATCCATATGCTGACCCT<br>GTCTCTGTGTGGTTGGGTTGGGAGGCGATCAGCAGATACC<br>ATAGTGAACGAAGAGGAAGGTTTGAACCATGGGCCCCATC<br>TTTAAAGAAAGTCATTAAAAGAAGGTAAACTTCAAAGTGA<br>TTCTGGAGTTCTTTGAAATGTGCTGGAAGACTTAAATTTA<br>TTAATCTTAAATCATGTACTTTTTTTCTGTAATAGAACTC<br>GGATTCTTTTGCATGATGGGGTAAAGCTTAGCAGAGAATC<br>ATGGGAGCTAACCTTTATCCCACCTTTGACACTACCCTCC<br>AATCTTGCAACACTATCCTGTTTCTCAGAACAGTTTTTAA<br>ATGCCAATCATAGAGGGTACTGTAAAGTGTACAAGTTACT<br>TTATATATGTAATGTTCACTTGAGTGGAACTGCTTTTTAC<br>ATTAAAGTTAAAATCGATCTTGTGTTTCTTCAACCTTCAA<br>AACTATCTCATCTGTCAGATTTTTAAAACTCCAACACAGG<br>TTTTGGCATCTTTTGTGCTGTATCTTTTAAGTGCATGTGA<br>AATTTGTAAAATAGAGATAAGTACAGTATGTATATTTTGT<br>AAATCTCCCATTTTTGTAAGAAAATATATATTGTATTTAT<br>ACATTTTTACTTTGGATTTTTGTTTTGTTGGCTTTAAAGG<br>TCTACCCCACTTTATCACATGTACAGATCACAAATAAATT<br>TTTTTAAATAC | |
| GLT8D1 | NM_001010983.2 | GACGGGCCGGTACAGCCCGTGTCCCCGCCCCGCGCCATCG<br>CTAGGCGACGTGCGCTTTTGCCGCGCCGTGCTGCCCGCGA<br>GGGCAGCTGAGGTGGTGGTGGCGGCCGCCTTGTCGAGGCA<br>TCGCGCGCCCGTGAAGTGTTCGCCGTCAGTGCTGTTGGGT<br>GCCTGGAGCCGCGTCCCCCGTCCCGAAAACTGTCCTTGAC<br>AGTACTTGCGCGGCCCAACGGCCGCCGGCGCCCCCGCGTC<br>TCCATGGCGACGGCCTTTTTCCCTGCGAGGACCCCGGCGG<br>CAGGGCTGCCCCGCGGCGCCTGCTTGGCGCGACGCTCTAG<br>CGGTTACCGCTGCGGGCTGGCTGGGCGTAGTGGGGCTGCG<br>CGGCTGCCACGGAGCTAGAGGGCAAGTGTGCTCGGCCCAG<br>CGTGCAGGGAACGCGGGCGGCCAGACAACGGGCTGGGCTC<br>CGGGGCCTGCGGCGCGGGCGCTGAGCTGGCAGGGCGGGTC<br>GGGGCGCGGGCTGCATCCGCATCTCCTCCATCGCCTGCAG<br>TAAGGGCGGCCGCGGCGAGCCTTTGAGGGGAACGACTTGT<br>CGGAGCCCTAACCAGGGGTATCTCTGAGCCTGGTGGGATC<br>CCCGGAGCGTCACATCACTTTCCGATCACTTCAAAGTACA<br>GCAGACCGAGGACACGGTTGTTACCAAGACCAGGCTGTTG<br>CCTTGGAAGAGCCCAGAGCGTGTCAAGGGAGACAGCCACA<br>TCACGCCAGAAATACATGACAGCTGGATTAGCCCTGGGAG<br>AGGGAGGCCCAGATGTGGGAGCTCAGGGGAGGTGCAGCTC<br>AACGTGGAGTTTGGAGGAGGCTACCTTGACCTTTGAATGC<br>CAAGTGGGAGCCAGCCAGATGAAAGGGGTTAAAAACTAAT<br>ATTTATATGACAGAAGAAAAAGATGTCATTCCGTAAAGTA<br>AACATCATCATCTTGGTCCTGGCTGTTGCTCTCTTCTTAC<br>TGGTTTTGCACCATAACTTCCTCAGCTTGAGCAGTTTGTT<br>AAGGAATGAGGTTACAGATTCAGGAATTGTAGGGCCTCAA<br>CCTATAGACTTTGTCCCAAATGCTCTCCGACATGCAGTAG<br>ATGGGAGACAAGAGGAGATTCCTGTGGTCATCGCTGCATC<br>TGAAGACAGGCTTGGGGGGGCCATTGCAGCTATAAACAGC<br>ATTCAGCACAACACTCGCTCCAATGTGATTTTCTACATTG<br>TTACTCTCAACAATACAGCAGACCATCTCCGGTCCTGGCT<br>CAACAGTGATTCCCTGAAAAGCATCAGATACAAAATTGTC<br>AATTTTGACCCTAAACTTTTGGAAGGAAAAGTAAAGGAGG<br>ATCCTGACCAGGGGGAATCCATGAAACCTTTAACCTTTGC<br>AAGGTTCTACTTGCCAATTCTGGTTCCCAGCGCAAAGAAG<br>GCCATATACATGGATGATGATGTAATTGTGCAAGGTGATA<br>TTCTTGCCCTTTACAATACAGCACTGAAGCCAGGACATGC<br>AGCTGCATTTTCAGAAGATTGTGATTCAGCCTCTACTAAA<br>GTTGTCATCCGTGGAGCAGGAAACCAGTACAATTACATTG<br>GCTATCTTGACTATAAAAAGGAAAGAATTCGTAAGCTTTC<br>CATGAAAGCCAGCACTTGCTCATTTAATCCTGGAGTTTTT<br>GTTGCAAACCTGACGGAATGGAAACGACAGAATATAACTA<br>ACCAACTGGAAAAATGGATGAAACTCAATGTAGAAGAGGG<br>ACTGTATAGCAGAACCCTGGCTGGTAGCATCACAACACCT<br>CCTCTGCTTATCGTATTTTATCAACAGCACTCTACCATCG<br>ATCCTATGTGGAATGTCCGCCACCTTGGTTCCAGTGCTGG<br>AAAACGATATTCACCTCAGTTTGTAAAGGCTGCCAAGTTA | 16 |

TABLE 1-continued

GEP-NEN Biomarker/Houskeeper Sequence Information

| Gene Name | RefSeq Accession | Sequence | SEQ ID NO: |
|---|---|---|---|
| | | CTCCATTGGAATGGACATTTGAAGCCATGGGGAAGGACTG<br>CTTCATATACTGATGTTTGGGAAAAATGGTATATTCCAGA<br>CCCAACAGGCAAATTCAACCTAATCCGAAGATATACCGAG<br>ATCTCAAACATAAAGTGAAACAGAATTTGAACTGTAAGCA<br>AGCATTTCTCAGGAAGTCCTGGAAGATAGCATGCGTGGGA<br>AGTAACAGTTGCTAGGCTTCAATGCCTATCGGTAGCAAGC<br>CATGGAAAAAGATGTGTCAGCTAGGTAAAGATGACAAACT<br>GCCCTGTCTGGCAGTCAGCTTCCCAGACAGACTATAGACT<br>ATAAATATGTCTCCATCTGCCTTACCAAGTGTTTTCTTAC<br>TACAATGCTGAATGACTGGAAAGAAGAACTGATATGGCTA<br>GTTCAGCTAGCTGGTACAGATAATTCAAAACTGCTGTTGG<br>TTTTAATTTTGTAACCTGTGGCCTGATCTGTAAATAAAAC<br>TTACATTTTTCAATAGGTAAAAAAAAAAAAAAAA | |
| HDAC9 | NM_001204144.1 | GCAGCGCGCACCGAGCCGGCCGCGCCGCGCCCGCCGCTCT<br>CGCCGCTTTCGCCGCGGTCTCCTCCTCTAGCGCCCGCCGC<br>GGCCGGTAAATCTCGGCTGGAGGAGCAGCGGCGGCCCCCG<br>AGTCAACTTTCATTCCCTTTTTGCTTCTGCCTCACCATTC<br>TCTTCTCCTCCTCGAAAGATGGCTGTTTGGAGAAGGGGGA<br>GAAGTTAAGAGGTCGCCAGCGCGGAGCGAAGGAGGGCGCG<br>ATAGCCTCAGCAGGAGCGGGCGGAGGTTTCTCCTCTGCCA<br>ACCCCTCCTGGACCATTGTCAGCAGTTGAACGACAAAGGC<br>TGTGAATCTGCATCCTAGTCTTAGCAGTCCCTCTGATTCT<br>CATGATGAGCTCACCTGCACAGCCTGACCTCATGTGGAAC<br>CTTGTACCATGGGTGCTATTCTGTGGCTGCTGTAGGATCT<br>TCCCAGATGGGGTGGCTGGACGAGAGCAGCTCTTGGCTCA<br>GCAAAGAATGCACAGTATGATCAGCTCAGTGGATGTGAAG<br>TCAGAAGTTCCTGTGGGCCTGGAGCCCATCTCACCTTTAG<br>ACCTAAGGACAGACCTCAGGATGATGATGCCCGTGGTGGA<br>CCCTGTTGTCCGTGAGAAGCAATTGCAGCAGGAATTACTT<br>CTTATCCAGCAGCAGCAACAAATCCAGAAGCAGCTTCTGA<br>TAGCAGAGTTTCAGAAACAGCATGAGAACTTGACACGGCA<br>GCACCAGGCTCAGCTTCAGGAGCATATCAAGGAACTTCTA<br>GCCATAAAACAGCAACAAGAACTCCTAGAAAAGGAGCAGA<br>AACTGGAGCAGCAGAGGCAAGAACAGGAAGTAGAGAGGCA<br>TCGCAGAGAACAGCAGCTTCCTCCTCTCAGAGGCAAAGAT<br>AGAGGACGAGAAAGGGCAGTGGCAAGTACAGAAGTAAAGC<br>AGAAGCTTCAAGAGTTCCTACTGAGTAAATCAGCAACGAA<br>AGACACTCCAACTAATGGAAAAAATCATTCCGTGAGCCGC<br>CATCCCAAGCTCTGGTACACGGCTGCCCACCACACATCAT<br>TGGATCAAAGCTCTCCACCCCTTAGTGGAACATCTCCATC<br>CTACAAGTACACATTACCAGGAGCACAAGATGCAAAGGAT<br>GATTTCCCCCTTCGAAAAACTGAATCCTCAGTCAGTAGCA<br>GTTCTCCAGGCTCTGGTCCCAGTTCACCAAACAATGGGCC<br>AACTGGAAGTGTTACTGAAAATGAGACTTCGGTTTTGCCC<br>CCTACCCCTCATGCCGAGCAAATGGTTTCACAGCAACGCA<br>TTCTAATTCATGAAGATTCCATGAACCTGCTAAGTCTTTA<br>TACCTCTCCTTCTTTGCCCAACATTACCTTGGGGCTTCCC<br>GCAGTGCCATCCCAGCTCAATGCTTCGAATTCACTCAAAG<br>AAAAGCAGAAGTGTGAGACGCAGACGCTTAGGCAAGGTGT<br>TCCTCTGCCTGGGCAGTATGGAGGCAGCATCCCGGCATCT<br>TCCAGCCACCCTCATGTTACTTTAGAGGGAAAGCCACCCA<br>ACAGCAGCCACCAGGCTCTCCTGCAGCATTTATTATTGAA<br>AGAACAAATGCGACAGCAAAAGCTTCTTGTAGCTGGTGGA<br>GTTCCCTTACATCCTCAGTCTCCCTTGGCAACAAAAGAGA<br>GAATTTCACCTGGCATTAGAGGTACCCACAAATTGCCCCG<br>TCACAGACCCCTGAACCGAACCCAGTCTGCACCTTTGCCT<br>CAGAGCACGTTGGCTCAGCTGGTCATTCAACAGCAACACC<br>AGCAATTCTTGGAGAAGCAGAAGCAATACCAGCAGCAGAT<br>CCACATGAACAAACTGCTTTCGAAATCTATTGAACAACTG<br>AAGCAACCAGGCAGTCACCTTGAGGAAGCAGAGGAAGAGC<br>TTCAGGGGGACCAGGCGATGCAGGAAGACAGAGCGCCCTC<br>TAGTGGCAACAGCACTAGGAGCGACAGCAGTGCTTGTGTG<br>GATGACACACTGGGACAAGTTGGGGCTGTGAAGGTCAAGG<br>AGGAACCAGTGGACAGTGATGAAGATGCTCAGATCCAGGA<br>AATGGAATCTGGGGAGCAGGCTGCTTTTATGCAACAGGTA<br>ATAGGCAAAGATTTAGCTCCAGGATTTGTAATTAAAGTCA<br>TTATCTGAACATGAAATGCATTGCAGGTTTGGTAAATGGA<br>TATGATTTCCTATCAGTTTATATTTCTCTATGATTTGAGT<br>TCAGTGTTTAAGGATTCTACCTAATGCAGATATATGTATA<br>TATCTATATAGAGGTCTTTCTATATACTGATCTCTATATA<br>GATATCAATGTTTCATTGAAAATCCACTGGTAAGGAAATA<br>CCTGTTATACTAAAATTATGATACATAATATCTGAGCAGT<br>TAATAGGCTTTAAATTTATCCCAAAGCCTGCTACACCAAT<br>TACTTCTAAAGAAAACAAATTCACTGTTATTTTGAGTTTA | 17 |

TABLE 1-continued

| GEP-NEN Biomarker/Houskeeper Sequence Information | | | |
|---|---|---|---|
| Gene Name | RefSeq Accession | Sequence | SEQ ID NO: |
| | | TGTGTTGAGATCAGTGACTGCTGGATAGTCTCCCAGTCTG<br>ATCAATGAAGCATTCGATTAGTTTTTGATTTTTTGCAACA<br>TCTAGAATTTAATTTTCACATCACTGTACATAATGTATCA<br>TACTATAGTCTTGAACACTGTTAAAGGTAGTCTGCCCCTT<br>CCTTCCTCTCTCTTTTTTTAGTTAAGTAGAAATGTTCTGG<br>TCACCATGCCAGTAGTCCTAGGTTATTGTGTAGGTTGCAA<br>TTGAACATATTAGGAATACAGGTGGTTTTAAATATATAGA<br>TGCAAATTGCAGCACTACTTTAAATATTAGATTATGTCTC<br>ACATAGCACTGCTCATTTTACTTTTATTTTGTGTAATTTG<br>ATGACACTGTCTATCAAAAAAGAGCAAATGAAGCAGATGC<br>AAATGTTAGTGAGAAGTAATGTGCAGCATTATGGTCCAAT<br>CAGATACAATATTGTGTCTACAATTGCAAAAAACACAGTA<br>ACAGGATGAATATTATCTGATATCAAGTCAAAATCAGTTT<br>GAAAAGAAGGTGTATCATATTTTATATTGTCACTAGAATC<br>TCTTAAGTATAATTCCATAATGACATGGGCATATACCGTA<br>ACATTCTGGCAAATAACAATTAGAAAAGATAGGTTTAACA<br>AAAAAATTTACTTGTATATAATGCACCTTCAGGAGGACTA<br>TGTCCTTTGATGCTATAAAATACAAACAACTTTGAAGGCA<br>ACAGAAGACACTGTTTATTCAAGTCAGTTCTTTGTCAGGT<br>TCCTGCTGTTCTCCTACAGAAAAGTGATTCTGTGAGGGTG<br>AACAGGAAATGCCTTGTGGAAACAGGAAGTCCAAGTGATT<br>CATGTACTGAGGAATGTAGGAAAAAAAATCTGAGGATAGT<br>GCTTTACTCTTTCTGTTTTTAAAGGGCACTCTATGAATTG<br>ATTTATTGTCTAAGAAAATAACACCACAAGTAGGGAAATT<br>GTTACGGAAGCTTTTCACTGGAACATTTCCTTCATATTCC<br>CTTTTGATATGTTTACCTTGTTTTATAGGTTTACTTTTGT<br>TAAGCTAGTTAAAGGTTCGTTGTATTAAGACCCCTTTAAT<br>ATGGATAATCCAAATTGACCTAGAATCTTTGTGAGGTTTT<br>TTCTATTAAAATATTTATATTTCTAAATCCGAGGTATTTC<br>AAGGTGTAGTATCCTATTTCAAAGGAGATATAGCAGTTTT<br>GCCAAATGTAGACATTGTTCAACTGTATGTTATTGGCACG<br>TGTTGTTTACATTTTGCTGTGACATTTAAAAATATTTCTT<br>TAAAAATGTTACTGCTAAAGATACATTATCCTTTTTTAAA<br>AAGTCTCCATTCAAATTAAATTAACATAACTAGAAGTTAG<br>AAAGTTTAAAAGTTTTCCACATAATGAAAGTCCTTCTGAT<br>AATTTGACAAATAGCTATAATAGGAACACTCCCTATCACC<br>AACATATTTTGGTTAGTATATTCCTTCATATTAAAATGAC<br>TTTTTGTCAGTTGTTTTGCATTAAAAATATGGCATGCCTA<br>AGATAAAATTGTATATTTTTTCCATCTCATAAATATTCAT<br>TTTCTTCAAAGTCTTTTTTCAATCTCATAAAAAAGGGATA<br>GTGCATCTTTTAAAATACATTTTATTTGGGGAGGAACATG<br>TGGCTGAGCAGACTTTTGTATAATATTACTTCAAAGATAT<br>GTAATCACAAACAAAAAAAACTATTTTTTATAATGTCATT<br>TGAGAGAGTTTCATCAGTACAGTTGGTGGACGTTAATTGT<br>TTGAATTTGATAGTCTTTGAATTTAATCAAGAAACTACCT<br>GGAACCAGTGAAAAGGAAAGCTGGACTTAAATAATCTTAG<br>AATTAATTGATAAATGTCTCTTTTAAAATCTACTGTATTT<br>ATTATAATTTACACCCTTGAAGGTGATCTCTTGTTTTGTG<br>TTGTAAATATATTGTTTGTATGTTTCCCTTCTTGCCTTCT<br>GTTATAAGTCTCTTCCTTTCTCAAATAAAGTTTTTTTTAA<br>AAGAAAAAAAAAAAAAAAAAAA | |
| HSF2 | NM_004506.3 | ACTTGTCCGTCACGTGCGGCCGCCCGGCCTCTCGGCCTTG<br>CCGCGCGCCTGGCGGGGTTGGGGGGGCGGGGACCAAGATC<br>TGCTGCGCCTGCGTTGTGGGCGTTCTCGGGGAGCTGCTGC<br>CGTAGCTGCCGCCGCCGCTACCACCGCGTTCGGGTGTAGA<br>ATTTGGAATCCCTGCGCCGCGTTAACAATGAAGCAGAGTT<br>CGAACGTGCCGGCTTTCCTCAGCAAGCTGTGGACGCTTGT<br>GGAGGAAACCCACACTAACGAGTTCATCACCTGGAGCCAG<br>AATGGCCAAAGTTTTCTGGTCTTGGATGAGCAACGATTTG<br>CAAAAGAAATTCTTCCCAAATATTTCAAGCACAATAATAT<br>GGCAAGCTTTGTGAGGCAACTGAATATGTATGGTTTCCGT<br>AAAGTAGTACATATCGACTCTGGAATTGTAAAGCAAGAAA<br>GAGATGGTCCTGTAGAATTTCAGCATCCTTACTTCAAACA<br>AGGACAGGATGACTTGTTGGAGAACATTAAAAGGAAGGTT<br>TCATCTTCAAAACCAGAAGAAAATAAAATTCGTCAGGAAG<br>ATTTAACAAAAATTATAAGTAGTGCTCAGAAGGTTCAGAT<br>AAAACAGGAAACTATTGAGTCCAGGCTTTCTGAATTAAAA<br>AGTGAGAATGAGTCCCTTTGGAAGGAGGTGTCAGAATTAC<br>GAGCAAAGCATGCACAACAGCAACAAGTTATTCGAAAGAT<br>TGTCCAGTTTATTGTTACATTGGTTCAAAATAACCAACTT<br>GTGAGTTTAAAACGTAAAAGGCCTCTACTTCTAAACACTA<br>ATGGAGCCCAAAAGAAGAACCTGTTTCAGCACATAGTCAA<br>AGAACCAACTGATAATCATCATCATAAAGTTCCACACAGT<br>AGGACTGAAGGTTTAAAGCCAAGGGAGAGGATTTCAGATG | 18 |

TABLE 1-continued

GEP-NEN Biomarker/Houskeeper Sequence Information

| Gene Name | RefSeq Accession | Sequence | SEQ ID NO: |
|---|---|---|---|
| | | ACATCATTATTTATGATGTTACTGATGATAATGCAGATGA<br>AGAAAATATCCCAGTTATTCCAGAAACTAATGAGGATGTT<br>ATATCTGATCCCTCCAACTGTAGCCAGTACCCTGATATTG<br>TCATCGTTGAAGATGACAATGAAGATGAGTATGCACCTGT<br>CATTCAGAGTGGAGAGCAGAATGAACCAGCCAGAGAATCC<br>CTAAGTTCAGGCAGTGATGGCAGCAGCCCTCTCATGTCTA<br>GTGCTGTCCAGCTAAATGGCTCATCCAGTCTGACCTCAGA<br>AGATCCAGTGACCATGATGGATTCCATTTTGAATGATAAC<br>ATCAATCTTTTGGGAAAGGTTGAGCTGTTGGATTATCTTG<br>ACAGTATTGACTGCAGTTTAGAGGACTTCCAGGCCATGCT<br>ATCAGGAAGACAATTTAGCATAGACCCAGATCTCCTGGTT<br>GATCTTTTCACTAGTTCTGTGCAGATGAATCCCACAGATT<br>ACATCAATAATACAAAATCTGAGAATAAAGGATTAGAAAC<br>TACCAAGAACAATGTAGTTCAGCCAGTTTCGGAAGAGGGA<br>AGAAAATCTAAATCCAAACCAGATAAGCAGCTTATCCAGT<br>ATACCGCCTTTCCACTTCTTGCATTCCTCGATGGGAACCC<br>TGCTTCTTCTGTTGAACAGGCGAGTACAACAGCATCATCA<br>GAAGTTTTGTCCTCTGTAGATAAACCCATAGAAGTTGATG<br>AGCTTCTGGATAGCAGCCTAGACCCAGAACCAACCCAAAG<br>TAAGCTTGTTCGCCTGGAGCCATTGACTGAAGCTGAAGCT<br>AGTGAAGCTACACTGTTTTATTTATGTGAACTTGCTCCTG<br>CACCTCTGGATAGTGATATGCCACTTTTAGATAGCTAAAT<br>CCCCAGGAAGTGGACTTTACATGTATATATTCATCAAAAT<br>GATGAACTATTTATTTTAAAGTATCATTTGGTACTTTTTT<br>TGTAAATTGCTTTGTTTTGTTTAATCAGATACTGTGGAAT<br>AAAAGCACCTTTTGCTTTTCTCACTAACCACACACTCTTG<br>CAGAGCTTTCAGGTGTTACTCAGCTGCATAGTTACGCAGA<br>TGTAATGCACATTATTGGCGTATCTTTAAGTTGGATTCAA<br>ATGGCCATTTTTCTCCAATTTTGGTAAATTGGATATCTTT<br>TTTTTACAAATACGACCATTAACCTCAGTTAAATTTTTGT<br>TTGTTTTCCTGTTTGATGCTGTCTATTTGCATTGAGTGTA<br>AGTCATTTGAACTAATGGTATAACTCCTAAAGCTTTCTCT<br>GCTCCAGTTATTTTTATTAAATATTTTTCACTTGGCTTAT<br>TTTTAAAACTGGGAACATAAAGTGCCTGTATCTTGTAAAA<br>CTTCATTTGTTTCTTTTGGTTCAGAGAAGTTCATTTATGT<br>TCAAAGACGTTTATTCATGTTCAACAGGAAAGACAAAGTG<br>TACGTGAATGCTCGCTGTCTGATAGGGTTCCAGCTCCATA<br>TATATAGAAAGATCGGGGGTGGGATGGGATGGAGTGAGCC<br>CCATCCAGTTAGTTGGACTAGTTTTAAATAAAGGTTTTCC<br>GGTTTGTGTTTTTTTGAACCATACTGTTTAGTAAAATAAA<br>TACAATGAATGTTGAGTACTAGTGTCTGTTATGTGTCTTC<br>TTTAGAGGTGACACTCACATGAAACAATTTTTTCTTCTCA<br>TAGGAAGCAGTAGCTTTAAACTGTCTGTGGTTCATTATTC<br>TCAATATGAATCATACCAAGATATTTGTGCCTCATCTCGA<br>AAATATATTGTATATTG | |
| Ki-67 | NM_001145966.1 | TACCGGGCGGAGGTGAGCGCGGCGCCGGCTCCTCCTGCGG<br>CGGACTTTGGGTGCGACTTGACGAGCGGTGGTTCGACAAG<br>TGGCCTTGCGGGCCGGATCGTCCCAGTGGAAGAGTTGTAA<br>ATTTGCTTCTGGCCTTCCCCTACGGATTATACCTGGCCTT<br>CCCCTACGGATTATACTCAACTTACTGTTTAGAAAATGTG<br>GCCCACGAGACGCCTGGTTACTATCAAAAGGAGCGGGGTC<br>GACGGTCCCCACTTTCCCCTGAGCCTCAGCACCTGCTTGT<br>TTGGAAGGGGTATTGAATGTGACATCCGTATCCAGCTTCC<br>TGTTGTGTCAAAACAACATTGCAAAATTGAAATCCATGAG<br>CAGGAGGCAATATTACATAATTTCAGTTCCACAAATCCAA<br>CACAAGTAAATGGGTCTGTTATTGATGAGCCTGTACGGCT<br>AAAACATGGAGATGTAATAACTATTATTGATCGTTCCTTC<br>AGGTATGAAAATGAAAGTCTTCAGAATGGAAGGAAGTCAA<br>CTGAATTTCCAAGAAAAATACGTGAACAGGAGCCAGCACG<br>TCGTGTCTCAAGATCTAGCTTCTCTTCTGACCCTGATGAG<br>AGTGAGGGAATACCTTTGAAAAGAAGGCGTGTGTCCTTTG<br>GTGGGCACCTAAGACCTGAACTATTTGATGAAAACTTGCC<br>TCCTAATACGCCTCTCAAAAGGGGAGAAGCCCCAACCAAA<br>AGAAAGTCTCTGGTAATGCACACTCCACCTGTCCTGAAGA<br>AAATCATCAAGGAACAGCCTCAACCATCAGGAAAACAAGA<br>GTCAGGTTCAGAAATCCATGTGGAAGTGAAGGCACAAAGC<br>TTGGTTATAAGCCCTCCAGCTCCTAGTCCTAGGAAAACTC<br>CAGTTGCCAGTGATCAACGCCGTAGGTCCTGCAAAACAGC<br>CCCTGCTTCCAGCAGCAAATCTCAGACAGAGGTTCCTAAG<br>AGAGGAGGGAGAAAGAGTGGCAACCTGCCTTCAAAGAGAG<br>TGTCTATCAGCCGAAGTCAACATGATATTTTACAGATGAT<br>ATGTTCCAAAAGAAGAAGTGGTGCTTCGGAAGCAAATCTG<br>ATTGTTGCAAAATCATGGGCAGATGTAGTAAAACTTGGTG<br>CAAAACAAACACAAACTAAAGTCATAAAACATGGTCCTCA | 19 |

TABLE 1-continued

GEP-NEN Biomarker/Houskeeper Sequence Information

| Gene Name | RefSeq Accession | Sequence | SEQ ID NO: |
|---|---|---|---|
| | | AAGGTCAATGAACAAAAGGCAAAGAAGACCTGCTACTCCA<br>AAGAAGCCTGTGGGCGAAGTTCACAGTCAATTTAGTACAG<br>GCCACGCAAACTCTCCTTGTACCATAATAATAGGGAAAGC<br>TCATACTGAAAAAGTACATGTGCCTGCTCGACCCTACAGA<br>GTGCTCAACAACTTCATTTCCAACCAAAAAATGGACTTTA<br>AGGAAGATCTTTCAGGAATAGCTGAAATGTTCAAGACCCC<br>AGTGAAGGAGCAACCGCAGTTGACAAGCACATGTCACATC<br>GCTATTTCAAATTCAGAGAATTTGCTTGGAAAACAGTTTC<br>AAGGAACTGATTCAGGAGAAGAACCTCTGCTCCCCACCTC<br>AGAGAGTTTTGGAGGAAATGTGTTCTTCAGTGCACAGAAT<br>GCAGCAAAACAGCCATCTGATAAATGCTCTGCAAGCCCTC<br>CCTTAAGACGGCAGTGTATTAGAGAAAATGGAAACGTAGC<br>AAAAACGCCCAGGAACACCTACAAAATGACTTCTCTGGAG<br>ACAAAAACTTCAGATACTGAGACAGAGCCTTCAAAAACAG<br>TATCCACTGCAAACAGGTCAGGAAGGTCTACAGAGTTCAG<br>GAATATACAGAAGCTACCTGTGGAAAGTAAGAGTGAAGAA<br>ACAAATACAGAAATTGTTGAGTGCATCCTAAAAAGAGGTC<br>AGAAGGCAACACTACTACAACAAAGGAGAGAAGGAGAGAT<br>GAAGGAAATAGAAAGACCTTTTGAGACATATAAGGAAAAT<br>ATTGAATTAAAAGAAAACGATGAAAAGATGAAAGCAATGA<br>AGAGATCAAGAACTTGGGGGCAGAAATGTGCACCAATGTC<br>TGACCTGACAGACCTCAAGAGCTTGCCTGATACAGAACTC<br>ATGAAAGACACGGCACGTGGCCAGAATCTCCTCCAAACCC<br>AAGATCATGCCAAGGCACCAAAGAGTGAGAAAGGCAAAAT<br>CACTAAAATGCCCTGCCAGTCATTACAACCAGAACCAATA<br>AACACCCCAACACACACAAAACAACAGTTGAAGGCATCCC<br>TGGGGAAAGTAGGTGTGAAAGAAGAGCTCCTAGCAGTCGG<br>CAAGTTCACACGGACGTCAGGGGAGACCACGCACACGCAC<br>AGAGAGCCAGCAGGAGATGGCAAGAGCATCAGAACGTTTA<br>AGGAGTCTCCAAAGCAGATCCTGGACCCAGCAGCCCGTGT<br>AACTGGAATGAAGAAGTGGCCAAGAACGCCTAAGGAAGAG<br>GCCCAGTCACTAGAAGACCTGGCTGGCTTCAAAGAGCTCT<br>TCCAGACACCAGGTCCCTCTGAGGAATCAATGACTGATGA<br>GAAAACTACCAAAATAGCCTGCAAATCTCCACCACCAGAA<br>TCAGTGGACACTCCAACAAGCACAAAGCAATGGCCTAAGA<br>GAAGTCTCAGGAAAGCAGATGTAGAGGAAGAATTCTTAGC<br>ACTCAGGAAACTAACACCATCAGCAGGGAAAGCCATGCTT<br>ACGCCCAAACCAGCAGGAGGTGATGAGAAAGACATTAAAG<br>CATTTATGGGAACTCCAGTGCAGAAACTGGACCTGGCAGG<br>AACTTTACCTGGCAGCAAAAGACAGCTACAGACTCCTAAG<br>GAAAAGGCCCAGGCTCTAGAAGACCTGGCTGGCTTTAAAG<br>AGCTCTTCCAGACTCCTGGTCACACCGAGGAATTAGTGGC<br>TGCTGGTAAAACCACTAAAATACCCTGCGACTCTCCACAG<br>TCAGACCCAGTGGACACCCCAACAAGCACAAAGCAACGAC<br>CCAAGAGAAGTATCAGGAAAGCAGATGTAGAGGGAGAACT<br>CTTAGCGTGCAGGAATCTAATGCCATCAGCAGGCAAAGCC<br>ATGCACACGCCTAAACCATCAGTAGGTGAAGAGAAAGACA<br>TCATCATATTTGTGGGAACTCCAGTGCAGAAACTGGACCT<br>GACAGAGAACTTAACCGGCAGCAAGAGACGGCCACAAACT<br>CCTAAGGAAGAGGCCCAGGCTCTGGAAGACCTGACTGGCT<br>TTAAAGAGCTCTTCCAGACCCCTGGTCATACTGAAGAAGC<br>AGTGGCTGCTGGCAAAACTACTAAAATGCCCTGCGAATCT<br>TCTCCACCAGAATCAGCAGACACCCCAACAAGCACAAGAA<br>GGCAGCCCAAGACACCTTTGGAGAAAAGGGACGTACAGAA<br>GGAGCTCTCAGCCCTGAAGAAGCTCACACAGACATCAGGG<br>GAAACCACACACACAGATAAAGTACCAGGAGGTGAGGATA<br>AAAGCATCAACGCGTTTAGGGAAACTGCAAAACAGAAACT<br>GGACCCAGCAGCAAGTGTAACTGGTAGCAAGAGGCACCCA<br>AAAACTAAGGAAAAGGCCCAACCCCTAGAAGACCTGGCTG<br>GCTTGAAAGAGCTCTTCCAGACACCAGTATGCACTGACAA<br>GCCCACGACTCACGAGAAAACTACCAAAATAGCCTGCAGA<br>TCACAACCAGACCCAGTGGACACACCAACAAGCTCCAAGC<br>CACAGTCCAAGAGAAGTCTCAGGAAAGTGGACGTAGAAGA<br>AGAATTCTTCGCACTCAGGAAACGAACACCATCAGCAGGC<br>AAAGCCATGCACACACCCAAACCAGCAGTAAGTGGTGAGA<br>AAAACATCTACGCATTTATGGGAACTCCAGTGCAGAAACT<br>GGACCTGACAGAGAACTTAACTGGCAGCAAGAGACGGCTA<br>CAAACTCCTAAGGAAAAGGCCCAGGCTCTAGAAGACCTGG<br>CTGGCTTTAAAGAGCTCTTCCAGACACGAGGTCACACTGA<br>GGAATCAATGACTAACGATAAAACTGCCAAAGTAGCCTGC<br>AAATCTTCACAACCAGACCCAGACAAAAACCCAGCAAGCT<br>CCAAGCGACGGCTCAAGACATCCCTGGGGAAAGTGGGCGT<br>GAAAGAAGAGCTCCTAGCAGTTGGCAAGCTCACACAGACA<br>TCAGGAGAGACTACACACACACACACAGAGCCAACAGGAG<br>ATGGTAAGAGCATGAAAGCATTTATGGAGTCTCCAAAGCA | |

TABLE 1-continued

GEP-NEN Biomarker/Houskeeper Sequence Information

| Gene Name | RefSeq Accession | Sequence | SEQ ID NO: |
|---|---|---|---|
| | | GATCTTAGACTCAGCAGCAAGTCTAACTGGCAGCAAGAGG<br>CAGCTGAGAACTCCTAAGGGAAAGTCTGAAGTCCCTGAAG<br>ACCTGGCCGGCTTCATCGAGCTCTTCCAGACACCAAGTCA<br>CACTAAGGAATCAATGACTAACGAAAAAACTACCAAAGTA<br>TCCTACAGAGCTTCACAGCCAGACCTAGTGGACACCCCAA<br>CAAGCTCCAAGCCACAGCCCAAGAGAAGTCTCAGGAAAGC<br>AGACACTGAAGAAGAATTTTTAGCATTTAGGAAACAAACG<br>CCATCAGCAGGCAAAGCCATGCACACACCCAAACCAGCAG<br>TAGGTGAAGAGAAAGACATCAACACGTTTTTGGGAACTCC<br>AGTGCAGAAACTGGACCAGCCAGGAAATTTACCTGGCAGC<br>AATAGACGGCTACAAACTCGTAAGGAAAAGGCCCAGGCTC<br>TAGAAGAACTGACTGGCTTCAGAGAGCTTTTCCAGACACC<br>ATGCACTGATAACCCCACGACTGATGAGAAAACTACCAAA<br>AAAATACTCTGCAAATCTCCGCAATCAGACCCAGCGGACA<br>CCCCAACAAACACAAAGCAACGGCCCAAGAGAAGCCTCAA<br>GAAAGCAGACGTAGAGGAAGAATTTTTAGCATTCAGGAAA<br>CTAACACCATCAGCAGGCAAAGCCATGCACACGCCTAAAG<br>CAGCAGTAGGTGAAGAGAAAGACATCAACACATTTGTGGG<br>GACTCCAGTGGAGAAACTGGACCTGCTAGGAAATTTACCT<br>GGCAGCAAGAGACGGCCACAAACTCCTAAAGAAAAGGCCA<br>AGGCTCTAGAAGATCTGGCTGGCTTCAAAGAGCTCTTCCA<br>GACACCAGGTCACACTGAGGAATCAATGACCGATGACAAA<br>ATCACAGAAGTATCCTGCAAATCTCCACAACCAGACCCAG<br>TCAAAACCCCAACAAGCTCCAAGCAACGACTCAAGATATC<br>CTTGGGGAAAGTAGGTGTGAAAGAAGAGGTCCTACCAGTC<br>GGCAAGCTCACACAGACGTCAGGGAAGACCACACAGACAC<br>ACAGAGAGACAGCAGGAGATGGAAAGAGCATCAAAGCGTT<br>TAAGGAATCTGCAAAGCAGATGCTGGACCCAGCAAACTAT<br>GGAACTGGGATGGAGAGGTGGCCAAGAACACCTAAGGAAG<br>AGGCCCAATCACTAGAAGACCTGGCCGGCTTCAAAGAGCT<br>CTTCCAGACACCAGACCACACTGAGGAATCAACAACTGAT<br>GACAAAACTACCAAAATAGCCTGCAAATCTCCACCACCAG<br>AATCAATGGACACTCCAACAAGCACAAGGAGGCGGCCCAA<br>AACACCTTTGGGGAAAAGGGATATAGTGGAAGAGCTCTCA<br>GCCCTGAAGCAGCTCACACAGACCACACACACAGACAAAG<br>TACCAGGAGATGAGGATAAAGGCATCAACGTGTTCAGGGA<br>AACTGCAAAACAGAAACTGGACCCAGCAGCAAGTGTAACT<br>GGTAGCAAGAGGCAGCCAAGAACTCCTAAGGGAAAAGCCC<br>AACCCCTAGAAGACTTGGCTGGCTTGAAAGAGCTCTTCCA<br>GACACCAATATGCACTGACAAGCCCACGACTCATGAGAAA<br>ACTACCAAAATAGCCTGCAGATCTCCACAACCAGACCCAG<br>TGGGTACCCCAACAATCTTCAAGCCACAGTCCAAGAGAAG<br>TCTCAGGAAAGCAGACGTAGAGGAAGAATCCTTAGCACTC<br>AGGAAACGAACACCATCAGTAGGGAAAGCTATGGACACAC<br>CCAAACCAGCAGGAGGTGATGAGAAAGACATGAAAGCATT<br>TATGGGAACTCCAGTGCAGAAATTGGACCTGCCAGGAAAT<br>TTACCTGGCAGCAAAAGATGGCCACAAACTCCTAAGGAAA<br>AGGCCCAGGCTCTAGAAGACCTGGCTGGCTTCAAAGAGCT<br>CTTCCAGACACCAGGCACTGACAAGCCCACGACTGATGAG<br>AAAACTACCAAAATAGCCTGCAAATCTCCACAACCAGACC<br>CAGTGGACACCCCAGCAAGCACAAAGCAACGGCCCAAGAG<br>AAACCTCAGGAAAGCAGACGTAGAGGAAGAATTTTTAGCA<br>CTCAGGAAACGAACACCATCAGCAGGCAAAGCCATGGACA<br>CACCAAAACCAGCAGTAAGTGATGAGAAAAATATCAACAC<br>ATTTGTGGAAACTCCAGTGCAGAAACTGGACCTGCTAGGA<br>AATTTACCTGGCAGCAAGAGACAGCCACAGACTCCTAAGG<br>AAAAGGCTGAGGCTCTAGAGGACCTGGTTGGCTTCAAAGA<br>ACTCTTCCAGACACCAGGTCACACTGAGGAATCAATGACT<br>GATGACAAAATCACAGAAGTATCCTGTAAATCTCCACAGC<br>CAGAGTCATTCAAAACCTCAAGAAGCTCCAAGCAAAGGCT<br>CAAGATACCCCTGGTGAAAGTGGACATGAAAGAAGAGCCC<br>CTAGCAGTCAGCAAGCTCACACGGACATCAGGGGAGACTA<br>CGCAAACACACACAGAGCCAACAGGAGATAGTAAGAGCAT<br>CAAAGCGTTTAAGGAGTCTCCAAAGCAGATCCTGGACCCA<br>GCAGCAAGTGTAACTGGTAGCAGGAGGCAGCTGAGAACTC<br>GTAAGGAAAAGGCCCGTGCTCTAGAAGACCTGGTTGACTT<br>CAAAGAGCTCTTCTCAGCACCAGGTCACACTGAAGAGTCA<br>ATGACTATTGACAAAAACACAAAAATTCCCTGCAAATCTC<br>CCCCACCAGAACTAACAGACACTGCCACGAGCACAAAGAG<br>ATGCCCCAAGACACGTCCCAGGAAAGAAGTAAAAGAGGAG<br>CTCTCAGCAGTTGAGAGGCTCACGCAAACATCAGGGCAAA<br>GCACACACACACACAAAGAACCAGCAAGCGGTGATGAGGG<br>CATCAAAGTATTGAAGCAACGTGCAAAGAAGAAACCAAAC<br>CCAGTAGAAGAGGAACCCAGCAGGAGAAGGCCAAGAGCAC<br>CTAAGGAAAAGGCCCAACCCCTGGAAGACCTGGCCGGCTT | |

TABLE 1-continued

GEP-NEN Biomarker/Houskeeper Sequence Information

| Gene Name | RefSeq Accession | Sequence | SEQ ID NO: |
|---|---|---|---|
| | | CACAGAGCTCTCTGAAACATCAGGTCACACTCAGGAATCA<br>CTGACTGCTGGCAAAGCCACTAAAATACCCTGCGAATCTC<br>CCCCACTAGAAGTGGTAGACACCACAGCAAGCACAAAGAG<br>GCATCTCAGGACACGTGTGCAGAAGGTACAAGTAAAAGAA<br>GAGCCTTCAGCAGTCAAGTTCACACAAACATCAGGGGAAA<br>CCACGGATGCAGACAAAGAACCAGCAGGTGAAGATAAAGG<br>CATCAAAGCATTGAAGGAATCTGCAAAACAGACACCGGCT<br>CCAGCAGCAAGTGTAACTGGCAGCAGGAGACGGCCAAGAG<br>CACCCAGGGAAAGTGCCCAAGCCATAGAAGACCTAGCTGG<br>CTTCAAAGACCCAGCAGCAGGTCACACTGAAGAATCAATG<br>ACTGATGACAAAACCACTAAAATACCCTGCAAATCATCAC<br>CAGAACTAGAAGACACCGCAACAAGCTCAAAGAGACGGCC<br>CAGGACACGTGCCCAGAAAGTAGAAGTGAAGGAGGAGCTG<br>TTAGCAGTTGGCAAGCTCACACAAACCTCAGGGGAGACCA<br>CGCACACCGACAAAGAGCCGGTAGGTGAGGGCAAAGGCAC<br>GAAAGCATTTAAGCAACCTGCAAAGCGGAAGCTGGACGCA<br>GAAGATGTAATTGGCAGCAGGAGACAGCCAAGAGCACCTA<br>AGGAAAAGGCCCAACCCCTGGAAGATCTGGCCAGCTTCCA<br>AGAGCTCTCTCAAACACCAGGCCACACTGAGGAACTGGCA<br>AATGGTGCTGCTGATAGCTTTACAAGCGCTCCAAAGCAAA<br>CACCTGACAGTGGAAAACCTCTAAAAATATCCAGAAGAGT<br>TCTTCGGGCCCCTAAAGTAGAACCCGTGGGAGACGTGGTA<br>AGCACCAGAGACCCTGTAAAATCACAAAGCAAAAGCAACA<br>CTTCCCTGCCCCCACTGCCCTTCAAGAGGGGAGGTGGCAA<br>AGATGGAAGCGTCACGGGAACCAAGAGGCTGCGCTGCATG<br>CCAGCACCAGAGGAAATTGTGGAGGAGCTGCCAGCCAGCA<br>AGAAGCAGAGGGTTGCTCCCAGGGCAAGAGGCAAATCATC<br>CGAACCCGTGGTCATCATGAAGAGAAGTTTGAGGACTTCT<br>GCAAAAAGAATTGAACCTGCGGAAGAGCTGAACAGCAACG<br>ACATGAAAACCAACAAAGAGGAACACAAATTACAAGACTC<br>GGTCCCTGAAAATAAGGGAATATCCCTGCGCTCCAGACGC<br>CAAAATAAGACTGAGGCAGAACAGCAAATAACTGAGGTCT<br>TTGTATTAGCAGAAAGAATAGAAATAAACAGAAATGAAAA<br>GAAGCCCATGAAGACCTCCCCAGAGATGGACATTCAGAAT<br>CCAGATGATGGAGCCCGGAAACCCATACCTAGAGACAAAG<br>TCACTGAGAACAAAAGGTGCTTGAGGTCTGCTAGACAGAA<br>TGAGAGCTCCCAGCCTAAGGTGGCAGAGGAGAGCGGAGGG<br>CAGAAGAGTGCGAAGGTTCTCATGCAGAATCAGAAAGGGA<br>AAGGAGAAGCAGGAAATTCAGACTCCATGTGCCTGAGATC<br>AAGAAAGACAAAAAGCCAGCCTGCAGCAAGCACTTTGGAG<br>AGCAAATCTGTGCAGAGAGTAACGCGGAGTGTCAAGAGGT<br>GTGCAGAAAATCCAAAGAAGGCTGAGGACAATGTGTGTGT<br>CAAGAAAATAAGAACCAGAAGTCATAGGGACAGTGAAGAT<br>ATTTGACAGAAAAATCGAACTGGGAAAAATATAATAAAGT<br>TAGTTTTGTGATAAGTTCTAGTGCAGTTTTTGTCATAAAT<br>TACAAGTGAATTCTGTAAGTAAGGCTGTCAGTCTGCTTAA<br>GGGAAGAAAACTTTGGATTTGCTGGGTCTGAATCGGCTTC<br>ATAAACTCCACTGGGAGCACTGCTGGGCTCCTGGACTGAG<br>AATAGTTGAACACCGGGGGCTTTGTGAAGGAGTCTGGGCC<br>AAGGTTTGCCCTCAGCTTTGCAGAATGAAGCCTTGAGGTC<br>TGTCACCACCCACAGCCACCCTACAGCAGCCTTAACTGTG<br>ACACTTGCCACACTGTGTCGTCGTTTGTTTGCCTATGTCC<br>TCCAGGGCACGGTGGCAGGAACAACTATCCTCGTCTGTCC<br>CAACACTGAGCAGGCACTCGGTAAACACGAATGAATGGAT<br>GAGCGCACGGATGAATGGAGCTTACAAGATCTGTCTTTCC<br>AATGGCCGGGGGCATTTGGTCCCCAAATTAAGGCTATTGG<br>ACATCTGCACAGGACAGTCCTATTTTTGATGTCCTTTCCT<br>TTCTGAAAATAAAGTTTTGTGCTTTGGAGAATGACTCGTG<br>AGCACATCTTTAGGGACCAAGAGTGACTTTCTGTAAGGAG<br>TGACTCGTGGCTTGCCTTGGTCTCTTGGGAATACTTTTCT<br>AACTAGGGTTGCTCTCACCTGAGACATTCTCCACCCGCGG<br>AATCTCAGGGTCCCAGGCTGTGGGCCATCACGACCTCAAA<br>CTGGCTCCTAATCTCCAGCTTTCCTGTCATTGAAAGCTTC<br>GGAAGTTTACTGGCTCTGCTCCCGCCTGTTTTCTTTCTGA<br>CTCTATCTGGCAGCCCGATGCCACCCAGTACAGGAAGTGA<br>CACCAGTACTCTGTAAAGCATCATCATCCTTGGAGAGACT<br>GAGCACTCAGCACCTTCAGCCACGATTTCAGGATCGCTTC<br>CTTGTGAGCCGCTGCCTCCGAAATCTCCTTTGAAGCCCAG<br>ACATCTTTCTCCAGCTTCAGACTTGTAGATATAACTCGTT<br>CATCTTCATTTACTTTCCACTTTGCCCCCTGTCCTCTCTG<br>TGTTCCCCAAATCAGAGAATAGCCCGCCATCCCCCAGGTC<br>ACCTGTCTGGATTCCTCCCCATTCACCCACCTTGCCAGGT<br>GCAGGTGAGGATGGTGCACCAGACAGGGTAGCTGTCCCCC<br>AAAATGTGCCCTGTGCGGGCAGTGCCCTGTCTCCACGTTT<br>GTTTCCCCAGTGTCTGGCGGGGAGCCAGGTGACATCATAA | |

TABLE 1-continued

GEP-NEN Biomarker/Houskeeper Sequence Information

| Gene Name | RefSeq Accession | Sequence | SEQ ID NO: |
|---|---|---|---|
| | | ATACTTGCTGAATGAATGCAGAAATCAGCGGTACTGACTT<br>GTACTATATTGGCTGCCATGATAGGGTTCTCACAGCGTCA<br>TCCATGATCGTAAGGGAGAATGACATTCTGCTTGAGGGAG<br>GGAATAGAAAGGGGCAGGGAGGGGACATCTGAGGGCTTCA<br>CAGGGCTGCAAAGGGTACAGGGATTGCACCAGGGCAGAAC<br>AGGGGAGGGTGTTCAAGGAAGAGTGGCTCTTAGCAGAGGC<br>ACTTTGGAAGGTGTGAGGCATAAATGCTTCCTTCTACGTA<br>GGCCAACCTCAAAACTTTCAGTAGGAATGTTGCTATGATC<br>AAGTTGTTCTAACACTTTAGACTTAGTAGTAATTATGAAC<br>CTCACATAGAAAAATTTCATCCAGCCATATGCCTGTGGAG<br>TGGAATATTCTGTTTAGTAGAAAAATCCTTTAGAGTTCAG<br>CTCTAACCAGAAATCTTGCTGAAGTATGTCAGCACCTTTT<br>CTCACCCTGGTAAGTACAGTATTTCAAGAGCACGCTAAGG<br>GTGGTTTTCATTTTACAGGGCTGTTGATGATGGGTTAAAA<br>ATGTTCATTTAAGGGCTACCCCCGTGTTTAATAGATGAAC<br>ACCACTTCTACACAACCCTCCTTGGTACTGGGGGAGGGAG<br>AGATCTGACAAATACTGCCCATTCCCCTAGGCTGACTGGA<br>TTTGAGAACAAATACCCACCCATTTCCACCATGGTATGGT<br>AACTTCTCTGAGCTTCAGTTTCCAAGTGAATTTCCATGTA<br>ATAGGACATTCCCATTAAATACAAGCTGTTTTTACTTTTT<br>CGCCTCCCAGGGCCTGTGGGATCTGGTCCCCCAGCCTCTC<br>TTGGGCTTTCTTACACTAACTCTGTACCTACCATCTCCTG<br>CCTCCCTTAGGCAGGCACCTCCAACCACCACACACTCCCT<br>GCTGTTTTCCCTGCCTGGAACTTTCCCTCCTGCCCCACCA<br>AGATCATTTCATCCAGTCCTGAGCTCAGCTTAAGGGAGGC<br>TTCTTGCCTGTGGGTTCCCTCACCCCCATGCCTGTCCTCC<br>AGGCTGGGGCAGGTTCTTAGTTTGCCTGGAATTGTTCTGT<br>ACCTCTTTGTAGCACGTAGTGTTGTGGAAACTAAGCCACT<br>AATTGAGTTTCTGGCTCCCCTCCTGGGGTTGTAAGTTTTG<br>TTCATTCATGAGGGCCGACTGCATTTCCTGGTTACTCTAT<br>CCCAGTGACCAGCCACAGGAGATGTCCAATAAAGTATGTG<br>ATGAAATGGTCTTAAAAAAAAAAAAAA | |
| KRAS | NM_004985.4 | TCCTAGGCGGCGGCCGCGGCGGCGGAGGCAGCAGCGGCGG<br>CGGCAGTGGCGGCGGCGAAGGTGGCGGCGGCTCGGCCAGT<br>ACTCCCGGCCCCCGCCATTTCGGACTGGGAGCGAGCGCGG<br>CGCAGGCACTGAAGGCGGCGGCGGGGCCAGAGGCTCAGCG<br>GCTCCCAGGTGCGGGAGAGAGGCCTGCTGAAAATGACTGA<br>ATATAAACTTGTGGTAGTTGGAGCTGGTGGCGTAGGCAAG<br>AGTGCCTTGACGATACAGCTAATTCAGAATCATTTTGTGG<br>ACGAATATGATCCAACAATAGAGGATTCCTACAGGAAGCA<br>AGTAGTAATTGATGGAGAAACCTGTCTCTTGGATATTCTC<br>GACACAGCAGGTCAAGAGGAGTACAGTGCAATGAGGGACC<br>AGTACATGAGGACTGGGGAGGGCTTTCTTTGTGTATTTGC<br>CATAAATAATACTAAATCATTTGAAGATATTCACCATTAT<br>AGAGAACAAATTAAAAGAGTTAAGGACTCTGAAGATGTAC<br>CTATGGTCCTAGTAGGAAATAAATGTGATTTGCCTTCTAG<br>AACAGTAGACACAAAACAGGCTCAGGACTTAGCAAGAAGT<br>TATGGAATTCCTTTTATTGAAACATCAGCAAAGACAAGAC<br>AGGGTGTTGATGATGCCTTCTATACATTAGTTCGAGAAAT<br>TCGAAAACATAAAGAAAAGATGAGCAAAGATGGTAAAAAG<br>AAGAAAAAGAAGTCAAAGACAAAGTGTGTAATTATGTAAA<br>TACAATTTGTACTTTTTTCTTAAGGCATACTAGTACAAGT<br>GGTAATTTTTGTACATTACACTAAATTATTAGCATTTGTT<br>TTAGCATTACCTAATTTTTTTCCTGCTCCATGCAGACTGT<br>TAGCTTTTACCTTAAATGCTTATTTTAAAATGACAGTGGA<br>AGTTTTTTTTTCCTCTAAGTGCCAGTATTCCCAGAGTTTT<br>GGTTTTTGAACTAGCAATGCCTGTGAAAAAGAAACTGAAT<br>ACCTAAGATTTCTGTCTTGGGGTTTTTGGTGCATGCAGTT<br>GATTACTTCTTATTTTTCTTACCAATTGTGAATGTTGGTG<br>TGAAACAAATTAATGAAGCTTTTGAATCATCCCTATTCTG<br>TGTTTTATCTAGTCACATAAATGGATTAATTACTAATTTC<br>AGTTGAGACCTTCTAATTGGTTTTTACTGAAACATTGAGG<br>GAACACAAATTTATGGGCTTCCTGATGATGATTCTTCTAG<br>GCATCATGTCCTATAGTTTGTCATCCCTGATGAATGTAAA<br>GTTACACTGTTCACAAAGGTTTTGTCTCCTTTCCACTGCT<br>ATTAGTCATGGTCACTCTCCCCAAAATATTATATTTTTTC<br>TATAAAAAGAAAAAAATGGAAAAAAATTACAAGGCAATGG<br>AAACTATTATAAGGCCATTTCCTTTTCACATTAGATAAAT<br>TACTATAAAGACTCCTAATAGCTTTTCCTGTTAAGGCAGA<br>CCCAGTATGAAATGGGGATTATTATAGCAACCATTTTGGG<br>GCTATATTTACATGCTACTAAATTTTTATAATAATTGAAA<br>AGATTTTAACAAGTATAAAAAATTCTCATAGGAATTAAAT<br>GTAGTCTCCCTGTGTCAGACTGCTCTTTCATAGTATAACT<br>TTAAATCTTTTCTTCAACTTGAGTCTTTGAAGATAGTTTT | 20 |

TABLE 1-continued

GEP-NEN Biomarker/Houskeeper Sequence Information

| Gene Name | RefSeq Accession | Sequence | SEQ ID NO: |
|---|---|---|---|
| | | AATTCTGCTTGTGACATTAAAAGATTATTTGGGCCAGTTA | |
| | | TAGCTTATTAGGTGTTGAAGAGACCAAGGTTGCAAGGCCA | |
| | | GGCCCTGTGTGAACCTTTGAGCTTTCATAGAGAGTTTCAC | |
| | | AGCATGGACTGTGTCCCCACGGTCATCCAGTGTTGTCATG | |
| | | CATTGGTTAGTCAAAATGGGGAGGGACTAGGGCAGTTTGG | |
| | | ATAGCTCAACAAGATACAATCTCACTCTGTGGTGGTCCTG | |
| | | CTGACAAATCAAGAGCATTGCTTTTGTTTCTTAAGAAAAC | |
| | | AAACTCTTTTTTAAAAATTACTTTTAAATATTAACTCAAA | |
| | | AGTTGAGATTTTGGGGTGGTGGTGTGCCAAGACATTAATT | |
| | | TTTTTTTTAAACAATGAAGTGAAAAAGTTTTACAATCTCT | |
| | | AGGTTTGGCTAGTTCTCTTAACACTGGTTAAATTAACATT | |
| | | GCATAAACACTTTTCAAGTCTGATCCATATTTAATAATGC | |
| | | TTTAAAATAAAAATAAAAACAATCCTTTTGATAAATTTAA | |
| | | AATGTTACTTATTTTAAAATAAATGAAGTGAGATGGCATG | |
| | | GTGAGGTGAAAGTATCACTGGACTAGGAAGAAGGTGACTT | |
| | | AGGTTCTAGATAGGTGTCTTTTAGGACTCTGATTTTGAGG | |
| | | ACATCACTTACTATCCATTTCTTCATGTTAAAAGAAGTCA | |
| | | TCTCAAACTCTTAGTTTTTTTTTTTTACAACTATGTAATT | |
| | | TATATTCCATTTACATAAGGATACACTTATTTGTCAAGCT | |
| | | CAGCACAATCTGTAAATTTTTAACCTATGTTACACCATCT | |
| | | TCAGTGCCAGTCTTGGGCAAAATTGTGCAAGAGGTGAAGT | |
| | | TTATATTTGAATATCCATTCTCGTTTTAGGACTCTTCTTC | |
| | | CATATTAGTGTCATCTTGCCTCCCTACCTTCCACATGCCC | |
| | | CATGACTTGATGCAGTTTTAATACTTGTAATTCCCCTAAC | |
| | | CATAAGATTTACTGCTGCTGTGGATATCTCCATGAAGTTT | |
| | | TCCCACTGAGTCACATCAGAAATGCCCTACATCTTATTTC | |
| | | CTCAGGGCTCAAGAGAATCTGACAGATACCATAAAGGGAT | |
| | | TTGACCTAATCACTAATTTTCAGGTGGTGGCTGATGCTTT | |
| | | GAACATCTCTTTGCTGCCCAATCCATTAGCGACAGTAGGA | |
| | | TTTTTCAAACCTGGTATGAATAGACAGAACCCTATCCAGT | |
| | | GGAAGGAGAATTTAATAAAGATAGTGCTGAAAGAATTCCT | |
| | | TAGGTAATCTATAACTAGGACTACTCCTGGTAACAGTAAT | |
| | | ACATTCCATTGTTTTAGTAACCAGAAATCTTCATGCAATG | |
| | | AAAAATACTTTAATTCATGAAGCTTACTTTTTTTTTTTGG | |
| | | TGTCAGAGTCTCGCTCTTGTCACCCAGGCTGGAATGCAGT | |
| | | GGCGCCATCTCAGCTCACTGCAACCTCCATCTCCCAGGTT | |
| | | CAAGCGATTCTCGTGCCTCGGCCTCCTGAGTAGCTGGGAT | |
| | | TACAGGCGTGTGCCACTACACTCAACTAATTTTTGTATTT | |
| | | TTAGGAGAGACGGGGTTTCACCCTGTTGGCCAGGCTGGTC | |
| | | TCGAACTCCTGACCTCAAGTGATTCACCCACCTTGGCCTC | |
| | | ATAAACCTGTTTTGCAGAACTCATTTATTCAGCAAATATT | |
| | | TATTGAGTGCCTACCAGATGCCAGTCACCGCACAAGGCAC | |
| | | TGGGTATATGGTATCCCCAAACAAGAGACATAATCCCGGT | |
| | | CCTTAGGTAGTGCTAGTGTGGTCTGTAATATCTTACTAAG | |
| | | GCCTTTGGTATACGACCCAGAGATAACACGATGCGTATTT | |
| | | TAGTTTTGCAAAGAAGGGGTTTGGTCTCTGTGCCAGCTCT | |
| | | ATAATTGTTTTGCTACGATTCCACTGAAACTCTTCGATCA | |
| | | AGCTACTTTATGTAAATCACTTCATTGTTTTAAAGGAATA | |
| | | AACTTGATTATATTGTTTTTTTATTTGGCATAACTGTGAT | |
| | | TCTTTTAGGACAATTACTGTACACATTAAGGTGTATGTCA | |
| | | GATATTCATATTGACCCAAATGTGTAATATTCCAGTTTTC | |
| | | TCTGCATAAGTAATTAAAATATACTTAAAAATTAATAGTT | |
| | | TTATCTGGGTACAAATAAACAGGTGCCTGAACTAGTTCAC | |
| | | AGACAAGGAAACTTCTATGTAAAAATCACTATGATTTCTG | |
| | | AATTGCTATGTGAAACTACAGATCTTTGGAACACTGTTTA | |
| | | GGTAGGGTGTTAAGACTTACACAGTACCTCGTTTCTACAC | |
| | | AGAGAAAGAAATGGCCATACTTCAGGAACTGCAGTGCTTA | |
| | | TGAGGGGATATTTAGGCCTCTTGAATTTTTGATGTAGATG | |
| | | GGCATTTTTTTAAGGTAGTGGTTAATTACCTTTATGTGAA | |
| | | CTTTGAATGGTTTAACAAAAGATTTGTTTTTGTAGAGATT | |
| | | TTAAAGGGGGAGAATTCTAGAAATAAATGTTACCTAATTA | |
| | | TTACAGCCTTAAAGACAAAAATCCTTGTTGAAGTTTTTTT | |
| | | AAAAAAAGCTAAATTACATAGACTTAGGCATTAACATGTT | |
| | | TGTGGAAGAATATAGCAGACGTATATTGTATCATTTGAGT | |
| | | GAATGTTCCCAAGTAGGCATTCTAGGCTCTATTTAACTGA | |
| | | GTCACACTGCATAGGAATTTAGAACCTAACTTTTATAGGT | |
| | | TATCAAAACTGTTGTCACCATTGCACAATTTTGTCCTAAT | |
| | | ATATACATAGAAACTTTGTGGGGCATGTTAAGTTACAGTT | |
| | | TGCACAAGTTCATCTCATTTGTATTCCATTGATTTTTTTT | |
| | | TTCTTCTAAACATTTTTTCTTCAAACAGTATATAACTTTT | |
| | | TTTAGGGGATTTTTTTTTAGACAGCAAAAACTATCTGAAG | |
| | | ATTTCCATTTGTCAAAAAGTAATGATTTCTTGATAATTGT | |
| | | GTAGTAATGTTTTTTAGAACCCAGCAGTTACCTTAAAGCT | |
| | | GAATTTATATTTAGTAACTTCTGTGTTAATACTGGATAGC | |
| | | ATGAATTCTGCATTGAGAAACTGAATAGCTGTCATAAAAT | |

TABLE 1-continued

GEP-NEN Biomarker/Houskeeper Sequence Information

| Gene Name | RefSeq Accession | Sequence | SEQ ID NO: |
|---|---|---|---|
| | | GAAACTTTCTTTCTAAAGAAAGATACTCACATGAGTTCTT<br>GAAGAATAGTCATAACTAGATTAAGATCTGTGTTTTAGTT<br>TAATAGTTTGAAGTGCCTGTTTGGGATAATGATAGGTAAT<br>TTAGATGAATTTAGGGGAAAAAAAAGTTATCTGCAGATAT<br>GTTGAGGGCCCATCTCTCCCCCCACACCCCCACAGAGCTA<br>ACTGGGTTACAGTGTTTTATCCGAAAGTTTCCAATTCCAC<br>TGTCTTGTGTTTTCATGTTGAAAATACTTTTGCATTTTTC<br>CTTTGAGTGCCAATTTCTTACTAGTACTATTTCTTAATGT<br>AACATGTTTACCTGGAATGTATTTTAACTATTTTTGTATA<br>GTGTAAACTGAAACATGCACATTTTGTACATTGTGCTTTC<br>TTTTGTGGGACATATGCAGTGTGATCCAGTTGTTTTCCAT<br>CATTTGGTTGCGCTGACCTAGGAATGTTGGTCATATCAAA<br>CATTAAAAATGACCACTCTTTTAATTGAAATTAACTTTTA<br>AATGTTTATAGGAGTATGTGCTGTGAAGTGATCTAAAATT<br>TGTAATATTTTTGTCATGAACTGTACTACTCCTAATTATT<br>GTAATGTAATAAAAATAGTTACAGTGACTATGAGTGTGTA<br>TTTATTCATGAAATTTGAACTGTTTGCCCCGAAATGGATA<br>TGGAATACTTTATAAGCCATAGACACTATAGTATACCAGT<br>GAATCTTTTATGCAGCTTGTTAGAAGTATCCTTTATTTCT<br>AAAAGGTGCTGTGGATATTATGTAAAGGCGTGTTTGCTTA<br>AACTTAAAACCATATTTAGAAGTAGATGCAAAACAAATCT<br>GCCTTTATGACAAAAAAATAGGATAACATTATTTATTTAT<br>TTCCTTTTATCAAAGAAGGTAATTGATACACAACAGGTGA<br>CTTGGTTTTAGGCCCAAAGGTAGCAGCAGCAACATTAATA<br>ATGGAAATAATTGAATAGTTAGTTATGTATGTTAATGCCA<br>GTCACCAGCAGGCTATTTCAAGGTCAGAAGTAATGACTCC<br>ATACATATTATTTATTTCTATAACTACATTTAAATCATTA<br>CCAGG | |
| LEO1 | NM_138792.3 | CGTAAAGAGAGGCCGGGAGCTGCCCCTAACCGAGGCAGCA<br>GCGGACGTGAGCGATAATGGCGGATATGGAGGATCTCTTC<br>GGGAGCGACGCCGACAGCGAAGCTGAGCGTAAAGATTCTG<br>ATTCTGGATCTGACTCAGATTCTGATCAAGAGAATGCTGC<br>CTCTGGCAGTAATGCCTCTGGAAGTGAAAGTGATCAGGAT<br>GAAAGAGGTGATTCAGGACAACCAAGTAATAAGGAACTGT<br>TTGGAGATGACAGTGAGGACGAGGGAGCTTCACATCATAG<br>TGGTAGTGATAATCACTCTGAAAGATCAGACAATAGATCA<br>GAAGCTTCTGAGCGTTCTGACCATGAGGACAATGACCCCT<br>CAGATGTAGATCAGCACAGTGGATCAGAAGCCCCTAATGA<br>TGATGAAGACGAAGGTCATAGATCGGATGGAGGGAGCCAT<br>CATTCAGAAGCAGAAGGTTCTGAAAAAGCACATTCAGATG<br>ATGAAAAATGGGGCAGAGAAGATAAAAGTGACCAGTCAGA<br>TGATGAAAAGATACAAAATTCTGATGATGAGGAGAGGGCA<br>CAAGGATCTGATGAAGATAAGCTGCAGAATTCTGACGATG<br>ATGAGAAAATGCAGAACACAGATGATGAGGAGAGGCCTCA<br>GCTTTCCGATGATGAGAGACAACAGCTATCTGAGGAGGAA<br>AAGGCTAATTCTGATGATGAACGGCCGGTAGCTTCTGATA<br>ATGATGATGAGAAACAGAATTCTGATGATGAAGAACAACC<br>ACAGCTGTCTGATGAAGAGAAAATGCAAAATTCTGATGAT<br>GAAAGGCCACAGGCCTCAGATGAAGAACACAGGCATTCAG<br>ATGATGAAGAGGAACAGGATCATAAATCAGAATCTGCAAG<br>AGGCAGTGATAGTGAAGATGAAGTTTTACGAATGAAACGC<br>AAGAATGCGATTGCATCTGATTCAGAAGCGGATAGTGACA<br>CTGAGGTGCCAAAAGATAATAGTGGAACCATGGATTTATT<br>TGGAGGTGCAGATGATATCTCTTCAGGGAGTGATGGAGAA<br>GACAAACCACCTACTCCAGGACAGCCTGTTGATGAAAATG<br>GATTGCCTCAGGATCAACAGGAAGAGGAGCCAATTCCTGA<br>GACCAGAATAGAAGTAGAAATACCCAAAGTAAACACTGAT<br>TTAGGAAACGACTTATATTTTGTTAAACTGCCCAACTTTC<br>TCAGTGTAGAGCCCAGACCTTTTGATCCTCAGTATTATGA<br>AGATGAATTTGAAGATGAAGAAATGCTGGATGAAGAAGGT<br>AGAACCAGGTTAAAATTAAAGGTAGAAAATACTATAAGAT<br>GGAGGATACGCCGAGATGAAGAAGGAAATGAAATTAAAGA<br>AAGCAATGCTCGGATAGTCAAGTGGTCAGATGGAAGCATG<br>TCCCTGCATTTAGGCAATGAAGTGTTTGATGTGTACAAAG<br>CCCCACTGCAGGGCGACCACAATCATCTTTTTATAAGACA<br>AGGTACTGGTCTACAGGGACAAGCAGTCTTTAAAACGAAA<br>CTCACCTTCAGACCTCACTCTACGGACAGTGCCACACATA<br>GAAAGATGACTCTGTCACTTGCAGATAGGTGTTCAAAGAC<br>ACAGAAGATTAGAATCTTGCCAATGGCTGGTCGTGATCCT<br>GAATGCCAACGCACAGAAATGATTAAGAAAGAAGAAGAAC<br>GTTTGAGGGCTTCCATACGTAGGGAATCTCAGCAGCGCCG<br>AATGAGAGAGAAACAGCACCAGCGGGGGCTGAGCGCCAGT<br>TACCTGGAACCTGATCGATACGATGAGGAGGAGGAAGGCG<br>AGGAGTCCATCAGCTTGGCTGCCATTAAAAACCGATATAA | 21 |

TABLE 1-continued

GEP-NEN Biomarker/Houskeeper Sequence Information

| Gene Name | RefSeq Accession | Sequence | SEQ ID NO: |
|---|---|---|---|
| | | AGGGGGCATTCGAGAGGAACGAGCCAGAATCTATTCATCA<br>GACAGTGATGAGGGATCAGAAGAAGATAAAGCTCAAAGAT<br>TACTCAAAGCAAAGAAACTTACCAGTGATGAGGAAGGTGA<br>ACCTTCCGGAAAGAGAAAAGCAGAAGATGATGATAAAGCA<br>AATAAAAAGCATAAGAAGTATGTGATCAGCGATGAAGAGG<br>AAGAAGATGATGATTGAAGTATGAAATATGAAAACATTTT<br>ATATATTTTATTGTACAGTTATAAATATGTAAACATGAGT<br>TATTTTGATTGAAATGAATCGATTTGCTTTTGTGTAATTT<br>TAATTGTAATAAAACAATTTAAAAGCAAAAAAAAAAAAAA<br>AA | |
| MORF4L2 | NM_001142418.1 | TTGATTATGGAACATTCTAAAACTTAGACAAGACGATTGT<br>GATTGGCTGAAGGGCATACGCCCTCCTCCAGGGTGACGTG<br>TCTGCCTATGGATATCAGTTGCCAGAGAAACCTGGCTTTA<br>CTATGGCGGTTGGAGGAACGGCAGTGATCACACGTCGGCT<br>GCTGGGAAGATCTGGATTCTCGTTTCAGGTCACCATCAGA<br>AAAGCTAAGTTTGCTGTATAGTGAGGATCAGGAGATCTGA<br>TCCTGATTGCAGAACCTTCCCTGATTACAGAATCTTGGGA<br>TTGTTGAGAGGATTACATGTAAAGTACCAGGACAGTGCAT<br>GGCACATATGATTTCACAAAAGTTCATCTTCATTGCAGAT<br>ACCTGCCTTTCTTTCTAGGTTGTATCTCCCACTTCACCCT<br>TCTAGACCATCCCAGAAGATCTATAAGATTTCATCTGGGA<br>AATCACTAGGAGTTCTTGGAAGGGAAAGAAGGAAGATTGT<br>TGGTTGGAATAAAAACAGGGTTGAATGAGTTCCAGAAAGC<br>AGGGTTCTCAACCTCGTGGACAGCAATCTGCAGAAGAAGA<br>GAACTTCAAAAAACCAACTAGAAGCAACATGCAGAGAAGT<br>AAAATGAGAGGGGCCTCCTCAGGAAAGAAGACAGCTGGTC<br>CACAGCAGAAAAATCTTGAACCAGCTCTCCCAGGAAGATG<br>GGGTGGTCGCTCTGCAGAGAACCCCCCTTCAGGATCCGTG<br>AGGAAGACCAGAAAGAACAAGCAGAAGACTCCTGGAAACG<br>GAGATGGTGGCAGTACCAGCGAAGCACCTCAGCCCCCTCG<br>GAAGAAAAGGGCCCGGGCAGACCCCACTGTTGAAAGTGAG<br>GAGGCGTTTAAGAATAGAATGGAGGTTAAAGTGAAGATTC<br>CTGAAGAATTAAAACCATGGCTTGTTGAGGACTGGGACTT<br>AGTTACCAGGCAGAAGCAGCTGTTTCAACTCCCTGCCAAG<br>AAAAATGTAGATGCAATTCTGGAGGAGTATGCAAATTGCA<br>AGAAATCGCAGGGAAATGTTGATAATAAGGAATATGCGGT<br>TAATGAAGTTGTGGCAGGAATAAAAGAATATTTCAATGTG<br>ATGTTGGGCACTCAGCTGCTCTACAAATTTGAGAGGCCCC<br>AGTATGCTGAAATCCTCTTGGCTCACCCTGATGCTCCAAT<br>GTCCCAGGTTTATGGAGCACCACACCTACTGAGATTATTT<br>GTAAGAATTGGAGCAATGTTGGCCTATACGCCCCTTGATG<br>AGAAAAGCCTTGCATTATTGTTGGGCTATTTGCATGATTT<br>CCTAAAATATCTGGCAAAGAATTCTGCATCTCTCTTTACT<br>GCCAGTGATTACAAAGTGGCTTCTGCTGAGTACCACCGCA<br>AAGCCCTGTGAGCGTCTACAGACAGCTCACCATTTTTGTC<br>CTGTATCTGTAAACACTTTTTGTTCTTAGTCTTTTTCTTG<br>TAAAATTGATGTTCTTTAAAATCGTTAATGTATAACAGGG<br>CTTATGTTTCAGTTTGTTTTCCGTTCTGTTTTAAACAGAA<br>AATAAAAGGAGTGTAAGCTCCTTTTCTCATTTCAAAGTTG<br>CTACCAGTGTATGCAGTAATTAGAACAAAGAAGAAACATT<br>CAGTAGAACATTTTATTGCCTAGTTGACAACATTGCTTGA<br>ATGCTGGTGGTTCCTATCCCTTTGACACTACACAATTTTC<br>TAATATGTGTTAATGCTATGTGACAAAACGCCCTGATTCC<br>TAGTGCCAAAGGTTCAACTTAATGTATATACCTGAAAACC<br>CATGCATTTGTGCTCTTTTTTTTTTTTTATGGTGCTTGAA<br>GTAAAACAGCCCATCCTCTGCAAGTCCATCTATGTTGTTC<br>TTAGGCATTCTATCTTTGCTCAAATTGTTGAAGGATGGTG<br>ATTTGTTTCATGGTTTTTGTATTTGAGTCTAATGCACGTT<br>CTAACATGATAGAGGCAATGCATTATTGTGTAGCCACGGT<br>TTTCTGGAAAAGTTGATATTTTAGGAATTGTATTTCAGAT<br>CTTAAATAAAATTTGTTTCTAAATTTCAAAGCAAAAAAAA<br>AAAAAAA | 22 |
| NAP1L1 | NM_139207.2 | AAAAGATATGGTGGGGTGCTTAACAGAGGAGGTTAGACAC<br>CGGCGGGAACCAGAGGAGCCCAAGCGCGGCGCCTGGGCCT<br>CGGGGCTGCAGGAGTCCTCGGTGGGGGTATGGAGGTCGCC<br>GGGGAAGGAGGACGGTTCAGTTGCTAGGCAACCCGGCCTG<br>GACCCGCCTCTCGCTCGCGTTGCTGGGAGACTACAAGGCC<br>GGGAGGAGGGCGGCGAAAGGGCCCTACGTGCTGACGCTAA<br>TTGTATATGAGCGCGAGCGGCGGGCTCTTGGGTCTTTTTT<br>AGCGCCATCTGCTCGCGGCGCCGCCTCCTGCTCCTCCCGC<br>TGCTGCTGCCGCTGCCGCCCTGAGTCACTGCCTGCGCAGC<br>TCCGGCCGCCTGGCTCCCCATACTAGTCGCCGATATTTGG<br>AGTTCTTACAACATGGCAGACATTGACAACAAAGAACAGT | 23 |

TABLE 1-continued

GEP-NEN Biomarker/Houskeeper Sequence Information

| Gene Name | RefSeq Accession | Sequence | SEQ ID NO: |
|---|---|---|---|
| | | CTGAACTTGATCAAGATTTGGATGATGTTGAAGAAGTAGA | |
| | | AGAAGAGGAAACTGGTGAAGAAACAAAACTCAAAGCACGT | |
| | | CAGCTAACTGTTCAGATGATGCAAAATCCTCAGATTCTTG | |
| | | CAGCCCTTCAAGAAAGACTTGATGGTCTGGTAGAAACACC | |
| | | AACAGGATACATTGAAAGCCTGCCTAGGGTAGTTAAAAGA | |
| | | CGAGTGAATGCTCTCAAAAACCTGCAAGTTAAATGTGCAC | |
| | | AGATAGAAGCCAAATTCTATGAGGAAGTTCACGATCTTGA | |
| | | AAGGAAGTATGCTGTTCTCTATCAGCCTCTATTTGATAAG | |
| | | CGATTTGAAATTATTAATGCAATTTATGAACCTACGGAAG | |
| | | AAGAATGTGAATGGAAACCAGATGAAGAAGATGAGATTTC | |
| | | GGAGGAATTGAAAGAAAAGGCCAAGATTGAAGATGAGAAA | |
| | | AAAGATGAAGAAAAAGAAGACCCCAAAGGAATTCCTGAAT | |
| | | TTTGGTTAACTGTTTTTAAGAATGTTGACTTGCTCAGTGA | |
| | | TATGGTTCAGGAACACGATGAACCTATTCTGAAGCACTTG | |
| | | AAAGATATTAAAGTGAAGTTCTCAGATGCTGGCCAGCCTA | |
| | | TGAGTTTTGTCTTAGAATTTCACTTTGAACCCAATGAATA | |
| | | TTTTACAAATGAAGTGCTGACAAAGACATACAGGATGAGG | |
| | | TCAGAACCAGATGATTCTGATCCCTTTTCTTTTGATGGAC | |
| | | CAGAAATTATGGGTTGTACAGGGTGCCAGATAGATTGGAA | |
| | | AAAAGGAAAGAATGTCACTTTGAAAACTATTAAGAAGAAG | |
| | | CAGAAACACAAGGGACGTGGGACAGTTCGTACTGTGACTA | |
| | | AAACAGTTTCCAATGACTCTTTCTTTAACTTTTTTGCCCC | |
| | | TCCTGAAGTTCCTGAGAGTGGAGATCTGGATGATGATGCT | |
| | | GAAGCTATCCTTGCTGCAGACTTCGAAATTGGTCACTTTT | |
| | | TACGTGAGCGTATAATCCCAAGATCAGTGTTATATTTTAC | |
| | | TGGAGAAGCTATTGAAGATGATGATGATGATTATGATGAA | |
| | | GAAGGTGAAGAAGCGGATGAGGAAGGGGAAGAAGAAGGAG | |
| | | ATGAGGAAAATGATCCAGACTATGACCCAAAGAAGGATCA | |
| | | AAACCCAGCAGAGTGCAAGCAGCAGTGAAGCAGGATGTAT | |
| | | GTGGCCTTGAGGATAACCTGCACTGGTCTACCTTCTGCTT | |
| | | CCCTGGAAAGGATGAATTTACATCATTTGACAAGCCTATT | |
| | | TTCAAGTTATTTGTTGTTTGTTTGCTTGTTTTTGTTTTTG | |
| | | CAGCTAAAATAAAAATTTCAAATACAATTTTAGTTCTTAC | |
| | | AAGATAATGTCTTAATTTTGTACCAATTCAGGTAGAAGTA | |
| | | GAGGCCTACCTTGAATTAAGGGTTATACTCAGTTTTTAAC | |
| | | ACATTGTTGAAGAAAAGGTACCAGCTTTGGAACGAGATGC | |
| | | TATACTAATAAGCAAGTGTAAAAAAAAAAAAAAAAGAGGA | |
| | | AGAAAATCTTAAGTGATTGATGCTGTTTTCTTTTAAAAAA | |
| | | AAAAAAAAAAATTCATTTTCTTTGGGTTAGAGCTAGAGAG | |
| | | AAGGCCCCAAGCTTCTATGGTTTCTTCTAATTCTTATTGC | |
| | | TTAAAGTATGAGTATGTCACTTACCCGTGCTTCTGTTTAC | |
| | | TGTGTAATTAAAATGGGTAGTACTGTTTACCTAACTACCT | |
| | | CATGGATGTGTTAAGGCATATTGAGTTAAATCTCATATAA | |
| | | TGTTTCTCAATCTTGTTAAAAGCTCAAAATTTTGGGCCTA | |
| | | TTTGTAATGCCAGTGTGACACTAAGCATTTTGTTCACACC | |
| | | ACGCTTTGATAACTAAACTGGAAAACAAAGGTGTTAAGTA | |
| | | CCTCTGTTCTGGATCTGGGCAGTCAGCACTCTTTTTAGAT | |
| | | CTTTGTGTGGCTCCTATTTTTATAGAAGTGGAGGGATGCA | |
| | | CTATTTCACAAGGTCCAAGATTTGTTTTCAGATATTTTTG | |
| | | ATGACTGTATTGTAAATACTACAGGGATAGCACTATAGTA | |
| | | TTGTAGTCATGAGACTTAAAGTGGAAATAAGACTATTTTT | |
| | | GACAAAAGATGCCATTAAATTTCAGACTGTAGAGCCACAT | |
| | | TTACAATACCTCAGGCTAATTACTGTTAATTTTGGGGTTG | |
| | | AACTTTTTTTTGACAGTGAGGGTGGATTATTGGATTGTCA | |
| | | TTAGAGGAAGGTCTAGATTTCCTGCTCTTAATAAAATTAC | |
| | | ATTGAATTGATTTTTAGAGGTAATGAAAACTTCCTTTCTG | |
| | | AGAAGTTAGTGTTAAGGTCTTGGAATGTGAACACATTGTT | |
| | | TGTAGTGCTATCCATTCCTCTCCTGAGATTTTAACTTACT | |
| | | ACTGGAAATCCTTAACCAATTATAATAGCTTTTTTTCTTT | |
| | | ATTTTCAAAATGATTTCCTTTGCTTTGATTAGACACTATG | |
| | | TGCTTTTTTTTTTTAACCATAGTTCATCGAAATGCAGCTT | |
| | | TTTCTGAACTTCAAAGATAGAATCCCATTTTTAATGAACT | |
| | | GAAGTAGCAAAATCATCTTTTTCATTCTTTAGGAAATAGC | |
| | | TATTGCCAAAGTGAAGGTGTAGATAATACCTAGTCTTGTT | |
| | | ACATAAAGGGGATGTGGTTTGCAGAAGAATTTTCTTTATA | |
| | | AAATTGAAGTTTTAAGGGACGTCAGTGTTTATGCCATTTT | |
| | | TCCAGTTCCAAAATGATTCCATTCCATTCTAGAAATTTGA | |
| | | AGTATGTAACCTGAAATCCTTAATAAAATTTGGATTTAAT | |
| | | TTTATAAAATGTACTGGTGATATTTTGGGTGTTTTTTTTT | |
| | | AAATGAATGTATATACTTTTTTTTTGAAGAGTGGAGAGTA | |
| | | GTGATGTCTAGAGGGAGCTATTTTGTGCTGAGGCCACTAT | |
| | | GTTCTGTAAATATATAATTTTAAGAGCAACCTCACAATCC | |
| | | CTGCTAAGTGGAGTTTATTATTTGAAGACTAAAATGGAAT | |
| | | TCCATAGTTCCTGATAGGTTATATTCTGGGTTATTATTCT | |
| | | GAGTTATCTACAAACATTTTTGAGATTTGTCTTTACACTC | |

TABLE 1-continued

GEP-NEN Biomarker/Houskeeper Sequence Information

| Gene Name | RefSeq Accession | Sequence | SEQ ID NO: |
|---|---|---|---|
| | | TGATTGTAGTTTCCAGCAGCCCATGCACACTGCCAAGTAA<br>GTCTCATTTTTTCCTGTTAGAAATGGTGAAATATCATATA<br>ATCACTTATAAAGAAAACTGATATGAAAAAATTTTAGAGT<br>TGTTTGCTTTATGGTCACTCAAGTAGGGTAAGTGTTCCAC<br>AAATTCCACAAGTTGATAGTTTAACATGGATGTCTGAAAG<br>CCACATATATAATTTCTTAGGATTCTTAAATTAGTAAATC<br>TAGCTTACTGAAGCAGTATTAGCATCACTATTTTAGATTG<br>CAAAAATACCTTAATTGTGTGGAACTGGCTTGTAGAGTGG<br>TACTTAAGAAAAATGGGATTCTACCTCTATTTCTGTTTTA<br>GCACACTTAATCAGGAAAGGATATATTAACTTTCATAAAA<br>ATATTTTTGTTGTGTGAATAGGTTAATGATATGGTAAGGC<br>CCCTAAAATAACTGAATTAATTGTTTATTGTAATTGTAGG<br>CCATTCCCATTATTAAAAATAAAGACAAAACTTGAAGTAA<br>CTGAAAATCTTATCGTGCTATGTAGAAATATTGAACTAAT<br>ATTCAAATATTTGAATGCTTTGGTTTCAGGGATTGGTTTA<br>AAATTGGAGTCCTTTTTTATGGGTTAGTCTTACAAAAATT<br>TAAGCCTTTATATTTTTGACTTTAAATCAAAACAAATGTT<br>ATTTTAAATGTACAGAATAGATTGGTAGTGCAGAAGAGTG<br>TAAGTTCTTCATAGGAGCTTTAGAAAAGAGAAATATGTGC<br>TAATTCAGTTTTTTTTTAATCTGCACTGTACATATATACT<br>TGGTAATTATGAGCTTGATTTTGTTTTTGGAAATATGTGT<br>TCATAATTTAGGTAATTTGCTACTTAAAGCACTAAGTCTC<br>TGATACCTGAAAAGTACATGTAAATGGTGATGGTGAAATA<br>ATACTGCAGTTAACTTAATAGATGTATACTGGTGATTTTT<br>GTATGCTGGATTAAAACTCCAGATATTAAAATATAACCTG<br>GATAAAAAGCC | |
| NOL3 | NM_001185057.2 | GGCATTCAGAGAGTAGATGCCAGTCCTGGGAAAGGCAGGG<br>GAGGAGAGGAGAGCCACGGCTGACGCTTGGGGACAGAAGG<br>AGGAGCCTGAGGAGGAGACAGGACAGAGCGTCTGGAGAGG<br>CAGGAGGACACCGAGTTCCCCGTGTTGGCCTCCAGGTCCT<br>GTGCTTGCGGAGCCGTCCGGCGGCTGGGATCGAGCCCCGA<br>CAATGGGCAACGCGCAGGAGCGGCCGTCAGAGACTATCGA<br>CCGCGAGCGGAAACGCCTGGTCGAGACGCTGCAGGCGGAC<br>TCGGGACTGCTGTTGGACGCGCTGCTGGCGCGGGGCGTGC<br>TCACCGGGCCAGAGTACGAGGCATTGGATGCACTGCCTGA<br>TGCCGAGCGCAGGGTGCGCCGCCTACTGCTGCTGGTGCAG<br>GGCAAGGGCGAGGCCGCCTGCCAGGAGCTGCTACGCTGTG<br>CCCAGCGTACCGCGGGCGCGCCGGACCCCGCTTGGGACTG<br>GCAGCACGCTACCGGGACCGCAGCTATGACCCTCCATGCC<br>CAGGCCACTGGACGCCGGAGGCACCCGGCTCGGGGACCAC<br>ATGCCCCGGGTTGCCCAGAGCTTCAGACCCTGACGAGGCC<br>GGGGGCCCTGAGGGCTCCGAGGCGGTGCAATCCGGGACCC<br>CGGAGGAGCCAGAGCCAGAGCTGGAAGCTGAGGCCTCTAA<br>AGAGGCTGAACCGGAGCCGGAGCCAGAGCCAGAGCTGGAA<br>CCCGAGGCTGAAGCAGAACCAGAGCCGGAACTGGAGCCAG<br>AACCGGACCCAGAGCCCGAGCCCGACTTCGAGGAAAGGGA<br>CGAGTCCGAAGATTCCTGAAGGCCAGAGCTCTGACAGGCG<br>GTGCCCCGCCCATGCTGGATAGGACCTGGGATGCTGCTGG<br>AGCTGAATCGGATGCCACCAAGGCTCGGTCCAGCCCAGTA<br>CCGCTGGAAGTGAATAAACTCCGGAGGGTCGGACGGGACC<br>TGGGCTCTCTCCACGATTCTGGCTGTTTGCCCAGGAACTT<br>AGGGTGGGTACCTCTGAGTCCCAGGGACCTGGGCAGGCCC<br>AAGCCCACCACGAGCATCATCCAGTCCTCAGCCCTAATCT<br>GCCCTTAGGAGTCCAGGCTGCACCCTGGAGATCCCAAACC<br>TAGCCCCCTAGTGGGACAAGGACCTGACCCTCCTGCCCGC<br>ATACACAACCCATTTCCCCTGGTGAGCCACTTGGCAGCAT<br>ATGTAGGTACCAGCTCAACCCCACGCAAGTTCCTGAGCTG<br>AACATGGAGCAAGGGGAGGGTGACTTCTCTCCACATAGGG<br>AGGGCTTAGAGCTCACAGCCTTGGGAAGTGAGACTAGAAG<br>AGGGGAGCAGAAAGGGACCTTGAGTAGACAAAGGCCACAC<br>ACATCATTGTCATTACTGTTTTAATTGTCTGGCTTCTCTC<br>TGGACTGGGAGCTCAGTGAGGATTCTGACCAGTGACTTAC<br>ACAAAAGGCGCTCTATACATATTATAATATATTCGCTTAC<br>TAAATGAATAAGGACTTTCCAAAAAAAAAAAAAAAAAAAA<br>AAAAAAAAAA | 24 |
| NUDT3 | NM_006703.3 | GGTGCAGCCTTACGCCGCTGACGCATCGCGCCCAAGATGG<br>CGGCGCGGTCGTCGTCGGGGGTGGCGGCGGCAGAGGGGGC<br>GGCGGCCCTGGCGGCAGCGGAGACGGCAGCCGTGACGGTG<br>GCAGCGGCGGCGCGGGACCTGGGCCTGGGGGAATGAGGCG<br>GCCGCGGCGGGCCAGCGGCGGAGCCGTGTAGCGGAGAAGC<br>TCCCCCTCCCTGCTTCCCTTGGCCGAGCCGGGGGCGCGCG<br>CGCACGCGGCCGTCCAGAGCGGGCTCCCCACCCCTCGACT<br>CCTGCGACCCGCACCGCACCCCCACCCGGGCCCGGAGGAT | 25 |

TABLE 1-continued

GEP-NEN Biomarker/Houskeeper Sequence Information

| Gene Name | RefSeq Accession | Sequence | SEQ ID NO: |
|---|---|---|---|
| | | GATGAAGCTCAAGTCGAACCAGACCCGCACCTACGACGGC<br>GACGGCTACAAGAAGCGGGCCGCATGCCTGTGTTTCCGCA<br>GCGAGAGCGAGGAGGAGGTGCTACTCGTGAGCAGTAGTCG<br>CCATCCAGACAGATGGATTGTCCCTGGAGGAGGCATGGAG<br>CCCGAGGAGGAGCCAAGTGTGGCAGCAGTTCGTGAAGTCT<br>GTGAGGAGGCTGGAGTAAAAGGGACATTGGGAAGATTAGT<br>TGGAATTTTTGAGAACCAGGAGAGGAAGCACAGGACGTAT<br>GTCTATGTGCTCATTGTCACTGAAGTGCTGGAAGACTGGG<br>AAGATTCAGTTAACATTGGAAGGAAGAGGGAATGGTTTAA<br>AATAGAAGACGCCATAAAAGTGCTGCAGTATCACAAACCC<br>GTGCAGGCATCATATTTTGAAACATTGAGGCAAGGCTACT<br>CAGCCAACAATGGCACCCCAGTCGTGGCCACCACATACTC<br>GGTTTCTGCTCAGAGCTCGATGTCAGGCATCAGATGACTG<br>AAGACTTCCTGTAAGAGAAATGGAAATTGGAAACTAGACT<br>GAAGTGCAAATCTTCCCTCTCACCCTGGCTCTTTCCACTT<br>CTCACAGGCCTCCTCTTTCAAATAAGGCATGGTGGGCAGC<br>AAAGAAAGGGTGTATTGATAATGTTGCTGTTTGGTGTTAA<br>GTGATGGGGCTTTTTCTTCTGTTTTTATTGAGGGTGGGGG<br>TTGGGTGTGTAATTTGTAAGTACTTTTGTGCATGATCTGT<br>CCCTCCCTCTTCCCACCCCTGCAGTCCTCTGAAGAGAGGC<br>CAACAGCCTTCCCCTGCCTTGGATTCTGAAGTGTTCCTGT<br>TTGTCTTATCCTGGCCCTGGCCAGACGTTTTCTTTGATTT<br>TTAATTTTTTTTTTTTATTAAAAGATACCAGTATGAGATG<br>AAAACTTCCAATAATTTGTCCTATAATGTGCTGTACAGTT<br>CAGTAGAGTGGTCACTTTCACTGCAGTATACATTTATCTA<br>CACATTATATATCGGACATATAATATGTAAATAAATGACT<br>TCTAGAAAGAGAAATTTGTTTAATTTTTCAAGGTTTTTTT<br>CTCTTTTAATTTGGGCATTTCTAGAATTGAGAGCCTCACA<br>ATTAACATACCTTTTTGTTTTCGATGCTAGTGGCTGGGCA<br>GGTTGCCCTGTCCTTTCTCTATTTCCCAGTCATTGACTGT<br>AGATATGGGAAGAGTTTAGCTACCTTCATAGTGCTCCCAG<br>GACTCATGGCCTTTCCTTCTTTAAGCTGTATTTCCCTGCC<br>CAGAAAGAAACAGGAAGAAACCTTTTTTTATTTTTTTATT<br>TTTTTTTAACCAAGCAAGGAGCAAATGGCCTCAGCCCAGA<br>TCTGTAAAAACAATGATAGAAATTGAATTCTGCCCCACAT<br>GTTGACAGTAGAGTTGGAACTGGATTCTTGGGATTACTTA<br>TCTAAAAAACTGGAGCATCAGGTCCATTTCTGTTCTGCTG<br>GTTTGGAATCTTTTCCGTAATGCTATTTATTGCCAACAAT<br>GGCCTCTCTTTGTGTCCATATATGCCTTACACCGTGCTGA<br>CCTGGGTATCATCCATGTGCTCTGAAGCATCCAACTTTAC<br>TTTGCAGGTGCATCAATGTAGTCCTGTCCCTGAACTGAGT<br>AACCGTGTTCCTGAAAAGTACACTAGGGAAATTCACCTGC<br>TTGCTTGTCTTTGTATTGGCATGGCACTTGTGATTGCACC<br>ATGGAGCATGCTCAGAGCTATTAAATTGGTCTCCCATCTC<br>CCACCAGGATATGAAAGGTCCATATGGGAGGCCACGTAAT<br>CACTTATTACAGTGGTTACATAATACACTGGCTCACTGCA<br>GACTCTCTTGTTTTTTGATACAGTTTCGTGCTGGCTTCAT<br>TTGCCAATTGTGTTGTTTAGTTCGGAAGTAAGAGGGTCTT<br>GAGATTGAGGGGTAGGGAGGGCTACACTGACTGATCCGTG<br>GCTTAAGACAGGAGATTATCTCTGTACTCCAGTGGCATCT<br>CCTTAGCCAAGATGTGAAATTAAAATCATAGTTCGCCTCA<br>TTTAAAAATTCTAATAAAGCACTCAAACTTTGAAAAAAAA<br>AAAAAAAAAA | |
| OAZ2 | NM_002537.3 | ATGCAGATGAGGCACTCGGGGGCGGGGCGGCGGCGGCGGC<br>GGCGGCGGTGGCGGCCGGGGAGGGTCAGTTGGAGGCAGGC<br>GCTCGCTGAGGCAAAAGGAGGCGCTCGGCCCGCGGCCTGA<br>CAGGGACTTAGCCCGCAGAGATCGACCCCGCGCGCGTGAC<br>CCCACACCCACCCACTCATCCATCTATCCACTCCCTGCGC<br>CGCCTCCTCCCACCCTGAGCAGAGCCGCCGAGGATGATAA<br>ACACCCAGGACAGTAGTATTTTGCCTTTGAGTAACTGTCC<br>CCAGCTCCAGTGCTGCAGGCACATTGTTCCAGGGCCTCTG<br>TGGTGCTCCTGATGCCCCTCACCCACTGTCGAAGATCCCC<br>GGTGGGCGAGGGGGCGGCAGGGATCCTTCTCTCTCAGCTC<br>TAATATATAAGGACGAGAAGCTCACTGTGACCCAGGACCT<br>CCCTGTGAATGATGGAAAACCTCACATCGTCCACTTCCAG<br>TATGAGGTCACCGAGGTGAAGGTCTCTTCTTGGGATGCAG<br>TCCTGTCCAGCCAGAGCCTGTTTGTAGAAATCCCAGATGG<br>ATTATTAGCTGATGGGAGCAAAGAAGGATTGTTAGCACTG<br>CTAGAGTTTGCTGAAGAGAAGATGAAAGTGAACTATGTCT<br>TCATCTGCTTCAGGAAGGGCCGAGAAGACAGAGCTCCACT<br>CCTGAAGACCTTCAGCTTCTTGGGCTTTGAGATTGTACGT<br>CCAGGCCATCCCTGTGTCCCCTCTCGGCCAGATGTGATGT<br>TCATGGTTTATCCCCTGGACCAGAACTTGTCCGATGAGGA<br>CTAATAGTCATAGAGGATGCTTTACCCAAGAGCCACAGTG | 26 |

TABLE 1-continued

| GEP-NEN Biomarker/Houskeeper Sequence Information | | | |
|---|---|---|---|
| Gene Name | RefSeq Accession | Sequence | SEQ ID NO: |
| | | GGGGAAGAGGGGAAGTTAGGCAGCCCTGGGACAGACGAGA<br>GGGCTCCTCGCTGTCTAGGGAAGGACACTGAGGGGCTCAG<br>GGTGAGGGTTGCCTATTGTGTTCTCGGAGTTGACTCGTTG<br>AAATTGTTTTCCATAAAGAACAGTATAAACATATTATTCA<br>CATGTAATCACCAATAGTAAATGAAGATGTTTATGAACTG<br>GCATTAGAAGCTTTCTAAACTGCGCTGTGTGATGTGTTCT<br>ATCTAGCCTAGGGGAGGACATTGCCTAGAGGGGGAGGGAC<br>TGTCTGGGTTCAGGGGCATGGCCTGGAGGGCTGGTGGGCA<br>GCACTGTCAGGCTCAGGTTTCCCTGCTGTTGGCTTTCTGT<br>TTTGGTTATTAAGACTTGTGTATTTTCTTTCTTTGCTTCC<br>TGTCACCCCAGGGGCTCCTGAGTATAGGCTTTTCAGTCCC<br>TGGGCAGTGTCCTTGAGTTGTTTTTTGACACTCTTACCTG<br>GGCTTCTCTGTGTGCATTTGCGTCTGGCCTGGAGTAAGCA<br>GGTCCGACCCCTCCTTCTTTACAGCTTAGTGTTATTCTGG<br>CATTTGGTTAAGCTGGCTTAATCTGTTTAATGTTATCAGT<br>ACATTTTAAATAGGGGCATTGAAATTTACTCCCACCACCA<br>GGGCTTTTTTGGGGGATGCCTGGGCCTTTAAAACACTAGC<br>CAAACTCTAATTAATTCTCAAATCACTGCCAGGAGTTCTT<br>GCTCCTGGCTGCAGGCCCAGGCCCCAAGGTCTCCTTCTTG<br>GGGTCACAAACAGCAGTAAGGAAGAGGAATATATAGCAAC<br>TCAGGGCCTGGGAATTGTGGGGCAATCCGTTCTTAGGGAC<br>TGGATACTTCTGGCTGGCTGAGTATAGTACTAGCTGCCTC<br>CCCACCAGGTTCCGAGTAGTGTCTGAGACTCTGCTCTGCA<br>GGGCCTAGGGTAGCGCTGGGAGTGTAGAAGTGGCCTGCCC<br>TTAACTGTTTTCACTAAACAGCTTTTTCTAAGGGGAGAGC<br>AAGGGGGAGAGATCTAGATTGGGTGAGGGGGACGGGGATG<br>TCAGGGAGGCAAGTGTGTTGTGTTACTGTGTCAATAAACT<br>GATTTAAAGTTGTGAAAAAAAAAAAAA | |
| PANK2 | NM_024960.4 | ATGCTGGGGGAGGGGCTGGCGGCCTCGACGGCAGCTGCGG<br>AACTAGGCCGAGGGACAAAGGCTAAGTTTTTCCATGGTTT<br>GGACTGGATATCGGTGGAACTCTGGTCAAGCTGGTATATT<br>TTGAACCCAAAGACATCACTGCTGAAGAAGAAGAGGAAGA<br>AGTGGAAAGTCTTAAAAGCATTCGGAAGTACCTGACCTCC<br>AATGTGGCTTATGGGTCTACAGGCATTCGGGACGTGCACC<br>TCGAGCTGAAGGACCTGACTCTGTGTGGACGCAAAGGCAA<br>TCTGCACTTTATACGCTTTCCCACTCATGACATGCCTGCT<br>TTTATTCAAATGGGCAGAGATAAAAACTTCTCGAGTCTCC<br>ACACTGTCTTTTGTGCCACTGGAGGTGGAGCGTACAAATT<br>TGAGCAGGATTTTCTCACAATAGGTGATCTTCAGCTTTGC<br>AAACTGGATGAACTAGATTGCTTGATCAAAGGAATTTTAT<br>ACATTGACTCAGTCGGATTCAATGGACGGTCACAGTGCTA<br>TTACTTTGAAAACCCTGCTGATTCTGAAAAGTGTCAGAAG<br>TTACCATTTGATTTGAAAAATCCGTATCCTCTGCTTCTGG<br>TGAACATTGGCTCAGGGGTTAGCATCTTAGCAGTATATTC<br>CAAAGATAATTACAAACGGGTCACAGGTACTAGTCTTGGA<br>GGAGGAACTTTTTTTGGTCTCTGCTGTCTTCTTACTGGCT<br>GTACCACTTTTGAAGAAGCTCTTGAAATGGCATCTCGTGG<br>AGATAGCACCAAAGTGGATAAACTAGTACGAGATATTTAT<br>GGAGGGGACTATGAGAGGTTTGGACTGCCAGGCTGGGCTG<br>TGGCTTCAAGCTTTGGAAACATGATGAGCAAGGAGAAGCG<br>AGAGGCTGTCAGTAAAGAGGACCTGGCCAGAGCGACTTTG<br>ATCACCATCACCAACAACATTGGCTCAATAGCAAGAATGT<br>GTGCCCTTAATGAAAACATTAACCAGGTGGTATTTGTTGG<br>AAATTTCTTGAGAATTAATACGATCGCCATGCGGCTTTTG<br>GCATATGCTTTGGATTATTGGTCCAAGGGGCAGTTGAAAG<br>CACTTTTTTCGGAACACGAGGGTTATTTTGGAGCTGTTGG<br>AGCACTCCTTGAGCTGTTGAAGATCCCGTGATCATTACCT<br>GGGGAGGGGTTCCTGAAACCTTCCACAATGGGATCTGTGG<br>ACTTTCATTTTTTTAAGAGACTTACTCAATTTCATGACTG<br>TACTACCTGAAACAAAGTGAGAAAGGACAGGTGTATTTTT<br>CTAAGTCATCAAGATAAATCCTTAAGAATTCAGTCTAAAT<br>TAGCAACCAGGAAGGAAAAATATATTAAAAACAACAAAAA<br>AGTGGCACATGTCCAGGCAGTGTGAGGATTTGCTGTATAT<br>AAGTTGCCTGCTTTGTATTTTTGAAATCTCTGCATCACTC<br>ATTGGAAGTGCTTCTGAAGAGAGCTGCTCTGTGTTCAGTT<br>GACTGGTTTTGTGTCCTGTTTGAACTTGCTGAATGTAAGG<br>CAGGCTACTATGCGTTATAATCTAATCACAATTTGTCAAT<br>ATGGTCTTGGCAATCATCTGTGCATTACTCTGGTTTGCAT<br>TAAGCCTGTGTGTGAACTTACTGTAAAACATGTTTTATTT<br>CAAGGTTCTGCAAAATTAATTGGGCAGGTTAATTGTGTAC<br>CTGAAACTTAACAAGCAGTTTTTGGAAGGGCA | 27 |
| PHF21A | NM_001101802.1 | GGTGAATGGGCTGGTGGTGCTCGCTGCTGCTGCTGAGAGG<br>AGGAGGAGGATGAAGAGTTGGGCTTGTTTGTCTCCTACAG | 28 |

TABLE 1-continued

GEP-NEN Biomarker/Houskeeper Sequence Information

| Gene Name | RefSeq Accession | Sequence | SEQ ID NO: |
|---|---|---|---|
| | | TTTCTCTCCTGCTGCTCTGATTCCCCCCTCCCGATTCCGG | |
| | | CCCGGGGCCTGTGTGTGTCCCTCCTGGAGGAGGAGGAGGA | |
| | | TCCAGTTCCTCCCCCCAACCCCCTCCTCCCCACCCCCCCT | |
| | | TGCCTGGGGAAGAGGAGGAAAGAAACAGCCCAGAGAGAGA | |
| | | GAGAGAGAGAGAGTGAGTGAGAGAGAGAGGAGAGGAGAGG | |
| | | AGGAGGAGGAGGAGGGAGAAGGGAACAACCTACCATCTTA | |
| | | ACACACTAATATCTAAAAAGTGCGAGAGGCCCAGAGCAGC | |
| | | AGCAGAAGCAGCAGCAGCAGCTCCAGCTTCTTCCCTCCCT | |
| | | CCCCATGAAGAAGAGTTCCCTCCTCCTCCTCCTCCTGCTT | |
| | | CTCCTGCTCAGAGTTCCTGCCTCCAGCTGCCAGGGGGGAC | |
| | | AGCCAGCCAGCAGCAGGAGGGGGGCTAGAGAGCTGAAGGA | |
| | | GAGCCAGTTTCCCCAAAATTGCTGCAGTGAGAAGAGGAGT | |
| | | TTGTTACTTTAAACAGAGGCTGAAGAAACTATAGAATTAG | |
| | | CAGAGAAAGTGGAGAAGGTAGAGGATGGAGTTGCAGACTC | |
| | | TACAGGAGGCTCTTAAAGTGGAAATTCAGGTTCACCAGAA | |
| | | ACTGGTTGCTCAAATGAAGCAGGATCCACAGAATGCTGAC | |
| | | TTAAAGAAACAGCTTCATGAACTCCAAGCCAAAATCACAG | |
| | | CTTTGAGTGAGAAACAGAAAAGAGTAGTTGAACAGCTACG | |
| | | GAAGAACCTGATAGTAAAGCAAGAACAACCGGACAAGTTC | |
| | | CAAATACAGCCATTGCCACAATCTGAAAACAAACTACAAA | |
| | | CAGCACAGCAGCAACCACTACAGCAACTACAACAACAGCA | |
| | | GCAGTACCACCACCACCACGCCCAGCAGTCAGCTGCAGCC | |
| | | TCTCCCAACCTGACTGCTTCACAGAAGACTGTAACTACAG | |
| | | CTTCTATGATTACCACAAAGACACTACCTCTCGTCTTGAA | |
| | | AGCAGCAACTGCGACCATGCCTGCCTCTGTGGTGGGCCAG | |
| | | AGACCTACCATTGCTATGGTGACCGCCATCAACAGTCAGA | |
| | | AGGCTGTGCTCAGCACTGATGTGCAGAACACACCAGTCAA | |
| | | CCTCCAGACGTCTAGTAAGGTCACTGGGCCTGGGGCAGAG | |
| | | GCTGTCCAAATTGTGGCAAAAAACACAGTCACTCTGGTTC | |
| | | AGGCAACACCTCCTCAGCCCATCAAAGTACCACAGTTTAT | |
| | | CCCCCCTCCTAGACTCACTCCACGTCCAAACTTTCTTCCA | |
| | | CAGGTTCGACCCAAGCCTGTGGCCCAGAATAACATTCCTA | |
| | | TTGCCCCAGCACCACCTCCCATGCTCGCAGCTCCTCAGCT | |
| | | TATCCAGAGGCCCGTCATGCTGACCAAGTTCACCCCCACA | |
| | | ACCCTTCCCACATCCCAGAATTCCATCCACCCCGTCCGTG | |
| | | TCGTCAATGGGCAGACTGCAACCATAGCCAAAACGTTCCC | |
| | | CATGGCCCAGCTCACCAGCATTGTGATAGCTACTCCAGGG | |
| | | ACCAGACTCGCTGGACCTCAAACTGTACAGCTTAGCAAGC | |
| | | CAAGTCTTGAAAAACAGACAGTTAAATCTCACACAGAAAC | |
| | | AGATGAGAAACAAACAGAGAGCCGCACCATCACCCCACCT | |
| | | GCTGCACCCAAACCAAAACGGGAGGAGAACCCTCAGAAAC | |
| | | TTGCCTTCATGGTGTCTCTAGGGTTGGTAACACATGACCA | |
| | | TCTAGAAGAAATCCAAAGCAAGAGGCAAGAGCGAAAAAGA | |
| | | AGAACAACAGCAAATCCGGTCTACAGTGGAGCAGTCTTTG | |
| | | AGCCAGAGCGTAAGAAGAGTGCAGTGACATACCTAAACAG | |
| | | CACAATGCACCCTGGGACCCGGAAGAGAGGTCGTCCTCCA | |
| | | AAATACAATGCAGTGCTGGGGTTTGGAGCCCTTACCCCAA | |
| | | CATCCCCCCAATCCAGTCATCCTGACTCCCCTGAAAATGA | |
| | | AAAGACAGAGACCACATTCACTTTCCCTGCACCTGTTCAG | |
| | | CCTGTGTCCCTGCCCAGCCCCACCTCCACAGACGGTGATA | |
| | | TTCATGAGGATTTTTGCAGCGTTTGCAGAAAAAGTGGCCA | |
| | | GTTACTGATGTGCGACACATGTTCCCGTGTATATCATTTG | |
| | | GACTGCTTAGACCCCCCTCTGAAAACAATTCCCAAGGGCA | |
| | | TGTGGATCTGTCCCAGATGTCAGGACCAGATGCTGAAGAA | |
| | | GGAAGAAGCAATTCCATGGCCTGGAACTTTAGCAATTGTT | |
| | | CATTCCTATATTGCCTACAAAGCAGCAAAAGAAGAAGAGA | |
| | | AACAGAAGTTACTTAAATGGAGTTCAGATTTAAAACAAGA | |
| | | ACGAGAACAACTAGAGCAAAAGGTGAAACAGCTCAGCAAT | |
| | | TCCATAAGTAAATGCATGGAAATGAAGAACACCATCCTGG | |
| | | CCCGGCAGAAGGAGATGCACAGCTCCCTGGAGAAGGTAAA | |
| | | ACAGCTGATTCGCCTCATCCACGGCATCGACCTCTCCAAA | |
| | | CCTGTAGACTCTGAGGCCACTGTGGGGGCCATCTCCAATG | |
| | | GCCCGGACTGCACCCCCCCTGCCAATGCCGCCACCTCCAC | |
| | | GCCGGCCCCTTCCCCCTCCTCCCAGAGCTGCACAGCGAAC | |
| | | TGTAACCAGGGGGAAGAGACTAAATAACAGAGCCCCTCTA | |
| | | GGAGAAGCCACGGGATCCCGGCGGCAAGGAGAACAGAACA | |
| | | CTGAAGACTCTAGAAAAGCAAAGCCGGATTTCTGGAAAGT | |
| | | GCAGAATTCTTTTGGTTCTTTGGTTCCAGAGAGAGAGAAG | |
| | | ATGCTTGTGCCAGGTGGCACCAGAGTTTGCCAATTGATCC | |
| | | TTCTTATTCTGTGTGTACATGCAAAGATTGGACCATGTTA | |
| | | CATGAAATAGTGCCAGCTGGAGGTTCTTTGCCAGCACCAT | |
| | | GCCAAGTGAAATAATATATTTACTCTCTCTATTATACACC | |
| | | AGTGTGTGCCTGCAGCAGCCTCCACAGCCACGATGGGTTT | |
| | | GTTTCTGTTTTCTTGGGTGGGGAGCAGGGACGGGCGGAGG | |
| | | GAGGAGAGCAGGTTTCAGATCCTTACTTGCCGAGCCGTTT | |

TABLE 1-continued

GEP-NEN Biomarker/Houskeeper Sequence Information

| Gene Name | RefSeq Accession | Sequence | SEQ ID NO: |
|---|---|---|---|
| | | GTTTAGGTAGAGAAGACAAGTCCAAAGAGTGTGTGGGCTT | |
| | | TCCTGTTTCTAAACTTTCGCTACTATAAAACCAAAAAAAG | |
| | | GAATTGAGATTTCACCAACCCCAGTGCCCAGAAGAGGGAA | |
| | | GGGGAGTGGCTGGAGGGAGCAGGGGGTGGGACAGTGTATC | |
| | | AAATAAGCAGTATTTAATCACCTCTGGCGGGGGCCTCGTG | |
| | | CAAGGGGAGACTGACACCAAGAACAGCCAGTAGGTTCTTC | |
| | | TCCCCTGCACTCTGCTCCCTGCGCGGTAACCCCACCACTC | |
| | | CTGAAGCCTGCCCAGTCTCCTTCCTTCCCTGCTTGGTGAG | |
| | | TCGCGCATCTCCGTGGTTATCCCGCTGTCTCCTCTCCAAG | |
| | | AACAAGCAGAGCCCGGGCCACTGGCCCTTGCCCAAGGCAG | |
| | | GGAAGAAGGATGTGTGTGTCCAGGAAGGAAAAAAAGGTGG | |
| | | ATCAGTGATTTTACTTGAAAACAAGCTCCATCCCTTTTCT | |
| | | ATATTTATAAGAAGAGAAGATCTTGAGTGAAGCAGCACGC | |
| | | GACCCAGGTGTGTGTGAATTGAATGGAGACGTTTCTTTTC | |
| | | TCTTTCTTTAATTTTTGTTTTTGTTCTTTTTTTCTTTAAG | |
| | | GAAAGTTTTATTTTACTGTTCATTTTACTTTCTTGGTAAC | |
| | | AAAAACTAAAATAAGGAATAGAAAAGCTGTTTTTCAGGCT | |
| | | GACAGTCCAATTAAGGGTAGCCAAGACCTTGCATGGTAGA | |
| | | GTAGGAATCATAGTGTCAGTGAGGTCCCGTGAGTCTTTGT | |
| | | GAGTCCTTGTGTCATCGTTCGGGCACTGTTTTTTTATGCA | |
| | | AGGGCAAAAATCTTTGTATCTGGGGAAAAAAAACTTTTTT | |
| | | TTAAATTAAAAAGGAAAATAAAAGATATTGAGGTCTTCCT | |
| | | AGTGTTACTTAAATTAAGATCAAGGTAAGAAACATTGTAA | |
| | | AAAAAAATTACAAAAGTGCTATTTGTTTCCTAAAAACAGT | |
| | | GATTTCTATTAAAAAGGTGTCAGAACTGGAGAAAATGCCG | |
| | | TGTAGTTATAATTTTTTAGCACAGACCCTGCTGATCACGA | |
| | | TGACATTTTGCCGTGTGTGTGTCTCTAGACTGGTGGGCCA | |
| | | GTCTCCTTGAAGGACAGAGGCGGAGCTCCCCACCCTTCTC | |
| | | TCTCCTCAGAAAAGACCGTGCTCTCTTCTTGGTGCAGGGA | |
| | | TCTTGTCTCCTGTTGTGAAGCCCAAATGGAAGCGTGGATG | |
| | | GTATCAGGGCCCTACCCGTGGTCTTCTCAGATTCTGCTAG | |
| | | AGCAAAAGGCTGGTGCCTAAATAAGATCCCTTCCTTTGGT | |
| | | GCTGCTTTTGGTCTTTCAGCCACCAGCATTATGAGTGCCT | |
| | | GGGGGACACCTCCGAGGGAACTGGCCAGCGGAGCTCTGTG | |
| | | GTGCGCACGCACCCTGGCCGTGACAGGAGGGTGCGGGAGT | |
| | | ACAGGCTGGCTGCATCAGCCCTTGGTGCTTAGAACAGAGG | |
| | | AGGAGTGACATGTTTTGAGGGTACGTCTCTGAGACAGAGC | |
| | | CCCAGCGTGGCCTTCGCTCTGTCTTGCCTTTGGGGAGAGG | |
| | | TCTGAAGCTCCCACTCCTTTCTCTGCCTGTTGGCTCCAGG | |
| | | CACCAGAAATTTACTCCACTCCACCCACCCACAAGCCTCC | |
| | | TGGGTGACCCTGGGCTAGAATTGCTGCGCTTGCCTCGGCT | |
| | | TGGCCGGTTGTGGCCTCTCCTTGAGAAAACCAGGGTTGTG | |
| | | AAAGACTCAGACCATTCTCTCATCTTGCCTTGTCAGAAGT | |
| | | AAATTGTGTCAGATTTGTGCTCTCGCTGGAGACCTTTGCC | |
| | | CCTTGCGTGCCCCTGGCCGATGGGAGGGCGGTGGAGGCTC | |
| | | TGTACCCTGGCCCTGCTGGAGCATCTCCCCCAAGCCCACT | |
| | | CCAGGCCCTGGGAATGGCCAGAGTCTAGGAGAGGTAGAAA | |
| | | CGATCCTATCAGCTTCTCTCCCACCCAATTAGGCCCAGAG | |
| | | AGACAAAGACAGATCTGAAAGCAAATGCAACAGAGAAGAG | |
| | | ACACTTCTTAGAGTAAAATGTGTCTCATCTCTATCAGCCA | |
| | | TCGCCTTTCATCTTCCCAGGGGCCTCAGAAGAAGGAATTA | |
| | | AGTTAGGCTGAACAGGCCTCAGAGTTAGGCCCTGGCTGCT | |
| | | TGATTGGCTGAGGGGGAAAGAGTTCCCTTTTCTCATTCAG | |
| | | AAACCAAGGTGCTGTGTCTAGTCAGGGAGCCTTGGAGATG | |
| | | CCTGGACTAGTTGGAGGAATCGTTGGCAGAGGATCAGAGA | |
| | | CCAGCAGCAGGCTGTCTGCCCTGTCTAGAGCTCTTCCCCT | |
| | | CAACTTGTCTGGGCCCATCTGGGGGTTGCCACACAACACC | |
| | | TAACTTACCTTTTCCTGAAAGAAGTTGGGAAACCATCATC | |
| | | ACTAGAGGCCTTTGCTCAGAGAGGAGCTGCCTTAGGAGTC | |
| | | TTGGGTCGGAGGACGGGGCTAGGAATTGACCAGGGCTTTG | |
| | | CCTGCCGCCCTCAGCAGTGTCGGGTACATTCTGACCTCGC | |
| | | CTGCAGCTGGGCTGTGGATTCTTCCTGACATTCAGATGTG | |
| | | AGCTGTTTTGGGAGTCAGCTAGTATGGAGTACGAGATGCA | |
| | | ACCCAGCCCCCAAACCTACATTCTGCACTCAAATTCCAAA | |
| | | ACACTGCTTTACTGTAAAGAAGAGGCCCCTGGCACCCAAT | |
| | | CTCCCTGTCCTTCACTGTCCCCTCAGACCTGGGCGGGGAG | |
| | | GGGGGGGGGCCTGTGACCACCTGAGACATACGCTCGTGAC | |
| | | ACTGCCCCACCCCAGCCACCTCCACTTGCTTCCTCCTCCT | |
| | | TCCCTCCGCTGCTCTTTCCCCACGGCCCAGAATTTAGCTG | |
| | | CTCTGACAGCCACTTTTGAGACCAGCTGGCTTTGTAGTCA | |
| | | CTTCAGAGAGCTGGAGCGGCTGCCCACTGGGCCCTGACTG | |
| | | GGAGTCCCCTGCCAGCTCCTGATCAGGCGCTGCGCCCTGG | |
| | | TGGCAGTGATGACTGGGAGTCCCCTGCCAGCTCCTGTCCA | |
| | | GGCGCTGCATCCTGGTAACAGTGAGGCCATGTTGCTGTCA | |
| | | TCTCCACCTCTGCATTCTTGCTGCCTGTGGGTCCTTTTTC | |

TABLE 1-continued

GEP-NEN Biomarker/Houskeeper Sequence Information

| Gene Name | RefSeq Accession | Sequence | SEQ ID NO: |
|---|---|---|---|
| | | TTTCATGGAGCCTGCTGGGTCTTGTCTCACCTGTGCTGAG CTCCTCTGGGGTTTTGATTTCTTCCTTCCTTATCAGGCCC TTTGGGGTAAGCCTGCTGGTTGTACCTGACATAGGGAGGC AGTTAGGGGCAGTCCCTGGTGGGGCCGCCCTGGCAGCCTC CAGCTGGCACCATCGTGTGCCTGGTTTCCCTGCAACACCT GCCTCTCTGTCCCTGCTGCTGCTTGGCTCAGGCCCAACAG GCAGCGTGCATGGAGGTGGTTACACACAGCTGTTTCCGTG AGGGTGACCGTGTCTGCAGCACGCTTCCGTCTCCGCATGC ACGGCTGCCTCTCCAGCCACCTCTGATACTTCTCTCTTGG GGCCATCAGAGCCTCCCTTGGGCTGTCACCTCCCAGCTCA CACACACTCTTCAGTGGTTTCCTCTCTTCATTCTCTTATA GGGCGTGGTCCTTCTTATTTATCTAAAGGGCTGAATTTAG GAGACTTTTTACCCAGGGGCAAAAGGCTCTTAGGGTAATG AGATGGATGGTGGCCCAGGTGCATTTTCCAGGGCCTGGGT TCTCCAGATCCCGTGGCTTCTGTTGAGTGGAGGCAACTTT GCTCTGTGTGAACCTCGCCCCTGTCCCTCTGCCGGGCACC CCTGGCAGGAAGCAGGACTCCCATCCTCACCCTGACTTAG ACTGTCCTCTGAGTCAGCTCCTCTCCAAGACAGGAGTGGG CAGCCCTGGGCAGTCTTCTGGCCCCTTGCTAAAGTGAGGG GCAGGAAGCTGGGGCTGCCCTCCAGAAAGCCGGGGTAGGA ACTCTGAAAAATACCTCCTCTAAACGGAAGCAGGGCTCTC CAGTTCCACTTGGCGCCCCCTCCCACAAGGCCCTTCCTCC CTGAGGACCCCACCCCCCTACCCCTTCCCCAGCAGCCTTT GGACCCTCACCTCTCTCCGGTGTCCGTGGGTCCTCAGCCC AGGGTGAGCTGCAGTCAGGCGGGATGGGACGGGCAGGCCA GAGGTCAGCCAGCTCCTAGCAGAGAAGAGCCAGCCAGACC CCAACCCTGTCTCTTGTCCATGCCCTTTGTGATTTCAGTC TTGGTAGACTTGTATTTGGAGTTTTGTGCTTCAAAGTTTT TGTTTTTGTTTGTTTGGTTTTTGTTTTGAGGGGGTGGGGG GGGATACAGAGCAGCTGATCAATTTGTATTTATTTATTTT AACATTTTACTAAATAAAGCCAATAAAGCCTCTCAAAAA AAAAAAAAAAAA | |
| PKD1 | NM_000296.3 | GCACTGCAGCGCCAGCGTCCGAGCGGGCGGCCGAGCTCCC GGAGCGGCCTGGCCCCGAGCCCCGAGCGGGCGTCGCTCAG CAGCAGGTCGCGGCCGCAGCCCCATCCAGCCCCGCGCCCG CCATGCCGTCCGCGGGCCCCGCCTGAGCTGCGGCCTCCGC GCGCGGGCGGGCCTGGGGACGGCGGGGCCATGCGCGCGCT GCCCTAACGATGCCGCCCGCCGCGCCCGCCCGCCTGGCGC TGGCCCTGGGCCTGGGCCTGTGGCTCGGGGCGCTGGCGGG GGGCCCCGGGCGCGGCTGCGGGCCCTGCGAGCCCCCCTGC CTCTGCGGCCCAGCGCCCGGCGCCGCCTGCCGCGTCAACT GCTCGGGCCGCGGGCTGCGGACGCTCGGTCCCGCGCTGCG CATCCCCGCGGACGCCACAGCGCTAGACGTCTCCCACAAC CTGCTCCGGGCGCTGGACGTTGGGCTCCTGGCGAACCTCT CGGCGCTGGCAGAGCTGGATATAAGCAACAACAAGATTTC TACGTTAGAAGAAGGAATATTTGCTAATTTATTTAATTTA AGTGAAATAAACCTGAGTGGGAACCCGTTTGAGTGTGACT GTGGCCTGGCGTGGCTGCCGCGATGGGCGGAGGAGCAGCA GGTGCGGGTGGTGCAGCCCGAGGCAGCCACGTGTGCTGGG CCTGGCTCCCTGGCTGGCCAGCCTCTGCTTGGCATCCCCT TGCTGGACAGTGGCTGTGGTGAGGAGTATGTCGCCTGCCT CCCTGACAACAGCTCAGGCACCGTGGCAGCAGTGTCCTTT TCAGCTGCCCACGAAGGCCTGCTTCAGCCAGAGGCCTGCA GCGCCTTCTGCTTCTCCACCGGCCAGGGCCTCGCAGCCCT CTCGGAGCAGGGCTGGTGCCTGTGTGGGGCGGCCCAGCCC TCCAGTGCCTCCTTTGCCTGCCTGTCCCTCTGCTCCGGCC CCCCGCCACCTCCTGCCCCCACCTGTAGGGGCCCCACCCT CCTCCAGCACGTCTTCCCTGCCTCCCCAGGGGCCACCCTG GTGGGGCCCCACGGACCTCTGGCCTCTGGCCAGCTAGCAG CCTTCCACATCGCTGCCCCGCTCCCTGTCACTGCCACACG CTGGGACTTCGGAGACGGCTCCGCCGAGGTGGATGCCGCT GGGCCGGCTGCCTCGCATCGCTATGTGCTGCCTGGGCGCT ATCACGTGACGGCCGTGCTGGCCCTGGGGGCCGGCTCAGC CCTGCTGGGGACAGACGTGCAGGTGGAAGCGGCACCTGCC GCCCTGGAGCTCGTGTGCCCGTCCTCGGTGCAGAGTGACG AGAGCCTTGACCTCAGCATCCAGAACCGCGGTGGTTCAGG CCTGGAGGCCGCCTACAGCATCGTGGCCCTGGGCGAGGAG CCGGCCCGAGCGGTGCACCCGCTCTGCCCCTCGGACACGG AGATCTTCCCTGGCAACGGGCACTGCTACCGCCTGGTGGT GGAGAAGGCGGCCTGGCTGCAGGCGCAGGAGCAGTGTCAG GCCTGGGCCGGGGCCGCCCTGGCAATGGTGGACAGTCCCG CCGTGCAGCGCTTCCTGGTCTCCCGGGTCACCAGGAGCCT AGACGTGTGGATCGGCTTCTCGACTGTGCAGGGGGTGGAG GTGGGCCCAGCGCCGCAGGGCGAGGCCTTCAGCCTGGAGA | 29 |

TABLE 1-continued

GEP-NEN Biomarker/Houskeeper Sequence Information

| Gene Name | RefSeq Accession | Sequence | SEQ ID NO: |
|---|---|---|---|
| | | GCTGCCAGAACTGGCTGCCCGGGGAGCCACACCCAGCCAC | |
| | | AGCCGAGCACTGCGTCCGGCTCGGGCCCACCGGGTGGTGT | |
| | | AACACCGACCTGTGCTCAGCGCCGCACAGCTACGTCTGCG | |
| | | AGCTGCAGCCCGGAGGCCCAGTGCAGGATGCCGAGAACCT | |
| | | CCTCGTGGGAGCGCCCAGTGGGGACCTGCAGGGACCCCTG | |
| | | ACGCCTCTGGCACAGCAGGACGGCCTCTCAGCCCCGCACG | |
| | | AGCCCGTGGAGGTCATGGTATTCCCGGGCCTGCGTCTGAG | |
| | | CCGTGAAGCCTTCCTCACCACGGCCGAATTTGGGACCCAG | |
| | | GAGCTCCGGCGGCCCGCCCAGCTGCGGCTGCAGGTGTACC | |
| | | GGCTCCTCAGCACAGCAGGGACCCCGGAGAACGGCAGCGA | |
| | | GCCTGAGAGCAGGTCCCCGGACAACAGGACCCAGCTGGCC | |
| | | CCCGCGTGCATGCCAGGGGGACGCTGGTGCCCTGGAGCCA | |
| | | ACATCTGCTTGCCGCTGGACGCCTCCTGCCACCCCCAGGC | |
| | | CTGCGCCAATGGCTGCACGTCAGGGCCAGGGCTACCCGGG | |
| | | GCCCCCTATGCGCTATGGAGAGAGTTCCTCTTCTCCGTTC | |
| | | CCGCGGGGCCCCCCGCGCAGTACTCGGTCACCCTCCACGG | |
| | | CCAGGATGTCCTCATGCTCCCTGGTGACCTCGTTGGCTTG | |
| | | CAGCACGACGCTGGCCCTGGCGCCCTCCTGCACTGCTCGC | |
| | | CGGCTCCCGGCCACCCTGGTCCCCAGGCCCCGTACCTCTC | |
| | | CGCCAACGCCTCGTCATGGCTGCCCCACTTGCCAGCCCAG | |
| | | CTGGAGGGCACTTGGGCCTGCCCTGCCTGTGCCCTGCGGC | |
| | | TGCTTGCAGCCACGGAACAGCTCACCGTGCTGCTGGGCTT | |
| | | GAGGCCCAACCCTGGACTGCGGCTGCCTGGGCGCTATGAG | |
| | | GTCCGGGCAGAGGTGGGCAATGGCGTGTCCAGGCACAACC | |
| | | TCTCCTGCAGCTTTGACGTGGTCTCCCCAGTGGCTGGGCT | |
| | | GCGGGTCATCTACCCTGCCCCCCGCGACGGCCGCCTCTAC | |
| | | GTGCCCACCAACGGCTCAGCCTTGGTGCTCCAGGTGGACT | |
| | | CTGGTGCCAACGCCACGGCCACGGCTCGCTGGCCTGGGGG | |
| | | CAGTGTCAGCGCCCGCTTTGAGAATGTCTGCCCTGCCCTG | |
| | | GTGGCCACCTTCGTGCCCGGCTGCCCCTGGGAGACCAACG | |
| | | ATACCCTGTTCTCAGTGGTAGCACTGCCGTGGCTCAGTGA | |
| | | GGGGGAGCACGTGGTGGACGTGGTGGTGGAAAACAGCGCC | |
| | | AGCCGGGCCAACCTCAGCCTGCGGGTGACGGCGGAGGAGC | |
| | | CCATCTGTGGCCTCCGCGCCACGCCCAGCCCCGAGGCCCG | |
| | | TGTACTGCAGGGAGTCCTAGTGAGGTACAGCCCCGTGGTG | |
| | | GAGGCCGGCTCGGACATGGTCTTCCGGTGGACCATCAACG | |
| | | ACAAGCAGTCCCTGACCTTCCAGAACGTGGTCTTCAATGT | |
| | | CATTTATCAGAGCGCGGCGGTCTTCAAGCTCTCACTGACG | |
| | | GCCTCCAACCACGTGAGCAACGTCACCGTGAACTACAACG | |
| | | TAACCGTGGAGCGGATGAACAGGATGCAGGGTCTGCAGGT | |
| | | CTCCACAGTGCCGGCCGTGCTGTCCCCCAATGCCACGCTA | |
| | | GCACTGACGGCGGGCGTGCTGGTGGACTCGGCCGTGGAGG | |
| | | TGGCCTTCCTGTGGACCTTTGGGGATGGGGAGCAGGCCCT | |
| | | CCACCAGTTCCAGCCTCCGTACAACGAGTCCTTCCCGGTT | |
| | | CCAGACCCCTCGGTGGCCCAGGTGCTGGTGGAGCACAATG | |
| | | TCATGCACACCTACGCTGCCCCAGGTGAGTACCTCCTGAC | |
| | | CGTGCTGGCATCTAATGCCTTCGAGAACCTGACGCAGCAG | |
| | | GTGCCTGTGAGCGTGCGCGCCTCCCTGCCCTCCGTGGCTG | |
| | | TGGGTGTGAGTGACGGCGTCCTGGTGGCCGGCCGGCCCGT | |
| | | CACCTTCTACCCGCACCCGCTGCCCTCGCCTGGGGGTGTT | |
| | | CTTTACACGTGGGACTTCGGGGACGGCTCCCCTGTCCTGA | |
| | | CCCAGAGCCAGCCGGCTGCCAACCACACCTATGCCTCGAG | |
| | | GGGCACCTACCACGTGCGCCTGGAGGTCAACAACACGGTG | |
| | | AGCGGTGCGGCGGCCCAGGCGGATGTGCGCGTCTTTGAGG | |
| | | AGCTCCGCGGACTCAGCGTGGACATGAGCCTGGCCGTGGA | |
| | | GCAGGGCGCCCCCGTGGTGGTCAGCGCCGCGGTGCAGACG | |
| | | GGCGACAACATCACGTGGACCTTCGACATGGGGGACGGCA | |
| | | CCGTGCTGTCGGGCCCGGAGGCAACAGTGGAGCATGTGTA | |
| | | CCTGCGGGCACAGAACTGCACAGTGACCGTGGGTGCGGCC | |
| | | AGCCCCGCCGGCCACCTGGCCCGGAGCCTGCACGTGCTGG | |
| | | TCTTCGTCCTGGAGGTGCTGCGCGTTGAACCCGCCGCCTG | |
| | | CATCCCCACGCAGCCTGACGCGCGGCTCACGGCCTACGTC | |
| | | ACCGGGAACCCGGCCCACTACCTCTTCGACTGGACCTTCG | |
| | | GGGATGGCTCCTCCAACACGACCGTGCGGGGGTGCCCGAC | |
| | | GGTGACACACAACTTCACGCGGAGCGGCACGTTCCCCCTG | |
| | | GCGCTGGTGCTGTCCAGCCGCGTGAACAGGGCGCATTACT | |
| | | TCACCAGCATCTGCGTGGAGCCAGAGGTGGGCAACGTCAC | |
| | | CCTGCAGCCAGAGAGGCAGTTTGTGCAGCTCGGGGACGAG | |
| | | GCCTGGCTGGTGGCATGTGCCTGGCCCCCGTTCCCCTACC | |
| | | GCTACACCTGGGACTTTGGCACCGAGGAAGCCGCCCCCAC | |
| | | CCGTGCCAGGGGCCCTGAGGTGACGTTCATCTACCGAGAC | |
| | | CCAGGCTCCTATCTTGTGACAGTCACCGCGTCCAACAACA | |
| | | TCTCTGCTGCCAATGACTCAGCCCTGGTGGAGGTGCAGGA | |
| | | GCCCGTGCTGGTCACCAGCATCAAGGTCAATGGCTCCCTT | |
| | | GGGCTGGAGCTGCAGCAGCCGTACCTGTTCTCTGCTGTGG | |

TABLE 1-continued

GEP-NEN Biomarker/Houskeeper Sequence Information

| Gene Name | RefSeq Accession | Sequence | SEQ ID NO: |
|---|---|---|---|
| | | GCCGTGGGCGCCCCGCCAGCTACCTGTGGATCTGGGGGA | |
| | | CGGTGGGTGGCTCGAGGGTCCGGAGGTCACCCACGCTTAC | |
| | | AACAGCACAGGTGACTTCACCGTTAGGGTGGCCGGCTGGA | |
| | | ATGAGGTGAGCCGCAGCGAGGCCTGGCTCAATGTGACGGT | |
| | | GAAGCGGCGCGTGCGGGGGCTCGTCGTCAATGCAAGCCGC | |
| | | ACGGTGGTGCCCCTGAATGGGAGCGTGAGCTTCAGCACGT | |
| | | CGCTGGAGGCCGGCAGTGATGTGCGCTATTCCTGGGTGCT | |
| | | CTGTGACCGCTGCACGCCCATCCCTGGGGGTCCTACCATC | |
| | | TCTTACACCTTCCGCTCCGTGGGCACCTTCAATATCATCG | |
| | | TCACGGCTGAGAACGAGGTGGGCTCCGCCCAGGACAGCAT | |
| | | CTTCGTCTATGTCCTGCAGCTCATAGAGGGGCTGCAGGTG | |
| | | GTGGGCGGTGGCCGCTACTTCCCCACCAACCACACGGTAC | |
| | | AGCTGCAGGCCGTGGTTAGGGATGGCACCAACGTCTCCTA | |
| | | CAGCTGGACTGCCTGGAGGGACAGGGGCCCGGCCCTGGCC | |
| | | GGCAGCGGCAAAGGCTTCTCGCTCACCGTGCTCGAGGCCG | |
| | | GCACCTACCATGTGCAGCTGCGGGCCACCAACATGCTGGG | |
| | | CAGCGCCTGGGCCGACTGCACCATGGACTTCGTGGAGCCT | |
| | | GTGGGGTGGCTGATGGTGGCCGCCTCCCCGAACCCAGCTG | |
| | | CCGTCAACACAAGCGTCACCCTCAGTGCCGAGCTGGCTGG | |
| | | TGGCAGTGGTGTCGTATACACTTGGTCCTTGGAGGAGGGG | |
| | | CTGAGCTGGGAGACCTCCGAGCCATTTACCACCCATAGCT | |
| | | TCCCCACACCCGGCCTGCACTTGGTCACCATGACGGCAGG | |
| | | GAACCCGCTGGGCTCAGCCAACGCCACCGTGGAAGTGGAT | |
| | | GTGCAGGTGCCTGTGAGTGGCCTCAGCATCAGGGCCAGCG | |
| | | AGCCCGGAGGCAGCTTCGTGGCGGCCGGGTCCTCTGTGCC | |
| | | CTTTTGGGGGCAGCTGGCCACGGGCACCAATGTGAGCTGG | |
| | | TGCTGGGCTGTGCCCGGCGGCAGCAGCAAGCGTGGCCCTC | |
| | | ATGTCACCATGGTCTTCCCGGATGCTGGCACCTTCTCCAT | |
| | | CCGGCTCAATGCCTCCAACGCAGTCAGCTGGGTCTCAGCC | |
| | | ACGTACAACCTCACGGCGGAGGAGCCCATCGTGGGCCTGG | |
| | | TGCTGTGGGCCAGCAGCAAGGTGGTGGCGCCCGGGCAGCT | |
| | | GGTCCATTTTCAGATCCTGCTGGCTGCCGGCTCAGCTGTC | |
| | | ACCTTCCGCCTGCAGGTCGGCGGGGCCAACCCCGAGGTGC | |
| | | TCCCCGGGCCCCGTTTCTCCCACAGCTTCCCCCGCGTCGG | |
| | | AGACCACGTGGTGAGCGTGCGGGGCAAAAACCACGTGAGC | |
| | | TGGGCCCAGGCGCAGGTGCGCATCGTGGTGCTGGAGGCCG | |
| | | TGAGTGGGCTGCAGGTGCCCAACTGCTGCGAGCCTGGCAT | |
| | | CGCCACGGGCACTGAGAGGAACTTCACAGCCCGCGTGCAG | |
| | | CGCGGCTCTCGGGTCGCCTACGCCTGGTACTTCTCGCTGC | |
| | | AGAAGGTCCAGGGCGACTCGCTGGTCATCCTGTCGGGCCG | |
| | | CGACGTCACCTACACGCCCGTGGCCGCGGGGCTGTTGGAG | |
| | | ATCCAGGTGCGCGCCTTCAACGCCCTGGGCAGTGAGAACC | |
| | | GCACGCTGGTGCTGGAGGTTCAGGACGCCGTCCAGTATGT | |
| | | GGCCCTGCAGAGCGGCCCCTGCTTCACCAACCGCTCGGCG | |
| | | CAGTTTGAGGCCGCCACCAGCCCCAGCCCCCGGCGTGTGG | |
| | | CCTACCACTGGGACTTTGGGGATGGGTCGCCAGGGCAGGA | |
| | | CACAGATGAGCCCAGGGCCGAGCACTCCTACCTGAGGCCT | |
| | | GGGGACTACCGCGTGCAGGTGAACGCCTCCAACCTGGTGA | |
| | | GCTTCTTCGTGGCGCAGGCCACGGTGACCGTCCAGGTGCT | |
| | | GGCCTGCCGGGAGCCGGAGGTGGACGTGGTCCTGCCCCTG | |
| | | CAGGTGCTGATGCGGCGATCACAGCGCAACTACTTGGAGG | |
| | | CCCACGTTGACCTGCGCGACTGCGTCACCTACCAGACTGA | |
| | | GTACCGCTGGGAGGTGTATCGCACCGCCAGCTGCCAGCGG | |
| | | CCGGGGCGCCCAGCGCGTGTGGCCCTGCCCGGCGTGGACG | |
| | | TGAGCCGGCCTCGGCTGGTGCTGCCGCGGCTGGCGCTGCC | |
| | | TGTGGGGCACTACTGCTTTGTGTTTGTCGTGTCATTTGGG | |
| | | GACACGCCACTGACACAGAGCATCCAGGCCAATGTGACGG | |
| | | TGGCCCCCGAGCGCCTGGTGCCCATCATTGAGGGTGGCTC | |
| | | ATACCGCGTGTGGTCAGACACACGGGACCTGGTGCTGGAT | |
| | | GGGAGCGAGTCCTACGACCCCAACCTGGAGGACGGCGACC | |
| | | AGACGCCGCTCAGTTTCCACTGGGCCTGTGTGGCTTCGAC | |
| | | ACAGAGGGAGGCTGGCGGGTGTGCGCTGAACTTTGGGCCC | |
| | | CGCGGGAGCAGCACGGTCACCATTCCACGGGAGCGGCTGG | |
| | | CGGCTGGCGTGGAGTACACCTTCAGCCTGACCGTGTGGAA | |
| | | GGCCGGCCGCAAGGAGGAGGCCACCAACCAGACGGTGCTG | |
| | | ATCCGGAGTGGCCGGGTGCCCATTGTGTCCTTGGAGTGTG | |
| | | TGTCCTGCAAGGCACAGGCCGTGTACGAAGTGAGCCGCAG | |
| | | CTCCTACGTGTACTTGGAGGGCCGCTGCCTCAATTGCAGC | |
| | | AGCGGCTCCAAGCGAGGGCGGTGGGCTGCACGTACGTTCA | |
| | | GCAACAAGACGCTGGTGCTGGATGAGACCACCACATCCAC | |
| | | GGGCAGTGCAGGCATGCGACTGGTGCTGCGGCGGGGCGTG | |
| | | CTGCGGGACGGCGAGGGATACACCTTCACGCTCACGGTGC | |
| | | TGGGCCGCTCTGGCGAGGAGGAGGGCTGCGCCTCCATCCG | |
| | | CCTGTCCCCCAACCGCCCGCCGCTGGGGGGCTCTTGCCGC | |
| | | CTCTTCCCACTGGGCGCTGTGCACGCCCTCACCACCAAGG | |

TABLE 1-continued

| GEP-NEN Biomarker/Houskeeper Sequence Information | | | |
|---|---|---|---|
| Gene Name | RefSeq Accession | Sequence | SEQ ID NO: |
| | | TGCACTTCGAATGCACGGGCTGGCATGACGCGGAGGATGC<br>TGGCGCCCCGCTGGTGTACGCCCTGCTGCTGCGGCGCTGT<br>CGCCAGGGCCACTGCGAGGAGTTCTGTGTCTACAAGGGCA<br>GCCTCTCCAGCTACGGAGCCGTGCTGCCCCCGGGTTTCAG<br>GCCACACTTCGAGGTGGGCCTGGCCGTGGTGGTGCAGGAC<br>CAGCTGGGAGCCGCTGTGGTCGCCCTCAACAGGTCTTTGG<br>CCATCACCCTCCCAGAGCCCAACGGCAGCGCAACGGGGCT<br>CACAGTCTGGCTGCACGGGCTCACCGCTAGTGTGCTCCCA<br>GGGCTGCTGCGGCAGGCCGATCCCCAGCACGTCATCGAGT<br>ACTCGTTGGCCCTGGTCACCGTGCTGAACGAGTACGAGCG<br>GGCCCTGGACGTGGCGGCAGAGCCCAAGCACGAGCGGCAG<br>CACCGAGCCCAGATACGCAAGAACATCACGGAGACTCTGG<br>TGTCCCTGAGGGTCCACACTGTGGATGACATCCAGCAGAT<br>CGCTGCTGCGCTGGCCCAGTGCATGGGGCCCAGCAGGGAG<br>CTCGTATGCCGCTCGTGCCTGAAGCAGACGCTGCACAAGC<br>TGGAGGCCATGATGCTCATCCTGCAGGCAGAGACCACCGC<br>GGGCACCGTGACGCCCACCGCCATCGGAGACAGCATCCTC<br>AACATCACAGGAGACCTCATCCACCTGGCCAGCTCGGACG<br>TGCGGGCACCACAGCCCTCAGAGCTGGGAGCCGAGTCACC<br>ATCTCGGATGGTGGCGTCCCAGGCCTACAACCTGACCTCT<br>GCCCTCATGCGCATCCTCATGCGCTCCCGCGTGCTCAACG<br>AGGAGCCCCTGACGCTGGCGGGCGAGGAGATCGTGGCCCA<br>GGGCAAGCGCTCGGACCCGCGGAGCCTGCTGTGCTATGGC<br>GGCGCCCCAGGGCCTGGCTGCCACTTCTCCATCCCCGAGG<br>CTTTCAGCGGGGCCCTGGCCAACCTCAGTGACGTGGTGCA<br>GCTCATCTTTCTGGTGGACTCCAATCCCTTTCCCTTTGGC<br>TATATCAGCAACTACACCGTCTCCACCAAGGTGGCCTCGA<br>TGGCATTCCAGACACAGGCCGGCGCCCAGATCCCCATCGA<br>GCGGCTGGCCTCAGAGCGCGCCATCACCGTGAAGGTGCCC<br>AACAACTCGGACTGGGCTGCCCGGGGCCACCGCAGCTCCG<br>CCAACTCCGCCAACTCCGTTGTGGTCCAGCCCCAGGCCTC<br>CGTCGGTGCTGTGGTCACCCTGGACAGCAGCAACCCTGCG<br>GCCGGGCTGCATCTGCAGCTCAACTATACGCTGCTGGACG<br>GCCACTACCTGTCTGAGGAACCTGAGCCCTACCTGGCAGT<br>CTACCTACACTCGGAGCCCCGGCCCAATGAGCACAACTGC<br>TCGGCTAGCAGGAGGATCCGCCCAGAGTCACTCCAGGGTG<br>CTGACCACCGGCCCTACACCTTCTTCATTTCCCCGGGGAG<br>CAGAGACCCAGCGGGGAGTTACCATCTGAACCTCTCCAGC<br>CACTTCCGCTGGTCGGCGCTGCAGGTGTCCGTGGGCCTGT<br>ACACGTCCCTGTGCCAGTACTTCAGCGAGGAGGACATGGT<br>GTGGCGGACAGAGGGGCTGCTGCCCCTGGAGGAGACCTCG<br>CCCCGCCAGGCCGTCTGCCTCACCCGCCACCTCACCGCCT<br>TCGGCGCCAGCCTCTTCGTGCCCCCAAGCCATGTCCGCTT<br>TGTGTTTCCTGAGCCGACAGCGGATGTAAACTACATCGTC<br>ATGCTGACATGTGCTGTGTGCCTGGTGACCTACATGGTCA<br>TGGCCGCCATCCTGCACAAGCTGGACCAGTTGGATGCCAG<br>CCGGGGCCGCGCCATCCCTTTCTGTGGGCAGCGGGGCCGC<br>TTCAAGTACGAGATCCTCGTCAAGACAGGCTGGGGCCGGG<br>GCTCAGGTACCACGGCCCACGTGGGCATCATGCTGTATGG<br>GGTGGACAGCCGGAGCGGCCACCGGCACCTGGACGGCGAC<br>AGAGCCTTCCACCGCAACAGCCTGGACATCTTCCGGATCG<br>CCACCCCGCACAGCCTGGGTAGCGTGTGGAAGATCCGAGT<br>GTGGCACGACAACAAAGGGCTCAGCCCTGCCTGGTTCCTG<br>CAGCACGTCATCGTCAGGGACCTGCAGACGGCACGCAGCG<br>CCTTCTTCCTGGTCAATGACTGGCTTTCGGTGGAGACGGA<br>GGCCAACGGGGGCCTGGTGGAGAAGGAGGTGCTGGCCGCG<br>AGCGACGCAGCCCTTTTGCGCTTCCGGCGCCTGCTGGTGG<br>CTGAGCTGCAGCGTGGCTTCTTTGACAAGCACATCTGGCT<br>CTCCATATGGGACCGGCCGCCTCGTAGCCGTTTCACTCGC<br>ATCCAGAGGGCCACCTGCTGCGTTCTCCTCATCTGCCTCT<br>TCCTGGGCGCCAACGCCGTGTGGTACGGGGCTGTTGGCGA<br>CTCTGCCTACAGCACGGGGCATGTGTCCAGGCTGAGCCCG<br>CTGAGCGTCGACACAGTCGCTGTTGGCCTGGTGTCCAGCG<br>TGGTTGTCTATCCCGTCTACCTGGCCATCCTTTTTCTCTT<br>CCGGATGTCCCGGAGCAAGGTGGCTGGGAGCCCGAGCCCC<br>ACACCTGCCGGGCAGCAGGTGCTGGACATCGACAGCTGCC<br>TGGACTCGTCCGTGCTGGACAGCTCCTTCCTCACGTTCTC<br>AGGCCTCCACGCTGAGGCCTTTGTTGGACAGATGAAGAGT<br>GACTTGTTTCTGGATGATTCTAAGAGTCTGGTGTGCTGGC<br>CCTCCGGCGAGGGAACGCTCAGTTGGCCGGACCTGCTCAG<br>TGACCCGTCCATTGTGGGTAGCAATCTGCGGCAGCTGGCA<br>CGGGGCCAGGCGGGCCATGGGCTGGGCCCAGAGGAGGACG<br>GCTTCTCCCTGGCCAGCCCCTACTCGCCTGCCAAATCCTT<br>CTCAGCATCAGATGAAGACCTGATCCAGCAGGTCCTTGCC<br>GAGGGGGTCAGCAGCCCAGCCCCTACCCAAGACACCCACA | |

TABLE 1-continued

GEP-NEN Biomarker/Houskeeper Sequence Information

| Gene Name | RefSeq Accession | Sequence | SEQ ID NO: |
|---|---|---|---|
| | | TGGAAACGGACCTGCTCAGCAGCCTGTCCAGCACTCCTGG<br>GGAGAAGACAGAGACGCTGGCGCTGCAGAGGCTGGGGGAG<br>CTGGGGCCACCCAGCCCAGGCCTGAACTGGGAACAGCCCC<br>AGGCAGCGAGGCTGTCCAGGACAGGACTGGTGGAGGGTCT<br>GCGGAAGCGCCTGCTGCCGGCCTGGTGTGCCTCCCTGGCC<br>CACGGGCTCAGCCTGCTCCTGGTGGCTGTGGCTGTGGCTG<br>TCTCAGGGTGGGTGGGTGCGAGCTTCCCCCCGGGCGTGAG<br>TGTTGCGTGGCTCCTGTCCAGCAGCGCCAGCTTCCTGGCC<br>TCATTCCTCGGCTGGGAGCCACTGAAGGTCTTGCTGGAAG<br>CCCTGTACTTCTCACTGGTGGCCAAGCGGCTGCACCCGGA<br>TGAAGATGACACCCTGGTAGAGAGCCCGGCTGTGACGCCT<br>GTGAGCGCACGTGTGCCCCGCGTACGGCCACCCCACGGCT<br>TTGCACTCTTCCTGGCCAAGGAAGAAGCCCGCAAGGTCAA<br>GAGGCTACATGGCATGCTGCGGAGCCTCCTGGTGTACATG<br>CTTTTTCTGCTGGTGACCCTGCTGGCCAGCTATGGGGATG<br>CCTCATGCCATGGGCACGCCTACCGTCTGCAAAGCGCCAT<br>CAAGCAGGAGCTGCACAGCCGGGCCTTCCTGGCCATCACG<br>CGGTCTGAGGAGCTCTGGCCATGGATGGCCCACGTGCTGC<br>TGCCCTACGTCCACGGGAACCAGTCCAGCCCAGAGCTGGG<br>GCCCCCACGGCTGCGGCAGGTGCGGCTGCAGGAAGCACTC<br>TACCCAGACCCTCCCGGCCCCAGGGTCCACACGTGCTCGG<br>CCGCAGGAGGCTTCAGCACCAGCGATTACGACGTTGGCTG<br>GGAGAGTCCTCACAATGGCTCGGGGACGTGGGCCTATTCA<br>GCGCCGGATCTGCTGGGGGCATGGTCCTGGGGCTCCTGTG<br>CCGTGTATGACAGCGGGGGCTACGTGCAGGAGCTGGGCCT<br>GAGCCTGGAGGAGAGCCGCGACCGGCTGCGCTTCCTGCAG<br>CTGCACAACTGGCTGGACAACAGGAGCCGCGCTGTGTTCC<br>TGGAGCTCACGCGCTACAGCCCGGCCGTGGGGCTGCACGC<br>CGCCGTCACGCTGCGCCTCGAGTTCCCGGCGGCCGGCCGC<br>GCCCTGGCCGCCCTCAGCGTCCGCCCCTTTGCGCTGCGCC<br>GCCTCAGCGCGGGCCTCTCGCTGCCTCTGCTCACCTCGGT<br>GTGCCTGCTGCTGTTCGCCGTGCACTTCGCCGTGGCCGAG<br>GCCCGTACTTGGCACAGGGAAGGGCGCTGGCGCGTGCTGC<br>GGCTCGGAGCCTGGGCGCGGTGGCTGCTGGTGGCGCTGAC<br>GGCGGCCACGGCACTGGTACGCCTCGCCCAGCTGGGTGCC<br>GCTGACCGCCAGTGGACCCGTTTCGTGCGCGGCCGCCCGC<br>GCCGCTTCACTAGCTTCGACCAGGTGGCGCAGCTGAGCTC<br>CGCAGCCCGTGGCCTGGCGGCCTCGCTGCTCTTCCTGCTT<br>TTGGTCAAGGCTGCCCAGCAGCTACGCTTCGTGCGCCAGT<br>GGTCCGTCTTTGGCAAGACATTATGCCGAGCTCTGCCAGA<br>GCTCCTGGGGGTCACCTTGGGCCTGGTGGTGCTCGGGGTA<br>GCCTACGCCCAGCTGGCCATCCTGCTCGTGTCTTCCTGTG<br>TGGACTCCCTCTGGAGCGTGGCCCAGGCCCTGTTGGTGCT<br>GTGCCCTGGGACTGGGCTCTCTACCCTGTGTCCTGCCGAG<br>TCCTGGCACCTGTCACCCCTGCTGTGTGTGGGGCTCTGGG<br>CACTGCGGCTGTGGGGCGCCCTACGGCTGGGGGCTGTTAT<br>TCTCCGCTGGCGCTACCACGCCTTGCGTGGAGAGCTGTAC<br>CGGCCGGCCTGGGAGCCCCAGGACTACGAGATGGTGGAGT<br>TGTTCCTGCGCAGGCTGCGCCTCTGGATGGGCCTCAGCAA<br>GGTCAAGGAGTTCCGCCACAAAGTCCGCTTTGAAGGGATG<br>GAGCCGCTGCCCTCTCGCTCCTCCAGGGGCTCCAAGGTAT<br>CCCCGGATGTGCCCCCACCCAGCGCTGGCTCCGATGCCTC<br>GCACCCCTCCACCTCCTCCAGCCAGCTGGATGGGCTGAGC<br>GTGAGCCTGGGCCGGCTGGGGACAAGGTGTGAGCCTGAGC<br>CCTCCCGCCTCCAAGCCGTGTTCGAGGCCCTGCTCACCCA<br>GTTTGACCGACTCAACCAGGCCACAGAGGACGTCTACCAG<br>CTGGAGCAGCAGCTGCACAGCCTGCAAGGCCGCAGGAGCA<br>GCCGGGCGCCCGCCGGATCTTCCCGTGGCCCATCCCCGGG<br>CCTGCGGCCAGCACTGCCCAGCCGCCTTGCCCGGGCCAGT<br>CGGGGTGTGGACCTGGCCACTGGCCCCAGCAGGACACCCC<br>TTCGGGCCAAGAACAAGGTCCACCCCAGCAGCACTTAGTC<br>CTCCTTCCTGGCGGGGGTGGGCCGTGGAGTCGGAGTGGAC<br>ACCGCTCAGTATTACTTTCTGCCGCTGTCAAGGCCGAGGG<br>CCAGGCAGAATGGCTGCACGTAGGTTCCCCAGAGAGCAGG<br>CAGGGGCATCTGTCTGTCTGTGGGCTTCAGCACTTTAAAG<br>AGGCTGTGTGGCCAACCAGGACCCAGGGTCCCCTCCCCAG<br>CTCCCTTGGGAAGGACACAGCAGTATTGGACGGTTTCTAG<br>CCTCTGAGATGCTAATTTATTTCCCCGAGTCCTCAGGTAC<br>AGCGGGCTGTGCCCGGCCCCACCCCCTGGGCAGATGTCCC<br>CCACTGCTAAGGCTGCTGGCTTCAGGGAGGGTTAGCCTGC<br>ACCGCCGCCACCCTGCCCCTAAGTTATTACCTCTCCAGTT<br>CCTACCGTACTCCCTGCACCGTCTCACTGTGTGTCTCGTG<br>TCAGTAATTTATATGGTGTTAAAATGTGTATATTTTTGTA<br>TGTCACTATTTTCACTAGGGCTGAGGGGCCTGCGCCCAGA<br>GCTGGCCTCCCCCAACACCTGCTGCGCTTGGTAGGTGTGG | |

TABLE 1-continued

GEP-NEN Biomarker/Houskeeper Sequence Information

| Gene Name | RefSeq Accession | Sequence | SEQ ID NO: |
|---|---|---|---|
| | | TGGCGTTATGGCAGCCCGGCTGCTGCTTGGATGCGAGCTT<br>GGCCTTGGGCCGGTGCTGGGGGCACAGCTGTCTGCCAGGC<br>ACTCTCATCACCCCAGAGGCCTTGTCATCCTCCCTTGCCC<br>CAGGCCAGGTAGCAAGAGAGCAGCGCCCAGGCCTGCTGGC<br>ATCAGGTCTGGGCAAGTAGCAGGACTAGGCATGTCAGAGG<br>ACCCCAGGGTGGTTAGAGGAAAAGACTCCTCCTGGGGGCT<br>GGCTCCCAGGGTGGAGGAAGGTGACTGTGTGTGTGTGTGT<br>GTGCGCGCGCGCACGCGCGAGTGTGCTGTATGGCCCAGGC<br>AGCCTCAAGGCCCTCGGAGCTGGCTGTGCCTGCTTCTGTG<br>TACCACTTCTGTGGGCATGGCCGCTTCTAGAGCCTCGACA<br>CCCCCCCAACCCCCGCACCAAGCAGACAAAGTCAATAAAA<br>GAGCTGTCTGACTGC | |
| PLD3 | NM_001031696.3 | GCATCCTCTCACCGCCGGAAGCTGAACTGACTCGTCCGCG<br>GCCGCTCTACCCCAACAGGCCGCCACCAGCGAGAGTGCGG<br>CCATAACCATCACGTGACCGCCCACCGACACCAGCGAGAG<br>TGCAGTCGTAACCGTCACGTGACCGCCCACCGTCGGCCCG<br>GCGCTCCCCTCCGCCCGAAGCTAGCAAGCGGCGCGGCCAA<br>TGAGAAAGGCGCATGCCTGGCCCCCGCCGGCCTGCAGTCT<br>AGCCGTAGTGCGCCTGCGCGCGGCTAGGAGGGGCCGTCAG<br>GCGGGGATACAGCCTGGAAGGTAATGCATGTCCATGGTAC<br>ACAAATTCACAAGTTTGGAGACCCTGACACACCCACCTTC<br>TCACCTGGGCTCTGCGTATCCCCCAGCCTTGAGGGAAGAT<br>GAAGCCTAAACTGATGTACCAGGAGCTGAAGGTGCCTGCA<br>GAGGAGCCCGCCAATGAGCTGCCCATGAATGAGATTGAGG<br>CGTGGAAGGCTGCGGAAAAGAAAGCCCGCTGGGTCCTGCT<br>GGTCCTCATTCTGGCGGTTGTGGGCTTCGGAGCCCTGATG<br>ACTCAGCTGTTTCTATGGGAATACGGCGACTTGCATCTCT<br>TTGGGCCCAACCAGCGCCCAGCCCCCTGCTATGACCCTTG<br>CGAAGCAGTGCTGGTGGAAAGCATTCCTGAGGGCCTGGAC<br>TTCCCCAATGCCTCCACGGGGAACCCTTCCACCAGCCAGG<br>CCTGGCTGGGCCTGCTCGCCGGTGCGCACAGCAGCCTGGA<br>CATCGCCTCCTTCTACTGGACCCTCACCAACAATGACACC<br>CACACGCAGGAGCCCTCTGCCCAGCAGGGTGAGGAGGTCC<br>TCCGGCAGCTGCAGACCCTGGCACCAAAGGGCGTGAACGT<br>CCGCATCGCTGTGAGCAAGCCCAGCGGGCCCCAGCCACAG<br>GCGGACCTGCAGGCTCTGCTGCAGAGCGGTGCCCAGGTCC<br>GCATGGTGGACATGCAGAAGCTGACCCATGGCGTCCTGCA<br>TACCAAGTTCTGGGTGGTGGACCAGACCCACTTCTACCTG<br>GGCAGTGCCAACATGGACTGGCGTTCACTGACCCAGGTCA<br>AGGAGCTGGGCGTGGTCATGTACAACTGCAGCTGCCTGGC<br>TCGAGACCTGACCAAGATCTTTGAGGCCTACTGGTTCCTG<br>GGCCAGGCAGGCAGCTCCATCCCATCAACTTGGCCCCGGT<br>TCTATGACACCCGCTACAACCAAGAGACACCAATGGAGAT<br>CTGCCTCAATGGAACCCCTGCTCTGGCCTACCTGGCGAGT<br>GCGCCCCCACCCCTGTGTCCAAGTGGCCGCACTCCAGACC<br>TGAAGGCTCTACTCAACGTGGTGGACAATGCCCGGAGTTT<br>CATCTACGTCGCTGTCATGAACTACCTGCCCACTCTGGAG<br>TTCTCCCACCCTCACAGGTTCTGGCCTGCCATTGACGATG<br>GGCTGCGGCGGGCCACCTACGAGCGTGGCGTCAAGGTGCG<br>CCTGCTCATCAGCTGCTGGGGACACTCGGAGCCATCCATG<br>CGGGCCTTCCTGCTCTCTCTGGCTGCCCTGCGTGACAACC<br>ATACCCACTCTGACATCCAGGTGAAACTCTTTGTGGTCCC<br>CGCGGATGAGGCCCAGGCTCGAATCCCATATGCCCGTGTC<br>AACCACAACAAGTACATGGTGACTGAACGCGCCACCTACA<br>TCGGAACCTCCAACTGGTCTGGCAACTACTTCACGGAGAC<br>GGCGGGCACCTCGCTGCTGGTGACGCAGAATGGGAGGGGC<br>GGCCTGCGGAGCCAGCTGGAGGCCATTTTCCTGAGGGACT<br>GGGACTCCCCTTACAGCCATGACCTTGACACCTCAGCTGA<br>CAGCGTGGGCAACGCCTGCCGCCTGCTCTGAGGCCCGATC<br>CAGTGGGCAGGCCAAGGCCTGCTGGGCCCCCGCGGACCCA<br>GGTGCTCTGGGTCACGGTCCCTGTCCCCGCGCCCCCGCTT<br>CTGTCTGCCCCATTGTGGCTCCTCAGGCTCTCTCCCCTGC<br>TCTCCCACCTCTACCTCCACCCCCACCGGCCTGACGCTGT<br>GGCCCCGGGACCCAGCAGAGCTGGGGGAGGGATCAGCCCC<br>CAAAGAAATGGGGGTGCATGCTGGGCCTGGCCCCCTGGCC<br>CACCCCCACTTTCCAGGGCAAAAAGGGCCCAGGGTTATAA<br>TAAGTAAATAACTTGTCTGTACAGCCTGAAAAAAAAAAAA<br>AAAAAAA | 30 |
| PNMA2 | NM_007257.5 | GAGCGGTGCTCAGGGGAGGGCTGGAGGGGAGGGAAGGAGA<br>GAGAGAGGGGAGGGCGGCACCGCCCCTAGCCCCGCGCTCC<br>GGAAGTGAAGCGGCCAGACCACCAGCTAATGGATGCGGAG<br>CGGAGGGCCCGCTGACCGCTCTCCGCGCCTGGAGCAGCTT<br>GGCTTGGCTGGAGCTAAGAGCCAGACACACCACTGTGTGG | 31 |

TABLE 1-continued

GEP-NEN Biomarker/Houskeeper Sequence Information

| Gene Name | RefSeq Accession | Sequence | SEQ ID NO: |
|---|---|---|---|
| | | AGGTGGGTGATGTCTTCCTGTGCTAAAAGGTGAATAAATA | |
| | | AGCTCCTCACCTCTCGCGGAACACTCGGGAACACATCAAC | |
| | | AGGGGTCCAAGCCGCCCTGCTGGGAGGCTTCTCTTCAAGA | |
| | | GTTCTGGGTCCCAGAGTGGAAGGCATTTTCCCATCAACTG | |
| | | GAGAGAGACGAAACATCAGAGACCAGGAGGCTGTGGAGAA | |
| | | AGCAGCTGTCCCAGGTGCCTCAACTATCAGAGAAGGGTCA | |
| | | GCGTCACGTGGCTGCCAGCATCTTTGAGAAAATCACTGGC | |
| | | AATCGGACTTCAGAGCTGCGGGCACAGGTGTGGTTAGAAC | |
| | | TGAGATACGACCTGCCCACCTGGGTCAGGCCTAAAGACAA | |
| | | GAAGTCCTGAGTTCTTGCCACTGAGTAGGCCAGGGTCATT | |
| | | TGTCCAGAAAACTTTGTGACTGTCTTTGAGTGACCTAGTC | |
| | | TGGGACCCATTCATTGGTGGGTTCTAAGGTTAGAAGCTCA | |
| | | TCCAGGATATTTTCAATATTAAGTCAGTGCATAGCTGCAC | |
| | | CACTAACAAATTGGTGCCTGTAGAGTCAGAGTGGGTCAAT | |
| | | TCTTAGGACAATGGCGCTGGCACTGTTAGAGGACTGGTGC | |
| | | AGGATAATGAGTGTGGATGAGCAGAAGTCACTGATGGTTA | |
| | | CGGGGATACCGGCGGACTTTGAGGAGGCTGAGATTCAGGA | |
| | | GGTCCTTCAGGAGACTTTAAAGTCTCTGGGCAGGTATAGA | |
| | | CTGCTTGGCAAGATATTCCGGAAGCAGGAGAATGCCAATG | |
| | | CTGTCTTACTAGAGCTTCTGGAAGATACTGATGTCTCGGC | |
| | | CATTCCCAGTGAGGTCCAGGGAAAGGGGGGTGTCTGGAAG | |
| | | GTGATCTTTAAGACCCCTAATCAGGACACTGAGTTTCTTG | |
| | | AAAGATTGAACCTGTTTCTAGAAAAAGAGGGGCAGACGGT | |
| | | CTCGGGTATGTTTCGAGCCCTGGGGCAGGAGGGCGTGTCT | |
| | | CCAGCCACAGTGCCCTGCATCTCACCAGAATTACTGGCCC | |
| | | ATTTGTTGGGACAGGCAATGGCACATGCGCCTCAGCCCCT | |
| | | GCTACCCATGAGATACCGGAAACTGCGAGTATTCTCAGGG | |
| | | AGTGCTGTCCCAGCCCCAGAGGAAGAGTCCTTTGAGGTCT | |
| | | GGTTGGAACAGGCCACGGAGATAGTCAAAGAGTGGCCAGT | |
| | | AACAGAGGCAGAAAAGAAAAGGTGGCTGGCGGAAAGCCTG | |
| | | CGGGGCCCTGCCCTGGACCTCATGCACATAGTGCAGGCAG | |
| | | ACAACCCGTCCATCAGTGTAGAAGAGTGTTTGGAGGCCTT | |
| | | TAAGCAAGTGTTTGGGAGCCTAGAGAGCCGCAGGACAGCC | |
| | | CAGGTGAGGTATCTGAAGACCTATCAGGAGGAAGGAGAGA | |
| | | AGGTCTCAGCCTATGTGTTACGGCTAGAAACCCTGCTCCG | |
| | | GAGAGCGGTGGAGAAACGCGCCATCCCTCGGCGTATTGCG | |
| | | GACCAGGTCCGCCTGGAGCAGGTCATGGCTGGGGCCACTC | |
| | | TTAACCAGATGCTGTGGTGCCGGCTTAGGGAGCTGAAGGA | |
| | | TCAGGGCCCGCCCCCCAGCTTCCTTGAGCTAATGAAGGTA | |
| | | ATACGGGAAGAAGAGGAGGAAGAGGCCTCCTTTGAGAATG | |
| | | AGAGTATCGAAGAGCCAGAGGAACGAGATGGCTATGGCCG | |
| | | CTGGAATCATGAGGGAGACGACTGAAAACCACCTGGGGGC | |
| | | AGGACCCACAGCCAGTGGGCTAAGACCTTTAAAAAATTTT | |
| | | TTTCTTTAATGTATGGGACTGAAATCAAACCATGAAAGCC | |
| | | AATTATTGACCTTCCTTCCTTCCTTCCTTCCCTCCCTTCC | |
| | | TCCTTCTCTCCTTCTCTCCTCCTCTCTCCTCTCCTCTCCT | |
| | | CTCTTTCCTTCCTTCCTTCCTTTTTTCTTTTTCTCTTTCT | |
| | | TCTTTATTTCTTGGGTCTCACTCTCATCACCCAGGCTAGA | |
| | | GTGCAGTGGCACAAAAATCTCGGCTCACTGCAGCCTTGAC | |
| | | TTCCCAGGCTCAGGCTCAGGTGATCCTCACACCTTAGCCT | |
| | | CCCAAGTACCTGGGACTACAGGCACGCACCACCATGCCTA | |
| | | GCTATTCTTTTGTATTTTTGGTAGAGACAGGGTTTTGCTG | |
| | | TGTTGCTCAGGCTGGTCTGGAACCCCTAGGCTCAAATGAT | |
| | | GTGCCCAACTCGGCCTCCCAAAGTGCTGGGATTACAGGCA | |
| | | TGAACCGCCATGCCTGGCCCTTGATTTTTCTTTTTAAGAA | |
| | | AAAAATATCTAGGAGTTTCTTAGACCCTATGTAGATTATT | |
| | | AATGAACAAAAGATTAAACTCCAAATATTAAATAGTAAGC | |
| | | CTGAAGGAATCTGAAACACTTGTACTTCCAATTTTCTTTA | |
| | | AATAATCCCAAATAGACCAGAATTGGCCCATACCATAGAA | |
| | | GAAAGAATTGGCAGTCAAAAAAAAAAATACCTTTTGTAAT | |
| | | GTTTGAAAAATAAAGCTGTTTGACTTGTCAGGTGTTTTCC | |
| | | TTTCTCAAATCAGCAAATTCTCTCTGAGTGCCTGGCTTTG | |
| | | TGAGACACTGTACAAGGAGTTACAAGACTACAGCTATAAC | |
| | | CTGCAGTTGAGCAGTTATAAACCTACAAAATGGGCCCTGC | |
| | | CCTCAGAGAGGTTCCAGTCTAGATGAGGAGCTGATCTAGA | |
| | | CAGGTAAAAGGCTAACTAACCCTTTGTGTAAATAAGTTCA | |
| | | TCACCCCAGTAAAAGTGTCATCACCCAGTGAATAGGACCA | |
| | | CCTCTGCCTGCAGATTTTTGTTGTTGTTGTTGTCATTGTT | |
| | | GTTGTTGTTTTAACCTGGGAAGTGTTCTTCCTGCCTTTCT | |
| | | GCTAGGTGTCAGATAGATGGTCCCAGAGCTAGGTGCTGTG | |
| | | TCAGGCCCTGAAGACACAGATGACTCAACCTAAGCTTTAC | |
| | | TTTCCAGAGGTCCACAGCCTGAGAGGTGTCCCCAAAGAAA | |
| | | GGGGGACATGAGGGGACTGCATGCTTGAGAGCAGGGTTGT | |
| | | TTAGGGCAGGTTTGGATTTAGTGAGCAGGCTGGTTTGCTT | |
| | | AGAGAAGGCTTTTAGTGGCAACAAAGGATGAAGAGGAGAG | |

TABLE 1-continued

GEP-NEN Biomarker/Houskeeper Sequence Information

| Gene Name | RefSeq Accession | Sequence | SEQ ID NO: |
|---|---|---|---|
| | | AAAAGGAACTCACATTTATTGAGGGCCTACTGTGTGCAAA<br>GTGTTTCATGTATATCTCATTGAATGTATACAGCCACCCT<br>GTTGTGGTATAATTTTGCTCTTTATAAAGAGAAAGACCGA<br>AGCTCAGATGAGTTAAGTGGTCTCCTCAACACCAAAATGC<br>CAAGAAGTGATGGAGCCTAGACAGAAGCCCAGAACTTTCT<br>GACTCACACTAGTCCATCCTCTACCATCACGATGACTTTC<br>AAATTGTGCTCTGCAGTTCTGCAGATTTTCTAGCAGTGCC<br>ATCTCCAAAATGTGTTTTAAACTCTTTATTTTTTTAATTA<br>TTATTAGTATTATTTTGAGACTGAGTCTTGCTCTATCACC<br>CAGGCTGGAGTGCAGTGGTGCAATCTCAGCTCACTGCAAC<br>CTCCGCCTCCCAGGTTCAAGCGATTTCGTGCCTCAGCCTC<br>CCGAGTAGCTGGGATTACAGGCACCCACCACCACGCCCAG<br>CTAATTTTTGTATTTTTAGTAGAAATGGGGTTTCACCATG<br>TTGGCCAGGCTGGTCTCGAACTCCTGACCTCAAGTGATCC<br>ACTCACCTCGGCCTCCCAAAGTGCTGGGATTACAGGTGTG<br>AGCCACCATGCCTGGGCTAAACTCTTTAAGTCTCTAGTAA<br>ATGCAGCTAGATTCAAATGGGCTGATAACCAAATTTTAAC<br>ACATCAGCATTCACCACCAGGTTTACTTTTATTTTCAGAT<br>TGGCTCATTTTGTGCAGACCTTAGAGCAAAGTTTCCTTTA<br>TGGTATCTGTGTACGTATCCAAACTTCTTTTAATTGTTCA<br>CAGATTTTAAAAGCGGTAGCACCACATGGTTGTGTAGATC<br>AGACCTGTGTATTTAGATCAGACCTGTGTATCACGTAAGT<br>GTGTGAGTGCAGTGCAGATGAGCACCATTTAGTTATATGT<br>GCTAGGCAAATCTCCAACACAGTTGATGTGTAGTCTTGTG<br>GTAGATTTGTGCATACTGTAAGCAAATTGCTTAGCTTCTC<br>TAGACATCAGTTTCCACATCTGAAAAATAAGAAGATGAGA<br>GTACACGGTTGTTATGAACAAATGACTTAATGCTTTTTAA<br>GCACGTTGCATGACATCTGGAACACAGAAAGCCCTCAATA<br>CATTGAAGCTCTTAGGATTTTCACGATGTTCCTGTCTGCT<br>CAATGCATGCTTTCTTTATTGTTCTGACAGTTGTGTGGTA<br>ACAAGCTAATATGCTTCCAGTTGACTTCCAGTCTACCCTG<br>GTGTTAGAAACCGTTTCATCTCTTATTGTAAATTTGAGTG<br>CTTGTTGTTTTTTATATTTGTGATGACTCTTCCAGCAGTT<br>GTTGACAATTGTTAGAGGTTTGACTTTTAAATAATTACTT<br>ATTTTTTCTGATTGTGGTTCAGTTTAACTGAAGAATATCC<br>TGAGATTGTAAGAAAAGCATTTTTTAAAAGGTATCACTTG<br>TGATCATTTATCTTTCTAAATTCTATTTTTAATACTGTTC<br>CACCAAAGTGATGCAGTGGTTACCATGACACCCTAATTTC<br>ATGTGTTTTTGTATTTATGAAAATAGTTTCATTGTCATTT<br>ATTGGCGGTATACAAAGTAAAATGTTATAAATGTGAAGTT<br>ATAAAATAAATATATGCTAATAAAATCCTGAGTTTTTCTG<br>TTTCCT | |
| PQBP1 | NM_001032381.1 | TGCCTCCTGAGCGTAGTCCAGTTACTTTCAGGCTCGGGGA<br>GTGAAGGCCTCGTTGAGAGAAGGTCTCATTCGGTGTTTTG<br>GGAAGAGAGTCGTGTGGGCCCAGGTCTGTCTGCTATCAGC<br>TATGCCGCTGCCCGTTGCGCTGCAGACCCGCTTGGCCAAG<br>AGAGGCATCCTCAAACATCTGGAGCCTGAACCAGAGGAAG<br>AGATCATTGCCGAGGACTATGACGATGATCCTGTGGACTA<br>CGAGGCCACCAGGTTGGAGGGCCTACCACCAAGCTGGTAC<br>AAGGTGTTCGACCCTTCCTGCGGGCTCCCTTACTACTGGA<br>ATGCAGACACAGACCTTGTATCCTGGCTCTCCCCACATGA<br>CCCCAACTCCGTGGTTACCAAATCGGCCAAGAAGCTCAGA<br>AGCAGTAATGCAGATGCTGAAGAAAAGTTGGACCGGAGCC<br>ATGACAAGTCGGACAGGGGCCATGACAAGTCGGACCGCAG<br>CCATGAGAAACTAGACAGGGGCCACGACAAGTCAGACCGG<br>GGCCACGACAAGTCTGACAGGGATCGAGAGCGTGGCTATG<br>ACAAGGTAGACAGAGAGAGAGAGCGAGACAGGGAACGGGA<br>TCGGGACCGCGGGTATGACAAGGCAGACCGGGAAGAGGGC<br>AAAGAACGGCGCCACCATCGCCGGGAGGAGCTGGCTCCCT<br>ATCCCAAGAGCAAGAAGGCAGTAAGCCGAAAGGATGAAGA<br>GTTAGACCCCATGGACCCTAGCTCATACTCAGACGCCCCC<br>CGGGGCACGTGGTCAACAGGACTCCCCAAGCGGAATGAGG<br>CCAAGACTGGCGCTGACACCACAGCAGCTGGGCCCCTCTT<br>CCAGCAGCGGCCGTATCCATCCCCAGGGGCTGTGCTCCGG<br>GCCAATGCAGAGGCCTCCCGAACCAAGCAGCAGGATTGAA<br>GCTTCGGCCTCCCTGGCCCTGGGTTAAAATAAAAGCTTTC<br>TGGTGATCCTGCCCACCAAAAAAAAAAAAAAAAAAAAAAA<br>AAAAAAAAAAAAAA | 32 |
| RAF1 | NM_002880.3 | AGAATCGGAGAGCCGGTGGCGTCGCAGGTCGGGAGGACGA<br>GCACCGAGTCGAGGGCTCGCTCGTCTGGGCCGCCCGAGAG<br>TCTTAATCGCGGGCGCTTGGGCCGCCATCTTAGATGGCGG<br>GAGTAAGAGGAAAACGATTGTGAGGCGGGAACGGCTTTCT<br>GCTGCCTTTTTTGGGCCCCGAAAAGGGTCAGCTGGCCGGG | 33 |

TABLE 1-continued

GEP-NEN Biomarker/Houskeeper Sequence Information

| Gene Name | RefSeq Accession | Sequence | SEQ ID NO: |
|---|---|---|---|
| | | CTTTGGGGCGCGTGCCCTGAGGCGCGGAGCGCGTTTGCTA<br>CGATGCGGGGGCTGCTCGGGGCTCCGTCCCCTGGGCTGGG<br>GACGCGCCGAATGTGACCGCCTCCCGCTCCCTCACCCGCC<br>GCGGGGAGGAGGAGCGGGCGAGAAGCTGCCGCCGAACGAC<br>AGGACGTTGGGGCGGCCTGGCTCCCTCAGGTTTAAGAATT<br>GTTTAAGCTGCATCAATGGAGCACATACAGGGAGCTTGGA<br>AGACGATCAGCAATGGTTTTGGATTCAAAGATGCCGTGTT<br>TGATGGCTCCAGCTGCATCTCTCCTACAATAGTTCAGCAG<br>TTTGGCTATCAGCGCCGGGCATCAGATGATGGCAAACTCA<br>CAGATCCTTCTAAGACAAGCAACACTATCCGTGTTTTCTT<br>GCCGAACAAGCAAAGAACAGTGGTCAATGTGCGAAATGGA<br>ATGAGCTTGCATGACTGCCTTATGAAAGCACTCAAGGTGA<br>GGGGCCTGCAACCAGAGTGCTGTGCAGTGTTCAGACTTCT<br>CCACGAACACAAAGGTAAAAAAGCACGCTTAGATTGGAAT<br>ACTGATGCTGCGTCTTTGATTGGAGAAGAACTTCAAGTAG<br>ATTTCCTGGATCATGTTCCCCTCACAACACACAACTTTGC<br>TCGGAAGACGTTCCTGAAGCTTGCCTTCTGTGACATCTGT<br>CAGAAATTCCTGCTCAATGGATTTCGATGTCAGACTTGTG<br>GCTACAAATTTCATGAGCACTGTAGCACCAAAGTACCTAC<br>TATGTGTGTGGACTGGAGTAACATCAGACAACTCTTATTG<br>TTTCCAAATTCCACTATTGGTGATAGTGGAGTCCCAGCAC<br>TACCTTCTTTGACTATGCGTCGTATGCGAGAGTCTGTTTC<br>CAGGATGCCTGTTAGTTCTCAGCACAGATATTCTACACCT<br>CACGCCTTCACCTTTAACACCTCCAGTCCCTCATCTGAAG<br>GTTCCCTCTCCCAGAGGCAGAGGTCGACATCCACACCTAA<br>TGTCCACATGGTCAGCACCACCCTGCCTGTGGACAGCAGG<br>ATGATTGAGGATGCAATTCGAAGTCACAGCGAATCAGCCT<br>CACCTTCAGCCCTGTCCAGTAGCCCCAACAATCTGAGCCC<br>AACAGGCTGGTCACAGCCGAAAACCCCCGTGCCAGCACAA<br>AGAGAGCGGGCACCAGTATCTGGGACCCAGGAGAAAAACA<br>AAATTAGGCCTCGTGGACAGAGAGATTCAAGCTATTATTG<br>GGAAATAGAAGCCAGTGAAGTGATGCTGTCCACTCGGATT<br>GGGTCAGGCTCTTTTGGAACTGTTTATAAGGGTAAATGGC<br>ACGGAGATGTTGCAGTAAAGATCCTAAAGGTTGTCGACCC<br>AACCCCAGAGCAATTCCAGGCCTTCAGGAATGAGGTGGCT<br>GTTCTGCGCAAAACACGGCATGTGAACATTCTGCTTTTCA<br>TGGGGTACATGACAAAGGACAACCTGGCAATTGTGACCCA<br>GTGGTGCGAGGGCAGCAGCCTCTACAAACACCTGCATGTC<br>CAGGAGACCAAGTTTCAGATGTTCCAGCTAATTGACATTG<br>CCCGGCAGACGGCTCAGGGAATGGACTATTTGCATGCAAA<br>GAACATCATCCATAGAGACATGAAATCCAACAATATATTT<br>CTCCATGAAGGCTTAACAGTGAAAATTGGAGATTTTGGTT<br>TGGCAACAGTAAAGTCACGCTGGAGTGGTTCTCAGCAGGT<br>TGAACAACCTACTGGCTCTGTCCTCTGGATGGCCCCAGAG<br>GTGATCCGAATGCAGGATAACAACCCATTCAGTTTCCAGT<br>CGGATGTCTACTCCTATGGCATCGTATTGTATGAACTGAT<br>GACGGGGGAGCTTCCTTATTCTCACATCAACAACCGAGAT<br>CAGATCATCTTCATGGTGGGCCGAGGATATGCCTCCCCAG<br>ATCTTAGTAAGCTATATAAGAACTGCCCCAAAGCAATGAA<br>GAGGCTGGTAGCTGACTGTGTGAAGAAAGTAAAGGAAGAG<br>AGGCCTCTTTTTCCCCAGATCCTGTCTTCCATTGAGCTGC<br>TCCAACACTCTCTACCGAAGATCAACCGGAGCGCTTCCGA<br>GCCATCCTTGCATCGGGCAGCCCACACTGAGGATATCAAT<br>GCTTGCACGCTGACCACGTCCCCGAGGCTGCCTGTCTTCT<br>AGTTGACTTTGCACCTGTCTTCAGGCTGCCAGGGGAGGAG<br>GAGAAGCCAGCAGGCACCACTTTTCTGCTCCCTTTCTCCA<br>GAGGCAGAACACATGTTTTCAGAGAAGCTGCTGCTAAGGA<br>CCTTCTAGACTGCTCACAGGGCCTTAACTTCATGTTGCCT<br>TCTTTTCTATCCCTTTGGGCCCTGGGAGAAGGAAGCCATT<br>TGCAGTGCTGGTGTGTCCTGCTCCCTCCCCACATTCCCCA<br>TGCTCAAGGCCCAGCCTTCTGTAGATGCGCAAGTGGATGT<br>TGATGGTAGTACAAAAAGCAGGGGCCCAGCCCCAGCTGTT<br>GGCTACATGAGTATTTAGAGGAAGTAAGGTAGCAGGCAGT<br>CCAGCCCTGATGTGGAGACACATGGGATTTTGGAAATCAG<br>CTTCTGGAGGAATGCATGTCACAGGCGGGACTTTCTTCAG<br>AGAGTGGTGCAGCGCCAGACATTTTGCACATAAGGCACCA<br>AACAGCCCAGGACTGCCGAGACTCTGGCCGCCCGAAGGAG<br>CCTGCTTTGGTACTATGGAACTTTTCTTAGGGGACACGTC<br>CTCCTTTCACAGCTTCTAAGGTGTCCAGTGCATTGGGATG<br>GTTTTCCAGGCAAGGCACTCGGCCAATCCGCATCTCAGCC<br>CTCTCAGGGAGCAGTCTTCCATCATGCTGAATTTTGTCTT<br>CCAGGAGCTGCCCCTATGGGGCGGGGCCGCAGGGCCAGCC<br>TTGTTTCTCTAACAAACAAACAAACAAACAGCCTTGTTTC<br>TCTAGTCACATCATGTGTATACAAGGAAGCCAGGAATACA<br>GGTTTTCTTGATGATTTGGGTTTTAATTTTGTTTTTATTG | |

TABLE 1-continued

GEP-NEN Biomarker/Houskeeper Sequence Information

| Gene Name | RefSeq Accession | Sequence | SEQ ID NO: |
|---|---|---|---|
| | | CACCTGACAAAATACAGTTATCTGATGGTCCCTCAATTAT<br>GTTATTTTAATAAAATAAATTAAATTTAGGTGTAAAAAAA<br>AAAAAAAAAAA | |
| RNF41 | NM_001242826.1 | GATGTCCCAGGGGTATTGGGGCGGGGGGTTGAAATAACTG<br>GGGTTCAGGAGGAGGGATGGTGGTAGAGATAAAAATGTGA<br>GAAGGGAGCAGCACTGGCGAGGAGTCGGGAGAGTACTCCT<br>GATTGTGACATCACATTCATCCCCTGGGCGATGGAGCTTG<br>TCACTGGGAAGGAATACTCAGTCGGAGAATAGCCAACAAG<br>ATGGGTTACTGGGAGAATCTCTTCAGTGGCACTGAGTGGA<br>GGCATCAGGGGGTTGGAGCCTTGTGAACAGGGAACCTGCC<br>CCCCAACACTTGGAAGGACCTGGGTTTCAGTGATGAGACA<br>TGGGGTATGATGTAACCCGTTTCCAGGGGGATGTTGACGA<br>AGATCTTATCTGCCCTATTTGCAGTGGAGTCTTGGAGGAG<br>CCAGTACAGGCACCTCATTGTGAACATGCTTTCTGCAACG<br>CCTGCATCACCCAGTGGTTCTCTCAGCAACAGACATGTCC<br>AGTGGACCGTAGTGTTGTGACGGTCGCCCATCTGCGCCCA<br>GTACCTCGGATCATGCGGAACATGTTGTCAAAGCTGCAGA<br>TTGCCTGTGACAACGCTGTGTTCGGCTGTAGTGCCGTTGT<br>CCGGCTTGACAACCTCATGTCTCACCTCAGCGACTGTGAG<br>CACAACCCGAAGCGGCCTGTGACCTGTGAACAGGGCTGTG<br>GCCTGGAGATGCCCAAAGATGAGCTGCCCAACCATAACTG<br>CATTAAGCACCTGCGCTCAGTGGTACAGCAGCAGCAGACA<br>CGCATCGCAGAGCTGGAGAAGACGTCAGCTGAACACAAAC<br>ACCAGCTGGCGGAGCAGAAGCGAGACATCCAGCTGCTAAA<br>GGCATACATGCGTGCAATCCGCAGTGTCAACCCCAACCTT<br>CAGAACCTGGAGGAGACAATTGAATACAACGAGATCCTAG<br>AGTGGGTGAACTCCCTTCAGCCAGCAAGAGTGACCCGCTG<br>GGGAGGGATGATCTCGACTCCTGATGCTGTGCTCCAGGCT<br>GTAATCAAGCGCTCCCTGGTGGAGAGTGGCTGTCCTGCTT<br>CTATTGTCAACGAGCTGATTGAAAATGCCCACGAGCGTAG<br>CTGGCCCCAGGGTCTGGCCACACTAGAGACTAGACAGATG<br>AACCGACGCTACTATGAGAACTACGTGGCCAAGCGCATCC<br>CTGGCAAGCAGGCTGTTGTCGTGATGGCCTGTGAGAACCA<br>GCACATGGGGGATGACATGGTGCAAGAGCCAGGCCTTGTC<br>ATGATATTTGCGCATGGCGTGGAAGAGATATAAGAGAACT<br>CGACTGGCTATCAGGAAGAGATGGAAATCAGAAAATCCCA<br>TCACTCCAGCAGCTGGGACCTGAGTCCTACCCACCATTCT<br>TAATACTGTGGCTTATACCTGAGCCACACATCTCCCTGCC<br>CTTCTGGCACTGAAGGGCCTTGGGGTAGTTTGCTCAGCCT<br>TTCAGGTGGGAAACCCAGATTTCCTCCCTTTGCCATATTC<br>CCCTAAAATGTCTATAAATTATCAGTCTGGGTGGGAAAGC<br>CCCCACCTCCATCCATTTTCCTGCTTAGGGTCCCTGGTTC<br>CAGTTATTTTCAGAAAGCACAAAGAGATTCAATTTCCCTG<br>GAGGATCAGGACAGAGGAAGGAATCTCTAATCGTCCCTCT<br>CCTCCAAAACCAGGGAATCAGAGCAGTCAGGCCTGTTGAC<br>TCTAAGCAGCAGACATCCTGAAGAAATGGTAAGGGTGGAG<br>CCAAATCTCTAGAAATAAGTAGTGAGGCCGTTAATTGGCC<br>ATCACTGATGGCCCTTAGGGAAAGACTGGACCTCTGTGCC<br>AAGCAGTATCCCTGTTCAGCCCACCTTAAAGGTGTAGGCA<br>CCCACTGGGTCTACCAGTATGCAGGTTGGGATACTGAAAA<br>TTTCCAGATGAGCTCTTCTTTCCTACAAGTTTTCATAATT<br>AGGGAATGCCAGGGTTTAGGGTAGGGGTTAATCTGTTGGG<br>GGTTGATGTGTTTAGCAAGAAGCTACTCCTAGCTTTTGCT<br>AAAATATGGTTGGCACTGCCTCTTGTGGCACAGGCCATAA<br>TTGTTCCATAGACCCCTCTCTAGCCCTGTGACTGTAGTTA<br>GTTACTTTGATAATTTTCTTTGGCCATTGTTTGTTTATAT<br>TTCACAAACTCCACCTACTGCCCCCCCCCCTCTTTTTTTT<br>AAGAATGGCCTGATCATGGCTATCTCAGCCACATTGTTGG<br>CAATTTAATTTATTTACTTCCTTTTTTTTTTTTTAAGAAA<br>GGAAAAAAGAAAAAAAAATCAAACTTGAAACTTTTCTTTT<br>GATGTTCCTATTGTGGGGGTTCTGGATAGGGTGGGACAGG<br>GATGGGGGTGTGTTTTATATTTTTTCCTTTTCAGCACAAC<br>CTTTGGCTTTAATATAGGAAGAGCCAAGGGAGTCCTCGGC<br>TGAACTTACGATATCTGCCCCAAACCTCTGTAACCCCAAC<br>TGAAATGAGGAGCTTCCTCTCTTCCTGTGAAGGATATGAC<br>AGTCCAGCATCGATGCCTGTGCCCTCTGGAAAAATTTCCT<br>CCTAGCCCTTCCAGGGCCTTATCATAAAACTCTGGATTTA<br>GAGTATTCATTTTGAAGGCAACTCCCCCTTCCCCAAGTTT<br>CCTTGGAGCTGTATAGCTGGGTTCTAAGCTTCACCATGCA<br>AATCAGAAATTTTATCTCTAAGTACAGGCTGTGCCGTGTC<br>TCACCCACACCCCCCTGGGGACTTCAGTTCCATTTCAGGT<br>TACCTGGGGTATACCTTGATCCCTAGAGTGACTGGCAGAG<br>TAAGAGAAGGGGAGAGATAATAGGTGTGATTATTTTAATA<br>TGGAGGTGGGAGTGTGGTTGGAGATAGAAAGGCTCCTCCC | 34 |

TABLE 1-continued

GEP-NEN Biomarker/Houskeeper Sequence Information

| Gene Name | RefSeq Accession | Sequence | SEQ ID NO: |
|---|---|---|---|
| | | CACCATGTAATGGCTTCCTCTCAGAATTTTATTCCAGGCT AGCTTGCTGCAGGTCTGGGTAGTTGGATCATGGCTCCACT GGGATTGGGGTGGAAAGCTTGAGGGGAGTAGGGTTCCAGC TCTGGGACATTGTGCTCAGGAATTTGAAAACGCTGCTATA CTTACTCTGGTTACTACATTTCTTCCACTCCCCTTTCCCC TACCTGCCTTAACCAAGGCTCATACTGTCCTGTCCTTACC CTCAGATGGAGCCAGGAAGCTCAGTGAAAGGCTTCCCTAC CCTTTGCACTAGTGTCTCTGCAGGTTGCTGGTTGTGTTGT ATGTGCTGTTCCATGGTGTTGACTGCACTAATAATAAACC TTTTACTCAACTCTCTAAATTCTTCAGCATTACTCCCTTT CTTGAGAAGGTTTCCCCTCTGCTTTTGCCTTTCTCTCACC TTAATTCCCTTTCTTCCTTACTTTGTTACCTACCCTTATC TTAGTGCTAACTTCTCTTTCAGGAGGATGTCTGGGAGTAG TGTGCACTTCACAGCTGCTTTCCCATGTACCCTCCTGCAT TCTTCCCTCCTATCTCCTGTTCTGTAGCAGCCAAAGCTCT CTAGTGATCTGAACTGTGTGCTTCCCAGGGTCTGCCTTTA TCCTAAATTCCATGTCTTCCCTGAGTGGTCCTGAGTTTTT GGGATAATTTCTACAGAAGATATGTATATATCTTTTTCCT TTGTCCCACAAGCAACTTTGCTTTAGAATCTAGAATTCCT TTGCAGGCAGAGAAGTCTCTACCTCCCAGTGTTTCCTAGC TAAGAACGTAAATGTGAGGAGGGAAATGTACTTGCAGAGG TTTCATAATTATTTACTTATAAAAATAGTCTTCATAGCCG GGCGCGGTGGCTCACGCCTGTAATCCCAGCACTTTGGGAG GCCGAGGTGGGTGGATCACAAGGTCAGGAGTTCGAGACCA TCCTGGCTAACACAGTGAAACCCCGTCTCTACTAAAAATA CAAAAAATTAGCCGGGCGTGGTGGCAGGCACCTGTAGTCC CAGCTACTTAGGAGGCTGAGGCAGGAGAATGGCGTGAACC CGGGAGGCAGAGCTTGCAGTGAGCAGAGATTGGGCCACTG CATTCCAGCCTGGGCGACAGAGCAAGGCTCCGTCTAAAAA AAAAAAAAAAAAAAAAAGTCTTCATAGGCCGGGCACGGTG GCTCACGTCTGTAATCCCAGCACTTTGGGAGGCCAAGGTG GGTGGATCACAACGTCAGGAGATCGAGACCATCCTGGCTA ACATGGTGAAACCCTGTCTCTACTAAAAATATAAATAAAT TAGCCGGACAGGCGCCTGTCCTCCCAGCTACTCAGGAGGC TGAGGCAGGAGAATGGTGTGAACCTGGGAGGCGGAGCTTG CAGTGAGCTGAGATCACGCCACTGCACTCCAGCCTGGGCA ACAGAGCAAGACTCCGTCTCAAAAAAAAAAAAAAAAAAAC CAGTCTTCATAAGTATTTGCTGCTACCTTTCCCTGTCATA AGAAAAAGGATAGCCAGACATGGTGGGACGCCACTATGAT CCCAGCTCCTTGGAAGGCTAAGGCACAAGAATCGCTTGAA CCTGGGAGGTGGAGGTTGCAGTGAGCTGAGATCATGCCAC TGCACTCCAGCCTGGTGACAGAGCAAGAGCCTGTCTCAAA AAAAAAAAAGAAAAGAAAAGAAAAAGGGATATCTTTTCCT CCTCCCAGAAGTTTGTTTTAAATTTGAGCATTTATCATGC ACCTGATGTAAACCTAATAGTACTCTTGATACTCTAGTGG CTTGAAAAAAAAAAAAAAGGCATTTCTGTGCTGAGTCTGC GCTTCTATGCACACAAGGTATGTTTATAAAATACTGATAA GCATGTCACAGTATAGAGCATAAGAGGCAATGTATGTATC CTAGTGACATTAGCAGTGCTTTTCCCCCCTTAAACTCCTT TAAAATTACTTTTAGAACTTGCTGCTCATTCTTGTGAATG TTATGAATGGTGTCATATTGTCCTTTTACAGAAGATACGA TTTTTAGAAACAAATATTCATTGAATGTCTGCCCTGTGAG ATACTCACTAGAGTGAACATGAGGAGGCTTATGTAGCAAA ATGGCACCTACCTGCAAAGAACTTAGTCCCTAATGGAGAT GAATATATAATAAGGGATCATAAATGTGCTAAGTGGATTT ACTAGTAATATGTGAGCCAAGGACGATAAAGCTCCTGATT CTGATGGGTATCAGGAAAGGCTTTTCAGGAAGTGTTACTT GTTATAGGTCAGAGGTCAGCAAACTACAGGTTACAACCCC ACTGCCTGCTTTTGTAAAAAACTTTATTGGAATACAGTTA TGCCCACTTGTTTATA | |
| RSF1 | NM_016578.3 | GATCCGCAGAGGAGCCCACTTGAGAGCGCCTCCTGTCGTC TGTAAGGTTGCCTTGCCATCCCTCGGCACCCCAACTTCCC CCGCCCCCCCATCGCCTCCTCCTCCATCCTCCAGTTCAAA ATGGCGACGGCGGCGGCAGCGGCGGCGGTGATGGCTCCTC CGGGCTGCCCGGGTTCGTGCCCCAACTTCGCCGTAGTCTG CTCCTTCTTGGAGCGCTACGGGCCGCTGCTAGACCTGCCT GAGTTGCCGTTCCCTGAGCTGGAGCGGGTGCTGCAGGCGC CGCCGCCGGACGTCGGCAACGGAGAAGTACCAAAAGAATT GGTGGAGCTCCATTTGAAGCTGATGAGGAAAATTGGCAAA TCTGTTACTGCAGACAGATGGGAAAAATATTTGATCAAGA TATGCCAAGAGTTTAACAGTACCTGGGCATGGGAGATGGA GAAGAAGGGCTATCTTGAAATGAGTGTTGAATGCAAACTA GCACTCTTAAAGTACCTCTGTGAGTGTCAGTTTGATGACA ATCTCAAATTCAAGAATATTATTAATGAGGAGGATGCCGA | 35 |

TABLE 1-continued

GEP-NEN Biomarker/Houskeeper Sequence Information

| Gene Name | RefSeq Accession | Sequence | SEQ ID NO: |
|---|---|---|---|
| | | TACTATGCGTCTCCAGCCAATTGGTCGAGACAAAGATGGC<br>CTCATGTACTGGTACCAATTGGATCAAGATCACAATGTCA<br>GAATGTACATAGAAGAACAAGATGATCAAGATGGCTCTTC<br>ATGGAAATGCATTGTCAGAAATCGAAACGAGTTGGCTGAG<br>ACTCTTGCACTCCTGAAAGCACAAATTGATCCTGTACTAT<br>TGAAAAACTCTAGCCAACAAGACAACTCTTCTCGGGAAAG<br>TCCCAGCTTAGAGGATGAGGAGACTAAAAAAGAGGAAGAA<br>ACACCTAAACAAGAGGAACAGAAAGAAAGTGAAAAGATGA<br>AAAGTGAGGAGCAGCCTATGGATTTAGAAAACCGTTCTAC<br>AGCCAATGTTCTAGAAGAGACTACTGTGAAAAAAGAAAAA<br>GAAGATGAAAAGGAACTTGTGAAACTGCCAGTCATAGTGA<br>AGCTAGAAAAACCTTTGCCAGAAAATGAAGAAAAAAAGAT<br>TATCAAAGAAGAAAGTGATTCCTTCAAGGAAAATGTCAAA<br>CCCATTAAAGTTGAGGTGAAGGAATGTAGAGCAGATCCTA<br>AAGATACCAAAAGTAGCATGGAGAAGCCAGTGGCACAGGA<br>GCCTGAAAGGATCGAATTTGGTGGCAATATTAAATCTTCT<br>CACGAAATTACTGAGAAATCTACTGAAGAAACTGAGAAAC<br>TTAAAAATGACCAGCAGGCCAAGATACCACTAAAAAAACG<br>AGAAATTAAACTGAGTGATGATTTTGACAGTCCAGTCAAG<br>GGACCTTTGTGTAAATCAGTTACTCCAACAAAAGAGTTTT<br>TGAAAGATGAAATAAAACAAGAGGAAGAGACTTGTAAAAG<br>GATCTCTACAATCACTGCTTTGGGTCATGAAGGGAAACAG<br>CTGGTAAATGGAGAAGTTAGTGATGAAAGGGTAGCTCCAA<br>ATTTTAAGACAGAACCAATAGAGACAAAGTTTTATGAGAC<br>AAAGGAAGAGAGCTATAGCCCCTCTAAGGACAGAAATATC<br>ATCACGGAGGGAAATGGAACAGAGTCCTTAAATTCTGTCA<br>TAACAAGTATGAAAACAGGTGAGCTTGAGAAAGAAACAGC<br>CCCTTTGAGGAAAGATGCAGATAGTTCAATATCAGTCTTA<br>GAGATCCATAGTCAAAAAGCACAAATAGAGGAACCCGATC<br>CTCCAGAAATGGAAACTTCTCTTGATTCTTCTGAGATGGC<br>AAAAGATCTCTCTTCAAAAACTGCTTTATCTTCCACCGAG<br>TCGTGTACCATGAAAGGTGAAGAGAAGTCTCCCAAAACTA<br>AGAAGGATAAGCGCCCACCAATCCTAGAATGTCTTGAAAA<br>GTTAGAGAAGTCCAAAAAGACTTTTCTTGATAAGGACGCA<br>CAAAGATTGAGTCCAATACCAGAAGAAGTTCCAAAGAGTA<br>CTCTAGAGTCAGAAAAGCCTGGCTCTCCTGAGGCAGCTGA<br>AACTTCTCCACCATCTAATATCATTGACCACTGTGAGAAA<br>CTAGCCTCAGAAAAAGAAGTGGTAGAATGCCAGAGTACAA<br>GTACTGTTGGTGGCCAGTCTGTGAAAAAAGTAGACCTAGA<br>AACCCTAAAAGAGGATTCTGAGTTCACAAAGGTAGAAATG<br>GATAATCTGGACAATGCCCAGACCTCTGGCATAGAGGAGC<br>CTTCTGAGACAAAGGGTTCTATGCAAAAAAGCAAATTCAA<br>ATATAAGTTGGTTCCTGAAGAAGAAACCACTGCCTCAGAA<br>AATACAGAGATAACCTCTGAAAGGCAGAAAGAGGGCATCA<br>AATTAACAATCAGGATATCAAGTCGGAAAAAGAAGCCCGA<br>TTCTCCCCCCAAAGTTCTAGAACCAGAAAACAAGCAAGAG<br>AAGACAGAAAAGGAAGAGGAGAAAACAAATGTGGGTCGTA<br>CTTTAAGAAGATCTCCAAGAATATCTAGACCCACTGCAAA<br>AGTGGCTGAGATCAGAGATCAGAAAGCTGATAAAAAAAGA<br>GGGGAAGGAGAAGATGAGGTGGAAGAAGAGTCAACAGCTT<br>TGCAAAAAACTGACAAAAAGGAAATTTTGAAAAAATCAGA<br>GAAAGATACAAATTCTAAAGTAAGCAAGGTAAAACCCAAA<br>GGCAAAGTTCGATGGACTGGTTCTCGGACACGTGGCAGAT<br>GGAAATATTCCAGCAATGATGAAAGTGAAGGGTCTGGCAG<br>TGAAAAATCATCTGCAGCTTCAGAAGAGGAGGAAGAAAAG<br>GAAAGTGAAGAAGCCATCCTAGCAGATGATGATGAACCAT<br>GCAAAAAATGTGGCCTTCCAAACCATCCTGAGCTAATTCT<br>TCTGTGTGACTCTTGCGATAGTGGATACCATACTGCCTGC<br>CTTCGCCCTCCTCTGATGATCATCCCAGATGGAGAATGGT<br>TCTGCCCACCTTGCCAACATAAACTGCTCTGTGAAAAATT<br>AGAGGAACAGTTGCAGGATTTGGATGTTGCCTTAAAGAAG<br>AAAGAGCGTGCCGAACGAAGAAAAGAACGCTTGGTGTATG<br>TTGGTATCAGTATTGAAAACATCATTCCTCCACAAGAGCC<br>AGACTTTTCTGAAGATCAAGAAGAAAAGAAAAAAGATTCA<br>AAAAAATCCAAAGCAAACTTGCTTGAAAGGAGGTCAACAA<br>GAACAAGGAAATGTATAAGCTACAGATTTGATGAGTTTGA<br>TGAAGCAATTGATGAAGCTATTGAAGATGACATCAAAGAA<br>GCCGATGGAGGAGGAGTTGGCCGAGGAAAAGATATCTCCA<br>CCATCACAGGTCATCGTGGGAAAGACATCTCTACTATTTT<br>GGATGAAGAAAGAAAAGAAAATAAACGACCCCAGAGGGCA<br>GCTGCTGCTCGAAGGAAGAAACGCCGGCGATTAAATGATC<br>TGGACAGTGATAGCAACCTGGATGAAGAAGAGAGCGAGGA<br>TGAATTCAAGATCAGTGATGGATCTCAAGATGAGTTTGTT<br>GTGTCTGATGAAAACCCAGATGAAAGTGAAGAAGATCCGC<br>CATCTAATGATGACAGTGACACTGACTTTTGTAGCCGTAG | |

TABLE 1-continued

GEP-NEN Biomarker/Houskeeper Sequence Information

| Gene Name | RefSeq Accession | Sequence | SEQ ID NO: |
|---|---|---|---|
| | | ACTGAGGCGACACCCCTCTCGGCCAATGAGGCAGAGCAGG CGTTTGCGAAGAAAGACCCCAAAGAAAAAATATTCCGATG ATGATGAAGAGGAGGAATCTGAGGAGAATAGTAGAGACTC TGAAAGTGACTTCAGTGATGATTTTAGTGATGATTTTGTA GAAACTCGGCGAAGGCGGTCAAGGAGAAATCAGAAAAGAC AAATTAACTACAAAGAAGACTCAGAAAGTGACGGTTCCCA GAAGAGTTTGCGACGTGGTAAAGAAATAAGGCGAGTACAC AAGCGAAGACTTTCCAGCTCAGAGAGTGAAGAGAGCTATT TGTCCAAGAACTCTGAAGATGATGAGCTAGCTAAAGAATC AAAGCGGTCAGTTCGAAAGCGGGGCCGAAGCACAGACGAG TATTCAGAAGCAGATGAGGAGGAGGAGGAAGAGGAAGGCA AACCATCCCGCAAACGGCTACACCGGATTGAGACGGATGA GGAGGAGAGTTGTGACAATGCTCATGGAGATGCAAATCAG CCTGCCCGTGACAGCCAGCCTAGGGTCCTGCCCTCAGAAC AAGAGAGCACCAAGAAGCCCTACCGGATAGAAAGTGATGA GGAAGAGGACTTTGAAAATGTAGGCAAAGTGGGGAGCCCA TTGGACTATAGCTTAGTGGACTTACCTTCAACCAATGGAC AGAGCCCTGGCAAAGCCATTGAGAACTTGATTGGCAAGCC TACTGAGAAGTCTCAGACCCCCAAGGACAACAGCACAGCC AGTGCAAGCCTAGCCTCCAATGGGACAAGTGGTGGGCAGG AGGCAGGAGCACCAGAAGAGGAGGAAGATGAGCTTTTGAG AGTGACTGACCTTGTTGATTATGTCTGTAACAGTGAACAG TTATAAGACTTTTTTTCCATTTTTGTGCTAATTTATTCCA CGGTAGCTCTCACACCAGCGGGCCAGTTATTAAAAGCTGT TTAATTTTTCCTAGAAAACTCCACTACAGAATGACTTTTA GAAGAAAAAATTTCAACAAATCCTGAAGTCTTTCTGTGAAG TGACCAGTTCTGAACTTTGAAGATAAATAATTGCTGTAAA TTCCTTTTGATTTTCTTTTTCCAGGTTCATGGTCCTTGGT AATTTCATTCATGGAAAAAAATCTTATTATAATAACAACA AAGATTTGTATATTTTTGACTTTATATTTCCTGAGCTCTC CTGACTTTGTGAAAAAGGGTGGATGAAAATGCATTCCGAA TCTGTGAGGGCCCAAAACAGAATTTAGGGGTGGGTGAAAG CACTTGTGCTTTAGCTTTTTCATATTAAATATATATTATA TTTAAACATTCATGGCATAGATGATGATTTACAGACAATT TAAAAGTTCAAGTCTGTACTGTTACAGTTTGAGAATTGTA GATAACATCATACATAAGTCATTTAGTAACAGCCTTTGTG AAATGAACTTGTTTACTATTGGAGATAACCACACTTAATA AAGAAGAGACAGTGAAAGTACCATCATAATTAACCTAAAT TTTTGTTATAGCAGAGTTTCTTGTTTAAAAAAAAATAAAA TCATCTGAAAAGCAAAAA | |
| RTN2 | NM_005619.4 | CGCGCGCTGCAGTGCCTTCCCCACCTCGGCCCCGCCCGCC CCCGCCGAGCCGAGCACCAGGGCGGCGGCGGCGGCGGCGG CGGCGGCGGCGGCTGGAGCAGCCCGGGAGGAGGAGGCGGC GAGAATGGCAGCGGCGTCGTGGGCGCGGCGGAGATGAGCG CCCGCGACCCCGGGCCCAGGGCGGCACAGCCGGAGTGGGC GGGGGTCCCGATGCAGGCCCGAGGGGGGCCATGGGGCAGG TCCTGCCGGTCTTCGCCCACTGCAAAGAAGCTCCGTCTAC AGCCTCCTCAACTCCTGATTCCACAGAAGGAGGGAACGAC GACTCTGATTTTCGAGAGCTGCACACAGCCCGGGAATTCT CAGAGGAGGACGAGGAGGAGACCACGTCGCAGGACTGGGG CACCCCCCGGGAGCTGACCTTCTCCTACATCGCCTTTGAT GGTGTAGTGGGCTCCGGGGGCCGCAGGGATTCAACTGCCC GCCGCCCCCGCCCCCAGGGCCGCTCAGTCTCGGAACCACG AGACCAGCACCCTCAGCCCAGCCTGGGCGACAGCTTGGAG AGCATCCCCAGCCTGAGCCAATCCCCGGAGCCTGGACGAC GGGGTGATCCTGACACCGCGCCTCCATCCGAGCGCCCTCT GGAAGACCTGAGGCTTCGGTTGGACCATCTGGGCTGGGTG GCCCGGGGAACGGGATCCGGGGAGGACTCTTCCACCAGCA GCTCCACCCCGCTGGAAGACGAAGAACCCCAAGAACCCAA CAGATTGGAGACAGGAGAAGCTGGGGAAGAACTGGACCTA CGACTCCGACTTGCTCAGCCCTCATCGCCCGAGGTCTTGA CTCCCCAGCTCAGTCCGGGCTCTGGGACACCCCAGGCCGG TACTCCGTCCCCATCCCGATCGCGAGATTCGAACTCTGGG CCCGAAGAGCCATTGCTGGAAGAGGAAGAAAAGCAGTGGG GGCCACTGGAGCGAGAGCCAGTAAGGGGACAGTGCCTCGA TAGCACGGACCAATTAGAATTCACGGTGGAGCCACGCCTT CTAGGAACAGCTATGGAATGGTTAAAGACATCATTGCTTT TGGCTGTTTACAAGACGGTTCCAATTTTGGAATTGTCCCC ACCTCTGTGGACAGCCATTGGCTGGGTCCAAAGGGGCCCC ACCCCCCCTACTCCTGTCCTCCGGGTTCTACTGAAGTGGG CAAAATCCCCGAGAAGCAGCGGTGTCCCCAGCCTCTCACT CGGAGCCGATATGGGGAGTAAAGTGGCGGACCTGCTGTAC TGGAAGGACACGAGGACGTCAGGAGTGGTCTTCACAGGCC TGATGGTCTCCCTCCTCTGCCTCCTGCACTTTAGCATCGT | 36 |

TABLE 1-continued

GEP-NEN Biomarker/Houskeeper Sequence Information

| Gene Name | RefSeq Accession | Sequence | SEQ ID NO: |
|---|---|---|---|
| | | GTCCGTGGCCGCGCACTTGGCTCTGTTGCTGCTCTGCGGC<br>ACCATCTCTCTCAGGGTTTACCGCAAAGTGCTGCAGGCCG<br>TGCACCGGGGGGATGGAGCCAACCCTTTCCAGGCCTACCT<br>GGATGTGGACCTCACCCTGACTCGGGAGCAGACGGAACGT<br>TTGTCCCACCAGATCACCTCCCGCGTGGTCTCGGCGGCCA<br>CGCAGCTGCGGCACTTCTTCCTGGTAGAAGACCTCGTGGA<br>TTCCCTCAAGCTGGCCCTCCTCTTCTACATCTTGACCTTC<br>GTGGGTGCCATCTTCAATGGTTTGACTCTTCTCATTCTGG<br>GAGTGATTGGTCTATTCACCATCCCCCTGCTGTACCGGCA<br>GCACCAGGCTCAGATCGACCAATATGTGGGGTTGGTGACC<br>AATCAGTTGAGCCACATCAAAGCTAAGATCCGAGCTAAAA<br>TCCCAGGGACCGGAGCCCTGGCCTCTGCAGCAGCCGCAGT<br>CTCCGGATCCAAAGCCAAAGCCGAATGAGAACGGTGTCTC<br>TGCCCGCAGGACGCCTGCCCCCAGCCCCCGCAGCCCTCTG<br>GCCCCCTCCATCTCTTGTCCGTTCCCACCCACCCCCCTCC<br>TCGGCCCGAGCCTTTTCCCGGTGGGTGTCAGGATCACTCC<br>CACTAGGGACTCTGCGCTAATTACCTGAGCGACCAGGACT<br>ACATTTCCCAAGAGGCTCTGCTCCAGGAGTCCAGGAAAGA<br>CGAGGCACCTTGGCCGCGGGGCCTGCTGGGACTTGTAGTT<br>GCCTAGACAGGGCACCACCCTGCACTTCCGGACCCGCCGC<br>TGGAGGCGCCGTGAGGCGTTGGTGTCTCCTGGATGCTACT<br>AGCCCCAACGCCGGGGCTTTGCATGGGGCCCAGGGGAGGC<br>CTGAGCTTGGATTTACACTGTAATAAAGACTCCTGTGGAA<br>AACCCGAG | |
| SMARCD3 | NM_001003801.1 | AGCAGGACTCAGAGGGGAGAGTTGGAGGAAAAAAAAAGGC<br>AGAAAAGGGAAAGAAAGAGGAAGAGAGAGAGAGAGTGAGA<br>GGAGCCGCTGAGCCCACCCCGATGGCCGCGGACGAAGTTG<br>CCGGAGGGGGCGCGCAAAGCCACGAAAAGCAAACTTTTGA<br>GTTTCTGGTCCATGGGGTGCGCCCCGGGATGCCGTCTGGA<br>GCCCGGATGCCCCACCAGGGGGCGCCCATGGGCCCCCCGG<br>GCTCCCCGTACATGGGCAGCCCCGCCGTGCGACCCGGCCT<br>GGCCCCCGCGGGCATGGAGCCCGCCCGCAAGCGAGCAGCG<br>CCCCCGCCCGGGCAGAGCCAGGCACAGAGCCAGGGCCAGC<br>CGGTGCCCACCGCCCCCGCGCGGAGCCGCAGTGCCAAGAG<br>GAGGAAGATGGCTGACAAAATCCTCCCTCAAAGGATTCGG<br>GAGCTGGTCCCCGAGTCCCAGGCTTACATGGACCTCTTGG<br>CATTTGAGAGGAAACTGGATCAAACCATCATGCGGAAGCG<br>GGTGGACATCCAGGAGGCTCTGAAGAGGCCCATGAAGCAA<br>AAGCGGAAGCTGCGACTCTATATCTCCAACACTTTTAACC<br>CTGCGAAGCCTGATGCTGAGGATTCCGACGGCAGCATTGC<br>CTCCTGGGAGCTACGGGTGGAGGGGAAGCTCCTGGATGAT<br>CCCAGCAAACAGAAGCGGAAGTTCTCTTCTTTCTTCAAGA<br>GTTTGGTCATCGAGCTGGACAAAGATCTTTATGGCCCTGA<br>CAACCACCTCGTTGAGTGGCATCGGACACCCACGACCCAG<br>GAGACGGACGGCTTCCAGGTGAAACGGCCTGGGGACCTGA<br>GTGTGCGCTGCACGCTGCTCCTCATGCTGGACTACCAGCC<br>TCCCCAGTTCAAACTGGATCCCCGCCTAGCCCGGCTGCTG<br>GGGCTGCACACACAGAGCCGCTCAGCCATTGTCCAGGCCC<br>TGTGGCAGTATGTGAAGACCAACAGGCTGCAGGACTCCCA<br>TGACAAGGAATACATCAATGGGGACAAGTATTTCCAGCAG<br>ATTTTTGATTGTCCCCGGCTGAAGTTTTCTGAGATTCCCC<br>AGCGCCTCACAGCCCTGCTATTGCCCCCTGACCCAATTGT<br>CATCAACCATGTCATCAGCGTGGACCCTTCAGACCAGAAG<br>AAGACGGCGTGCTATGACATTGACGTGGAGGTGGAGGAGC<br>CATTAAAGGGGCAGATGAGCAGCTTCCTCCTATCCACGGC<br>CAACCAGCAGGAGATCAGTGCTCTGGACAGTAAGATCCAT<br>GAGACGATTGAGTCCATAAACCAGCTCAAGATCCAGAGGG<br>ACTTCATGCTAAGCTTCTCCAGAGACCCCAAAGGCTATGT<br>CCAAGACCTGCTCCGCTCCCAGAGCCGGGACCTCAAGGTG<br>ATGACAGATGTAGCCGGCAACCCTGAAGAGGAGCGCCGGG<br>CTGAGTTCTACCACCAGCCCTGGTCCCAGGAGGCCGTCAG<br>TCGCTACTTCTACTGCAAGATCCAGCAGCGCAGGCAGGAG<br>CTGGAGCAGTCGCTGGTTGTGCGCAACACCTAGGAGCCCA<br>AAAATAAGCAGCACGACGGAACTTTCAGCCGTGTCCCGGG<br>CCCCAGCATTTTGCCCCGGGCTCCAGCATCACTCCTCTGC<br>CACCTTGGGGTGTGGGGCTGGATTAAAAGTCATTCATCTG<br>ACAAAAAAAAAAAAAAAAAA | 37 |
| SPATA7 | NM_001040428.3 | ACAATAGCGACTCACTGGACCCAGCCCTTAGCAACGGCCT<br>GGCGACGGTTTCCCTGCTGCTGCAGCCCCCGTCGGCTCCT<br>CTTTTCCAGTCCTCCACTGCCGGGGCTGGGCCCGGCCGCG<br>GGAAGGACCGAAGGGGATACAGCGTGTCCCTGCGGCGGCT<br>GCAAGAGGACTAAGCATGGATGGCAGCCGGAGAGTCAGAG<br>CAACCTCTGTCCTTCCCAGATATGGTCCACCGTGCCTATT | 38 |

TABLE 1-continued

| GEP-NEN Biomarker/Houskeeper Sequence Information | | | |
|---|---|---|---|
| Gene Name | RefSeq Accession | Sequence | SEQ ID NO: |
| | | TAAAGGACACTTGAGCACCAAAAGTAATGCTGCAGTAGAC<br>TGCTCGGTTCCAGTAAGCGTGAGTACCAGCATAAAGTATG<br>CAGACCAACAACGAAGAGAGAAACTCAAAAAGGAATTAGC<br>ACAATGTGAAAAAGAGTTCAAATTAACTAAAACTGCAATG<br>CGAGCCAATTATAAAAATAATTCCAAGTCACTTTTTAATA<br>CCTTACAAAAGCCCTCAGGCGAACCGCAAATTGAGGATGA<br>CATGTTAAAAGAAGAAATGAATGGATTTTCATCCTTTGCA<br>AGGTCACTAGTACCCTCTTCAGAGAGACTACACCTAAGTC<br>TACATAAATCCAGTAAAGTCATCACAAATGGTCCTGAGAA<br>GAACTCCAGTTCCTCCCCGTCCAGTGTGGATTATGCAGCC<br>TCCGGGCCCCGGAAACTGAGCTCTGGAGCCCTGTATGGCA<br>GAAGGCCCAGAAGCACATTCCCAAATTCCCACCGGTTTCA<br>GTTAGTCATTTCGAAAGCACCCAGTGGGGATCTTTTGGAT<br>AAACATTCTGAACTCTTTTCTAACAAACAATTGCCATTCA<br>CTCCTCGCACTTTAAAAACAGAAGCAAAATCTTTCCTGTC<br>ACAGTATCGCTATTATACACCTGCCAAAAGAAAAAAGGAT<br>TTTACAGATCAACGGATAGAAGCTGAAACCCAGACTGAAT<br>TAAGCTTTAAATCTGAGTTGGGGACAGCTGAGACTAAAAA<br>CATGACAGATTCAGAAATGAACATAAAGCAGGCATCTAAT<br>TGTGTGACATATGATGCCAAAGAAAAAATAGCTCCTTTAC<br>CTTTAGAAGGGCATGACTCAACATGGGATGAGATTAAGGA<br>TGATGCTCTTCAGCATTCCTCACCAAGGGCAATGTGTCAG<br>TATTCCCTGAAGCCCCCTTCAACTCGTAAAATCTACTCTG<br>ATGAAGAAGAACTGTTGTATCTGAGTTTCATTGAAGATGT<br>AACAGATGAAATTTTGAAACTTGGTTTATTTTCAAACAGG<br>TTTTTAGAACGACTGTTCGAGCGACATATAAAACAAAATA<br>AACATTTGGAGGAGGAAAAAATGCGCCACCTGCTGCATGT<br>CCTGAAAGTAGACTTAGGCTGCACATCGGAGGAAAACTCG<br>GTAAAGCAAAATGATGTTGATATGTTGAATGTATTTGATT<br>TTGAAAAGGCTGGGAATTCAGAACCAAATGAATTAAAAAA<br>TGAAAGTGAAGTAACAATTCAGCAGGAACGTCAACAATAC<br>CAAAAGGCTTTGGATATGTTATTGTCGGCACCAAAGGATG<br>AGAACGAGATATTCCCTTCACCAACTGAATTTTTCATGCC<br>TATTTATAAATCAAAGCATTCAGAAGGGGTTATAATTCAA<br>CAGGTGAATGATGAAACAAATCTTGAAACTTCAACTTTGG<br>ATGAAAATCATCCAAGTATTTCAGACAGTTTAACAGATCG<br>GGAAACTTCTGTGAATGTCATTGAAGGTGATAGTGACCCT<br>GAAAAGGTTGAGATTTCAAATGGATTATGTGGTCTTAACA<br>CATCACCCTCCCAATCTGTTCAGTTCTCCAGTGTCAAAGG<br>CGACAATAATCATGACATGGAGTTATCAACTCTTAAAATC<br>ATGGAAATGAGCATTGAGGACTGCCCTTTGGATGTTTAAT<br>CTTCATTAATAAATACCTCAAATGGCCAGTAACTCAAAAA<br>AAAAAAAAAAAAAAA | |
| SST1 | NM_001049.2 | TGGTCATCGCACGGCGGCAGCTCCTCACCTGGATTTAGAA<br>GAGCTGGCGTCCCCGCCCGCCCAAGCCTTTAAACTCTCGT<br>CTGCCAGAACCCGCCAACTCTCCAGGCTTAGGGCCAGTTT<br>CCGCGATTCTAAGAGTAATTGCGTGGGCACCTGTGCTGGG<br>GCCAGGCGCAAAGAAGGGAGTTGGTCTGCGCGAAGATCGT<br>CAACCTGCTAACAGACCGCACATGCACTTTGCACCGACCA<br>TCTACGTCTCAGTCTGGAGGTTGCGCACTTTGGCTGCTGA<br>CGCGCTGGTGGTGCCTATTAATCATTTACCAGTCCAGAGC<br>CGCGCCAGTTAATGGCTGTGCCGTGCGGTGCTCCCACATC<br>CTGGCCTCTCCTCTCCACGGTCGCCTGTGCCCGGGCACCC<br>CGGAGCTGCAAACTGCAGAGCCCAGGCAACCGCTGGGCTG<br>TGCGCCCCGCCGGCGCCGGTAGGAGCCGCGCTCCCCGCAG<br>CGGTTGCGCTCTACCCGGAGGCGCTGGGCGGCTGTGGGCT<br>GCAGGCAAGCGGTCGGGTGGGGAGGGAGGGCGCAGGCGGC<br>GGGTGCGCGAGGAGAAAGCCCCAGCCCTGGCAGCCCCACT<br>GGCCCCCCTCAGCTGGGATGTTCCCCAATGGCACCGCCTC<br>CTCTCCTTCCTCCTCTCCTAGCCCCAGCCCGGGCAGCTGC<br>GGCGAAGGCGGCGGCAGCAGGGGCCCCGGGGCCGGCGCTG<br>CGGACGGCATGGAGGAGCCAGGGCGAAATGCGTCCCAGAA<br>CGGGACCTTGAGCGAGGGCCAGGGCAGCGCCATCCTGATC<br>TCTTTCATCTACTCCGTGGTGTGCCTGGTGGGGCTGTGTG<br>GGAACTCTATGGTCATCTACGTGATCCTGCGCTATGCCAA<br>GATGAAGACGGCCACCAACATCTACATCCTAAATCTGGCC<br>ATTGCTGATGAGCTGCTCATGCTCAGCGTGCCCTTCCTAG<br>TCACCTCCACGTTGTTGCGCCACTGGCCCTTCGGTGCGCT<br>GCTCTGCCGCCTCGTGCTCAGCGTGGACGCGGTCAACATG<br>TTCACCAGCATCTACTGTCTGACTGTGCTCAGCGTGGACC<br>GCTACGTGGCCGTGGTGCATCCCATCAAGGCGGCCCGCTA<br>CCGCCGGCCCACCGTGGCCAAGGTAGTAAACCTGGGCGTG<br>TGGGTGCTATCGCTGCTCGTCATCCTGCCCATCGTGGTCT<br>TCTCTCGCACCGCGGCCAACAGCGACGGCACGGTGGCTTG | 39 |

TABLE 1-continued

GEP-NEN Biomarker/Houskeeper Sequence Information

| Gene Name | RefSeq Accession | Sequence | SEQ ID NO: |
|---|---|---|---|
| | | CAACATGCTCATGCCAGAGCCCGCTCAACGCTGGCTGGTG | |
| | | GGCTTCGTGTTGTACACATTTCTCATGGGCTTCCTGCTGC | |
| | | CCGTGGGGGCTATCTGCCTGTGCTACGTGCTCATCATTGC | |
| | | TAAGATGCGCATGGTGGCCCTCAAGGCCGGCTGGCAGCAG | |
| | | CGCAAGCGCTCGGAGCGCAAGATCACCTTAATGGTGATGA | |
| | | TGGTGGTGATGGTGTTTGTCATCTGCTGGATGCCTTTCTA | |
| | | CGTGGTGCAGCTGGTCAACGTGTTTGCTGAGCAGGACGAC | |
| | | GCCACGGTGAGTCAGCTGTCGGTCATCCTCGGCTATGCCA | |
| | | ACAGCTGCGCCAACCCCATCCTCTATGGCTTTCTCTCAGA | |
| | | CAACTTCAAGCGCTCTTTCCAACGCATCCTATGCCTCAGC | |
| | | TGGATGGACAACGCCGCGGAGGAGCCGGTTGACTATTACG | |
| | | CCACCGCGCTCAAGAGCCGTGCCTACAGTGTGGAAGACTT | |
| | | CCAACCTGAGAACCTGGAGTCCGGCGGCGTCTTCCGTAAT | |
| | | GGCACCTGCACGTCCCGGATCACGACGCTCTGAGCCCGGG | |
| | | CCACGCAGGGGCTCTGAGCCCGGGCCACGCAGGGGCCCTG | |
| | | AGCCAAAAGAGGGGGAGAATGAGAAGGGAAGGCCGGGTGC | |
| | | GAAAGGGACGGTATCCAGGGCGCCAGGGTGCTGTCGGGAT | |
| | | AACGTGGGGCTAGGACACTGACAGCCTTTGATGGAGGAAC | |
| | | CCAAGAAAGGCGCGCGACAATGGTAGAAGTGAGAGCTTTG | |
| | | CTTATAAACTGGGAAGGCTTTCAGGCTACCTTTTTCTGGG | |
| | | TCTCCCACTTTCTGTTCCTTCCTCCACTGCGCTTACTCCT | |
| | | CTGACCCTCCTTCTATTTTCCCTACCCTGCAACTTCTATC | |
| | | CTTTCTTCCGCACCGTCCCGCCAGTGCAGATCACGAACTC | |
| | | ATTAACAACTCATTCTGATCCTCAGCCCCTCCAGTCGTTA | |
| | | TTTCTGTTTGTTTAAGCTGAGCCACGGATACCGCCACGGG | |
| | | TTTCCCTCGGCGTTAGTCCCTAGCCGCGCGGGGCCGCTGT | |
| | | CCAGGTTCTGTCTGGTGCCCCTACTGGAGTCCCGGGAATG | |
| | | ACCGCTCTCCCTTTGCGCAGCCCTACCTTAAGGAAAGTTG | |
| | | GACTTGAGAAAGATCTAAGCAGCTGGTCTTTTCTCCTACT | |
| | | CTTGGGTGAAGGTGCATCTTTCCCTGCCCTCCCCTGTCCC | |
| | | CCTCTCGCCGCCCGCCCGCCACCACCACTCTCACTCCACC | |
| | | CAGAGTAGAGCCAGGTGCTTAGTAAAATAGGTCCCGCGCT | |
| | | TCGAACTCCAGGCTTTCTGGAGTTCCCACCCAAGCCCTCC | |
| | | TTTGGAGCAAAGAAGGAGCTGAGAACAAGCCGAATGAGGA | |
| | | GTTTTTATAAGATTGCGGGGTCGGAGTGTGGGCGCGTAAT | |
| | | AGGAATCACCCTCCTACTGCGCGTTTTCAAAGACCAAGCG | |
| | | CTGGGCGCTCCCGGGCCGCGCGTCTGCGTTAGGCAGGGCA | |
| | | GGGTAGTGCAGGGCACACCTTCCCCGGGGTTCGGGGTTCG | |
| | | GGGTTCGGTTGCAGGGCTGCAGCCCGCCTTGGCTTTCTCC | |
| | | CTCACCCAAGTTTCCGGAGGAGCCGACCTAAAAGTAACAA | |
| | | TAGATAAGGTTTCCTGCTCCAGTGTATCTCAAAAGACCGG | |
| | | GCGCCAGGGGCGGGGGACCTAGGGCGACGTCTTCAGAGTC | |
| | | CGCCAGTGTTGGCGGTGTCGCCGCAACCTGCAGGCTCCCG | |
| | | AGTGGGGCCTGCCTGGTCTCTAGAGGGTTGCTGCCTTTCA | |
| | | AGCGGTGCCTAAGAAGTTATTTTCTTGTTTAACATATATA | |
| | | TTTATTAATTTATTTGTCGTGTTGGAAAATGTGTCTCTGC | |
| | | TTTCCTTTTCTCTGCTTGCCTAGCCCCAGGTCTTTTCTTT | |
| | | GGGACCCTGGGGGCGGGCATGGAAGTGGAAGTAGGGGCAA | |
| | | GCTCTTGCCCCACTCCCTGGCCATCTCAACGCCTCTCCTC | |
| | | AATGCTGGGCCCTCTTATCTCATCCTTTCCTCTAGCTTTT | |
| | | CTATTTTTGATTGTGTTGAGTGAAGTTTGGAGATTTTTCA | |
| | | TACTTTTCTTACTATAGTCTCTTGTTTGTCTTATTAGGAT | |
| | | AATACATAAATGATAATGTGGGTTATCCTCCTCTCCATGC | |
| | | ACAGTGGAAAGTCCTGAACTCCTGGCTTTCCAGGAGACAT | |
| | | ATATAGGGGAACATCACCCTATATATAATTTGAGTGTATA | |
| | | TATATTTATATATATGATGTGGACATATGTATACTTATCT | |
| | | TGCTCCATTGTCATGAGTCCATGAGTCTAAGTATAGCCAC | |
| | | TGATGGTGACAGGTGTGAGTCTGGCTGGAACACTTTCAGT | |
| | | TTCAGGAGTGCAAGCAGCACTCAAACCTGGAGCTGAGGAA | |
| | | TCTAATTCAGACAGAGACTTTAATCACTGCTGAAGATGCC | |
| | | CCTGCTCCCTCTGGGTTCCAGCAGAGGTGATTCTTACATA | |
| | | TGATCCAGTTAACATCATCACTTTTTTTGAGGACATTGAA | |
| | | AGTGAAATAATTTGTGTCTGTGTTTAATATTACCAACTAC | |
| | | ATTGGAAGCCTGAGCAGGGCGAGGACCAATAATTTTAATT | |
| | | ATTTATATTTCCTGTATTGCTTTAGTATGCTGGCTTGTAC | |
| | | ATAGTAGGCACTAAATACATGTTTGTTGGTTGATTGTTTA | |
| | | AGCCAGAGTGTATTACAACAATCTGGAGATACTAAATCTG | |
| | | GGGTTCTCAGGTTCACTCATTGACATGATATACAATGGTT | |
| | | AAAATCACTATTGAAAAATACGTTTTGTGTATATTTGCTT | |
| | | CAACAACTTTGTGCTTTCCTGAAAGCAGTAACCAAGAGTT | |
| | | AAGATATCCCTAATGTTTTGCTTAAACTAATGAACAAATA | |
| | | TGCTTTGGGTCATAAATCAGAAAGTTTAGATCTGTCCCTT | |
| | | AATAAAAATATATATTACTACTCCTTTGGAAAATAGATTT | |
| | | TTAATGGTTAAGAACTGTGAAATTTACAAATCAAAATCTT | |
| | | AATCATTATCCTTCTAAGAGGATACAAATTTAGTGCTCTT | |

TABLE 1-continued

GEP-NEN Biomarker/Houskeeper Sequence Information

| Gene Name | RefSeq Accession | Sequence | SEQ ID NO: |
|---|---|---|---|
| | | AACTTGTTACCATTGTAATATTAACTAAATAAACAGATGT<br>ATTATGCTGTTAAAAAAAAAAAAAAAAAAAAAAAAAAAAA<br>AAAAAAAAAAAAAAAAAAAAAAA | |
| SST3 | NM_001051.4 | CTGCATCTCTCCCTCTCACCCGTGTCTCCTCTCCTCTCTT<br>TCCTTCTCGTCTTCTCCCTGTCACGCATCTCTCATCACTC<br>CCCCTCATTCTGCCTTTCCTCCTACTCACGGTCTCCTCTC<br>CCTCTCCCTCTCTCTCTCTCCCCCTCCCTCTTTCTCTCTC<br>TCTCTCTTTCTCCACCTCCTCCCGACCCCCTTTCCCCTCT<br>ATTTCTATTGGCTTCTGTGTCCCTTGCTCCCCTCTTCTCT<br>TCCTCACCCTGGGAAGCTTCTCCCCCCTATCCTTGCCCCT<br>GCCCCCCCAGGATGTGTCCTGGAGATGGGGGGTGACGTAC<br>CAGGCTCTGGTTGGGAAGTCAGGGCCGGAGACCAGATGGG<br>AGAGGCTCTGTGGACAGCCGTGGCCGAGGGCCTGGGAGGG<br>AACCTGAGCCCGCAAGCGGTCTAGAAGTGGGTGCCTTGTG<br>GGGACCCTAGTTAGGAGTGCCCTGGGGGCACCTGGGGACT<br>GGGCAGGGAGAGGGGACAGCAGAATGATAACCAGCCTGGC<br>GGCAAGGAGGGAAGCCCTCACCCCATGGGCAGGCAAATAG<br>CTGACTGCTGACCACCCTCCCCTCAGCCATGGACATGCTT<br>CATCCATCATCGGTGTCCACGACCTCAGAACCTGAGAATG<br>CCTCCTCGGCCTGGCCCCCAGATGCCACCCTGGGCAACGT<br>GTCGGCGGGCCCAAGCCCGGCAGGGCTGGCCGTCAGTGGC<br>GTTCTGATCCCCCTGGTCTACCTGGTGGTGTGCGTGGTGG<br>GCCTGCTGGGTAACTCGCTGGTCATCTATGTGGTCCTGCG<br>GCACACGGCCAGCCCTTCAGTCACCAACGTCTACATCCTC<br>AACCTGGCGCTGGCCGACGAGCTCTTCATGCTGGGGCTGC<br>CCTTCCTGGCCGCCCAGAACGCCCTGTCCTACTGGCCCTT<br>CGGCTCCCTCATGTGCCGCCTGGTCATGGCGGTGGATGGC<br>ATCAACCAGTTCACCAGCATATTCTGCCTGACTGTCATGA<br>GCGTGGACCGCTACCTGGCCGTGGTACATCCCACCCGCTC<br>GGCCCGCTGGCGCACAGCTCCGGTGGCCCGCACGGTCAGC<br>GCGGCTGTGTGGGTGGCCTCAGCCGTGGTGGTGCTGCCCG<br>TGGTGGTCTTCTCGGGAGTGCCCCGCGGCATGAGCACCTG<br>CCACATGCAGTGGCCCGAGCCGGCGGCGGCCTGGCGAGCC<br>GGCTTCATCATCTACACGGCCGCACTGGGCTTCTTCGGGC<br>CGCTGCTGGTCATCTGCCTCTGCTACCTGCTCATCGTGGT<br>GAAGGTGCGCTCAGCTGGGCGCCGGGTGTGGGCACCCTCG<br>TGCCAGCGGCGGCGGCGCTCCGAACGCAGGGTCACGCGCA<br>TGGTGGTGGCCGTGGTGGCGCTCTTCGTGCTCTGCTGGAT<br>GCCCTTCTACGTGCTCAACATCGTCAACGTGGTGTGCCCA<br>CTGCCCGAGGAGCCTGCCTTCTTTGGGCTCTACTTCCTGG<br>TGGTGGCGCTGCCCTATGCCAACAGCTGTGCCAACCCCAT<br>CCTTTATGGCTTCCTCTCCTACCGCTTCAAGCAGGGCTTC<br>CGCAGGGTCCTGCTGCGGCCCTCCCGCCGTGTGCGCAGCC<br>AGGAGCCCACTGTGGGGCCCCCGGAGAAGACTGAGGAGGA<br>GGATGAGGAGGAGGAGGATGGGGAGGAGAGCAGGGAGGGG<br>GGCAAGGGGAAGGAGATGAACGGCCGGGTCAGCCAGATCA<br>CGCAGCCTGGCACCAGCGGGCAGGAGCGGCCGCCCAGCAG<br>AGTGGCCAGCAAGGAGCAGCAGCTCCTACCCCAAGAGGCT<br>TCCACTGGGGAGAAGTCCAGCACGATGCGCATCAGCTACC<br>TGTAGGGGCCTGGGGAAAGCCAGGATGGCCCGAGGAAGAG<br>GCAGAAGCCGTGGGTGTGCCTAGGGCCTACTTCCCAAGGT<br>GCCACAGGCCCATGATGGGATGTTGAGGGGCCTGGACTTT<br>GATGCTATTGCTGCCAGGTCTTGCTGTGTGACCTTGGGTA<br>GGTTGCTTCTACTCTCTGGGCCTTGTTTTCTCCTCTGTGA<br>CTCAGGGATAGGAGTCATCAGCCTGGATGAGCTATGTCAG<br>ATGAGAGGTTTGGAGGGCACTGTTGCTGGGCTGACCTGGC<br>TGAGCAGGCAAAAGGTGGGTGCAGACTGGCCTCCCCCCAG<br>GGATGGAGTGTCTTGGGGCATCAACTAGAATCTTGGCCCT<br>CAGAGGGATAAACCAAGGCCAGGATTTCTTGGGCTCAGAG<br>TCAGGAACACAGGAGCTGCTGGGGGCTGGGCTGGAAACCT<br>AAACAGAAGAAAGCCTAACCCGGTGGGAGGAGTGGGGCAG<br>AAATGGTCAGGCCCCAGATCAGCTCCCTCCCCTCGACTGT<br>GAGGCCTTGGACCAGCTCTGCTCCTCTCTAGGCCTCAGGC<br>TTCACCTGGGTAAAACCCAACAACCTCTACACCCTTTTGG<br>CCCAGGCAGTCAATGCTGGAGGTCCTGTGCTCCTGGACGG<br>GAAGAGCAGGTGAATTTCCTGCTCATGGAAGCGAATGAAG<br>TCCAGCTTCAGGGTCTCTCACTGCCTGGGCTTTTGCAAGG<br>CCCTGCATCTACTTTTGTACTTGTCATTTTGTATTCGTTT<br>TCTTAAAGAGGGACCTCGAACTGCATAAGCTTAGGCCACC<br>CAAAGCCTGGCTCTGCCCCTGCTGAGGTCAGCCACCCAAT<br>CCCCAAGGAAGCTCATGTTGGGTCTTATGGCTGGAGTAGG<br>GGCCCCCGGGGGTTCCCAGGTCTTTTGAGGGCTTCCAGGC<br>ACCTCCTTGTAGGAAGGGCCATCCCTGTTCCTCTCCTTGT<br>GACCCATATTCTCCCTTCCTGGAGACCGAGACAGGGACCC | 40 |

TABLE 1-continued

GEP-NEN Biomarker/Houskeeper Sequence Information

| Gene Name | RefSeq Accession | Sequence | SEQ ID NO: |
|---|---|---|---|
| | | AGCCCATGAGGACTGGCATGGAAAGGCAGAGTGTCTGAAG<br>AGCGCTGTGAGGAGAAGGAAGAGGAAGGGAGAAGAGGAAG<br>AGGAAGGAGAAGGAAGAGGAAGACAAGGGGGAAAGGGGAG<br>GATGAGGAGGGGGAAGGAGAAGTACAGATCTGTTTCCTGG<br>AGCCGTCTTTGGCCCCCCTGGGCTGAGCTCAGTGGTAGCA<br>TCTGTGAACCTGAGTTGCCGACAACAGCCCCACCCAACCA<br>GTACTGAGGGAAGGACACGATCAGGGTGGAACAGCCAGGG<br>TGCAATGGCAAATGCACAGAGTACAGACAGGCACAGGGCC<br>TGCGTCCCTGAGGGGCCTCAGAGTGCTGCCAAGAGGGCTC<br>AGGCCTTAATAAAGCCCTAGGGTGGAGCTGGCTACCAGGG<br>ACATTGGGAGGACTGGGGAGCTCCCTCCCCATGCTCTATC<br>ATCCTGGAGACTACAGGTCGGGAGGCCCAGGGAAGACAAG<br>AAGAGGCTGAAGTGGGACTGTGGAGGGGGACCATGGGGAG<br>CAGCCACCATCCAAGGCTGGGCCTAGACTCCCTCCCAGAG<br>ATGGTCCCTCAGAGCTGTGGTGAGGCTGGCCCTGGGAGGG<br>TGAGACCCCCGGTGAAATCCTTCCGCTTCCCCACCCCTTG<br>CAGAGGGCAGGGGTCCTCAGGGAAAGCACAGGAACCAGAC<br>TTTTGGAGACTTGGATCTTCAGCACACCTCAGGGTCCTGG<br>GCTGGCATTGGCCTTCCGGGCCTCAATTTCCCCATCAACA<br>AATGGAGATGAATCCCAGCTTGGCTGCCTCCTGGGATCTA<br>ACGAGAAAATGAGTCATGTGAGGTAACTTCCAGGCTCACT<br>GCAATGGGTACGGTGGGGTGTATCAGATTATAAAGTGGGG<br>GTGCCCTCCTCACCCCCAGGCTTGGCCTATACCCCCCTCT<br>CCATCAAGTGGCCTCTCTGTGTCTGTCCTTTGGGGTGAGG<br>ACACTGTAGGCCATGAGAAATGGGCAGTTGGGGGGTCAGA<br>GGCCAAGGGTTAGGGAGGCAGGGCTTGGGGAGAGTGTGGG<br>ACCATCAGAAGAGAAGGAAGTTTACAAAACCACATTTTGT<br>GTGGAGATGGAGGCTGGAGGCCCGGCCCTGGGACTTGGTC<br>TGGGGTTTCTTGAGGAAGATCTGAGGGTCCAAGGGAGGAA<br>GGATGCCCTGGCCTTCTGGCCTTCTCTGGCTGATCCTGCC<br>TTCTTGCTGCCTAGGACAGGAGAGTAATGTCCTAGAATGG<br>TCCCTGGGAGGCCAGTTAGGAAACCCTTTGCTGCTTCTGT<br>CTCTAGCTCTTGTCAATAAAGACGGTGACACCTGAAAAAA<br>AAAAAAAAAAA | |
| SST4 | NM_001052.2 | CCGAGCTCTCTGGCGCAGCGCTAGCTCCGCCGCGCTCAGC<br>TGCCCTGCGCCGGCACCCCTGGTCATGAGCGCCCCCTCGA<br>CGCTGCCCCCCGGGGGCGAGGAAGGGCTGGGGACGGCCTG<br>GCCCTCTGCAGCCAATGCCAGTAGCGCTCCGGCGGAGGCG<br>GAGGAGGCGGTGGCGGGGCCCGGGGACGCGCGGGCGGCGG<br>GCATGGTCGCTATCCAGTGCATCTACGCGCTGGTGTGCCT<br>GGTGGGGCTGGTGGGCAACGCCCTGGTCATCTTCGTGATC<br>CTTCGCTACGCCAAGATGAAGACGGCTACCAACATCTACC<br>TGCTCAACCTGGCCGTAGCCGACGAGCTCTTCATGCTGAG<br>CGTGCCCTTCGTGGCCTCGTCGGCCGCCCTGCGCCACTGG<br>CCCTTCGGCTCCGTGCTGTGCCGCGCGGTGCTCAGCGTCG<br>ACGGCCTCAACATGTTCACCAGCGTCTTCTGTCTCACCGT<br>GCTCAGCGTGGACCGCTACGTGGCCGTGGTGCACCCTCTG<br>CGCGCGGCGACCTACCGGCGGCCCAGCGTGGCCAAGCTCA<br>TCAACCTGGGCGTGTGGCTGGCATCCCTGTTGGTCACTCT<br>CCCCATCGCCATCTTCGCAGACACCAGACCGGCTCGCGGC<br>GGCCAGGCCGTGGCCTGCAACCTGCAGTGGCCACACCCGG<br>CCTGGTCGGCAGTCTTCGTGGTCTACACTTTCCTGCTGGG<br>CTTCCTGCTGCCCGTGCTGGCCATTGGCCTGTGCTACCTG<br>CTCATCGTGGGCAAGATGCGCGCCGTGGCCCTGCGCGCTG<br>GCTGGCAGCAGCGCAGGCGCTCGGAGAAGAAAATCACCAG<br>GCTGGTGCTGATGGTCGTGGTCGTCTTTGTGCTCTGCTGG<br>ATGCCTTTCTACGTGGTGCAGCTGCTGAACCTCTTCGTGA<br>CCAGCCTTGATGCCACCGTCAACCACGTGTCCCTTATCCT<br>TAGCTATGCCAACAGCTGCGCCAACCCCATTCTCTATGGC<br>TTCCTCTCCGACAACTTCCGCCGATTCTTCCAGCGGGTTC<br>TCTGCCTGCGCTGCTGCCTCCTGGAAGGTGCTGGAGGTGC<br>TGAGGAGGAGCCCCTGGACTACTATGCCACTGCTCTCAAG<br>AGCAAAGGTGGGGCAGGGTGCATGTGCCCCCCACTCCCCT<br>GCCAGCAGGAAGCCCTGCAACCAGAACCCGGCCGCAAGCG<br>CATCCCCCTCACCAGGACCACCACCTTCTGAGGAGCCCTT<br>CCCCTACCCACCCTGCGT | 41 |
| SST5 | NM_001053.3 | ATGCCTGCATGTGCTGGTTCAGGGACTCACCACCCTGGCG<br>TCCTCCCTTCTTCTCTTGCAGAGCCTGACGCACCCCAGGG<br>CTGCCGCCATGGAGCCCCTGTTCCCAGCCTCCACGCCCAG<br>CTGGAACGCCTCCTCCCCGGGGGCTGCCTCTGGAGGCGGT<br>GACAACAGGACGCTGGTGGGGCCGGCGCCCTCGGCAGGGG<br>CCCGGGCGGTGCTGGTGCCCGTGCTGTACCTGCTGGTGTG<br>TGCGGCCGGGCTGGGCGGGAACACGCTGGTCATCTACGTG | 42 |

TABLE 1-continued

GEP-NEN Biomarker/Houskeeper Sequence Information

| Gene Name | RefSeq Accession | Sequence | SEQ ID NO: |
| --- | --- | --- | --- |
| | | GTGCTGCGCTTCGCCAAGATGAAGACCGTCACCAACATCT<br>ACATTCTCAACCTGGCAGTGGCCGACGTCCTGTACATGCT<br>GGGGCTGCCTTTCCTGGCCACGCAGAACGCCGCGTCCTTC<br>TGGCCCTTCGGCCCCGTCCTGTGCCGCCTGGTCATGACGC<br>TGGACGGCGTCAACCAGTTCACCAGTGTCTTCTGCCTGAC<br>AGTCATGAGCGTGGACCGCTACCTGGCAGTGGTGCACCCG<br>CTGAGCTCGGCCCGCTGGCGCCGCCCGCGTGTGGCCAAGC<br>TGGCGAGCGCCGCGGCCTGGGTCCTGTCTCTGTGCATGTC<br>GCTGCCGCTCCTGGTGTTCGCGGACGTGCAGGAGGGCGGT<br>ACCTGCAACGCCAGCTGGCCGGAGCCCGTGGGGCTGTGGG<br>GCGCCGTCTTCATCATCTACACGGCCGTGCTGGGCTTCTT<br>CGCGCCGCTGCTGGTCATCTGCCTGTGCTACCTGCTCATC<br>GTGGTGAAGGTGAGGGCGGCGGGCGTGCGCGTGGGCTGCG<br>TGCGGCGGCGCTCGGAGCGGAAGGTGACGCGCATGGTGTT<br>GGTGGTGGTGCTGGTGTTTGCGGGATGTTGGCTGCCCTTC<br>TTCACCGTCAACATCGTCAACCTGGCCGTGGCGCTGCCCC<br>AGGAGCCCGCCTCCGCCGGCCTCTACTTCTTCGTGGTCAT<br>CCTCTCCTACGCCAACAGCTGTGCCAACCCCGTCCTCTAC<br>GGCTTCCTCTCTGACAACTTCCGCCAGAGCTTCCAGAAGG<br>TTCTGTGCCTCCGCAAGGGCTCTGGTGCCAAGGACGCTGA<br>CGCCACGGAGCCGCGTCCAGACAGGATCCGGCAGCAGCAG<br>GAGGCCACGCCACCCGCGCACCGCGCCGCAGCCAACGGGC<br>TTATGCAGACCAGCAAGCTGTGAGAGTGCAGGCGGGGGGT<br>GGGCGGCCCCGTGTCACCCCCAGGAGCGGAGGTTGCACTG<br>CGGTGACCCCCACCCATGACCTGCCAGTCAGGATGCTCCC<br>CGGCGGTGGTGTGAGGACAGAGCTGGCTGAAGCCAGGCTG<br>GGGTAGACACAGGGCAGTAGGTTCCCCACCGTGACCGACC<br>ATCCCCTCTAACCGTCTGCCACACAGCGGGGGCTCCCGGG<br>AGGTAGGGGAGGTGGCCAGACCGGTGGGGGGCTCCGCCAT<br>GCCGTGCAAGTGCTCAGGGCCGCCTCACCCTCCATCTGGC<br>CCCAGCCCATGCCGGCCTTCCCTCTGGGGAGCGACTTTTC<br>CAGAAGGCCGGCCAGGCGAGAGGGTCTTCCTGACGGCGGA<br>GCTGACCTGCCCGGCCCACCAGCTGCATGTCAGCTCCGAG<br>CCACCGGGTCCCCGTCCAAGGCTGCTCTGCTAAGTTAAAG<br>ACACCCGAAAGCGCTTGACTCAGGTCCCCGGAGTCCCTGG<br>CCAGGGCCCCAGCCCCTCGCTTGCCCTGCACTGTGTGGAC<br>TCTGGGGATGCAGGTGTAAGGGGAGTGTGGCTGGGCAGCC<br>CCTGGTCAGCCAGGGTCACGCCTGTCCTGGGGGCCCCACC<br>CTGCTGCCCGACACCCCCCATGGGAGGCTGCGGGCGGCAG<br>TTGCTGTCTCAGAGAGGGGAGTGTGGGGGCTTGGGCGCTG<br>GCCTAGCCAGGGGCGAGGTGGGGAGGCGGCTGGTGCAGAG<br>GAGAGCTGGGGGCTGAGGTTGGGGTGAAGGCTGCAGCCCT<br>CCAGGCTGCTGGGGGTGCAGATGGCTGTGCCGTGCTGAGA<br>TTGGCTCTGTCTGGAGGGGTCCAGTGTGGGGTGCCTGAGG<br>GCACTAGGGAGAGGTGCTCCTGCTGCAGGAGGACCTGAGG<br>GTCAGGGCTTGGAGAGGACAGGGAACCTGCGGCCGTCTCT<br>TCTGCTTTGGGGCAGGGGCTCTGGCCCGGGAGAGGGAACG<br>GGGACAGGAGCAGAGGACGGTCATCCAGGCGCAGCGGGGA<br>GCTGCTCCCCAGGCCACAGCAGACAGCACTGCTGAGAGGC<br>AGCGGCCGCGCGGGTGACGCAAATGGCAGGCCCTGGGAAT<br>CCCGCCGCCTCCCACCTAGAATTGTCCTACCTCCCCCACC<br>CCAAACACCAGCTTTTCCTGGCGCCCCAGGCCCAGAACGT<br>GGGCCCAGAGAGCCTTGCTGGGGTCTCTGGGGCACCTTGG<br>CCTTGCTCTGAGGCTGGAAGGAGAAGGACCAGGGTGCGGC<br>ATCACTCGGCCTCAGGGACCCCTCTGCCCTGCCCAGCACT<br>GGCCCCGACCCGTGCTCCCGCCGTCTGCCCAGAGCAGGAC<br>CTCAACCTCCTGGAGGGCACAGGGAGCGGCTGAGTGGGCA<br>CAAATCCTGGCAGGAGAAAGGCCCAGGCTGAGGCCAGGCC<br>TGGGAAACATCCAAGCAGTGAGGACACGCGTGTTTGACAA<br>CTGCTCCCCTGAATAAATGCGAGGATAAATGTTT | |
| TECPR2 | NM_001172631.1 | CCCCCGGCGGAGCCAGCTGCTGCTCTTCGGTGCTGGCCCC<br>GGTGCCGGCCCCGTTGCCCAGGGAACAGGCTCCCGGCAGC<br>CCCCGCGGCCCGGAGTCCATCCCGCCTCCTCCGGCCCGGC<br>GGGGCCGACGAGTCCGGAGGGGCTGCCGCGGGAGCCCCCA<br>GGTTTCCCTAGATGACAAATAAACATTCCTTTTCCTGCGT<br>GAAGATAGTCTGTGGAAACCTTGGCCATGGCATCGATATC<br>AGAGCCTGTTACATTCAGAGAGTTCTGCCCGTTGTACTAT<br>CTCCTCAATGCCATTCCGACAAAGATCCAGAAGGGTTTCC<br>GCTCTATCGTGGTCTATCTCACGGCCCTCGACACCAACGG<br>GGACTACATCGCGGTGGGCAGCAGCATCGGCATGCTCTAT<br>CTGTACTGCCGGCACCTCAACCAGATGAGGAAGTACAACT<br>TTGAGGGGAAGACGGAATCTATCACTGTGGTGAAGCTGCT<br>GAGCTGCTTTGATGACCTGGTGGCAGCAGGCACAGCCTCT<br>GGCAGGGTTGCAGTTTTTCAACTTGTATCTTCATTGCCAG | 43 |

TABLE 1-continued

GEP-NEN Biomarker/Houskeeper Sequence Information

| Gene Name | RefSeq Accession | Sequence | SEQ ID NO: |
|---|---|---|---|
| | | GGAGAAATAAACAGCTTCGGAGATTTGATGTCACTGGTAT<br>TCACAAAAATAGCATTACAGCTCTGGCTTGGAGCCCCAAT<br>GGAATGAAATTGTTCTCTGGAGATGACAAAGGCAAAATTG<br>TTTATTCTTCTCTGGATCTAGACCAGGGGCTCTGTAACTC<br>CCAGCTGGTGTTGGAGGAGCCATCTTCCATTGTGCAGCTG<br>GATTATAGCCAGAAAGTGCTGCTGGTCTCTACTCTGCAAA<br>GAAGTCTGCTCTTTTACACTGAAGAAAAGTCTGTAAGGCA<br>AATTGGAACACAACCAAGGAAAAGTACTGGGAAATTTGGT<br>GCTTGTTTTATACCAGGACTCTGTAAGCAAAGTGATCTAA<br>CCTTGTATGCGTCACGGCCCGGGCTCCGGCTATGGAAGGC<br>TGATGTCCACGGGACTGTTCAAGCCACGTTTATCTTAAAA<br>GATGCTTTTGCCGGGGGAGTCAAGCCTTTTGAACTGCACC<br>CGCGTCTGGAATCCCCCAACAGTGGAAGTTGCAGCTTACC<br>TGAGAGGCACCTGGGGCTTGTTTCATGTTTCTTTCAAGAA<br>GGCTGGGTGCTGAGTTGGAATGAATATAGTATCTATCTCC<br>TAGACACAGTCAACCAGGCCACAGTTGCTGGTTTGGAAGG<br>ATCCGGTGATATTGTGTCTGTTTCGTGCACAGAAAATGAA<br>ATATTTTTCTTGAAAGGAGATAGGAACATTATAAGAATTT<br>CAAGCAGGCCTGAAGGATTAACATCAACAGTGAGAGATGG<br>TCTGGAGATGTCTGGATGCTCAGAGCGTGTCCACGTGCAG<br>CAAGCGGAGAAGCTGCCAGGGGCCACAGTTTCTGAGACGA<br>GGCTCAGAGGCTCTTCCATGGCCAGCTCCGTGGCCAGCGA<br>GCCAAGGAGCAGGAGCAGCTCGCTCAACTCCACCGACAGC<br>GGCTCCGGGCTCCTGCCCCCTGGGCTCCAGGCCACCCCTG<br>AGCTGGGCAAGGGCAGCCAGCCCCTGTCACAGAGATTCAA<br>CGCCATCAGCTCAGAGGACTTTGACCAGGAGCTTGTCGTG<br>AAGCCTATCAAAGTGAAAAGGAAGAAGAAGAAGAAGAAGA<br>CAGAAGGTGGAAGCAGGAGCACCTGTCACAGCTCCCTGGA<br>ATCGACACCCTGCTCCGAATTTCCTGGGGACAGTCCCCAG<br>TCCTTGAACACAGACTTGCTGTCGATGACCTCAAGTGTCC<br>TGGGCAGTAGCGTGGATCAGTTAAGTGCAGAGTCTCCAGA<br>CCAGGAAAGCAGCTTCAATGGTGAAGTGAACGGTGTCCCA<br>CAGGAAAATACTGACCCCGAAACGTTTAATGTCCTGGAGG<br>TGTCAGGATCAATGCCTGATTCTCTGGCTGAGGAAGATGA<br>CATTAGAACTGAAATGCCACACTGTCACCATGCACATGGG<br>CGGGAGCTGCTCAATGGAGCGAGGGAAGATGTGGGAGGCA<br>GTGATGTCACGGGACTCGGAGATGAGCCGTGTCCTGCAGA<br>TGATGGACCAAATAGCACACAGTTACCCTTCCAAGAACAG<br>GACAGCTCTCCTGGGGCGCATGATGGGGAAGACATCCAAC<br>CCATTGGCCCCCAAAGCACTTTTTGTGAAGTCCCCCTCCT<br>GAACTCACTCACTGTGCCTTCCAGCCTCAGCTGGGCCCCA<br>AGTGCTGAACAGTGGCTGCCTGGGACCAGAGCTGATGAAG<br>GCAGCCCCGTGGAGCCCAGCCAAGAGCAGGACATCCTAAC<br>CAGCATGGAGGCCTCTGGCCACCTCAGCACAAATCTCTGG<br>CATGCTGTCACTGATGATGACACAGGTCAGAAAGAAATAC<br>CCATTTCTGAACGTGTCTTGGGGAGTGTGGGAGGACAGCT<br>GACTCCGGTCTCTGCCTTGGCAGCCAGCACTCACAAGCCC<br>TGGCTTGAGCAGCCTCCACGGGATCAGACATTGACGTCCA<br>GCGATGAGGAGGACATCTATGCCCACGGGCTTCCTTCTTC<br>ATCCTCAGAGACGAGTGTGACAGAGCTCGGACCTAGTTGC<br>TCCCAGCAGGACCTGAGCCGGCTGGGTGCAGAGGACGCCG<br>GGCTGCTCAAGCCAGATCAGTTTGCAGAAAGCTGGATGGG<br>CTACTCGGGTCCCGGCTATGGCATCCTCAGCTTGGTGGTC<br>TCCGAGAAGTATATCTGGTGCCTGGACTACAAAGGCGGCC<br>TGTTCTGCAGCGCGTTGCCGGGCGCCGGGCTGCGCTGGCA<br>GAAGTTTGAAGATGCTGTCCAGCAGGTGGCAGTCTCGCCC<br>TCAGGAGCCCTTCTCTGGAAGATTGAACAGAAATCTAACC<br>GGGCTTTTGCTTGTGGGAAAGTCACCATCAAGGGGAAGCG<br>GCACTGGTACGAAGCCCTGCCCCAGGCAGTGTTTGTGGCC<br>CTGAGCGATGACACGGCCTGGATCATCAGGACCAGTGGGG<br>ACCTATACTTGCAGACAGGTCTGAGCGTGGATCGCCCTTG<br>TGCCAGAGCCGTAAAGGTGGACTGTCCCTACCCGCTGTCC<br>CAGATCACAGCCCGGAACAATGTGGTGTGGGCGCTGACAG<br>AGCAGAGGGCCCTCCTGTACCGGGAGGGCGTGAGCAGCTT<br>CTGTCCGGAAGGCGAGCAGTGGAAGTGTGACATTGTCAGC<br>GAAAGGCAAGCTTTAGAACCCGTCTGCATAACGCTCGGGG<br>ATCAGCAGACTCTCTGGGCCCTGGACATCCATGGGAACCT<br>GTGGTTCAGAACTGGCATTATTTCCAAGAAGCCCCAAGGA<br>GATGACGACCATTGGTGGCAAGTGAGCATCACGGACTATG<br>TGGTGTTTGACCAGTGCAGCTTATTTCAGACGATAATCCA<br>TGCCACTCACTCGGTGGCCACAGCAGCCCAAGCCCCCGTA<br>GAAAAGGTGGCAGATAAGCTGCGCATGGCGTTTTGGTCCC<br>AGCAGCTTCAGTGCCAGCCAAGCCTTCTCGGGGTCAATAA<br>CAGCGGTGTCTGGATCTCCTCGGGCAAGAATGAATTCCAC<br>GTCGCTAAGGGAAGTCTCATAGGCACCTACTGGAATCATG | |

TABLE 1-continued

GEP-NEN Biomarker/Houskeeper Sequence Information

| Gene Name | RefSeq Accession | Sequence | SEQ ID NO: |
|---|---|---|---|
| | | TGGTTCCCCGTGGGACAGCTTCTGCTACAAAATGGGCCTT | |
| | | TGTGTTGGCTTCTGCAGCTCCCACGAAGGAAGGAAGCTTC | |
| | | CTGTGGCTGTGCCAGAGCAGCAAGGACCTGTGCAGCGTCA | |
| | | GCGCCCAGAGCGCACAGTCGCGGCCCTCCACGGTGCAGCT | |
| | | GCCTCCCGAAGCCGAGATGCGCGCCTATGCCGCCTGCCAG | |
| | | GATGCGCTGTGGGCGCTGGACAGCCTCGGCCAGGTGTTCA | |
| | | TCAGGACGCTCTCCAAGAGCTGCCCCACGGGCATGCACTG | |
| | | GACCAGGCTGGACCTCTCCCAGCTAGGAGCTGTAAAATTG | |
| | | ACAAGCTTGGCATGTGGAAATCAGCACATCTGGGCCTGTG | |
| | | ATTCCAGGGGTGGAGTTTACTTCCGTGTAGGGACTCAGCC | |
| | | TCTCAATCCCAGTCTCATGCTTCCAGCCTGGATAATGATT | |
| | | GAGCCACCTGTCCAGGTAAGCAGAAGTTAGCTGGTGGAAC | |
| | | TCACTCTTCAGTAAGACAGAAACTGTGAGGATGCTGGTAC | |
| | | TGGGAAAAAGGATCTGCACAGCCTCTAGAGGCCTCCCAGC | |
| | | AAATGCGGGGAGCCATGCCCCCAGGGTCTACACACTCTCG | |
| | | TTCATCAACATCACAACTGGAATTCGGGATTTGTGAAGTT | |
| | | TAGAGCTGAACAGACTGTTACAGATTATGAGTCAACACGT | |
| | | ATATTTTCTCTTTCAAAATAATAATATTTCGTTTTTGACT | |
| | | TTTTACTAAGTGAATATTATTTTTTAAATCTGCCTATATA | |
| | | TTGGAACCTCTATTTTATAATAATAATGATAATAAATCAG | |
| | | TACCCAGAAGTATAAAGAAGGTAAAAGTTACTTTGAAAAA | |
| | | AAAAAAAAAAAAAAAAAAAAAAAAAAA | |
| TPH1 | NM_004179.2 | TTTTAGAGAATTACTCCAAATTCATCATGATTGAAGACAA | 44 |
| | | TAAGGAGAACAAAGACCATTCCTTAGAAAGGGGAAGAGCA | |
| | | AGTCTCATTTTTTCCTTAAAGAATGAAGTTGGAGGACTTA | |
| | | TAAAAGCCCTGAAAATCTTTCAGGAGAAGCATGTGAATCT | |
| | | GTTACATATCGAGTCCCGAAAATCAAAAAGAAGAAACTCA | |
| | | GAATTTGAGATTTTTGTTGACTGTGACATCAACAGAGAAC | |
| | | AATTGAATGATATTTTTCATCTGCTGAAGTCTCATACCAA | |
| | | TGTTCTCTCTGTGAATCTACCAGATAATTTTACTTTGAAG | |
| | | GAAGATGGTATGGAAACTGTTCCTTGGTTTCCAAAGAAGA | |
| | | TTTCTGACCTGGACCATTGTGCCAACAGAGTTCTGATGTA | |
| | | TGGATCTGAACTAGATGCAGACCATCCTGGCTTCAAAGAC | |
| | | AATGTCTACCGTAAACGTCGAAAGTATTTTGCGGACTTGG | |
| | | CTATGAACTATAAACATGGAGACCCCATTCCAAAGGTTGA | |
| | | ATTCACTGAAGAGGAGATTAAGACCTGGGGAACCGTATTC | |
| | | CAAGAGCTCAACAAACTCTACCCAACCCATGCTTGCAGAG | |
| | | AGTATCTCAAAAACTTACCTTTGCTTTCTAAATATTGTGG | |
| | | ATATCGGGAGGATAATATCCCACAATTGGAAGATGTCTCC | |
| | | AACTTTTTAAAAGAGCGTACAGGTTTTTCCATCCGTCCTG | |
| | | TGGCTGGTTACTTATCACCAAGAGATTTCTTATCAGGTTT | |
| | | AGCCTTTCGAGTTTTTCACTGCACTCAATATGTGAGACAC | |
| | | AGTTCAGATCCCTTCTATACCCCAGAGCCAGATACCTGCC | |
| | | ATGAACTCTTAGGTCATGTCCCGCTTTTGGCTGAACCTAG | |
| | | TTTTGCCCAATTCTCCCAAGAAATTGGCTTGGCTTCTCTT | |
| | | GGCGCTTCAGAGGAGGCTGTTCAAAAACTGGCAACGTGCT | |
| | | ACTTTTTCACTGTGGAGTTTGGTCTATGTAAACAAGATGG | |
| | | ACAGCTAAGAGTCTTTGGTGCTGGCTTACTTTCTTCTATC | |
| | | AGTGAACTCAAACATGCACTTTCTGGACATGCCAAAGTAA | |
| | | AGCCCTTTGATCCCAAGATTACCTGCAAACAGGAATGTCT | |
| | | TATCACAACTTTTCAAGATGTCTACTTTGTATCTGAAAGT | |
| | | TTTGAAGATGCAAAGGAGAAGATGAGAGAATTTACCAAAA | |
| | | CAATTAAGCGTCCATTTGGAGTGAAGTATAATCCATATAC | |
| | | ACGGAGTATTCAGATCCTGAAAGACACCAAGAGCATAACC | |
| | | AGTGCCATGAATGAGCTGCAGCATGATCTCGATGTTGTCA | |
| | | GTGATGCCCTTGCTAAGGTCAGCAGGAAGCCGAGTATCTA | |
| | | ACAGTAGCCAGTCATCCAGGAACATTTGAGCATCAATTCG | |
| | | GAGGTCTGGGCCATCTCTTGCTTTCCTTGAACACCTGATC | |
| | | CTGGAGGGACAGCATCTTCTGGCCAAACAATATTATCGAA | |
| | | TTCCACTACTTAAGGAATCACTAGTCTTTGAAAATTTGTA | |
| | | CCTGGATATTCTATTTACCACTTATTTTTTTGTTTAGTTT | |
| | | TATTTCTTTTTTTTTTTGGTAGCAGCTTTAATGAGACAAT | |
| | | TTATATACCATACAAGCCACTGACCACCCATTTTTAATAG | |
| | | AGAAGTTGTTTGACCCAATAGATAGATCTAATCTCAGCCT | |
| | | AACTCTATTTTCCCCAATCCTCCTTGAGTAAAATGACCCT | |
| | | TTAGGATCGCTTAGAATAACTTGAGGAGTATTATGGCGCT | |
| | | GACTCATATTGTTACCTAAGATCCCCTTATTTCTAAAGTA | |
| | | TCTGTTACTTATTGC | |
| TRMT112 | NM_016404.2 | GGCCACCCGCAGAACAGAGCTTCCGGGACCCACGCCTCGT | 45 |
| | | TTGCACTGGGTGCTGGACAGCCGACGCAACTACAAATGGG | |
| | | GCGGAGCTTTCGGCACTGGAGCAGCTAATTTGCATATAGG | |
| | | AATGAGGTGCGGCTCGGCTTCCATGGGCCTAATTTACAGA | |
| | | TAGGGCGGTATTTCTGCCCCTTAACCGAAAGTGGGATACA | |

TABLE 1-continued

| GEP-NEN Biomarker/Houskeeper Sequence Information | | | |
|---|---|---|---|
| Gene Name | RefSeq Accession | Sequence | SEQ ID NO: |
| | | GAGGACGACGGTGTTAGGCGCCTGTGTAGGAGTAAAATGT<br>GTTTATTTTGCATTCAACGAGAGCTCCTGCATTGCAGCTA<br>TTTTGCATATGATTTGCATCTTACGAAGAATTTGTGGCAA<br>AAAAAAGCTGGGCGTGCGCCGTAGGAACCTCCTGCTGAGA<br>CGCTTCCGGTAGCGGCGCGTGACCCGACAGGTCTTTCACC<br>TACCTACCTCAGCTCCCACAAACACGAGAAGTTCCAGCAA<br>GTTCGCCACTTCCGGTTCTCCTGGCTATCCAATAGCATCG<br>AGAGGAGCATCCCCGGAAGTGAGGCAGCGGAGGACGACCT<br>TTTTCCGGTTCCGGCCTGGCGAGAGTTTGTGCGGCGACAT<br>GAAACTGCTTACCCACAATCTGCTGAGCTCGCATGTGCGG<br>GGGGTGGGGTCCCGTGGCTTCCCCCTGCGCCTCCAGGCCA<br>CCGAGGTCCGTATCTGCCCTGTGGAATTCAACCCCAACTT<br>CGTGGCGCGTATGATACCTAAAGTGGAGTGGTCGGCGTTC<br>CTGGAGGCGGCCGATAACTTGCGTCTGATCCAGGTGCCGA<br>AAGGGCCGGTTGAGGGATATGAGGAGAATGAGGAGTTTCT<br>GAGGACCATGCACCACCTGCTGCTGGAGGTGGAAGTGATA<br>GAGGGCACCCTGCAGTGCCCGGAATCTGGACGTATGTTCC<br>CCATCAGCCGCGGGATCCCCAACATGCTGCTGAGTGAAGA<br>GGAAACTGAGAGTTGATTGTGCCAGGCGCCAGTTTTTCTT<br>GTTATGACTGTGTATTTTTGTTGATCTATACCCTGTTTCC<br>GAATTCTGCCGTGTGTATCCCCAACCCTTGACCCAATGAC<br>ACCAAACACAGTGTTTTTGAGCTCGGTATTATATATTTTT<br>TTCTCATTAAAGGTTTAAAACCAAAAGCGGTTTCTCTTTG<br>CAGCAAATATACATTAAAATAGAGTCTCTGTACAGCCAAG<br>GGCTCTGGGCCCTGGCTTGCCCCATGTCCCTGCGCCTCCC<br>TGGCCAAACCCAAAAATAAATATAGTGTTATTGCTCTGCA<br>GGGCATAGAGGCAGTGCTCTCCTACCCCCTGAGGAGGCTC<br>GTTGGGAGCTGATGGGGAAGCCCTG | |
| VMAT1 | NM_003053.3 | CACACACACACATACACAGAATCCTCAGATAACAGGAGGC<br>AATAAATCCAACAGCACATCCACGTTCAGAGAACAGTGTC<br>CCTGCTGTCTTGCTAACAGCTGCCAATACCTCACTGAGTG<br>CCTCACACCAACATGGGCTCCAAGTGAGTTTCCTTCGTCT<br>GGGCAGACTCCCTCCCCTCTTCCATAAAGGCTGCAGGAGA<br>CCTGTAGCTGTCACAGGACCTTCCCTAAGAGCCCGCAGGG<br>GAAGACTGCCCCAGTCCGGCCATCACCATGCTCCGGACCA<br>TTCTGGATGCTCCCCAGCGGTTGCTGAAGGAGGGGAGAGC<br>GTCCCGGCAGCTGGTGCTGGTGGTGGTATTCGTCGCTTTG<br>CTCCTGGACAACATGCTGTTTACTGTGGTGGTGCCAATTG<br>TGCCCACCTTCCTATATGACATGGAGTTCAAAGAAGTCAA<br>CTCTTCTCTGCACCTCGGCCATGCCGGAAGTTCCCCACAT<br>GCCCTCGCCTCTCCTGCCTTTTCCACCATCTTCTCCTTCT<br>TCAACAACAACACCGTGGCTGTTGAAGAAAGCGTACCTAG<br>TGGAATAGCATGGATGAATGACACTGCCAGCACCATCCCA<br>CCTCCAGCCACTGAAGCCATCTCAGCTCATAAAAACAACT<br>GCTTGCAAGGCACAGGTTTCTTGGAGGAAGAGATTACCCG<br>GGTCGGGGTTCTGTTTGCTTCAAAGGCTGTGATGCAACTT<br>CTGGTCAACCCATTCGTGGGCCCTCTCACCAACAGGATTG<br>GATATCATATCCCCATGTTTGCTGGCTTTGTTATCATGTT<br>TCTCTCCACAGTTATGTTTGCTTTTTCTGGGACCTATACT<br>CTACTCTTTGTGGCCCGAACCCTTCAAGGCATTGGATCTT<br>CATTTTCATCTGTTGCAGGTCTTGGAATGCTGGCCAGTGT<br>CTACACTGATGACCATGAGAGAGGACGAGCCATGGGAACT<br>GCTCTGGGGGGCCTGGCCTTGGGGTTGCTGGTGGGAGCTC<br>CCTTTGGAAGTGTAATGTACGAGTTTGTTGGGAAGTCTGC<br>ACCCTTCCTCATCCTGGCCTTCCTGGCACTACTGGATGGA<br>GCACTCCAGCTTTGCATCCTACAGCCTTCCAAAGTCTCTC<br>CTGAGAGTGCCAAGGGGACTCCCCTCTTTATGCTTCTCAA<br>AGACCCTTACATCCTGGTGGCTGCAGGGTCCATCTGCTTT<br>GCCAACATGGGGGTGGCCATCCTGGAGCCCACACTGCCCA<br>TCTGGATGATGCAGACCATGTGCTCCCCCAAGTGGCAGCT<br>GGGTCTAGCTTTCTTGCCTGCCAGTGTGTCCTACCTCATT<br>GGCACCAACCTCTTTGGTGTGTTGGCCAACAAGATGGGTC<br>GGTGGCTGTGTTCCCTAATCGGGATGCTGGTAGTAGGTAC<br>CAGCTTGCTCTGTGTTCCTCTGGCTCACAATATTTTTGGT<br>CTCATTGGCCCCAATGCAGGGCTTGGCCTTGCCATAGGCA<br>TGGTGGATTCTTCTATGATGCCCATCATGGGGCACCTGGT<br>GGATCTACGCCACACCTCGGTGTATGGGAGTGTCTACGCC<br>ATCGCTGATGTGGCTTTTTGCATGGGCTTTGCTATAGGTC<br>CATCCACCGGTGGTGCCATTGTAAAGGCCATCGGTTTTCC<br>CTGGCTCATGGTCATCACTGGGGTCATCAACATCGTCTAT<br>GCTCCACTCTGCTACTACCTGCGGAGCCCCCCGGCAAAGG<br>AAGAGAAGCTTGCTATTCTGAGTCAGGACTGCCCCATGGA<br>GACCCGGATGTATGCAACCCAGAAGCCCACGAAGGAATTT<br>CCTCTGGGGGAGGACAGTGATGAGGAGCCTGACCATGAGG | 46 |

TABLE 1-continued

GEP-NEN Biomarker/Houskeeper Sequence Information

| Gene Name | RefSeq Accession | Sequence | SEQ ID NO: |
|---|---|---|---|
| | | AGTAGCAGCAGAAGGTGCTCCTTGAATTCATGATGCCTCA<br>GTGACCACCTCTTTCCCTGGGACCAGATCACCATGGCTGA<br>GCCCACGGCTCAGTGGGCTTCACATACCTCTGCCTGGGAA<br>TCTTCTTTCCTCCCCTCCCATGGACACTGTCCCTGATACT<br>CTTCTCACCTGTGTAACTTGTAGCTCTTCCTCTATGCCTT<br>GGTGCCGCAGTGGCCCATCTTTTATGGGAAGACAGAGTGA<br>TGCACCTTCCCGCTGCTGTGAGGTTGATTAAACTTGAGCT<br>GTGACGGGTTCTGCAAGGGGTGACTCATTGCATAGAGGTG<br>GTAGTGAGTAATGTGCCCCTGAAACCAGTGGGGTGACTGA<br>CAAGCCTCTTTAATCTGTTGCCTGATTTTCTCTGGCATAG<br>TCCCAACAGATCGGAAGAGTGTTACCCTCTTTTCCTCAAC<br>GTGTTCTTTCCCGGGTTTTCCCAGCCGAGTTGAGAAAATG<br>TTCTCAGCATTGTCTTGCTGCCAAATGCCAGCTTGAAGAG<br>TTTTGTTTTGTTTTTTTTCATTTATTTTTTTTTTTAATAA<br>AGTGAGTGATTTTTCTGTGGCTAAATCTAGAGCTGCTAAA<br>AGGGCTTTACCCTCAGTGAAAAGTGTCTTCTATTTTCATT<br>ATCTTTCAGAAACAGGAGCCCATTTCTCTTCTGCTGGAGT<br>TATTGACATTCTCCTGACCTCCCCTGTGTGTTCCTACCTT<br>TTCTGAACCTCTTAGACTCTTAGAAATAAAAGTAGAAGAA<br>AGACAGAAAAAATAACTGATTAGACCCAAGATTTCATGGG<br>AAGAAGTTAAAAGAAACTGCCTTGAAATCCCTCCTGATTG<br>TAGATTTCCTAACAGGAGGGGTGTAATGTGACATTGTTCA<br>TACTTGCTAATAAATACATTATTGCCTAATTCAAAAAAAA<br>AAAAAAAAAA | |
| VMAT2 | NM_003054.4 | AGAGCCGGACGGGGTAAACTGAGCGGCGGCGGCGGGGCGC<br>TGGGGCGGAGACTGCGACCCGGAGCCGCCCGGACTGACGG<br>AGCCCACTGCGGTGCGGGCGTTGGCGCGGGCACGGAGGAC<br>CCGGGCAGGCATCGCAAGCGACCCCGAGCGGAGCCCCGGA<br>GCCATGGCCCTGAGCGAGCTGGCGCTGGTCCGCTGGCTGC<br>AGGAGAGCCGCCGCTCGCGGAAGCTCATCCTGTTCATCGT<br>GTTCCTGGCGCTGCTGCTGGACAACATGCTGCTCACTGTC<br>GTGGTCCCCATCATCCCAAGTTATCTGTACAGCATTAAGC<br>ATGAGAAGAATGCTACAGAAATCCAGACGGCCAGGCCAGT<br>GCACACTGCCTCCATCTCAGACAGCTTCCAGAGCATCTTC<br>TCCTATTATGATAACTCGACTATGGTCACCGGGAATGCTA<br>CCAGAGACCTGACACTTCATCAGACCGCCACACAGCACAT<br>GGTGACCAACGCGTCCGCTGTTCCTTCCGACTGTCCCAGT<br>GAAGACAAAGACCTCCTGAATGAAAACGTGCAAGTTGGTC<br>TGTTGTTTGCCTCGAAAGCCACCGTCCAGCTCATCACCAA<br>CCCTTTCATAGGACTACTGACCAACAGAATTGGCTATCCA<br>ATTCCCATATTTGCGGGATTCTGCATCATGTTTGTCTCAA<br>CAATTATGTTTGCCTTCTCCAGCAGCTATGCCTTCCTGCT<br>GATTGCCAGGTCGCTGCAGGGCATCGGCTCGTCCTGCTCC<br>TCTGTGGCTGGGATGGGCATGCTTGCCAGTGTCTACACAG<br>ATGATGAAGAGAGAGGCAACGTCATGGGAATCGCCTTGGG<br>AGGCCTGGCCATGGGGGTCTTAGTGGGCCCCCCCTTCGGG<br>AGTGTGCTCTATGAGTTTGTGGGGAAGACGGCTCCGTTCC<br>TGGTGCTGGCCGCCCTGGTACTCTTGGATGGAGCTATTCA<br>GCTCTTTGTGCTCCAGCCGTCCCGGGTGCAGCCAGAGAGT<br>CAGAAGGGGACACCCCTAACCACGCTGCTGAAGGACCCGT<br>ACATCCTCATTGCTGCAGGCTCCATCTGCTTTGCAAACAT<br>GGGCATCGCCATGCTGGAGCCAGCCCTGCCCATCTGGATG<br>ATGGAGACCATGTGTTCCCGAAAGTGGCAGCTGGGCGTTG<br>CCTTCTTGCCAGCTAGTATCTCTTATCTCATTGGAACCAA<br>TATTTTTGGGATACTTGCACACAAAATGGGGAGGTGGCTT<br>TGTGCTCTTCTGGGAATGATAATTGTTGGAGTCAGCATTT<br>TATGTATTCCATTTGCAAAAAACATTTATGGACTCATAGC<br>TCCGAACTTTGGAGTTGGTTTTGCAATTGGAATGGTGGAT<br>TCGTCAATGATGCCTATCATGGGCTACCTCGTAGACCTGC<br>GGCACGTGTCCGTCTATGGGAGTGTGTACGCCATTGCGGA<br>TGTGGCATTTTGTATGGGGTATGCTATAGGTCCTTCTGCT<br>GGTGGTGCTATTGCAAAGGCAATTGGATTTCCATGGCTCA<br>TGACAATTATTGGGATAATTGATATTCTTTTTGCCCCTCT<br>CTGCTTTTTTCTTCGAAGTCCACCTGCCAAAGAAGAAAAA<br>ATGGCTATTCTCATGGATCACAACTGCCCTATTAAAACAA<br>AAATGTACACTCAGAATAATATCCAGTCATATCCGATAGG<br>TGAAGATGAAGAATCTGAAAGTGACTGAGATGAGATCCTC<br>AAAAATCATCAAAGTGTTTAATTGTATAAAACAGTGTTTC<br>CAGTGACACAACTCATCCAGAACTGTCTTAGTCATACCAT<br>CCATCCCTGGTGAAAGAGTAAAACCAAAGGTTATTATTTC<br>CTTTCCATGGTTATGGTCGATTGCCAACAGCCTTATAAAG<br>AAAAAGAAGCTTTTCTAGGGGTTTGTATAAATAGTGTTGA<br>AACTTTATTTTATGTATTTAATTTTATTAAATATCATACA<br>ATATATTTTGATGAAATAGGTATTGTGTAAATCTATAAAT | 47 |

TABLE 1-continued

GEP-NEN Biomarker/Houskeeper Sequence Information

| Gene Name | RefSeq Accession | Sequence | SEQ ID NO: |
|---|---|---|---|
| | | ATTTGAATCCAAACCAAATATAATTTTTTAACTTACATTA | |
| | | ACAAACATTTGGGCAAAAATCATATTGGTAATGAGTGTTT | |
| | | AAAATTAAAGCACACATTATCTCTGAGACTCTTCCAACAA | |
| | | AGAGAAACTAGAATGAAGTCTGAAAAACAGAATCAAGTAA | |
| | | GACAGCATGTTATATAGTGACACTGAATGTTATTTAACTT | |
| | | GTAGTTACTATCAATATATTTATGCGTTAAACAGCTAGTT | |
| | | CTCTCAAGTGTAGAGGACAAGAACTTGTGTCAGTTATCTT | |
| | | TTGAATCCATAAATCTTAGCTGGCATTAGTTTTCTATGTA | |
| | | ATCACCTACCTAGAGAGAGTTGTAAATTATATGTTAACAT | |
| | | GTTATCTGGTTGGCAGCAAACACTAAAGCCAATAAAGGAA | |
| | | AAACAGTAAATGTTCCGAAAGCAGAGAAAAGCAACCAAAC | |
| | | ATATTGTTATGAACTAAAAGCTTTCCCTTTAAGATGCATA | |
| | | CTTGTCTTACTGGATGAAGAAAATTGAGGGTACATGTACC | |
| | | TTATACTGTCAAGGTTGTTTAAACATGATAAGGTTAATCG | |
| | | CCATCTACTTCAAGTTTTAGAAAAGGAAACAAGAAGCTGA | |
| | | AAACAGCTGCTCTGACTTTAATATCTGACTATATCTTTGA | |
| | | TCTGTTTGCAGGTCATCCAAGTGTTTTCTAGGAATATATT | |
| | | TATTTTAGGTTGTCTGAAACTACTATTTTTTAGACTCCTG | |
| | | AAAGTTGTTCACATCAATGTGAAGACAAATTTTAAATGAA | |
| | | AATGAAGAATGAAATTATGTCTTGAATCATATATTAAGAA | |
| | | GTAAAAATAATAGTGATCAGGCAGAAAAGAAAAATGGAAC | |
| | | ATCTAAAAATGTATGTGCTAACTATATCATCCAGTGTGCA | |
| | | GTGTTGTGTATTTTTCTAAGCATGACAACATTGATGTGCC | |
| | | TTTTCAGTGTAACAGCAAATACTGTTAGTGAACATTGTCA | |
| | | ATTTATGTCATTTTGTTAAGAGATATGACTGGAGTGTGCA | |
| | | GTGTGGAATGTCTCTAATACTACTTGTGAATCCTGCAGTT | |
| | | CTATAATCATAAACAAAAATTACTTAGTTTCGTTAAGCTA | |
| | | AGATTGTGTTTGTGTTAACTTCGACATCAAGGAGCAAAGA | |
| | | ACTTTAGAACAGACTCCTCAATCTTGTGACTTTCTTATTC | |
| | | TCTAGGAAAGTAACACTTCGTTTCATGAAGCTTTTCTGTG | |
| | | GGGCTTCGATTATTTCAAGTCTGGTTTCTAAGTGCAGTGT | |
| | | GTTTGAAGCAAACGAACTTCCAACTCACTTATTTGGCATT | |
| | | GGGCAACTTGGCCAAGTCTGCCACTTTGGAAGATGGCTCT | |
| | | GGAGGAAACTCTCATATGGCTAAAAAGGCAGGCTAGTTTC | |
| | | TTACTTCTACAGGGGTAGAGCCTTAAAAAAGAACGTGCTA | |
| | | CAAATTGGTTCTCTTTGAGGGTTTCTGGTTCTCCCTGCCC | |
| | | CCAATACCATATACTTTATTGCAATTTTATTTTTGCCTTT | |
| | | ACGGCTCTGTGTCTTTCTGCAAGAAGGCCTGGCAAAGGTA | |
| | | TGCCTGCTGTTGGTCCCTCGGGATAAGATAAAATATAAAT | |
| | | AAAACCTTCAGAACTGTTTTGGAGCAAAAGATAGCTTGTA | |
| | | CTTGGGGAAAAAAATTCTAAGTTCTTTTATATGACTAATA | |
| | | TTCTTGGTTAGCAAGACTGGAAAGAGGTGTTTTTTTAAAA | |
| | | TGTACATACCAGAACAAAGAACATACAGCTCTCTGAACAT | |
| | | TTATTTTTTGAACAGAGGTGGTTTTTATGTTTGGACCTGG | |
| | | TAATACAGATACAAAAACTTTAATGAGGTAGCAATGAATA | |
| | | TTCAACTGTTTGACTGCTAAGTGTATCTGTCCATATTTTA | |
| | | GCAAGTTTACTTAATAAATCTTCTGAACCATGAAAAAAAA | |
| | | AAAAA | |
| VPS13C | NM_001018088.2 | CCGGAGGGGCTGTCATTTGCAGCGCTGGTCGCAGCCCTCA | 48 |
| | | GCTGCGCCGGGCGGTTCCGGCTCCTCCCTCTCCTTGTGCC | |
| | | TCAGCGCCACCATGGTGCTGGAGTCGGTGGTCGCGGACTT | |
| | | GCTGAACCGCTTCCTGGGGGACTATGTGGAGAACCTGAAC | |
| | | AAGTCCCAGCTGAAGCTGGGCATCTGGGGCGGAAATGTGG | |
| | | CTTTAGATAATCTACAGATAAAAGAAAATGCCCTGAGTGA | |
| | | ATTGGATGTTCCTTTTAAAGTCAAGGCTGGCCAAATTGAT | |
| | | AAATTAACTTTGAAGATTCCTTGGAAGAACCTTTATGGAG | |
| | | AAGCAGTTGTTGCGACCCTGGAAGGATTATACCTGCTTGT | |
| | | TGTCCCTGGAGCAAGTATTAAGTATGATGCTGTAAAAGAA | |
| | | GAAAAATCCTTGCAGGATGTTAAACAGAAAGAGCTATCCC | |
| | | GAATTGAAGAAGCCCTTCAAAAAGCAGCAGAAAAAGGCAC | |
| | | ACATTCAGGGGAGTTCATATATGGCTTGGAGAACTTTGTT | |
| | | TACAAGGACATCAAGCCTGGACGTAAACGTAAAAAGCACA | |
| | | AAAAACATTTTAAGAAACCTTTTAAAGGTCTTGATCGTTC | |
| | | AAAAGATAAGCCAAAAGAAGCCAAAAAGGATACATTTGTG | |
| | | GAAAAATTGGCAACTCAAGTAATAAAAAATGTACAAGTAA | |
| | | AAATCACAGATATTCACATTAAATATGAAGATGATGTCAC | |
| | | TGATCCAAAGCGGCCTCTTTCATTTGGTGTCACACTGGGA | |
| | | GAGCTTAGTCTACTGACTGCAAATGAACACTGGACTCCAT | |
| | | GCATATTAAATGAAGCAGACAAAATTATATACAAGCTTAT | |
| | | ACGACTTGATAGTCTTAGCGCCTACTGGAATGTAAATTGC | |
| | | AGCATGTCTTACCAGAGATCAAGGGAACAGATTTTGGATC | |
| | | AGCTGAAAAATGAAATTCTTACAAGTGGAAATATACCCCC | |
| | | AAATTATCAATACATTTTCCAGCCAATATCAGCCTCTGCA | |
| | | AAACTCTACATGAATCCTTATGCAGAATCAGAGCTCAAAA | |

TABLE 1-continued

GEP-NEN Biomarker/Houskeeper Sequence Information

| Gene Name | RefSeq Accession | Sequence | SEQ ID NO: |
|---|---|---|---|
| | | CGCCCAAACTGGATTGCAACATAGAAATACAAAATATTGC | |
| | | CATTGAACTGACCAAACCTCAGTACTTAAGTATGATTGAC | |
| | | CTTTTGGAGTCAGTGGATTATATGGTTAGGAATGCGCCTT | |
| | | ATAGGAAATACAAGCCTTATTTACCACTTCATACCAATGG | |
| | | TCGACGATGGTGGAAATATGCAATTGATTCTGTTCTTGAA | |
| | | GTTCATATAAGAAGGTATACACAGATGTGGTCATGGAGTA | |
| | | ACATAAAAAAGCACAGGCAGTTACTCAAGAGTTATAAAAT | |
| | | TGCCTACAAAAACAAGTTAACACAGTCTAAAGTCTCAGAA | |
| | | GAAATACAGAAAGAAATTCAGGACTTGGAGAAGACTCTAG | |
| | | ATGTTTTTAACATAATTTTAGCAAGGCAACAAGCACAAGT | |
| | | TGAGGTGATTCGGTCTGGGCAAAAATTAAGGAAAAAGTCT | |
| | | GCTGACACAGGCGAGAAACGTGGAGGCTGGTTTAGTGGGT | |
| | | TGTGGGGTAAGAAAGAGTCTAAGAAAAAGGACGAAGAATC | |
| | | ATTGATTCCTGAAACTATTGATGACCTTATGACTCCAGAG | |
| | | GAAAAAGATAAACTCTTCACTGCCATTGGTTATAGTGAGA | |
| | | GTACCCACAACCTAACTTTACCTAAGCAGTATGTTGCCCA | |
| | | TATTATGACCCTGAAGTTAGTAAGCACCTCTGTTACGATA | |
| | | AGAGAAAACAAGAATATTCCAGAAATACTAAAAATTCAGA | |
| | | TAATTGGCCTGGGCACTCAAGTATCTCAGCGACCAGGAGC | |
| | | ACAAGCACTTAAGGTAGAAGCGAAATTAGAACACTGGTAT | |
| | | ATAACAGGTTTGAGACAGCAGGATATTGTGCCATCACTTG | |
| | | TGGCTTCAATTGGTGACACTACATCATCCTTGCTTAAAAT | |
| | | TAAATTTGAAACCAATCCGGAGGATAGTCCTGCTGACCAG | |
| | | ACTCTGATTGTTCAGTCCCAGCCTGTGGAGGTCATCTATG | |
| | | ATGCTAAAACTGTCAATGCAGTGGTTGAATTCTTTCAATC | |
| | | AAATAAGGGATTGGATCTTGAGCAAATAACATCAGCAACA | |
| | | TTGATGAAGCTGGAAGAAATTAAGGAGAGAACAGCTACAG | |
| | | GACTTACACATATTATTGAAACTCGAAAAGTCCTTGATTT | |
| | | AAGGATAAATCTGAAGCCTTCTTATCTAGTAGTTCCACAG | |
| | | ACGGGTTTCCACCATGAAAAGTCAGATCTTCTGATTTTAG | |
| | | ATTTTGGTACATTTCAGCTCAACAGTAAAGATCAAGGTTT | |
| | | ACAGAAGACTACTAATTCATCTCTGGAAGAAATAATGGAT | |
| | | AAGGCATATGACAAGTTTGATGTTGAAATAAAAAATGTAC | |
| | | AACTACTTTTTGCAAGAGCAGAGGAAACCTGGAAAAAGTG | |
| | | TCGATTTCAGCATCCATCAACTATGCATATATTGCAACCC | |
| | | ATGGATATTCATGTTGAGTTGGCTAAGGCCATGGTAGAAA | |
| | | AAGACATTAGAATGGCCAGATTTAAAGTGTCAGGAGGACT | |
| | | TCCTTTGATGCATGTGAGAATTTCTGACCAGAAGATGAAA | |
| | | GATGTGCTATATTTGATGAACAGTATACCTTTGCCACAGA | |
| | | AATCATCAGCCCAGTCTCCAGAGAGACAGGTATCCTCAAT | |
| | | TCCTATTATTTCAGGTGGTACAAAAGGTCTACTTGGTACT | |
| | | TCACTATTGCTAGACACTGTGGAATCAGAGTCTGATGATG | |
| | | AGTATTTTGATGCTGAAGATGGAGAACCACAGACTTGTAA | |
| | | AAGTATGAAAGGATCAGAACTTAAAAAAGCTGCAGAGGTC | |
| | | CCAAATGAGGAGCTCATCAATCTTCTACTCAAGTTTGAAA | |
| | | TTAAAGAAGTGATTTTGGAATTTACTAAACAGCAGAAAGA | |
| | | AGAAGATACAATTCTAGTATTTAATGTTACTCAGTTAGGA | |
| | | ACAGAGGCCACAATGAGAACATTTGACTTAACTGTGGTAT | |
| | | CTTATTTAAAGAAAATCAGCTTGGATTATCATGAAATTGA | |
| | | AGGATCCAAAAGGAAGCCCCTTCACTTGATTAGCTCTTCT | |
| | | GACAAACCTGGATTAGATCTTTTGAAAGTGGAGTATATTA | |
| | | AGGCTGATAAGAATGGACCTAGTTTTCAAACTGCTTTTGG | |
| | | AAAAACTGAACAAACAGTTAAGGTGGCCTTTTCATCTTTA | |
| | | AATCTGTTGCTGCAAACACAAGCTCTTGTCGCTTCTATTA | |
| | | ATTACCTCACAACCATTATTCCATCTGATGATCAAAGCAT | |
| | | AAGTGTTGCTAAGGAGGTACAAATTTCAACTGAAAAACAA | |
| | | CAAAAAAATTCAACTCTGCCAAAAGCGATTGTATCCTCCA | |
| | | GAGATAGTGACATTATTGATTTCAGGCTATTTGCCAAGTT | |
| | | GAATGCTTTCTGTGTCATTGTTTGCAACGAAAAGAACAAT | |
| | | ATCGCCGAAATCAAGATTCAAGGACTGGATTCCTCCCTTT | |
| | | CTCTCCAGTCAAGAAAGCAGTCACTTTTTGCCCGACTAGA | |
| | | AAATATTATTGTCACAGATGTTGATCCAAAGACAGTTCAT | |
| | | AAGAAAGCTGTGTCAATAATGGGAAATGAAGTTTTCCGTT | |
| | | TTAATTTGGATTTGTATCCAGATGCTACTGAGGGGGATTT | |
| | | GTATACTGACATGTCCAAAGTGGATGGTGTGCTGTCTCTG | |
| | | AATGTTGGCTGTATTCAGATTGTCTATCTTCATAAATTCC | |
| | | TTATGTCACTTCTGAACTTCCTGAATAATTTCCAGACAGC | |
| | | CAAAGAGTCTCTGAGTGCTGCCACTGCCCAGGCTGCAGAA | |
| | | AGGGCTGCCACAAGTGTGAAAGATCTTGCCCAGAGGAGTT | |
| | | TTCGTGTTTCCATCAATATTGATTTGAAAGCACCGGTTAT | |
| | | AGTCATCCCACAGTCTTCTATTTCCACCAATGCAGTAGTG | |
| | | GTAGATCTTGGGTTAATCAGAGTTCATAATCAGTTCAGTC | |
| | | TGGTGTCTGATGAAGACTACTTAAATCCTCCAGTAATTGA | |
| | | TAGAATGGATGTGCAGCTAACAAAGCTTACACTTTATAGG | |
| | | ACAGTGATCCAGCCAGGCATCTACCATCCTGATATTCAGC | |

TABLE 1-continued

GEP-NEN Biomarker/Houskeeper Sequence Information

| Gene Name | RefSeq Accession | Sequence | SEQ ID NO: |
|---|---|---|---|
| | | TGTTGCACCCAATTAACTTGGAATTTCTTGTAAATCGGAA | |
| | | TCTAGCTGCATCTTGGTACCACAAGGTGCCTGTTGTGGAA | |
| | | ATTAAAGGACATCTTGATTCAATGAATGTTAGTCTAAATC | |
| | | AAGAAGATCTTAATCTTTTATTTAGGATACTAACAGAAAA | |
| | | TCTCTGTGAGGGTACTGAAGACTTGGATAAAGTGAAACCA | |
| | | AGAGTACAAGAGACAGGTGAAATTAAAGAGCCCCTTGAAA | |
| | | TCTCTATATCACAAGATGTACATGATTCAAAAAATACTTT | |
| | | AACAACTGGAGTGGAAGAAATTAGGTCTGTAGACATCATT | |
| | | AATATGCTGCTGAATTTTGAAATTAAAGAGGTTGTGGTTA | |
| | | CTTTGATGAAAAAATCAGAAAAGAAAGGAAGGCCTTTACA | |
| | | TGAGCTAAATGTCCTGCAACTTGGAATGGAAGCTAAAGTT | |
| | | AAAACCTATGACATGACTGCTAAAGCTTATCTAAAAAAAA | |
| | | TTAGTATGCAGTGCTTTGATTTCACTGACTCTAAAGGGGA | |
| | | ACCTCTTCACATTATTAACTCTTCTAATGTGACTGACGAA | |
| | | CCCCTTCTGAAAATGTTACTGACAAAGGCAGACAGTGATG | |
| | | GACCAGAATTTAAAACTATTCATGACAGTACCAAACAGAG | |
| | | ACTGAAGGTTTCATTTGCATCCTTAGACTTAGTACTTCAT | |
| | | TTGGAAGCTTTACTTTCCTTCATGGATTTTTTATCATCTG | |
| | | CTGCTCCATTCTCTGAGCCTTCCTCTTCTGAGAAGGAATC | |
| | | CGAGCTGAAACCACTTGTGGGGGAGTCCAGAAGTATCGCT | |
| | | GTCAAAGCTGTATCCAGCAACATTTCCCAAAAGGATGTGT | |
| | | TTGATTTAAAGATCACAGCTGAATTAAATGCATTTAATGT | |
| | | CTTTGTCTGTGATCAGAAGTGTAACATTGCAGATATTAAA | |
| | | ATACATGGAATGGATGCCTCTATTTCTGTGAAGCCTAAGC | |
| | | AGACTGATGTGTTTGCCAGACTTAAAGATATTATAGTTAT | |
| | | GAATGTAGATTTGCAGTCCATTCACAAAAAGGCTGTCTCT | |
| | | ATTTTGGGAGATGAAGTCTTTAGGTTCCAACTGACTCTTT | |
| | | ATCCAGATGCCACAGAAGGAGAGGCCTATGCTGATATGTC | |
| | | CAAAGTAGACGGCAAACTTAGTTTTAAAGTGGGTTGTATT | |
| | | CAGATTGTTTATGTTCATAAATTCTTCATGTCTCTTTTGA | |
| | | ACTTCCTCAACAATTTCCAAACTGCTAAAGAAGCTTTGAG | |
| | | TACAGCCACAGTCCAGGCTGCAGAAAGAGCTGCTTCCAGC | |
| | | ATGAAAGACTTGGCTCAAAAGAGTTTCCGCCTTTTGATGG | |
| | | ATATTAATTTGAAAGCACCAGTTATTATTATTCCTCAGTC | |
| | | TTCAGTATCACCTAATGCTGTTATAGCAGATCTGGGTTTA | |
| | | ATCAGAGTTGAAAACAAGTTTAGCTTGGTTCCTATGGAAC | |
| | | ATTATTCTCTTCCTCCAGTCATTGATAAAATGAACATCGA | |
| | | ACTCACTCAGTTGAAGCTGTCAAGAACTATTTTGCAGGCT | |
| | | AGCTTGCCACAAAATGACATTGAAATTTTAAAACCAGTCA | |
| | | ACATGCTTTTGTCCATACAGCGAAACTTAGCAGCAGCATG | |
| | | GTATGTGCAAATTCCAGGGATGGAGATAAAAGGAAAACTA | |
| | | AAACCTATGCAGGTTGCTCTCAGTGAAGATGACTTGACAG | |
| | | TTTTAATGAAAATTTTGCTAGAAAATCTTGGAGAAGCTTC | |
| | | CTCACAACCAAGCCCTACACAGTCTGTGCAGGAGACTGTA | |
| | | AGAGTGAGAAAAGTTGATGTTTCAAGTGTACCTGACCATC | |
| | | TCAAAGAACAAGAAGATTGGACAGACTCAAAGCTCTCTAT | |
| | | GAACCAGATTGTCAGTCTCCAATTTGACTTTCACTTTGAA | |
| | | TCTCTTTCCATTATCCTTTATAACAATGATATCAACCAGG | |
| | | AATCTGGAGTTGCATTTCATAATGACAGTTTCCAACTTGG | |
| | | TGAACTCAGACTACATCTTATGGCCTCCTCAGGGAAGATG | |
| | | TTTAAGGATGGCTCAATGAATGTCAGCGTTAAACTTAAGA | |
| | | CATGCACCCTTGATGATCTCAGAGAAGGAATTGAGAGAGC | |
| | | AACATCGAGAATGATTGACAGAAAGAATGACCAAGATAAC | |
| | | AACAGTTCTATGATTGATATAAGTTACAAACAAGACAAAA | |
| | | ATGGAAGTCAAATTGATGCTGTTCTTGACAAGCTGTATGT | |
| | | ATGTGCCAGTGTGGAATTTCTGATGACTGTGGCAGATTTC | |
| | | TTTATCAAAGCTGTGCCTCAGAGTCCAGAAAATGTGGCAA | |
| | | AAGAAACACAGATTTTACCAAGACAGACTGCCACAGGGAA | |
| | | GGTCAAGATAGAGAAAGATGACTCTGTTAGACCAAATATG | |
| | | ACTTTAAAGGCCATGATCACAGATCCAGAAGTGGTATTTG | |
| | | TTGCCAGCCTGACAAAGGCTGATGCTCCTGCTCTGACAGC | |
| | | CTCGTTTCAGTGCAACCTTTCTCTGTCAACATCCAAACTC | |
| | | GAACAGATGATGGAAGCTTCTGTGAGAGATCTGAAAGTGC | |
| | | TCGCTTGCCCTTTTCTCAGAGAAAAGAGAGGGAAAAACAT | |
| | | TACCACAGTCTTGCAGCCCTGTTCTTTATTTATGGAAAAA | |
| | | TGTACGTGGGCTTCAGGAAAGCAAAATATAAATATTATGG | |
| | | TTAAAGAATTTATAATTAAGATTTCACCCATAATTCTTAA | |
| | | TACTGTGTTGACAATCATGGCTGCATTGTCTCCAAAAACA | |
| | | AAAGAAGATGGATCCAAAGATACGTCTAAGGAAATGGAAA | |
| | | ATCTTTGGGGTATCAAATCGATTAATGATTATAACACTTG | |
| | | GTTTCTTGGTGTTGACACGGCAACAGAAATAACGGAAAGC | |
| | | TTCAAAGGCATTGAACATTCACTGATAGAGGAAAATTGTG | |
| | | GTGTTGTTGTAGAATCCATTCAAGTTACCTTAGAATGTGG | |
| | | CCTTGGACATCGAACTGTACCTTTATTATTGGCAGAGTCT | |
| | | AAGTTTTCAGGAAATATTAAAAATTGGACTTCTCTAATGG | |

TABLE 1-continued

| GEP-NEN Biomarker/Houskeeper Sequence Information | | | |
|---|---|---|---|
| Gene Name | RefSeq Accession | Sequence | SEQ ID NO: |
| | | CTGCTGTTGCTGACGTGACACTACAGGTGCACTATTACAA | |
| | | TGAGATCCATGCTGTCTGGGAGCCACTGATTGAGAGAGTG | |
| | | GAGGGGAAGAGACAATGGAATTTAAGGCTTGATGTAAAGA | |
| | | AGAACCCAGTTCAGGATAAAAGTTTGCTGCCAGGAGATGA | |
| | | TTTTATTCCTGAGCCACAAATGGCAATTCATATTTCTTCA | |
| | | GGAAATACAATGAATATAACAATATCCAAAAGTTGTCTTA | |
| | | ATGTTTTCAACAATTTAGCAAAAGGTTTTTCAGAGGGCAC | |
| | | TGCTTCTACTTTTGACTACTCTTTAAAGGACAGAGCTCCT | |
| | | TTTACGGTAAAAAATGCTGTAGGTGTTCCCATTAAGGTGA | |
| | | AGCCCAATTGTAATCTCAGAGTAATGGGCTTCCCTGAGAA | |
| | | AAGTGATATTTTTGATGTTGATGCTGGCCAGAATTTGGAA | |
| | | CTGGAGTATGCCAGCATGGTACCTTCAAGTCAAGGGAACC | |
| | | TATCTATATTGAGCCGTCAAGAAAGCTCCTTCTTCACTCT | |
| | | GACCATTGTACCTCATGGATATACAGAAGTTGCAAATATC | |
| | | CCTGTGGCCAGACCTGGACGGCGATTGTATAATGTACGGA | |
| | | ATCCCAATGCCAGTCATTCTGACTCTGTCTTGGTACAAAT | |
| | | TGATGCAACTGAAGGGAATAAAGTAATTACCCTTCGCTCT | |
| | | CCTCTACAGATCAAAAACCATTTCTCCATTGCATTTATCA | |
| | | TCTATAAATTTGTTAAGAATGTTAAGCTATTGGAGCGCAT | |
| | | TGGGATAGCCAGACCTGAAGAGGAGTTCCATGTTCCTTTA | |
| | | GATTCATATAGATGTCAATTGTTTATCCAGCCAGCTGGAA | |
| | | TCTTAGAGCATCAGTACAAAGAATCTACCACTTATATTTC | |
| | | CTGGAAGGAAGAACTTCATAGGAGCAGGGAAGTCAGATGC | |
| | | ATGTTGCAGTGTCCATCAGTAGAAGTCAGCTTCTTACCTC | |
| | | TCATAGTGAATACAGTTGCTCTGCCTGATGAATTGAGCTA | |
| | | CATATGTACACATGGGGAAGACTGGGATGTAGCTTACATT | |
| | | ATTCATCTTTATCCTTCTCTCACTTTGCGGAATCTTCTCC | |
| | | CATATTCCCTAAGATATTTACTTGAGGGAACAGCAGAAAC | |
| | | TCATGAGCTGGCAGAAGGCAGTACTGCTGATGTTCTGCAT | |
| | | TCGAGAATCAGTGGTGAAATAATGGAATTAGTCCTGGTGA | |
| | | AATACCAGGGCAAAAACTGGAATGGACATTTCCGCATACG | |
| | | TGATACACTACCAGAATTCTTTCCTGTGTGTTTTTCTTCT | |
| | | GACTCCACAGAAGTGACGACAGTCGACCTGTCAGTCCACG | |
| | | TCAGGAGAATTGGCAGCCGGATGGTGCTGTCTGTCTTTAG | |
| | | TCCCTATTGGTTAATCAACAAGACTACCCGGGTTCTCCAG | |
| | | TATCGTTCAGAAGATATTCATGTGAAACATCCAGCTGATT | |
| | | TCAGGGATATTATTTTATTTTCTTTCAAGAAGAAGAACAT | |
| | | TTTTACTAAAAATAAGGTACAATTAAAAATTTCAACCAGT | |
| | | GCCTGGTCCAGTAGTTTCTCATTGGATACAGTGGGAAGTT | |
| | | ATGGGTGTGTGAAGTGTCCTGCCAACAATATGGAGTACCT | |
| | | GGTTGGTGTTAGCATCAAAATGAGCAGTTTCAACCTTTCA | |
| | | CGAATAGTTACCCTGACTCCCTTTTGTACCATTGCAAACA | |
| | | AGTCATCATTAGAACTAGAAGTTGGCGAGATTGCATCTGA | |
| | | TGGCTCAATGCCAACTAATAAATGGAACTATATTGCTTCT | |
| | | TCAGAGTGCCTTCCATTTTGGCCAGAAAGTTTGTCAGGCA | |
| | | AACTTTGTGTGAGAGTGGTGGGCTGTGAAGGATCTTCCAA | |
| | | ACCATTCTTTTATAACCGACAGGATAATGGCACTTTATTG | |
| | | AGCTTAGAAGATCTGAATGGGGGTATCTTGGTGGATGTAA | |
| | | ACACTGCCGAACATTCAACTGTCATAACTTTTTCTGATTA | |
| | | CCATGAGGGATCTGCACCTGCCTTGATAATGAACCATACA | |
| | | CCATGGGACATCCTCACATACAAACAGAGTGGGTCACCAG | |
| | | AAGAAATGGTCTTGCTGCCAAGACAGGCTCGACTTTTTGC | |
| | | CTGGGCAGATCCTACTGGTACCAGAAAACTTACATGGACA | |
| | | TATGCAGCAAATGTTGGGGAACATGATCTGTTAAAGGATG | |
| | | GATGTGGACAGTTTCCATATGATGCAAACATCCAGATACA | |
| | | CTGGGTATCATTTCTGGATGGGCGCCAGAGAGTTTTGCTT | |
| | | TTCACCGATGATGTTGCCTTGGTTTCCAAAGCACTGCAGG | |
| | | CAGAAGAAATGGAACAGGCTGATTATGAAATAACCTTGTC | |
| | | TCTCCACAGTCTTGGGCTTTCACTGGTTAACAATGAAAGC | |
| | | AAGCAGGAAGTTTCCTATATTGGGATAACCAGTTCTGGTG | |
| | | TTGTTTGGGAGGTGAAACCAAAGCAGAAATGGAAGCCATT | |
| | | TAGTCAAAAGCAGATAATCTTATTGGAACAATCCTATCAG | |
| | | AAACATCAAATATCAAGAGACCATGGCTGGATTAAGCTAG | |
| | | ATAATAATTTTGAGGTCAATTTTGATAAAGATCCAATGGA | |
| | | AATGCGCCTCCCTATTCGTAGCCCTATTAAACGAGACTTT | |
| | | TTATCAGGAATTCAGATTGAATTTAAGCAGTCTTCTCACC | |
| | | AGAGAAGTTTAAGGGCCAGGTTGTACTGGCTTCAGGTTGA | |
| | | TAATCAGTTACCAGGTGCAATGTTCCCTGTTGTATTTCAT | |
| | | CCTGTTGCCCCTCCAAAATCTATTGCTTTAGATTCAGAGC | |
| | | CCAAGCCTTTCATTGATGTGAGTGTCATCACAAGATTTAA | |
| | | TGAGTACAGTAAAGTCTTACAGTTCAAGTATTTTATGGTC | |
| | | CTCATTCAGGAAATGGCCTTAAAAATTGATCAAGGGTTTC | |
| | | TAGGAGCTATTATTGCACTGTTTACCCCAACAACAGACCC | |
| | | TGAAGCTGAAAGAAGACGGACAAAGTTAATCCAACAAGAT | |
| | | ATTGATGCTCTAAATGCAGAATTAATGGAGACTTCAATGA | |

TABLE 1-continued

GEP-NEN Biomarker/Houskeeper Sequence Information

| Gene Name | RefSeq Accession | Sequence | SEQ ID NO: |
|---|---|---|---|
| | | CTGATATGTCAATTCTTAGTTTCTTTGAACATTTCCATAT | |
| | | TTCTCCTGTGAAGTTGCATTTGAGTTTGTCTTTGGGTTCC | |
| | | GGAGGTGAAGAATCAGACAAAGAAAAACAGGAAATGTTTG | |
| | | CAGTTCATTCTGTCAACTTGCTGTTGAAAAGCATAGGTGC | |
| | | TACTCTGACTGATGTGGATGACCTTATATTCAAACTTGCT | |
| | | TATTATGAAATTCGATATCAGTTCTACAAGAGAGATCAGC | |
| | | TTATATGGAGTGTTGTTAGGCATTACAGTGAACAGTTCTT | |
| | | GAAACAGATGTATGTCCTTGTATTGGGGTTAGATGTACTT | |
| | | GGAAACCCATTTGGATTAATTAGAGGTCTGTCTGAAGGAG | |
| | | TTGAAGCTTTATTCTATGAACCCTTCCAGGGTGCTGTTCA | |
| | | AGGCCCTGAAGAATTTGCAGAGGGGTTAGTGATTGGAGTG | |
| | | AGAAGCCTCTTTGGACACACAGTAGGTGGTGCAGCAGGAG | |
| | | TTGTATCTCGAATCACCGGTTCTGTTGGGAAAGGTTTGGC | |
| | | AGCAATTACAATGGACAAGGAATATCAGCAAAAAAGAAGA | |
| | | GAAGAGTTGAGTCGACAGCCCAGAGATTTTGGAGACAGCC | |
| | | TGGCCAGAGGAGGAAAGGGCTTTCTGCGAGGAGTTGTTGG | |
| | | TGGAGTGACTGGAATAATAACAAAACCTGTGGAAGGTGCC | |
| | | AAAAAGGAAGGAGCTGCTGGATTCTTTAAAGGAATTGGAA | |
| | | AAGGGCTTGTGGGTGCTGTGGCCCGTCCAACTGGTGGAAT | |
| | | CGTAGATATGGCCAGTAGTACCTTCCAAGGCATTCAGAGG | |
| | | GCAGCAGAATCAACTGAGGAAGTATCTAGCCTCCGTCCCC | |
| | | CTCGCCTGATCCATGAAGATGGCATCATTCGTCCTTATGA | |
| | | CAGACAGGAATCTGAGGGCTCTGACTTACTTGAGCAAGAA | |
| | | CTGGAAATACAGGAATAAATGTTTCCTAAACTACTACTTG | |
| | | ATTTCATCCTTAAAAATCAAAACAAACTGTGGTGTTAATT | |
| | | GACTGTGTGTGAATTCCATTGTCAATTTTAATGAAATTTT | |
| | | CTTTAAAACTCTCACCTCCATCTGAACTTTTCATAGTAGT | |
| | | GGGATTGACTACAAATAAAAACTTGTGGTATTCCTGGTAA | |
| | | TACTGTCCAGAAATAAGAGATTAGTATAAAATATTAAAGG | |
| | | ATGCAGAGAATCAGCTCTCTTCTGCGTTTAATAGATGAAA | |
| | | GCCTTTATTGAGCTCAGAAGCAGATACTGTTACTATCATT | |
| | | TCGAAAATTTTATCTTATGGTGTTCATGTGCATTTCAGGT | |
| | | AAAATTGAAAAACAGGACAATTATTATGTCCAATTAATAT | |
| | | GTTTATGTTTGTGAGTCTTGATGATGGAATTACATAGCTT | |
| | | TCTGTTTCACAAATGGCTCTAAATTTGCTTAAGTTACGGG | |
| | | ACTATTACCTGGAGCATCTGCTTTAATAATTGAATTGTCA | |
| | | GTTGCTCTGAGCCTGCCCTTAGACCTCAAGTAATAAATAG | |
| | | TTGGCACATGAATTTTGAGGATATGTTTCCTCTTCCCTCT | |
| | | TTTTCCTATTTAACCCCTTGGTACTGTTGCTAAATAAATG | |
| | | ATAGCCATTTTATAATTATGTTATATACATTTTCAGCCTT | |
| | | TAGCATTTCTGCTTTTCAAAAATTGAATCTCCTTGTTGGT | |
| | | TATGCTTATTTCATAATTATTAGTTTTAATTAATGTAGAT | |
| | | AGAAGTTGAACATGTAATTAGGCAAATTGCTGTGTGGCAC | |
| | | TTGAATACATAGATTTCTTTATTTTCAAAAACCAACCTTT | |
| | | TGCTTTTAAATCCTTAGAGAGGGTTTATTATCTTAGAGAA | |
| | | AAAATAATTATAATCATTATTTTTGAAATTAGTATCCTCT | |
| | | TAATTCTCAACATAAGTTATGTTTCAATTTCTTTTTTTTG | |
| | | TAATAAATGATGGAAATGTTTAACAATGTCTTATCTAGCA | |
| | | ACTTTCATGCTTCTCCTCAGAAATGAAGCCAAAGTATAAA | |
| | | CTTAGATTTAATGTGTTGTATATTTGAAGAGAATGAAACT | |
| | | ATTAACATATAATTGTTCAGTTGGATTATGTATTTTAAGG | |
| | | ATTGCAGTTATCAAAATAATAAATTGAATGTTTTATGTTT | |
| | | AACCACTTTAAAGAAGAAAGACTGACATCCAAAAACCAGC | |
| | | GTGTGCTAGATATACAAAGGAAATTACTTCTGTCCTTAAG | |
| | | GGACCAAGTATAACAAAACATGTAACTGTTAAAAGTAGCT | |
| | | GACAAACCTTTCTTGTGCCTAGATAATTTAGCATTGGCAA | |
| | | AAATGTCACCACATGCAGTTTTCTAGGAGAGTCAAGCACA | |
| | | AATAACTAATTCAAGATGCTGACTTAAATCATCTCCAATA | |
| | | GTTACCCTTCCTGAGATTCTAAAGTAACAATTTTTAATTT | |
| | | TACTGGTTATATTGCTGTTTTACTGAGACTTACTTTTAAG | |
| | | AACCCCTGTAACTTAAGATTTTTTCTTAATTGTTTTGTTT | |
| | | AGCTCTGTTATTAATTTTTTCCTTGTGATATCTTTTTATA | |
| | | ACTCTCTGTCAAAAAGCACAAAACTTCAAGAAACTTTTAA | |
| | | TTATTTTGTCTGAACATATAATCTTGTCTGATTTCTTAGT | |
| | | TTTTATTAAGATATCAGACAACTTTTAAAACTTTAGTGCA | |
| | | TTATTATAATTACTGGAAGAAAAAGAATGATTATACACTA | |
| | | ATGAGAGGACTTGGTAGTTTTTGTCGTGGATGTCAAGTGT | |
| | | GGGCATGGATAATTGAAATATTTAGGCTATTTCATTCTTT | |
| | | GCCCATCTTGCTGTGATCAGTTAGTTGGGTAAAAATATTT | |
| | | ATTGATTATTTAGACTGTACTGGATATACAAAAGAAGCCT | |
| | | TCTGTCCTTAAGGGACCGAGTAAAACAAAACATGGAAATA | |
| | | TTAAAGAGTATTAGAGTATAAAAGTATATCTTTTTAGCCC | |
| | | TTTGTAATATGGCCAAATTCTAAATAATTTATTTGGGGAT | |
| | | CTTTTGATCCTCATGTTCCTTTTTCTCCTAAGTACTACTT | |
| | | TGTATTCTTTAATATGCAGCTTTGAGAGTTACTGAATCAT | |

TABLE 1-continued

GEP-NEN Biomarker/Houskeeper Sequence Information

| Gene Name | RefSeq Accession | Sequence | SEQ ID NO: |
|---|---|---|---|
| | | ATATTATATTTCCATGAGATGTACTATTCTACTTATCCTC<br>TAATCTTCATATATATATACACACACACATATATATACAC<br>ATACATATATACACACGTACATATATGTACACATACAGAT<br>ATACATACACACAAACACATATATACACACATACATATAC<br>ACACATATATATACACATACAAATATACACATATATACAC<br>ATACATATATATACACACATACAAATATACCCATATGTAC<br>ACATACATATATACACATACATATATACACACACATATAC<br>ACACATATATACGCAAACATACACATATTTACACATACAT<br>ATATACATACATTATATGTATGTATATATAGTCATTTAAT<br>ACTCATTTTGGTTCACATACTTATGATCATGCAACGTTTA<br>AAACAGCATTTCTTGCTTTTTAGTTTTAGTTATATTTTTC<br>CATGTTCTTAGAAATGCCTCATTAACATTTTTAATTCTTG<br>TATTGCCATCTATTGAGGTGACATTACATTGTGTTTTTAT<br>CTCGTCTTAATTCATGACATTAAATTATTCTACTAACAGT<br>AATAATGCTGTAATAAACATCATTATAGATTTTGCTTTTT<br>TATATCTTGTTTGCTTTTTCATATTTCCTTAGAATTTACT<br>TGAAAAAATTGAATTACTGGGTAAAGGGCTTTTGCAAAGT<br>ATTGTTAAATTCCTCGAGTTGCATTTTTGGAAAGGGGACG<br>TGAATATTTTATCAACTAATTTGGTCTCCCTGCTGCCATT<br>AGTGACTGAATATCTTAATCTGAATCTCAGAGTGTAGTGG<br>GTTTTTAGTAGTGCTGAAGACAAGTTTTCTAAAGTGTATT<br>ATGGTGATAAATTATATTTTAAAAACTGTCAATGGCTTGA<br>AGCACAATAGCCTAATAACTAACGAAAATACATACAAGAT<br>AGAAAGTGGGTAGTATTTCTTGTACTTGCATTTCAGATCT<br>AAATATTTTAACATATTTAAATTTCAAGCTGCAGATAAAT<br>GCATTACATTATTAAATTCATTTCCCATTTTCTCTTTGAA<br>GAAATTAAGGCAAAAGTGTTAAAAGATTTTAACTAATTCG<br>CACAAGTGAATTGTGAAACAAGTAGCTATTGCTGTGAAAT<br>CTGCACTCCTCTCTGAGACTCATTCTGAAGATGAGATCCC<br>AGTTCTTTGTGGATTCCTCTTCCTTATTCATGGCTTTTTG<br>CAATTGTCAAGGAATGACTAGGTACCAAGCAACTTTAAAA<br>AATGTATATTTAAGCATTGAAATAATATCAAATGTGATTT<br>CTCTGCTTGTGGTTATATTGATTATATTATCCTTTTAATA<br>ATATTGGCATTATATTCTTGGTCGTAAAATGTCAAGGTCT<br>TATTTATTCAGTATATTTATGTTCTGTATTTTCATATATA<br>TTATCTATTTTCAGCCATGCATTATATATAATGTCAGTAA<br>TAGTATTTCATTAGCATTCATTATAAAAAAACTCGTTTTT<br>AATATTTGACTAATTCAAGTCACAGTACTTTTGAGATAGC<br>TGAAAAGGAAAATAAATGTGTTTTAATGTGCTACTAAAAA<br>AAAAAAA | |
| WDFY3 | NM_014991.4 | GCGGCCGCAGAATCGAGCTCGGGCCCCGGCCCCCGGCCCG<br>CGGCGCGGGGCTCCCGGGCCCCGCCGCGGACGTCGCGCCG<br>GTCGCCCCTTCCCCGTAGCCCGTGCGCCCTCGGCGCGGAG<br>CCCCGGCCCGCCGCGGTCCCGTCTCCTGGGCCTGTCCCGC<br>CCGCGCCCTCCGCCGGCCCTCAGGTATAATACTTCTCCAC<br>GTCTGCTTCAGGAAGAAAGTGCCTGCCATTCTTATCATTT<br>CTAAGCAGGTTCATGCCAGCCCAGAACAGAGAATCAGCTG<br>GAGCCCAGATTTCAAGTTTTGAGTAAAATACCTTCAAGCG<br>AATGGGCCCTATTGTGCTCACACATTCAGAACCTGTTACC<br>CAAGGAATTCCCTAAAGAATTAGAAGTGCGTCTCACCAAC<br>CAGCCAAGATGAACATGGTGAAGAGGATCATGGGGCGGCC<br>GAGGCAGGAGGAGTGCAGCCCACAAGACAACGCCTTAGGA<br>CTGATGCACCTCCGCCGGCTCTTCACGGAGTTGTGCCATC<br>CTCCCCGGCACATGACTCAGAAGGAACAAGAAGAGAAACT<br>GTATATGATGCTGCCAGTGTTTAACAGGGTTTTTGGAAAT<br>GCTCCGCCGAATACAATGACAGAAAAATTTTCTGATCTTC<br>TGCAGTTCACAACACAAGTCTCACGACTAATGGTGACAGA<br>AATTCGAAGGAGAGCATCAAACAAATCCACAGAGGCTGCA<br>AGTCGGGCCATAGTTCAGTTCCTAGAGATTAATCAGAGTG<br>AAGAAGCCAGTAGAGGCTGGATGCTTCTAACGACAATTAA<br>TTTGTTAGCTTCCTCTGGTCAGAAAACCGTGGACTGCATG<br>ACAACAATGTCAGTGCCTTCCACCCTGGTTAAATGTTTAT<br>ATCTGTTTTTTGACCTTCCACATGTGCCTGAGGCAGTTGG<br>AGGTGCACAGAATGAGCTACCTCTAGCAGAACGTCGAGGA<br>CTACTCCAGAAAGTTTTTGTACAGATCTTAGTGAAACTGT<br>GCAGTTTTGTTTCCCCTGCGGAGGAGCTGGCTCAGAAAGA<br>TGATCTCCAGCTTCTATTCAGTGCAATAACCTCTTGGTGC<br>CCTCCCTATAACCTGCCTTGGAGAAAGAGTGCTGGAGAAG<br>TCCTCATGACCATATCTCGTCATGGTCTTAGTGTCAATGT<br>AGTGAAGTATATTCATGAGAAAGAGTGTTTATCTACATGT<br>GTTCAGAATATGCAGCAATCAGATGACCTGTCTCCCCTAG<br>AAATTGTCGAAATGTTTGCTGGGCTTTCTTGTTTCCTCAA<br>AGATTCCAGCGATGTTTCCCAAACACTTCTGGATGATTTT<br>CGGATATGGCAAGGATATAATTTTCTTTGTGATCTCTTGC | 49 |

TABLE 1-continued

| GEP-NEN Biomarker/Houskeeper Sequence Information | | | |
|---|---|---|---|
| Gene Name | RefSeq Accession | Sequence | SEQ ID NO: |
| | | TTAGATTGGAACAAGCAAAAGAGGCAGAATCCAAAGATGC<br>CTTGAAAGATCTGGTTAATCTGATAACTTCCCTAACAACA<br>TATGGTGTCAGTGAACTAAAACCAGCTGGTATTACCACAG<br>GGGCACCCTTTTTATTGCCTGGATTTGCAGTACCTCAGCC<br>TGCAGGCAAAGGTCACAGTGTGAGAAACGTCCAGGCCTTT<br>GCAGTTCTTCAGAATGCATTTTTAAAAGCAAAAACCAGCT<br>TCCTTGCCCAAATCATCCTTGATGCTATCACAAATATTTA<br>CATGGCTGACAATGCCAATTACTTCATCCTAGAGTCACAG<br>CACACATTGTCACAGTTTGCAGAGAAGATTTCTAAACTCC<br>CAGAAGTACAAAACAAATACTTTGAGATGCTGGAGTTTGT<br>TGTTTTTAGCTTAAATTATATACCTTGTAAAGAACTTATT<br>AGTGTCAGTATCCTCTTAAAATCTAGCTCTTCTTATCACT<br>GTAGCATTATTGCAATGAAAACACTTCTTAAGTTTACAAG<br>ACATGACTACATATTTAAAGACGTGTTCAGGGAGGTTGGC<br>CTTTTGGAGGTCATGGTAAACCTTTTGCATAAATATGCTG<br>CCCTGTTGAAGGATCCAACTCAGGCACTAAATGAACAAGG<br>GGACTCAAGAAATAATAGTTCAGTTGAAGACCAAAAACAC<br>CTGGCTTTATTGGTTATGGAGACCTTGACAGTGCTTCTTC<br>AAGGATCAAACACAAATGCAGGAATTTTTCGAGAATTTGG<br>AGGTGCAAGATGTGCACATAATATAGTAAAGTACCCTCAA<br>TGCCGGCAGCATGCCTTGATGACTATCCAACAGCTGGTGC<br>TCTCCCCAAATGGGGACGATGACATGGGCACTCTCCTGGG<br>GCTAATGCATTCAGCCCCACCGACGGAATTGCAGTTGAAG<br>ACTGATATTTTAAGGGCCCTCCTGTCGGTCCTTCGAGAAA<br>GCCATCGTTCAAGAACAGTTTTTAGGAAAGTTGGAGGATT<br>TGTGTACATTACATCCTTGCTCGTTGCTATGGAAAGATCT<br>TTGAGCTGTCCACCCAAGAATGGCTGGGAGAAAGTGAACC<br>AGAATCAAGTGTTTGAACTTCTTCACACTGTGTTCTGCAC<br>GTTGACTGCAGCAATGCGCTATGAGCCAGCCAACTCTCAT<br>TTCTTCAAAACAGAGATTCAGTATGAGAAGTTGGCAGATG<br>CTGTTCGATTTCTTGGCTGCTTCTCAGACCTAAGAAAAAT<br>AAGCGCCATGAATGTCTTCCCCTCAAATACACAGCCATTT<br>CAAAGACTTTTAGAGGAAGATGTAATCTCAATAGAATCAG<br>TGTCACCCACGTTACGGCACTGCAGTAAACTTTTTATTTA<br>TCTTTACAAAGTAGCCACAGATTCTTTTGACAGTCGTGCA<br>GAACAGATCCCTCCTTGCCTGACAAGTGAGTCTTCTCTCC<br>CCTCTCCTTGGGGTACACCAGCTTTGTCCAGGAAAAGGCA<br>TGCATATCATTCTGTTTCAACTCCCCCTGTTTACCCTCCT<br>AAAAATGTTGCCGACCTGAAACTACATGTGACAACTTCAT<br>CTCTGCAGAGTTCTGATGCAGTCATCATTCATCCTGGAGC<br>CATGCTTGCCATGCTGGACCTACTGGCCTCTGTTGGGTCA<br>GTGACACAGCCAGAACATGCTTTGGATCTTCAACTTGCCG<br>TGGCAAATATTTTACAATCCCTGGTGCACACAGAAAGGAA<br>CCAGCAAGTCATGTGTGAAGCTGGTCTTCATGCACGACTG<br>CTGCAGAGGTGCAGTGCTGCATTGGCTGATGAGGACCACT<br>CACTGCACCCGCCCCTGCAGCGGATGTTTGAACGATTAGC<br>CTCTCAGGCTCTGGAACCCATGGTGTTGAGGGAGTTTTTA<br>CGTTTGGCAAGTCCTTTAAATTGTGGTGCCTGGGACAAAA<br>AACTGCTAAAACAATATAGGGTCCACAAACCAAGTTCACT<br>GAGTTATGAACCAGAAATGAGAAGTAGTATGATCACATCT<br>CTGGAAGGTCTGGGTACTGATAATGTTTTTAGCTTACATG<br>AAGATAACCATTACCGGATAAGCAAGAGCCTGGTAAAATC<br>TGCGGAAGGAAGTACTGTACCCCTGACCAGGGTGAAGTGT<br>CTGGTCTCCATGACAACCCCACATGACATCAGACTTCATG<br>GGTCATCAGTTACTCCAGCTTTTGTTGAATTTGACACATC<br>ACTTGAAGGGTTTGGATGTCTTTTTTTGCCCAGTTTGGCC<br>CCTCATAATGCTCCTACAAATAATACCGTCACAACAGGTC<br>TTATTGATGGGGCTGTGGTCAGTGGCATTGGTTCTGGTGA<br>AAGATTCTTCCCTCCTCCCTCCGGCTTAAGTTACTCTAGC<br>TGGTTTTGTATTGAACATTTTAGTTCTCCTCCAAATAACC<br>ACCCTGTCAGACTTCTTACTGTTGTGCGCCGAGCAAATTC<br>TTCTGAGCAACATTACGTGTGCCTTGCAATAGTTCTATCA<br>GCAAAAGACCGATCTCTGATTGTTTCCACCAAAGAGGAAC<br>TCCTCCAAAATTATGTTGATGATTTTAGTGAAGAGTCCTC<br>ATTTTATGAAATTCTCCCATGCTGTGCTCGCTTTCGATGT<br>GGAGAGCTTATCATTGAGGGACAGTGGCATCATTTGGTCC<br>TGGTAATGAGCAAAGGCATGTTGAAAAACAGTACTGCAGC<br>CCTTTATATTGATGGACAGCTTGTTAACACTGTAAAGCTT<br>CATTATGTCCACAGTACTCCAGGGGGTTCAGGTTCGGCAA<br>ATCCACCAGTGGTGAGCACGGTCTATGCCTACATTGGTAC<br>TCCACCTGCCCAACGCCAAATTGCCTCATTGGTTTGGCGC<br>CTGGGACCCACACATTTTCTAGAAGAAGTTTTACCTTCTT<br>CAAATGTTACTACCATTTATGAACTTGGACCAAATTATGT<br>TGGAAGCTTTCAGGCTGTATGTATGCCATGTAAAGATGCA<br>AAATCCGAAGGGGTGGTGCCATCCCCTGTGTCATTAGTAC | |

TABLE 1-continued

GEP-NEN Biomarker/Houskeeper Sequence Information

| Gene Name | RefSeq Accession | Sequence | SEQ ID NO: |
|---|---|---|---|
| | | CAGAGGAGAAAGTGTCATTTGGCCTCTATGCACTCTCTGT | |
| | | GTCGTCTCTAACAGTGGCAAGAATCCGGAAAGTGTATAAC | |
| | | AAATTGGATAGCAAAGCCATTGCTAAGCAGTTAGGCATTT | |
| | | CCTCACATGAGAATGCCACTCCTGTGAAGTTGATACACAA | |
| | | TTCAGCAGGACATCTTAATGGATCTGCACGGACAATTGGG | |
| | | GCCGCTCTGATTGGATACTTGGGAGTAAGAACATTTGTCC | |
| | | CTAAGCCTGTTGCCACTACTTTGCAGTACGTTGGTGGAGC | |
| | | TGCAGCCATCCTGGGCCTGGTGGCCATGGCCTCTGATGTG | |
| | | GAAGGGTTATATGCAGCAGTCAAGGCCCTGGTTTGTGTGG | |
| | | TCAAGAGTAACCCACTAGCCAGCAAAGAAATGGAAAGAAT | |
| | | CAAGGGCTACCAGTTGCTGGCAATGTTGCTTAAGAAGAAA | |
| | | CGTTCCCTTCTTAACAGCCACATCCTCCATCTAACTTTTT | |
| | | CTTTGGTGGGAACTGTTGATAGTGGACATGAGACCTCCAT | |
| | | TATTCCAAATTCAACTGCTTTCCAGGACCTCCTCTGTGAT | |
| | | TTTGAAGTCTGGCTCCATGCACCATATGAACTTCATCTTT | |
| | | CCTTATTTGAACACTTTATTGAACTGCTCACAGAGTCCAG | |
| | | TGAAGCCTCAAAGAATGCCAAATTAATGAGAGAATTCCAG | |
| | | TTAATCCCAAAGCTGCTCCTGACTCTTCGAGATATGTCTT | |
| | | TATCCCAGCCTACTATTGCTGCTATTAGTAATGTCCTGAG | |
| | | CTTCTTACTGCAAGGTTTTCCTAGCAGCAATGATCTGCTC | |
| | | AGATTTGGGCAGTTTATTTCTTCTACTTTGCCAACCTTTG | |
| | | CGGTTTGTGAGAAATTTGTAGTAATGGAAATAAATAATGA | |
| | | AGAGAAGCTTGACACTGGAACTGAAGAGGAGTTTGGAGGT | |
| | | CTTGTATCAGCTAATCTTATACTTTTGAGGAACAGACTTC | |
| | | TGGATATCTTGCTAAAACTAATTTATACATCTAAAGAAAA | |
| | | GACAAGCATTAATTTGCAAGCTTGTGAAGAACTGGTGAAG | |
| | | ACACTGGGTTTTGACTGGATCATGATGTTTATGGAGGAAC | |
| | | ACTTACATTCCACCACAGTTACAGCAGCCATGAGGATTCT | |
| | | TGTTGTCCTACTAAGTAATCAGTCTATTCTCATCAAGTTT | |
| | | AAAGAAGGACTCAGTGGTGGAGGATGGCTTGAACAGACAG | |
| | | ATTCTGTCTTAACTAATAAGATTGGAACTGTATTAGGATT | |
| | | CAACGTGGGCAGAAGTGCTGGTGGGAGATCGACGGTCAGG | |
| | | GAGATTAACCGAGATGCTTGTCATTTTCCTGGTTTTCCAG | |
| | | TCCTTCAGTCATTCCTTCCTAAACACACTAATGTCCCTGC | |
| | | CCTCTATTTTCTCCTCATGGCCTTGTTTCTGCAGCAGCCA | |
| | | GTTAGTGAGCTGCCTGAGAACCTGCAGGTCAGTGTGCCTG | |
| | | TCATCAGCTGCCGGAGTAAGCAGGGTTGCCAGTTTGATTT | |
| | | GGATTCCATTTGGACATTCATCTTTGGAGTTCCTGCCTCC | |
| | | AGCGGAACTGTGGTCTCTTCTATCCATAACGTATGCACAG | |
| | | AAGCTGTTTTTTTATTATTGGGAATGCTCCGCAGCATGCT | |
| | | GACTTCACCTTGGCAATCAGAAGAAGAGGGATCTTGGCTC | |
| | | CGAGAATATCCTGTGACCCTGATGCAGTTCTTCAGATATT | |
| | | TGTATCACAACGTGCCAGACCTTGCCTCCATGTGGATGAG | |
| | | CCCTGACTTCCTGTGTGCATTAGCAGCCACCGTCTTCCCC | |
| | | TTCAATATTCGCCCTTACTCAGAGATGGTGACTGACCTTG | |
| | | ATGATGAAGTTGGATCTCCAGCAGAAGAGTTTAAAGCGTT | |
| | | TGCAGCAGACACAGGGATGAACAGGAGCCAATCAGAGTAC | |
| | | TGCAATGTGGGCACCAAGACATATCTGACCAATCACCCGG | |
| | | CTAAAAAGTTCGTTTTTGACTTCATGCGGGTCTTAATCAT | |
| | | AGACAACCTCTGTCTCACTCCTGCCAGCAAGCAAACTCCA | |
| | | CTAATTGATCTTTTGTTGGAGGCTTCCCCTGAAAGGTCTA | |
| | | CAAGAACTCAGCAAAAAGAATTTCAAACTTACATTTTGGA | |
| | | TAGCGTGATGGACCATTTGCTTGCAGCTGATGTGTTATTA | |
| | | GGGGAAGATGCATCTCTGCCTATTACCAGTGGAGGAAGCT | |
| | | ACCAGGTATTGGTGAACAATGTGTTTTATTTCACACAGCG | |
| | | TGTGGTGGACAAGCTTTGGCAAGGCATGTTCAACAAAGAA | |
| | | TCTAAACTTCTTATAGATTTTATAATTCAACTAATTGCAC | |
| | | AGTCAAAGAGAAGATCACAGGGATTGTCACTGGATGCAGT | |
| | | GTATCATTGCCTCAATAGGACCATCTTGTACCAGTTCTCA | |
| | | CGGGCACACAAAACCGTTCCTCAGCAAGTAGCTCTGCTTG | |
| | | ATTCACTCAGGGTCCTCACTGTAAACAGAAACTTGATCCT | |
| | | GGGACCTGGGAACCATGACCAAGAATTCATTAGCTGTCTG | |
| | | GCCCACTGCTTGATAAATCTACATGTTGGAAGCAACGTGG | |
| | | ATGGATTTGGACTGGAAGCAGAAGCCCGCATGACCACATG | |
| | | GCACATTATGATCCCCTCGGACATTGAACCAGATGGTAGT | |
| | | TACAGCCAAGATATTAGTGAAGGGCGTCAGCTTCTCATAA | |
| | | AAGCTGTCAACAGAGTTTGGACTGAACTGATACATAGTAA | |
| | | GAAACAAGTCTTAGAGGAACTTTTCAAAGTAACTCTACCT | |
| | | GTGAATGAAAGGGGCCACGTGGACATAGCTACAGCAAGGC | |
| | | CACTCATTGAAGAAGCTGCCCTGAAGTGCTGGCAGAATCA | |
| | | TTTGGCCCATGAAAAGAAATGCATAAGTCGAGGAGAAGCT | |
| | | TTAGCGCCCACCACACAGTCCAAATTATCCCGTGTCAGCA | |
| | | GTGGCTTTGGTCTTTCCAAGTTAACAGGATCAAGAAGGAA | |
| | | TCGAAAAGAAAGTGGTCTTAATAAACACAGTCTTTCCACC | |
| | | CAGGAGATTTCGCAGTGGATGTTTACTCACATTGCTGTTG | |

TABLE 1-continued

GEP-NEN Biomarker/Houskeeper Sequence Information

| Gene Name | RefSeq Accession | Sequence | SEQ ID NO: |
|---|---|---|---|
| | | TTCGTGACTTAGTAGATACACAATATAAAGAATATCAGGA | |
| | | GCGTCAGCAGAATGCCCTGAAGTACGTGACAGAAGAGTGG | |
| | | TGTCAGATCGAGTGCGAGCTGTTGAGGGAGCGGGGGCTGT | |
| | | GGGGCCCTCCCATCGGCTCCCACCTCGACAAGTGGATGCT | |
| | | GGAGATGACAGAAGGGCCCTGCAGGATGAGGAAAAAGATG | |
| | | GTGCGAAATGATATGTTTTATAACCATTACCCTTACGTGC | |
| | | CAGAAACTGAGCAAGAGACAAATGTGGCGTCTGAGATCCC | |
| | | AAGTAAACAGCCTGAGACACCCGATGATATTCCTCAAAAG | |
| | | AAACCTGCTCGATATAGAAGAGCCGTAAGTTATGACAGTA | |
| | | AAGAGTACTACATGCGACTGGCCTCTGGCAATCCCGCCAT | |
| | | TGTCCAAGACGCCATTGTGGAGAGTTCAGAAGGTGAAGCT | |
| | | GCTCAGCAAGAACCAGAGCATGGGGAAGACACTATTGCTA | |
| | | AAGTCAAAGGTTTGGTCAAGCCTCCTCTAAAACGCTCCCG | |
| | | ATCTGCACCTGATGGAGGAGATGAGGAGAACCAGGAGCAG | |
| | | CTACAAGACCAGATTGCTGAGGGCAGCTCCATAGAAGAGG | |
| | | AGGAGAAAACAGATAATGCTACCTTACTGCGCCTGTTAGA | |
| | | GGAAGGAGAAAAGATCCAACACATGTACCGCTGTGCTCGA | |
| | | GTCCAGGGCCTAGATACCAGTGAGGGGCTCCTTCTTTTTG | |
| | | GTAAAGAGCATTTTTATGTGATTGATGGATTTACCATGAC | |
| | | AGCAACCAGGGAAATAAGAGATATTGAAACCTTACCTCCA | |
| | | AATATGCATGAGCCTATTATTCCTAGAGGAGCCAGGCAAG | |
| | | GCCCTAGTCAACTCAAGAGAACATGCAGCATTTTTGCATA | |
| | | TGAAGATATCAAGGAAGTTCATAAAAGGAGATATCTCCTG | |
| | | CAGCCTATTGCTGTGGAAGTTTTCTCTGGAGATGGACGGA | |
| | | ATTACCTCCTTGCTTTTCAGAAAGGAATCAGAAACAAAGT | |
| | | CTATCAAAGGTTTTTGGCTGTAGTGCCATCTCTAACGGAC | |
| | | AGTTCAGAATCTGTATCTGGGCAACGACCAAACACGAGTG | |
| | | TGGAGCAGGGATCTGGGTTACTTAGCACTTTGGTTGGAGA | |
| | | GAAGTCTGTGACTCAGAGATGGGAGAGAGGTGAAATCAGC | |
| | | AACTTCCAATATTTGATGCATTTGAACACTTTGGCTGGCA | |
| | | GATCATATAATGATCTCATGCAGTATCCTGTCTTCCCCTG | |
| | | GATCCTTGCAGATTATGACTCAGAGGAGGTGGATCTTACT | |
| | | AATCCCAAGACGTTTAGAAACCTGGCTAAGCCAATGGGAG | |
| | | CACAAACAGATGAACGATTAGCTCAGTATAAGAAGCGGTA | |
| | | TAAAGACTGGGAGGATCCTAATGGAGAAACTCCTGCATAC | |
| | | CACTATGGGACCCACTATTCATCTGCAATGATTGTGGCCT | |
| | | CATACCTTGTAAGGATGGAGCCTTTCACACAGATATTCTT | |
| | | AAGGCTACAGGGTGGCCACTTTGACCTGGCTGACCGGATG | |
| | | TTTCACAGTGTGCGCGAGGCCTGGTATTCAGCGTCAAAGC | |
| | | ACAATATGGCAGATGTAAAAGAACTTATCCCAGAGTTCTT | |
| | | TTATTTACCAGAATTCCTGTTCAATTCCAACAACTTTGAT | |
| | | CTAGGCTGTAAACAAAATGGCACCAAGCTTGGAGATGTTA | |
| | | TCCTTCCACCCTGGGCAAAAGGGGACCCACGAGAATTCAT | |
| | | CAGAGTCCATCGTGAGGCTTTGGAGTGTGATTACGTGAGT | |
| | | GCCCATCTACATGAGTGGATTGACTTAATCTTCGGTTATA | |
| | | AACAGCAAGGCCCTGCTGCAGTAGAAGCTGTAAATGTCTT | |
| | | CCATCATCTTTTTTATGAGGGTCAAGTGGATATCTACAAC | |
| | | ATCAATGACCCACTAAAGGAGACAGCCACAATTGGGTTCA | |
| | | TTAATAACTTCGGTCAGATCCCTAAACAGTTATTTAAAAA | |
| | | ACCTCATCCACCAAAGCGAGTGAGAAGTCGACTCAATGGA | |
| | | GACAATGCAGGAATCTCTGTCCTACCAGGATCTACAAGTG | |
| | | ACAAGATCTTTTTTCATCATCTAGACAACTTGAGGCCTTC | |
| | | TCTAACACCTGTAAAAGAACTCAAAGAACCTGTAGGACAA | |
| | | ATCGTATGTACAGATAAAGGTATTCTTGCGGTGGAACAGA | |
| | | ATAAGGTTCTTATCCCACCAACCTGGAATAAAACTTTTGC | |
| | | TTGGGGCTATGCAGACCTCAGTTGCAGACTGGGAACCTAT | |
| | | GAGTCAGACAAGGCCATGACTGTTTATGAATGCTTGTCTG | |
| | | AGTGGGGCCAGATTCTCTGTGCAATCTGCCCCAACCCCAA | |
| | | GCTGGTCATCACGGGTGGAACAAGCACGGTTGTGTGTGTG | |
| | | TGGGAGATGGGCACCTCCAAAGAAAAGGCCAAGACCGTCA | |
| | | CCCTCAAACAGGCCTTACTGGGCCACACTGATACCGTCAC | |
| | | CTGCGCCACAGCATCATTAGCCTATCACATAATTGTCAGT | |
| | | GGGTCCCGTGATCGAACCTGTATCATTTGGGATTTGAACA | |
| | | AACTGTCATTTCTAACCCAGCTTCGAGGGCATCGAGCTCC | |
| | | AGTTTCTGCTCTTTGTATCAATGAATTAACAGGGGACATT | |
| | | GTGTCCTGCGCTGGCACATATATCCATGTGTGGAGCATCA | |
| | | ATGGGAACCCTATCGTGAGTGTCAACACGTTCACAGGTAG | |
| | | GAGCCAGCAGATCATCTGCTGCTGCATGTCGGAGATGAAC | |
| | | GAATGGGACACGCAGAACGTCATAGTGACAGGACACTCAG | |
| | | ATGGAGTGGTTCGGTTTTGGAGAATGGAATTTTTGCAAGT | |
| | | TCCTGAAACACCAGCTCCTGAGCCTGCTGAAGTCCTAGAA | |
| | | ATGCAGGAAGACTGTCCAGAAGCACAAATAGGGCAGGAAG | |
| | | CCCAAGACGAGGACAGCAGTGATTCAGAAGCAGATGAGCA | |
| | | GAGCATCAGCCAGGACCCTAAGGACACTCCAAGCCAACCC | |
| | | AGCAGCACCAGCCACAGGCCCCGGGCAGCCTCCTGCCGCG | |

TABLE 1-continued

GEP-NEN Biomarker/Houskeeper Sequence Information

| Gene Name | RefSeq Accession | Sequence | SEQ ID NO: |
|---|---|---|---|
| | | CAACAGCCGCCTGGTGTACTGACAGTGGCTCTGACGACTC | |
| | | CAGACGCTGGTCCGACCAGCTCAGTCTAGATGAGAAAGAC | |
| | | GGCTTCATATTTGTGAACTATTCAGAGGGCCAGACCAGAG | |
| | | CCCATCTGCAGGGCCCCCTTAGCCACCCCCACCCCAATCC | |
| | | CATTGAGGTGCGGAATTACAGCAGATTGAAACCTGGGTAC | |
| | | CGATGGGAACGGCAGCTGGTGTTCAGGAGTAAGCTGACTA | |
| | | TGCACACAGCCTTTGATCGAAAGGACAATGCACACCCAGC | |
| | | TGAGGTCACTGCCTTGGGCATCTCCAAGGATCACAGTAGG | |
| | | ATCCTCGTTGGTGACAGTCGAGGCCGAGTTTTCAGCTGGT | |
| | | CTGTGAGTGACCAGCCAGGCCGTTCTGCTGCTGATCACTG | |
| | | GGTGAAGGATGAAGGTGGTGACAGCTGCTCAGGCTGCTCG | |
| | | GTGAGGTTTTCACTCACAGAAAGACGACACCATTGCAGGA | |
| | | ACTGTGGTCAGCTCTTCTGCCAGAAGTGCAGTCGCTTTCA | |
| | | ATCTGAAATCAAACGCTTGAAAATCTCATCCCCGGTGCGT | |
| | | GTTTGTCAGAACTGTTATTATAACTTACAGCATGAGAGAG | |
| | | GTTCAGAAGATGGGCCTCGAAATTGTTGAAGATTCAACAA | |
| | | GCTGAGTGGAGACCATGGTCTGTAGACCCCTTCCCGATTC | |
| | | TCCTGTCCCAGCTTGGAAGGCATTGAAAACAGTCTCCGTT | |
| | | TACACATCTCTTCATACCACGTGTTTGAAGTGTTAAAATT | |
| | | CAAAGGGATCATTGAATAAAACGGGTGTAGAGTACAGGAA | |
| | | TGGGGCAGACGCGATTCAGGTGAACAGCACAAGAAGAATA | |
| | | TGAGGTGGTTCCTAGGAGCAACACTTTCGACCTCCAGTTC | |
| | | TCCCTGATGACAGTAGCTGTCTCCAAGAGAAAAATCCTCA | |
| | | CTTATTAACTCTCTTTTCTTGCATCTCATTTTTATAGAGC | |
| | | TACTCATCCTTATTTGGAAAAACCAACAACAAAAAAGGCT | |
| | | TTTAGAAAATGGTTGTAAATCTGACTTCTTTGCAAGTAAC | |
| | | TATGTATATTGTAAATAGATATAAAAGGCCTTTTTTCTAA | |
| | | ATAAGGACTTAACTGCCTGTAACATGAAACTTCAAACTAA | |
| | | ACCACTAACTCAATGAACTACTTATGGTTTGTCTGACATC | |
| | | CCTCACTTACCAATTAATTATAAATATGTTTTTTTAAATC | |
| | | CCCAAAGACATTATCTGTGGTCTTTTTTTCCTTTCAAGCT | |
| | | CAGCCTGTGTGCCTGATGTCATTTCTTTCAAGTTGCCCAC | |
| | | AGTATCTCCACTTAAACTAGGCTAGTAACCAAAATAATGT | |
| | | GGACCTTCTTTAGGAAACAGTGTGGGAGAATAGGAGTCCA | |
| | | GCCGTAAGATAAACTGGAAATATTTGGGCGTCTTGTACCT | |
| | | GGCTACGCACCACCTCAGTGTTGTTCCTACATAAACAGGG | |
| | | CCCCTTTTAAACTTGTATGTGGACTGCTGTTTGGTCAAAG | |
| | | AATACCTTCTTAGCATTGCAGAAAGGTGGTCAGATGACCA | |
| | | GTGTAGTGCAGGAAACAGCCCTGTCTCAACTAATGGAAAT | |
| | | ATATTTGCATGTAACCCAAAATTAGCTTATCTTGCATAGA | |
| | | ACATAATAAGTATGTGTCTTTGGTGACACTAATGTTCTAC | |
| | | TATAGCTTATTTTCAAACAAGGGGTAAAAAAAGGAAAGAA | |
| | | AGAAGTGTACAGAATTAACATATAAACTTTGTTGTAAAAC | |
| | | TGAATCATGTCAGAACTGCTTAAAATTAACCTTTACCATT | |
| | | TAATGTCATCTACCTGAAAACAGTGAGATTTATACTGTAT | |
| | | CAATGTCTATTTTTTTGTTTTTGCTATGAATATAATTACA | |
| | | GTATTTTAATATTTAGTTATTTAATTTGTTCTACTAGTTG | |
| | | GATACAGAACACACAAATCCAGGGGGATTAAAGCTGGAAG | |
| | | GGGCTAAGAGATTAGTTTACAGAGAAAAGGCTTGGTGGTG | |
| | | GGATTTTTTTAAATGTGTGTTATGTACATATATATATATA | |
| | | TATAATATATATTAAAAATGAAACAATTAATCTAGATTTT | |
| | | AACATTTTCAGAAACTTAGTGATAACATTATGAACAATTC | |
| | | TAAAAGCCCTGTGATTTGAAAAATATAGAATCATTAATGG | |
| | | CCCAAGATAGGCCTTCACACCTTCACAGGTGCGAAAGGAA | |
| | | AGGCCTTCACACCCTCACAGAGGCATCATGCAAAGGACAG | |
| | | CGGCTTTGGCTTTTCCAATTTTCCATCTTTAGGCCCTGGT | |
| | | GAGAGGCACACTTATGCACTAAAATGCACATATATGCACA | |
| | | TGCATTCAAAAATAGGCATTTGGTACAATGGTGATCTTGT | |
| | | ACCTGATGGGCTGAAACCAGCTTAAGAACAAATTTGTTCT | |
| | | TCCTGATATGATAACTAGGTCTCCAAGAGAAAATAGAAAG | |
| | | GCTGCTTTAGTGCCTTACGCTTACTAAATTTAAATCTTTA | |
| | | TTTACCTGGGTTTGAGCCTACAGTCTATTTATGATTACAT | |
| | | ATCAAAATTGATTAAAACACTTCCATTTCTAAAAGTTCAA | |
| | | ATATACTTGTTAATAAAAGGATTATCGGCATTAATACTTT | |
| | | AATTTAAAGAAAAGTTGTGTTCTGTTTTCCTTTCTGTGTC | |
| | | TTACTCCCCCCACACTCTCCCTCCCCCATCACCATCTTCA | |
| | | ATTCTAATAAATAATGCTGATGTTCAACAGTTGCAGAAAT | |
| | | TGTGCTATTATGTAACTGTGGGCCTTGCCCCTGTCTGGCC | |
| | | CTCTAGATGATTTGTAGCAGTGTTATTCTACACTTTTTAA | |
| | | AAGAAGCGTCCTCCTTTTGTCCATGAATCATGTTTACCCC | |
| | | ATACCCAGTGGCAGAGGTGTTCTTTAAAGACTTGAATATA | |
| | | TGAATGTGTGTGTGTAGTTACTTAAAGGTTATTCCTCTTT | |
| | | GTAATAGGAAACTATATGGGATGAACACTTTTAAACTTTC | |
| | | CGACACAACTTCCATTACTAACTTTCTAACAGAACTTCCA | |
| | | TAACTAGAAGGTGGAAACCAAAACCCTCATGGTAGTATTT | |

TABLE 1-continued

GEP-NEN Biomarker/Houskeeper Sequence Information

| Gene Name | RefSeq Accession | Sequence | SEQ ID NO: |
|---|---|---|---|
| | | CCTCTGGCAGCTGGTGCTGTGGGCAACTGTTTTGTTCAAT<br>CGGGTTTCTTTTCTTTTTGCCTCTAATGCAGAAATCAACA<br>GAATCACTCACACATACAAGTACACTCACATACATAAACT<br>AATTATTTCTCTGGATATCTTTCTGTGTTCCATGTAAATT<br>TATTTACCAACATCTATTGTCAACATGTACATCTACCTTA<br>GTATGGTCTGCATTCTTTTTCTGAGAGTACCTCATAGGGC<br>TCCTGCCTGATCTTTGTAGTTTGTTCATTCATCCATCCAC<br>CTGTTCATTTGTTCATCCATGTATTCTAACATTTCTATGT<br>AGTGTGCAACTCTAATGTCATGCTTTTGAAGAAGAGAATA<br>GCTGCCCATAGCAGCCATCCGTCTGGATAATAGCAAAACA<br>CTCTAGATAAGTTATTTTGCACTTTCTTATGTATAAAGTT<br>GGTAGAAACTTATTTTTGCTTTGTATCATTTAAATACATT<br>TTGTTTTGGTAAATGAACTGTGTATAAAATATTTATGCCG<br>TTAAAACTGTTTTTAGAAAGTATTTTTAATTTCAGCAAGT<br>TTGGTTACTTGTTGCATGACTCTTAACACAGCTGACTTTT<br>TGTGTCAGTGCAATGTATATTTTTTGTCCTGTTATTAACT<br>TGTAAGCCCTAGTAATGGCCAATTATTTGTACAGCAACAG<br>AAGTAAATTGAAGATACTGGCTAAGACTGGATTGATTGTG<br>GACTTTTATACTATATTGCAGAAACCAATATCTGTTTCTT<br>GGTGGTTATGTAAAAGACCTGAAGAATTACTATCTAGTGT<br>GCAGTCTGTGATATCTGAATGTTCATTGTATATTTGTCTC<br>TGATGCAAAAAGGTAGAGTAACACAATTACAATACATGAT<br>TAAATGCAATAGTCCAGGTACTTAAGTAATTTTTTTTTCA<br>TTTCAAATAAATACCTATTTACCACCAAAAGAAAGAAAAA<br>AAAAAAAAA | |
| ZFHX3 | NM_001164766.1 | CGCGGCCCGAGCGCCTCTTTTCGGGATTAAAAGCGCCGCC<br>AGCTCCCGCCGCCGCCGCCGTCGCCAGCAGCGCCGCTGCA<br>GCCGCCGCCGCCGGAGAAGCAACCGCTGGGCGGTGAGATC<br>CCCCTAGACATGCGGCTCGGGGGCGGGCAGCTGGTGTCAG<br>AGGAGCTGATGAACCTGGGCGAGAGCTTCATCCAGACCAA<br>CGACCCGTCGCTGAAGCTCTTCCAGTGCGCCGTCTGCAAC<br>AAGTTCACGACGGACAACCTGGACATGCTGGGCCTGCACA<br>TGAACGTGGAGCGCAGCCTGTCGGAGGACGAGTGGAAGGC<br>GGTGATGGGGGACTCATACCAGTGCAAGCTCTGCCGCTAC<br>AACACCCAGCTCAAGGCCAACTTCCAGCTGCACTGCAAGA<br>CAGACAAGCACGTGCAGAAGTACCAGCTGGTGGCCCACAT<br>CAAGGAGGGCGGCAAGGCCAACGAGTGGAGGCTCAAGTGT<br>GTGGCCATCGGCAACCCCGTGCACCTCAAGTGCAACGCCT<br>GTGACTACTACACCAACAGCCTGGAGAAGCTGCGGCTGCA<br>CACGGTCAACTCCAGGCACGAGGCCAGCCTGAAGTTGTAC<br>AAGCACCTGCAGCAGCATGAGAGTGGTGTAGAAGGTGAGA<br>GCTGCTACTACCACTGCGTTCTGTGCAACTACTCCACCAA<br>GGCCAAGCTCAACCTCATCCAGCATGTGCGCTCCATGAAG<br>CACCAGCGAAGCGAGAGCCTGCGAAAGCTGCAGCGGCTGC<br>AGAAGGGCCTTCCAGAGGAGGACGAGGACCTGGGGCAGAT<br>CTTCACCATCCGCAGGTGCCCCTCCACGGACCCAGAAGAA<br>GCCATTGAAGATGTTGAAGGACCCAGTGAAACAGCTGCTG<br>ATCCAGAGGAGCTTGCTAAGGACCAAGAGGGCGGAGCATC<br>GTCCAGCCAAGCAGAGAAGGAGCTGACAGATTCTCCTGCA<br>ACCTCCAAACGCATCTCCTTCCCAGGTAGCTCAGAGTCTC<br>CCCTCTCTTCGAAGCGACCAAAAACAGCTGAGGAGATCAA<br>ACCGGAGCAGATGTACCAGTGTCCCTACTGCAAGTACAGT<br>AATGCCGATGTCAACCGGCTCCGGGTGCATGCCATGACGC<br>AGCACTCGGTGCAACCCATGCTTCGCTGCCCCCTGTGCCA<br>GGACATGCTCAACAACAAGATCCACCTCCAGCTGCACCTC<br>ACCCACCTCCACAGCGTGGCACCTGACTGCGTGGAGAAGC<br>TCATTATGACGGTGACCACCCCTGAGATGGTGATGCCAAG<br>CAGCATGTTCCTCCCAGCAGCTGTTCCAGATCGAGATGGG<br>AATTCCAATTTGGAAGAGGCAGGAAAGCAGCCTGAAACCT<br>CAGAGGATCTGGGAAAGAACATCTTGCCATCCGCAAGCAC<br>AGAGCAAAGCGGAGATTTGAAACCATCCCCTGCTGACCCA<br>GGCTCTGTGAGAGAAGACTCAGGCTTCATCTGCTGGAAGA<br>AGGGGTGCAACCAGGTTTTCAAAACTTCTGCTGCCCTTCA<br>GACGCATTTTAATGAAGTGCATGCCAAGAGGCCTCAGCTG<br>CCGGTGTCAGATCGCCATGTGTACAAGTACCGCTGTAATC<br>AGTGTAGCCTGGCCTTCAAGACCATTGAAAAGTTGCAGCT<br>CCATTCTCAGTACCATGTGATCAGAGCTGCCACCATGTGC<br>TGTCTTTGTCAGCGCAGTTTCCGAACTTTCCAGGCTCTGA<br>AGAAGCACCTTGAGACAAGCCACCTGGAGCTGAGTGAGGC<br>TGACATCCAACAGCTTTATGGTGGCCTGCTGGCCAATGGG<br>GACCTCCTGGCAATGGGAGACCCCACTCTGGCAGAGGACC<br>ATACCATAATTGTTGAGGAAGACAAGGAGGAAGAGAGTGA<br>CTTGGAAGATAAACAGAGCCCAACGGGCAGTGACTCTGGG<br>TCAGTACAAGAAGACTCGGGCTCAGAGCCAAAGAGAGCTC | 50 |

TABLE 1-continued

GEP-NEN Biomarker/Houskeeper Sequence Information

| Gene Name | RefSeq Accession | Sequence | SEQ ID NO: |
|---|---|---|---|
| | | TGCCTTTCAGAAAAGGTCCCAATTTTACTATGGAAAAGTT | |
| | | CCTAGACCCTTCTCGCCCTTACAAGTGTACCGTCTGCAAG | |
| | | GAATCTTTCACTCAAAAGAATATCCTGCTAGTACACTACA | |
| | | ATTCTGTCTCCCACCTGCATAAGTTAAAGAGAGCCCTTCA | |
| | | AGAATCAGCAACCGGTCAGCCAGAACCCACCAGCAGCCCA | |
| | | GACAACAAACCTTTTAAGTGTAACACTTGTAATGTGGCCT | |
| | | ACAGCCAGAGTTCCACTCTGGAGATCCATATGAGGTCTGT | |
| | | GTTACATCAAACCAAGGCCCGGGCAGCCAAGCTGGAGGCT | |
| | | GCAAGTGGCAGCAGCAATGGGACTGGGAACAGCAGCAGTA | |
| | | TTTCCTTGAGCTCCTCCACGCCAAGTCCTGTGAGCACCAG | |
| | | TGGCAGTAACACCTTTACCACCTCCAATCCAAGCAGTGCT | |
| | | GGCATTGCTCCAAGCTCTAACTTACTAAGCCAAGTGCCCA | |
| | | CTGAGAGTGTAGGGATGCCACCCCTGGGGAATCCTATTGG | |
| | | TGCCAACATTGCTTCCCCTTCAGAGCCCAAAGAGGCCAAT | |
| | | CGGAAGAAACTGGCAGATATGATTGCATCCAGGCAGCAGC | |
| | | AACAACAGCAGCAGCAACAGCAACAACAACAACAACAACA | |
| | | ACAACAACAAGCACAAACGCTGGCCCAGGCCCAGGCTCAA | |
| | | GTTCAAGCTCACCTGCAGCAGGAGCTGCAGCAACAGGCTG | |
| | | CCCTGATCCAGTCTCAGCTGTTTAACCCCACCCTCCTTCC | |
| | | TCACTTCCCCATGACAACTGAGACCCTGCTGCAACTACAG | |
| | | CAGCAGCAGCACCTCCTCTTCCCTTTCTACATCCCCAGTG | |
| | | CTGAGTTCCAGCTTAACCCCGAGGTGAGCTTGCCAGTGAC | |
| | | CAGTGGGGCACTGACACTGACTGGGACAGGCCCAGGCCTG | |
| | | CTGGAAGATCTGAAGGCTCAGGTTCAGGTCCCACAGCAGA | |
| | | GCCATCAGCAGATCTTGCCGCAGCAGCAGCAGAACCAACT | |
| | | CTCTATAGCCCAGAGTCACTCTGCCCTCCTTCAGCCAAGC | |
| | | CAGCACCCCGAAAAGAAGAACAAATTGGTCATCAAAGAAA | |
| | | AGGAAAAAGAAAGCCAGAGAGAGAGGGACAGCGCCGAGGG | |
| | | GGGAGAGGGCAACACCGGTCCGAAGGAAACACTGCCAGAT | |
| | | GCCTTGAAGGCCAAAGAGAAGAAAGAGTTGGCACCAGGGG | |
| | | GTGGTTCTGAGCCTTCCATGCTCCCTCCACGCATTGCTTC | |
| | | AGATGCCAGAGGGAACGCCACCAAGGCCCTGCTGGAGAAC | |
| | | TTTGGCTTTGAGTTGGTCATCCAGTATAATGAGAACAAGC | |
| | | AGAAGGTGCAGAAAAAGAATGGGAAGACTGACCAGGGAGA | |
| | | GAACCTGGAAAAGCTCGAGTGTGACTCCTGCGGCAAGTTG | |
| | | TTTTCCAACATCTTGATTTTAAAGAGTCATCAAGAGCACG | |
| | | TTCATCAGAATTACTTTCCTTTCAAACAGCTCGAGAGGTT | |
| | | TGCCAAACAGTACAGAGACCACTACGATAAACTGTACCCA | |
| | | CTGAGGCCCCAGACCCCAGAGCCACCACCACCTCCCCCTC | |
| | | CACCCCCTCCACCCCCACTTCCGGCAGCGCCGCCTCAGCC | |
| | | GGCGTCCACACCAGCCATCCCCGCATCAGCCCCACCCATC | |
| | | ACCTCACCTACAATTGCACCGGCCCAGCCATCAGTGCCGC | |
| | | TCACCCAGCTCTCCATGCCGATGGAGCTGCCCATCTTCTC | |
| | | GCCGCTGATGATGCAGACGATGCCGCTGCAGACCTTGCCG | |
| | | GCTCAGCTACCCCCGCAGCTGGGACCTGTGGAGCCTCTGC | |
| | | CTGCGGACCTGGCCCAACTCTACCAGCATCAGCTCAATCC | |
| | | AACCCTGCTCCAGCAGCAGAACAAGAGGCCTCGCACCAGG | |
| | | ATCACAGATGATCAGCTCCGAGTCTTGCGGCAATATTTTG | |
| | | ACATTAACAACTCCCCCAGTGAAGAGCAAATAAAAGAGAT | |
| | | GGCAGACAAGTCCGGGTTGCCCCAGAAAGTGATCAAGCAC | |
| | | TGGTTCAGGAACACTCTCTTCAAAGAGAGGCAGCGTAACA | |
| | | AGGACTCCCCTTACAACTTCAGTAATCCTCCTATCACCAG | |
| | | CCTGGAGGAGCTCAAGATTGACTCCCGGCCCCCTTCGCCG | |
| | | GAACCTCCAAAGCAGGAGTACTGGGGAAGCAAGAGGTCTT | |
| | | CAAGAACAAGGTTTACGGACTACCAGCTGAGGGTCTTACA | |
| | | GGACTTCTTCGATGCCAATGCTTACCCAAAGGATGATGAA | |
| | | TTTGAGCAACTCTCTAATTTACTGAACCTTCCAACCCGAG | |
| | | TGATAGTGGTGTGGTTTCAGAATGCCCGACAGAAGGCCAG | |
| | | GAAGAATTATGAGAATCAGGGAGAGGGCAAAGATGGAGAG | |
| | | CGGCGTGAGCTTACAAATGATAGATACATTCGAACAAGCA | |
| | | ACTTGAACTACCAGTGCAAAAAATGTAGCCTGGTGTTTCA | |
| | | GCGCATCTTTGATCTCATCAAGCACCAGAAGAAGCTGTGT | |
| | | TACAAGGATGAGGATGAGGAGGGGCAGGACGACAGCCAAA | |
| | | ATGAGGATTCCATGGATGCCATGGAAATCCTGACGCCTAC | |
| | | CAGCTCATCCTGCAGTACCCCGATGCCCTCACAGGCTTAC | |
| | | AGCGCCCCAGCACCATCAGCCAATAATACAGCTTCCTCCG | |
| | | CTTTCTTGCAGCTTACAGCGGAGGCTGAGGAACTGGCCAC | |
| | | CTTCAATTCAAAAACAGAGGCAGGCGATGAGAAACCAAAG | |
| | | CTGGCGGAAGCTCCCAGTGCACAGCCAAACCAAACCCAAG | |
| | | AAAAGCAAGGACAACCAAAGCCAGAGCTGCAGCAGCAAGA | |
| | | GCAGCCCGAGCAGAAGACCAACACTCCCCAGCAGAAGCTC | |
| | | CCCCAGCTGGTGTCCCTGCCTTCGTTGCCACAGCCTCCTC | |
| | | CACAAGCGCCCCCTCCACAGTGCCCCTTACCCCAGTCGAG | |
| | | CCCCAGTCCTTCCCAGCTCTCCCACCTGCCCCTCAAGCCC | |
| | | CTCCACACATCAACTCCTCAACAGCTCGCAAACCTACCTC | |

TABLE 1-continued

GEP-NEN Biomarker/Houskeeper Sequence Information

| Gene Name | RefSeq Accession | Sequence | SEQ ID NO: |
|---|---|---|---|
| | | CTCAGCTAATCCCCTACCAGTGTGACCAGTGTAAGTTGGC<br>ATTTCCGTCATTTGAGCACTGGCAGGAGCATCAGCAGCTC<br>CACTTCCTGAGCGCGCAGAACCAGTTCATCCACCCCCAGT<br>TTTTGGACAGGTCCCTGGATATGCCTTTCATGCTCTTTGA<br>TCCCAGTAACCCACTCCTGGCCAGCCAGCTGCTCTCTGGG<br>GCCATACCTCAGATTCCAGCAAGCTCAGCCACTTCTCCTT<br>CAACTCCAACCTCCACAATGAACACTCTCAAGAGGAAGCT<br>GGAGGAAAAGGCCAGTGCAAGCCCTGGCGAAAACGACAGT<br>GGGACAGGAGGAGAAGAGCCTCAGAGAGACAAGCGTTTGA<br>GAACAACCATCACACCGGAACAACTAGAAATTCTCTACCA<br>GAAGTATCTACTGGATTCCAATCCGACTCGAAAGATGTTG<br>GATCACATTGCACACGAGGTGGGCTTGAAGAAACGTGTGG<br>TACAAGTCTGGTTTCAGAACACCCGAGCTCGGGAAAGGAA<br>AGGACAGTTCCGGGCTGTAGGCCCAGCGCAGGCCCACAGG<br>AGATGCCCTTTTTGCAGAGCGCTCTTCAAAGCCAAGACTG<br>CTCTTGAGGCTCATATCCGGTCCCGTCACTGGCATGAAGC<br>CAAGAGAGCTGGCTACAACCTAACTCTGTCTGCGATGCTC<br>TTAGACTGTGATGGGGGACTCCAGATGAAAGGAGATATTT<br>TTGACGGAACTAGCTTTTCCCACCTACCCCCAAGCAGTAG<br>TGATGGTCAGGGTGTCCCCCTCTCACCTGTGAGTAAAACC<br>ATGGAATTGTCACCCAGAACTCTTCTAAGCCCTTCCTCCA<br>TTAAGGTGGAAGGGATTGAAGACTTTGAAAGCCCCTCCAT<br>GTCCTCAGTTAATCTAAACTTTGACCAAACTAAGCTGGAC<br>AACGATGACTGTTCCTCTGTCAACACAGCAATCACAGATA<br>CCACAACTGGAGACGAGGGCAACGCAGATAACGACAGTGC<br>AACGGGAATAGCAACTGAAACCAAATCCTCTTCTGCACCC<br>AACGAAGGGTTGACCAAAGCGGCCATGATGGCAATGTCTG<br>AGTATGAAGATCGGTTGTCATCTGGTCTGGTCAGCCCGGC<br>CCCGAGCTTTTATAGCAAGGAATATGACAATGAAGGTACA<br>GTGGACTACAGTGAAACCTCAAGCCTTGCAGATCCCTGCT<br>CCCCGAGTCCTGGTGCGAGTGGATCTGCAGGCAAATCTGG<br>TGACAGCGGAGATCGGCCTGGGCAGAAACGTTTTCGCACT<br>CAAATGACCAATCTGCAGCTGAAGGTCCTCAAGTCATGCT<br>TTAATGACTACAGGACACCCACTATGCTAGAATGTGAGGT<br>CCTGGGCAATGACATTGGACTGCCAAAGAGAGTCGTTCAG<br>GTCTGGTTCCAGAATGCCCGGGCAAAAGAAAAGAAGTCCA<br>AGTTAAGCATGGCCAAGCATTTTGGTATAAACCAAACGAG<br>TTATGAGGGACCCAAAACAGAGTGCACTTTGTGTGGCATC<br>AAGTACAGCGCTCGGCTGTCTGTACGTGACCATATCTTTT<br>CCCAACAGCATATCTCCAAAGTTAAAGACACCATTGGAAG<br>CCAGCTGGACAAGGAGAAAGAATACTTTGACCCAGCCACC<br>GTACGTCAGTTGATGGCTCAACAAGAGTTGGACCGGATTA<br>AAAAGGCCAACGAGGTCCTTGGACTGGCAGCTCAGCAGCA<br>AGGGATGTTTGACAACACCCCTCTTCAGGCCCTTAACCTT<br>CCTACAGCATATCCAGCGCTCCAGGGCATTCCTCCTGTGT<br>TGCTCCCGGGCCTCAACAGCCCCTCCTTGCCAGGCTTTAC<br>TCCATCCAACACAGCTTTAACGTCTCCTAAGCCGAACTTG<br>ATGGGTCTGCCCAGCACAACTGTTCCTTCCCCTGGCCTCC<br>CCACTTCTGGATTACCAAATAAACCGTCCTCAGCGTCGCT<br>GAGCTCCCCAACCCCAGCACAAGCCACGATGGCGATGGGC<br>CCTCAGCAACCCCCCCAGCAGCAGCAGCAGCAGCAGCAAC<br>CACAGGTGCAGCAGCCTCCCCCGCCGCCAGCAGCCCAGCC<br>GCCACCCACACCACAGCTCCCACTGCAACAGCAGCAGCAA<br>CGCAAGGACAAAGACAGTGAGAAAGTAAAGGAGAAGGAAA<br>AGGCACACAAAGGGAAAGGGGAACCCCTGCCTGTCCCCAA<br>GAAGGAGAAAGGAGAGGCCCCCACGGCAACTGCAGCCACG<br>ATCTCAGCCCCGCTGCCCACCATGGAGTATGCGGTAGACC<br>CTGCACAGCTGCAGGCCCTGCAGGCCGCGTTGACTTCGGA<br>CCCCACAGCATTGCTCACAAGCCAGTTCCTTCCTTACTTT<br>GTACCAGGCTTTTCTCCTTATTATGCTCCCCAGATCCCTG<br>GCGCCCTGCAGAGCGGGTACCTGCAGCCTATGTATGGCAT<br>GGAAGGCCTGTTCCCCTACAGCCCTGCACTGTCGCAGGCC<br>CTGATGGGGCTGTCCCCAGGCTCCCTACTGCAGCAGTACC<br>AGCAATACCAGCAGAGTCTGCAGGAGGCAATTCAGCAGCA<br>GCAGCAGCGGCAACTACAGCAGCAGCAGCAGCAAAAAGTG<br>CAGCAGCAGCAGCCCAAAGCAAGCCAAACCCCAGTCCCCC<br>CCGGGGCTCCTTCCCCAGACAAAGACCCTGCCAAAGAATC<br>CCCCAAACCAGAAGAACAGAAAAACACCCCCCGTGAGGTG<br>TCCCCCCTCCTGCCGAAACTCCCTGAAGAGCCAGAAGCAG<br>AAAGCAAAAGTGCGGACTCCCTCTACGACCCCTTCATTGT<br>TCCAAAGGTGCAGTACAAGTTGGTCTGCCGCAAGTGCCAG<br>GCGGGCTTCAGCGACGAGGAGGCAGCGAGGAGCCACCTGA<br>AGTCCCTCTGCTTCTTCGGCCAGTCTGTGGTGAACCTGCA<br>AGAGATGGTGCTTCACGTCCCCACCGGCGGCGGCGGCGGT<br>GGCAGTGGCGGCGGCGGCGGCGGTGGCGGCGGCGGCGGCG | |

TABLE 1-continued

GEP-NEN Biomarker/Houskeeper Sequence Information

| Gene Name | RefSeq Accession | Sequence | SEQ ID NO: |
|---|---|---|---|
| | | GCGGCGGCTCGTACCACTGCCTGGCGTGCGAGAGCGCGCT<br>CTGTGGGGAGGAAGCTCTGAGTCAACATCTCGAGTCGGCC<br>TTGCACAAACACAGAACAATCACGAGAGCAGCAAGAAACG<br>CCAAAGAGCACCCTAGTTTATTACCTCACTCTGCCTGCTT<br>CCCCGATCCTAGCACCGCATCTACCTCGCAGTCTGCCGCT<br>CACTCAAACGACAGCCCCCCTCCCCCGTCGGCCGCCGCCC<br>CCTCCTCCGCTTCCCCCCACGCCTCCAGGAAGTCTTGGCC<br>GCAAGTGGTCTCCCGGGCTTCGGCAGCGAAGCCCCCTTCT<br>TTTCCTCCTCTCTCCTCATCTTCAACGGTTACCTCAAGTT<br>CATGCAGCACCTCAGGGGTTCAGCCCTCGATGCCAACAGA<br>CGACTATTCGGAGGAGTCTGACACGGATCTCAGCCAAAAG<br>TCCGACGGACCGGCGAGCCCGGTGGAGGGTCCCAAAGACC<br>CCAGCTGCCCCAAGGACAGTGGTCTGACCAGTGTAGGAAC<br>GGACACCTTCAGATTGTAAGCTTTGAAGATGAACAATACA<br>AACAAATGAATTTAAATACAAAAATTAATAACAAACCAAT<br>TTCAAAAATAGACTAACTGCAATTCCAAAGCTTCTAACCA<br>AAAAACAAAAAAAAAAAAAAAAAGAAAAAAAAGAAAAAGC<br>GTGGGTTGTTTTCCCATATACCTATCTATGCCGGTGATTT<br>TACATTCTTGTCTTTTTCTTTTCTTTTAATATTAAAAAAA<br>AAAAAAAAGCCCTAACCCTGTTACATTGTGTCCTTTTGAA<br>GGTACTATTGGTCTGGGAAACAGAAGTCCGCAGGGCCTCC<br>CTAATGTCTTTGGAGCTTAAACCCCTTGTATATTTGCCCC<br>TTTTCAATAAACGCCCCACGCTGATAGCACAGAGGAGCCC<br>GGCATGCACTGTATGGGAAAGCAGTCCACCTTGTTACAGT<br>TTTAAATTTCTTGCTATCTTAGCATTCAGATACCAATGGC<br>TTGCTAAAAGAAAAAAAGAAATGTAATGTCTTTTTATTCT<br>CAGGTCAATCGCTCACACTTTGTTTTCAGAATCATTGTTT<br>TATATATTATTGTTTTTTCAGTTTTTTTTTTTTTTTTTGT<br>TCCAGAAAAGATTTTTTGTTTTGTTAACTTAAAAATGGGC<br>AGAAAGTATTCAAGAAAAACAATGTGAACTGCTTTAGCTT<br>TCTGGGGATTTTTAAGGATAGCTTTTCTGCTGAAGCCAAT<br>TTCAAGGGGAAAAGTTAAGCACTCCCACTTTCAAAAAAAA<br>AAAAAAATAATAACCCACACACACAAAGAGTGTTGAGGAC<br>TTGTAGCTTAAAAAAAATAAGTTTTAAAAACTGACTTTCT<br>GTATTTATGATAGATATGACCATTTTTGGTGTTGAGTAGA<br>TTGTTGCATTGGAAATGAACTGAAGCAGTATGGTAGATTT<br>AAAAGGAAAAAAAAAAAAAAAACCTTTTGTGTACATTTAGC<br>TTTTTGTATGGTCCAGCTGACAGCTCCTCATTTGATGTTG<br>TCTTGTTCATTCCTAGCAGATGATAGATTGCAATCCGTTG<br>ATTCGCCTAAGCTTTTCTCCCCTTGTCCCTTAATTCCACT<br>TTCTCTTTCTTGTCCCTTAATTCCACTTTCTCTTTCCTTC<br>TCCCACCTCCCGTCCTATAATCTCCCACTTAAGGTAGCTG<br>CCTTCATTTCTTAGAGGGAGCTGCAGAATTATTTTATAAA<br>ACTAAAGAAAGAATTTCAAGGGATTCTAGGGGTCATTAGG<br>ATCCTCACAGATTATTTTTGGTTGGGGAGTTGAAACTTTT<br>TAAAGGCATATAATTCTAGTTACCTGTGTCTGTTAGCTTT<br>GTGCATTTATTTTTTATTTATCCTTCTTTTGGCTTTTTTT<br>TCTTTGTACCCCTTCTTTTCCTCCTTGTTTGGTAGGAGCT<br>TCAAATATTCTTTTTTTTTCTATACTAAAGGATTTGTTTC<br>CATTTGTGTAATTGGCTGTGTACTTTTCTTTTCTAAAAAA<br>AGTTTTTGGTTAGGGATTTGGTTTTTGGTTTTGTGTTTGT<br>TTTTTCTTTCCTCTCTCAGAAAAAAAAAATTTCATGCTTTA<br>AATAAAATCCAAAGACACACCCTTTCACTGCTGATGCAGA<br>AAAAAGGGAAAGGGTTCTTGTTACTTGAGAATTTGTTTCT<br>GATTTAAACAAACAAGACTTAGTTTAATAAAAGAAAGAGA<br>AAAACAAAAGATTCCCAGGTTGTTATGTGCTTCTTCTGCA<br>AGCAGAGAGGCAAATGTTAATGACAATTCCATATACCAAA<br>AGACACATTTTTTACTTCAAAGTTTTGTCCTTGTGTTAGG<br>CAGTCTGAGCAGCGAGTGATCCAGAGCGCAGCCAACAAAG<br>CAGCAGATAGCAGTGTACAGAAAGCAAAAAAGGAACTGTA<br>TGTGAGGCACTTGTTTCTGTTAATATCCATATTCCTGTTA<br>ACACACACCCTTTCTCATGTAAAAAGAAAAATAAATAAAT<br>GGTCTGAACTTTGAAAACTTTGTGCTGCTAAAACATAGAT<br>TTTGGAGACAAATAAATAGATGCTTTGCTGTTTCACTTTC<br>ATAGCTAAACATCAACAGAAACCATCTCCCCTTGCCCCCA<br>AAGTGTGAAATCCTTCTTCCCTTCGTTTTCTTCCTTATGT<br>TTCAAAAGGGAACTTTGAAGACTGTGAATACAGGTTCCAT<br>TGGTCACCTTTCGGGCTTCTTTCCCCAGTGCTGAAGCCAC<br>TCATCGACTTTGCAAAAGACTGGAGCATTCCAAGATCTGA<br>AAATGGATTTTTTTTCTTTTTTTCTTTTTTAGCCGGGACT<br>ATTTTATTTTTATGAATTTGTTTTTAGTTTAATGAAATAG<br>TAGATCCTGAAATGTTGTACATATTTCTAACTAGGCTGAT<br>GCACAGTGCAAATTCCTTTTTTAATTGTTTTTTTTAAGTA<br>GAAATACTAAAGAAAGAATACCATCTAACTATTCATACCA<br>GTATCCAGTTGTAGCATAAGGTGTCAAAAGCAAGTACGCA | |

TABLE 1-continued

GEP-NEN Biomarker/Houskeeper Sequence Information

| Gene Name | RefSeq Accession | Sequence | SEQ ID NO: |
|---|---|---|---|
| | | AAACATTTACTGTTTTAACAAGCTATTTCCTTTTAACAAG<br>AAATCTTGTATTTCTTCCTGTGTTTGAGATGAACATTTTT<br>AAATTTTAAAGTTGTACAGTTTTTTGTTTTCCATTATTTT<br>ATCTTGTTTGTAACTCTATGAAATATATATATATATATTT<br>TTTGCCATTTAACTGTTGTATGTTACTCTGTGTCTGTACC<br>ATATAGAAAAAAAATTGTTTTTGTTTTTGGTTCTCTATGT<br>GATATCAGTTAACAATGTAACACTAGCTTTACCTGTCAAA<br>TTCTGCTAGGTCTTCTCTGAAAACGTTGTTTTTAAAAATG<br>ATATTGCTTGGTAATAGTGCAATTTCTATCCTTTTCCCTC<br>CCCCCTCAACTTTTAAGTTCTTTTCTTTATAATTTTGCTG<br>CCCCCTCCCTGATGGTTTGGGTTTTTGTTTTTGTTTTTGT<br>TTTTTTTTTTCATGGAGCTACTATGCCATCCTCCCTCTGT<br>GAGGCAGAGTGACTGTCAGTGTTTTGTTATGCCATGCCTT<br>GAGCTGTGGGTGTTTGGCGACAATAAGGTGGTTGAATAGA<br>TTGGCTGAGCACACTTCCACCCACCTAGTGTTCTCAGAGG<br>GGTTATGTGATTGTTTCAACCTGGAGTGGGTTGCACCCTT<br>AATGCTTTCCTCTGCAACTAAACCGCCCACATATATGTTC<br>ATTGAAAAAAGTAAGAATAATTCTCAGCACTAACCCAGAA<br>GTAGCAAAGCAGTCAGTGATGGTGAACATTAGAGGTCAAA<br>CATGAGTTAGATGTTTGTGGGCTGACAGCCATCGTGGCTA<br>TGACCAGTACTATTTACAAAGCATGAATTCACTACAATGC<br>TCAACTGTTTGTTTAGCTTTATCTCACTTGGGGAATTTAT<br>TCCTGTCTGCTGCATTGTAGGTAGCTGGGTAGGATATATT<br>TCCACTTGCTTTTTAAATTAGTTCTTCACCTCCATTGACA<br>CTCGTTTTTTGGTTTTCTCCCTATAGTGTGGGTTGGTGCT<br>AGACACCAGTCTGACCCACAGAATGGGAGTTATTTCATCC<br>ATCTTTCCTCCATCCTTCCAAAAACCACATATCTACACAA<br>GGAAAAATTTAATACATCTAGGAATTTTTTTTTTAATTAC<br>AAGCTATTTAAAGAGATGAATGTGGCCAAAGTTTTACACA<br>ATTGAAAATAAAGTAAAACAGACGGCATGTGTTTAAACCT<br>GAGTTTATCAGGCATGGCAGGAAGTTGCAGGAGAGAGAGG<br>CAGTGACCCAAGCCAGTGCACTTGATGTTCATGGACATAT<br>ATTTTTTTTAAATAATAAATTAAAACATTTTAAATAGAAG<br>CATAAATTGAGTTGTTTGTTGGCGCTGAGATACTGCCCAC<br>TGTGAAACAAAGCTTTGACTAGTTTTTTGTTTGTTTACTT<br>TCTTCAGGGGGGAGGGGGGCAAGTTTGGGTAGGAAAGAAA<br>GCATAAATGAACGTGACCCTGAGGTGAAGAGGTATATGAA<br>CAGCCTTTGCAATGTACAAAAAGAAAAAAAAACAAAAAAC<br>AACAAAAAAAAATAGAGCAAGTGAAACCAAAAATGATGTTC<br>TTGGTGTTTTTCTATAATGTAGTCTTGTTAGCTTTTTTGT<br>TACTGTAACAATGCTGATCTCGAACTGTACCAAAATACAT<br>GGAGACTAACAAACAGAACCACATGGAACTTTCAAACTGA<br>AAAAAAAATTTGTCACAAAAACTTTGTTGTCATAGTTAAG<br>TTGATTGTAGATGGTAATTGAATATACTCCTTTGAAAATA<br>TTTCATCAAGTATGTTTCCTGCTCATTGTGATACATTAAA<br>AAAAAAATATGAGCAAAA | |
| ZXDC | NM_001040653.3 | GGGCGCGGGCAGCTCTGCGTCCGAAGCTGCTCCGACGCCG<br>TCGCTGGGACCAAGATGGACCTCCCGGCGCTGCTCCCCGC<br>CCCGACTGCGCGCGGAGGGCAACATGGCGGCGGCCCCGGC<br>CCGCTCCGCCGAGCCCCAGCGCCGCTCGGCGCGAGCCCCG<br>CGCGCCGCCGCCTGCTACTGGTGCGGGGCCCTGAAGATGG<br>CGGGCCCGGGGCGCGGCCCGGGGAGGCCTCCGGGCCAAGC<br>CCGCCGCCCGCCGAGGACGACAGCGACGGCGACTCTTTCT<br>TGGTGCTGCTGGAAGTGCCGCACGGCGGCGCTGCCGCCGA<br>GGCTGCCGGATCACAGGAGGCCGAGCCTGGCTCCCGTGTC<br>AACCTGGCGAGCCGCCCCGAGCAGGGCCCCAGCGGCCCGG<br>CCGCCCCCCCCGGCCCTGGCGTAGCCCCGGCGGGCGCCGT<br>CACCATCAGCAGCCAGGACCTGCTGGTGCGTCTCGACCGC<br>GGCGTCCTCGCGCTGTCTGCGCCGCCCGGCCCCGCAACCG<br>CGGGCGCCGCCGCTCCCCGCCGCGCGCCCCAGGCCTCCGG<br>CCCCAGCACGCCCGGCTACCGCTGCCCCGAGCCGCAGTGC<br>GCGCTGGCCTTCGCCAAGAAGCACCAGCTCAAGGTGCACC<br>TGCTCACGCACGGCGGCGGTCAGGGCCGGCGGCCCTTCAA<br>GTGCCCACTGGAGGGCTGTGGTTGGGCCTTCACAACGTCC<br>TACAAGCTCAAGCGGCACCTGCAGTCGCACGACAAGCTGC<br>GGCCCTTCGGCTGTCCAGTGGGCGGCTGTGGCAAGAAGTT<br>CACTACGGTCTATAACCTCAAGGCGCACATGAAGGGCCAC<br>GAGCAGGAGAGCCTGTTCAAGTGCGAGGTGTGCGCCGAGC<br>GCTTCCCCACGCACGCCAAGCTCAGCTCCCACCAGCGCAG<br>CCACTTCGAGCCCGAGCGCCCTTACAAGTGTGACTTTCCC<br>GGCTGTGAGAAGACATTTATCACAGTGAGTGCCCTGTTTT<br>CCCATAACCGAGCCCACTTCAGGGAACAAGAGCTCTTTTC<br>CTGCTCCTTTCCTGGGTGCAGCAAGCAGTATGATAAAGCC<br>TGTCGGCTGAAAATTCACCTGCGGAGCCATACAGGTGAAA | 51 |

TABLE 1-continued

GEP-NEN Biomarker/Houskeeper Sequence Information

| Gene Name | RefSeq Accession | Sequence | SEQ ID NO: |
|---|---|---|---|
| | | GACCATTTATTTGTGACTCTGACAGCTGTGGCTGGACCTT | |
| | | CACCAGCATGTCCAAACTTCTAAGGCACAGAAGGAAACAT | |
| | | GACGATGACCGGAGGTTTACCTGCCCTGTCGAGGGCTGTG | |
| | | GGAAATCATTCACCAGAGCAGAGCATCTGAAAGGCCACAG | |
| | | CATAACCCACCTAGGCACAAAGCCGTTCGAGTGTCCTGTG | |
| | | GAAGGATGTTGCGCGAGGTTCTCCGCTCGTAGCAGTCTGT | |
| | | ACATTCACTCTAAGAAACACGTGCAGGATGTGGGTGCTCC | |
| | | GAAAAGCCGTTGCCCAGTTTCTACCTGCAACAGACTCTTC | |
| | | ACCTCCAAGCACAGCATGAAGGCGCACATGGTCAGACAGC | |
| | | ACAGCCGGCGCCAAGATCTCTTACCTCAGCTAGAAGCTCC | |
| | | GAGTTCTCTTACTCCCAGCAGTGAACTCAGCAGCCCAGGC | |
| | | CAAAGTGAGCTCACTAACATGGATCTTGCTGCACTCTTCT | |
| | | CTGACACACCTGCCAATGCTAGTGGTTCTGCAGGTGGGTC | |
| | | GGATGAGGCTCTGAACTCCGGAATCCTGACTATTGACGTC | |
| | | ACTTCTGTGAGCTCCTCTCTGGGAGGGAACCTCCCTGCTA | |
| | | ATAATAGCTCCCTAGGGCCGATGGAACCCCTGGTCCTGGT | |
| | | GGCCCACAGTGATATTCCCCCAAGCCTGGACAGCCCTCTG | |
| | | GTTCTCGGGACAGCAGCCACGGTTCTGCAGCAGGGCAGCT | |
| | | TCAGTGTGGATGACGTGCAGACTGTGAGTGCAGGAGCATT | |
| | | AGGCTGTCTGGTGGCTCTGCCCATGAAGAACTTGAGTGAC | |
| | | GACCCACTGGCTTTGACCTCCAATAGTAACTTAGCAGCAC | |
| | | ATATCACCACACCGACCTCTTCGAGCACCCCCCGAGAAAA | |
| | | TGCCAGTGTCCCGGAACTGCTGGCTCCAATCAAGGTGGAG | |
| | | CCGGACTCGCCTTCTCGCCCAGGAGCAGTTGGGCAGCAGG | |
| | | AAGGAAGCCATGGGCTGCCCCAGTCCACGTTGCCCAGTCC | |
| | | AGCAGAGCAGCACGGTGCCCAGGACACAGAGCTCAGTGCA | |
| | | GGCACTGGCAACTTCTATTTGGTATGAAGCACTCTATTCA | |
| | | GTCACCACCATATAGGTCACTTCTCTCATACTCGGTCTTG | |
| | | AGGATATTCTGGATTAATCCTTTCTATGCAGACGTTTCTG | |
| | | GTTTACAAAAGGACGCAGCCCTGGACTACAAGTCTGGAAC | |
| | | TGACAAGTTCTTATGACCTTGACAAATCACCTTAACCCAT | |
| | | CTGAGCCTTAAATTCTCATTTATTTCCTGCATAAGGAGAT | |
| | | TTGGCTAAATGCTTTCTGAGGTCCTTTGGAGTCCTGTGGC | |
| | | TCCATGGTAATGTGCTCCTTTCCTTGAAGATTGGGGGTTT | |
| | | TGTAATGTTGAGATACTTTGCCTCTATGCTTGTCAGCTCA | |
| | | TGACCAGTCCTAGAAGAGGAGTCGAGACATAAGCCACCTT | |
| | | CAGAGGTTCAATGGAAACTTTAAAACCATACCAAACTCTT | |
| | | TTTTAAAATTAGAATTAACAAGAAAAAAAAAAAGGGTGGG | |
| | | GTTTATGAGCCTTAGTTCTTGGAGGATTATAAGAGTACTT | |
| | | CCCCAGTTTTGAGGCTGGACAGTTAATATACTTTATATCA | |
| | | ATTATACATTTAATATAATTTAATTTAAAATAATTTAAAG | |
| | | ATTCTTAGGAGATAGTCTGACTTTCCTGACCTAGATGGGA | |
| | | ATGATCAGATAGGGATTTTTTTTGTGGCACAGGCTAAATT | |
| | | TGATGGTGACATTTATATTGTTGAGAATGTTACATCTTAT | |
| | | TTTACCACAACTTTTAAAAAATGTTACATCTTTTGCAGTA | |
| | | GGATCAGTTGTGAGGCACATAGTAGCTGAGGCTCCATGGA | |
| | | GCCACCTTTCATTTCTTTCAGTCAGAGAGGAGGACAGTCT | |
| | | CTGTCTCTGCATTTCTGGTGTCTTGCTTGTCGGTGGCAGA | |
| | | GCCATGCTTGCCGGCATTTGCTTAGGCGGCCATAGTAGTT | |
| | | GCTAAGTGTACAGGTGACTGGGCAGGGATGGGAGGTGGCC | |
| | | ACAGGTCAGAGACAAGTGCTCAGTCAGTCCCTGGTGCCAG | |
| | | GACTGTGTGCCTCGGTGCCTTGGGAAATGGAAGCTCCCTG | |
| | | GTGCAGCTGCAGCTGTGGGTGGAGGTAGAGAAGCCAGCAA | |
| | | GACCTTGGTCTTAACCCCGTGTTCATTTTCTTGCTAGCTG | |
| | | TGTGACGTTGGGCTACCTCGCTTCTCTGAGTACAAATGGT | |
| | | GTGTGGTGAATGGGTCCCAGGTATGCTACGAGCTTTGAGG | |
| | | GCTGCTCTTTTTCTCTTCATAGCGATAAGTGTTAAACTGT | |
| | | CTTTCTTAGGAAACGTTCACAGACTTGCAACAGCTGATGT | |
| | | CCTCTGAGTACTGTCTGACTCCCTCAGGCAAGTTCCTGAA | |
| | | TTCAGTACCATCATTATTATTTTTGTGTAAGACTTTGACA | |
| | | AAGTATAGCCCCTGCCACCAGAGCAGCCTGTACAGTGGGT | |
| | | CTCTAAGGTGGGACCTGCCCCGGGCCTGCCATGCACGTGT | |
| | | GTGAAACAGCGTGAAAAGTGTCGCGGTAAGGTGACCCTGG | |
| | | GTTACCCAGGCAAGGCTCGGTGTTTGTTTCAGAAAGCAGA | |
| | | GAAGTATGTAATTGATTTTAAAAGTTTCTGTTTAAAATAT | |
| | | TTGGCTATGTTTTAGACTATGAAGGAATGAACTTTGCTTC | |
| | | TCTGGATAAGAAAGTCACATACATTGTTCCAGCTCCAAGT | |
| | | TTGTTCGGCCCTCGCCACAAGTGGATGTAGCGTTTGGCCC | |
| | | TTTGTGTGCCTTGCTGGTGACTCTGGTTTTGGGAGCTCGG | |
| | | ATATGTCCCAGAAGCAGGCTTATGGCACTTCTGTAGCTCC | |
| | | CTTGCTACCCTTCCTTTGTGTCTAGATAAGTGACTGACAT | |
| | | GCTTTTCTTTGGTCTCAGGAAAGTGGGGGCTCAGCAAGAA | |
| | | CTGATTACCGAGCCATTCAACTAGCCAAGGAAAAAAAGCA | |
| | | GAGAGGAGCGGGGAGCAATGCAGGTGAGGCCGTGTGTGCT | |
| | | GCAGCCGGACGAGCAAGGGCCTGAGGGTTCTCTGTCACTG | |

TABLE 1-continued

GEP-NEN Biomarker/Houskeeper Sequence Information

| Gene Name | RefSeq Accession | Sequence | SEQ ID NO: |
|---|---|---|---|
| | | TTACTGGCAGAAGAAACACAGCAGGTGTTTCTGTGCTCTT | |
| | | GGTTTTACTTTTCTGTTCAGAATACCCTTTTATCAACTCC | |
| | | TTAGTTTTATTTGAACTTAAGGGAAAAAATTAGTAACAAA | |
| | | ATTCCCAGCATCAGTATGAACATATTTTATTTGCCTAAAC | |
| | | AAGCTTTGTGAAAGTTAAGCGTTCAAACACCAGTGTCAGT | |
| | | TACCTGGAAGGCTACTAAGGTAAATAAGCAAAGCAGGCCA | |
| | | GTTGTCAGGAAAGCAGAGATTGTGCCTGGTGCTGAATGGC | |
| | | CTTGGGGCCTGATCTTGGCATGGCAGAGACCTGGGGACTG | |
| | | CCACTGTCCCCAGGTACGTGTACATGGAGCCAAACTGTGT | |
| | | GTCCTGTGGCATTGTCAGAGTTATGTTGAAATCTTATTTG | |
| | | AAAATGTTAGCAACTTACTTGCATTTTTAAAGACCAAACA | |
| | | AGAGCTGGTAACCTATGGCCTCAAGCATCTGTCCTTCCTA | |
| | | AAAATGGAATAGTGGGATGTAGTGCTTAATGGAAACTGCT | |
| | | AAATCTTTTTCTAAAAACTAACAGTGGATTTTTAAAATAT | |
| | | ATTGTTTTTTGTGTATTTCATTTGTCCTTTGTATTTATCT | |
| | | AAAAGGGTTGATATGATTTTATATCTTGCTCTCTATTCCT | |
| | | AATAGTATTATGACTTCTTATTTAAAATAAATAACAATTG | |
| | | CCGGTTTTCTGTTAAAAAAAAAAAAA | |
| ZZZ3 | NM_015534.4 | GTTGGCAGAGCAGTTGTCCTGGATGGCGGAGCCTTGGGTT | 52 |
| | | CCGGGGGCCTGGGACCTGCAACTCTTTCTACAAGATATCA | |
| | | AGTTATTCTAGTACAACCATATAAATAAATAATACCTGAA | |
| | | GTCTCAGTGTAACATGGACAATTAACAGTGATGACAGATA | |
| | | AATACAGACGCATGGGGATCAAATACTAGGCAAAACGCTT | |
| | | TTTAAAAGTGTATCAGGCTTTTAAGAAACACTGCAGGATC | |
| | | CTGTCTATCTTAATGCTGATAGAGCTCAGCTAAAAATTTA | |
| | | GGAGGTTCTAGTATTCTTCATGGCTGAAGCTGAGAGAGTC | |
| | | TGAAACCCTGATGCTTAAGCTCCATTCTAGATCATAGCTC | |
| | | CAACTCCTTCAGGATATAAGGAAAAGAGATTATATTTCCA | |
| | | CAATGATAGATCTTTGGTTGTACAGGTTTCCCAATGAGTG | |
| | | GATCATGATGACCGTATTGTAGGGACTTGCCATAGTATGG | |
| | | CTGCTTCCCGATCTACTCGTGTTACAAGATCAACAGTGGG | |
| | | GTTAAACGGCTTGGATGAATCTTTTTGTGGTAGAACTTTA | |
| | | AGGAATCGTAGCATTGCGCATCCTGAAGAAATCTCTTCTA | |
| | | ATTCTCAAGTACGATCAAGATCACCAAAGAAGAGACCAGA | |
| | | GCCTGTGCCAATTCAGAAAGGAAATAATAATGGGAGAACC | |
| | | ACTGATTTAAAACAGCAGAGTACCCGAGAATCATGGGTAA | |
| | | GCCCTAGGAAAAGAGGACTTTCTTCTTCAGAAAAGGATAA | |
| | | CATAGAAAGGCAGGCTATAGAAAATTGTGAGAGAAGGCAA | |
| | | ACAGAACCTGTTTCACCAGTTTTAAAAAGAATTAAGCGTT | |
| | | GTCTTAGATCTGAAGCACCAAACAGTTCAGAAGAAGATTC | |
| | | TCCTATAAAATCAGACAAGGAGTCAGTAGAACAGAGGAGT | |
| | | ACAGTAGTGGACAATGATGCAGATTTTCAAGGGACTAAAC | |
| | | GAGCTTGTCGATGTCTTATACTGGATGATTGTGAGAAAAG | |
| | | GGAAATTAAAAAGGTGAATGTCAGTGAGGAAGGGCCACTT | |
| | | AATTCTGCAGTAGTTGAAGAAATCACAGGCTATTTGGCTG | |
| | | TCAATGGTGTTGATGACAGTGATTCAGCTGTTATAAACTG | |
| | | TGATGACTGTCAGCCTGATGGGAACACTAAACAAAATAGC | |
| | | ATTGGTTCCTATGTGTTACAGGAAAAATCAGTAGCTGAAA | |
| | | ATGGGGATACGGATACCCAAACTTCAATGTTCCTTGATAG | |
| | | TAGGAAGGAGGACAGTTATATAGACCATAAGGTGCCTTGC | |
| | | ACAGATTCACAAGTGCAGGTCAAGTTGGAGGACCACAAAA | |
| | | TAGTAACTGCCTGCTTGCCTGTGGAACATGTTAATCAGCT | |
| | | GACTACTGAGCCAGCTACAGGGCCCTTTTCTGAAACTCAG | |
| | | TCATCTTTAAGGGATTCTGAGGAGGAAGTAGATGTGGTGG | |
| | | GAGATAGCAGTGCCTCAAAAGAGCAGTGTAAAGAAAACAC | |
| | | CAATAACGAACTGGACACAAGTCTTGAGAGTATGCCAGCC | |
| | | TCCGGAGAACCTGAACCATCTCCTGTTCTAGACTGTGTTT | |
| | | CAGCTCAAATGATGTCTTTATCAGAACCTCAAGAACATCG | |
| | | TTATACTCTGAGAACCTCACCACGAAGGGCAGCCCCTACC | |
| | | AGAGGTAGTCCCACTAAAAACAGTTCTCCTTACAGAGAAA | |
| | | ATGGACAATTTGAGGAGAATAATCTTAGTCCTAATGAAAC | |
| | | AAATGCAACTGTTAGTGATAATGTAAGTCAATCTCCTACA | |
| | | AATCCTGGTGAAATTTCTCAAAATGAAAAAGGGATATGTT | |
| | | GTGACTCTCAAAATAATGGAAGTGAAGGAGTAAGTAAACC | |
| | | ACCCTCAGAGGCAAGACTCAATATTGGACATTTGCCATCT | |
| | | GCCAAAGAGAGTGCCAGTCAGCACATTACAGAAGAGGAAG | |
| | | ATGATGATCCTGATGTTTATTACTTTGAATCAGATCATGT | |
| | | GGCACTGAAACACAACAAAGATTATCAGAGACTATTACAG | |
| | | ACGATTGCTGTACTCGAGGCTCAGCGTTCTCAAGCAGTCC | |
| | | AAGACCTTGAAAGTTTAGGCAGGCACCAGAGAGAAGCACT | |
| | | GAAAAATCCCATTGGATTTGTGGAAAAACTCCAGAAGAAG | |
| | | GCTGATATTGGGCTTCCATATCCACAGAGAGTTGTTCAAT | |
| | | TGCCTGAGATCGTATGGGACCAATATACCCATAGCCTTGG | |
| | | GAATTTTGAAAGAGAATTTAAAAATCGTAAAAGACATACT | |

TABLE 1-continued

GEP-NEN Biomarker/Houskeeper Sequence Information

| Gene Name | RefSeq Accession | Sequence | SEQ ID NO: |
|---|---|---|---|
| | | AGAAGAGTTAAGCTAGTTTTTGATAAAGTAGGTTTACCTG<br>CTAGACCAAAAAGTCCTTTAGATCCTAAGAAGGATGGAGA<br>GTCCCTTTCATATTCTATGTTGCCTTTGAGTGATGGTCCA<br>GAAGGCTCAAGCAGTCGTCCTCAGATGATAAGAGGACGCT<br>TGTGTGATGATACCAAACCTGAAACATTTAACCAGTTGTG<br>GACTGTTGAAGAACAGAAAAAGCTGGAACAGCTACTCATC<br>AAATACCCTCCTGAAGAAGTAGAATCTCGACGCTGGCAGA<br>AGATAGCAGATGAATTGGGCAACAGGACAGCAAAACAGGT<br>TGCCAGCCGAGTACAGAAGTATTTCATAAAGCTAACTAAA<br>GCTGGCATTCCAGTACCAGGCAGAACACCAAACTTATATA<br>TATACTCCAAAAAGTCTTCAACAAGCAGACGACAGCACCC<br>TCTTAATAAGCATCTCTTTAAGCCTTCCACTTTCATGACT<br>TCACATGAACCGCCAGTGTATATGGATGAAGATGATGACC<br>GATCTTGTTTTCATAGCCACATGAACACTGCTGTTGAAGA<br>TGCATCAGATGACGAAAGTATTCCTATCATGTATAGGAAT<br>TTACCTGAATATAAAGAACTATTACAGTTTAAAAAGTTAA<br>AGAAGCAGAAACTTCAGCAAATGCAAGCTGAAAGTGGATT<br>TGTGCAACATGTGGGCTTTAAGTGTGATAACTGTGGCATA<br>GAACCCATCCAGGGTGTTCGGTGGCATTGCCAGGATTGTC<br>CTCCAGAAATGTCTTTGGATTTCTGTGATTCTTGTTCAGA<br>CTGTCTACATGAAACAGATATTCACAAGGAAGATCACCAA<br>TTAGAACCTATTTATAGGTCAGAGACATTCTTAGACAGAG<br>ACTACTGTGTGTCTCAGGGCACCAGTTACAATTACCTTGA<br>CCCAAACTACTTTCCAGCAAACAGATGACATGGAAGAGAA<br>CATCATTTACTAGTCCTCTTCAACACATAGCAATGGTATC<br>ATTGTTAATTATGTGCACAGTTTGGAAAGATTCTCTGCTT<br>TCCCAGAAATGACACTCACAGCATGAGAGCTTCCTGAGTG<br>TTCTCGTCAAGTACAGCTCTGCACCGTTGTGGCTCTAGAT<br>CACTGTTCAGCAGCTGAACATTCCTGGTGAGCAAAGGTTT<br>CCCTGGTGAATTTTTCACCACTGCGTTTTAGGTGGTGATC<br>TTAAATGGGTGAGATGGAACGAGAGCACACATTAAAGAGA<br>GAGTAAATTCCAAAGGTTTCAAAGAACTTGGTCATAAATA<br>TGATAATGAGAAGACAAAGTATTTATATTAAAACAGTTTA<br>GTAGCCTTCAGTTTTGTGAAAATAGTTTTCAGCACAGAAA<br>CTGACTTCTTTAGACAAAGTTTTAACCAATGATGGTGTTT<br>GCTTCTAGGATATACACTTTAAAAGAACTCACTGTCCCAG<br>TGGTGGTCATTGATGGCCTTTAGTAAATTGGAGCTGCTTA<br>ATCATATTGATATCTAATTTCTTTTAACCACAATGAATTG<br>TCCTTAATTACCAACAGTGAAGCACTACAGGAGGCAACTG<br>TGGCATTGCTTCCTTAACCAGCTCATGGTGTGTGAATGTT<br>ATAAAATTGTCACTCAGATATATTTTTTAAATGTAATGTT<br>ATATAAGATGATCATGTGATGTGTACAAACTATGGTGAAA<br>AGTGCCAGTGGTAGTAACTGTGTAAAGTTTCTAATTCACA<br>ACATTAATTCCTTTAAAATACACAGCCTTCTGCCTCTGTA<br>TTTGGAGTTGTCAGTACAACTCATCAAAGAAAACTGCCTA<br>ATATAAAAATCATATATATGGTAATAATTTCCCTCTTTTG<br>TAGTCTGCACAAGATCCATAAAAGATTGTATTTTTATTAC<br>TATTTAAACAAGTGATTAAATTTAGTCTGCACAGTGAGCA<br>AGGGTTCACATGCATTCTTTTATACTGCTGGATTTTGTTG<br>TGCATCATTTAAAACATTTTGTATGTTTCTTCTTATCTGT<br>GTATACAGTATGTTCTTGAATGATGTTCATTTGTCAGGAG<br>AACTGTGAGAAATAAACTATGTGGATACTGTCTGTTTATA<br>TTAAAAGAAAAAAAAAAAAAAAAAA | |

The 51 GEP-NEN biomarkers include: AKAP8L (A kinase (PRKA) anchor protein 8-like), APLP2 (amyloid beta (A4) precursor-like protein 2), ARAF1 (v-raf murine sarcoma 3611 viral oncogene homolog), ATP6V1H (ATPase, H+ transporting, lysosomal 50/57 kDa, VI subunit H), BNIP3L (BCL2/adenovirus E1B19 kDa interacting protein 3-like), BRAF (v-raf murine sarcoma viral oncogene homolog B1), C21ORF7 (chromosome 21 open reading frame 7), CD59 (CD59 molecule, complement regulatory protein), COMMD9 (COMM domain containing 9), CTGF (connective tissue growth factor), ENPP4 (ectonucleotide pyrophosphatase/phosphodiesterase 4), FAM131A (family with sequence similarity 131, member A, transcript variant 2), FLJ10357 (Rho guanine nucleotide exchange factor (GEF) 40 (ARHGEF40), FZD7 (frizzled homolog 7 (*Drosophila*)), GLT8D1 (glycosyltransferase 8 domain containing 1, transcript variant 3), HDAC9 (histone deacetylase 9, transcript variant 6), HSF2 (heat shock transcription factor 2, transcript variant 1), Ki-67 (antigen identified by monoclonal antibody Ki-67), KRAS (v-Ki-ras2 Kirsten rat sarcoma viral oncogene homolog), LEO1 (Paf1/RNA polymerase II complex component homolog (*S. cerevisiae*)), MORF4L2 (mortality factor 4 like 2, transcript variant 1), NAP1L1 (nucleosome assembly protein 1-like 1), NOL3 (nucleolar protein 3 (apoptosis repressor with CARD domain), transcript variant 3), NUDT3 (nudix (nucleoside diphosphate linked moiety X)-type motif 3), OAZ2 (ornithine decarboxylase antizyme 2), PANK2 (pantothenate kinase 2), PHF21A (PHD finger protein 21A, transcript variant 1), PKD1 (polycystic kidney disease 1 (autosomal dominant), transcript variant 2), PLD3 (phospholipase D family, member 3, transcript variant 1), PNMA2 (paraneoplastic antigen MA2), PQBP1 (polyglutamine binding protein 1, transcript variant 2), RAF1 (v-raf-1 murine leukemia viral oncogene homolog 1), RNF41 (ring finger protein 41, transcript variant 4), RSF1 (remodeling and spacing factor 1), RTN2 (reticulon 2, transcript variant 1), SMARCD3 (SWL/SNF related, matrix associated, actin dependent regulator of chromatin, subfamily d, member 3, transcript variant 3), SPATA7 (spermatogenesis associated 7, transcript variant 2), SST1 (somatostatin receptor 1), SST3 (somatostatin receptor 3), SST4 (somatostatin receptor 4), SST5 (somatostatin receptor 5, transcript variant 1). TECPR2 (tectonin beta-propeller repeat containing 2, transcript variant 2), TPH1 (tryptophan hydroxylase 1), TRMT112 (tRNA methyltransferase 11-2 homolog (*S. cerevisiae*)), VMAT1 (solute carrier family 18 (vesicular monoamine), member 1), VMAT2 (solute carrier family 18 (vesicular monoamine), member 2), VPS13C (vacuolar protein sorting 13 homolog C (*S. cerevisiae*), transcript variant 2B), WDFY3 (WD repeat and FYVE domain containing 3), ZFHX3 (zinc finger homeobox 3, transcript variant B), ZXDC (zinc finger C, transcript variant 2), and ZZZ3 (zinc finger, ZZ-type containing 3), including gene products typically human gene products, including transcripts, mRNA, cDNA, coding sequences, proteins and polypeptides, as well as polynucleotides (nucleic acids) encoding the proteins and polypeptides, including naturally occurring variants, e.g., allelic variants, splice variants, transcript variants, and single nucleotide polymorphism (SNP) variants. For example, the biomarkers include polynucleotides, proteins, and polypeptides having the sequences disclosed herein, and naturally occurring variants thereof.

The housekeeping gene used to normalize expression of the 51 marker genes is the human ALG9 (asparagine-linked glycosylation 9, alpha-1,2-mannosyltransferase homolog).

Of these 51 differentially expressed biomarker genes, 38 biomarker genes are useful for the generation of mathematically-derived expression level scores for diagnosing, monitoring, and/or prognosticating the presence of GEP-NEN and/or different states of GEP-NENs. These 38 GEP-NEN biomarkers include: PNMA2, NAP1L1, FZD7, SLC18A2/VMAT2, NOL3, SSTR5, TPH1, RAF1, RSF1, SSTR3, SSTR1. CD59. ARAF, APLP2, KRAS, MORF4L2, TRMT112, MKI67/KI67, SSTR4, CTGF, SPATA7, ZFHX3, PHF21A, SLC18A1/VMAT1, ZZZ3, TECPR2, ATP6V1H, OAZ2, PAN K2, PLD3, PQBP1, RNF41, SMARCD3, BNIP3L, WDFY3, COMMD9, BRAF, and GLT8D1.

Of the 38 biomarker genes useful for the generation of a mathematically-derived expression level score for diagnosing, monitoring, and/or prognosticating the presence of GEP-NENs, at least 22 biomarker genes may be needed to generate an adequate classifier. These at least 22 biomarker genes include PNMA2, NAP1L1, FZD7, SLC18A2, NOL3, SSTR5, TPH1, RAF1, RSF1, SSTR3, SSTR1, CD59, ARAF, APLP2, KRAS, MORF4L2, TRMT112, MKI67, SSTR4, CTGF, SPATA7, and ZFHX3.

The ALG9 biomarkers/housekeeping genes include human ALG9 gene products, including natural variants, e.g., allelic variants, and homologs and analogs thereof. In one example, the ALG9 biomarker/housekeeping gene is a polynucleotide having the nucleotide sequence set forth in SEQ ID NO: 1 (referenced at NM_024740.2), or containing a protein-coding portion thereof, a natural variant thereof, or a protein encoded by such a polynucleotide.

The AKAP8L biomarkers include human AKAP8L gene products, including natural variants, e.g., allelic variants, and homologs and analogs thereof. In one example, the AKAP8L biomarker is a polynucleotide having the nucleotide sequence set forth in SEQ ID NO: 2 (referenced at NM_014371.3), or containing a protein-coding portion thereof, a natural variant thereof, or a protein encoded by such a polynucleotide.

The APLP2 biomarkers include human APLP2 gene products, including natural variants, e.g., allelic variants, and homologs and analogs thereof. In one example, the APLP2 biomarker is a polynucleotide having the nucleotide sequence set forth in SEQ ID NO: 3 (referenced at NM_001142276.1) or containing a protein-coding portion thereof, a natural variant thereof, or a protein encoded by such a polynucleotide.

The ARAF1 biomarkers include human ARAF1 gene products, including natural variants, e.g., allelic variants, and homologs and analogs thereof. In one example, the ARAF1 biomarker is a polynucleotide having the nucleotide sequence set forth in SEQ ID NO: 4 (referenced at NM_001654.4), or containing a protein-coding portion thereof, a natural variant thereof, or a protein encoded by such a polynucleotide.

The ATP6V1H biomarkers include human ATP6VIH gene products, including natural variants, e.g., allelic variants, and homologs and analogs thereof. In one example, the ATP6V1H biomarker is a polynucleotide having the nucleotide sequence set forth in SEQ ID NO: 5 (referenced at NM_015941.3), or containing a protein-coding portion thereof, a natural variant thereof, or a protein encoded by such a polynucleotide.

The BNIP3L biomarkers include human BNIP3L gene products, including natural variants, e.g., allelic variants, and homologs and analogs thereof. In one example, the BNIP3L biomarker is a polynucleotide having the nucleotide sequence set forth in SEQ ID NO: 6 (referenced at NM_004331.2), or containing a protein-coding portion thereof, a natural variant thereof, or a protein encoded by such a polynucleotide.

The BRAF biomarkers include BRAF gene products, including natural variants, e.g., allelic variants, and homologs and analogs thereof. In one example, the BRAF biomarker is a polynucleotide having the nucleotide sequence set forth in SEQ ID NO: 7 (referenced at NM_004333.4), or containing a protein-coding portion thereof, a natural variant thereof, or a protein encoded by such a polynucleotide.

The C21ORF7 biomarkers include C21ORF7 gene products, including natural variants, e.g., allelic variants, and homologs and analogs thereof. In one example, the C21ORF7 biomarker is a polynucleotide having the nucleotide sequence set forth in SEQ ID NO: 8 (referenced at NM_020152.3), or containing a protein-coding portion thereof, a natural variant thereof, or a protein encoded by such a polynucleotide.

The CD59 biomarkers include CD59 gene products, including natural variants, e.g., allelic variants, and homologs and analogs thereof. In one example, the CD59 biomarker is a polynucleotide having the nucleotide sequence set forth in SEQ ID NO: 9 (referenced at NM_203331.2), or containing a protein-coding portion thereof, a natural variant thereof, or a protein encoded by such a polynucleotide.

The COMMD9 biomarkers include COMMD9 gene products, including natural variants, e.g., allelic variants, and homologs and analogs thereof. In one example, the COMMD9 biomarker is a polynucleotide having the nucleotide sequence set forth in SEQ ID NO: 10 (referenced at NM_001101653.1), or containing a protein-coding portion thereof, a natural variant thereof, or a protein encoded by such a polynucleotide.

The CTGF biomarkers include CTGF gene products, including natural variants, e.g., allelic variants, and homologs and analogs thereof. In one example, the CTGF biomarker is a polynucleotide having the nucleotide sequence set forth in SEQ ID NO: 11 (referenced at NM_001901.2), or containing a protein-coding portion thereof, a natural variant thereof, or a protein encoded by such a polynucleotide.

The ENPP4 biomarkers include ENPP4 gene products, including natural variants, e.g., allelic variants, and homologs and analogs thereof. In one example, the ENPP4 biomarker is a polynucleotide having the nucleotide sequence set forth in SEQ ID NO: 12 (referenced at NM_014936.4), or containing a protein-coding portion thereof, a natural variant thereof, or a protein encoded by such a polynucleotide.

The FAM131A biomarkers include FAM131A gene products, including natural variants, e.g., allelic variants, and homologs and analogs thereof. In one example, the FAM131A biomarker is a polynucleotide having the nucleotide sequence set forth in SEQ ID NO: 13 (referenced at NM_001171093.1), or containing a protein-coding portion thereof, a natural variant thereof, or a protein encoded by such a polynucleotide.

The FLJ1035 biomarkers include FLJ1035 gene products, including natural variants, e.g., allelic variants, and homologs and analogs thereof. In one example, the FLJ1035 biomarker is a polynucleotide having the nucleotide sequence set forth in SEQ ID NO: 14 (referenced at NM_018071.4), or containing a protein-coding portion thereof, a natural variant thereof, or a protein encoded by such a polynucleotide.

The FZD7 biomarkers include FZD7 gene products, including natural variants, e.g., allelic variants, and homologs and analogs thereof. In one example, the FZD7 biomarker is a polynucleotide having the nucleotide sequence set forth in SEQ ID NO: 15 (referenced at NM_003507.1), or containing a protein-coding portion thereof, a natural variant thereof, or a protein encoded by such a polynucleotide.

The GLT8D1 biomarkers include GLT8D1 gene products, including natural variants, e.g., allelic variants, and homologs and analogs thereof. In one example, the GLT8D1 biomarker is a polynucleotide having the nucleotide sequence set forth in SEQ ID NO: 16 (referenced at NM_001010983.2), or containing a protein-coding portion thereof, a natural variant thereof, or a protein encoded by such a polynucleotide.

The HDAC9 biomarkers include HDAC9 gene products, including natural variants, e.g., allelic variants, and homologs and analogs thereof. In one example, the HDAC9 biomarker is a polynucleotide having the nucleotide sequence set forth in SEQ ID NO: 17 (referenced at NM_001204144.1), or containing a protein-coding portion thereof, a natural variant thereof, or a protein encoded by such a polynucleotide.

The HSF2 biomarkers include HSF2 gene products, including natural variants, e.g., allelic variants, and homologs and analogs thereof. In one example, the HSF2 biomarker is a polynucleotide having the nucleotide sequence set forth in SEQ ID NO: 18 (referenced at NM_004506.3), or containing a protein-coding portion thereof, a natural variant thereof, or a protein encoded by such a polynucleotide.

The Ki-67 biomarkers include Ki-67 gene products, including natural variants, e.g., allelic variants, and homologs and analogs thereof. In one example, the Ki-67 biomarker is a polynucleotide having the nucleotide sequence set forth in SEQ ID NO: 19 (referenced at NM_001145966.1), or containing a protein-coding portion thereof, a natural variant thereof, or a protein encoded by such a polynucleotide.

The KRAS biomarkers include KRAS gene products, including natural variants, e.g., allelic variants, and homologs and analogs thereof. In one example, the KRAS biomarker is a polynucleotide having the nucleotide sequence set forth in SEQ ID NO: 20 (referenced at NM_004985.4), or containing a protein-coding portion thereof, a natural variant thereof, or a protein encoded by such a polynucleotide.

The LEO1 biomarkers include LEO1 gene products, including natural variants, e.g., allelic variants, and homologs and analogs thereof. In one example, the LEO1 biomarker is a polynucleotide having the nucleotide sequence set forth in SEQ ID NO: 21 (referenced at NM_138792.3), or containing a protein-coding portion thereof, a natural variant thereof, or a protein encoded by such a polynucleotide.

The MORF4L2 biomarkers include MORF4L2 gene products, including natural variants, e.g., allelic variants, and homologs and analogs thereof. In one example, the MORF4L2 biomarker is a polynucleotide having the nucleotide sequence set forth in SEQ ID NO: 22 (referenced at NM_001142418.1), or containing a protein-coding portion thereof, a natural variant thereof, or a protein encoded by such a polynucleotide.

The NAP1L1 biomarkers include NAP1L1 gene products, including natural variants, e.g., allelic variants, and homologs and analogs thereof. In one example, the NAP1L1 biomarker is a polynucleotide having the nucleotide sequence set forth in SEQ ID NO: 23 (referenced at NM_139207.2), or containing a protein-coding portion thereof, a natural variant thereof, or a protein encoded by such a polynucleotide.

The NOL3 biomarkers include NOL3 gene products, including natural variants, e.g., allelic variants, and homologs and analogs thereof. In one example, the NOL3 biomarker is a polynucleotide having the nucleotide sequence set forth in SEQ ID NO: 24 (referenced at NM_001185057.2), or containing a protein-coding portion thereof, a natural variant thereof, or a protein encoded by such a polynucleotide.

The NUDT3 biomarkers include NUDT3 gene products, including natural variants, e.g., allelic variants, and homologs and analogs thereof. In one example, the NUDT3 biomarker is a polynucleotide having the nucleotide sequence set forth in SEQ ID NO: 25 (referenced at NM_006703.3), or containing a protein-coding portion thereof, a natural variant thereof, or a protein encoded by such a polynucleotide.

The OAZ2 biomarkers include OAZ2 gene products, including natural variants, e.g., allelic variants, and homologs and analogs thereof. In one example, the OAZ2 biomarker is a polynucleotide having the nucleotide sequence set forth in SEQ ID NO: 26 (referenced at NM_002537.3), or containing a protein-coding portion thereof, a natural variant thereof, or a protein encoded by such a polynucleotide.

The PANK2 biomarkers include PANK2 gene products, including natural variants, e.g., allelic variants, and homologs and analogs thereof. In one example, the PANK2 biomarker is a polynucleotide having the nucleotide sequence set forth in SEQ ID NO: 27 (referenced at NM_024960.4), or containing a protein-coding portion thereof, a natural variant thereof, or a protein encoded by such a polynucleotide.

The PHF21A biomarkers include PHF21A gene products, including natural variants, e.g., allelic variants, and homologs and analogs thereof. In one example, the PHF21A biomarker is a polynucleotide having the nucleotide sequence set forth in SEQ ID NO: 28 (referenced at NM_001101802.1), or containing a protein-coding portion thereof, a natural variant thereof, or a protein encoded by such a polynucleotide.

The PKD1 biomarkers include PKD1 gene products, including natural variants, e.g., allelic variants, and homologs and analogs thereof. In one example, the PKD1 biomarker is a polynucleotide having the nucleotide sequence set forth in SEQ ID NO: 29 (referenced at NM_000296.3), or containing a protein-coding portion thereof, a natural variant thereof, or a protein encoded by such a polynucleotide.

The PLD3 biomarkers include PLD3 gene products, including natural variants, e.g., allelic variants, and homologs and analogs thereof. In one example, the PLD3 biomarker is a polynucleotide having the nucleotide sequence set forth in SEQ ID NO: 30 (referenced at NM_001031696.3), or containing a protein-coding portion thereof, a natural variant thereof, or a protein encoded by such a polynucleotide.

The PNMA2 biomarkers include PNMA2 gene products, including natural variants, e.g., allelic variants, and homologs and analogs thereof. In one example, the PNMA2 biomarker is a polynucleotide having the nucleotide sequence set forth in SEQ ID NO: 31 (referenced at NM_007257.5), or containing a protein-coding portion thereof, a natural variant thereof, or a protein encoded by such a polynucleotide.

The PQBP1 biomarkers include PQBP1 gene products, including natural variants, e.g., allelic variants, and homologs and analogs thereof. In one example, the PQBP1 biomarker is a polynucleotide having the nucleotide sequence set forth in SEQ ID NO: 32 (referenced at NM_001032381.1), or containing a protein-coding portion thereof, a natural variant thereof, or a protein encoded by such a polynucleotide.

The RAF1 biomarkers include RAF1 gene products, including natural variants, e.g., allelic variants, and homologs and analogs thereof. In one example, the RAF1 biomarker is a polynucleotide having the nucleotide sequence set forth in SEQ ID NO: 33 (referenced at NM_002880.3), or containing a protein-coding portion thereof, a natural variant thereof, or a protein encoded by such a polynucleotide.

The RNF41 biomarkers include RNF41 gene products, including natural variants, e.g., allelic variants, and homologs and analogs thereof. In one example, the RNF41 biomarker is a polynucleotide having the nucleotide sequence set forth in SEQ ID NO: 34 (referenced at NM_001242826.1), or containing a protein-coding portion thereof, a natural variant thereof, or a protein encoded by such a polynucleotide.

The RSF1 biomarkers include RSF1 gene products, including natural variants, e.g., allelic variants, and homologs and analogs thereof. In one example, the RSF1 biomarker is a polynucleotide having the nucleotide sequence set forth in SEQ ID NO: 35 (referenced at NM_016578.3), or containing a protein-coding portion thereof, a natural variant thereof, or a protein encoded by such a polynucleotide.

The RTN2 biomarkers include RTN2 gene products, including natural variants, e.g., allelic variants, and homologs and analogs thereof. In one example, the RTN2 biomarker is a polynucleotide having the nucleotide sequence set forth in SEQ ID NO: 36 (referenced at NM_005619.4), or containing a protein-coding portion thereof, a natural variant thereof, or a protein encoded by such a polynucleotide.

The SMARCD3 biomarkers include SMARCD3 gene products, including natural variants, e.g., allelic variants, and homologs and analogs thereof. In one example, the SMARCD3 biomarker is a polynucleotide having the nucleotide sequence set forth in SEQ ID NO: 37 (referenced at NM_001003801.1), or containing a protein-coding portion thereof, a natural variant thereof, or a protein encoded by such a polynucleotide.

The SPATA7 biomarkers include SPATA7 gene products, including natural variants, e.g., allelic variants, and homologs and analogs thereof. In one example, the SPATA7 biomarker is a polynucleotide having the nucleotide sequence set forth in SEQ ID NO: 38 (referenced at NM_001040428.3), or containing a protein-coding portion thereof, a natural variant thereof, or a protein encoded by such a polynucleotide.

The SSTR1 biomarkers include SSTR1 gene products, including natural variants, e.g., allelic variants, and homologs and analogs thereof. In one example, the SSTR1 biomarker is a polynucleotide having the nucleotide sequence set forth in SEQ ID NO: 39 (referenced at NM_001049.2), or containing a protein-coding portion thereof, a natural variant thereof, or a protein encoded by such a polynucleotide.

The SSTR3 biomarkers include SSTR3 gene products, including natural variants, e.g., allelic variants, and homologs and analogs thereof. In one example, the SSTR3 biomarker is a polynucleotide having the nucleotide sequence set forth in SEQ ID NO: 40 (referenced at NM_001051.4), or containing a protein-coding portion thereof, a natural variant thereof, or a protein encoded by such a polynucleotide.

The SST4 biomarkers include SST4 gene products, including natural variants, e.g., allelic variants, and homologs and analogs thereof. In one example, the SST4 biomarker is a polynucleotide having the nucleotide sequence set forth in SEQ ID NO: 41 (referenced at NM_001052.2), or containing a protein-coding portion thereof, a natural variant thereof, or a protein encoded by such a polynucleotide.

The SST5 biomarkers include SST5 gene products, including natural variants, e.g., allelic variants, and homologs and analogs thereof. In one example, the SST5 biomarker is a polynucleotide having the nucleotide sequence set forth in SEQ ID NO: 42 (referenced at NM_001053.3), or containing a protein-coding portion thereof, a natural variant thereof, or a protein encoded by such a polynucleotide.

The TECPR2 biomarkers include TECPR2 gene products, including natural variants, e.g., allelic variants, and homologs and analogs thereof. In one example, the TECPR2 biomarker is a polynucleotide having the nucleotide sequence set forth in SEQ ID NO: 43 (referenced at NM_001172631.1), or containing a protein-coding portion thereof, a natural variant thereof, or a protein encoded by such a polynucleotide.

The TPH1 biomarkers include TPH1 gene products, including natural variants, e.g., allelic variants, and homologs and analogs thereof. In one example, the TPH1 biomarker is a polynucleotide having the nucleotide sequence set forth in SEQ ID NO: 44 (referenced at NM_004179.2), or containing a protein-coding portion thereof, a natural variant thereof, or a protein encoded by such a polynucleotide.

The TRMT112 biomarkers include TRMT112 gene products, including natural variants, e.g., allelic variants, and homologs and analogs thereof. In one example, the TRMT112 biomarker is a polynucleotide having the nucleotide sequence set forth in SEQ ID NO: 45 (referenced at NM_016404.2), or containing a protein-coding portion thereof, a natural variant thereof, or a protein encoded by such a polynucleotide.

The VMAT1 biomarkers include VMAT1 gene products, including natural variants, e.g., allelic variants, and homologs and analogs thereof. In one example, the VMAT1 biomarker is a polynucleotide having the nucleotide sequence set forth in SEQ ID NO: 46 (referenced at NM_003053.3), or containing a protein-coding portion thereof, a natural variant thereof, or a protein encoded by such a polynucleotide.

The VMAT2 biomarkers include VMAT2 gene products, including natural variants, e.g., allelic variants, and homologs and analogs thereof. In one example, the VMAT2 biomarker is a polynucleotide having the nucleotide sequence set forth in SEQ ID NO: 47 (referenced at NM_003054.4), or containing a protein-coding portion thereof, a natural variant thereof, or a protein encoded by such a polynucleotide.

The VPS13C biomarkers include VPS13C gene products, including natural variants, e.g., allelic variants, and homologs and analogs thereof. In one example, the VPS3C biomarker is a polynucleotide having the nucleotide sequence set forth in SEQ ID NO: 48 (referenced at NM_001018088.2), or containing a protein-coding portion thereof, a natural variant thereof, or a protein encoded by such a polynucleotide.

The WDFY3 biomarkers include WDFY3 gene products, including natural variants, e.g., allelic variants, and homologs and analogs thereof. In one example, the WDFY3 biomarker is a polynucleotide having the nucleotide sequence set forth in SEQ ID NO: 49 (referenced at NM_014991.4), or containing a protein-coding portion thereof, a natural variant thereof, or a protein encoded by such a polynucleotide.

The ZFHX3 biomarkers include ZFHX3 gene products, including natural variants, e.g., allelic variants, and homologs and analogs thereof. In one example, the ZFHX3 biomarker is a polynucleotide having the nucleotide sequence set forth in SEQ ID NO: 50 (referenced at NM_001164766.1), or containing a protein-coding portion thereof, a natural variant thereof, or a protein encoded by such a polynucleotide.

The ZXDC biomarkers include ZXDC gene products, including natural variants, e.g., allelic variants, and homologs and analogs thereof. In one example, the ZXDC biomarker is a polynucleotide having the nucleotide sequence set forth in SEQ ID NO: 51 (referenced at NM_001040653.3), or containing a protein-coding portion thereof, a natural variant thereof, or a protein encoded by such a polynucleotide.

The ZZZ3 biomarkers include ZZZ3 gene products, including natural variants, e.g., allelic variants, and homologs and analogs thereof. In one example, the ZZZ3 biomarker is a polynucleotide having the nucleotide sequence set forth in SEQ ID NO: 52 (referenced at NM_015534.4), or containing a protein-coding portion thereof, a natural variant thereof, or a protein encoded by such a polynucleotide.

In some embodiments, the panel of polynucleotides further includes one or more polynucleotide able to specifically hybridize to "housekeeping," or reference genes, for example, genes for which differences in expression is known or not expected to correlate with differences in the variables analyzed, for example, with the presence or absence of GEP-NEN or other neoplastic disease, differentiation of various GEP-NEN sub-types, metastasis, mucosal or other tissue types, prognostic indications, and/or other phenotype, prediction, or outcome. In some aspects, expression levels of such housekeeping genes are detected and used as an overall expression level standards, such as to normalize expression data obtained for GEP-NEN biomarkers across various samples.

Housekeeping genes are well known in the art. Typically, the housekeeping genes include one or more genes characterized as particularly appropriate for analyzing GEP-NEN samples, such as ALG9. See Kidd M, et al., "GeneChip, geNorm and Gastrointestinal tumors: novel reference genes for real-time PCR." Physiol Genomics 2007; 30:363-70. In the current application, ALG9 is the housekeeping gene of choice.

The present invention provides methods, compositions, and systems, for the detection of the GEP-NEN biomarkers and for identifying, isolating, and enriching tumors and cells that express the GEP-NEN biomarkers. For example, provided are agents, sets of agents, and systems for detecting the GEP-NEN biomarkers and methods for use of the same, including for diagnostic and prognostic uses.

In one embodiment, the agents are proteins, polynucleotides or other molecules which specifically bind to or specifically hybridize to the GEP-NEN biomarkers. The agents include polynucleotides, such as probes and primers, e.g. sense and antisense PCR primers, having identity or complementarity to the polynucleotide biomarkers, such as mRNA, or proteins, such as antibodies, which specifically bind to such biomarkers. Sets and kits containing the agents, such as agents specifically hybridizing to or binding the panel of biomarkers, also are provided.

Thus, the systems, e.g., microarrays, sets of polynucleotides, and kits, provided herein include those with nucleic acid molecules, typically DNA oligonucleotides, such as primers and probes, the length of which typically varies between 15 bases and several kilo bases, such as between 20 bases and 1 kilobase, between 40 and 100 bases, and between 50 and 80 nucleotides or between 20 and 80 nucleotides. In one aspect, most (i.e. at least 60% of) nucleic acid molecules of a nucleotide microarray, kit, or other system, are capable of hybridizing to GEP-NEN biomarkers.

In one example, systems containing polynucleotides that specifically hybridize to the biomarkers, e.g., nucleic acid microarrays, are provided to detect and measure changes in expression levels and determine expression profiles of the biomarkers according to the provided methods. Among such systems, e.g., microarrays, are those comprising polynucleotides able to hybridize to at least as at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following sets of biomarkers:

PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and GLT8D1 gene products;

In some aspects, at least 60%, or at least 70%, at least 80%, or more, of the nucleic acid molecules of the system, e.g., microarray, are able to hybridize to biomarkers in the panel of biomarkers. In one example, probes immobilized on such nucleotide microarrays comprise at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more nucleic acid molecules able to hybridize to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more of the biomarkers, where each of the nucleic acid molecules is capable of specifically hybridizing to a different one of the biomarkers, such that at least that many different biomarkers can be bound.

In one example, the remaining nucleic acid molecules, such as 40% or at most 40% of the nucleic acid molecules on the microarray or in the set of polynucleotides are able to hybridize to a set of reference genes or a set of normalization genes (such as housekeeping genes), for example, for normalization in order to reduce systemic bias. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment. To reduce systemic bias, the determined RNA levels are preferably corrected for background non-specific hybridization and normalized.

The use of such reference probes is advantageous but not mandatory. In one embodiment a set of polynucleotides or system, e.g., microarray, is provided wherein at least 90% of the nucleic acid sequences are able to hybridize to the GEP-NEN biomarkers; further embodiments include such systems and sets in which at least 95% or even 100% of the polynucleotides hybridize to the biomarkers.

Disclosed herein are exemplary suitable polynucleotides, such as PCR primers. Other nucleic acid probes and primers, able to hybridize to different regions of the biomarkers are of course also suitable for use in connection with the provided systems, kits and methods.

The present invention provides methods for detecting and quantifying the biomarkers, including detecting the presence, absence, amount or relative amount, such as expression levels or expression profile of the biomarkers. Typically, the methods are nucleic acid based methods, for example, measuring the presence, amount or expression levels of biomarker mRNA expression. Such methods typically are carried out by contacting polynucleotide agents to biological samples, such as test samples and normal and reference samples, for example, to quantify expression levels of nucleic acid biomarkers (e.g., mRNA) in the samples.

Detection and analysis of biomarkers according to the provided embodiments can be performed with any suitable method known in the art. For example, where the biomarkers are RNA biomarkers, RNA detection and quantification methods are used.

Exemplary methods for quantifying or detecting nucleic acid expression levels, e.g., mRNA expression, are well known, and include northern blotting and in situ hybridization (Parker and Barnes, Methods in Molecular Biology 106:247-283, 1999); RNAse protection assays (Hod. Biotechniques 13:852-854, 1992); and quantitative or semi-quantitative reverse transcription polymerase chain reaction (RT-PCR) (Weis et al., Trends in Genetics 8:263-264, 1992), representative methods for sequencing-based gene expression analysis include Serial Analysis of Gene Expression (SAGE), and gene expression analysis by massively parallel signature sequencing (MPSS).

Therefore, in one embodiment, expression of the biomarker or biomarker panel includes RNA expression; the methods include determining levels of RNA of the biomarkers, such as RNA obtained from and/or present in a sample of a patient, and performing analysis, diagnosis, or predictive determinations based upon the RNA expression levels determined for the biomarkers or panel of biomarkers.

RNA samples can be processed in numerous ways, as is known to those in the art. Several methods are well known for isolation of RNA from samples, including guanidinium thiocyanate-phenol-chloroform extraction, which may be carried out using the TRIZOL® reagent, a proprietary formulation (see Chomczynski P, Sacchi N (2006). "The single-step method of RNA isolation by acid guanidinium thiocyanate-phenol-chloroform extraction: twenty-something years on". Nat Protoc 1 (2): 581-5). In this method, TRIZOL® is used to extract RNA and DNA; chloroform and centrifugation are used to separate RNA from other nucleic acids, followed by a series of washes with ethanol for cleanup of the RNA sample.

The RNA samples can be freshly prepared from samples e.g., cells or tissues at the moment of harvesting; alternatively, they can be prepared from samples that stored at −70° C. until processed for sample preparation. Alternatively, tissues or cell samples can be stored under and/or subjected to other conditions known in the art to preserve the quality of the RNA, including fixation for example with formalin or similar agent; and incubation with RNase inhibitors such as RNASIN® (ribonuclease inhibitors) or RNASECURE™ (RNase inactivation reagents); aqueous solutions such as RNALATER® (RNA stabilization solutions), Hepes-Glutamic acid buffer mediated Organic solvent Protection Effect (HOPE®), and RCL2® (formalin-free tissue fixatives); and non-aqueous solutions such as Universal Molecular Fixative (Sakura Finetek USA Inc.). A chaotropic nucleic acid isolation lysis buffer (Boom method, Boom et al. J Clin Microbiol. 1990; 28:495-503) may also be used for RNA isolation.

In one embodiment, RNA is isolated from buffy coat by incubating samples with TRIZOL®, followed by RNA clean-up. RNA is dissolved in diethyl pyrocarbonate water and measured spectrophotometrically, and an aliquot analyzed on a Bioanalyzer (Agilent Technologies, Palo Alto, Calif.) to assess the quality of the RNA (Kidd M, et al. "The role of genetic markers—NAP1L1, MAGE-D2, and MTA1—in defining small-intestinal carcinoid neoplasia," Ann Surg Oncol 2006; 13(2):253-62). In another embodiment, RNA is isolated from plasma using the QIAamp RNA Blood Mini Kit; in some cases, this method allows better detection by real-time PCR of significantly more housekeeping genes from plasma compared to the TRIZOL® approach. In another embodiment, RNA is isolated directly from whole blood, for example, using the QIAamp RNA Blood Mini Kit in a similar manner.

Methods for isolating RNA from fixed, paraffin-embedded tissues as the RNA source are well-known and generally include mRNA isolation, purification, primer extension and amplification (for example: T. E. Godfrey et al, Molec. Diagnostics 2: 84-91 [2000]; K. Specht et al., Am. J. Pathol. 158: 419-29 [2001]). In one example, RNA is extracted from a sample such as a blood sample using the QIAamp RNA Blood Mini Kit RNA. Typically, RNA is extracted from tissue, followed by removal of protein and DNA and analysis of RNA concentration. An RNA repair and/or amplification step may be included, such as a step for reverse transcription of RNA for RT-PCR.

Expression levels or amounts of the RNA biomarkers may be determined or quantified by any method known in the art, for example, by quantifying RNA expression relative to housekeeping gene or with relation to RNA levels of other genes measured at the same time. Methods to determine RNA levels of genes are known to a skilled person and include, but are not limited to, Northern blotting, (quantitative) PCR, and microarray analysis.

RNA biomarkers can be reverse transcribed to produce cDNA and the methods of the present invention can include detecting and quantifying that produced cDNA. In some embodiments, the cDNA is detected by forming a complex with a labeled probe. In some embodiments, the RNA biomarkers are directed detected by forming a complex with a labeled probe or primer.

Northern blotting may be performed for quantification of RNA of a specific biomarker gene or gene product, by hybridizing a labeled probe that specifically interacts with the RNA, following separation of RNA by gel electrophoresis. Probes are for example labeled with radioactive isotopes or chemiluminescent substrates. Quantification of the labeled probe that has interacted with said nucleic acid expression product serves as a measure for determining the level of expression. The determined level of expression can be normalized for differences in the total amounts of nucleic acid expression products between two separate samples with for instance an internal or external calibrator by comparing the level of expression of a gene that is known not to differ in expression level between samples or by adding a known quantity of RNA before determining the expression levels.

For RT-PCR, biomarker RNA is reverse transcribed into cDNA. Reverse transcriptase polymerase chain reaction (RT-PCR) is, for example, performed using specific primers that hybridize to an RNA sequence of interest and a reverse transcriptase enzyme. Furthermore, RT-PCR can be performed with random primers, such as for instance random hexamers or decamers which hybridize randomly along the RNA, or oligo d(T) which hybridizes to the poly(A) tail of mRNA, and reverse transcriptase enzyme.

In some embodiments, RNA expression levels of the biomarkers in a sample, such as one from a patient suffering from or suspected of suffering from GEP-NEN or associated symptom or syndrome, are determined using quantitative methods such as by real-time rt-PCR (qPCR) or microarray analysis. In some embodiments, quantitative Polymerase Chain Reaction (QPCR) is used to quantify the level of expression of nucleic acids. In one aspect, detection and determining expression levels of the biomarkers is carried out using RT-PCR, GeneChip analysis, quantitative real-time PCR (Q RT-PCR), or carcinoid tissue microarray (TMA) immunostaining/quantitation, for example, to compare biomarker RNA, e.g., mRNA, or other expression product, levels in different sample populations, characterize patterns of gene expression, to discriminate between closely related mRNAs, and to analyze RNA structure.

In one example, QPCR is performed using real-time PCR (RTPCR), where the amount of product is monitored during the amplification reaction, or by end-point measurements, in which the amount of a final product is determined. As is known to a skilled person, rtPCR is for instance performed by the use of a nucleic acid intercalator, such as for example ethidium bromide or SYBR® Green 1 dye, which interacts which all generated double stranded products resulting in an increase in fluorescence during amplification, or for instance by the use of labeled probes that react specifically with the generated double stranded product of the gene of interest. Alternative detection methods that can be used are provided by amongst other things dendrimer signal amplification, hybridization signal amplification, and molecular beacons.

In one embodiment, reverse transcription on total RNA is carried out using the High Capacity cDNA Archive Kit (Applied Biosystems (ABI), Foster City, Calif.) following the manufacturer's suggested protocol (briefly, using 2 micrograms of total RNA in 50 microliters water, mixing with 50 uL of 2×RT mix containing Reverse Transcription Buffer, deoxynucleotide triphosphate solution, random primers, and Multiscribe Reverse Transcriptase). RT reaction conditions are well known. In one example, the RT reaction is performed using the following thermal cycler conditions: 10 mins, 25° C.; 120 min., 37° C. {see Kidd M, et al., "The role of genetic markers—NAP1L1, MAGE-D2, and MTA1—in defining small-intestinal carcinoid neoplasia," Ann Surg Oncol 2006; 13(2):253-62).

For measurement of individual transcript levels, in one embodiment, Assays-on-Demand™ products are used with the ABI 7900 Sequence Detection System according to the manufacturer's suggestions see Kidd M, Eick G, Shapiro M D, et al. Microsatellite instability and gene mutations in transforming growth factor-beta type II receptor are absent in small bowel carcinoid tumors. Cancer 2005; 103(2):229-36). In one example, cycling is performed under standard conditions, using the TaqMan® Universal PCR Master Mix Protocol, by mixing cDNA in 7.2 uL water, 0.8 uL 20. ASSAYS-ON-DEMAND™ (gene expression products) primer and probe mix and 8 uL of 2× TaqMan Universal Master mix, in a 384-well optical reaction plate, under the following conditions: 50° C., 2 min.; 95° C.; 10 min.; 50 cycles at 95° C. for 15 min., 60° for 1 min {see Kidd M, et al, "The role of genetic markers—NAP 1 LI, MAGE-D2, and MTA1 in defining small-intestinal carcinoid neoplasia," Ann Surg Oncol 2006; 13(2):253-62).

Typically, results from real-time PCR are normalized, using internal standards and/or by comparison to expression levels for housekeeping genes. For example, in one embodiment, Raw $AC_T$ (delta $C_T$=change in cycle time as a function of amplification) data from QPCR as described above is normalized using well-known methods, such as geNorm {see Vandesompele J, De Preter K, Pattyn F, et al. Accurate normalization of real-time quantitative RT-PCR data by geometric averaging of multiple internal control genes. Genome Biol 2002; 3(7):RESEARCH0034). Normalization by house-keeping gene expression levels is also well-known. See Kidd M, et al., "GeneChip, geNorm, and gastrointestinal tumors: novel reference genes for real-time PCR." Physiol Genomics 2007; 30(3):363-70.

Microarray analysis involves the use of selected nucleic acid molecules that are immobilized on a surface. These nucleic acid molecules, termed probes, are able to hybridize to nucleic acid expression products. In a preferred embodiment the probes are exposed to labeled sample nucleic acid, hybridized, washed and the (relative) amount of nucleic acid expression products in the sample that are complementary to a probe is determined. Microarray analysis allows simultaneous determination of nucleic acid expression levels of a large number of genes. In a method according to the invention it is preferred that at least 5 genes according to the invention are measured simultaneously.

Background correction can be performed for instance according to the "offset" method that avoids negative intensity values after background subtraction. Furthermore, normalization can be performed in order to make the two channels on each single array comparable for instance using global loess normalization, and scale normalization which ensures that the log-ratios are scaled to have the same median-absolute-deviation (MAD) across arrays.

Protein levels may, for example, be measured using antibody-based binding assays. Enzyme labeled, radioactively labeled or fluorescently labeled antibodies may be used for detection of protein. Exemplary assays include enzyme-linked immunosorbent assays (ELISA), radio-immuno assays (RIA), Western Blot assays and immunohistochemical staining assays. Alternatively, in order to determine the expression level of multiple proteins simultaneously protein arrays such as antibody-arrays are used.

Typically, the biomarkers and housekeeping markers are detected in a biological sample, such as a tissue or fluid sample, such as a blood, such as whole blood, plasma, serum, stool, urine, saliva, tears, serum or semen sample, or a sample prepared from such a tissue or fluid, such as a cell preparation, including of cells from blood, saliva, or tissue, such as intestinal mucosa, tumor tissue, and tissues containing and/or suspected of containing GEP-NEN metastases or shed tumor cells, such as liver, bone, and blood. In one embodiment, a specific cell preparation is obtained by fluorescence-activated cell sorting (FACS) of cell suspensions or fluid from tissue or fluid, such as mucosa, e.g., intestinal mucosa, blood or buffy coat samples.

In some embodiments, the sample is taken from a GEP-NEN patient, a patient suspected of having GEP-NEN, a patient having and/or suspected of having cancer generally, a patient exhibiting one or more GEP-NEN symptoms or syndromes or determined to be at-risk for GEP-NEN, or a GEP-NEN patient undergoing treatment or having completed treatment, including patients whose disease is and/or is thought to be in remission.

In other embodiments, the sample is taken from a human without GEP-NEN disease, such as a healthy individual or an individual with a different type of cancer, such as an adenocarcinoma, for example, a gastrointestinal adenocarcinoma or one of the breast, prostate, or pancreas, or a gastric or hepatic cancer, such as esophageal, pancreatic, gallbladder, colon, or rectal cancer.

In some embodiments, the sample is taken from the GEP-NEN tumor or metastasis. In other embodiments, the sample is taken from the GEP-NEN patient, but from a tissue or fluid not expected to contain GEP-NEN or GEP-NEN cells; such samples may be used as reference or normal samples. Alternatively, the normal or reference sample may be a tissue or fluid or other biological sample from a patient without GEP-NEN disease, such as a corresponding tissue, fluid or other sample, such as a normal blood sample, a normal small intestinal (SI) mucosa sample, a normal enterochromaffin (EC) cell preparation.

In some embodiments, the sample is a whole blood sample. As neuroendocrine tumors metastasize, they typically shed cells into the blood. Accordingly, detection of the panels of GEP-NEN biomarkers provided herein in plasma and blood samples may be used for identification of GEP-NENs at an early time point and for predicting the presence of tumor metastases, e.g., even if anatomic localization studies are negative. Accordingly, the provided agents and methods are useful for early diagnosis.

Thus, in some embodiments, the methods can identify a GEP-NEN molecular signature or expression profile in 1 mL or about 1 mL of whole blood. In some aspects, the molecular signature or expression profile is stable for up to four hours (for example, when samples are refrigerated 4-8° C. following phlebotomy) prior to freezing. In one aspect, the approach able to diagnose, prognosticate or predict a given GEP-NEN-associated outcome using a sample obtained from tumor tissue is also able to make the same diagnosis, prognosis, or prediction using a blood sample.

A number of existing detection and diagnostic methodologies require 7 to 10 days to produce a possible positive result, and can be costly. Thus, in one aspect, the provided methods and compositions are useful in improving simplicity and reducing costs associated with GEP-NEN diagnosis, and make early-stage diagnosis feasible.

Thus in one example, the biomarkers are detected in circulation, for example by detection in a blood sample, such as a serum, plasma, cells, e.g., peripheral blood mononuclear cells (PBMCs), obtained from buffy coat, or whole blood sample.

Tumor-specific transcripts have been detected in whole blood in some cancers. See Sicuwerts A M, et al., "Molecular characterization of circulating tumor cells in large quantities of contaminating leukocytes by a multiplex real-time PCR," Breast Cancer Res Treat 2009; 118(3):455-68 and Mimori K, et al, "A large-scale study of MT1-MMP as a marker for isolated tumor cells in peripheral blood and bone marrow in gastric cancer cases," Ann Surg Oncol 2008; 15(10):2934-42.

The CELLSEARCH® CTC Test (circulating tumor cell kits) (described by Kahan L., "Medical devices; immunology and microbiology devices; classification of the immunomagnetic circulating cancer cell selection and enumeration system. Final rule," Fed Regist 2004; 69:26036-8) uses magnetic beads coated with EpCAM-specific antibodies that detects epithelial cells (CK—8/18/19) and leukocytes (CD45), as described by Sieuwerts A M, Kraan J, Bolt-de Vries J, et al., "Molecular characterization of circulating tumor cells in large quantities of contaminating leukocytes by a multiplex real-time PCR," Breast Cancer Res Treat 2009; 118(3):455-68. This method has been used to detect circulating tumor cells (CTCs), and monitoring disease progression and therapy efficacy in metastatic prostate (Danila D C, Heller G, Gignac G A, et al. Circulating tumor cell number and prognosis in progressive castration-resistant prostate cancer. Clin Cancer Res 2007; 13(23):7053-8), colorectal (Cohen S J, Alpaugh R K, Gross S, et al.) Isolation and characterization of circulating tumor cells in patients with metastatic colorectal cancer. Clin Colorectal Cancer 2006; 6(2): 125-32, and breast (Cristofanilli M, Budd G T. Ellis M J, et al., Circulating tumor cells, disease progression, and survival in metastatic breast cancer. N Engl J Med 2004; 351(8):781-91).

This and other existing approaches have not been entirely satisfactory for detection of GEP-NEN cells, which can exhibit variable expression and/or not express cytokeratin (See Van Ecden S, et al, Classification of low-grade neuroendocrine tumors of midgut and unknown origin," Hum Pathol 2002; 33(11): 1126-32; Cai Y C, et al., "Cytokeratin 7 and 20 and thyroid transcription factor 1 can help distinguish pulmonary from gastrointestinal carcinoid and pancreatic endocrine tumors," Hum Pathol 2001; 32(10): 1087-93, and studies described herein, detecting EpCAM transcript expression in two of twenty-nine GEP-NEN samples).

Factors to consider in the available detection methods for circulating tumor cells are relatively low numbers of the cells in peripheral blood, typically about 1 per $10^6$ peripheral blood mononuclear cells (PBMCs) (see Ross A A. et al. "Detection and viability of tumor cells in peripheral blood stem cell collections from breast cancer patients using immunocytochemical and clonogenic assay techniques." Blood 1993; 82(9):2605-10), and the potential for leukocyte contamination. See Sieuwerts A M, et al. "Molecular characterization of circulating tumor cells in large quantities of contaminating leukocytes by a multiplex real-time PCR," Breast Cancer Res Treat 2009; 118(3):455-68; Mimori K, et al) and technical complexity of available approaches. These factors can render available methods not entirely satisfactory for use in the clinical laboratory.

In some embodiments, Neuroendocrine cells are FACS-sorted to heterogeneity, using known methods, following acridine orange (AO) staining and uptake, as described Kidd M, et al., "Isolation, Purification and Functional Characterization of the Mastomys E C cell," Am J Physiol 2006; 291:G778-91; Modlin E V I, et al., "The functional characterization of normal and neoplastic human enterochromaffin cells," Clin Endocrinol Metab 2006; 91(6):2340-8.

In some embodiments, the provided detection methods are used to detect, isolate, or enrich for the GEP-NEN cells and/or biomarkers in two to three mL of blood or less. The methods are performed using standard laboratory apparatuses and thus are easily performed in the clinical laboratory setting. In one example, a readout is obtained within 12 hours, at an average cost of approximately 20-30 per sample.

The present invention provides diagnostic, prognostic, and predictive uses for the agents and detection methods provided herein, such as for the diagnosis, prognosis, and prediction of GEP-NEN, associated outcomes, and treatment responsiveness. For example, available GEP-NEN classification methods are limited, in part due to incorrect classifications and that individual lesions or tumors can evolve into different GEP-NEN sub-types or patterns, and/or contain more than one GEP-NEN sub-type. Known classification frameworks are limited, for example, in the ability to predict response to treatment or discriminate accurately between tumors with similar histopathologic features that may vary substantially in clinical course and treatment response, and to predict treatment responsiveness.

There is therefore a need for molecular or gene-based classification schemes. The provided methods and systems, including GEP-NEN-specific predictive gene-based models, address these issues, and may be used in identifying and analyzing molecular parameters that are predictive of biologic behavior and prediction based on such parameters.

Among the provided diagnostic, prognostic, and predictive methods are those which employ statistical analysis and biomathematical algorithms and predictive models to analyze the detected information about expression of GEP-NEN biomarkers and other markers such as housekeeping genes. In some embodiments, expression levels, detected binding or other information is normalized and assessed against reference value(s), such as expression levels in normal samples or standards. Provided embodiments include methods and systems for classification and prediction of GEP-NENs using the detected and measured information about the expression of the GEP-NEN biomarkers, for example, in classification, staging, prognosis, treatment design, evaluation of treatment options, and prediction of GEP-NEN disease outcomes, e.g., predicting development of metastases.

In some embodiments, the methods are used to establish GEP-NEN diagnosis, such as diagnosis or detection of early-stage disease or metastasis, define or predict the extent of disease, identify early spread or metastasis, predict outcome or prognosis, predict progression, classify disease activity, monitor treatment responsiveness, detect or monitor for recurrence, and to facilitate early therapeutic intervention. For example, among the provided methods and algorithms are those for use in classification, staging, prognosis, treatment design, evaluation of treatment options, and prediction of GEP-NEN disease outcomes, e.g., predicting development of metastases.

In one embodiment, the methods, algorithms and models are useful for diagnostic surveillance, such as routine surveillance and patient follow-up. In some embodiments, the methods, algorithms and models provide for early diagnosis; in one aspect, the methods are capable of detection of low-volume tumors, and detection of circulating tumor cells, including at early stages of disease, such as detection of as few as at or about 3 circulating GEP-NEN cells per milliliter of blood. In some embodiments, early evidence of disease allows early therapeutic intervention, at a time when therapies are more effective, which can improve survival rates and disease outcomes.

For example, in one embodiment, the methods useful for early detection of the recurrence and/or metastasis of GEP-NEN, such as after treatment for example following surgical or chemical intervention. In some aspect, the methods are performed weekly or monthly following therapeutic intervention, for example, on human blood samples. In some aspects, the methods are capable of detecting micrometastases that are too small to be detected by conventional means, such as by imaging methods. For example, in one aspect the methods are capable of detecting metastases less than one centimeter (cm), such as at or about 1 cm, 0.9 cm, 0.8 cm, 0.7 cm, 0.6 cm, 0.5 cm, 0.4 cm, 0.3 cm, 0.2 cm, or 0.1 cm metastases, such as in the liver.

For example, among the provided methods and systems are those that determine the presence or absence (or both) of a GEP-NEN in a subject or sample with a correct call rate of between 56 and 92%, such as at least or at least about a 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% correct call rate. In some cases, the methods are useful for diagnosis with a specificity or sensitivity of at least or at least about 70%, 7%5, 80%, 81%, 82%, 83%, 84%, 85%, 86%, 87%, 88%, 89%, 90%, 91%, 92%, 93%, 94%, 95%, 96%, 97%, 98%, 99%, or 100%.

In other aspects, the methods are capable of detecting the recurrence, metastasis, or spread of GEP-NEN following treatment or during initial disease progression at an earlier stage as compared with other diagnostic methods, such as imaging and detection of available biomarkers. In some aspects, the detected expression levels and/or expression signature of the biomarkers correlate significantly with the progression of disease, disease severity or aggressiveness, lack of responsiveness of treatment, reduction in treatment efficacy, GEP-NEN-associated events, risk, prognosis, type or class of GEP-NEN or disease stage.

Among the provided embodiments are methods that use the provided biomarkers and detection thereof in treatment development, strategy, and monitoring, including evaluation of response to treatment and patient-specific or individualized treatment strategies that take into consideration the likely natural history of the tumor and general health of the patient.

GEP-NEN management strategies include surgery—for cure (rarely achieved) or cytoreduction—radiological intervention—for example, by chemoembolization or radiofrequency ablation—chemotherapy, cryoablation, and treatment with somatostatin and somatostatin analogues (such as SANDOSTATIN® LAR (Octreotide acetate injection)) to control symptoms caused by released peptides and neuroamines. Biological agents, including interferon, and hormone therapy, and somatostatin-tagged radionucleotides are under investigation.

In one example, Cryoablation liberates GEP-NEN tissue for entry into the blood, which in turn induces symptoms, as described by Mazzaglia P J, et ah, “Laparoscopic radiofrequency ablation of neuroendocrine liver metastases: a 10-year experience evaluating predictors of survival,” Surgery 2007; 142(1): 10-9. Chemo therapeutic agents, e.g., systemic cytotoxic chemo therapeutic agents, include etoposide, cisplatin, 5-fluorouracil, streptozotocin, doxorubicin; vascular endothelial growth factor inhibitors, receptor tyrosine kinase inhibitors (e.g., Sunitinib, Sorafenib, and Vatalanib), and mammalian target of rapamycin (mTOR) inhibitors (e.g., Temsirolimus and Everolimus), and combinations thereof, for example to treat disseminated and/or poorly differentiated/aggressive disease. Other treatment approaches are well known.

In some embodiments, the detection and diagnostic methods are used in conjunction with treatment, for example, by performing the methods weekly or monthly before and/or after treatment. In some aspects, the expression levels and profiles correlate with the progression of disease, ineffectiveness or effectiveness of treatment, and/or the recurrence or lack thereof of disease. In some aspects, the expression information indicates that a different treatment strategy is preferable. Thus, provided herein are therapeutic methods, in which the GEP-NEN biomarker detection methods are performed prior to treatment, and then used to monitor therapeutic effects.

At various points in time after initiating or resuming treatment, significant changes in expression levels or expression profiles of the biomarkers (e.g., as compared to expression or expression profiles before treatment, or at some other point after treatment, and/or in a normal or reference sample) indicates that a therapeutic strategy is or is not successful, that disease is recurring, or that a different therapeutic approach should be used. In some embodiments, the therapeutic strategy is changed following performing of the detection methods, such as by adding a different therapeutic intervention, either in addition to or in place of the current approach, by increasing or decreasing the aggressiveness or frequency of the current approach, or stopping or reinstituting the treatment regimen.

In another aspect, the detected expression levels or expression profile of the biomarkers identifies the GEP-NEN disease for the first time or provides the first definitive diagnosis or classification of GEP-NEN disease. In some aspects of this embodiment, a treatment approach is designed based upon the expression levels or expression profiles, and/or the determined classification. The methods include iterative approaches, whereby the biomarker detection methods are followed by initiation or shift in therapeutic intervention, followed by continued periodic monitoring, reevaluation, and change, cessation, or addition of a new therapeutic approach, optionally with continued monitoring.

In some aspects, the methods and systems determine whether or not the assayed subject is responsive to treatment, such as a subject who is clinically categorized as in complete remission or exhibiting stable disease. In some aspects, the methods and systems determine whether or not the subject is untreated (or treatment-I, i.e., has not received treatment) or is non-responsive (i.e., clinically categorized as “progressive.” For example, methods are provided for distinguishing treatment-responsive and non-responsive patients, and for distinguishing patients with stable disease or those in complete remission, and those with progressive disease. In various aspects, the methods and systems make such calls with at least at or about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% correct call rate (i.e., accuracy), specificity, or sensitivity.

In some aspects, the sensitivity or correct call rate for the diagnostic or predictive or prognostic outcome is greater than, e.g., significantly greater than, that obtained using a known diagnosis or prognostic method, such as detection and measurement of circulating CgA or other single protein.

Typically, the diagnostic, prognostic, and predictive methods, often in an initial step, select a subset of biomarkers based on their ability to build a classifier that may accurately predict and classify GEP-NEN and/or different stages of GEP-NEN.

Any of a number of well-known methods for evaluating differences in gene expression may be used to select the subset of biomarkers. For example, an accurate classifier may be based on topographic, pattern-recognition based protocols e.g., support vector machines (SVM) (Noble W S. What is a support vector machine? Nat Biotechnol. 2006; 24(12): 1565-7). Machine-learning based techniques are typically desirable for developing sophisticated, automatic, and/or objective algorithms for analyzing high-dimensional and multimodal biomedical data. In some examples, SVM—a variant of the supervised learning algorithm—is used in connection with the provided methods and systems. SVMs have been used to predict the grading of astrocytomas with a >90 accuracy, and prostatic carcinomas with an accuracy of 74-80% (Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11; Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11).

Other algorithms for building an accurate classifier include linear discriminant analysis (LDA), naive Bayes (NB), and K-nearest neighbor (KNN) protocols. Such approaches are useful for identifying individual or multivariable alterations in neoplastic conditions (Drozdov I, Tsoka S, Ouzounis C A, Shah A M. Genome-wide expression patterns in physiological cardiac hypertrophy. BMC Genomics. 2010; 11: 55; Freeman T C, Goldovsky L, Brosch M, et al. Construction, visualization, and clustering of transcription networks from microarray expression data. PLoS Comput Biol 2007; 3(10): 2032-42; Zampetaki A, Kiechl S, Drozdov I, et al. Plasma microRNA profiling reveals loss of endothelial miR-126 and other microRNAs in type 2 diabetes. Circ Res. 2010; 107(6): 810-7. Epub 2010 Jul. 22; Dhawan M, Selvaraja S, Duan Z H. Application of committee kNN classifiers for gene expression profile classification. Int J Bioinform Res Appl. 2010:6(4): 344-52; Kawarazaki S, Taniguchi K, Shirahata M, et al. Conversion of a molecular classifier obtained by gene expression profiling into a classifier based on real-time PCR: a prognosis predictor for gliomas. BMC Med Genomics. 2010; 3: 52; Vandebriel R J, Van Loveren H, Meredith C. Altered cytokine (receptor) mRNA expression as a tool in immunotoxicology. Toxicology. 1998; 130(1): 43-67; Urgard E, Vooder T, Vosa U, et al. Metagenes associated with survival in non-small cell lung cancer. Cancer Inform. 2011; 10: 175-83. Epub 2011 Jun. 2; Pimentel M, Amichai M, Chua K, Braham L. Validating a New Genomic Test for Irritable Bowel Syndrome Gastroenterology 2011; 140 (Suppl 1): S-798; Lawlor G, Rosenberg L. Ahmed A, et al. Increased Peripheral Blood GATA-3 Expression in Asymptomatic Patients With Active Ulcerative Colitis at Colonoscopy. Gastroenterology 2011; 140 (Suppl 1)).

In some embodiments, an accurate classifier for GEP-NEN and/or different stages of GEP-NEN is based on a combination of the SVM, LDA, NB, and KNN protocols. This is termed the Multi-Analyte-Algorithm Risk Classifier for NETs (MAARC-NET).

Methods using the predictive algorithms and models use statistical analysis and data compression methods, such as those well known in the art. For example, expression data may be transformed, e.g., In-transformed, and imported into a statistical analysis program, such as PARTEK® GENOMICS SUITE® (genomic data analysis software) or similar program, for example. Data are compressed and analyzed for comparison.

Whether differences in expression level score or values are deemed significant may be determined by well-known statistical approaches, and typically is done by designating a threshold for a particular statistical parameter, such as a threshold p-value (e.g., $p<0.05$), threshold S-value (e.g., +0.4, with $S<-0.4$ or $S>0.4$), or other value, at which differences are deemed significant, for example, where expression of a biomarker is considered significantly down- or up-regulated, respectively, among two different samples, for example, representing two different GEP-NEN subtypes, tumors, stages, localizations, aggressiveness, or other aspect of GEP-NEN or normal or reference sample.

In one aspect, the algorithms, predictive models, and methods are based on biomarkers expressed from genes associated with regulatory gene clusters (i.e., SSTRome, Proliferome. Signalome. Metabolome, Secretome, Secretome, Plurome, EpiGenome, and Apoptome) underlying various GEP-NEN subtypes.

In one aspect, the methods apply the mathematical formulations, algorithms or models identify specific cutoff points, for example, pre-determined expression level scores, which distinguish between normal and GEP-NEN samples, between GEP-NEN and other cancers, and between various sub-types, stages, and other aspects of disease or disease outcome. In another aspect, the methods are used for prediction, classification, prognosis, and treatment monitoring and design. In one aspect, the predictive embodiments are useful for identifying molecular parameters predictive of biologic behavior, and prediction of various GEP-NEN-associated outcomes using the parameters. In one aspect of these embodiments, machine learning approaches are used, e.g., to develop sophisticated, automatic and objective algorithms for the analysis of high-dimensional and multimodal biomedical data.

A "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a subset or panel of GEP-NEN biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a subset or panel of GEP-NEN has an AUC in the range of about 0.75 to 1.0. In certain of these embodiments, the AUC is in the range of about 0.50 to 0.85, 0.85 to 0.9, 0.9 to 0.95, or 0.95 to 1.0.

For the comparison of expression level scores or other values, and to identify expression profiles (expression signatures) or regulatory signatures based on GEP-NEN biomarker expression, data are compressed. Compression typically is by Principal Component Analysis (PCA) or similar technique for describing and visualizing the structure of high-dimensional data. PCA allows the visualization and comparison of GEP-NEN biomarker expression and determining and comparing expression profiles (expression signatures, expression patterns) among different samples, such as between normal or reference and test samples and among different tumor types.

In some embodiments, expression level data are acquired, e.g., by real-time PCR, and reduced or compressed, for example, to principal components.

PCA is used to reduce dimensionality of the data (e.g., measured expression values) into uncorrelated principal components (PCs) that explain or represent a majority of the variance in the data, such as about 50%, 60%, 70%, 75%, 80%. 85%, 90%, 95%, or 99% of the variance.

In one example, the PCA is 3-component PCA, in which three PCs are used that collectively represent most of the variance, for example, about 75%, 80%, 85%. 90%, or more variance in the data (Jolliffe I T, "Principle Component Analysis," Springer, 1986).

PCA mapping, e.g., 3-component PCA mapping is used to map data to a three dimensional space for visualization, such as by assigning first ($1^{st}$), second ($2^{nd}$) and third ($3^{rd}$) PCs to the X-, Y-, and Z-axes, respectively.

PCA may be used to determine expression profiles for the biomarkers in various samples. For example, reduced expression data for individual sample types (e.g., each tumor type, sub-type or grade, or normal sample type) are localized in a PCA coordinate system and localized data used to determine individual transcript expression profiles or signatures.

In one aspect, the expression profile is determined for each sample by plotting or defining a centroid (center of mass; average expression), corresponding to or representing the sample's individual transcript expression profile (regulatory signature), as given by the principal component vector, as determined by PCA for the panel of biomarkers.

Generally, two centroids or points of localization separated by a relatively large distance in this coordinate system represent two relatively distinct transcript expression profiles. Likewise, relatively close centroids represent relatively similar profiles. In this representation, the distance between centroids is inversely equivalent to the similarity measure (greater distance=less similarity) for the different samples, such that large distances or separation between centroids indicates samples having distinct transcript expression signatures. Proximity of centroids indicates similarity between samples. For example, the relative distance between centroids for different GEP-NEN tumor samples represents the relative similarity of their regulatory signatures or transcript expression profiles.

In one aspect, the statistical and comparative analysis includes determining the inverse correlation between expression levels or values for two biomarkers. In one example, this correlation and the cosine of the angle between individual expression vectors (greater angle=less similarity), is used to identify related gene expression clusters (Gabriel K R, "The biplot graphic display of matrices with application to principal component analysis," Biometrika 1971; 58(3):453).

In some embodiments, there is a linear correlation between expression levels of two or more biomarkers, and/or the presence or absence of GEP-NEN, sub-type, stage, or other outcome. In one aspect, there is an expression-dependent correlation between the provided GEP-NEN biomarkers and characteristics of the biological samples, such as between biomarkers (and expression levels thereof) and various GEP-NEN sub-types (e.g., benign versus active disease).

Pearson's Correlation (PC) coefficients ($R^2$) may be used to assess linear relationships (correlations) between pairs of values, such as between expression levels of a biomarker for different biological samples (e.g., tumor sub-types) and between pairs of biomarkers. This analysis may be used to linearly separate distribution in expression patterns, by calculating PC coefficients for individual pairs of the biomarkers (plotted on x- and y-axes of individual Similarity Matrices). Thresholds may be set for varying degrees of linear correlation, such as a threshold for highly linear correlation of ($R>0.50$, or 0.40). Linear classifiers can be applied to the datasets. In one example, the correlation coefficient is 1.0.

In one embodiment, regulatory clusters are determined by constructing networks of correlations using statistical analyses, for example, to identify regulatory clusters composed of subsets of the panel of biomarkers. In one example, PC correlation coefficients are determined and used to construct such networks of correlations. In one example, the networks are identified by drawing edges between transcript pairs having R above the pre-defined threshold. Degree of correlation can provide information on reproducibility and robustness.

Also provided herein are objective algorithms, predictive models, and topographic analytical methods, and methods using the same, to analyze high-dimensional and multimodal biomedical data, such as the data obtained using the provided methods for detecting expression of the GEP-NEN biomarker panels. As discussed above, the objective algorithms, models, and analytical methods include mathematical analyses based on topographic, pattern-recognition based protocols e.g., support vector machines (SVM) (Noble W S. What is a support vector machine? Nat Biotechnol. 2006; 24(12): 1565-7), linear discriminant analysis (LDA), naive Bayes (NB), and K-nearest neighbor (KNN) protocols, as well as other supervised learning algorithms and models, such as Decision Tree, Perceptron, and regularized discriminant analysis (RDA), and similar models and algorithms well-known in the art (Gallant S I, "Perceptron-based learning algorithms," Perceptron-based learning algorithms 1990; 1(2): 179-91).

In some embodiments, Feature Selection (FS) is applied to remove the most redundant features from a dataset, such as a GEP-NEN biomarker expression dataset, and generate a relevant subset of GEP-NEN biomarkers. FS enhances the generalization capability, accelerates the learning process, and improves model interpretability. In one aspect, FS is employed using a "greedy forward" selection approach, selecting the most relevant subset of features for the robust learning models. (Peng H, Long F, Ding C, "Feature selection based on mutual information: criteria of max-dependency, max-relevance, and min-redundancy," IEEE Transactions on Pattern Analysis and Machine Intelligence, 2005; 27(8): 1226-38).

In some embodiments, Support Vector Machines (SVM) algorithms are used for classification of data by increasing the margin between the n data sets (Cristianini N, Shawe-Taylor J. An Introduction to Support Vector Machines and other kernel-based learning methods. Cambridge: Cambridge University Press, 2000).

In some embodiments, the predictive models include Decision Tree, which maps observations about an item to a conclusion about its target value (Zhang H, Singer B. "Recursive Partitioning in the Health Sciences," (Statistics for Biology and Health): Springer, 1999.). The leaves of the tree represent classifications and branches represent conjunctions of features that devolve into the individual classifications. It has been used effectively (70-90%) to predict prognosis of metastatic breast cancer (Yu L et al "TGF-beta receptor-activated p38 MAP kinase mediates Smad-independent TGF-beta responses," Embo J 2002; 21(14):3749-59), as well as colon cancer (Zhang H et al "Recursive partitioning for tumor classification with gene expression microarray data.," Proc Natl Acad Sci USA 2001; 98(12): 6730-5), to predict the grading of astrocytomas (Glotsos D et al "Automated diagnosis of brain tumours astrocytomas using probabilistic neural network clustering and support vector machines," Int J Neural Syst 2005; 15(1-2): 1-11) with a >90% accuracy, and prostatic carcinomas with an accuracy of 74-80% (Mattfeldt T et al. "Classification of prostatic carcinoma with artificial neural networks using comparative genomic hybridization and quantitative stereological data," Pathol Res Pract 2003; 199(12):773-84). The efficiency of this technique has been measured by 10-fold cross-validation (Pirooznia M et al "A comparative study of different machine learning methods on microarray gene expression data," BMC Genomics 2008; 9 Suppl 1:S13).

The predictive models and algorithms further include Perceptron, a linear classifier that forms a feed forward neural network and maps an input variable to a binary classifier (Gallant S I. "Perceptron-based learning algorithms," Perceptron-based learning algorithms 1990; 1(2): 179-91). It has been used to predict malignancy of breast cancer (Markey M K et al. "Perceptron error surface analysis: a case study in breast cancer diagnosis," Comput Biol Med 2002; 32(2):99-109). In this model, the learning rate is a constant that regulates the speed of learning. A lower learning rate improves the classification model, while increasing the time to process the variable (Markey M K et al. "Perceptron error surface analysis: a case study in breast cancer diagnosis," Comput Biol Med 2002; 32(2):99-109). In one example, a learning rate of 0.05 is used. In one aspect, a Perceptron algorithm is used to distinguish between localized or primary tumors and corresponding metastatic tumors. In one aspect, three data scans are used to generate decision boundaries that explicitly separate data into classes.

The predictive models and algorithms further include Regularized Discriminant Analysis (RDA), which can be used as a flexible alternative to other data mining techniques, including Linear and Quadratic Discriminant Analysis (LDA, QDA) (Lilien R H, Farid H, Donald B R. "Probabilistic disease classification of expression-dependent proteomic data from mass spectrometry of human serum.," J Comput Biol 2003; 10(6):925-46.; Cappellen D, Luong-Nguyen N H, Bongiovanni S, et al. "Transcriptional program of mouse osteoclast differentiation governed by the macrophage colony-stimulating factor and the ligand for the receptor activator of NFkappa B." J Biol Chem 2002; 277(24):21971-82.). RDA's regularization parameters, $\gamma$ and $\lambda$, are used to design an intermediate classifier between LDA and QDA. QDA is performed when $\gamma$=0 and $\lambda$^O while LDA is performed when $\gamma$=0 and $\lambda$=1 (Picon A, Gold L I, Wang J, Cohen A, Friedman E. A subset of metastatic human colon cancers expresses elevated levels of transforming growth factor beta 1. Cancer Epidemiol. Biomarkers Prev. 1998; 7(6):497-504).

To reduce over-fitting, RDA parameters are selected to minimize cross-validation error while not being equal 0.0001, thus forcing RDA to produce a classifier between LDA, QDA, and L2 (Pima I, Aladjem M., "Regularized discriminant analysis for face recognition," Pattern Recognition 2003; 37(9): 1945-48). Finally, regularization itself has been used widely to overcome over-fitting in machine learning (Evgeniou T, Pontil M, Poggio T. "Regularization Networks and Support Vector Machines.," Advances in Computational Math 2000; 13(1): 1-50.; Ji S, Ye J. Kernel "Uncorrelated and Regularized Discriminant Analysis: A Theoretical and Computational Study.," IEEE Transactions on Knowledge and Data Engineering 2000; 20(10): 1311-21.).

In one example, regularization parameters are defined as $\gamma$=0.002 and $\lambda$=0. In one example, for each class pair, S-values are assigned to all transcripts which are then arranged by a decreasing S-value. RDA is performed, e.g., 21 times, such that the $N^{th}$ iteration consists of top N scoring transcripts. Error estimation can be carried out by a 10-fold cross-validation of the RDA classifier. This can be done by partitioning the tissue data set into complementary subsets, performing the analysis on one subset (called the training set), and validating the analysis on the other subset (called the validation set or testing set).

In one example, misclassification error is averaged to reduce variability in the overall predictive assessment, which can provide a more accurate approach to error estimation compared to other approaches, including bootstrapping and leave-one-out cross-validation (Kohavi R. "A study of cross-validation and bootstrap for accuracy estimation and model selection.," Proceedings of the Fourteenth International Joint Conference on Artificial Intelligence, 1995; 2(12): 1137-43.).

In one example, selection for tissue classification is performed, for example, by computing the rank score (S) for each gene and for each class pair as:

$$S = \frac{|\mu_{c2} - \mu_{c1}|}{\sigma_{c1} + \sigma_{c2}}$$

where $\mu_{C1}$ and $\mu_{C2}$ represent means of first and second class respectively and $\alpha_{C1}$ and $\sigma_{C2}$ are inter-class standard deviations. A large S value is indicative of a substantial differential expression ("Fold Change") and a low standard deviation ("transcript stability") within each class. Genes may be sorted by a decreasing S-value and used as inputs for the regularized discriminant analysis algorithm (RDA).

The algorithms and models may be evaluated, validated and cross-validated, for example, to validate the predictive and classification abilities of the models, and to evaluate specificity and sensitivity. In one example, radial basis function is used as a kernel, and a 10-fold cross-validation used to measure the sensitivity of classification (Cristianini N, Shawe-Taylor J. "An Introduction to Support Vector Machines and other kernel-based learning methods.," Cambridge: Cambridge University Press, 2000.). Various classification models and algorithms may be compared by the provided methods, for example, using training and cross-validation, as provided herein, to compare performance of the predictive models for predicting particular outcomes.

Embodiments of the provided methods, systems, and predictive models are reproducible, with high dynamic range, can detect small changes in data, and are performed using simple methods, at low cost, e.g., for implementation in a clinical laboratory.

Kits and other articles of manufacture are provided for use in the diagnostic, prognostic, predictive, and therapeutic applications described herein. In some embodiments, the kits include a carrier, package, or packaging, compartmentalized to receive one or more containers such as vials, tubes, plates, and wells, in which each of the containers includes one of the separate elements for use in the methods provided herein, and in some aspects further include a label or insert with instructions for use, such as the uses described herein. In one example, the individual containers include individual agents for detection of the GEP-NEN biomarkers as provided herein; in some examples, individual containers include agents for detection of housekeeping genes and/or normalization.

For example, the container(s) can comprise an agent, such as a probe or primer, which is or can be detectably labeled. Where the method utilizes nucleic acid hybridization for detection, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody.

The kits will typically comprise the container(s) described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapeutic or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as GEP-NEN.

In another embodiment, an article(s) of manufacture containing compositions, such as amino acid sequence(s), small molecule(s), nucleic acid sequence(s), and/or antibody(s), e.g., materials useful for the diagnosis, prognosis, or therapy of GEP-NEN is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of GEP-NEN biomarkers in biological samples, e.g., blood or cells and tissues, or for relevant laboratory, prognostic, diagnostic, prophylactic and therapeutic purposes; indications and/or directions for such uses can be included on or with such container, as can reagents and other compositions or tools used for these purposes.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Differential Expression of NET Marker GENESIN Primary NETs—An exon-level screen of localized small intestinal NETs using Affymetrix Human Exon 1.0 ST arrays was performed to define alternative splicing events in neuroendocrine tumor tissue in comparison to a control (normal intestinal mucosa). Exon expression analysis identified 1287 differentially expressed genes between normal intestinal mucosa and NET tumor tissues. Five hundred and twenty nine genes were upregulated and 758 were downregulated. As an example, a subset of NET marker genes was focused on, in particular CgA, Tph1, VMAT2, SCG5, and PTPRN2. The RMA-normalized exon expression of the NET marker genes in this subset is shown in FIGS. 1A-1E in normal (green) and tumor (red) samples. Of these genes, Tph1 was the only gene where all exons were differentially expressed in tumor (FC>1.5, p<0.05), while CgA was the only gene where all exon expressions remained constant between tumor and normal samples.

Two of 17 differentially expressed exons were identified in VMAT2 and eight of 9 in SCG5. In PTPRN2 six of 30 exons were differentially expressed. These results demonstrate that specific primer/probe sets are required to maximize differences between neoplasia and normal gene expression.

Validating Alternative Splicing in NET Marker Genes by RT-PCR—With reference to FIGS. 2A-2E, the findings of differential exon transcript levels was validated using reverse transcriptase polymerase chain reaction (RT-PCR). All marker gene exons, including $Tph1_{1-2}$, $VMAT2_{9-10}$, $SCG5_{2-3}$, and $PTPRN2_{12-13}$, were confirmed to be differentially expressed in tumor samples versus normal mucosa, with the exception of $CgA_{4-5}$.

Genomic and RT-PCR data from FIGS. 1A-1E and 2A-2E, respectively, identify that differential splicing occurs in NETs and that candidate biomarkers, e.g., VMAT2, require the use of specific primer/probe sets to effectively capture differences in expression of target transcripts.

To evaluate the relevance in blood, a microarray analysis of peripheral NET blood samples was performed. Up-regulated genes (n=1,397) included GO-Fat terms such as "RNA splicing", "Vesicle-mediated transport", and "Chromatin modification" which is consistent with known roles for these processes in NET pathobiology. Comparisons of the blood transcriptome with GEP-NET transcriptomes identified 236 up-regulated genes, 72 of which were examined for utility as biomarkers. A preliminary screen identified 51 genes as upregulated in tumor blood samples compared to controls. Forty-two genes (83%) were transcribed from multiple exons. A minimum of two primer/probe sets were tested for these genes in blood to define the most relevant combinations for target amplification. The housekeeping gene and 51 validated targets and exons of interest for primer/probe sets are described in TABLE 2. The amplicon positions identified for each GEN-NEN biomarker in Table 2 are the identified as underlined sequences in Table 1.

TABLE 2

| Primer Details | | | | | | | |
|---|---|---|---|---|---|---|---|
| GEP-NEN Biomarker | | NCBI Chromosome | UniGene | | Amplicon Size | Exon | |
| Symbol | Name | location | ID | RefSeq | Length | Boundary | Position |
| ALG9 | asparagine-linked glycosylation 9, alpha-1,2-mannosyl transferase homolog | Chr. 11 - 111652919-111742305 | Hs.503850 | NM_024740.2 | 68 | 4-5 | 541-600 |
| AKAP8L | A kinase (PRKA) anchor protein 8-like | Chr. 19: 15490859-15529833 | Hs.399800 | NM_014371.3 | 75 | 12-13 | 1596-1670 |
| APLP2 | amyloid beta (A4) precursor-like protein 2 | Chr. 11 - 129939716-130014706 | Hs.370247 | NM_001142276.1 | 102 | 14-15 | 2029-2132 |
| ARAF1 | v-raf murine sarcoma 3611 viral oncogene homolog | Chr. X - 47420578-47431320 | Hs.446641 | NM_001654.4 | 74 | 10-11 | 1410-1475 |
| ATP6V1H | ATPase, H+ transporting, lysosomal 50/57 kDa, V1, Subunit H | Chr. 8: 54628115-54755850 | Hs.491737 | NM_015941.3 | 102 | 13-14 | 1631-1732 |

TABLE 2-continued

| Primer Details | | | | | | | |
|---|---|---|---|---|---|---|---|
| GEP-NEN Biomarker | | NCBI Chromosome | UniGene | | Amplicon Size | Exon | |
| Symbol | Name | location | ID | RefSeq | Length | Boundary | Position |
| BNIP3L | BCL2/adenovirus E1B 19 kDa interacting protein 3-like | Chr. 8: 26240523-26270644 | Hs.131226 | NM_004331.2 | 69 | 2-3 | 374-342 |
| BRAF | v-raf murine sarcoma viral oncogene homolog B1 | Chr. 7 - 140433812-140624564 | Hs.550061 | NM_004333.4 | 77 | 1-2 | 165-233 |
| C21ORF7 | chromosome 21 open reading frame 7 | Chr. 21: 30452873-30548204 | Hs.222802 | NM_020152.3 | 76 | — | 611-686 |
| CD59 | CD59 molecule, complement regulatory protein | Chr. 11 - 33724556-33758025 | Hs.278573 | NM_203331.2 | 70 | 3-4 | 193-264 |
| COMMD9 | COMM domain containing 9 | Chr. 11: 36293842-36310999 | Hs.279836 | NM_001101653.1 | 85 | 2-3 | 191-275 |
| CTGF | connective tissue growth factor | Chr. 6 - 132269316-132272518 | Hs.410037 | NM_001901.2 | 60 | 4-5 | 929-990 |
| ENPP4 | ectonucleotide pyrophosphatase/ phosphodiesterase 4 | Chr. 6: 46097701-46114436 | Hs.643497 | NM_014936.4 | 82 | 3-4 | 1221-1303 |
| FAM131A | family with sequence similarity 131, member A, transcript variant 2 | Chr. 3: 184053717-184064063 | Hs.591307 | NM_001171093.1 | 64 | 4-5 | 498-561 |
| FLJ10357 | Rho guanine nucleotide exchange factor (GEF) 40 (ARHGEF40) | Chr. 14: 21538527-21558036 | Hs.35125 | NM_018071.4 | 102 | 16-17 | 3557-3658 |
| FZD7 | frizzled homolog 7 (*Drosophila*) | Chr. 2 - 202899310-202903160 | Hs.173859 | NM_003507.1 | 70 | 1-1 | 1-70 |
| GLT8D1 | glycosyltransferase 8 domain containing 1, transcript variant 3 | Chr. 3: 52728504-52740048 | Hs.297304 | NM_001010983.2 | 87 | 4-5 | 924-1010 |
| HDAC9 | histone deacetylase 9, transcript variant 6 | Chr. 7: 18535369-19036993 | Hs.196054 | NM_001204144.1 | 69 | 11-12 | 1777-1845 |
| HSF2 | heat shock transcription factor 2, transcript variant 1 | Chr. 6: 122720696-122754264 | Hs.158195 | NM_004506.3 | 82 | 10-11 | 1324-1405 |
| Ki-67 | antigen identified by monoclonal antibody Ki-67 | Chr. 10 - 129894923-129924655 | Hs.689823 | NM_001145966.1 | 78 | 6-7 | 556-635 |
| KRAS | v-Ki-ras2 Kirsten rat sarcoma viral oncogene homolog | Chr. 12 - 25358180-25403854 | Hs.505033 | NM_004985.4 | 130 | 4-5 | 571-692 |
| LEO1 | Leo1, Paf1/RNA polymerase II complex component homolog (*S. cerevisiae*) | Chr. 15: 52230222-52263958 | Hs.567662 | NM_138792.3 | 122 | 10-11 | 1753-1874 |
| MORF4L2 | mortality factor 4 like 2, transcript variant 1 | Chr. X: 102930426-102943086 | Hs.326387 | NM_001142418.1 | 153 | 5-5 | 1294-1447 |
| NAP1L1 | nucleosome assembly protein 1-like 1 | Chr. 12 - 76438672-76478738 | Hs.524599 | NM_139207.2 | 139 | 16-16 | 1625-1764 |
| NOL3 | nucleolar protein 3 (apoptosis repressor with CARD domain), transcript variant 3 | Chr. 16: 67204405-67209643 | Hs.513667 | NM_001185057.2 | 118 | 1-2 | 131-248 |
| NUDT3 | nudix (nucleoside diphosphate linked moiety X)-type motif 3 | Chr. 6: 34255997-34360441 | Hs.188882 | NM_006703.3 | 62 | 2-3 | 500-561 |
| OAZ2 | ornithine decarboxylase antizyme 2 | Chr. 15: 64979773-64995462 | Hs.713816 | NM_002537.3 | 96 | 1-2 | 189-284 |
| PANK2 | pantothenate kinase 2 | Chr. 20: 3869486-3904502 | Hs.516859 | NM_024960.4 | 126 | 4-5 | 785-910 |
| PHF21A | PHD finger protein 21A, transcript variant 1 | Chr. 11: 45950870-46142985 | Hs.502458 | NM_001101802.1 | 127 | 16-17 | 2241-2367 |
| PKD1 | polycystic kidney disease 1 (autosomal dominant), transcript variant 2 | Chr. 16: 2138711-2185899 | Hs.75813 | NM_000296.3 | 110 | 16-17 | 7224-7333 |
| PLD3 | phospholipase D family, member 3, transcript variant 1 | Chr. 19: 40854332-40884390 | Hs.257008 | NM_001031696.3 | 104 | 6-7 | 780-883 |
| PNMA2 | paraneoplastic antigen MA2 | Chr. 8 - 26362196-26371483 | Hs.591838 | NM_007257.5 | 60 | 3-3 | 283-343 |
| PQBP1 | polyglutamine binding protein 1, transcript variant 2 | Chr. X: 48755195-48760422 | Hs.534384 | NM_001032381.1 | 68 | 2-3 | 157-224 |
| RAF1 | v-raf-1 murine leukemia viral oncogene homolog 1 | Chr. 3 - 12625100-12705700 | Hs.159130 | NM_002880.3 | 90 | 7-8 | 1186-1277 |
| RNF41 | ring finger protein 41, transcript variant 4 | Chr. 12: 56598285-56615735 | Hs.524502 | NM_001242826 | 72 | 2-3 | 265-336 |
| RSF1 | remodeling and spacing factor 1 | Chr. 11: 77377274-77531880 | Hs.420229 | NM_016578.3 | 60 | 7-8 | 2804-2863 |
| RTN2 | reticulon 2, transcript variant 1 | Chr. 19: 45988550-46000313 | Hs.47517 | NM_005619.4 | 87 | 9-10 | 1681-1766 |

TABLE 2-continued

| Primer Details | | | | | | | |
|---|---|---|---|---|---|---|---|
| GEP-NEN Biomarker | | NCBI Chromosome | UniGene | | Amplicon Size | Exon | |
| Symbol | Name | location | ID | RefSeq | Length | Boundary | Position |
| SMARCD3 | SWI/SNF related, matrix associated, actin dependent regulator of chromatin, subfamily d, member 3, transcript variant 3 | Chr. 7: 150936059-150974231 | Hs.647067 | NM_001003801.1 | 109 | 8-9 | 986-1094 |
| SPATA7 | spermatogenesis associated 7, transcript variant 2 | Chr. 14: 88851988-88904804 | Hs.525518 | NM_001040428.3 | 81 | 1-2 | 160-241 |
| SST1 | somatostatin receptor 1 | Chr. 14: 38677204-38682268 | Hs.248160 | NM_001049.2 | 85 | 3-3 | 724-808 |
| SST3 | somatostatin receptor 3 | Chr. 22: 37602245-37608353 | Hs.225995 | NM_001051.4 | 84 | 2-2 | 637-720 |
| SST4 | somatostatin receptor 4 | Chr. 20: 23016057-23017314 | Hs.673846 | NM_001052.2 | 104 | 1-1 | 91-194 |
| SST5 | somatostatin receptor 5, transcript variant 1 | Chr. 16: 1122756-1131454 | Hs.449840 | NM_001053.3 | 157 | 1-1 | 1501-1657 |
| TECPR2 | tectonin beta-propeller repeat containing 2, transcript variant 2 | Chr. 14: 102829300-102968818 | Hs.195667 | NM_001172631.1 | 61 | 12-13 | 3130-3191 |
| TPH1 | tryptophan hydroxylase 1 | Chr. 11 - 18042538-18062309 | Hs.591999 | NM_004179.2 | 145 | 1-2 | 73-219 |
| TRMT112 | tRNA methyltransferase 11-2 homolog (*S. cerevisiae*) | Chr. 11: 64084163-64085033 | Hs.333579 | NM_016404.2 | 91 | 1-2 | 45-135 |
| VMAT1 | solute carrier family 18 (vesicular monoamine), member 1 | Chr. 8 - 20002366-20040717 | Hs.158322 | NM_003053.3 | 102 | 1-2 | 93-196 |
| VMAT2 | solute carrier family 18 (vesicular monoamine), member 2 | Chr. 10 - 119000716-119037095 | Hs.596992 | NM_003054.4 | 60 | 9-10 | 896-957 |
| VPS13C | vacuolar protein sorting 13 homolog C (*S. cerevisiae*), transcript variant 2B | Chr. 15: 62144588-62352647 | Hs.511668 | NM_001018088.2 | 65 | 69-70 | 9685-9749 |
| WDFY3 | WD repeat and FYVE domain containing 3 | Chr. 4: 85590690-85887544 | Hs.480116 | NM_014991.4 | 81 | 64-65 | 10190-10270 |
| ZFHX3 | zinc finger homeobox 3, transcript variant B | Chr. 16: 72816784-73092534 | Hs.598297 | NM_001164766.1 | 68 | 5-6 | 886-953 |
| ZXDC | zinc finger C, transcript variant 2 | Chr. 3: 126156444-126194762 | Hs.440049 | NM_001040653.3 | 61 | 1-2 | 936-1001 |
| ZZZ3 | zinc finger, ZZ-type containing 3 | Chr. 1: 78030190-78148343 | Hs.480506 | NM_015534.4 | 62 | 13-14 | 2909-2971 |

Figure 3:
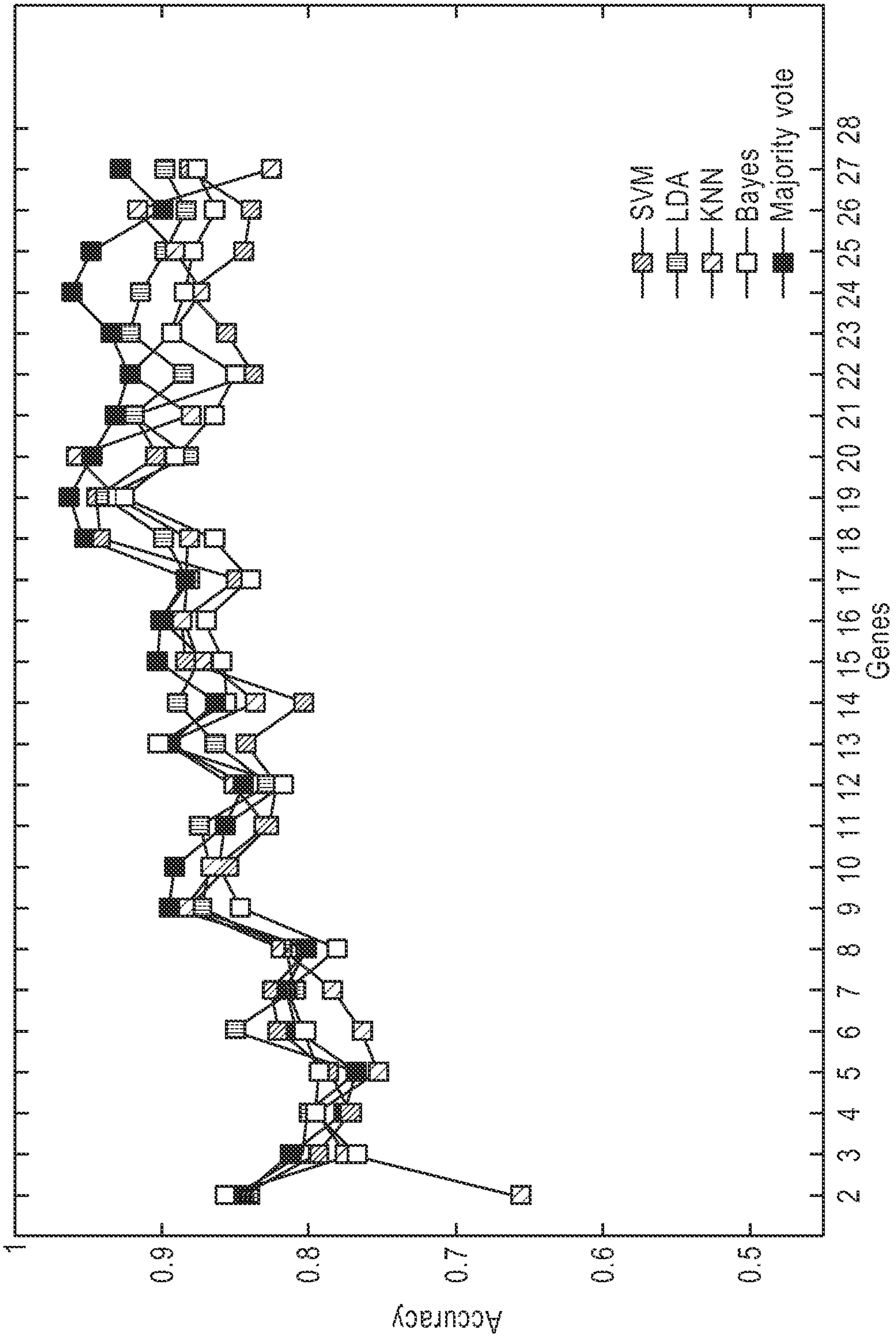
FIG. 3 is a line graph showing the prediction accuracy of four classification algorithms (SVM, LDA, KNN, and Bayes) using sequential addition of up to 22 significantly up-regulated genes ($p<0.05$) in GEP-NET samples obtained using the results of 10-fold cross validation.

Delineation of Minimum Gene Set for Mathematically-Derived (MAARC-NET) Scoring System-Four classification algorithms (SVM, LDA, KNN, and Bayes) and a 10-fold cross-validation design were used to build a classifier for the identification of GEP-NETs in blood. See Modlin I, Drozdov I, Kidd M: The Identification of gut neuroendocrine tumor disease by multiple synchronous transcript analysis in blood. *Plos One* 2013, e63364. These classifiers were built on a training set and significantly up-regulated features between control and tumor cases were calculated by t-test. With reference to FIG. 3, an examination of the 51 genes featured in TABLE 2 identified that inclusion of at least 22 genes was sufficient to build an accurate (>0.85) classifier. FIG. 3 shows the prediction accuracy of each classifier algorithm using sequential addition of up to 27 significantly up-regulated genes ($p<0.05$) in the GEP-NET samples obtained using results of the 10-fold cross validation. The average accuracy of the SVM, LDA, KNN, and Bayes algorithms to distinguish GEP-NET from control blood samples using the sequentially added 27 genes was comparable—0.89 (0.85-1.0), 0.89 (0.86-0.93), 0.88 (0.85-0.93), and 0.86 (0.85-0.93) respectively. The “majority voting” combination of the four classifiers achieved an accuracy of 0.88. The at least 22 genes sufficient to build an accurate classifier were used to develop the MAARC-NET scoring system, and are featured in TABLE 3.

TABLE 3

| Twenty Two Genes Included in the Mathematically-Derived MAARC-NET Scoring System | | | |
|---|---|---|---|
| | Fold Change | p-value | Adjusted p-value |
| PNMA2 | 0.819515 | 6.74E−21 | 3.43E−19 |
| NAP1L1 | 0.662434 | 4.9E−18 | 1.25E−16 |
| FZD7 | 0.799858 | 3.82E−15 | 6.5E−14 |
| SLC18A2 | 0.524046 | 1.08E−12 | 1.37E−11 |
| NOL3 | 0.809571 | 7.22E−10 | 7.36E−09 |
| SSTR5 | 0.877322 | 1.64E−09 | 1.4E−08 |
| TPH1 | 0.459185 | 1.75E−07 | 1.27E−06 |
| RAFT | 0.316509 | 1.54E−06 | 7.86E−06 |
| RSF1 | 0.530054 | 1.74E−06 | 8.07E−06 |
| SSTR3 | 0.555269 | 3.82E−06 | 1.62E−05 |
| SSTR1 | 0.493052 | 1.73E−05 | 6.81E−05 |
| CD59 | 0.26257 | 2.7E−05 | 9.82E−05 |
| ARAF | 0.228332 | 4.07E−05 | 0.000138 |
| APLP2 | 0.228153 | 4.42E−05 | 0.000141 |
| KRAS | 0.205822 | 9.92E−05 | 0.000298 |
| MORF4L2 | 0.319826 | 0.000169 | 0.000453 |
| TRMT112 | 0.269618 | 0.001125 | 0.002524 |
| MKI67 | 0.191245 | 0.003468 | 0.007074 |
| SSTR4 | 0.313807 | 0.003734 | 0.007324 |
| CTGF | 0.196845 | 0.007665 | 0.01303 |
| SPATA7 | 0.288625 | 0.01467 | 0.02338 |
| ZFHX3 | 0.13248 | 0.031354 | 0.045687 |

Figure 4C:
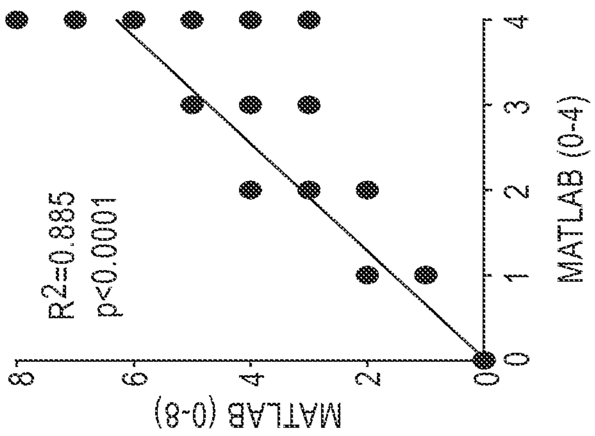
FIGS. 4A-4C are graphs showing mathematically-derived MAARC-NET scores in the test set.
Figure 4B:
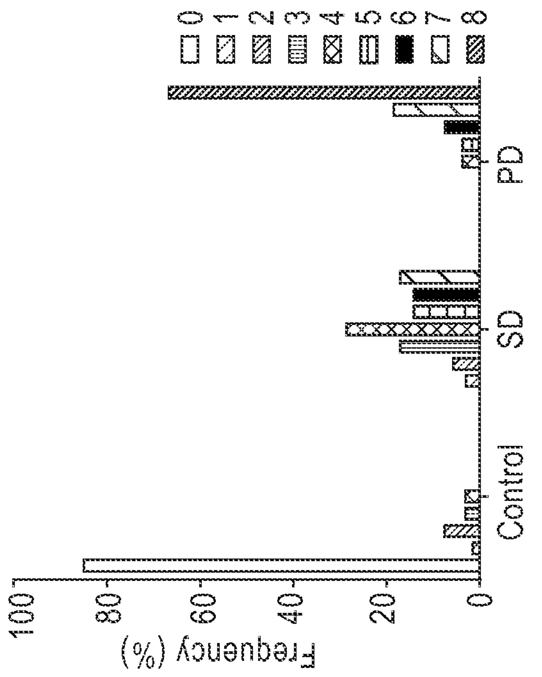
Figure 4A:
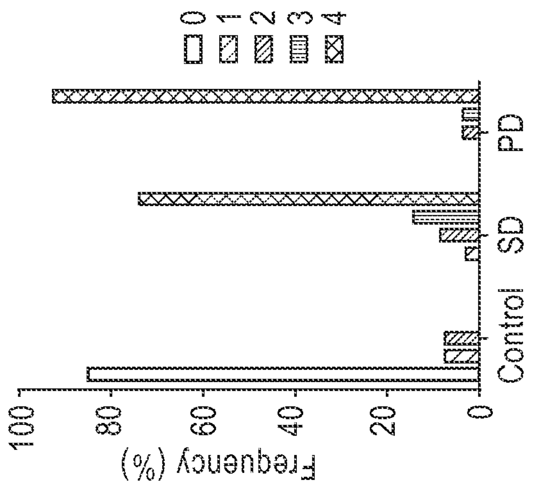

Refinement of Mathematically-Derived MAARC-NET Scoring System—Individual PCR-based gene expressions are included in a score. See Modlin I, Drozdov I, Kidd M, *Plos One* 2013. The score is based on a “majority vote”

strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naive Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN. With reference to FIG. 4A, an audit of samples identified that 85% of controls exhibited a score of "0." No tumors scored "0." ROC analyses identified that a score of 2 was the cut-off for normal samples (controls) versus tumors (score ≥2). This approach exhibited correct call rates of 91-97% with sensitivities and specificities of 85-98% and 93-97% for the identification of GEP-NETs in two independent sets. See Modlin I, Drozdov I, Kidd M, *Plos One* 2013.

These data were initially derived from a test data set of 130 samples (n=67 controls, n=63 NETs). Inherent in the test set are two classes of NETs—clinically defined as treated, stable disease (SD: n=35) and untreated, progressive disease (PD: n=28). The classification algorithm also segregated the tumor call into two units "treated" and "untreated." The 0-4 binary classification was therefore amended to represent 3 possible calls for each particular sample: "normal", "tumor (treated)" and "tumor (untreated)".

A number of rules were implemented to generate an amended majority vote strategy. A call of "normal" was assigned a value of 0; a call of tumor "treated" was assigned a value of 1; a call of tumor "untreated" was assigned a value of 2. By way of example, if a sample results in four calls of "normal," a value of 0 was assigned for each call, thereby totaling a score of 0. If a sample results in four calls of tumor "treated," a value of 1 was assigned for call, thereby totaling a score of 4. If a sample results in four calls of tumor "untreated," a "2" is assigned for each, thereby totaling a score of 8. Scores in the amended majority vote strategy can therefore range between 0 and 8.

Examination of the test dataset (n=130) was used to establish whether the amended majority vote-derived score could serve as a measure of "treatment" responses. Similarly to the published 0-4 score shown in FIG. 4A, the majority of NET patients exhibited an amended majority vote score ≥2 as shown in FIG. 4B. With reference to FIG. 4C, majority vote and amended majority vote scores were significantly related ($R^2=0.89$, $p<0.0001$).

Figure 5A:
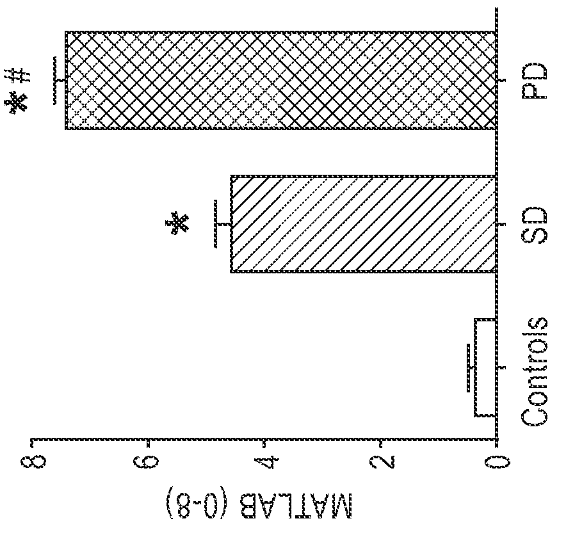
FIGS. 5A-5B are graphs showing MAARC-NET scores in the test set and a Receiver Operating Characteristics (ROC) analysis. In FIGURE SA, NETs had a significantly elevated score compared to controls, where values for PD were higher than SD. In FIGURE SB, a ROC curve of controls versus GEP-NETS is shown, wherein the AUC was >0.98, p<0.0001. *p<0.05 vs. controls, #p<0.05 vs. SD (2-tailed Mann-Whitney U-test).

With reference to FIG. 5A, analysis of the data in the test set identified that an amended mathematically-derived score (0-8) was significantly elevated in tumors compared to controls and was highest in PD relative to SD.

Figure 5B:
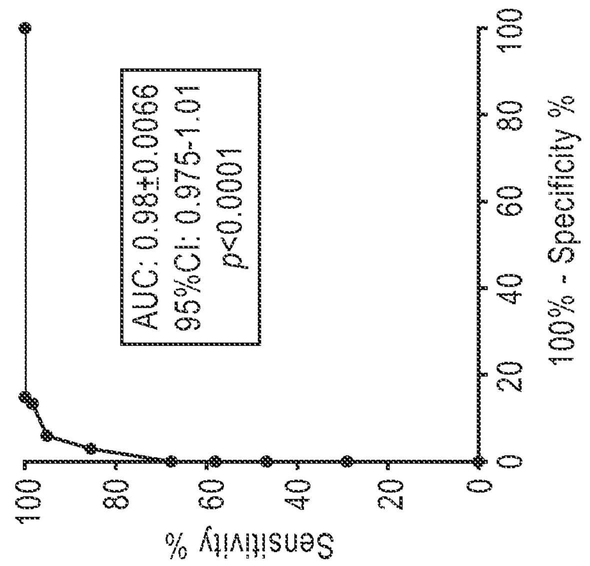

With reference to FIG. 5B, a receiver operating characteristic (ROC) curve was generated of controls versus GEP-NETs (SD and PD combined). A ROC curve is a generalization of the set of potential combinations of sensitivity and specificity possible for predictors. A ROC curve is a plot of the true positive rate (sensitivity) against the false positive rate (1-specificity) for the different possible cut-points of a diagnostic test. FIG. 5B is a graphical representation of the functional relationship between the distribution of the sensitivity and specificity values in the test set and in a cohort of control samples. The area under the curve (AUC) is an overall indication of the diagnostic accuracy of (1) the amended mathematically-derived scores and (2) a receiver operating characteristic (ROC) curve. AUC may be determined by the "trapezoidal rule." For a given ROC curve, the data points are connected by straight line segments, perpendiculars are erected from the abscissa to each data point, and the sum of the areas of the triangles and trapezoids so constructed is computed.

The ROC curve in FIG. 5B identifies that the amended mathematically-derived score may be utilized to differentiate between controls and GEP-NETs—exhibiting an AUC of >0.98, and a $p<0.0001$; *$p<0.05$ vs. controls; #$p<0.05$ vs. SD (2-tailed Mann-Whitney U-test).

Figure 6A:
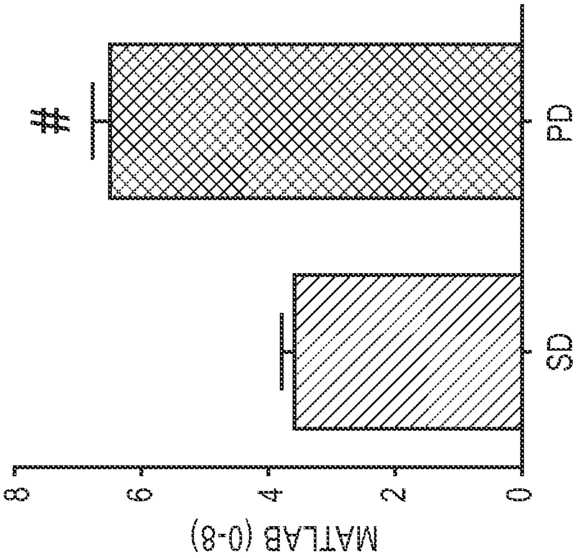
FIG. 6A-6B are (FIG. 6A) a graph of MAARC-NET scores in the independent set, wherein Progressive Disease (PD) NETs had a significantly higher elevated score compared to Stable Disease (SD)
Figure 6B:
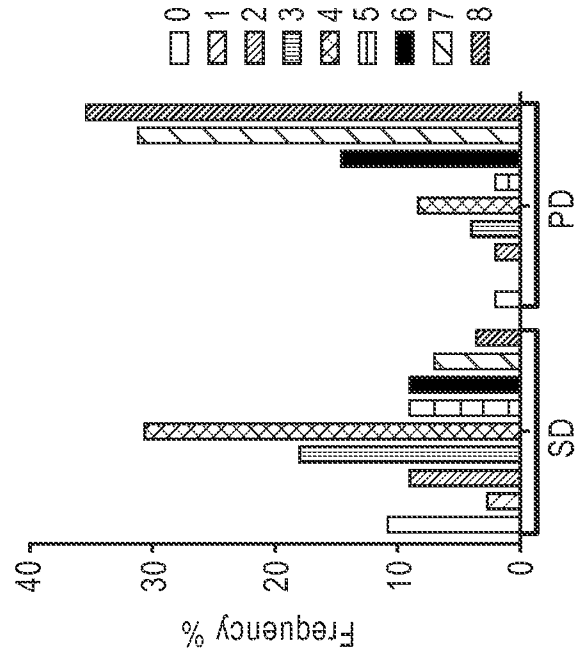

Amended mathematically-derived scores were subsequently examined in an independent set (SD: n=111, PD: n=48). With reference to FIG. 6A, the scores were significantly elevated in the independent set, exhibiting a $p<0.0001$. With reference to FIG. 6B, a frequency distribution plot of amended mathematically-derived scores in SD and PD patients confirmed that PD samples exhibited higher scores, with #$p<0.0001$ vs. SD (2-tailed Mann-Whitney U-test).

Figure 7B:
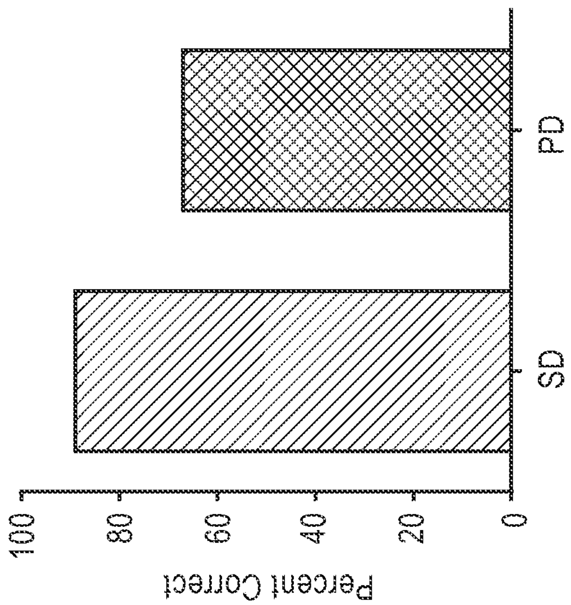
FIGS. 7A-7B are (FIG. 7A) a graph of ROC of SD versus PD NETs with an AUC of >0.93, p<0.0001 and (FIG. 7B) a graph of the percentage of SD and PD NETs correctly called using a cut-off score of ≥7.
Figure 7A:
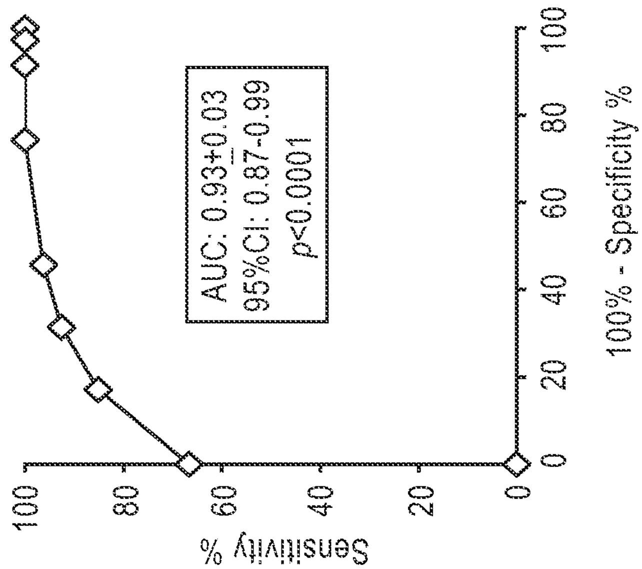

With reference to FIG. 7A, a second ROC curve was generated to determine whether the amended mathematically-derived score could be utilized to differentiate SD from PD.

In the test set (SD: n=35, PD: n=28), the ROC analysis identified that the score could be used to differentiate PD from SD tumors with an AUC of 0.93. A score cutoff of >6.5 (i.e. a score of ≥7) had a sensitivity of 85% and 83% specificity for detecting PDs (Likelihood ratio: 4.97).

With reference to FIG. 7B, the utility of the amended mathematically-derived scoring system to differentiate between SD and PD in the independent set (n=111 SD, n=48 PD) was assessed. The percentage correctly called ranged between 70-90% using a cut-off of ≥7. For SD, 89% of NETs were correctly predicted using the cut-off of ≥7 while 67% of PD were correctly predicted. The performance metrics were: sensitivity=67%, specificity=89%, PPV=73% and NPV=86%. Accordingly, the data indicate that a mathematically-derived MAARC-NET score ranging from 0-8 has utility for discriminating between controls and GEP-NETs.

Application of Scoring System and Developing a Nomogram for "NETEST 1"—To differentiate between controls and NETs, a cut-off of ≥3 has a sensitivity of 95% and 94% specificity. The sensitivity can be improved to 98% using a cut-off of ≥2. To differentiate between SD and PD, a cut-off of ≥7 can be used (sensitivity of 85% and 83% specificity). The sensitivity can be improved to 96% using a cut-off of ≥5.

The mathematically-derived MAARC-NET scores therefore range from 0-2 (control); 2-5 (SD); and 5-8 (PD). These scores can be converted to a percentage as displayed in TABLE 4.

TABLE 4

| Mathematically-Derived Scores Percentage | | | | |
|---|---|---|---|---|
| Mathematically-derived Score | 0-2 | 2-5 | 5-7 | 7-8 |
| Disease Nomogram Score | 0 | 0-55% | 55-75% | 75-100% |
| | | Low | Moderate | High |

Figure 8:
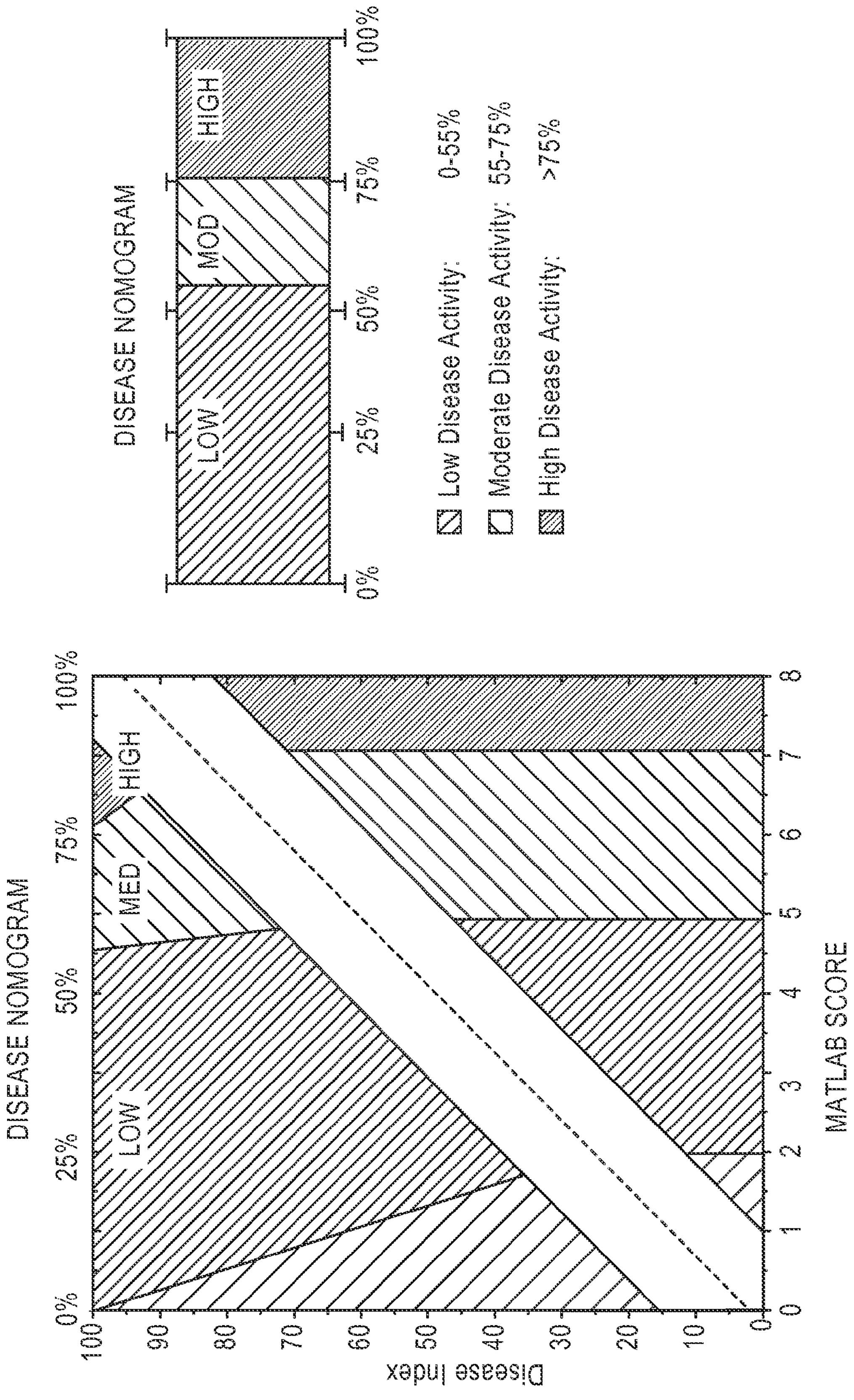
FIG. 8 is a nomogram for NETest 1 demonstrating how the score is achieved and categorizing patients into different disease classes.

With reference to FIG. 8, the score percentages from TABLE 4 can be displayed within a nomogram representing "NETest 1." The NETest 1 nomogram demonstrates how the amended mathematically-derived score is achieved and how it categorizes patients into different classes of GEP-NEN (no disease, stable disease, or progressive disease).

Figure 9:
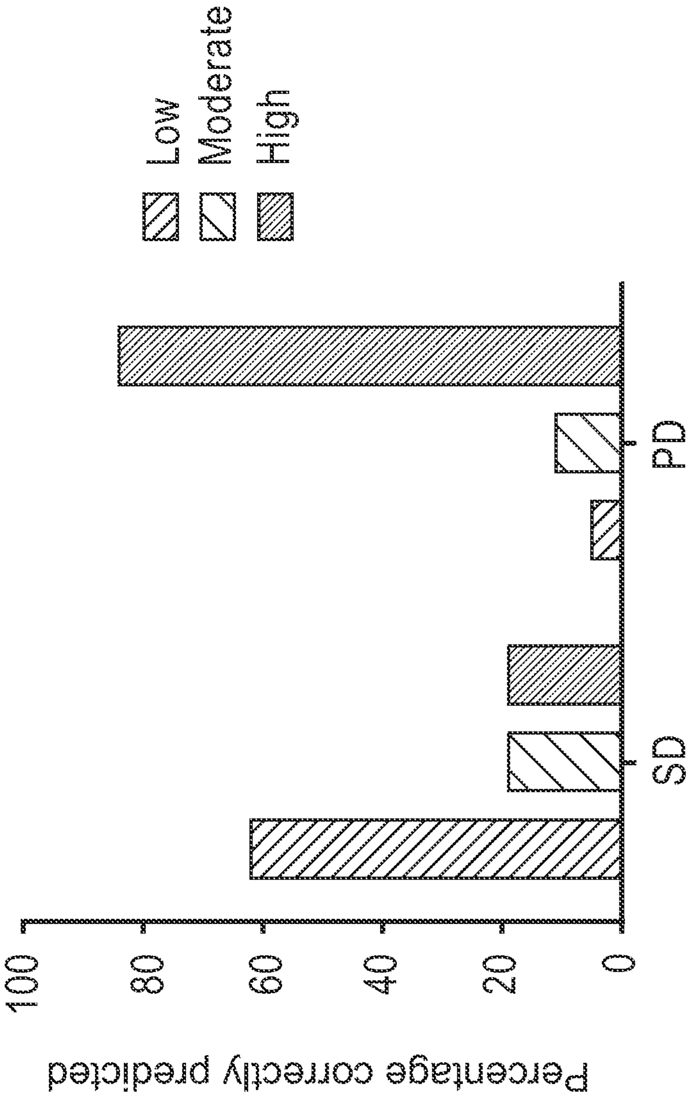
FIG. 9 is a graph of the utility of the nomogram of FIG. 8. The percentages of correctly predicted SD and PD NETs, including the level of disease activity, using the nomogram of FIG. 8 are shown.

With reference to FIG. 9, the utility of the NETest 1 nomogram was assessed. Values for the correct predictions of SD and PD using the NETest 1 nomogram of FIG. 8 are shown. Overall, the NETest 1 nomogram identified 80% of SD patients as exhibiting low or moderate disease activity and 84% of PD patients as exhibiting high disease activity.

Figure 10A:
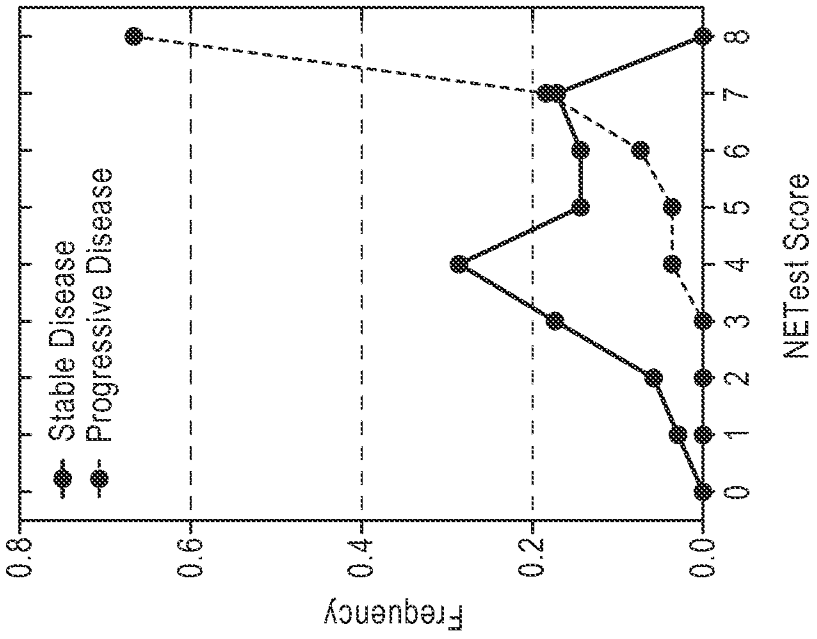
FIGS. 10A-10B are graphs each showing the frequency distribution for the 0-8 score in SD and PD NET tumors in (FIG. 10A) the test set and (FIG. 10B) the independent set.
Figure 10B:
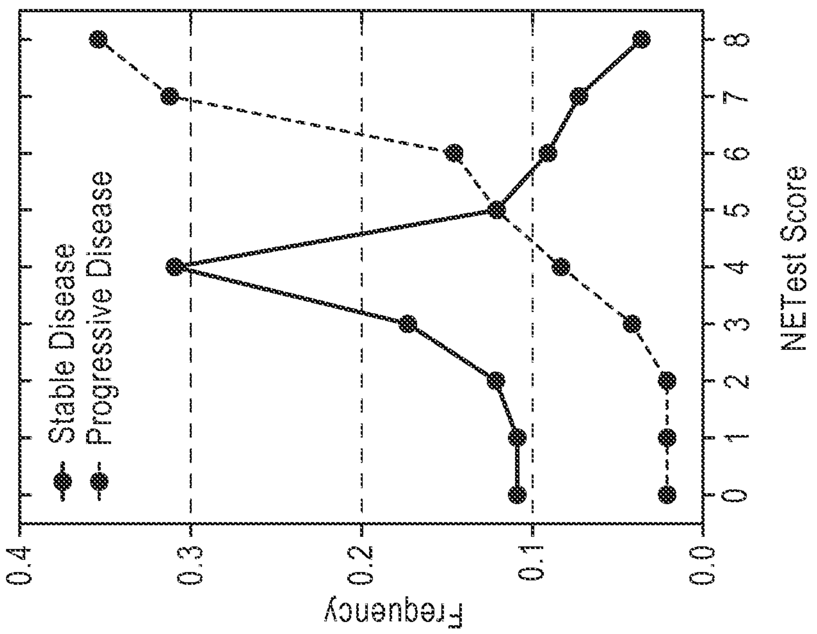

Application of Scoring System and Developing a Nomogram for "NETEST 2"-MAARC-NET-derived NETest Scores (0-8) in patients clinically defined as either stable or progressive disease (best clinical judgment and/or imaging data) were examined. The frequency distribution of scores for each subtype in both the test set (FIG. 10A) or the independent set (FIG. 10B) demonstrate that SD patients have a median NETest value of 4 and PD patients range from 7-8. However, SD patients can exhibit MAARC-NET-derived scores >4 while PD can exhibit scores <7.

Figure 11B:
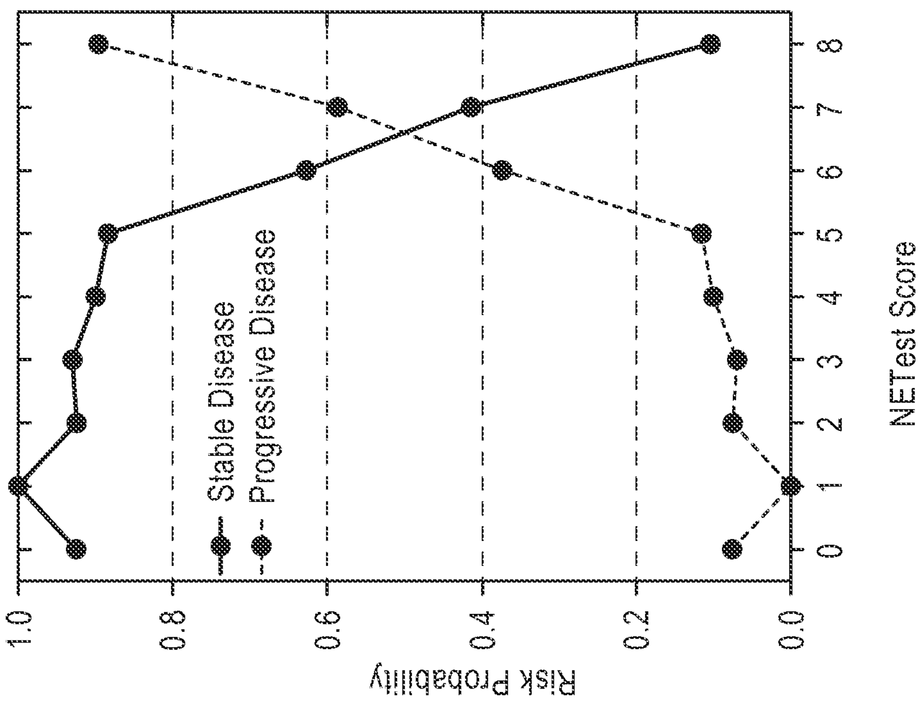
FIGS. 11A-11B are graphs of (FIG. 11A) the frequency distribution for the 0-8 score in SD and PD in the combined sets and (FIG. 11B) the risk probability for a score being either SD or PD vs. NETest Score.
Figure 11A:
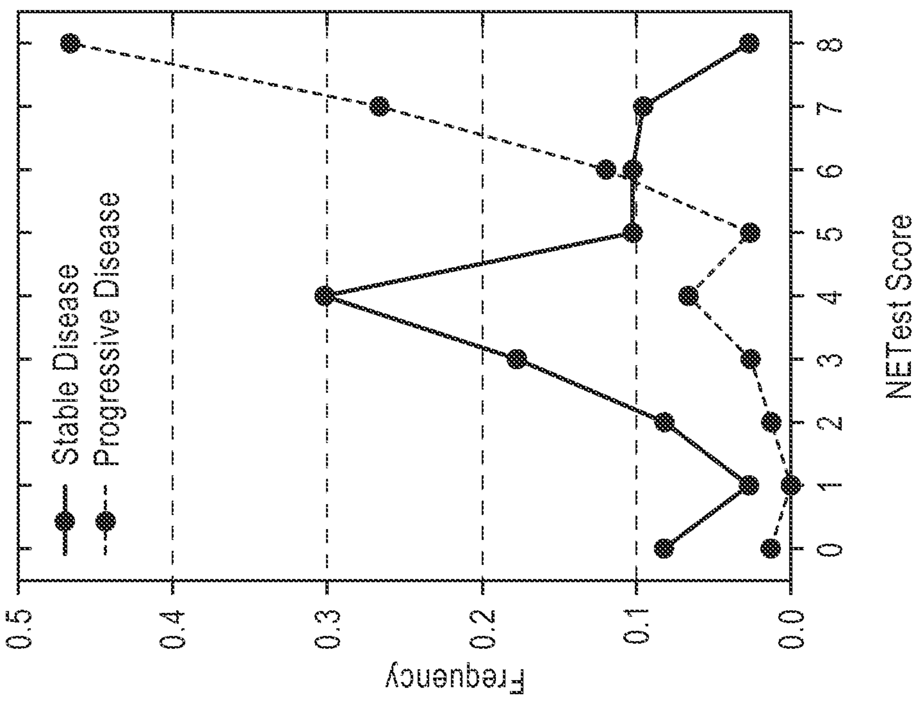

An assessment of the complete patient group (test set+independent set) demonstrated that the highest frequency SD score was 4 (30%—FIG. 11A), while 46% of PD had a score of 8 (FIG. 11A). A risk probability assessment identified that NETest scores ranging between 0-5 were associated with SD with a ≥90% certainty (FIG. 11B). A score of 8 was most likely PD (>90%). However, scores of 6 and 7 could not accurately differentiate SD versus PD.

Based on these results from FIGS. 11A and 11B, the NETest 1 nomogram from FIG. 8 can be updated to include risk values. The NETest 2a nomogram of FIG. 12 includes the NETest with the inclusion of score and risk categorizations.

To upgrade the risk assessment NETest 2a nomogram, individual gene expression in SD and PD samples may be evaluated. The genes that were most differentially expressed in SD and PD samples were identified and used in decision trees to generate the rules for defining whether a NETest score was SD or PD. This approach provides the basis for NETest 2.

Figure 12:
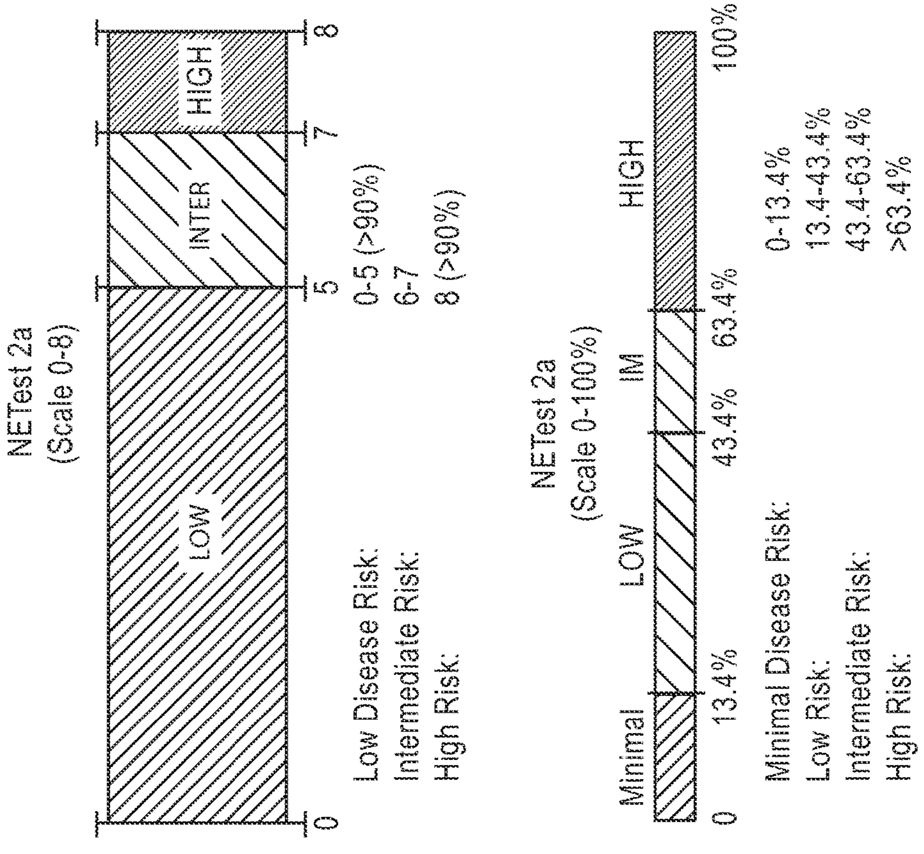
FIG. 12 is a nomogram of NETest 2a with the inclusion of score and risk categorizations. Top figure includes MAARC-NET as 0-8 scores; bottom figure is the 0-100% scaled version.

A NETest score of 5 has a >90% chance of identifying an SD sample (as shown in FIGS. 11A-11B and 12). Comparisons of the individual 51 gene expression profiles between patients scored as 5 (SD versus PD) identified expression of SMARCD3 and TPH1 as candidate differentiation markers. Using the rule:

If SMARCD3≤0.13 and TPH1<4 then call PD.

This allowed for 100% accuracy in defining progressive disease.

A NETest score of 6 has a ~50% chance of differentiating SD from PD samples. Gene expression profile analysis identified VMAT1 and PHF21A as candidates. A ROC analysis defined the AUCs for each to differentiate PD from SD to be:

VMAT1: ROC=0.835

PHF21A: ROC=0.733

Using the rule:

If VMAT1≥0 and PHF21A<1.2 then SD

If VMAT1≥0 and PHF21A≥1.2 then PD

This allowed for 100% accuracy in defining progressive disease and 90% accuracy in defining SD. The overall accuracy was 93%.

A NETest score of 7 has a ~50% chance of differentiating SD from PD samples.

As for NETest scores of 6, gene expression profile analysis identified both VMAT1 and PHF21A as candidates. A ROC analysis defined the AUCs for each to differentiate PD from SD to be:

VMAT1: ROC=0.835

PHF21A: ROC=0.733

Using the rule:

If VMAT1≥0 and PHF21A>1 then SD

If VMAT1≥0 and PHF21A≤1 then PD

This allowed for a 100% accuracy for defining progressive disease and 95% accuracy for SD. The overall accuracy was 97.5%.

A NETest score of 8 has a >90% chance of identifying a sample as PD. Expression of ZZZ3 was identified as a candidate. A ROC analysis defined the AUC for this gene to be 1.0.

Using the rule:

If ZZZ3≤14 then PD

This allowed for a 100% accuracy for defining progressive disease and differentiating from SD.

Figure 13:
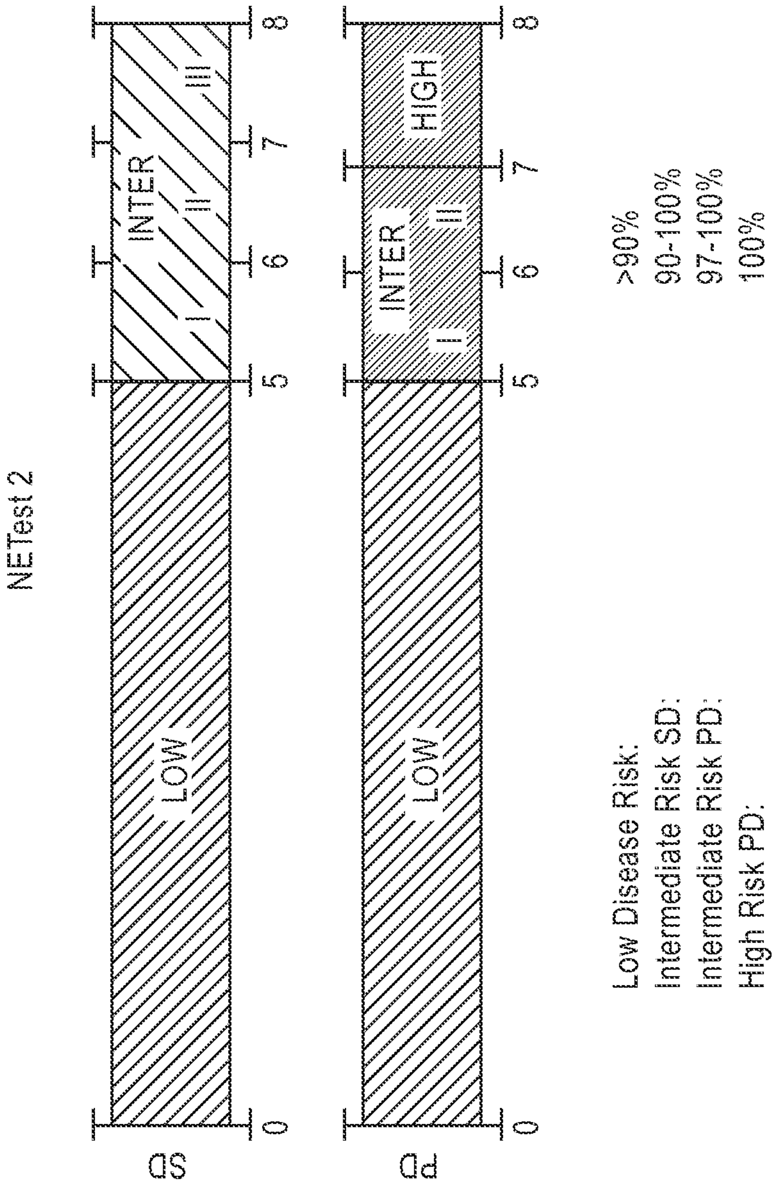
FIG. 13 is a nomogram of NETest 2 with the inclusion of risk category delineation.

With reference to FIG. 13, this individual gene expression information was used to finalize the "NETest 2" nomogram, which provides an accurate disease categorization profile for the patient. The combination of NETest scores and individual gene expression information used in the NETest 2 nomogram of FIG. 13 is further detailed in TABLE 5.

TABLE 5

NETEST 2 Nomogram Information

| | | Accuracy |
|---|---|---|
| Low risk stable disease | NETest score 0-5 | 90-100% |
| Intermediate risk stable disease (I) | NETest score 6 (low PHF21A) | 90-100% |
| Intermediate risk stable disease (II) | NETest score 7 (high PHF21A) | 95-100% |
| Intermediate risk stable disease (III) | NETest score 8 (high ZZZ3) | 100% |
| Intermediate risk progressive disease (I) | NETest score 6 (high PHF21A) | 100% |
| Intermediate risk progressive disease (II) | NETest score 7 (low PHF21A) | 97.5-100% |
| High risk progressive disease | NETest score 8 (low ZZZ3) | 100% |

Defining Clinically Relevant Genes—To further refine the scoring system, gene cluster expression was examined and algorithms were developed to capture the information. Individual gene clusters incorporate biological information that may augment the mathematically-derived MAARC-NET scoring systems. One focus may be given to literature-curated gene clusters which are included in TABLE 6.

TABLE 6

Genes included in each Cluster

| Cluster Name | Genes |
|---|---|
| Proliferome | Ki67, NAP1L1, NOL3, TECPR2 |
| Growth Factor Signalome | ARAF1, BRAF, KRAS, RAF1 |
| Metabolome | ATP6V1H, OAZ2, PANK2, PLD3 |
| Secretome I (General) | PNMA2, VMAT2 |
| Secretome II (Progressive) | PQBP1, TPH1 |
| Epigenome | MORF4L2, NAP1L1, PQBP1, RNF41, RSF1, SMARCD3, ZFHX3 |
| Apoptome | BNIP3L, WDFY3 |
| Plurome | COMMD9 |
| SSTRome | SSTR1, SSTR3, SSTR4, SSTR5 |

Figure 14A:
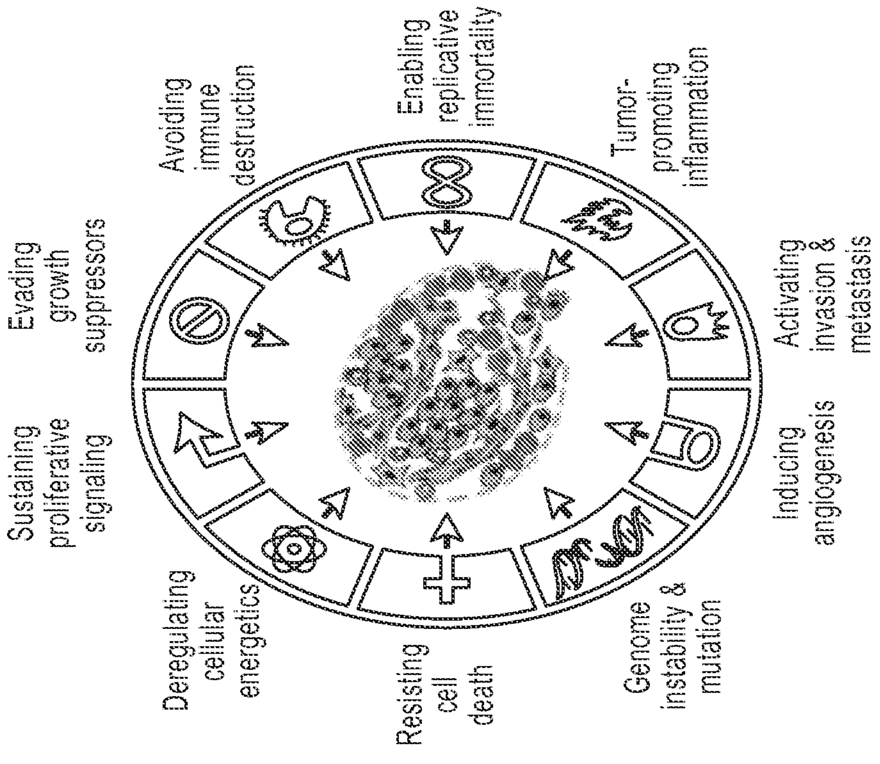
FIGS. 14A-14B are illustrations representing the Hallmarks of Neoplasia refocused on NETs.
Figure 14B:
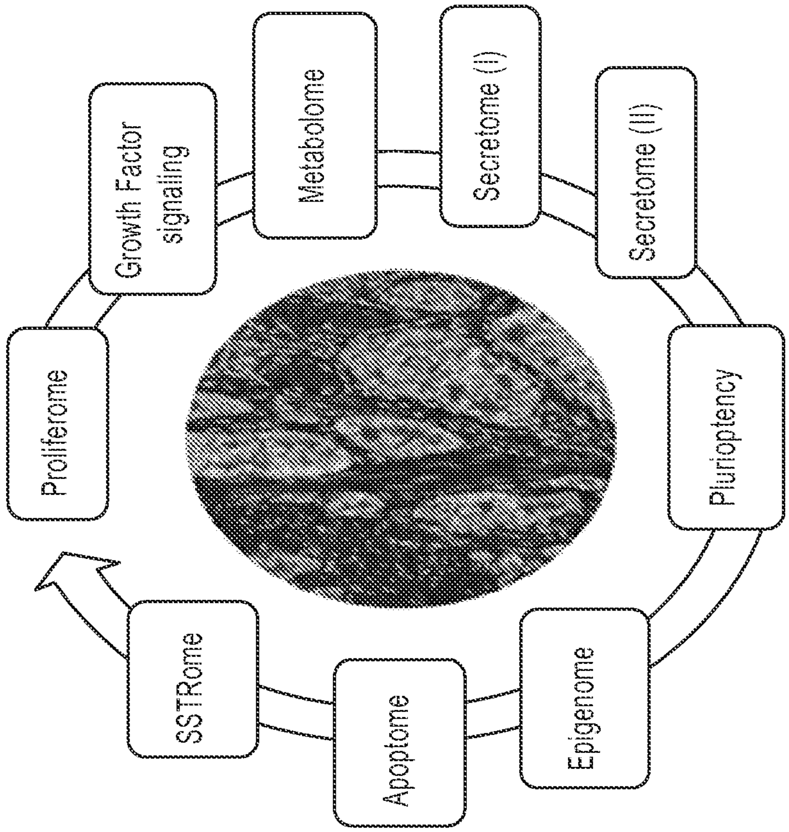

With reference to FIG. 14A, the Hallmarks of Neoplasia are illustrated, including the delineation of tumor (adenocarcinoma)-derived hallmarks. With reference to FIG. 14B, the NET hallmarks based on the Hanahan and Weinberg classifications are illustrated.

Values for the nine clusters represented in FIGS. 14A-14B were derived from gene addition. In addition to the gene clusters, two algorithms were also assessed:

1) the "PDA" algorithm, which included a summation of the proliferome, signalome, secretome II, plurome and epigenome (the PDA algorithm is also referred to as Progressive Diagnostic I);

2) the "NDA" algorithm, which included expression of 15 genes associated with disease: these included ARAF1, BRAF, KRAS, RAF1, Ki67, NAP1L1, NOL3, GLT8D1, PLD3, PNMA2, VMAT2, TPH1, FZD7, MORF4L2 and ZFHX3 (the NDA algorithm is also referred to as Progressive Diagnostic II). Genes were summated and an averaged value was derived.

Figure 15A:
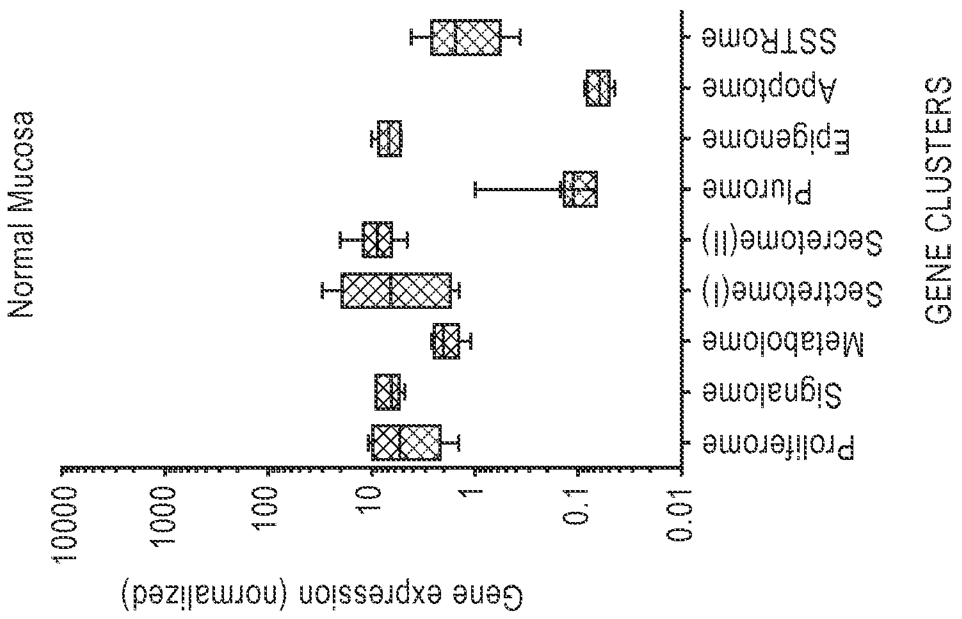
FIGS. 15A-15B are graphs showing normalized gene expression of gene clusters in (FIG. 15A) normal mucosa and (FIG. 15B) NETs.
Figure 15B:
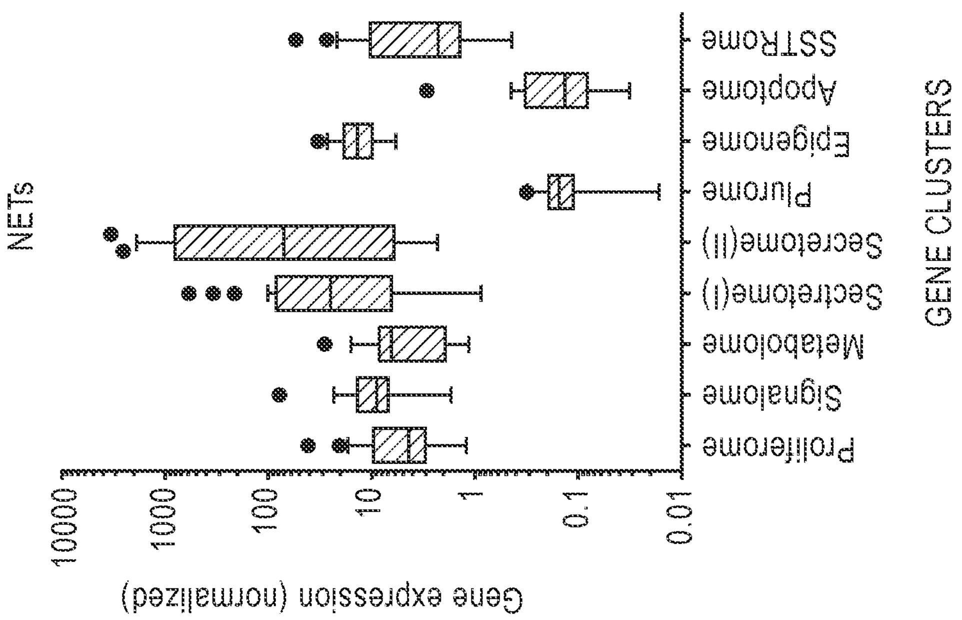
Figure 16:
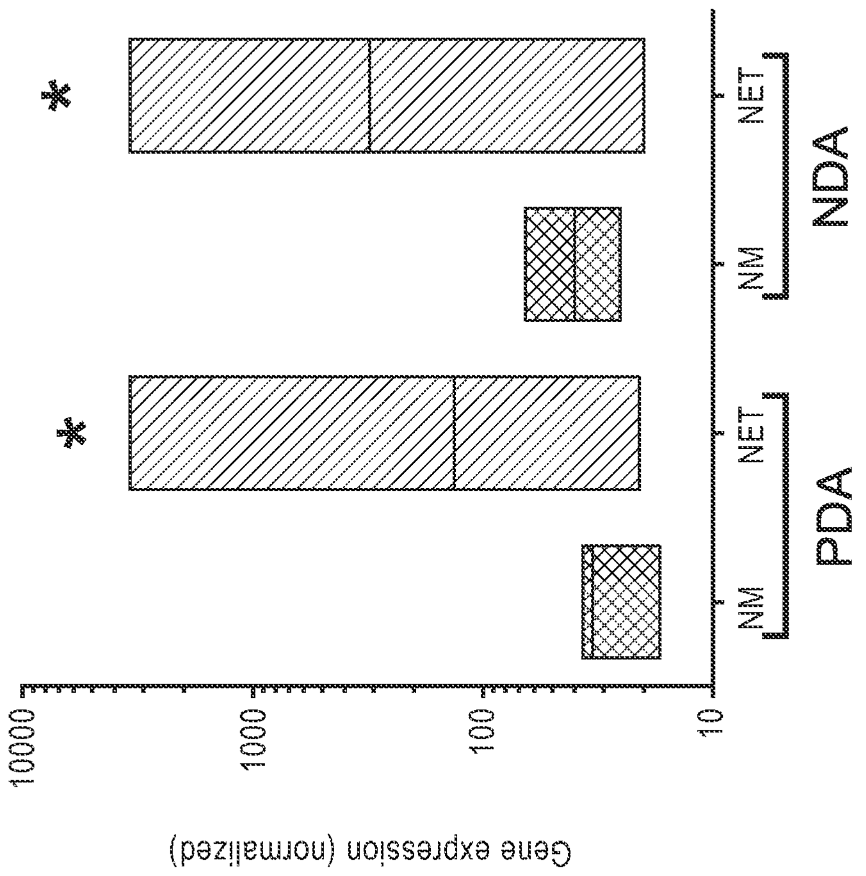
FIG. 16 is a graph of normalized gene expression as evaluated by the PDA and NDA algorithms in normal mucosa (NM) and NET.

Prior to assessing the value of the nine gene clusters and two algorithms in blood samples, their expression in NET tumor tissue was assessed to confirm that these were NET-relevant. With reference to FIGS. 15B and 15A, respectively, expression in 22 NETs may be compared to expression in normal mucosa (n=10). Assessment identified that seven of the nine clusters were specific to NETs (in comparison to normal mucosa). In particular, expression of the signalome, metabolome, secretome (I) and (II), epigenome, apoptome and SSTRome were elevated in NETs ($p<0.05$). Genes in the apoptome were decreased in NETs, while the proliferome was not different between NETs and normal mucosa. With respect to the algorithms, FIG. 16 shows that each of the PDA and NDA were significantly increased ($p<0.05$) in NET tumor tissue compared to normal mucosa.

Figure 17A:
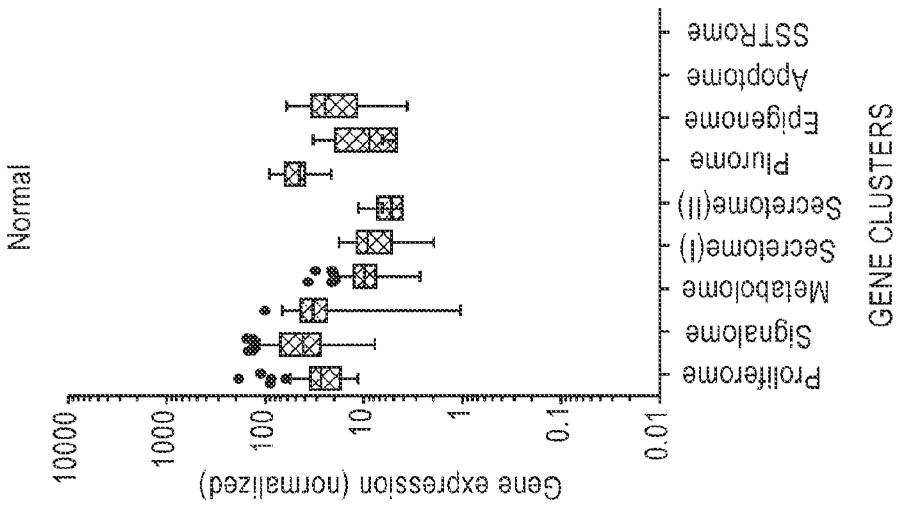
FIGS. 17A-17C are graphs of normalized gene expression in (FIG. 17A) normal mucosa, (FIG. 17B) a SD related gene cluster, and (FIG. 17C) a PD related gene cluster.
Figure 17B:
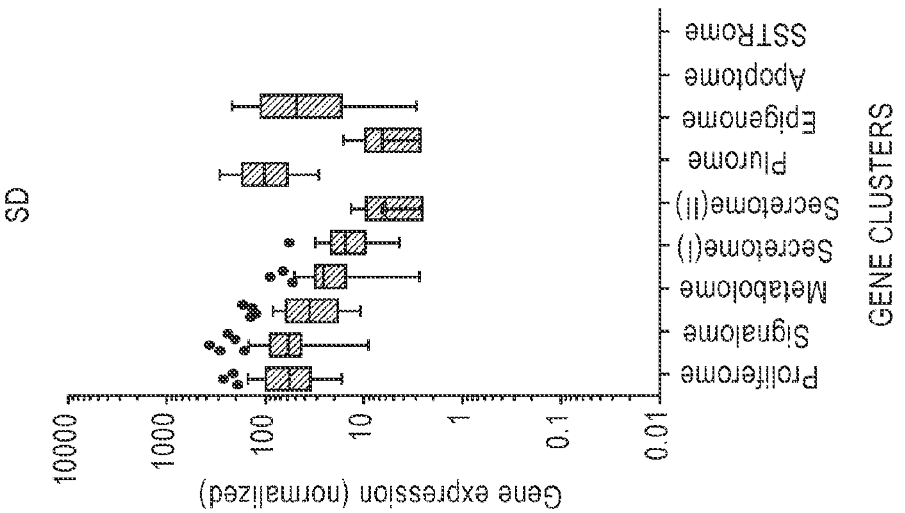
Figure 17C:
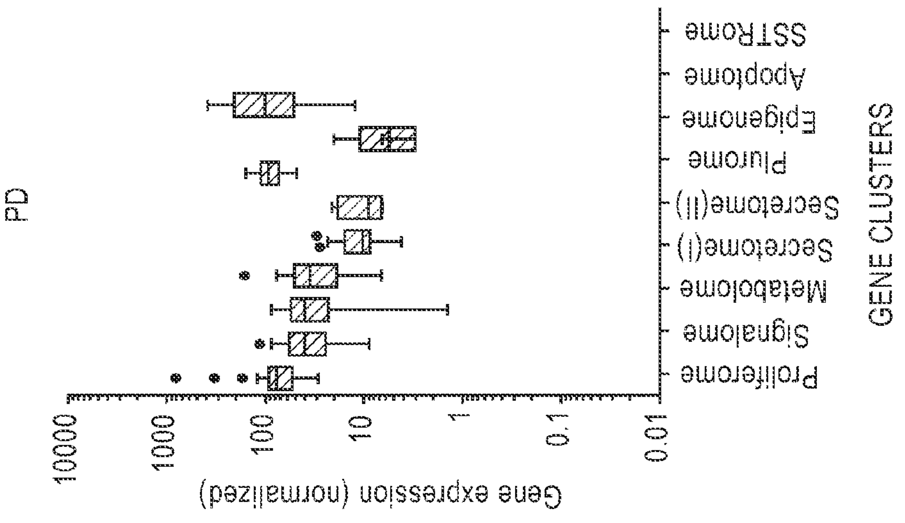

Thereafter, the expression of each of the clusters was assessed in blood samples. We examined the test (n=130) set and evaluated whether expression they were related to SD or PD. Significant differences were noted in gene expression between controls and SD/PD, as shown in FIGS. 17A-17C and TABLE 7.

TABLE 7

Gene Clusters and Clinical Outcome

| Cluster Name | Con vs SD | Con vs PD | SD vs PD |
|---|---|---|---|
| Proliferome | p < 0.05 | p < 0.05 | ns |
| Growth Factor Signalome | p < 0.05 | ns | p < 0.05 |
| Metabolome | ns | p < 0.05 | ns |
| Secretome I (General) | p < 0.05 | p < 0.05 | p < 0.05 |
| Secretome II (Progressive) | p < 0.05 | p < 0.05 | p < 0.05 |
| Epigenome | ns | p < 0.05 | p < 0.05 |
| Apoptome | p < 0.05 | p < 0.05 | ns |
| Plurome | p < 0.05 | p < 0.05 | ns |
| SSTRome | p < 0.05 | p < 0.05 | p < 0.05 |

ns = not significant
Two-tailed Mann-Whitney U-test

These data demonstrate that gene clusters can be used to differentiate SD and PD from controls as well as identify differences between SD and PD.

Figure 18:
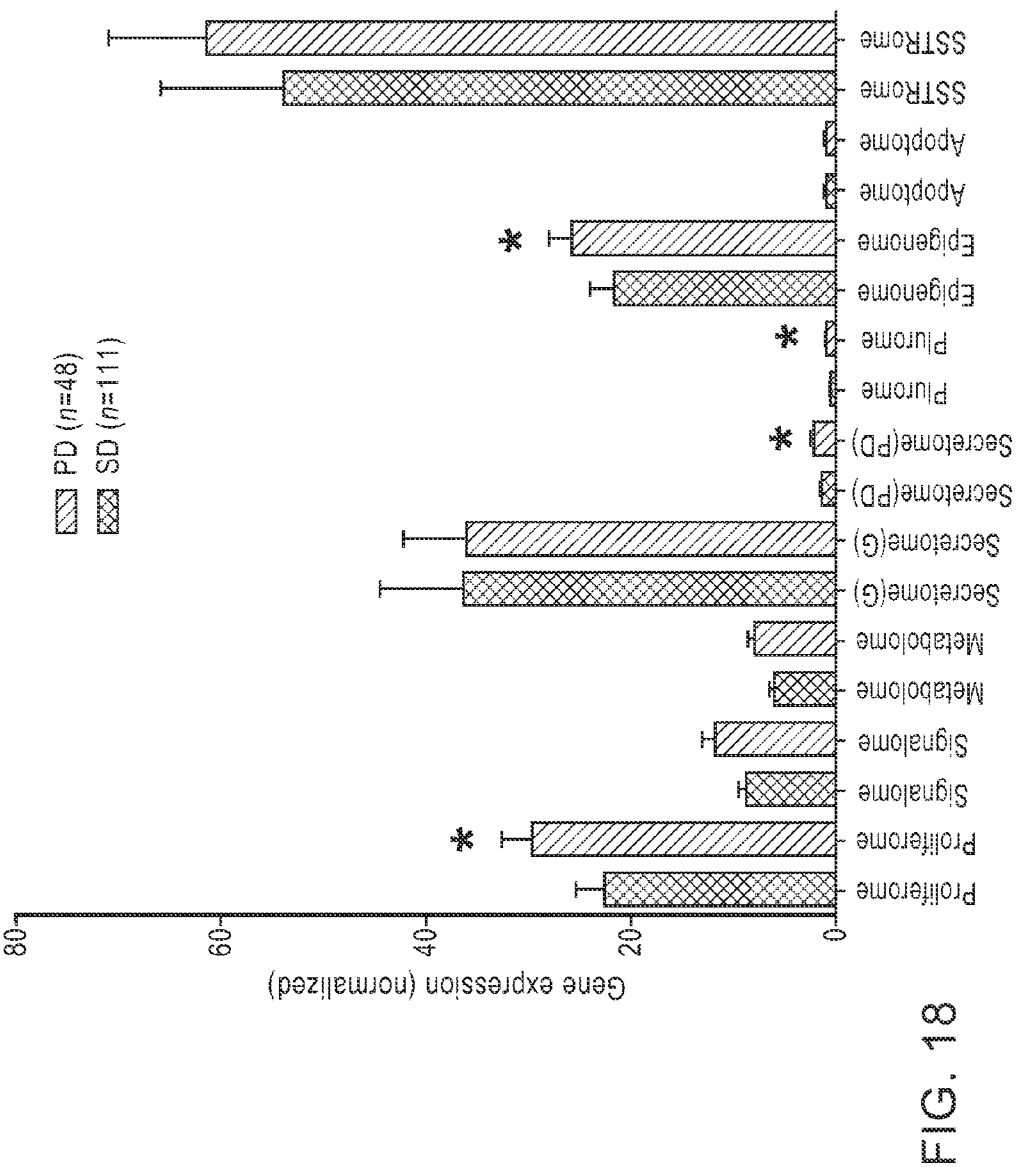
FIG. 18 is a graph of normalized gene expression in an independent test set, where the genes in PD and SD tumors were evaluated.

With reference to FIG. 18, gene cluster results were examined in the independent set (n=159), evaluating each of the clusters in SD vs PD. In the independent set, the proliferome, secretome (II), plurome and epigenome were significantly increased.

Figure 19B:
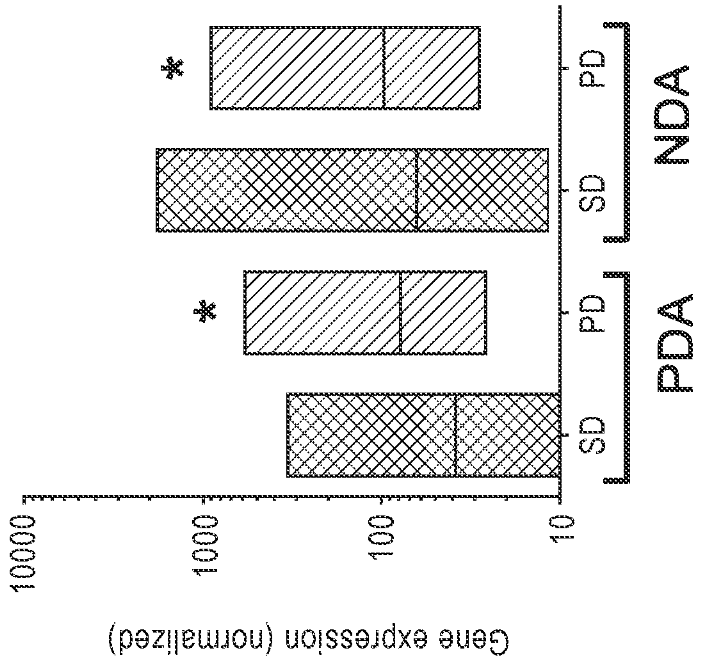
FIGS. 19A-19B are graphs showing normalized gene expression of PDA and NDA gene cluster algorithms in (FIG. 19A) the test set and (FIG. 19B) the independent set.
Figure 19A:
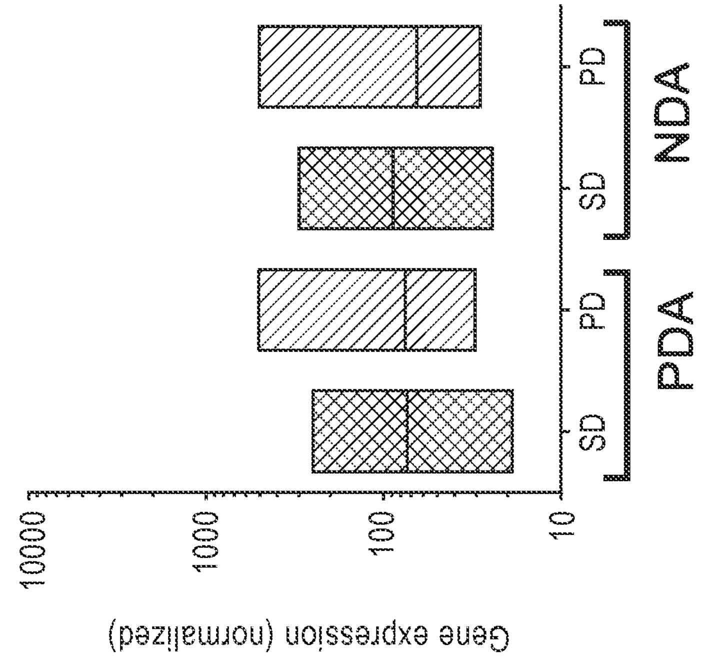

Next the PDA and NDA were evaluated in each of the two datasets (independent and test sets). With reference to FIG. 19A, no significant differences were identified between SD and PD for either of the two algorithms in the test set. With reference to FIG. 19B, each of the PDA and NDA were elevated in the independent set.

Figure 20A:
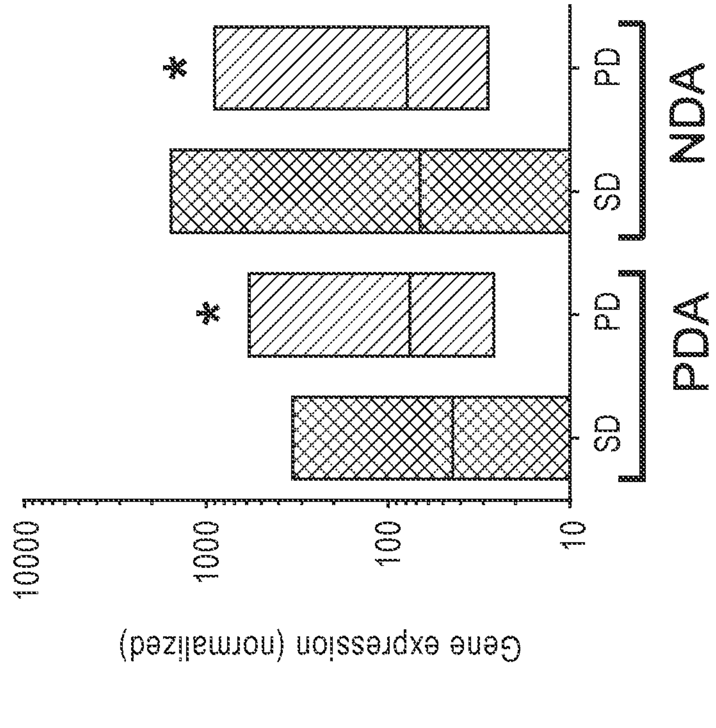
FIGS. 20A-20B are graphs showing (FIG. 20A) normalized gene expression of PDA and NDA gene cluster algorithms in the combined set, and (FIG. 20B) a ROC analysis curve of PDA and NDA for differentiating SD from PD, where *p<0.05 vs. SD.
Figure 20B:
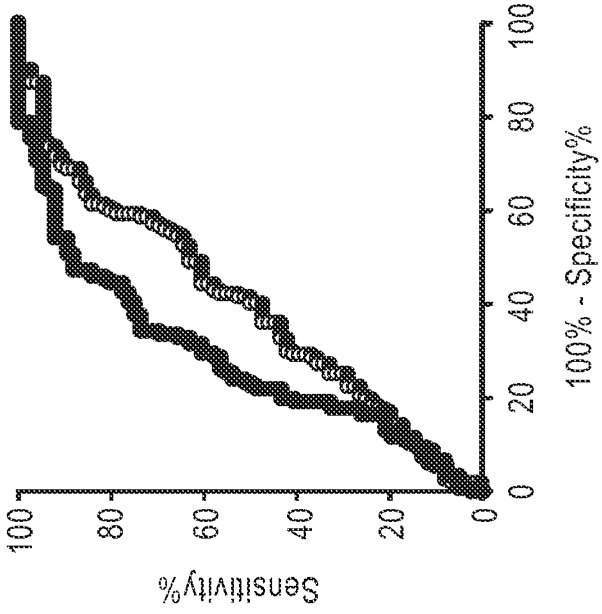

Next each of the algorithms were included in a combined set (test+independent: n=222) and their utility to predict SD versus PD was evaluated. With reference to FIG. 20A, both PDA and NDA were elevated in PD compared to SD in the combined sets. With reference to FIG. 20B, a ROC analysis identified the following parameters for PDA and NDA listed in TABLE 8.

TABLE 8

ROC Analysis Parameters, PDA and NDA in Combined Set

| | PDA | NDA |
|---|---|---|
| AUC | 0.72 ± 0.034 | 0.6 ± 0.038 |
| 95% CI | 0.652-0.785 | 0.525-0.675 |
| p-value | <0.0001 | 0.014 |
| ROC cut-off | 58 | 74 |

Two additional algorithms based on gene cluster expression differences in the test (TDA) and independent (IDA) set were evaluated. TDA included a summation of gene clusters significantly different between SD and PD in the test set.

These included TDA: Secretome (I), Plurome and SSTRome (the TDA algorithm is also referred to as Progressive Diagnostic III); and IDA: Proliferome, secretome (II), plurome and epigenome (the IDA algorithm is also referred to as Progressive Diagnostic IV).

Each of the algorithms in the test set and independent set were evaluated. With reference to FIG. 21A, TDA was significantly elevated in PD compared to SD in the test set.

Figure 21B:
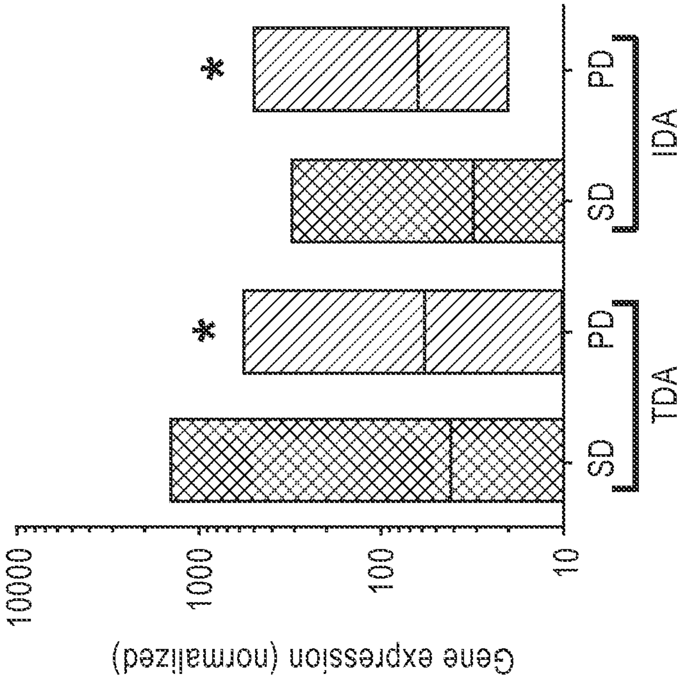
FIGS. 21A-21B are graphs showing normalized gene expression as evaluated by TDA and IDA gene cluster algorithms in (FIG. 21A) the test set, and (FIG. 21B) the independent set.
Figure 21A:
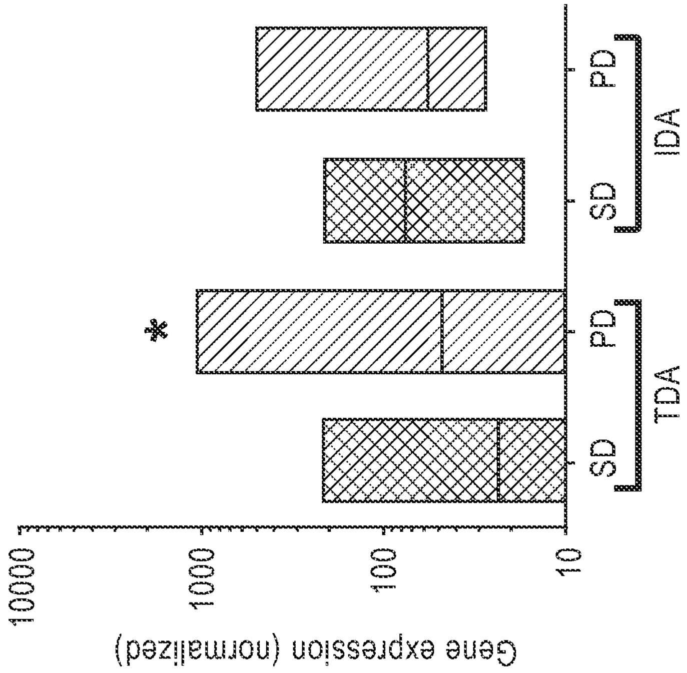

With reference to FIG. 21B, both TDA and IDA algorithms were significantly elevated in the independent set.

Next, a ROC analyses with both algorithms in the combined dataset was performed. The ROC analysis identified the following parameters for TDA and IDA listed in TABLE 9.

TABLE 9

ROC Analysis Parameters, TDA and IDA in Combined Set

| | TDA | IDA |
|---|---|---|
| AUC | 0.62 ± 0.04 | 0.70 ± 0.034 |
| 95% CI | 0.542-0.698 | 0.637-0.770 |
| p-value | 0.003 | <0.001 |
| ROC-cut-off | >43 | >46 |

Figure 22A:
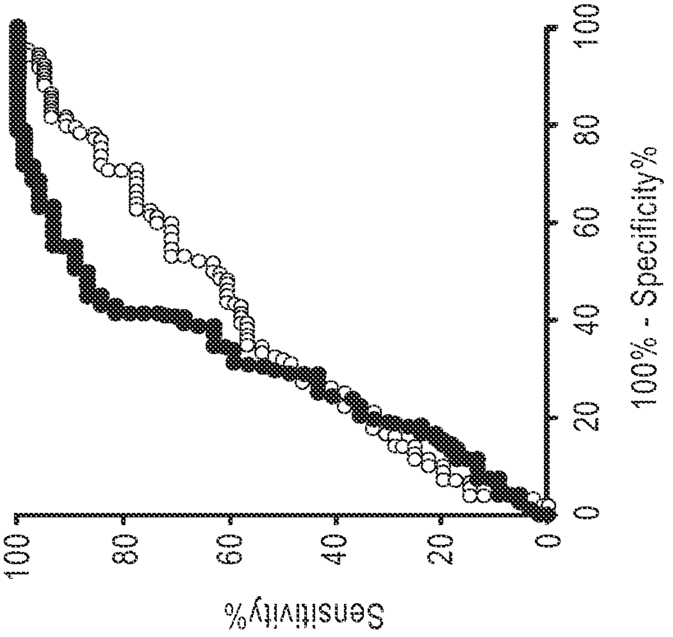
FIGS. 22A-22B are graphs showing a ROC analysis of (FIG. 22A) TDA and IDA for differentiating SD from PD, and (FIG. 22B) for each of the individual gene clusters.
Figure 22B:
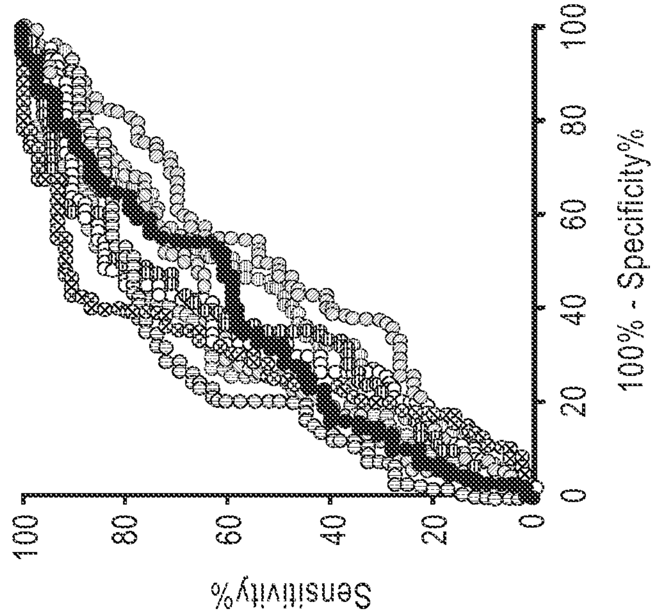

Algorithm-generated ROC curves of TDA and IDA for differentiating between SD and PD are shown in FIG. 22A. Algorithm-generated ROC curves for each of the clusters for differentiating between SD and PD are shown in FIG. 22B. The ROC curves in FIGS. 22A and 22B demonstrate that AUCs range from 0.51 (GF signalome) to 0.72 (plurome) for the differentiation of SD and PD.

Accordingly, individual gene cluster expression and algorithms that capture this information contain biologically relevant information that correlates with clinical observations. These provide the basis for defining clinically relevant MAARC-NET scoring systems.

Demonstration of Clinical Utility of NETEST Genes—The clinical utility of NETest scores, as well as the scores from pertinent gene clusters and algorithms, will now be defined. An examination of how surgical removal of a NET altered the circulating gene signature was performed to demonstrate how the test will have utility as a measure of the completeness of surgical therapy.

Figure 23A:
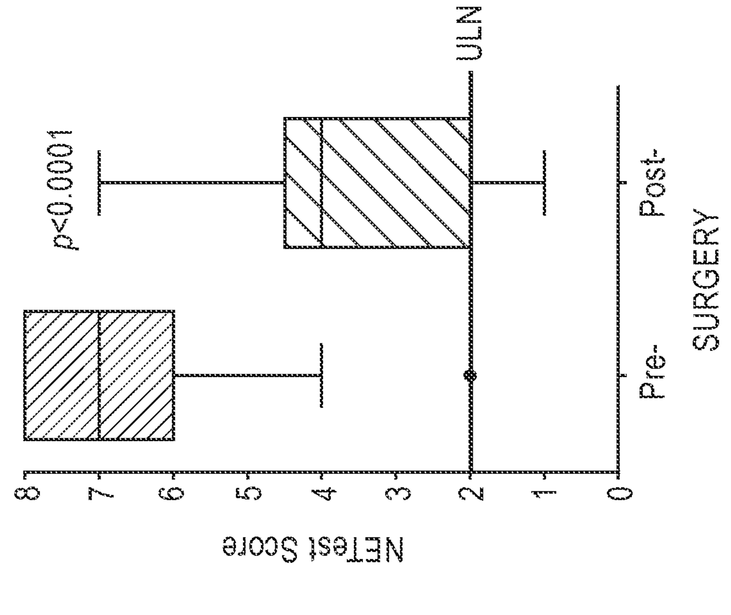
FIGS. 23A-23B are graphs showing the alternation in (FIG. 23A) NETest Score in Pre- and Post-Surgery conditions and (FIG. 23B) circulating Chromogranin A (CgA) levels in Pre- and Post-Surgery conditions.
Figure 23B:
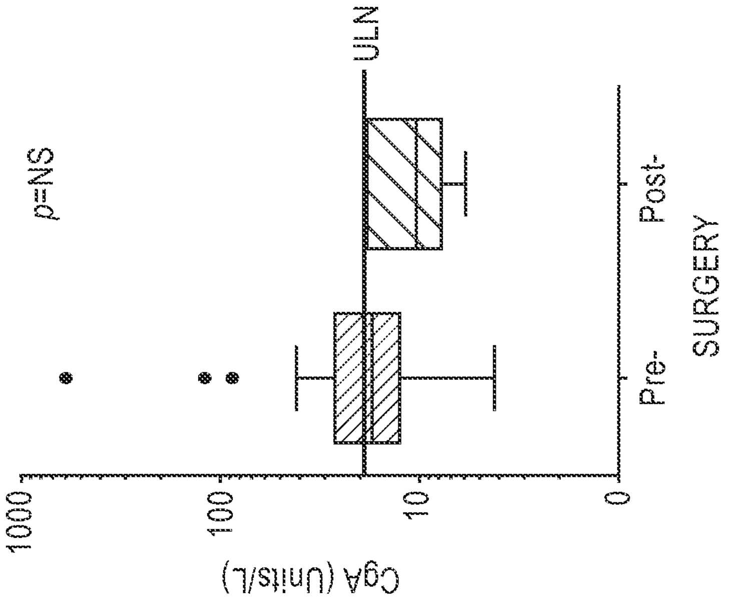

Parameters in 29 surgically treated patients prior to surgery and >1 month post-surgery was examined. As a group, MAARC-NET scores were significantly decreased ($p<0.0001$) from a mean of 6.58±1.48 to 3.65±1.6, as shown in in FIG. 23A. Chromogranin A (CgA), a gene used in a prior known single biomarker assay for NETs, was not significantly decreased (58.5±137.9 ng/ml vs. 55.25154.8), as shown in FIG. 23B.

Figures 24A, 24B:
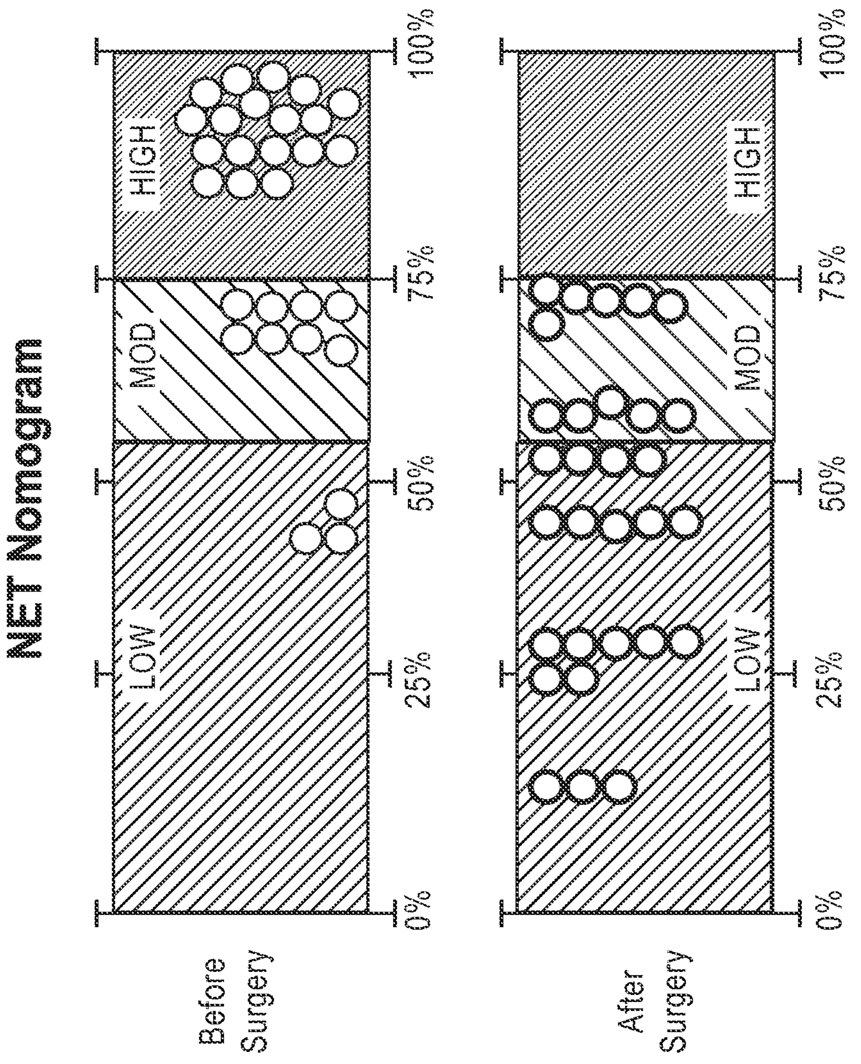
FIGS. 24A-24B are illustrations showing differences in the NETest nomogram in (FIG. 24A) pre-surgical therapy conditions and (FIG. 24B) post-surgical therapy conditions.

An examination of how NETest 1 performed, i.e. changes in NETest score pre- and post-surgical therapy, is included in FIGS. 24A-24B. Prior to surgery, 62% of patients were included in the high disease category; after surgery this was 0% ($\chi^2=24$, $p=5\times10^{-8}$).

Figure 25B:
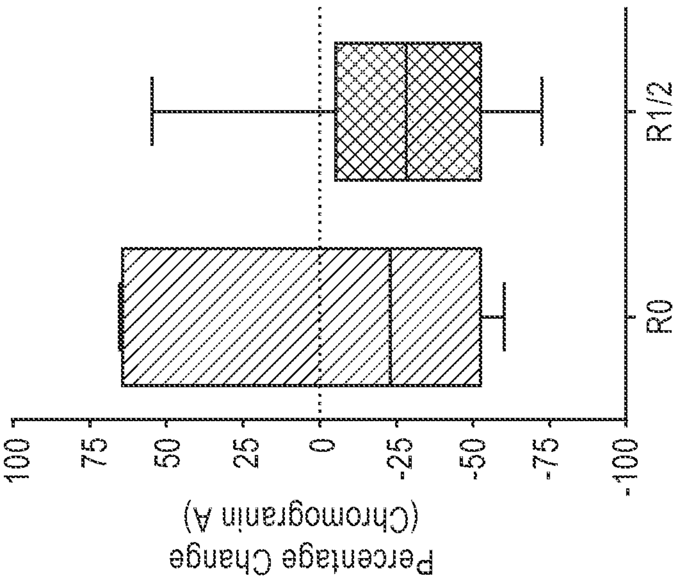
FIGS. 25A-25B are graphs showing the percentage change in (FIG. 25A) mathematically-derived score and (FIG. 25B) Chromogranin A in both R0 (complete resections) and R1/2 (incomplete sections) conditions.
Figure 25A:
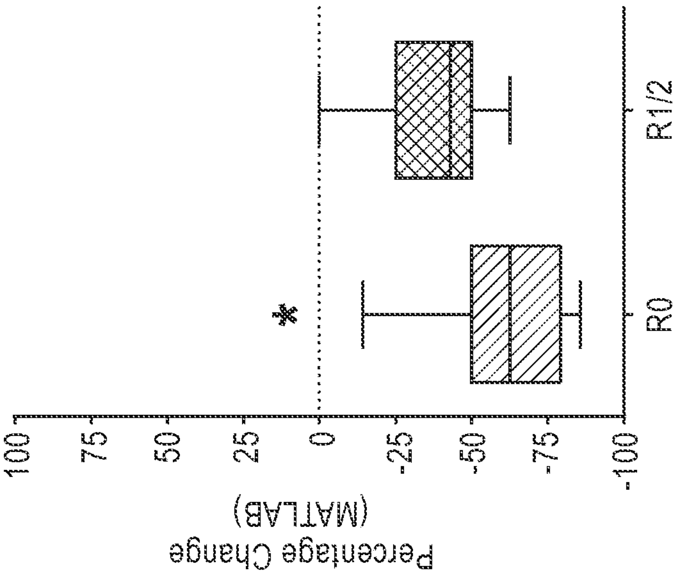

An alternative assessment of how surgery affected disease status is provided by the percentage changes in surgical approaches—no evidence of residual disease (R0) versus evidence of residual disease including metastases. With reference to FIG. 25A, levels for the MAARC-NET score were significantly decreased ($p<0.003$) in the R0 group (complete resection) compared to the R1/R2 group (incomplete resection).

Figure 26A:
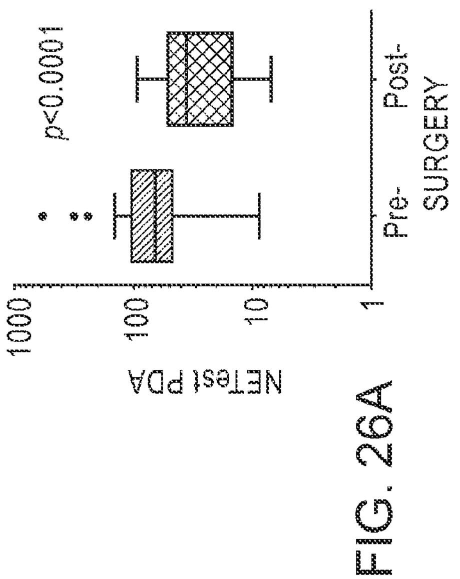
FIGS. 26A-26D are graphs showing the difference in NETest score for gene-derived algorithms, (FIG. 26A) PDA, (FIG. 26B) NDA, (FIG. 26C) TDA, and (FIG. 26D) IDA, in pre- and post-surgery conditions.
Figure 26B:
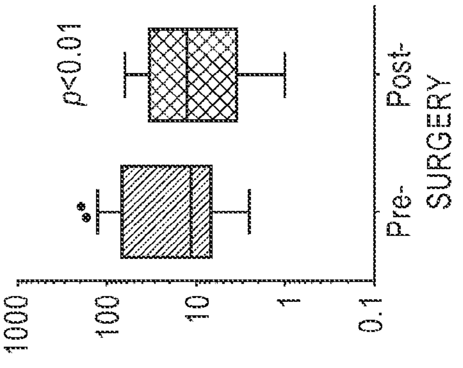
Figure 26C:
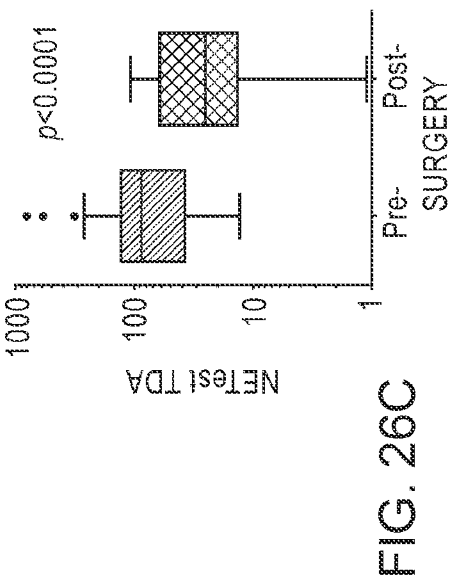
Figure 26D:
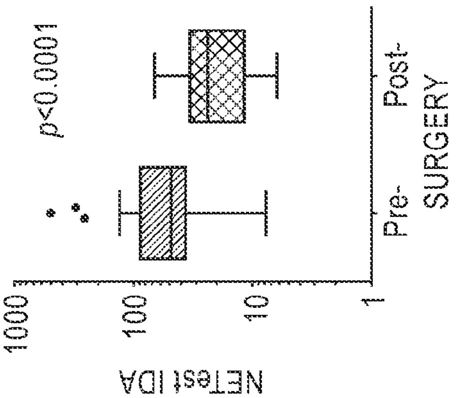
Figures 27A, 27B, 27C, 27D, 27E, 27F, 27G, 27H, 27I:
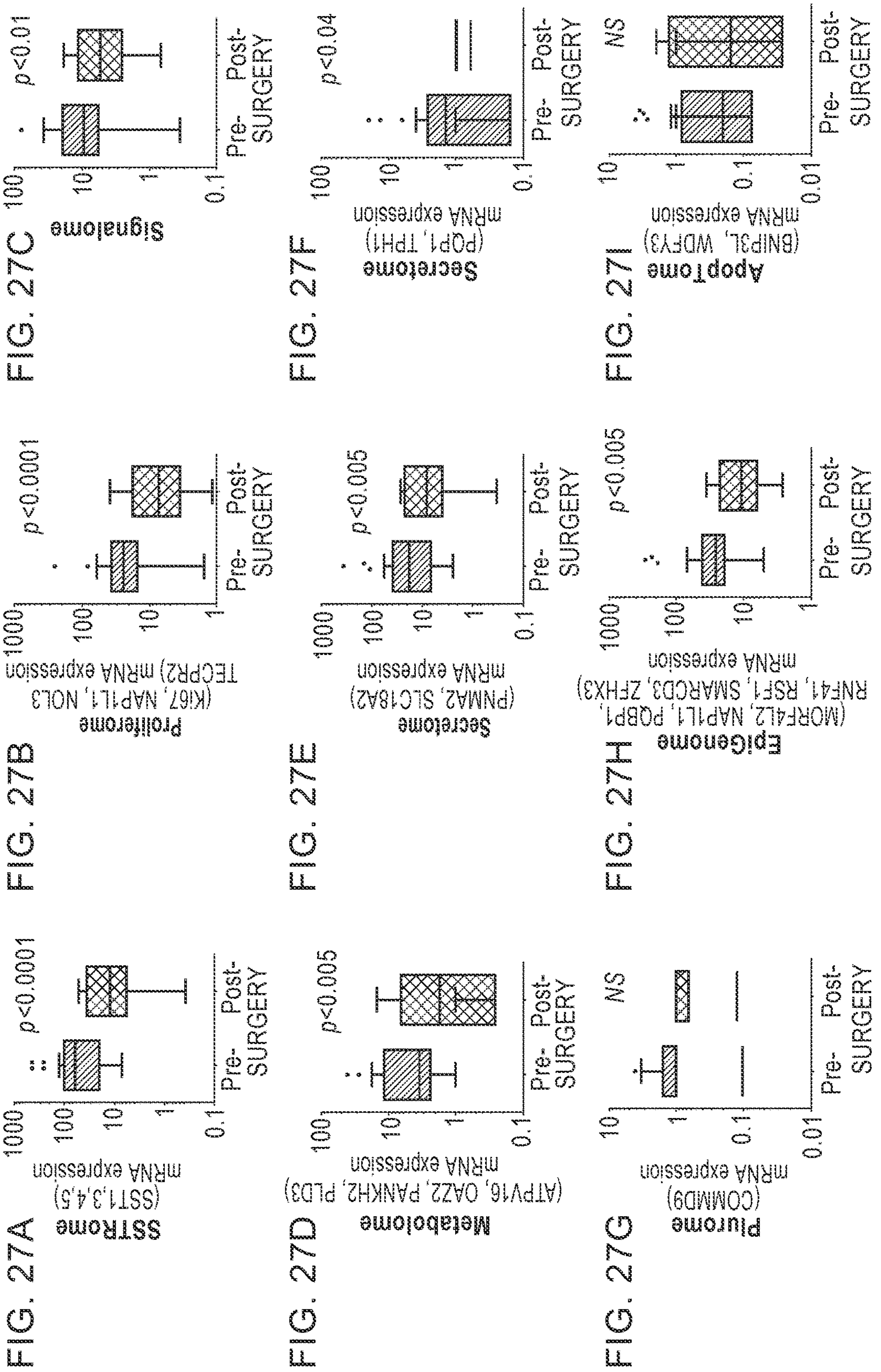
FIGS. 27A-27I are graphs showing the differences in NETest score for gene-derived clusters, (FIG. 27A) SSTRome, (FIG. 27B) Proliferome, (FIG. 27C) Signalome, (FIG. 27D) Metabolome, (FIG. 27E) Secretome, (FIG. 27F) Secretome, (FIG. 27G) Plurome, (FIG. 27H) EpiGenome, and (FIG. 27I) ApopTome, in pre- and post-surgery conditions.

To better define the role of surgery each of the four algorithms were examined. Significant decreases were identified (post-surgery) in PDA (99.3±21 vs. 41.1±7.5, $p<0.0001$; FIG. 26A), NDA (45.8±10.3 vs. 29.6±7.8, $p<0.01$; FIG. 26B), TDA (133.3±32.3 vs. 43.8±9.3, $p<0.0001$; FIG. 26C) and IDA (86.1±19.3 vs. 34.1±7.2, $p<0.0001$; FIG. 26D).

With reference to FIGS. 27A-27I, an examination of individual clusters identified significant decreases in the SSTRome, proliferome, GF signalome, metabolome, secretome I/II and the epigenome pre- and post-surgery.

With reference to TABLE 10, surgical removal of the tumor tissue was associated with decreases in circulating gene expression to levels not different to or below ROC cut-off values for SD for each of the four algorithms and for 6 of the 9 gene clusters.

TABLE 10

Relationship Between Surgical Excision, Gene Clusters and Each of the Algorithms

| Algorithm/ Cluster | p-value | Change | Pre-surgery | Post-surgery | ROC for SD |
|---|---|---|---|---|---|
| NDA | 0.009 | ↓ | 45 | 30 | <74 |
| PDA | <0.0001 | ↓ | 99 | 41 | <58 |
| TDA | <0.0001 | ↓ | 133 | 44 | <74 |
| IDA | <0.0001 | ↓ | 86 | 34 | <46 |
| SSTRome | <0.0001 | ↓ | 93 | 23 | <25.5 |
| Proliferome | <0.0001 | ↓ | 34 | 15 | <20 |
| GF Signalome | 0.009 | ↓ | 14.8 | 8 | <9 |
| Metabolome | 0.004 | ↓ | 8.2 | 6.8 | <6.5 |
| Secretome (I) | 0.004 | ↓ | 39.2 | 19.5 | <11 |
| Secretome (II) | 0.04 | ↓ | 2.4 | 0.85 | <1.6 |
| Plurome | NS | ↔ | 0.8 | 0.8 | <0.9 |
| Epigenome | 0.005 | ↓ | 48.7 | 17.7 | <2.3 |
| Apoptome | NS | ↔ | 0.72 | 0.84 | >0.5 |

All patients who had surgery can be considered as exhibiting progressive/active disease. Following surgery, the scores or algorithms were indicative of progressive disease in 3-7 of the twenty-nine patients (10-24%) depending on the algorithm used.

Surgery significantly reduced the circulating tumor signature and can provide evidence for the degree both of tumor removal as well as for evidence of residual active disease.

The clinical utility of the test therefore is defined by the examination of scores, algorithms and clusters and evaluation in comparison to pre-surgical bloods. Evidence of elevated expression of e.g., PDA or proliferome in post-surgical samples is indicative of residual progressive (highly active disease).

Figure 28:
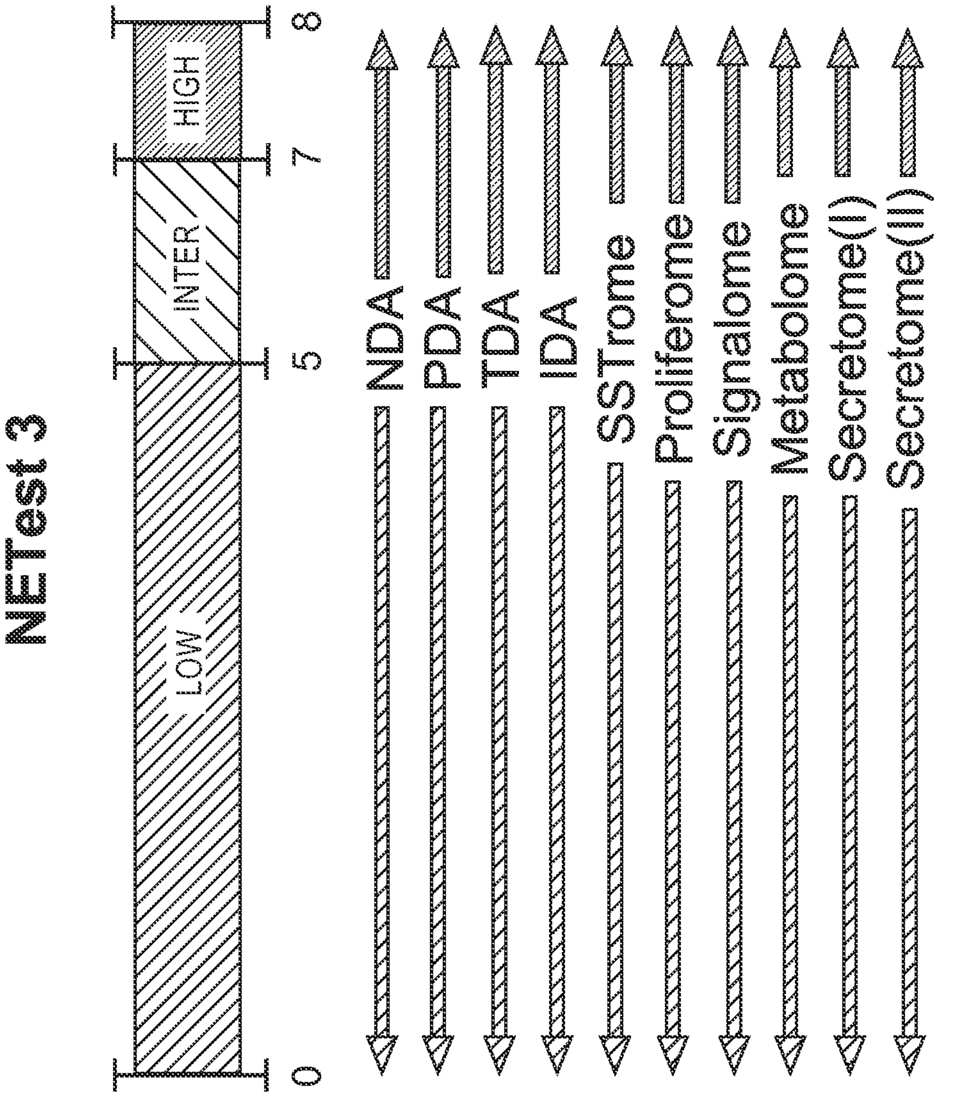
FIG. 28 is a nomogram of NETest 3 with the inclusion of surgically-relevant algorithms and gene clusters.

With reference to FIG. 28, a NETest 3 nomogram is illustrated with the inclusion of surgically-relevant algorithms and gene clusters. A combination score, as well as alterations in gene clusters e.g., a significant increase in the proliferome, will be indicative of disease regrowth following surgery. Of note, is that while post-operative imaging identified disease in n=1 (10%) of the R0 patients, elevated gene scores were evident in 6 (60%) at 1 month. Subsequently, two R0 individuals developed positive imaging at 6 months.

Effect of Standard Drug Therapies on Circulating NET Signature—The efficacy of a standard pharmacological therapy for NETs, somatostatin (used to treat >80% of patients), was evaluated on the circulating NET signature. Signatures were evaluated in patients treated with a somatostatin analog who were considered as either SD (n=63) or PD (n=26) by imaging and best clinical judgment. Those patients who were SD on somatostatin analogs were considered to be stable-treated patients, while those patients who were PD on somatostatin analogs were considered to be failing therapy.

Figure 29B:
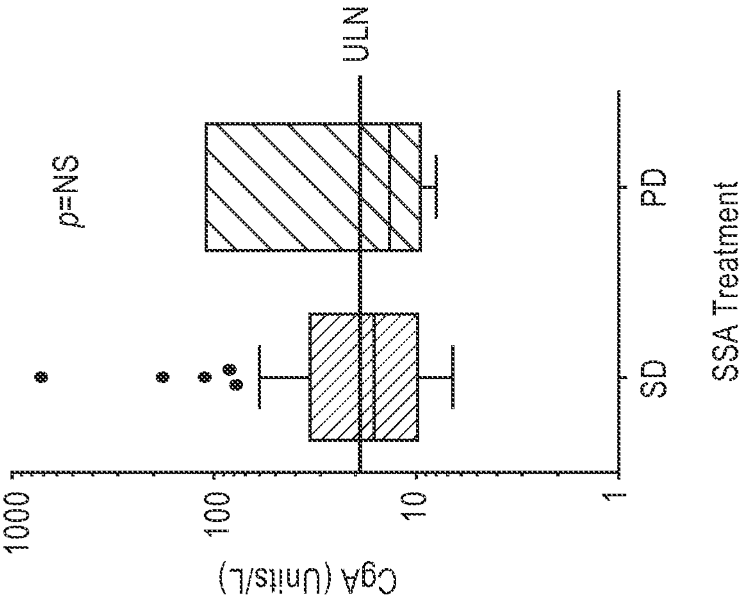
FIGS. 29A-29B are graphs showing the differences in (FIG. 29A) NETest score and (FIG. 29B) circulating CgA levels, each in in stable disease (SD) conditions and somatostatin analog (SSA) treatment failure (equivalent of PD conditions).
Figure 29A:
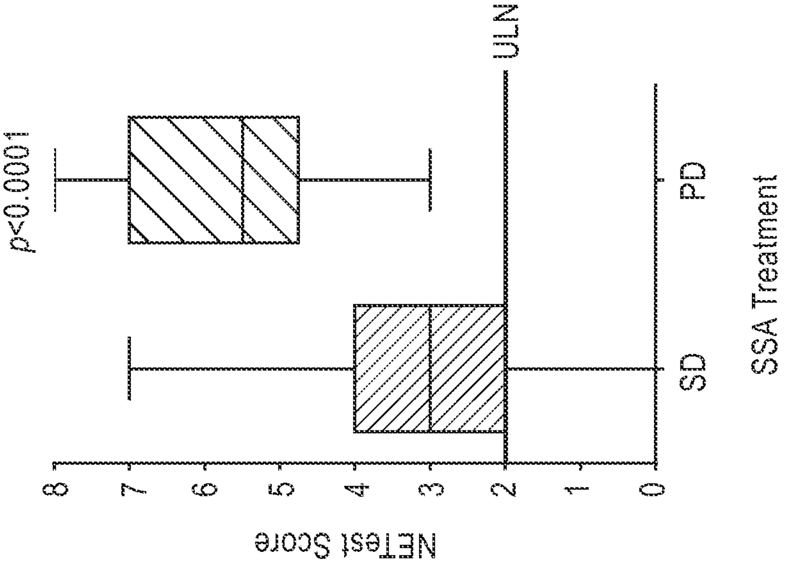

With reference to FIG. 29A, MAARC-NET scores were significantly lower in the SD group than those failing therapy: 3.33±0.21 vs 5.77±0.3 ($p<0.001$). With reference to FIG. 29B, Chromogranin A was not significantly different in the two groups (44.7±17.2 ng/ml vs. 102.4±58.7).

Figure 30A:
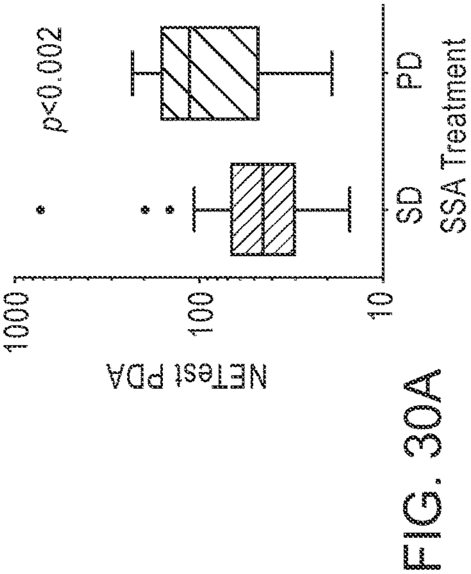
FIGS. 30A-30D are graphs showing the differences in gene-derived algorithms, (FIG. 30A) PDA, (FIG. 30B) NDA, (FIG. 30C) TDA, and (FIG. 30D) IDA, in stably treated patients (SD) and treatment failure (PD).
Figure 30B:
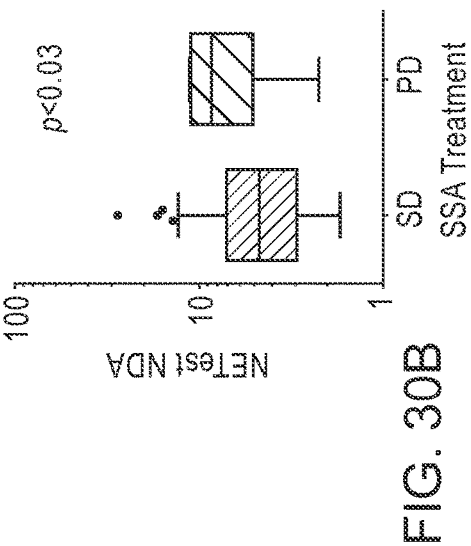
Figure 30C:
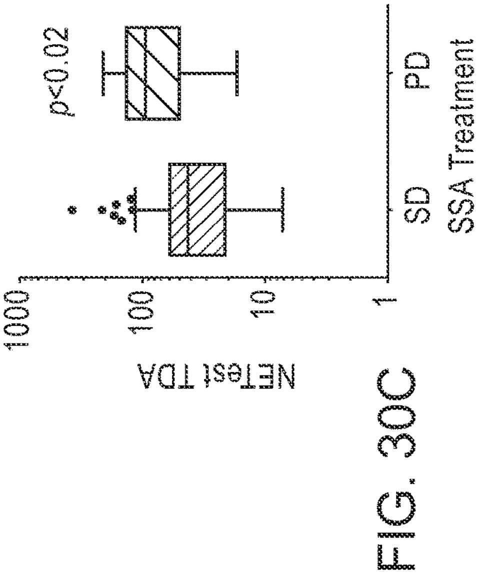
Figure 30D:
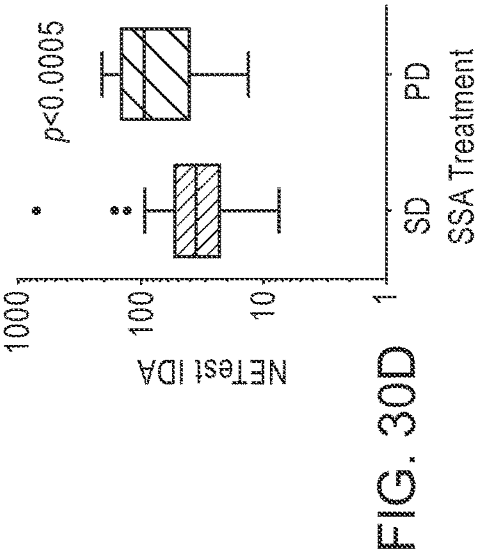
Figures 31A, 31B, 31C, 31D, 31E, 31F, 31G, 31H, 31I:
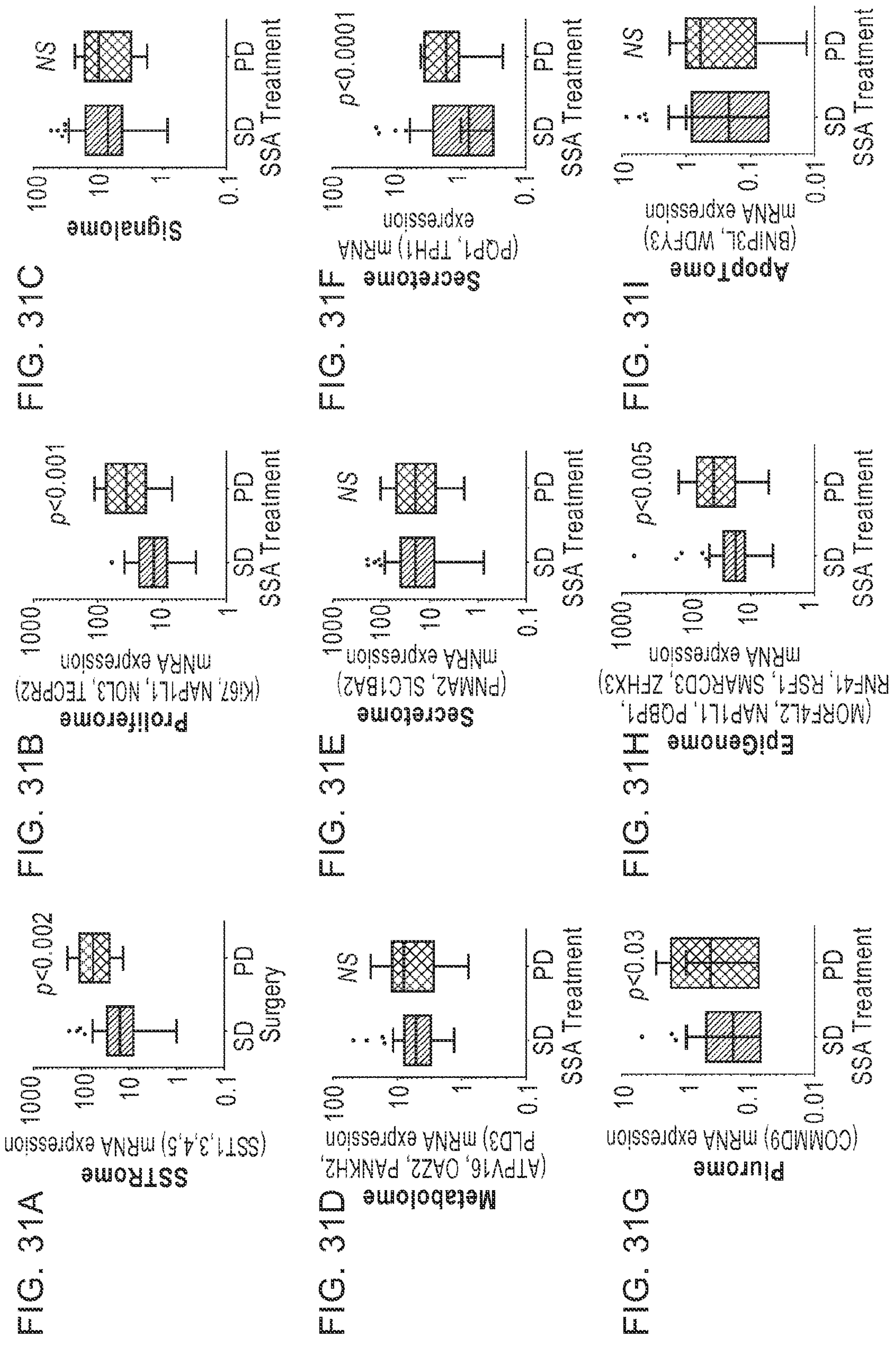
FIGS. 31A-31I are graphs showing the differences in gene-derived clusters, specifically (FIG. 31A) SSTrome, (FIG. 31B) Proliferome, (FIG. 31C) Signalome, (FIG. 31D) Metabolome, (FIG. 31E) Secretome, (FIG. 31F) Secretome, (FIG. 31G) Plurome, (FIG. 31H) EpiGenome, and (FIG. 31I) ApopTome, in stably treated patients (SD) and SSA treatment failure (equivalent of PD conditions).

An assessment of the algorithms demonstrated significant differences in each of them in SD compared to PD. Specifically, PDA (62.8±11.4 vs. 153.9±36.2, $p<0.002$; FIG. 30A), NDA (6±0.6 vs. 13.5±3, $p<0.03$; FIG. 30B), TDA (56.8±7.4 vs. 154±37.2, $p<0.02$; FIG. 30C) and IDA (51.7±11.1 vs. 140.5±36, $p<0.0005$; FIG. 30D).

With reference to FIGS. 31A-31I, examination of individual clusters identified that the SSTRome, proliferome, secretome II, plurome and the epigenome were significantly lower in the SD group relative to the PD group.

These data demonstrate that patients who exhibit progressive disease despite somatostatin analog (SSA) therapy exhibit increases in the MAARC-NET score, as well as each of the four algorithms and specific gene clusters including an increase in proliferation, as well as the epigenome. One mechanism to evaluate whether the SSA treatment is effective therefore is to evaluate whether scores for these parameters alter. However, given the overlap in each of these parameters between the SD and PD groups, it would be helpful to better define the PD group. To do this, the expression may be compared of the circulating signature in those failing therapy to that in controls. The hypothesis behind this approach was that an effective therapy (i.e. SD) would normalize the signatures. The corollary is that PD will be significantly different to normal. To establish this, ROC analyses were used to examine normal circulating transcripts and compared to PD. All four algorithms were examined as well as the gene clusters.

Figure 32A:
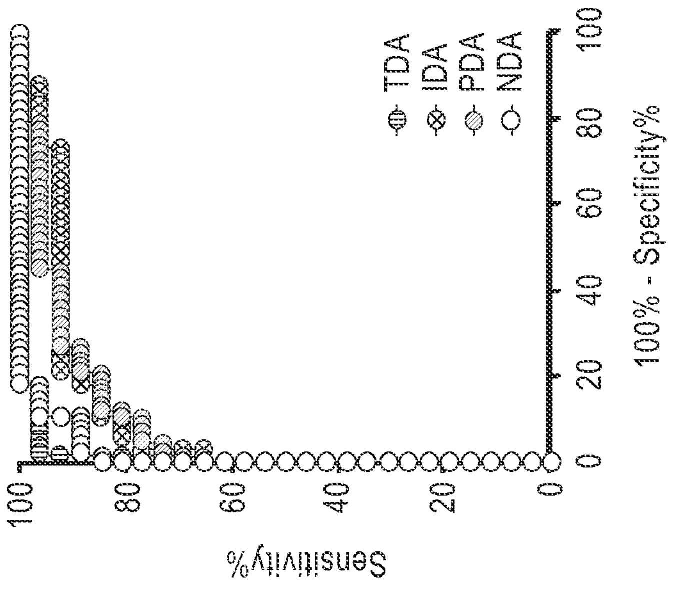
FIGS. 32A-32B are graphs showing a ROC analysis according to (FIG. 32A) gene-derived cluster algorithms and (FIG. 32B) gene clusters for differentiating treatment failure (equivalent of PD conditions) from controls.
Figure 32B:
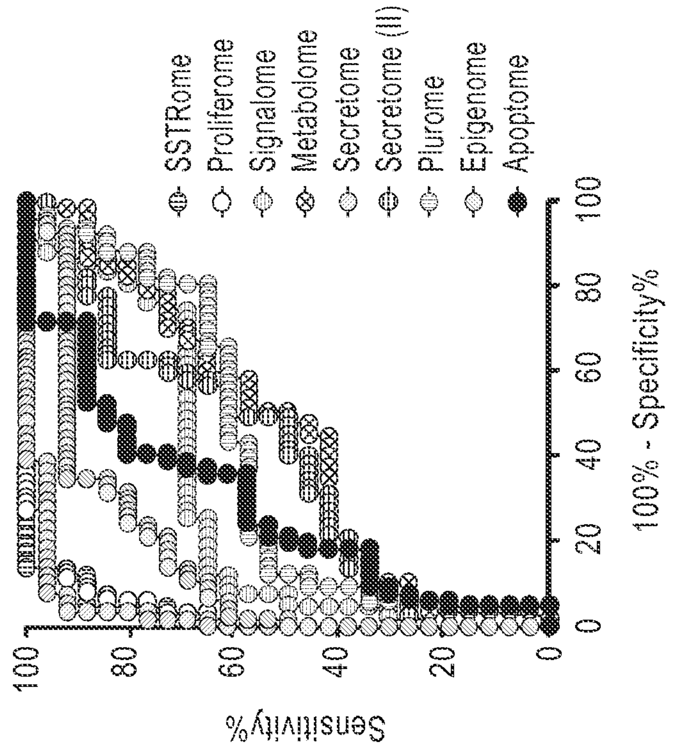

With reference to FIGS. 32A-32B, analysis of the data identified that algorithms (FIG. 32A) and selected clusters (FIG. 32B) differentiated controls from PD treated with SSAs. Data for the individual clusters are included in TABLE 11.

TABLE 11

Relationship between Gene Clusters and each of the Algorithms for those Failing SSA Therapyand Controls

| Algorithm/ Cluster | AUC | 95% CI | p-value | ROC for PD |
|---|---|---|---|---|
| NDA | 0.98 ± 0.01 | 0.965-1.00 | <0.0001 | >3 |
| PDA | 0.92 ± 0.04 | 0.851-0.994 | <0.0001 | >40 |
| TDA | 0.99 ± 0.01 | 0.975-1.01 | <0.0001 | >29 |
| IDA | 0.91 ± 0.04 | 0.828-0.998 | <0.0001 | >31 |
| SSTRome | 0.98 ± 0.01 | 0.95-1 | <0.0001 | >22 |
| Proliferome | 0.97 ± 0.02 | 0.94-1 | <0.0001 | >14 |
| GF Signalome | 0.71 ± 0.07 | 0.564-0.855 | <0.002 | >5 |
| Metabolome | 0.56 ± 0.07 | 0.41-0.7 | NS | <8 |
| Secretome (I) | 0.98 ± 0.02 | 0.944-1 | <0.0001 | >4 |
| Secretome (II) | 0.62 ± 0.07 | 0.486-0.759 | NS | >1.6 |
| Plurome | 0.61 ± 0.08 | 0.454-0.763 | NS | <0.7 |
| Epigenome | 0.86 ± 0.05 | 0.756-0.962 | <0.0001 | >16 |
| Apoptome | 0.73 ± 0.06 | 0.618-0.834 | <0.001 | <0.95 |

Based on the data in TABLE 11, NDA and TDA were examined as well as the SSTRome, Proliferome, and Secretome (I) in the SD cases to evaluate whether these parameters correlated with clinical assessments of therapeutic efficacy.

Figure 33A:
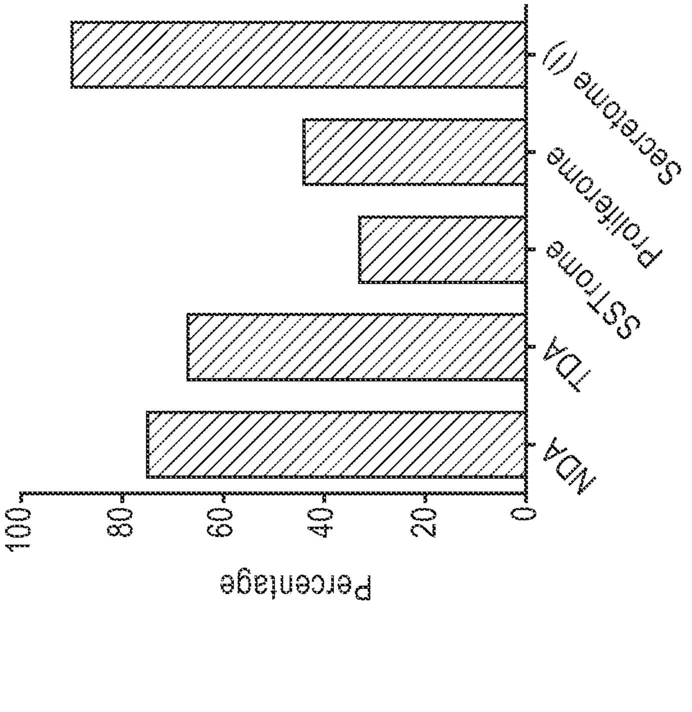
FIGS. 33A-33B are graphs showing the percentage of correct calls for each of (FIG. 33A) the gene-derived cluster algorithms and clusters for defining treatment failure in patients categorized as SD and (FIG. 33B) a Best-of-3 outperformed by a combination of SSTRome and Proliferome.
Figure 33B:
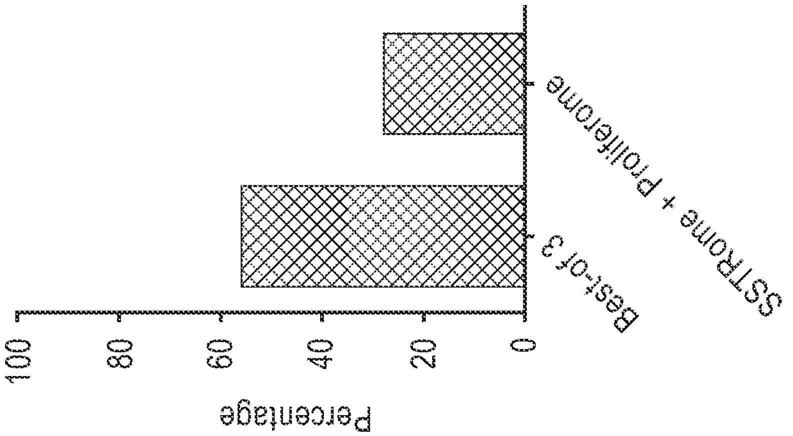
Figure 34:
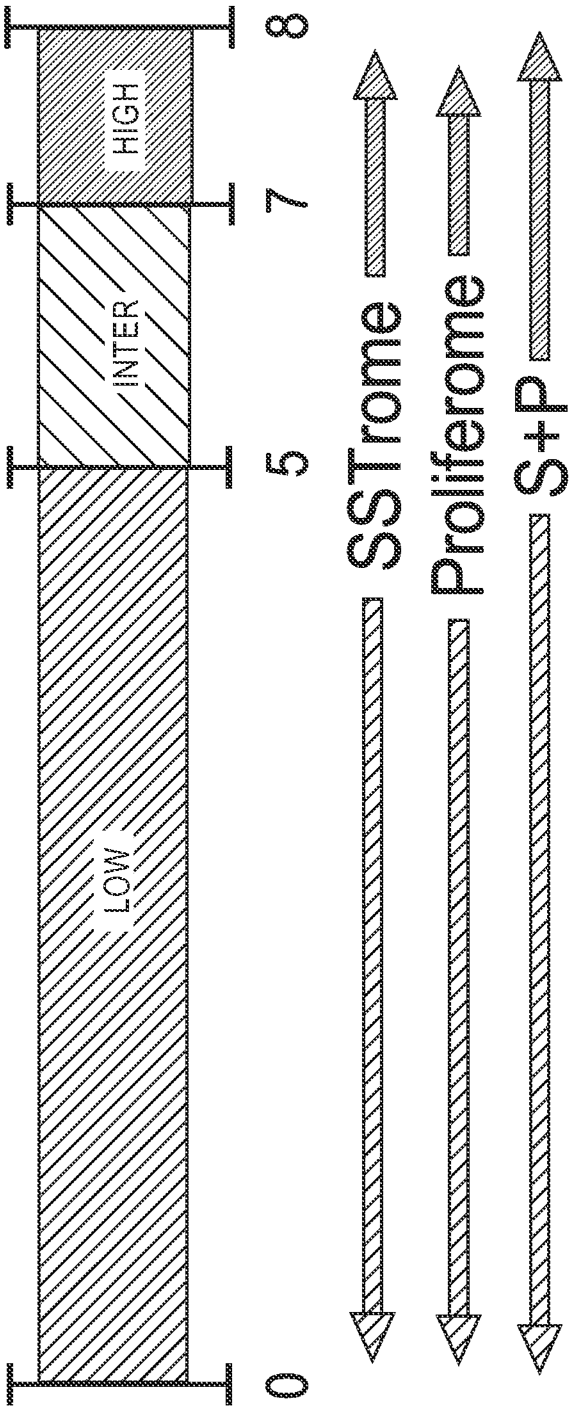
FIG. 34 is a nomogram for somatostatin analog treated patients including the mathematically-derived score as well as the SSTRome, Proliferome, and their combination.

An assessment of individual algorithms or gene clusters identified that samples would be categorized as exhibiting disease in 33-75% of cases (FIG. 33A). In comparison to a best of 3 score (56%) a combination of elevations in the SSTRome and Proliferome resulted in the lowest number of cases (28%) predicted as exhibiting progressive disease (FIG. 33B). With reference to FIG. 34, the nomogram for somatostatin analog treated patients, named "NETest 4," therefore includes the MAARC-NET score as well as the SSTRome, proliferome and their combination.

Figure 35A:
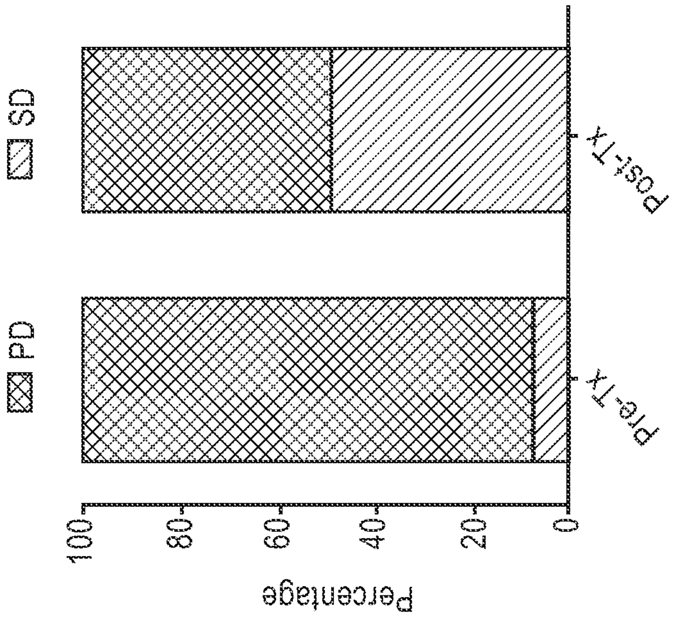
FIGS. 35A-35B are graphs that demonstrate therapeutic efficacy of SSAs and the proportion of patients with low/high NETest scores that developed disease recurrence.

Utility of NETEST and Gene Expression for the Prediction of Somatostatin Analog Efficacy—To evaluate the utility of the NETest in therapy, the relationship between SSAs and clinically defined outcomes (per RECIST criteria) were evaluated. Samples were collected both pre-therapy as well as monthly in twenty-eight patients. Imaging was available to stage and categorize disease patterns pre- and during therapy (up to 12 months follow-up). In this prospective sample set, SSA resulted in a significant reduction in the number of patients with progressive disease (FIG. 35A).

Scores were also determined in blood samples collected prior to as well as monthly during SSA treatment to evaluate whether early alterations were predictive of outcome, i.e., response to therapy.

Figure 35B:
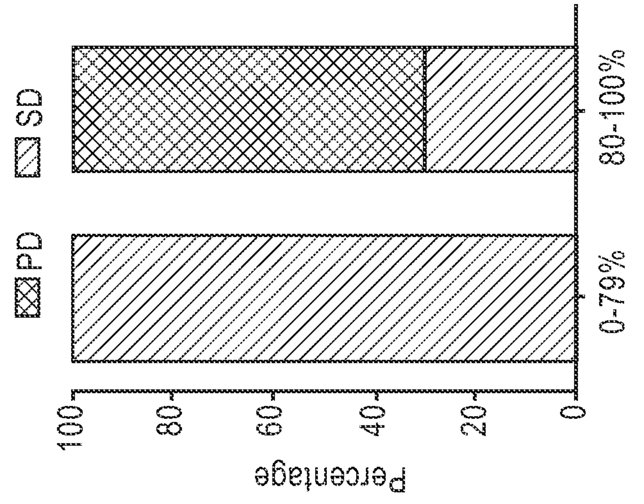

With reference to FIG. 35B, the results identify that elevated NETest scores (80-100% activity) measured at any time point during therapy were predictive of therapeutic responsiveness. With reference to FIG. 36A, a significant rise in the NETest (80-100%) occurred from 48-252 days (mean=105 days) prior to the detection of clinically significant disease (PD). The mean time for CgA was 70 days (range: 0-196 days). The NETest was more informative, occurring at an earlier time (p=0.04), and in more patients (high activity was noted in 100%) than CgA (57% exhibited >25% elevation, p=0.016).

Figure 36B:
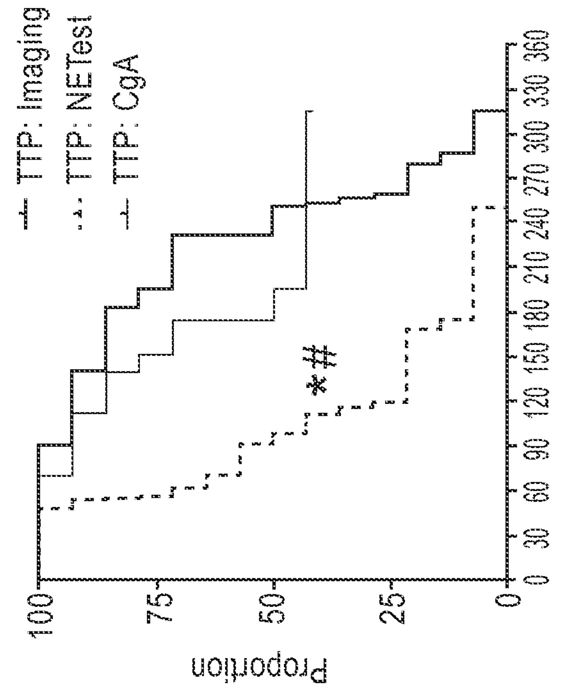
FIGS. 36A-36B are graphs that demonstrate the time point when either the NETest was elevated (>80%) or CgA was abnormal prior to the development of image positive disease recurrence as well as the times that these events occurred prior to image-positive disease recurrence.
Figure 36A:
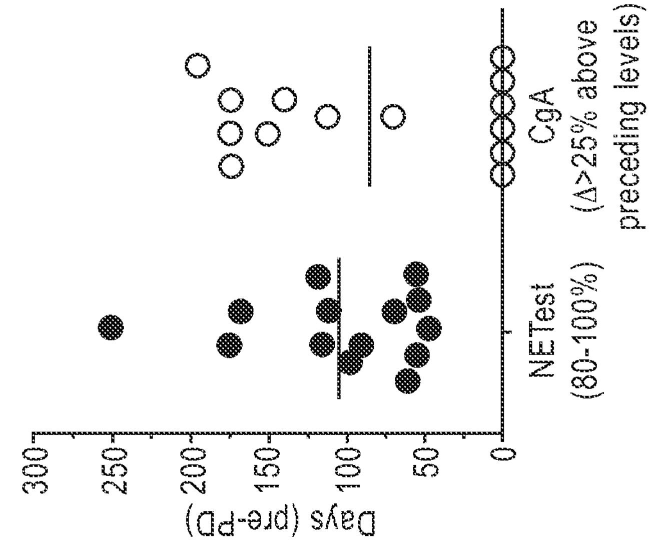

With reference to FIG. 36B, the elevation in NETest (80-100% score) occurred at a significantly earlier time (94.5 days) than image-identifiable disease progression (241 days) in the 14 patients (*p<0.0001, $Chi^2$=19). A similar analysis for CgA identified that this was not different to image-based assessment (FIG. 36B, 185.5 days vs. 241 days). CgA alterations occurred significantly later than the NETest (p=0.002, $Chi^2$=13.6).

Utility of NETEST and Gene Expression for the Prediction of Disease Recurrence—Utility of NETEST To evaluate the utility of the NETest disease recurrence, the relationship between the NETest and clinically defined outcomes (per RECIST criteria) was evaluated in a long-term prospective study. Samples were collected both pre-therapy as well as at intervals up to five years in thirty four patients. Imaging was available to stage and categorize disease patterns pre- and during therapy (up to 65 months follow-up).

Figure 37A:
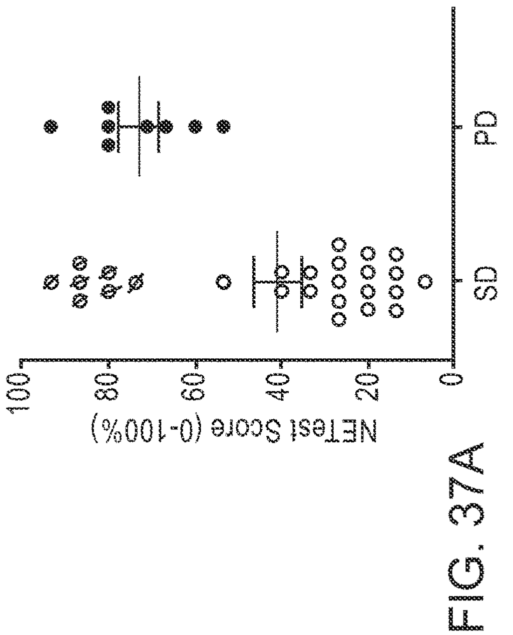
FIGS. 37A-37D are graphs that demonstrate the NETest scores prior to long-term follow up (FIG. 37A), and the times to relapse in patients with elevated scores (FIGS. 37B, 37D) or disease-free time (FIG. 37C).
Figure 37B:
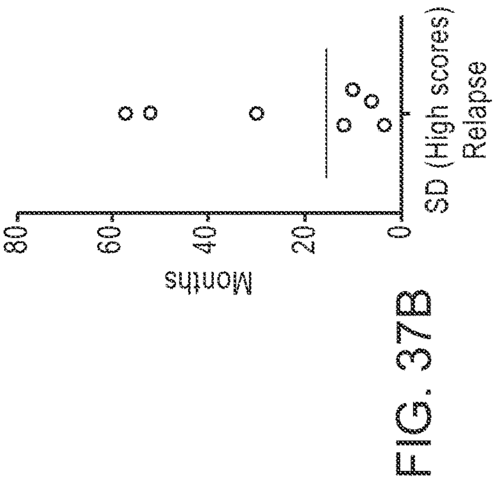
Figure 37C:
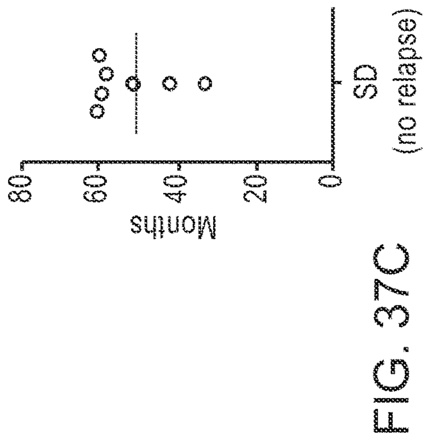

In this prospective sample set, the initial NETest scores were significantly elevated in the PD patients (median: 75%, range 53-94%) compared to the SD patients (median: 26%, range 7-94%; p=0.01) (FIG. 37A). Eight SD patients had levels >40%. Of these 7 developed disease recurrence in a median of 12.2 months (range 3.6-57.7; FIG. 37B). With reference to FIG. 37C, seven of the initial SD patients (with low NETest scores) did not develop recurrent disease. The median follow-up time was 58 months (range: 32-64).

Figure 37D:
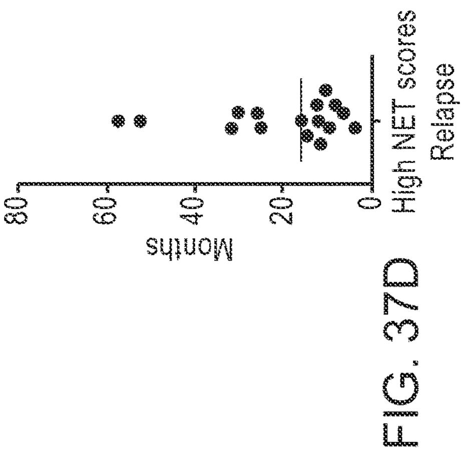

Sixteen events of progressive disease were identified over the time course. Each was associated with elevated NETest (scores >80%). With reference to FIG. 37D, the median time to progression for patients with elevated scores was 13.4 months (range: 3.6-57).

Overall, 23/24 events where the NETest was elevated was associated with development of disease recurrence in median ~13 months. Seven of seven with consistently low scores were disease free (up to 5 years). The accuracy of the test was 97%.

Utility of NET Genes as Surrogate Measure of Tumor Proliferation and Imaging—The utility of NETest genes as well as clusters of genes to function as surrogate markers of histopathological and imaging parameters was evaluated. A particular focus was placed on the Ki-67 index (a marker of tumor proliferation) and on somatostatin-based imaging e.g., $^{68}$Ga-PET. This was undertaken to demonstrate that the NETest and elements thereof could have clinical utility as adjuncts for standard clinical measures. As an example, Ki-67 measurements are tissue based and therefore are invasive. Demonstrating a blood-derived correlate would provide a real-time measure of tumor growth without the need for a biopsy.

These analyses were conducted in two separate datasets: Dataset 1 (n=28) and Dataset 2 (n=22). Dataset 1 included patients who were collected for therapeutic intervention, namely peptide receptor radionucleotide therapy (PRRT). Dataset 2 included patients who exhibited stable disease and were undergoing routine follow-up.

Figure 38A:
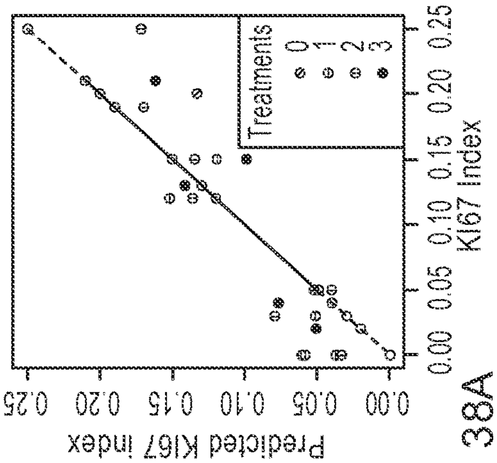
FIGS. 38A-38F are graphs including predicted Ki67 index versus Ki67 index in (FIGS. 38A-38B) SSTRome, (FIGS. 38C-38E) All genes, and (FIGS. 38D-38F) high relevant genes (KRAS, SSTR4, and VPS13C).

A Surrogate for the Ki-67 Index: Multivariate regression analysis did not identify any significant correlation between individual gene expression and the Ki-67 index (a marker of tumor proliferation) in either of the two groups. With reference to FIGS. 38A and 38B, examination of somatostatin receptor expression identified significant correlations (R=0.9, $p=2\times10^{-8}$) with Ki67 in each of the tumor groups.

Figure 38C:
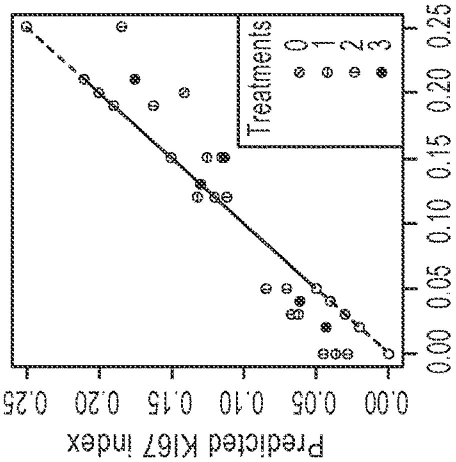
Figure 38D:
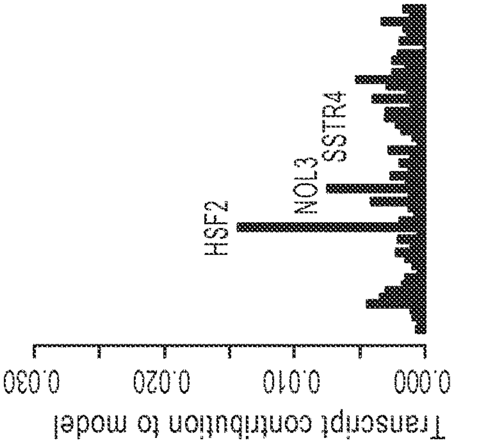
Figure 38B:
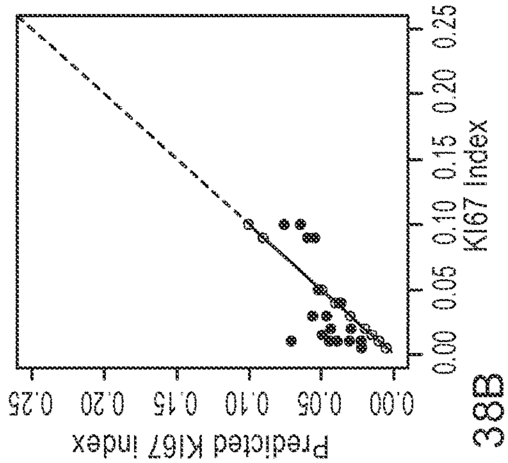
Figure 38E:
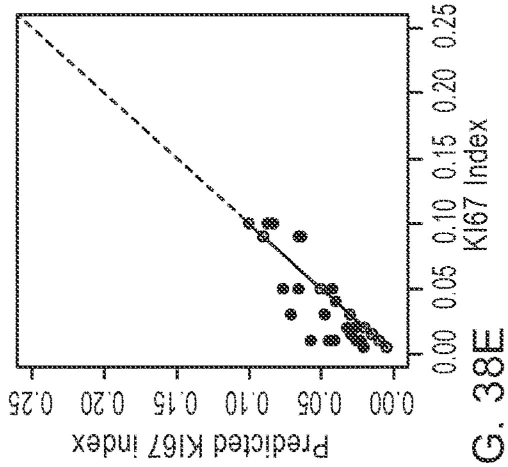
Figure 38F:
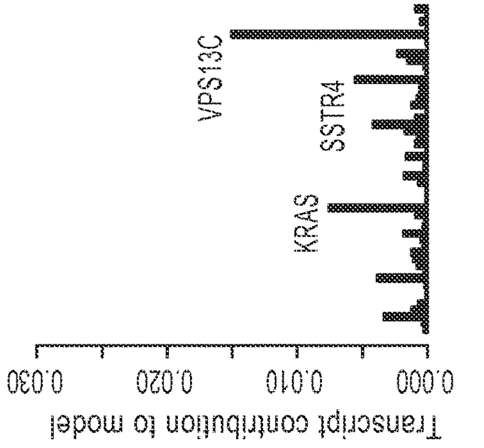
Figure 39D:
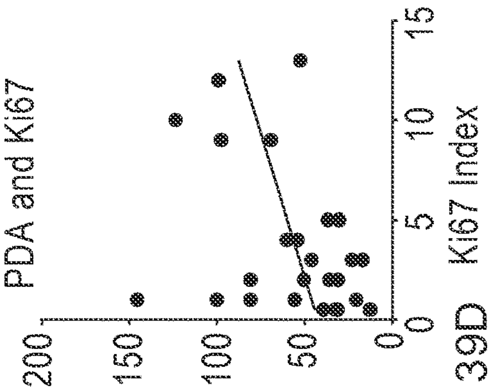
FIGS. 39A-39F are graphs showing the correlations (linear regression) between gene clusters or algorithms, (FIG. 39A) SSTRome and Ki67, (FIG. 39B) TDA and Ki67, (FIG. 39C) Proliferome and Ki67, (FIG. 39D) PDA and Ki67, (FIG. 39E) IDA and Ki67, and (FIG. 39F) PDA and Ki67, each versus the Ki-67 index.
Figure 39F:
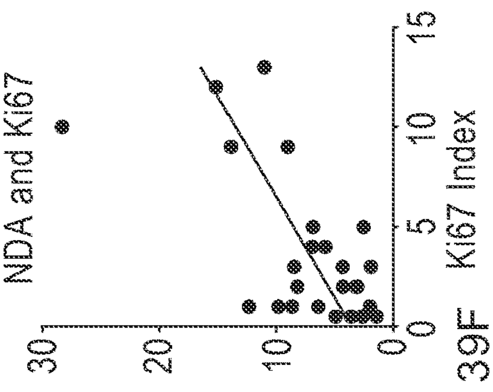
Figure 39C:
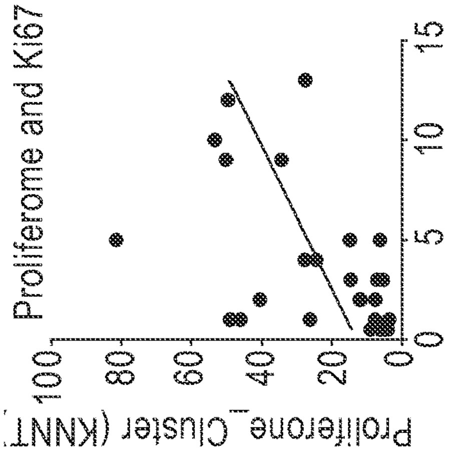
Figure 39E:
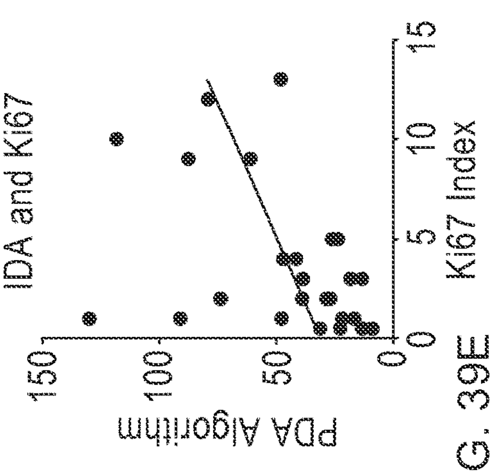
Figure 39A:
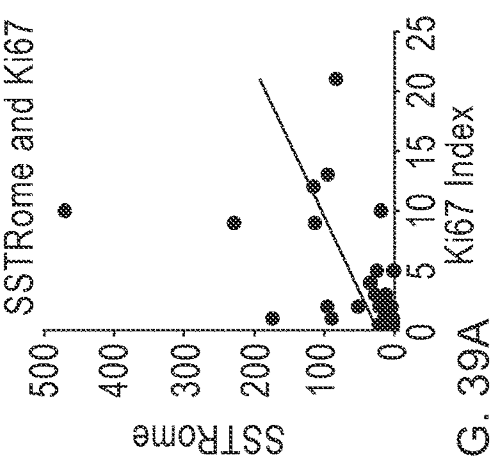
Figure 39B:
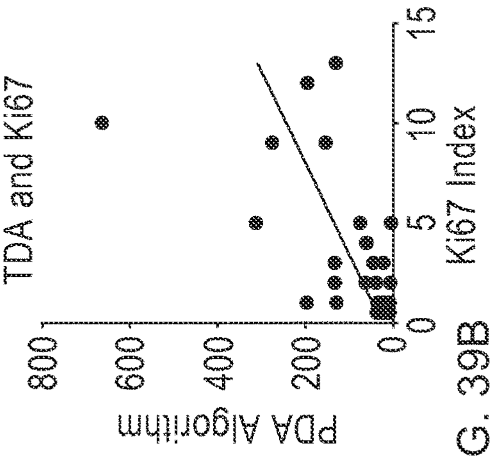

An examination of all genes in the NETest identified significantly higher correlations with Ki-67 (R=0.93-98, $p=10^{-9}$-$10^{-13}$, FIGS. 38C-38E). The single most informative gene was SSTR4 (FIG. 38D-38F). These data demonstrate firstly, that the NETest as a whole can be used as a liquid biopsy to determine the proliferative index of the tumor i.e., provides a surrogate marker for a tissue-based histopathological measurement. Secondly, expression of circulating somatostatin receptor genes can also be used as a measure of tumor proliferation.

Proliferome+SSTRome algorithm is also referred to as Progressive Diagnostic V; the highly relevant genes (KRAS, SSTR4, and VPS13C) algorithm is also referred to as Progressive Diagnostic VI; the highly relevant genes+SSTRome algorithm is also referred to as Progressive Diagnostic VII.

With reference to FIGS. 39A-39F, correlations (linear regression) between gene clusters (SSTRome and proliferome) or each of the algorithms and the Ki-67 index, are shown. Examination of individual gene clusters confirmed that the SSTRome and Proliferome correlated with the Ki-67 index (R=0.16-0.25, p<0.05, FIGS. 39A, 39C). Analysis of the algorithms identified that the NDA and TDA algorithms were highly correlated with the Ki-67 index (R=0.34-0.42, p<0.002, FIGS. 39B, 39F) while the PDA and IDA were less well-correlated (R=0.14-0.17, p=0.06, FIGS. 39D, 39E). These results demonstrate that gene clusters and algorithms including biologically relevant tumor information e.g., SSTRome can be utilized as a measure of tumor tissue proliferation.

Figure 40A:
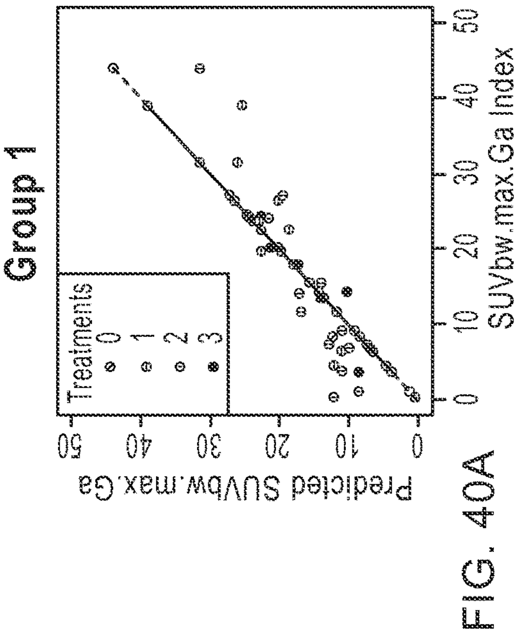
FIGS. 40A-40D are graphs modeling predicted SUVmax (tumor uptake—a measure of receptor density/target availability) for SSTRome (Group I.
Figure 40B:
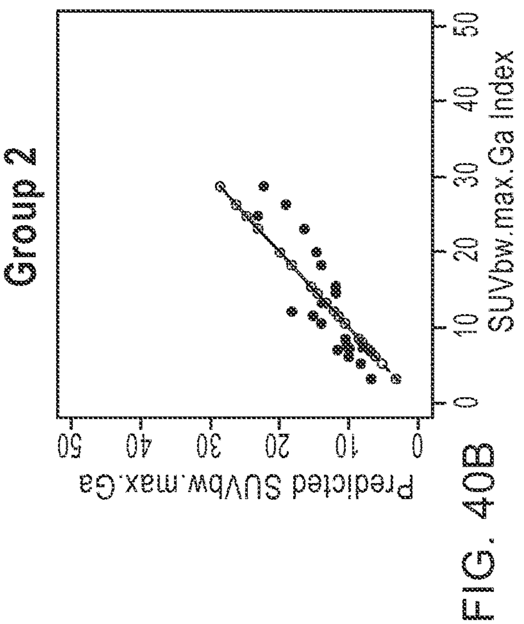
Figure 40C:
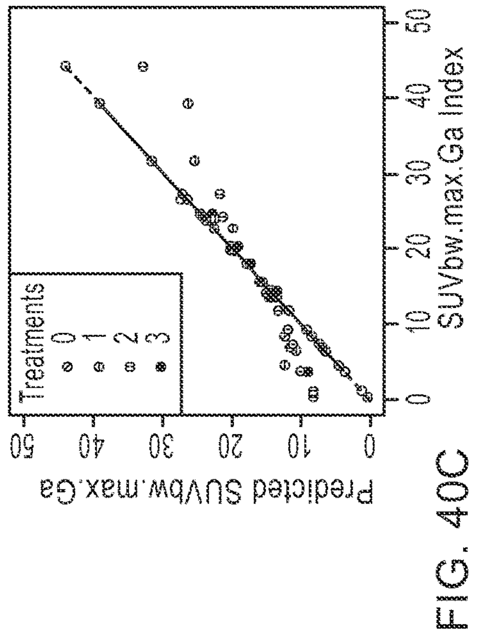
Figure 40D:
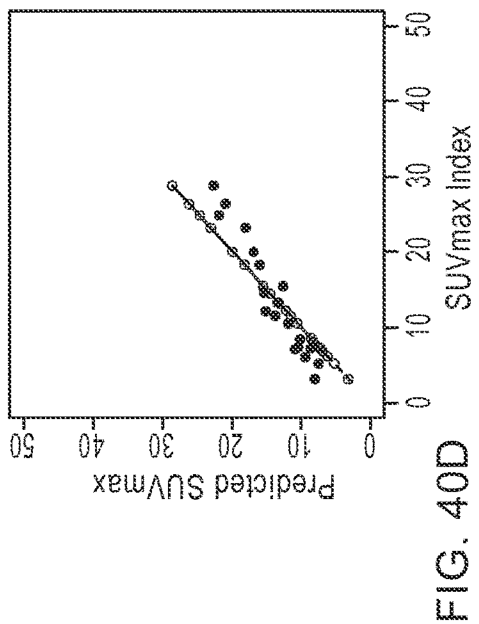

Relationship with Somatostatin-Based Imaging: Next was examined whether genes in the test correlated with two variables from somatostatin-based imaging, the SUVbmax (tumor uptake—a measure of receptor density/target availability) and the MTV (molecular tumor volume—a measure of the tumor burden). Multivariate regression analysis did not identify any single gene to correlate with the SUVmax. However, both the SSTRome as well as the NETest genes as a group were well correlated with the SUVmax. Correlations in both groups ranged between R=0.88-0.94 ($p<10^{-7}$) for the SSTRome (FIGS. 40A-40B) and R=0.97-0.98, $p<10^{-13}$ for the NET gene set (FIGS. 40C-40D).

Figures 41A, 41B, 41C, 41D, 41E, 41F:
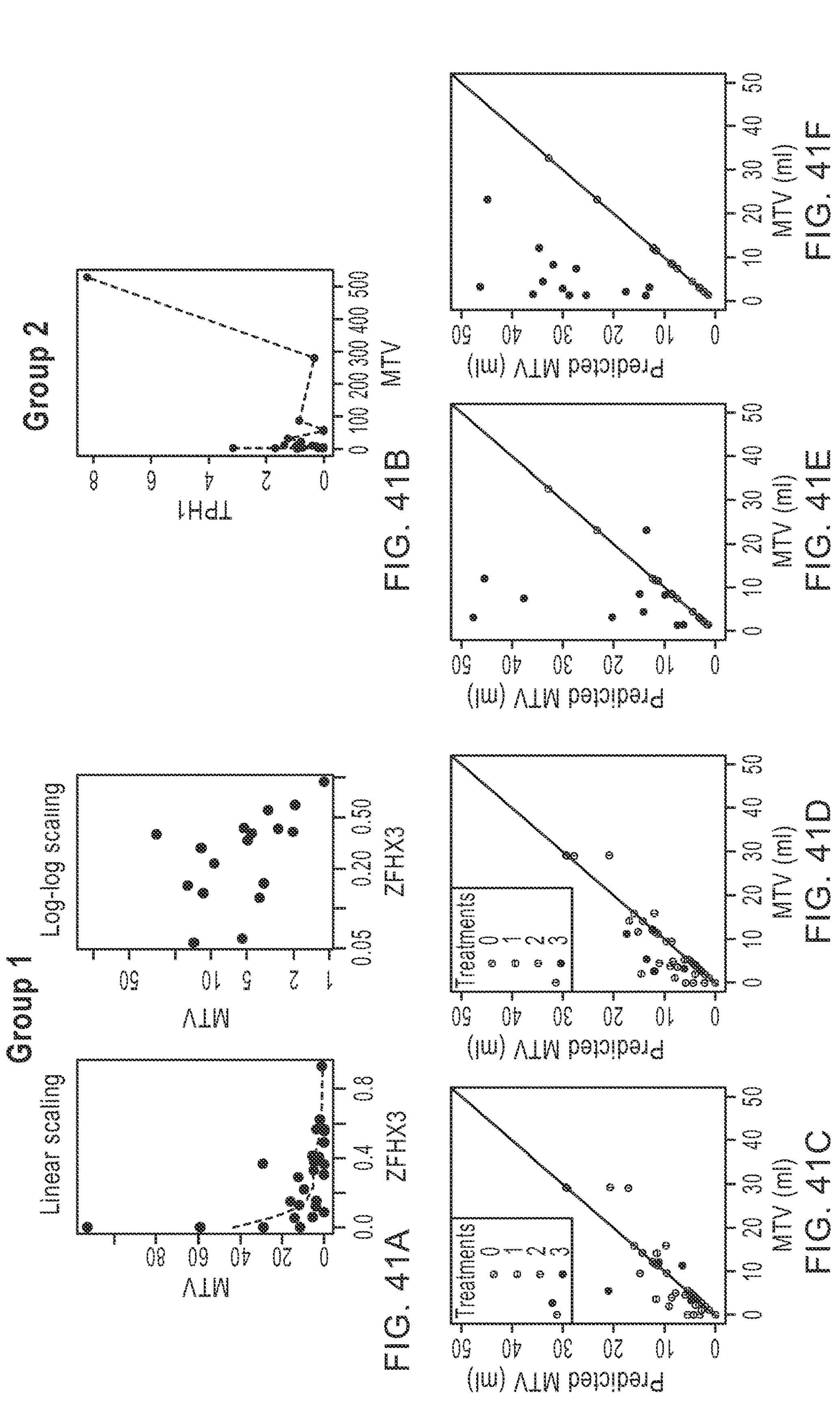
FIGS. 41A-41F are graphs modeling MTV (molecular tumor volume—a measure of the tumor burden) in individual genes (FIGS. 41A-41B), SSTRome (FIGS. 41C-41E), and all genes (FIGS. 41D-41F).

Multivariate regression analysis identified ZFHX3 as a marker of MTV in Group 1 (R=0.98, FIG. 41A) while TPH1 was correlated with MTV in Group 2 (R=0.76, FIG. 41B).

Similarly to the SUVmax, both the SSTRome as well as the NETest genes as a group were well correlated with the MTV. Correlations in both groups ranged between R=0.72-0.77 ($p<10^{-4}$) for the SSTRome (FIGS. 41C-41E) and R=0.91-0.95, $p<10^{-12}$ for the NET gene set (FIGS. 41D-41F).

These data demonstrate that genes in the NETest correlate and can be used to estimate both the target availability for somatostatin analog-based therapies as well as provide a measure of the tumor burden. Both these aspects are critical for directing therapy as well as measuring the efficacy of therapy.

ZFHX3 as a Marker for Disease Assessment: The identification of ZFHX3 as the best marker for MTV, as shown in FIG. 41A, suggests that expression of this gene may have clinical utility as a measure of tumor burden and changes thereof. ZFHX3 is a zinc finger protein involved in the regulation of neuronal differentiation through the control of cell cycle arrest. Loss of ZFHX3 expression with a subsequent loss of cell cycle arrest therefore is related to tumor proliferation and the development of new lesions and/or progression of disease.

It was examined whether measurements of ZFHX3 may provide a marker of new growth/progression in NETs and if that alteration in ZFHX3 may reflect response to therapy or therapy failure (progression). Expression of this gene was initially assessed in patients who had evidence of new lesions.

Figures 42A, 42B, 42C:
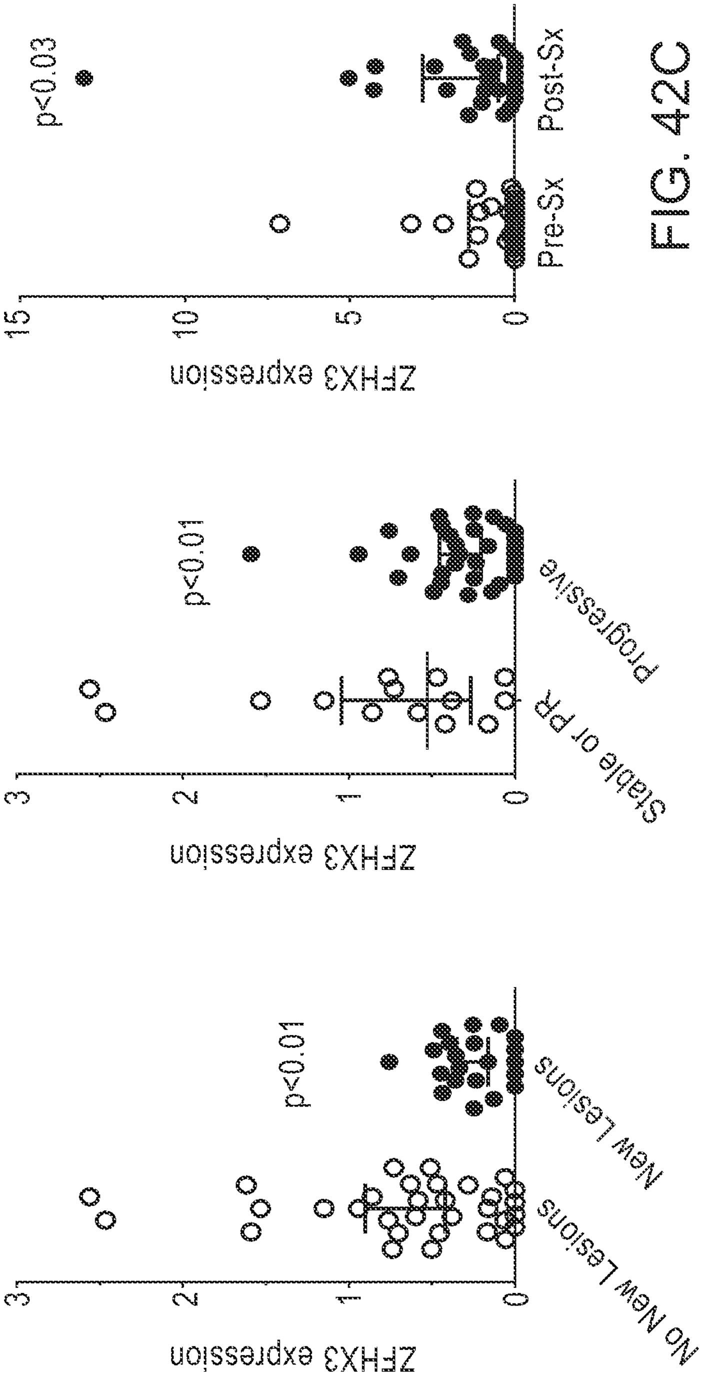
FIGS. 42A-42C are graphs showing ZFHX3 expression in patients identified with (FIG. 42A) new lesions by imaging, with (FIG. 42B) progressive disease by RECIST, and (FIG. 42C) following surgery.

With reference to FIG. 42A, patients who had developed new lesions (identified by imaging) expressed significantly decreased ZFHX3. With reference to FIG. 42B, those patients that were determined as SD also have significantly higher levels than those who were progressive. Moreover, with reference to FIG. 42C, expression of the gene was increased following surgery.

Figure 43B:
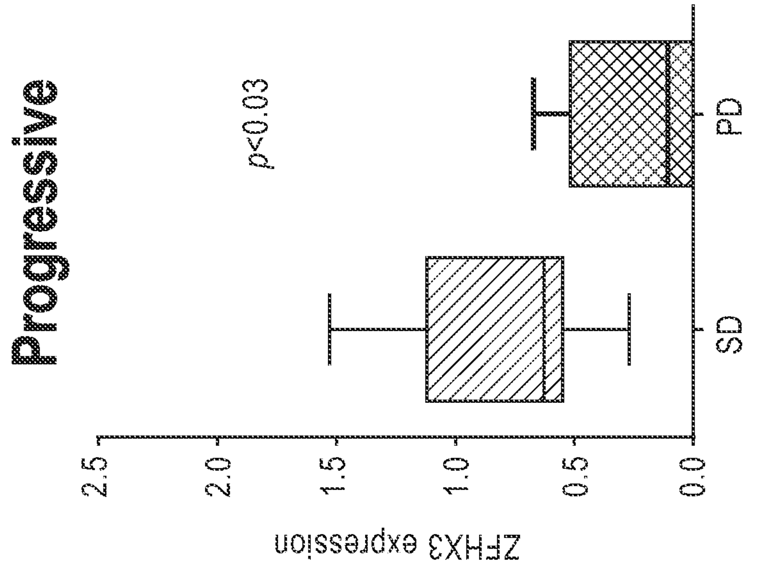
FIGS. 43A-43B are graphs showing ZFHX3 expression in (FIG. 43A) patients who remain in a stable disease state of GEP-NEN versus (FIG. 43B) those who develop a progressive disease state of GEP-NEN.
Figure 43A:
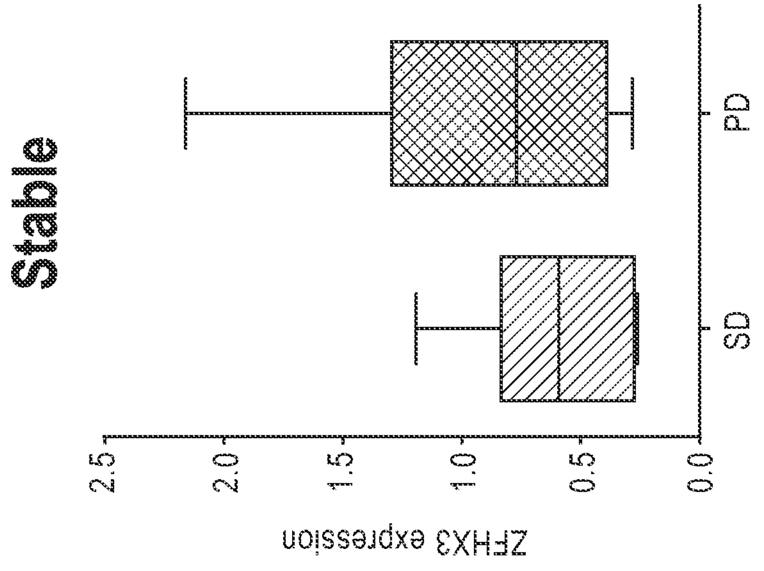

With reference to FIGS. 43A-43B, long-term follow-up (>3 years) in a group identified that patients who remained stable exhibited no changes in ZFHX3 expression over this time period, while patients who developed progressive disease had significantly lower expression levels.

These data demonstrate that ZFHX3 expression correlates with the development of new lesions and a decrease in expression can be used to define disease progression.

Utility of NETEST and Gene Expression for the Prediction of Therapeutic Efficacy—To further evaluate the utility of the NETest in therapy, the relationship between PRRT and clinically defined (per RECIST criteria) outcomes were evaluated. Samples were collected both pre-therapy as well as at follow-up in fifty-four patients. Imaging was available to stage and categorize disease patterns pre- and post-therapy (at 3 and 6 month follow-up).

Figure 44A:
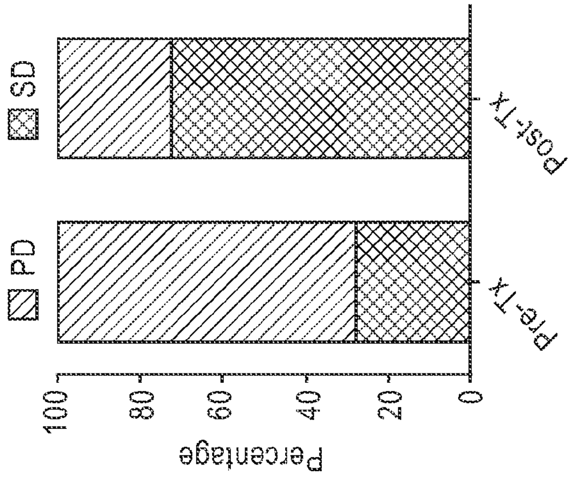
FIGS. 44A-44C are graphs representing (FIG. 44A) the effectiveness of peptide receptor radionucleotide therapy (PRRT), (FIG. 44B) changes in NETest Score versus clinical status at 6M Follow-up (FuP) in responders (R) and non-responders (NR)
Figure 44B:
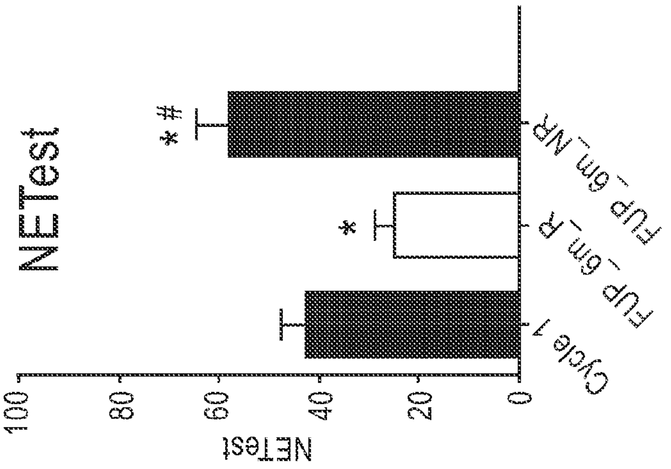
Figure 44C:
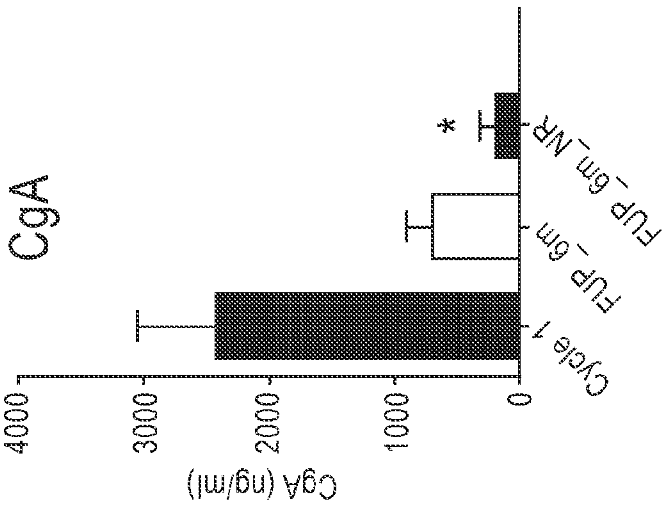
Figure 45:
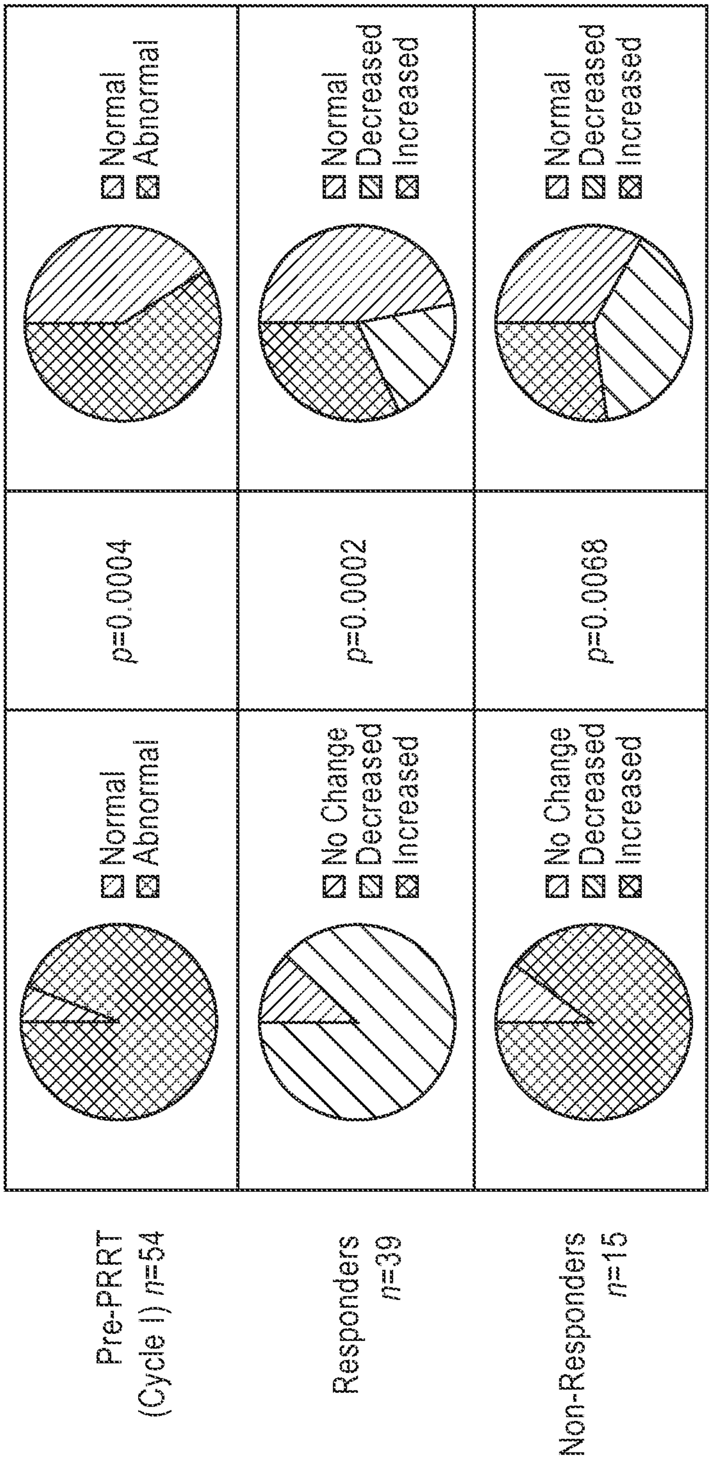
FIG. 45 are graphs showing concordance between the NETest in responders and non-responders prior to and after therapy and in addition the comparison to CgA.
Figure 46B:
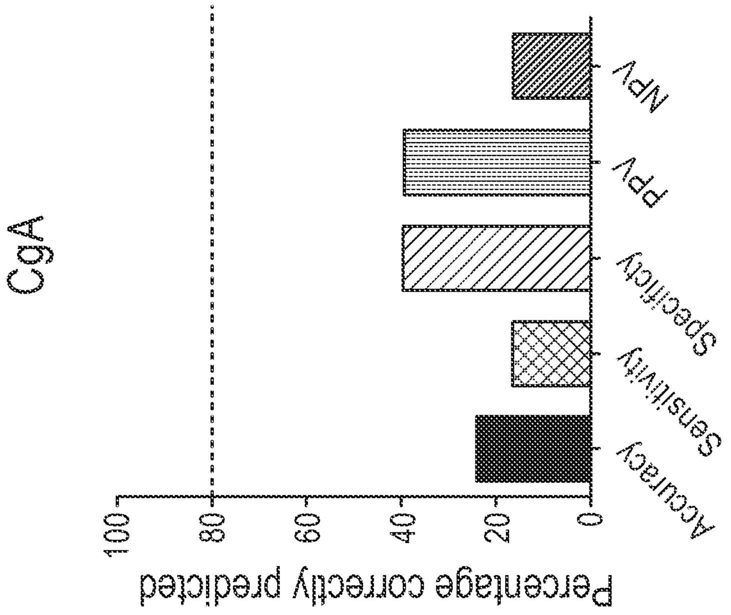
FIGS. 46A-46B shows the accuracy of the NETest Score versus CgA for treatment responses.
Figure 46A:
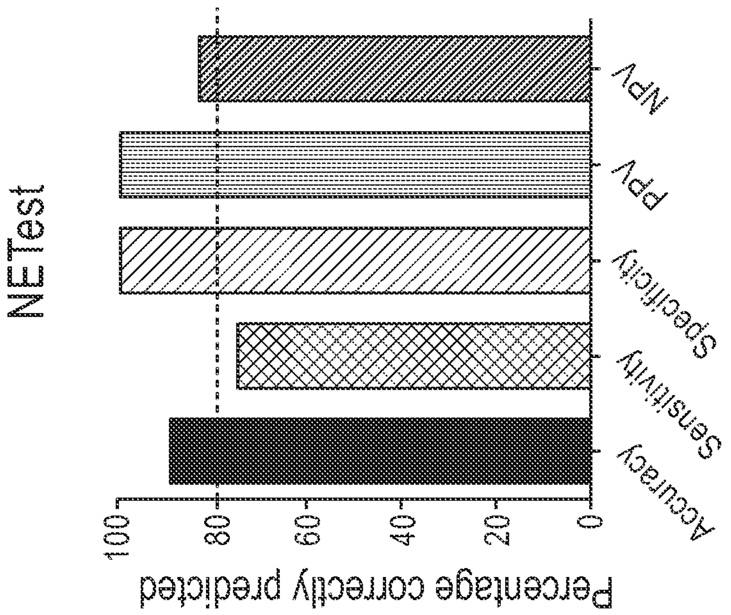

In this prospective sample set, radiotherapy significantly resulted in a reduction in the number of patients with progressive disease (FIG. 44A). Patients who did not respond to therapy i.e., categorized as progressive disease at the 6 month follow-up period exhibited an increase in the NETest score. The score was significantly reduced in patients with SD at this time point (FIG. 44B). No significant alterations were noted for CgA (FIG. 44C). Alterations in NETest paralleled changes in therapeutic responses (FIG. 45). The metrics for biomarkers and outcome identified that the NETest had an accuracy of 89%, sensitivity 75%, specificity 100%, PPV 100% and NPV 83% (FIG. 46A). With reference to FIG. 46B, CgA had an accuracy of 24%, sensitivity 17%, specificity 40%, PPV 40% and NPV 17%. The NETest significantly outperformed CgA (Chi-square=27.4; $p=1.2\times10^{-7}$).

Pre-treatment NETest scores as well as grading were available and used to identify whether a combination of gene expression and clinical parameters were predictive of outcome, i.e., response to therapy.

Figure 47A:
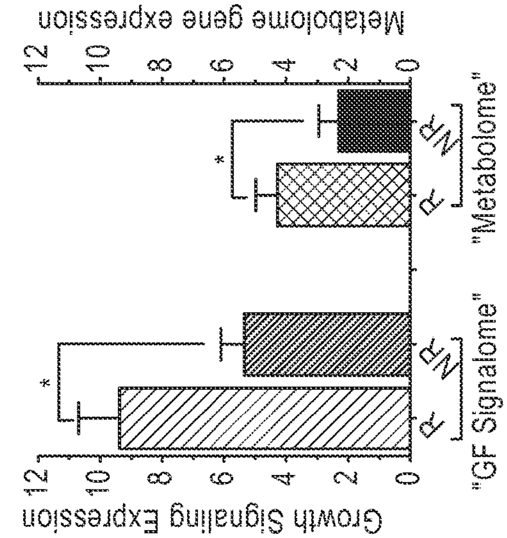
FIG. 47A-47D shows expression of two subsets of NETest genes, the signalome and metabolome in blood samples prior to therapy and the differences between responders (R) and non-responders (NR), the predictive utility of each as well as when combined into a biological index (FIG. 47B), the utility for predicting treatment response alone (Quotient) or as a combination with grade (Combination) (FIG. 47C) and the metrics of the combination for predicting the outcome of PRRT therapy (FIG. 47D).
Figure 47B:
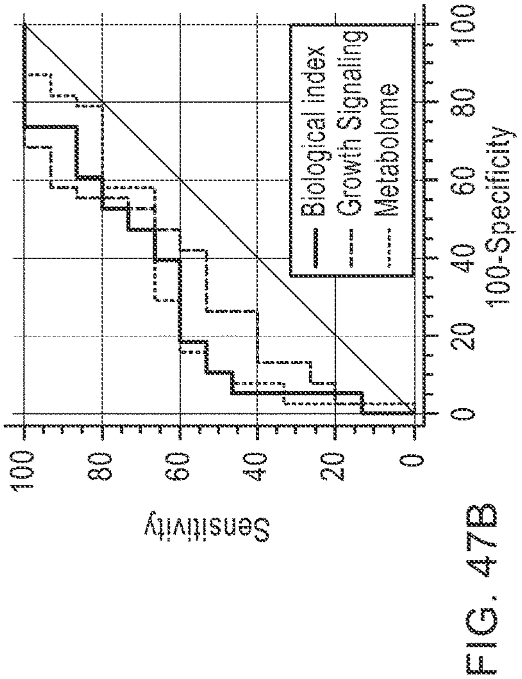

With reference to FIG. 47A, a subset of NETest gene expression levels were significantly different between responders and non-responders prior to therapy. These included genes linked to growth factor signaling (GF signalome: ARA4F, BRAF, KRAS and RAF1) as well as genes linked to metabolism (including A TP6V1H, OAZ2, PANK2, PLD3). Specifically, PRRT-responders exhibited significantly elevated growth factor signaling (9.4±1.3 vs. 5.3±0.7, p=0.05) and significantly elevated metabolomic gene expression (4.37 vs. 2.3±0.6, p=0.03) prior to PRRT. An integration of the two “clusters” (GF signalome+metabolome) into a “Biological Index” through summation of gene expression enabled prediction of future PRRT-responders from non-responders. A cut-off of 5.9 (normalized gene expression) exhibited >85% specificity for predicting response (>5.9 predicted PRRT responders) and resulted in an AUC of 0.74±0.08 (z-statistic=2.915, p=0.0036) (FIG. 47B).

Figure 47C:
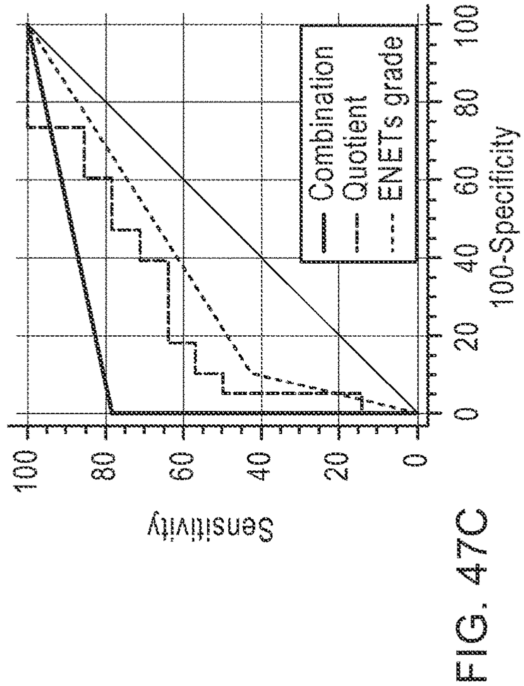

No clinical parameters were predictive of PRRT response except tumor grade. Low grade tumors responded (77%) to therapy while ~50% of high grade lesions were associated with responses. Grading alone was only 65% accurate (p=0.1). In contrast a “Prediction Quotient” which comprised the combination of the Biological Index (“GF signalome”+“metabolome”) and the tumor grade was significantly (92%) more accurate. The Prediction Quotient had a significantly better AUC (0.90±0.07) than histological grade alone for predicting treatment response (AUC=0.66, difference between areas 0.23, z-statistic 2.25, p=0.024) (FIG. 47C).

Figure 47D:
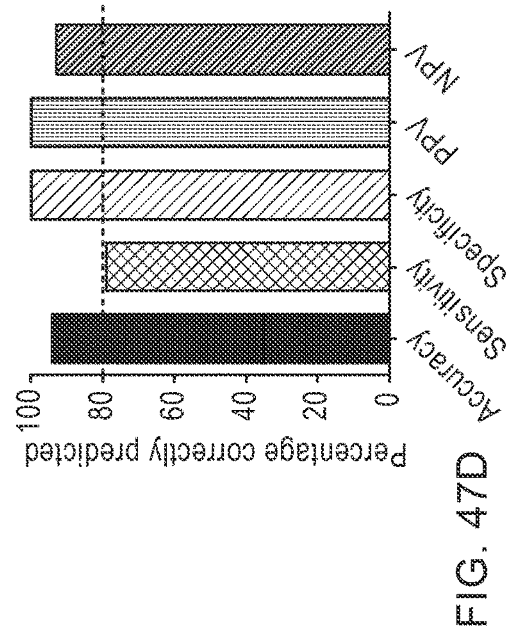

The Prediction Quotient was also clinically useful. Patients could be segregated into Low Grade/High Ome and High Grade/Low Ome groups. The latter had a significantly lower PFS (17 months) than the low grade/high Ome group (PFS not reached, Log-rank: 26.8; p<0.0001: FIG. 47D). The Hazard Ratio was 53.3.

These results demonstrate that alterations in score correlate with treatment responses and that circulating NET transcript measurements prior to therapy are predictive of outcome to PRRT.

We claim:

1. A method for treating a gastroenteropancreatic neuroendocrine neoplasm (GEP-NEN) in a human subject in need thereof, comprising:

determining the expression levels of at least 23 biomarkers from a test sample from the human subject by performing reverse transcription polymerase chain reaction (RT-PCR) with a plurality of probes or primers specific to detect the expression of the at least 23 biomarkers, wherein the at least 23 biomarkers comprise APLP2, ARAF, CD59, CTGF, FZD7, KRAS, MKI67/K167, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, ZFHX3, and ALG9, wherein the test sample is blood, serum, plasma, or neoplastic tissue;

normalizing the expression levels of APLP2, ARAF, CD59, CTGF, FZD7, KRAS, MKI67/K167, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, and ZFHX3 to the expression level of ALG9 to obtain normalized expression levels;

classifying the test sample with respect to the presence or development of a GEP-NEN using the normalized expression levels in a classification system, wherein the classification system is a machine learning system that comprises four different algorithms: Support Vector Machine, Linear Discrimination Analysis, K-Nearest Neighbor, and Naïve Bayes;

assigning a score based on a result of each of the four different algorithms;

comparing the score with a predetermined cutoff value;

determining the presence of a GEP-NEN in the subject when the score is equal to or greater than the predetermined cutoff value, wherein the predetermined cutoff value is 2 on a MAARC-NET scoring system scale of 0-8;

identifying a level of risk for the human subject to develop a progressive GEP-NEN comprising (a) identifying an intermediate level of risk for developing a progressive GEP-NEN when the score is equal to or greater than a predetermined cutoff value of 5 and less than a predetermined cutoff value of 7 on the MAARC-NET scoring system scale of 0-8; or (b) identifying a high level of risk for developing a progressive GEP-NEN when the score is equal to or greater than a predetermined cutoff value of 7 on the MAARC-NET scoring system scale of 0-8; and administering a treatment to the subject identified as having an intermediate level or high level of risk for developing a progressive GEP-NEN, wherein the treatment comprises surgery or drug therapy.

2. The method of claim 1, further comprising, determining the presence of a progressive GEP-NEN in the human subject when the score is equal to or higher than the predetermined cutoff value, wherein the predetermined cutoff value is 5 on the MAARC-NET scoring system scale of 0-8.

3. The method of claim 1, wherein the biomarker is RNA or cDNA.

4. The method of claim 3, wherein when the biomarker is RNA, the RNA is reverse transcribed to produce cDNA, and the produced cDNA expression level is detected.

5. The method of claim 3, wherein when the biomarker is RNA or cDNA, the RNA or cDNA detected by forming a complex between the RNA or cDNA and a labeled nucleic acid probe or primer.

6. The method of claim 5, wherein when the label is a fluorescent label.

7. The method of claim 5, wherein the complex between the RNA or cDNA and the labeled nucleic acid probe or primer is a hybridization complex.

8. The method of claim 1, wherein the expression level of the biomarker is detected by forming a complex between the biomarker and a labeled probe or primer.

9. The method of claim 1, wherein a subject in need thereof is a subject diagnosed with a GEP-NEN, a subject having at least one GEP-NEN symptom or a subject having a predisposition or familial history for developing a GEP-NEN.

* * * * *

SEQUENCE LISTING

```
<160> NUMBER OF SEQ ID NOS: 52

<210> SEQ ID NO 1
<211> LENGTH: 6158
<212> TYPE: DNA
<213> ORGANISM: Homo sapiens

<400> SEQUENCE: 1

gtcttttgtc cctcggcgga caccgtttgc cagccaaagc tatgtctgcg cgctcaccga     60

cttcataggg tgccgaattc ttttttcccc aggcttgcca tggctagtcg aggggctcgg    120

cagcgcctga agggcagcgg ggccagcagt ggggatacgg ccccggctgc ggacaagctg    180

cgggagctgc tgggcagccg agaggcgggc ggcgcggagc accggaccga gttatctggg    240

aacaaagcag gacaagtctg ggcacctgaa ggatctactg ctttcaagtg tctgctttca    300

gcaaggttat gtgctgctct cctgagcaac atctctgact gtgatgaaac attcaactac    360

tgggagccaa cacactacct catctatggg gaagggtttc agacttggga atattcccca    420

gcatatgcca ttcgctccta tgcttacctg ttgcttcatg cctggccagc tgcatttcat    480

gcaagaattc tacaaactaa taagattctt gtgttttact tttgcgatg tcttctggct    540

tttgtgagct gtatttgtga actttacttt tacaaggctg tgtgcaagaa gtttgggttg    600

cacgtgagtc gaatgatgct agccttcttg gttctcagca ctggcatgtt ttgctcatca    660

tcagcattcc ttcctagtag cttctgtatg tacactacgt tgatagccat gactggatgg    720

tatatggaca agacttccat tgctgtgctg ggagtagcag ctggggctat cttaggctgg    780

ccattcagtg cagctcttgg tttacccatt gcctttgatt tgctggtcat gaaacacagg    840

tggaagagtt tctttcattg gtcgctgatg gccctcatac tatttctggt gcctgtggtg    900

gtcattgaca gctactatta tgggaagttg gtgattgcac cactcaacat tgttttgtat    960

aatgtcttta ctcctcatgg acctgatctt tatggtacag aaccctggta tttctattta   1020

attaatggat ttctgaattt caatgtagcc tttgctttgg ctctcctagt cctaccactg   1080

acttctctta tggaatacct gctgcagaga tttcatgttc agaatttagg ccacccgtat   1140

tggcttacct tggctccaat gtatatttgg tttataattt tcttcatcca gcctcacaaa   1200

gaggagagat ttcttttccc tgtgtatcca cttatatgtc tctgtggcgc tgtggctctc   1260

tctgcacttc agcacagttt tctgtacttc cagaaatgtt accactttgt gtttcaacga   1320

tatcgcctgg agcactatac tgtgacatcg aattggctgg cattaggaac tgtcttcctg   1380

tttgggctct tgtcattttc tcgctctgtg gcactgttca gaggatatca cgggcccctt   1440

gatttgtatc cagaatttta ccgaattgct acagacccaa ccatccacac tgtcccagaa   1500

ggcagacctg tgaatgtctg tgtgggaaaa gagtggtatc gatttcccag cagcttcctt   1560

cttcctgaca attggcagct tcagttcatt ccatcagagt tcagaggtca gttaccaaaa   1620

ccttttgcag aaggacctct ggccacccgg attgttccta ctgacatgaa tgaccagaat   1680

ctagaagagc catccagata tattgatatc agtaaatgcc attatttagt ggatttggac   1740

accatgagag aaacaccccg ggagccaaaa tattcatcca ataaagaaga atggatcagc   1800
```

```
ttggcctata gaccattcct tgatgcttct agatcttcaa agctgctgcg ggcattctat   1860
gtccccttcc tgtcagatca gtatacagtg tacgtaaact acaccatcct caaaccccgg   1920
aaagcaaagc aaatcaggaa gaaaagtgga ggttagcaac acacctgtgg ccccaaagga   1980
caaccatctt gttaactatt gattccagtg acctgactcc ctgcaagtca tcgcctgtaa   2040
catttgtaat aaaggtcttc tgacatgaat actggaatct gggtgctctg ggctagtcaa   2100
agtctatttc aaagtctaat caaagtcaca tttgctccct gtgtgtgtct ctgttctgca   2160
tgtaaacttt ttgcagctag gcagagaaag gccctaaagc acagatagat atattgctcc   2220
acatctcatt gtttttcctc tgttcaatta tttactagac cggagaagag cagaaccaac   2280
ttacaggaag aattgaaaat cctggtactg gatggctgtg ataagctgtt ctccacactc   2340
tggcctggca tctgagaact agcaagcctc tcttaggcca tatgggcttc tccaccaaag   2400
ctgtttggca gctcctagca gaccttctta ttgaaatcct catgctgaaa atgaacacag   2460
cctagttgcc aacccacatg tccttttcac ctccagcaag actaagcttc tttaaagcac   2520
ttcacaggac taggaccctg tcctggagct atctcaggaa aaaggtgacc atttgaggaa   2580
ctgtgaccta attttattat aatgatgcct ctaattttca tttcctttac aaccaactgt   2640
aactataagg ttgtattgct tttttgttca gttttagcat gctatttttt gaattctaga   2700
ctcctccatg tgaagatatc aacagacaaa actacaactg tataggacat atttggagaa   2760
aattctatca attgatacat ttggatgaca tcacattttt aagtaatgta atctgaggcc   2820
attgctgagg aaattaagaa ttttcctttt tttttaacca cccccagtga aaaggatcag   2880
tgtatattta tagcacctat tttttagttc tgtctgttgt gaggcacatc ctgcatgggg   2940
cacttctagt caaataggca atgataagga cctaattaaa atgtgataag tgtatactat   3000
tactttaaaa gcctttacag tcagtacttc agtttacaag gcactttcac agcatctcgt   3060
ttgatcctca cagtcacaac atgtggtaga caaggcaggt gatttttatc cccattttac   3120
agataaggaa acaggctgcg ggtggggagt gaggggaggt aaagatagtt agttgcctaa   3180
ggtcacacag ccagtaagta atagagctgg gactggaacc caggtttcct tactctcatc   3240
tattgctcct ccatattcct cactcaacca tgaaaacatt acttgaaagg actgatgagg   3300
ttaaccagag acctaactga tattgtaact ttctatttta aggaagaatt gtgtctgtat   3360
ttgagttctt tggagcctcc agtctgcctg tgtgttagac cagcacagca gtgctgtgtg   3420
atgcagcctg acctgtggca ggaaagtagt gcttctgttt ggaagtcatg ttcttttgca   3480
gccacacagg atccaaatat cagtactatt cctgtagtca atctggggtc acattatagg   3540
tgccttattt ccctaagggt aactgatctg aatatctgca aataggatga atctattttt   3600
cagaagttcc atctttcatt tttctttttt tttttgagac agagtctcat tctgtcgccc   3660
atgctggagt gcagtggcgc gatctcggct cgctgcaacc tctgcctccc aggttgaagc   3720
aattctcatg cctcagccac ccgagtagct gggattacag gcatgcgcca tcatgcccag   3780
ctaatttatg tatttttagt agagttggag tttcaccatg ttggccaggc tggtcttgga   3840
ctcctgacct caggtcatcc acccgcctca gcctcccaaa gtgctggtat tacaggcgtg   3900
agccaccgca cccagcccca tctttcattt tcaaagagaa gggcattcta ataggaactg   3960
gtgccaagag agaagaaaag aagtgataac agaagaaatg gctagttaca atattaaaaa   4020
gctcctcttt gagatctcct ctgcaggaat atcagagacg gagttgaagc gctggagagg   4080
taataggtct agacagtaca gaacaataac tggggagtgt gtgaggatag actgggctcc   4140
```

-continued cccttgcttg aaagatctct ggcatttaat tctcaattct tgattactat tttccagtgt 4200
aaaactagca catatgatct gactacagga cagagaattt taagtgaaac atttgcctta 4260
cttgcagtaa taatgtgctg ttcttcacag tagctaaggc cctctatgtt tcccagaggt 4320
aaataagaat ccaggaatgg aggtccatct gtgatgaatg gctttttct aatcaaagta 4380 gtataatgct gttttatctg ttttgtcatc ttgtttttt tttttttaa aaaaacaaaa 4440 ccttaattat aatatagcgc aaagaaaggc caggactgat gcagggattc cttggaaata 4500
tcagttccta tcacttttaa aacctgattt tggatctctc tgttctatgt atgtctttag 4560
tgagagcaca atacatggca gaacgctgtg ccaaatgtta taggtaagga atatagaaat 4620
gaatgttttt tgttgtgaag gtgttttcat gtgatatttt ataaacacat tttaaaaaat 4680
ctccatcact ttttagtata ggaaggatag ctttgcctgg gaaaaacagt ttcaacacac 4740
ctgctcagag tagcagttct ccctcaaaaa agcagtgttc agcctgcact gactgttctg 4800
cttgccaaaa ggaggaagca tgcaagatac ttatttctcc atagattgtg gagtatagag 4860
ggatgtggga ctacagatta ttattttttt tccccgagac agagtcttgc tctgtcgccc 4920
aggttggaac acaatggcac gacctcagct cactgcaacc tctgtctccc gggttcaagc 4980
aattctcctg cttcagcctc ctgagtagct gggattacag gcacacacca ccaccgcact 5040
cagctaattt ttgtattttt agtagaggtg gggttttacc atgttggcca ggctggtctt 5100
aaactcctga ccttgtaatc atcccgcctc ggcctcctaa agtgctagga ttacaggcat 5160
gagccaccgc acccggccca gataattttt aatagccttt gatcatgggg tgagtgaggg 5220
agtaggtata cttggcaaat gcatggttct ctgatttcta gctctaaagc agccttatct 5280
gaatccccaa atcttgtgat gctgagtacc attactgaac cagtctgcac ggtaggcatc 5340
tgctaccaaa atttacctcc tacctggtag gtgtcatctg ataagaaaga agacaggtta 5400
ttttaatttt ttgagataat cacagaaaat tgcagcccat actctttatt accgaattca 5460
agtttggaaa tagacccttt gttttaaatc atgatgggtc tttatcccaa tcatttatct 5520
gggtcatttt tccaactttg gagttctagg aaagaacctt gaaaacctga tatgattctg 5580
cagcatgagg tctacggtga ccatttgggc aaagctccag tggcaatcat ttattgtgtt 5640
ttgcatttcc tgggatttat tgaaataaga attcactgtg attatgtagt cttctggcta 5700
gtatcaggca gctctgcttt taatttggtt aattttattt tctctgaaga gggagaagag 5760
gtacaattta atcttggcct ccacaagcat attaaagctc acgtgttaat cagtgcattc 5820
ttatgctcct acattaaatg ccttgggtaa atggataaat ggacatgtgc ccagctttaa 5880 tttttttgc aacagaaaga tcagacttcc gtatggcatc gttggatttc agaggctttc 5940
tggtgtatct gtaaatctga atgttgcctt ctgccagtct gtataaccag gtgattcatg 6000
ctgcaaatga aatcaggaag cagtaaagtg ttaaagcaag agtattgtcc aattcacttg 6060
tcttcctgat ccttgtactt tatttcacgt gtcggtgttt acattacata cttatatttc 6120
ctgtgaaaga aagagttaaa taaattgtag cagtttga 6158

<210> SEQ ID NO 2
<211> LENGTH: 2231
<212> TYPE: DNA
<213> ORGANISM: Homo sapiens

<400> SEQUENCE: 2
actgatatga ggaggcatag agatagacag cggttccttc caatagacgt gaagccgagg 60
ccggtatgag ccaatgcggt cgggaggcgg ggctcgggtg tgtgtggagg ggaccctgtg 120

-continued

```
gttagcagca gctatcgcag cgtcggatgt tcagagcagc agaagccggc gtcgtcggat    180
gttgtgttgc ccgccaccat gagctacaca ggctttgtcc agggatctga aaccactttg    240
cagtcgacat actcggatac cagcgctcag cccacctgtg attatggata tggaacttgg    300
aactctggga caaatagagg ctacgagggc tatggctatg gctatggcta tggccaggat    360
aacaccacca actatgggta tggtatggcc acttcacact cttgggaaat gcctagctct    420
gacacaaatg caaacactag tgcctcgggt agcgccagtg ccgattccgt tttatccaga    480
attaaccagc gcttagatat ggtgccgcat ttggagacag acatgatgca aggaggcgtg    540
tacggctcag gtggagaaag gtatgactct tatgagtcct gcgactcgag ggccgtcctg    600
agtgagcgcg acctgtaccg gtcaggctat gactacagcg agcttgaccc tgagatggaa    660
atggcctatg agggccaata cgatgcctac cgcgaccagt tccgcatgcg tggcaacgac    720
accttcggtc ccagggcaca gggctgggcc cgggatgccc ggagcggccg gccaatggcc    780
tcaggctatg ggcgcatgtg ggaagacccc atgggggccc ggggccagtg catgtctggt    840
gcctctcggc tgccctccct cttctcccag aacatcatcc ccgagtacgg catgttccag    900
ggcatgcgag gtgggggcgc cttcccgggc ggctcccgct ttggtttcgg gtttggcaat    960
ggcatgaagc agatgaggcg gacctggaag acctggacca cagccgactt ccgaaccaag   1020
aagaagaaga gaaagcaggg cggcagtcct gatgagccag atagcaaagc cacccgcacg   1080
gactgctcgg acaacagcga ctcagacaat gatgagggca ccgaggggga agccacagag   1140
ggccttgaag gcaccgaggc tgtggagaag ggctccagag tggacggaga ggatgaggag   1200
ggaaaagagg atgggagaga agaaggcaaa gaggatccag agaagggggc cctaaccacc   1260
caggatgaaa atggccagac caagcgcaag ttgcaggcag gcaagaagag tcaggacaag   1320
cagaaaaagc ggcagcgaga ccgcatggtg gaaaggatcc agtttgtgtg ttctctgtgc   1380
aaataccgga ccttctatga ggacgagatg gccagccatc ttgacagcaa gttccacaag   1440
gaacacttta agtacgtagg caccaagctc cctaagcaga cggctgactt tctgcaggag   1500
tacgtcacta acaagaccaa gaagacagag gagctccgaa aaaccgtgga ggaccttgat   1560
ggcctcatcc agcaaatcta cagagaccag gatctgaccc aggaaattgc catggagcat   1620
tttgtgaaga aggtggaggc agcccattgt gcagcctgcg acctcttcat tcccatgcag   1680
tttgggatca tccagaagca tctgaagacc atggatcaca accggaaccg caggctcatg   1740
atggagcagt ccaagaagtc ctccctcatg gtggcccgca gtattctcaa caacaagctc   1800
atcagcaaga agctggagcg ctacctgaag ggcgagaacc ctttcaccga cagcccccgag   1860
gaggagaagg agcaggagga ggctgagggc ggtgccctgg acgagggggc gcagggcgaa   1920
gcggcaggga tctcggaggg cgcagagggc gtgccggcgc agcctcccgt gcccccagag   1980
ccagcccccg gggccgtgtc gccgccaccg ccgccgcccc cagaggagga ggaggagggc   2040
gccgtgccct tgctgggagg ggcgctgcaa cgccagatcc gcggcatccc gggcctcgac   2100
gtggaggacg acgaggaggg cggcgggggc gccccgtgac ccgagctcgg ggcgggcgga   2160
gcccgcgtgg ccgaagctgg aaaccaaacc taataaagtt ttcccatccc accaaaaaaa   2220
aaaaaaaaaa a                                                        2231
```

<210> SEQ ID NO 3
<211> LENGTH: 3791
<212> TYPE: DNA
<213> ORGANISM: Homo sapiens

<400> SEQUENCE: 3

```
agaaggaggg cgtggtaata tgaagtcagt tccggttggt gtaaaacccc cggggcggcg     60
gcgaactggc tttagatgct tctgggtcgc ggtgtgctaa gcgaggagtc cgagtgtgtg    120
agcttgagag ccgcgcgcta gagcgacccg gcgagggatg gcggccaccg ggaccgcggc    180
cgccgcagcc acgggcaggc tcctgcttct gctgctggtg gggctcacgg cgcctgcctt    240
ggcgctggcc ggctacatcg aggctcttgc agccaatgcc ggaacaggat ttgctgttgc    300
tgagcctcaa atcgcaatgt tttgtgggaa gttaaatatg catgtgaaca ttcagactgg    360
gaaatgggaa cctgatccaa caggcaccaa gagctgcttt gaaacaaaag aagaagttct    420
tcagtactgt caggagatgt atccagagct acagatcaca aatgtgatgg aggcaaacca    480
gcgggttagt attgacaact ggtgccggag ggacaaaaag caatgcaaga gtcgctttgt    540
tacacctttc aagtgtctcg tgggtgaatt tgtaagtgat gtcctgctag ttccagaaaa    600
gtgccagttt ttccacaaag agcggatgga ggtgtgtgag aatcaccagc actggcacac    660
ggtagtcaaa gaggcatgtc tgactcaggg aatgacctta tatagctacg gcatgctgct    720
cccatgtggg gtagaccagt tccatggcac tgaatatgtg tgctgccctc agacaaagat    780
tattggatct gtgtcaaaag aagaggaaga ggaagatgaa gaggaagagg aagaggaaga    840
tgaagaggaa gactatgatg tttataaaag tgaatttcct actgaagcag atctggaaga    900
cttcacagaa gcagctgtgg atgaggatga tgaggatgag gaagaagggg aggaagtggt    960
ggaggaccga gattactact atgacacctt caaaggagat gactacaatg aggagaatcc   1020
tactgaaccc ggcagcgacg gcaccatgtc agacaaggaa attactcatg atgtcaaagc   1080
tgtctgctcc caggaggcga tgacggggcc ctgccgggcc gtgatgcctc gttggtactt   1140
cgacctctcc aagggaaagt gcgtgcgctt tatatatggt ggctgcggcg gcaacaggaa   1200
caattttgag tctgaggatt attgtatggc tgtgtgtaaa gcgatgattc ctccaactcc   1260
tctgccaacc aatgatgttg atgtgtattt cgagacctct gcagatgata atgagcatgc   1320
tcgcttccag aaggctaagg agcagctgga gattcggcac cgcaaccgaa tggacagggt   1380
aaagaaggaa tgggaagagg cagagcttca agctaagaac ctccccaaag cagagaggca   1440
gactctgatt cagcacttcc aagccatggt taaagcttta gagaaggaag cagccagtga   1500
gaagcagcag ctggtggaga cccacctggc ccgagtggaa gctatgctga atgaccgccg   1560
tcggatggct ctggagaact acctggctgc cttgcagtct gacccgccac ggcctcatcg   1620
cattctccag gccttacggc gttatgtccg tgctgagaac aaagatcgct tacataccat   1680
ccgtcattac cagcatgtgt tggctgttga cccagaaaag gcggcccaga tgaaatccca   1740
ggtgatgaca catctccacg tgattgaaga aaggaggaac caaagcctct ctctgctcta   1800
caaagtacct tatgtagccc aagaaattca agaggaaatt gatgagctcc ttcaggagca   1860
gcgtgcagat atggaccagt tcactgcctc aatctcagag acccctgtgg acgtccgggt   1920
gagctctgag gagagtgagg agatcccacc gttccacccc ttccacccct tcccagccct   1980
acctgagaac gaaggatctg gagtgggaga gcaggatggg ggactgatcg gtgccgaaga   2040
gaaagtgatt aacagtaaga ataaagtgga tgaaaacatg gtcattgacg agactctgga   2100
tgttaaggaa atgattttca atgccgagag agttggaggc ctcgaggaag agcgggaatc   2160
cgtgggccca ctgcgggagg acttcagtct gagtagcagt gctctcattg gcctgctggt   2220
catcgcagtg gccattgcca cggtcatcgt catcagcctg gtgatgctga ggaagaggca   2280
gtatggcacc atcagccacg ggatcgtgga ggttgatcca atgctcaccc cagaagagcg   2340
```

```
tcacctgaac aagatgcaga accatggcta tgagaacccc acctacaaat acctggagca   2400
gatgcagatt taggtggcag ggagcgcggc agccctggcg gagggatgca ggtgggccgg   2460
aagatcccac gattccgatc gactgccaag cagcagccgc tgccaggggc tgcgtctgac   2520
atcctgacct cctggactgt aggactatat aaagtactac tgtagaactg caatttccat   2580
tcttttaaat gggtgaaaaa tggtaatata acaatatatg atatataaac cttaaatgaa   2640
aaaaatgatc tattgcagat atttgatgta gttttctttt ttaaattaat cagaaacccc   2700
acttccattg tattgtctga cacatgctct caatatataa taaatgggaa atgtcgattt   2760
tcaataatag acttatatgc aggctgtcgt tccggttatg ttgtgtaagt caactcttca   2820
gcctcattca ctgtcctggc ttttatttaa agaaaaaaaa ggcagtattc ccttttttaaa   2880
tgagctttca ggaagttgct gagaaatggg gtggaatagg gaactgtaat ggccactgaa   2940
gcacgtgaga gaccctcgca aaatgatgtg aaaggaccag tttcttgaag tccagtgttt   3000
ccacggctgg atacctgtgt gtctccataa aagtcctgtc accaaggacg ttaaaggcat   3060
tttattccag cgtcttctag agagcttagt gtatacagat gagggtgtcc gctgctgctt   3120
tccttcggaa tccagtgctt ccacagagat tagcctgtag cttatatttg acattcttca   3180
ctgtctgttg tttacctacc gtagcttttt accgttcact tccccttcca actatgtcca   3240
gatgtgcagg ctcctcctct ctggactttc tccaaaggca ctgaccctcg gcctctactt   3300
tgtcccctca cctccacccc ctcctgtcac cggccttgtg acattcactc agagaagacc   3360
acaccaagga ggcggccgct ggcccaggag agaacacggg gaggtttgtt tgtgtgaaag   3420
gaaagtagtc caggctgtcc ctgaaactga gtctgtggac actgtggaaa gctttgaaca   3480
attgtgtttt cgtcacagga gtctttgtaa tgcttgtaca gttgatgtcg atgctcactg   3540
cttctgcttt ttctttcttt ttattttaaa tctgaaggtt ctggtaacct gtggtgtatt   3600
tttattttcc tgtgactgtt tttgttttgt ttttttcctt tttcctcccc tttgacccta   3660
ttcatgtctc tacccactat gcacagatta aacttcacct acaaactcct taatatgatc   3720
tgtggagaat gtacacagtt taaacacatc aataaatact ttaacttcca ccgagaaaaa   3780
aaaaaaaaaa a                                                        3791
```

<210> SEQ ID NO 4
<211> LENGTH: 2562
<212> TYPE: DNA
<213> ORGANISM: Homo sapiens

<400> SEQUENCE: 4

```
cttgacagac gtgaccctga cccaataagg gtggaaggct gagtcccgca gagccaataa     60
cgagagtccg agaggcgacg gaggcggact ctgtgaggaa acaagaagag aggcccaaga    120
tggagacggc ggcggctgta gcggcgtgac aggagcccca tggcacctgc ccagccccac    180
ctcagcccat cttgacaaaa tctaaggctc catggagcca ccacggggcc cccctgccaa    240
tggggccgag ccatcccggg cagtgggcac cgtcaaagta tacctgccca acaagcaacg    300
cacggtggtg actgtccggg atggcatgag tgtctacgac tctctagaca aggccctgaa    360
ggtgcggggt ctaaatcagg actgctgtgt ggtctaccga ctcatcaagg gacgaaagac    420
ggtcactgcc tgggacacag ccattgctcc cctggatggc gaggagctca ttgtcgaggt    480
ccttgaagat gtcccgctga ccatgcacaa ttttgtacgg aagaccttct tcagcctggc    540
gttctgtgac ttctgcctta agtttctgtt ccatggcttc cgttgccaaa cctgtggcta    600
```

caagttccac cagcattgtt cctccaaggt ccccacagtc tgtgttgaca tgagtaccaa 660
ccgccaacag ttctaccaca gtgtccagga tttgtccgga ggctccagac agcatgaggc 720
tccctcgaac cgccccctga atgagttgct aaccccccag ggtcccagcc cccgcaccca 780
gcactgtgac ccggagcact tccccttccc tgccccagcc aatgcccccc tacagcgcat 840
ccgctccacg tccactccca acgtccatat ggtcagcacc acggccccca tggactccaa 900
cctcatccag ctcactggcc agagtttcag cactgatgct gccggtagta gaggaggtag 960
tgatggaacc ccccggggga gccccagccc agccagcgtg tcctcgggga ggaagtcccc 1020
acattccaag tcaccagcag agcagcgcga gcggaagtcc ttggccgatg acaagaagaa 1080
agtgaagaac ctggggtacc gggactcagg ctattactgg gaggtaccac ccagtgaggt 1140
gcagctgctg aagaggatcg ggacgggctc gtttggcacc gtgtttcgag ggcggtggca 1200
tggcgatgtg gccgtgaagg tgctcaaggt gtcccagccc acagctgagc aggcccaggc 1260
tttcaagaat gagatgcagg tgctcaggaa gacgcgacat gtcaacatct tgctgtttat 1320
gggcttcatg acccggccgg gatttgccat catcacacag tggtgtgagg gctccagcct 1380
ctaccatcac ctgcatgtgg ccgacacacg cttcgacatg gtccagctca tcgacgtggc 1440
ccggcagact gcccagggca tggactacct ccatgccaag aacatcatcc accgagatct 1500
caagtctaac aacatcttcc tacatgaggg gctcacggtg aagatcggtg actttggctt 1560
ggccacagtg aagactcgat ggagcggggc ccagcccttg gagcagccct caggatctgt 1620
gctgtggatg gcagctgagg tgatccgtat gcaggacccg aacccctaca gcttccagtc 1680
agacgtctat gcctacgggg ttgtgctcta cgagcttatg actggctcac tgccttacag 1740
ccacattggc tgccgtgacc agattatctt tatggtgggc cgtggctatc tgtccccgga 1800
cctcagcaaa atctccagca actgccccaa ggccatgcgg cgcctgctgt ctgactgcct 1860
caagttccag cgggaggagc ggcccctctt cccccagatc ctggccacaa ttgagctgct 1920
gcaacggtca ctccccaaga ttgagcggag tgcctcggaa ccctccttgc accgcaccca 1980
ggccgatgag ttgcctgcct gcctactcag cgcagcccgc cttgtgcctt aggccccgcc 2040
caagccacca gggagccaat ctcagccctc cacgccaagg agccttgccc accagccaat 2100
caatgttcgt ctctgccctg atgctgcctc aggatccccc attccccacc ctgggagatg 2160
agggggtccc catgtgcttt tccagttctt ctggaattgg gggacccccg ccaaagactg 2220
agccccctgt ctcctccatc atttggtttc ctcttggctt tggggatact tctaaatttt 2280
gggagctcct ccatctccaa tggctgggat ttgtggcagg gattccactc agaacctctc 2340
tggaatttgt gcctgatgtg ccttccactg gattttgggg ttcccagcac cccatgtgga 2400
ttttgggggg tccctttgt gtctccccg ccattcaagg actcctctct ttcttcacca 2460
agaagcacag aattctgctg ggcctttgct tgtttaaaaa aaaaaaaaaa aaaaaaaaaa 2520
aaaaaaaaaa aaaaaaaaaa aaaaaaaaaa aaaaaaaaaa aa 2562

<210> SEQ ID NO 5
<211> LENGTH: 2186
<212> TYPE: DNA
<213> ORGANISM: Homo sapiens

<400> SEQUENCE: 5
agcagtcacg tgcctccgat cacgtgaccg gcgcctctgt cattctactg cggccgccct 60
ggcttccttc tacctgtgcg gccctcaacg tctccttggt gcgggacccg cttcactttc 120
ggctcccgga gtctccctcc actgctcaga cctctggacc tgacaggaga cgcctacttg 180
gctctgacgc ggcgccccag cccggctgtg tccccggcgc cccggaccac cctccctgcc 240
ggctttgggt gcgttgtggg gtcccgagga ttcgcgagat ttgttgaaag acattcaaga 300
ttacgaagtt tagatgacca aaatggatat ccgaggtgct gtggatgctg ctgtccccac 360
caatattatt gctgccaagg ctgcagaagt tcgtgcaaac aaagtcaact ggcaatccta 420
tcttcaggga cagatgattt ctgctgaaga ttgtgagttt attcagaggt ttgaaatgaa 480
acgaagccct gaagagaagc aagagatgct tcaaactgaa ggcagccagt gtgctaaaac 540
atttataaat ctgatgactc atatctgcaa agaacagacc gttcagtata tactaactat 600
ggtggatgat atgctgcagg aaaatcatca gcgtgttagc attttctttg actatgcaag 660
atgtagcaag aacactgcgt ggccctactt tctgccaatg ttgaatcgcc aggatccctt 720
cactgttcat atggcagcaa gaattattgc caagttagca gcttggggaa aagaactgat 780
ggaaggcagt gacttaaatt actatttcaa ttggataaaa actcagctga gttcacagaa 840
actgcgtggt agcggtgttg ctgttgaaac aggaacagtc tcttcaagtg atagttcgca 900
gtatgtgcag tgcgtggccg ggtgtttgca gctgatgctc cgggtcaatg agtaccgctt 960
tgcttgggtg gaagcagatg gggtaaattg cataatggga gtgttgagta acaagtgtgg 1020
ctttcagctc cagtatcaaa tgattttttc aatatggctc ctggcattca gtcctcaaat 1080
gtgtgaacac ctgcggcgct ataatatcat tccagttctg tctgatatcc ttcaggagtc 1140
tgtcaaagag aaagtaacaa gaatcattct tgcagcattt cgtaactttt tagaaaaatc 1200
aactgaaaga gaaactcgcc aagaatatgc cctggctatg attcagtgca aagttctgaa 1260
acagttggag aacttggaac agcagaagta cgatgatgaa gatatcagcg aagatatcaa 1320
atttcttttg gaaaaacttg gagagagtgt ccaggacctt agttcatttg atgaatacag 1380
ttcagaactt aaatctggaa ggttggaatg gagtcctgtg cacaaatctg agaaattttg 1440
gagagagaat gctgtgaggt taaatgagaa gaattatgaa ctcttgaaaa tcttgacaaa 1500
acttttggaa gtgtcagatg atccccaagt cttagctgtt gctgctcacg atgttggaga 1560
atatgtgcgg cattatccac gaggcaaacg ggtcatcgag cagctcggtg ggaagcagct 1620
ggtcatgaac cacatgcatc atgaagacca gcaggtccgc tataatgctc tgctggccgt 1680
gcagaagctc atggtgcaca actgggaata ccttggcaag cagctccagt ccgagcagcc 1740
ccagaccgct gccgcccgaa gctaagcctg cctctggcct tcccctccgc ctcaatgcag 1800
aaccagtagt gggagcactg tgtttagagt taagagtgaa cactgtttga ttttacttgg 1860
aatttcctct gttatatagc ttttcccaat gctaatttcc aaacaacaac aacaaaataa 1920
catgtttgcc tgttaagttg tataaaagta ggtgattctg tatttaaaga aaatattact 1980
gttacatata ctgcttgcaa tttctgtatt tattgttctc tggaaataaa tatagttatt 2040
aaaggattct cactccaaac atggcctctc tctttacttg gactttgaac aaaagtcaac 2100
tgttgtctct tttcaaacca aattgggaga attgttgcaa agtagtgaat ggcaaataaa 2160
tgttttaaaa tctatcgctc tatcaa 2186

<210> SEQ ID NO 6
<211> LENGTH: 3505
<212> TYPE: DNA
<213> ORGANISM: Homo sapiens

<400> SEQUENCE: 6
cgtcaggggc aggggaggga cggcgcaggc gcagaaaagg gggcggcgga ctcggcttgt 60

-continued

```
tgtgttgctg cctgagtgcc ggagacggtc ctgctgctgc cgcagtcctg ccagctgtcc    120
gacaatgtcg tcccacctag tcgagccgcc gccgcccctg cacaacaaca acaacaactg    180
cgaggaaaat gagcagtctc tgcccccgcc ggccggcctc aacagttcct gggtggagct    240
acccatgaac agcagcaatg gcaatgataa tggcaatggg aaaaatgggg ggctggaaca    300
cgtaccatcc tcatcctcca tccacaatgg agacatggag aagattcttt tggatgcaca    360
acatgaatca ggacagagta gttccagagg cagttctcac tgtgacagcc cttcgccaca    420
agaagatggg cagatcatgt ttgatgtgga aatgcacacc agcagggacc atagctctca    480
gtcagaagaa gaagttgtag aaggagagaa ggaagtcgag gctttgaaga aaagtgcgga    540
ctgggtatca gactggtcca gtagacccga aaacattcca cccaaggagt tccacttcag    600
acaccctaaa cgttctgtgt ctttaagcat gaggaaaagt ggagccatga agaaaggggg    660
tattttctcc gcagaatttc tgaaggtgtt cattccatct ctcttccttt ctcatgtttt    720
ggctttgggg ctaggcatct atattggaaa gcgactgagc acaccctctg ccagcaccta    780
ctgagggaaa ggaaaagccc ctggaaatgc gtgtgacctg tgaagtggtg tattgtcaca    840
gtagcttatt tgaacttgag accattgtaa gcatgaccca acctaccacc ctgtttttac    900
atatccaatt ccagtaactc tcaaattcaa tattttattc aaactctgtt gaggcatttt    960
actaacctta taccctttttt ggcctgaaga cattttagaa tttcctaaca gagtttactg   1020
ttgtttagaa atttgcaagg gcttcttttc cgcaaatgcc accagcagat tataattttg   1080
tcagcaatgc tattatctct aattagtgcc accagactag acctgtatca ttcatggtat   1140
aaattttact cttgcaacat aactaccatc tctctcttaa aacgagatca ggttagcaaa   1200
tgatgtaaaa gaagctttat tgtctagttg tttttttcc cccaagacaa aggcaagttt   1260
ccctaagttt gagttgatag ttattaaaaa gaaaacaaaa caaaaaaaaa aggcaaggca   1320
caacaaaaaa atatcctggg caataaaaaa aatattttaa accagctttg gagccacttt   1380
tttgtctaag cctcctaata gcgtctttta atttatagga ggcaaactgt ataaatgata   1440
ggtatgaaat agaataagaa gtaaaataca tcagcagatt ttcatactag tatgttgtaa   1500
tgctgtcttt tctatggtgt agaatctttc tttctgataa ggaacgtctc aggcttagaa   1560
atatatgaaa ttgctttttg agatttttgc gtgtgtgttt gatatttttt acgataatta   1620
gctgcatgtg aatttttcat gaccttcttt acatttttta tttttattt ctttattttt   1680
ttttctctaa gaagaggctt tggaatgagt tccaatttgt gatgttaata caggcttctt   1740
gttttaggaa gcatcaccta tactctgaag cctttaaact ctgaagagaa ttgtttcaga   1800
gttattccaa gcacttgtgc aacttggaaa aacagacttg ggttgtggga acagttgaca   1860
gcgttctgaa aagatgccat ttgtttcctt ctgatctctc actgaataat gtttactgta   1920
cagtcttccc aaggtgattc ctgcgactgc aggcactggt cattttctca tgtagctgtc   1980
ttttcagtta tggtaaactc ttaaagttca gaacactcaa cagattcctt cagtgatata   2040
cttgttcgtt catttctaaa atgtgaagct ttaggaccaa attgttagaa agcatcagga   2100
tgaccagtta tctcgagtag attttcttgg atttcagaac atctagcatg actctgaagg   2160
ataccacatg ttttatatat aaataattac tgtttatgat atagacattg atattgacta   2220
tttagagaac cgttgttaat tttaaaacta gcaatctata aagtgcacca ggtcaacttg   2280
aataaaaaca ctatgacaga caggtttgcc agtttgcaga aactaactct tttctcacat   2340
caacatttgt aaaattgatg tgttatagtg gaaaataaca tatagattaa acaaaatttt   2400
tatctttttt caagaatata gctggctatc tttaagaaag atgatatatc ctagttttga   2460
```

```
aagtaatttt ctttttttctt tctagcattt gatgtctaaa taattttgga catctttttc   2520
ctagaccatg tttctgtctt actcttaaac ctggtaacac ttgatttgcc ttctataacc   2580
tatttatttc aagtgttcat atttgaattt ctttgggaag aaagtaaatc tgatggctca   2640
ctgatttttg aaaagcctga ataaaattgg aaagactgga aagttaggag aactgactag   2700
ctaaactgct acagtatgca atttctatta caattggtat tacagggggg aaaagtaaaa   2760
ttacacttta cctgaaagtg acttcttaca gctagtgcat tgtgctcttt ccaagttcag   2820
cagcagttct atcagtggtg ccactgaaac tgggtatatt tatgatttct ttcagcgtta   2880
aaaagaaaca tagtgttgcc ctttttctta aagcatcagt gaaattatgg aaaattactt   2940
aaaacgtgaa tacatcatca cagtagaatt tattatgaga gcatgtagta tgtatctgta   3000
gccctaacac atgggatgaa cgttttactg ctacacccag atttgtgttg aacgaaaaca   3060
ttgtggtttg gaaaggagaa ttcaacaatt aatagttgaa attgtgaggt taatgtttaa   3120
aaagctttac acctgtttac aatttgggga caaaaaggca ggcttcattt ttcatatgtt   3180
tgatgaaaac tggctcaaga tgtttgtaaa tagaatcaag agcaaaactg cacaaacttg   3240
cacattggaa agtgcaacaa gttcccgtga ttgcagtaaa aatatttact attctaaaaa   3300
aatgagaatt gaagacttag ccagtcagat aagtttttc atgaacccgt tgtggaaatt   3360
attggaatta actgagccaa agtgattatg cattcttcat ctattttagt tagcactttg   3420
tatcgttata tacagtttac aatacatgta taacttgtag ctataaacat tttgtgccat   3480
taaagctctc acaaaacttt aaaaa                                          3505
```

<210> SEQ ID NO 7
<211> LENGTH: 2949
<212> TYPE: DNA
<213> ORGANISM: Homo sapiens

<400> SEQUENCE: 7

```
cgcctccctt cccccctcccc gcccgacagc ggccgctcgg gccccggctc tcggttataa     60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
```

acccgcctcg gactctattg ggccccaaat tctcaccagt ccgtctcctt caaaatccat 1080
tccaattcca cagcccttcc gaccagcaga tgaagatcat cgaaatcaat ttgggcaacg 1140
agaccgatcc tcatcagctc ccaatgtgca tataaacaca atagaacctg tcaatattga 1200
tgacttgatt agagaccaag gatttcgtgg tgatggagga tcaaccacag gtttgtctgc 1260 tacccccccct gcctcattac ctggctcact aactaacgtg aaagccttac agaaatctcc 1320
aggacctcag cgagaaagga agtcatcttc atcctcagaa gacaggaatc gaatgaaaac 1380
acttggtaga cgggactcga gtgatgattg ggagattcct gatgggcaga ttacagtggg 1440
acaaagaatt ggatctggat catttggaac agtctacaag ggaaagtggc atggtgatgt 1500
ggcagtgaaa atgttgaatg tgacagcacc tacacctcag cagttacaag ccttcaaaaa 1560
tgaagtagga gtactcagga aaacacgaca tgtgaatatc ctactcttca tgggctattc 1620
cacaaagcca caactggcta ttgttaccca gtggtgtgag ggctccagct tgtatcacca 1680
tctccatatc attgagacca aatttgagat gatcaaactt atagatattg cacgacagac 1740
tgcacagggc atggattact tacacgccaa gtcaatcatc cacagagacc tcaagagtaa 1800
taatatattt cttcatgaag acctcacagt aaaaataggt gattttggtc tagctacagt 1860
gaaatctcga tggagtgggt cccatcagtt tgaacagttg tctggatcca ttttgtggat 1920
ggcaccagaa gtcatcagaa tgcaagataa aaatccatac agctttcagt cagatgtata 1980
tgcatttgga attgttctgt atgaattgat gactggacag ttaccttatt caaacatcaa 2040
caacagggac cagataattt ttatggtggg acgaggatac ctgtctccag atctcagtaa 2100
ggtacggagt aactgtccaa aagccatgaa gagattaatg gcagagtgcc tcaaaaagaa 2160
aagagatgag agaccactct ttccccaaat tctcgcctct attgagctgc tggcccgctc 2220
attgccaaaa attcaccgca gtgcatcaga accctccttg aatcgggctg gtttccaaac 2280
agaggatttt agtctatatg cttgtgcttc tccaaaaaca cccatccagg caggggggata 2340 tggtgcgttt cctgtccact gaaacaaatg agtgagagag ttcaggagag tagcaacaaa 2400
aggaaaataa atgaacatat gtttgcttat atgttaaatt gaataaaata ctctcttttt 2460
ttttaaggtg aaccaaagaa cacttgtgtg gttaaagact agatataatt tttccccaaa 2520
ctaaaattta tacttaacat tggattttta acatccaagg gttaaaatac atagacattg 2580
ctaaaaattg gcagagcctc ttctagaggc tttactttct gttccgggtt tgtatcattc 2640
acttggttat tttaagtagt aaacttcagt ttctcatgca acttttgttg ccagctatca 2700
catgtccact agggactcca gaagaagacc ctacctatgc ctgtgtttgc aggtgagaag 2760
ttggcagtcg gttagcctgg gttagataag gcaaactgaa cagatctaat ttaggaagtc 2820
agtagaattt aataattcta ttattattct taataatttt tctataacta tttcttttta 2880
taacaatttg gaaaatgtgg atgtctttta tttccttgaa gcaataaact aagtttcttt 2940
ttataaaaa 2949

<210> SEQ ID NO 8
<211> LENGTH: 2260
<212> TYPE: DNA
<213> ORGANISM: Homo sapiens

<400> SEQUENCE: 8
cgcagccccg gttcctgccc gcacctctcc ctccacacct ccccgcaagc tgagggagcc 60
ggctccggcc tcggccagcc caggaaggcg ctcccacagc gcagtggtgg gctgaagggc 120
tcctcaagtg ccgccaaagt gggagcccag gcagaggagg cgccgagagc gagggagggc 180

```
tgtgaggact gccagcacgc tgtcacctct caatagcagc ccaaacagat taagacatgg    240
gagatgtaca agggcagccg tggggctggc aacagcttcg taatcctggc ttcctgcttt    300
ctgggtcaaa gccctggtgg tgtgttcttg atatcggtcc atctagtggc gttgtttgat    360
tcctcccacc ttgctgatca ttcgtagtgt agcccccaag gtgtggaata acccttaagc    420
ccttaccggg gtccttctgg actgagaatt gttgtaaagt aatactgctc aggtgaaaga    480
caacttgagt ggttaaatta ctgtcatgca aagcgactag atggttcagc tgattgcacc    540
tttagaagtt atgtggaacg aggcagcaga tcttaagccc cttgctctgt cacgcaggct    600
ggaatgcagt ggtggaatca tggctcacta cagccctgac ctcctgggcc cagagatgga    660
gtctcgctat tttgcccagg ttggtcttga acacctggct tcaagcagtc ctcctgcttt    720
tggcttcttg aagtgcttgg attacagtat ttcagtttta tgctctgcaa caagtttggc    780
catgttggag gacaatccaa aggtcagcaa gttggctact ggcgattgga tgctcactct    840
gaagccaaag tctattactg tgcccgtgga aatccccagc tcccctctgg atgatacacc    900
ccctgaagac tccattcctt tggtctttcc agaattagac cagcagctac agcccctgcc    960
gccttgtcat gactccgagg aatccatgga ggtgttcaaa cagcactgcc aaatagcaga   1020
agaataccat gaggtcaaaa aggaaatcac cctgcttgag caaaggaaga aggagctcat   1080
tgccaagtta gatcaggcag aaaaggagaa ggtggatgct gctgagctgg ttcgggaatt   1140
cgaggctctg acggaggaga atcggacgtt gaggttggcc cagtctcaat gtgtggaaca   1200
actggagaaa cttcgaatac agtatcagaa gaggcagggc tcgtcctaac tttaaatttt   1260
tcagtgtgag catacgaggc tgatgactgc cctgtgctgg ccaaaagatt tttattttaa   1320
atgaatagtg agtcagatct attgcttctc tgtattaccc acatgacaac tgtctataat   1380
gagtttactg cttgccagct tctagcttga gagaagggat attttaaatg agatcattaa   1440
cgtgaaacta ttactagtat atgtttttgg agatcagaat tcttttccaa agatatatgt   1500
tttttctttt tttaggaaga tatgatcatg ctgtacaaca gggtagaaaa tgataaaaat   1560
agactattga ctgacccagc taagaatcgt gggctgagca gagttaaacc atgggacaaa   1620
cccataacat gttcaccata gtttcacgta tgtgtatttt taaatttcat gcctttaata   1680
tttcaaatat gctcaaattt aaactgtcag aaacttctgt gcatgtattt atatttgcca   1740
gagtataaac ttttatactc tgatttttat ccttcaatga ttgattatac taagaataaa   1800
tggtcacata tcctaaaagc ttcttcatga aattattagc agaaaccatg tttgtaacca   1860
aagcacattt gccaatgcta actggctgtt gtaataataa acagataagg ctgcatttgc   1920
ttcatgccat gtgacctcac agtaaacatc tctgcctttg cctgtgtgtg ttctggggga   1980
ggggggacat ggaaaaatat tgtttggaca ttacttgggt gagtgcccat gaaaacatca   2040
gtgaacttgt aactattgtt ttgttttgga tttaaggaga tgttttagat cagtaacagc   2100
taataggaat atgcgagtaa attcagaatt gaaacaattt ctccttgttc tacctatcac   2160
cacattttct caaattgaac tctttgttat atgtccattt ctattcatgt aacttctttt   2220
tcattaaaca tggatcaaaa ctgacaaaaa aaaaaaaaaa                          2260
```

<210> SEQ ID NO 9
<211> LENGTH: 7680
<212> TYPE: DNA
<213> ORGANISM: Homo sapiens

<400> SEQUENCE: 9

-continued

```
ggggccgggg ggcggagcct tgcgggctgg agcgaaagaa tgcgggggct gagcgcagaa     60
gcggctcgag gctggaagag gatcttgggc gccgccagtc tttagcacca gttggtgtag    120
gagttgagac ctacttcaca gtagttctgt ggacaatcac aatgggaatc caaggagggt    180
ctgtcctgtt cgggctgctg ctcgtcctgg ctgtcttctg ccattcaggt catagcctgc    240
agtgctacaa ctgtcctaac ccaactgctg actgcaaaac agccgtcaat tgttcatctg    300
attttgatgc gtgtctcatt accaaagctg ggttacaagt gtataacaag tgttggaagt    360
ttgagcattg caatttcaac gacgtcacaa cccgcttgag ggaaaatgag ctaacgtact    420
actgctgcaa gaaggacctg tgtaacttta acgaacagct tgaaaatggt gggacatcct    480
tatcagagaa aacagttctt ctgctggtga ctccatttct ggcagcagcc tggagccttc    540
atccctaagt caacaccagg agagcttctc ccaaactccc cgttcctgcg tagtccgctt    600
tctcttgctg ccacattcta aaggcttgat attttccaaa tggatcctgt tgggaaagaa    660
taaaattagc ttgagcaacc tggctaagat agaggggctc tgggagactt tgaagaccag    720
tcctgtttgc agggaagccc cacttgaagg aagaagtcta agagtgaagt aggtgtgact    780
tgaactagat tgcatgcttc ctcctttgct cttgggaaga ccagctttgc agtgacagct    840
tgagtgggtt ctctgcagcc ctcagattat ttttcctctg gctccttgga tgtagtcagt    900
tagcatcatt agtacatctt tggagggtgg ggcaggagta tatgagcatc ctctctcaca    960
tggaacgctt tcataaactt cagggatccc gtgttgccat ggaggcatgc caaatgttcc   1020
atatgtgggt gtcagtcagg gacaacaaga tccttaatgc agagctagag gacttctggc   1080
agggaagtgg ggaagtgttc cagatagcag ggcatgaaaa cttagagagg tacaagtggc   1140
tgaaaatcga gtttttcctc tgtctttaaa ttttatatgg gctttgttat cttccactgg   1200
aaaagtgtaa tagcatacat caatggtgtg ttaaagctat ttccttgcct tttttttatt   1260
ggaatggtag gatatcttgg ctttgccaca cacagttaca gagtgaacac tctactacat   1320
gtgactggca gtattaagtg tgcttatttt aaatgttact ggtagaaagg cagttcaggt   1380
atgtgtgtat atagtatgaa tgcagtgggg acaccctttg tggttacagt ttgagacttc   1440
caaaggtcat ccttaataac aacagatctg caggggtatg ttttaccatc tgcatccagc   1500
ctcctgctaa ctcctagctg actcagcata gattgtataa aataccttg taacggctct   1560
tagcacactc acagatgttt gaggctttca gaagctcttc taaaaaatga tacacacctt   1620
tcacaagggc aaactttttc cttttccctg tgtattctag tgaatgaatc tcaagattca   1680
gtagacctaa tgacatttgt attttatgat cttggctgta tttaatggca taggctgact   1740
tttgcagatg gaggaatttc ttgattaatg ttgaaaaaaa acccttgatt atactctgtt   1800
ggacaaaccg agtgcaatga atgatgcttt tctgaaaatg aaatataaca agtgggtgaa   1860
tgtggttatg gccgaaaagg atatgcagta tgcttaatgg tagcaactga aagaagacat   1920
cctgagcagt gccagctttc ttctgttgat gccgttccct gaacatagga aaatagaaac   1980
ttgcttatca aaacttagca ttaccttggt gctctgtgtt ctctgttagc tcagtgtctt   2040
tccttacatc aataggtttt tttttttttt tttggcctga ggaagtactg accatgccca   2100
cagccaccgg ctgagcaaag aagctcattt catgtgagtt ctaaggaatg agaaacaatt   2160
ttgatgaatt taagcagaaa atgaatttct gggaactttt ttgggggcgg gggggtgggg   2220
aattcagcca cactccagaa agccaggagt cgacagtttt ggaagcctct ctcaggattg   2280
agattctagg atgagattgg cttactgcta tcttgtgtca tgtacccact ttttggccag   2340
actacactgg gaagaaggta gtcctctaaa gcaaaatctg agtgccacta aatggggaga   2400
```

-continued

```
tggggctgtt aagctgtcca aatcaacaag ggtcatataa atggccttaa actttggggt   2460
tgctttctgc aaaaagttgc tgtgactcat gccatagaca aggttgagtg cctggaccca   2520
aaggcaatac tgtaatgtaa agacatttat agtactaggc aaacagcacc ccaggtactc   2580
caggccctcc tggctggaga gggctgtggc aatagaaaat tagtgccaac tgcagtgagt   2640
cagcctaggt taaatagaga gtgtaagagt gctggacagg aacctccacc ctcatgtcac   2700
atttcttcaa tgtgaccctt ctggcccctc tcctcctgac agcggaacaa tgactgcccc   2760
gataggtgag gctggaggaa gaatcagtcc tgtccttggc aagctcttca ctatgacagt   2820
aaaggctctc tgcctgctgc caaggcctgt gactttctaa cctggcctca cgctgggtaa   2880
gcttaaggta gaggtgcagg attagcaagc ccacctggct accaggccga cagctacatc   2940
ctccaactga ccctgatcaa cgaagaggga ttcatgtgtc tgtctcagtt ggttccaaat   3000
gaaaccaggg agcaggggag ttaggaatcg aacaccagtc atgcctactg gctctctgct   3060
cgagagccaa taccctgtgc cctccactca tctggattta caggaactgt catagtgttc   3120
agtattgggt ggtgataagc ccattggatt gtccccttgg ggggatgagc taggggtgca   3180
aggaacacct gatgagtaga taagtggagc tcatggtatt tcctgaaaga tgctaatcta   3240
tttgccaaac ttggtcttga atgtactggg ggcttcaagg tatgggtata tttttcttgt   3300
gtccttgcag ttagccccca tgtcttatgt gtgtcctgaa aaaataagag cctgcccaag   3360
actttgggcc tcttgacaga attaaccact tttatacatc tgagttctct tggtaagttc   3420
tttagcagtg ttcaaagtct actagctcgc attagtttct gttgctgcca acagatctga   3480
actaatgcta acagatcccc ctgagggatt cttgatgggc tgagcagctg gctggagcta   3540
gtactgactg acattcattg tgatgagggc agctttctgg tacaggattc taagctctat   3600
gttttatata cattttcatc tgtacttgca cctcacttta cacaagagga aactatgcaa   3660
agttagctgg atcgctcaag gtcacttagg taagttggca agtccatgct tcccactcag   3720
ctcctcaggt cagcaagtct acttctctgc ctattttgta tactctcttt aatatgtgcc   3780
tagctttgga aagtctagaa tgggtccctg gtgccttttt actttgaaga aatcagtttc   3840
tgcctctttt tggaaaagaa aacaaagtgc aattgttttt tactggaaag ttacccaata   3900
gcatgaggtg aacaggacgt agttaggcct tcctgtaaac agaaaatcat atcaaaacac   3960
tatcttccca tctgtttctc aatgcctgct acttcttgta gatatttcat ttcaggagag   4020
cagcagttaa acccgtggat tttgtagtta ggaacctggg ttcaaaccct cttccactaa   4080
ttggctatgt ctctggacaa gttttttttt tttttttttt ttaaaccctt tctgaacttt   4140
cactttctat gtctacctca aagaattgtt gtgaggcttg agataatgca tttgtaaagg   4200
gtctgccaga taggaagatg ctagttatgg atttacaagg ttgttaaggc tgtaagagtc   4260
taaaacctac agtgaatcac aatgcattta cccccactga cttggacata agtgaaaact   4320
agccagaagt ctctttttca aattacttac aggttattca atataaaatt tttgtaatgg   4380
ataatcttat ttatctaaac taaagcttcc tgtttataca cactcctgtt attctgggat   4440
aagataaatg accacagtac cttaatttct aggtgggtgc ctgtgatggt tcattgtagg   4500
taaggacatt ttctcttttt cagcagctgt gtaggtccag agcctctggg agaggagggg   4560
ggtagcatgc acccagcagg ggactgaact gggaaactca aggttctttt tactgtgggg   4620
tagtgagctg cctttctgtg atcggtttcc ctagggatgt tgctgttccc ctccttgcta   4680
ttcgcagcta catacaacgt ggccaacccc agtaggctga tcctatatat gatcagtgct   4740
```

ggtgctgact ctcaatagcc ccacccaagc tggctatagg tttacagata cattaattag 4800
gcaacctaaa atattgatgc tggtgttggt gtgacataat gctatggcca gaactgaaac 4860
ttagagttat aattcatgta ttagggttct ccagagggac agaattagta ggatatatgt 4920
atatatgaaa gggaggttat tagggagaac tggctcccac agttagaagg cgaagtcgca 4980
caataggccg tctgcaagct gggttagaga gaagccagta gtggctcagc ctgagttcaa 5040
aaacctcaaa actggggaag ctgacagtgc agccagcctt cagtctgtgg ccaaaggccc 5100
aagagcccct ggcaaccaac ccactggtgc aagtcctaga ttccaaaggc tgaagaacct 5160
ggagtctgat gtccaagagc aggaagagtg gaagaaagcc agaagactca gcaaacaagg 5220
tagacagtgt ctaccaccat agtggccata ccaaagaggc taccgattcc ttcctgctac 5280
ctggatccct gaagttgccc tggtctctgc accttctaaa cctagttctt aagagctttc 5340
cattacatga gctgtctcaa agccctccaa taaattctca gtgtaagctt ctgttgcttg 5400
tggacagaaa attctgacag acctacccta taagtgttac tgtcaggata acatgagaac 5460
gcacaacagt aagtggtcac taagtgttag ctacggttat tttgcccaag gtagcatggc 5520
tagttgatgc cggttgatgg ggcttaaacc cagctccctc atcttccagg cctctgtact 5580
ccctattcca ctaaactacc tctcaggttt attttttaa attcttactc tgcaagtaca 5640
taggaccaca tttacctggg aaaacaagaa taaaggctgc tctgcatttt ttagaaactt 5700
ttttgaaagg gagatgggaa tgcctgcacc cccaagtcca gaccaacaca atggttaatt 5760
gagatgaata ataaaggaaa gactgttctg ggcttcccag aatagcttgg tccttaaatt 5820
gtggcacaaa caacctcctg tcagagccag cctcctgcca ggaagagggg taggagacta 5880
gaggccgtgt gtgcagcctt gccctgaagg ctagggtgac aatttggagg ctgtccaaac 5940
accctggcct ctagagctgg cctgtctatt tgaaatgccg gctctgatgc taatcggcga 6000
ccctcaggca agttacttaa ccttacatgc ctcagttttc tcatctggaa aatgagaacc 6060
ctaggtttag ggttgttaga aaagttaaat gagttaagac aagtgcctgg gacacagtag 6120
cctcttgtgt gtgtttatca ttatgtcctc agcaggtcgt agaagcagct tctcaggtgt 6180
gaggctggcg cgattatctg gagtgggttg ggttttctag gatggacccc ctgctgcatt 6240
ttcctcattc atccaccagg gcttaatggg gaatcaagga atccatgtgt aactgtataa 6300
taactgtagc cacactccaa tgaccaccta ctagttgtcc ctggcactgc ttatacatat 6360
gtccatcaaa tcaatcctat gaagtagata ctgtcttcat tttatagatc agagacaatt 6420
ggggttcaga gagctgatgt gattttccca gggtcacaga gagtcccaga ttcaggcaca 6480
actcttgtat tccaagacac aaccactaca tgtccaaagg ctgcccagag ccaccgggca 6540
cggcaaattg tgacatatcc ctaaagaggc tgagcacctg gtcaggatct gatggctgac 6600
agtgtgtcca gatgcagagc tggagtgggg gaggggaagg ggggctcctt gggacagaga 6660
aggctttctg tgctttctct gaagggagca gtctgaggac caagggaacc cggcaaacag 6720
cacctcaggt actccaggcc ctcctggctg gagagggctg tggcaatgga aaattagtgc 6780
caactgcaat gagtcagcct cggttaaata gagagtgaag aatgctggac aggaacctcc 6840
accctcatgt cacatttctt cagtgtgacc cttctggccc ctctcctcct gacagcggaa 6900
caatgactgc cccgataggt gaggctggag gaagaatcag tcctgtcctt ggcaagctct 6960
tcactatgac agtaaaggct ctctgcctgc tgccaaggcc tgtgactttc taacctggcc 7020
tcacgctggg taagcttaag gtagaggtgc aggattagca agcccacctg gctaccaggc 7080
cgacagctac atctttcaac tgaccctgat caacgaagag ggacttgtgt ctctcagttg 7140
gttccaaatg aaaccaggga gcaggggcgt taggaagctc caacaggatg gtacttaatg 7200
gggcatttga gtggagaggt aggtgacata gtgctttgga gcccagggag ggaaaggttc 7260
tgctgaagtt gaattcaaga ctgttctttc atcacaaact tgagtttcct ggacatttgt 7320
ttgcagaaac aaccgtaggg ttttgcctta acctcgtggg tttattatta cctcataggg 7380
actttgcctc ctgacagcag tttatgggtg ttcattgtgg cacttgagtt ttcttgcata 7440
cttgttagag aaaccaagtt tgtcatcaac ttcttattta accccctggc tataacttca 7500
tggattatgt tataattaag ccatccagag taaaatctgt ttagattatc ttggagtaag 7560
ggggaaaaaa tctgtaattt tttctcctca actagatata tacataaaaa atgattgtat 7620
tgcttcattt aaaaaatata acgcaaaatc tcttttcctt ctaaaaaaaa aaaaaaaaaa 7680

<210> SEQ ID NO 10
<211> LENGTH: 2880
<212> TYPE: DNA
<213> ORGANISM: Homo sapiens

<400> SEQUENCE: 10
gcttccctgg gtgccacggt catgtgactt cggcaagatg gctgccctga cagcggagca 60
ttttgcagca ctccagagcc tgctcaagct gctccaggct ctgcaccgcc tcactaggct 120
ggtggcattc cgtgacctgt cctctgccga ggcaattctg gctctctttc cagaaaattt 180
ccaccaaaac ctcaaaaacc tgctgacaaa gatcatccta gaacatgtgt ctacttggag 240
aaccgaagcc caggcaaatc agatctctct gccacgcctg gtcgatctgg actggagagt 300
ggatatcaaa acctcctcag acagcatcag ccgcatggcc gtccccacct gcctgctcca 360
gatgaagatc caagaagatc ccagcctatg cggagacaaa ccctccatct cagctgtcac 420
cgtggagctg agcaaagaaa cactggacac catgttagat ggcctgggcc gcatccgaga 480
ccaactctct gccgtggcca gtaaatgatc cagccagctg ccagggccac tgccatgacc 540
cagctgctca tgagtgataa atgtctcccc atatgcaggc tgcccttgca gctgcagctg 600
acaacaggca ggatggtggg gacagcaggg ggctactgcc atccagaagt tacagttgga 660
ttgggaagaa gcagccagat cccccgctgt tctcactcat cttctttctc tttctgaagc 720
tggagagcag aagcccccat ctttgaaaag ctcctgagtg caacttaatt accaccatgg 780
cagggtgagg gaacatttgc atcgtcagct gcctctgcat agctgtttga gaaattcagg 840
cccaaatcat gcagcctatc caataagtaa gtttatttcc aacattagct ctaattagtt 900
catttccaat cccagaacac atggagggaa tcggacaggt gatgccagca gttcctgctc 960
ctctgtcagg gaagccaggc agagcccaca gagcatggtc catccagagt gttccctgag 1020
ccccctccac catactggaa cccctcttca gtgtaggaag tctgaaatgg gtgctaattc 1080
ccttcttcat gaaaccaggg ccctcttcct tcatctaatg cagccactcc taggtgaaga 1140
agtgggaata attggaaata aacaacagtt ctaaaacttc catgattttt gtagcttctt 1200
ttgtccccaa gttgaagctt ttggccagta ccttctctag tttttaaaga tgatcccaac 1260
ttcctaattc ccagctaagc ccttgaccca tggtgtgaca tgaaatcagg caattgaatc 1320
gcaccacttt ctgtgttttc acctgttacg tagaacaaaa ggaagcaagg tggccaggcg 1380
caatggctca cgcctgtaat cccagcactt tgggaggccg aggcaggcag atcatgaggt 1440
caggagatcg agaccatggt gaaaccccat ctctactaaa aatacaaaaa attagctggg 1500
cgcggtggcg ggcatctgta gtcccagctc ctcgggaggc tgaggcagga gaatggcgtg 1560
aacctgggag gcagagcttg cagtgagccg agatcgtgcc actgcactcc agtctgggtg 1620
acagagaagg actcgtctca aaaaataaaa ataaataaaa aggaagcaag gctaatcatc 1680
agtatgtgct tgttacaaga gctatgatga aggcactcct tcgagtttaa ccaaatgaga 1740
tcatctctgt catgtgcctc acgcctcaca gggactccat gtgtgaagat tccccccttca 1800 ctcaccagat catctccatg gcaacagctt gcagcctgct cttggagtgc tttgttttgg 1860
cagcttctct gctagtttgt gtatggagtg aatggaggag gtaaatccac agattaagaa 1920
tatgctgtca ggagtcaggc agccaaggtc agaagccagc tctgcttctc agtggtaagg 1980
tgcttgactt ctacatctca attttcaccc actttgtact tttttcctaa attaaatgag 2040
tataatagta gtacctactt gataggactt ttgtgaaaat taaatgatat aatgcaccta 2100
aaaacagtac tgttacaact aataggaaag gctttgatta ttaatggatg agagtagaaa 2160
gcttggtgca tttattgtct catctactat aacagagttg gtgtgagaat tagtattatc 2220
atcctccctt tattgaccag gaaaccagct cattgagatt gagtcatctg ctggtaaatg 2280
gtctcattaa gaggtggacc catatttctc tagctttctc tttacaacac aggactttgc 2340
aaggaacata taattctgtg actagcgcca tttggaaaat gttgaaactg aagtagagat 2400
gagagatctt acgtctgcct acccagtgag atacgaggaa ggtcaaggga aaaaaaattc 2460
caagctcttc tttatctgct ataggaaatg aacattcaat tttttgcatg caacgacaag 2520
aggtcaagga ccccagaagc cagcccgcta cttccaagtt gagagcccct ggtcataccc 2580
tccagttgag ctcagatttg tcacaaattt acccctctcc tttccttcca ttccccatga 2640
cctgcagaga gagatgtcag ataccttcct cttggcctcc catgggcatc cataagaaac 2700
ttacttgaag caagaagccc agtataggtg tctgggcagt tggacatttc ctctagccag 2760
atctgtccga atagagccat ctgggtacat gacgcagagg gcatttgata aataactgga 2820
aaagtcaata aatctttgct acccttcaaa aaaaaaaaaa aaaaaaaaaa aaaaaaaaaa 2880

<210> SEQ ID NO 11
<211> LENGTH: 2358
<212> TYPE: DNA
<213> ORGANISM: Homo sapiens

<400> SEQUENCE: 11
aaactcacac aacaactctt ccccgctgag aggagacagc cagtgcgact ccaccctcca 60
gctcgacggc agccgccccg gccgacagcc ccgagacgac agcccggcgc gtcccggtcc 120
ccacctccga ccaccgccag cgctccaggc cccgccgctc cccgctcgcc gccaccgcgc 180
cctccgctcc gcccgcagtg ccaaccatga ccgccgccag tatgggcccc gtccgcgtcg 240
ccttcgtggt cctcctcgcc ctctgcagcc ggccggccgt cggccagaac tgcagcgggc 300
cgtgccggtg cccggacgag ccggcgccgc gctgcccggc gggcgtgagc ctcgtgctgg 360
acggctgcgg ctgctgccgc gtctgcgcca agcagctggg cgagctgtgc accgagcgcg 420
acccctgcga cccgcacaag ggcctcttct gtgacttcgg ctccccggcc aaccgcaaga 480
tcggcgtgtg caccgccaaa gatggtgctc cctgcatctt cggtggtacg gtgtaccgca 540
gcggagagtc cttccagagc agctgcaagt accagtgcac gtgcctggac ggggcggtgg 600
gctgcatgcc cctgtgcagc atggacgttc gtctgcccag ccctgactgc cccttcccga 660
ggagggtcaa gctgcccggg aaatgctgcg aggagtgggt gtgtgacgag cccaaggacc 720
aaaccgtggt tgggcctgcc ctcgcggctt accgactgga agacacgttt ggcccagacc 780
caactatgat tagagccaac tgcctggtcc agaccacaga gtggagcgcc tgttccaaga 840
cctgtgggat gggcatctcc acccgggtta ccaatgacaa cgcctcctgc aggctagaga 900
agcagagccg cctgtgcatg gtcaggcctt gcgaagctga cctggaagag aacattaaga 960
agggcaaaaa gtgcatccgt actcccaaaa tctccaagcc tatcaagttt gagctttctg 1020
gctgcaccag catgaagaca taccgagcta aattctgtgg agtatgtacc gacggccgat 1080
gctgcacccc ccacagaacc accaccctgc cggtggagtt caagtgccct gacggcgagg 1140
tcatgaagaa gaacatgatg ttcatcaaga cctgtgcctg ccattacaac tgtcccggag 1200
acaatgacat ctttgaatcg ctgtactaca ggaagatgta cggagacatg gcatgaagcc 1260
agagagtgag agacattaac tcattagact ggaacttgaa ctgattcaca tctcattttt 1320
ccgtaaaaat gatttcagta gcacaagtta tttaaatctg tttttctaac tgggggaaaa 1380
gattcccacc caattcaaaa cattgtgcca tgtcaaacaa atagtctatc aaccccagac 1440
actggtttga agaatgttaa gacttgacag tggaactaca ttagtacaca gcaccagaat 1500
gtatattaag gtgtggcttt aggagcagtg ggagggtacc agcagaaagg ttagtatcat 1560
cagatagcat cttatacgag taatatgcct gctatttgaa gtgtaattga gaaggaaaat 1620
tttagcgtgc tcactgacct gcctgtagcc ccagtgacag ctaggatgtg cattctccag 1680
ccatcaagag actgagtcaa gttgttcctt aagtcagaac agcagactca gctctgacat 1740
tctgattcga atgacactgt tcaggaatcg gaatcctgtc gattagactg gacagcttgt 1800
ggcaagtgaa tttgcctgta acaagccaga tttttaaaa tttatattgt aaatattgtg 1860
tgtgtgtgtg tgtgtgtata tatatatata tgtacagtta tctaagttaa tttaaagttg 1920
tttgtgcctt tttatttttg tttttaatgc tttgatattt caatgttagc ctcaatttct 1980
gaacaccata ggtagaatgt aaagcttgtc tgatcgttca aagcatgaaa tggatactta 2040
tatggaaatt ctgctcagat agaatgacag tccgtcaaaa cagattgttt gcaaagggga 2100
ggcatcagtg tccttggcag gctgatttct aggtaggaaa tgtggtagcc tcacttttaa 2160
tgaacaaatg gcctttatta aaaactgagt gactctatat agctgatcag ttttttcacc 2220
tggaagcatt tgtttctact ttgatatgac tgtttttcgg acagtttatt tgttgagagt 2280
gtgaccaaaa gttacatgtt tgcacctttc tagttgaaaa taaagtgtat atttttttcta 2340 taaaaaaaaa aaaaaaaa 2358

<210> SEQ ID NO 12
<211> LENGTH: 4697
<212> TYPE: DNA
<213> ORGANISM: Homo sapiens

<400> SEQUENCE: 12
agacgctcgc ctggcagctg cgcacactcg gagcgccccg agcggcgcag atagggacgt 60
tggggctgtg ccccgcggcg cggcgcctgc cactgcgcag gcgcctcagg aagagctcgg 120
catcgcccct cttcctccag gtccccccttc cccgcaactt cccacgagtg ccaggtgccg 180
cgagcgccga gttccgcgca ttggaaagaa gcgaccgcgg cggctggaac cctgattgct 240
gtccttcaac gtgttcatta tgaagttatt agtaatactt ttgttttctg gacttataac 300
tggttttaga agtgactctt cctctagttt gccacctaag ttactactag tatcctttga 360
tggcttcaga gctgattatc tgaagaacta tgaatttcct catctccaga attttatcaa 420
agaaggtgtt ttggtagagc atgttaaaaa tgtttttatc acaaaaaacat ttccaaacca 480 ctacagtatt gtgacaggct tgtatgaaga aagccatggc attgtggcta attccatgta 540

-continued

```
tgatgcagtc acaaagaaac acttttctga ctctaatgac aaggatcctt tttggtggaa    600
tgaggcagta cctatttggg tgaccaatca gcttcaggaa aacagatcaa gtgctgctgc    660
tatgtggcct ggtactgatg tacccattca cgataccatc tcttcctatt ttatgaatta    720
caactcctca gtgtcatttg aggaaagact aaataatatt actatgtggc taaacaattc    780
gaacccacca gtcacctttg caacactata ttgggaagaa ccagatgcaa gtggccacaa    840
atacggacct gaagataaag aaaacatgag cagagtgttg aaaaaaatag atgatcttat    900
cggtgactta gtccaaagac tcaagatgtt agggctatgg gaaaatctta atgtgatcat    960
tacaagtgat catgggatga cccagtgttc tcaggacaga ctgataaacc tggattcctg   1020
catcgatcat tcatactaca ctcttataga tttgagccca gttgctgcaa tacttcccaa   1080
aataaataga acagaggttt ataacaaact gaaaaactgt agccctcata tgaatgttta   1140
tctcaaagaa gacattccta acagatttta ttaccaacat aatgatcgaa ttcagcccat   1200
tattttggtt gccgatgaag gctggacaat tgtgctaaat gaatcatcac aaaaattagg   1260
tgaccatggt tatgataatt ctttgcctag tatgcatcca tttctagctg cccacggacc   1320
tgcatttcac aaaggctaca agcatagcac aattaacatt gtggatattt atccaatgat   1380
gtgccacatc ctgggattaa aaccacatcc caataatggg acctttggtc atactaagtg   1440
cttgttagtt gaccagtggt gcattaatct cccagaagcc atcgcgattg ttatcggttc   1500
actcttggtg ttaaccatgc taacatgcct cataataatc atgcagaata gactttctgt   1560
acctcgtcca ttttctcgac ttcagctaca agaagatgat gatgatcctt taattgggtg   1620
acatgtgcta gggcttatac aaagtgtctt tgattaatca caaaactaag aatacatcca   1680
aagaatagtg ttgtaactat gaaaaagaat actttgaaag acaaagaact tagactaagc   1740
atgttaaaat tattactttg ttttccttgt gttttgtttc ggtgcatttg ctaataagat   1800
aacgctgacc atagtaaaat tgttagtaaa tcattaggta acatcttgtg gtaggaaatc   1860
attaggtaac atcaatccta actagaaata ctaaaaatgg cttttgagaa aaatacttcc   1920
tctgcttgta ttttgcgatg aagatgtgat acatctttaa atgaaaatat accaaaattt   1980
agtaggcatg tttttctaat aaatttatat atttgtaaag aaaacaacag aaatctttat   2040
gcaatttgtg aattttgtat attagggagg aaaagcttcc tatattttta tatttacctt   2100
taattagttt gtatctcaag taccctcttg aggtaggaaa tgctctgtga tggtaaataa   2160
aattggagca gacagaaaag atatagcaaa tgaagaaata ttttaaggaa acctatttga   2220
aaaaaaaagc aaagaccatt tgataaaagc ctgagttgtc accattatgt cttaagctgt   2280
tagtcttaaa gattattgtt aaaaaattca gaagaaaaga gagacaagtg ctcttctctc   2340
tatctatgct taatgccttt atgtaagtta cttagttgtt tgcgtgtgcc tgtgcaagtg   2400
tgtttgtgtg tggttgtgtg gacattatgt gatttactat ataaggaggt cagagatgga   2460
ctgtggccag gcttccacat tcctgaagca cacagatctc aggaaaggtt atttttgcac   2520
ttcatatttg tttactttct cctaactcac aagttaaaat cataacttaa tttcattaac   2580
ttttatcatt taactctctc atgtttgttg taacctgagg tatccaaatg ctacagaaaa   2640
atttatgacc caaatacaaa tctcaatttg actgggacag aatgaggaat ggagattttt   2700
gtatttatct ttgggacttt atgccttact ttttaggcta tagaatagtt aagaaatttt   2760
aaacaaaatt tagtatcttt tggtctttca caccattcat atgttaagtg gcagaatagc   2820
cttagtgcta cctccacttt tttctccagt atttgcatca cagaaataat ccctctgttt   2880
aacatgtttg ttcagagcca agggtttatt gtgaagaact gtcatcctgc ctttgctagc   2940
```

tggtaccttc tagtaatcaa aattaatatg aagaaactag gttgtgacag actagattat 3000
atttagtagg ggaaaaattg ggctcaagaa ccattcatca gtacgtgaga caagcagtta 3060
atagtatgat ctttaaagtt ttgacaatat aaaataaact tggtaactgt tttacaaata 3120
taaaagtata ataaatatgc agcccagtta aatattgatt atctgtgatg gtaaagaaca 3180
acagtggtgc cagtcatcaa acatacagtg cgtcctattg agtcactgct aatttcttga 3240
gcctggtatt tgctgcctat tgtatttgtg gttgttgaga ggcattttca aaccctgtat 3300
aaataatcca tgctgttggt cataagttaa ctgtattaag aacagtaaaa taaataaaaa 3360
ccaatagtac taattttgct ttaaaaaaat ttctaatttt tttcacataa aacaattatc 3420
ctaaaggtta atagttgatc gaaacagaat aatagaaaaa ttctacttta atttccatta 3480
aaaagcaaat agcattgaca catttaaagc ttttcattta aagtagtgga tgtttttgaa 3540
gtatctaaaa tagtagcaga atattttata cttggtcctt gcaatggtgt gagttttaat 3600
gattgcatta tcgtgattgg tggttatgag tttcagaaat ctatacttgg catccaactc 3660
atgagtggat tttatatagg atggaacagg aaggtatgtc ctgtcagtat cttaaccctt 3720
tcaacaagac atttacctat ttgtctttcc ttacgttctc aaaatattaa ctcgaattgt 3780
aaattaagca aaaatttaaa aagtatatgt tgatgggaca agaagaatag tatttattta 3840
ataaaacata tattatattg aactatgtgt taattcattt gtatctttta aaaaattatc 3900
actgttaaag ccattgactc ctttagtaca ctgagaaaaa tcttatagta aaactagcct 3960
ttcacattaa ggttttggtg tgtattttgt taaataacta acatgctgct ctattttctg 4020
ggtgtagaaa gtatttggct ctaggaaaca tttacttgtt tgtgaaaaca ataccccaag 4080
gtaataggaa aagtttgagt taagtgtttt taattcagtc agtgaattca gaataagtac 4140
attcatgtat aacataggga cagttctgct gctgttattt atatgcaatt cttctggtaa 4200
atagcaatag aataaaacat atttcaatgt ttgtgtatag gttttatatt attattccac 4260
taggaatggc ataagaattt atagataaat tcttgtaaca ttaaaggatt aaaatgtttt 4320
tacattgttt ttgggtgtct ccttcttgtg cccatatctg ataagcttta tggattattg 4380
catttaattc cttttatttg gagggtttta cttccttgtt aacatataaa gttataaatg 4440
aaggacaagg aggagatgga aaatgtgtat ttattgttaa ttcttaaaat agtgtgtaaa 4500
taaaataaca tcagtgtgct ttaaagaaat gtgtatgtag tgccttaatt taaattaaaa 4560
tatttttgac tgttacttga gttcagaatt aatgactttg ttcatgattt ttaaaatgtg 4620
tgtgaataaa atctaccaaa aaattcttac tgtaattatt aaatataaag ttcagtgtca 4680
aaaaaaaaaa aaaaaaa 4697

<210> SEQ ID NO 13
<211> LENGTH: 2448
<212> TYPE: DNA
<213> ORGANISM: Homo sapiens

<400> SEQUENCE: 13
accggcccgg ttccctctcc ggggagcggc ggcggacgcg cggctcccac ccctcccctc 60
tcacgggctc tcccctcccc agtgtggccg cgaccctacc ctctgcaagg cgatggcccg 120
cgccccgagc gcaggctagc gtgcctgggt gcccggccat gggctgtatc ggctctcgga 180
gcccggcggg tcaggcattt ctggggacca acagctggcc gaggctcagg gatagagacg 240
gctgctccag ctaaaggtga atgttggaga cacagtcgcg atgctgccca agtcccggcg 300
agccctaact atccaggaga tcgctgcgct ggccaggtcc tccctgcatg gtatttccca 360
ggtggtgaag gaccacgtga ccaagcctac cgccatggcc cagggccgag tggctcacct 420
cattgagtgg aagggctgga gcaagccgag tgactcacct gctgccctgg aatcagcctt 480
ttcctcctat tcagacctca gcgagggcga acaagaggct cgctttgcag caggagtggc 540
tgagcagttt gccatcgcgg aagccaagct ccgagcatgg tcttcggtgg atggcgagga 600
ctccactgat gactcctatg atgaggactt tgctggggga atggacacag acatggctgg 660
gcagctgccc ctggggccgc acctccagga cctgttcacc ggccaccggt tctcccggcc 720
tgtgcgccag ggctccgtgg agcctgagag cgactgctca cagaccgtgt ccccagacac 780
cctgtgctct agtctgtgca gcctggagga tgggttgttg ggctccccgg cccggctggc 840
ctcccagctg ctgggcgatg agctgcttct cgccaaactg ccccccagcc gggaaagtgc 900
cttccgcagc ctgggcccac tggaggccca ggactcactc tacaactcgc ccctcacaga 960
gtcctgcctt tcccccgcgg aggaggagcc agccccctgc aaggactgcc agccactctg 1020
cccaccacta acgggcagct gggaacggca gcggcaagcc tctgacctgg cctcttctgg 1080
ggtggtgtcc ttagatgagg atgaggcaga gccagaggaa cagtgaccca catcatgcct 1140
ggcagtggca tgcatccccc ggctgctgcc aggggcagag cctctgtgcc caagtgtggg 1200
ctcaaggctc ccagcagagc tccacagcct agagggctcc tgggagcgct cgcttctccg 1260
ttgtgtgttt tgcatgaaag tgtttggaga ggaggcaggg gctgggctgg gggcgcatgt 1320
cctgccccca ctcccggggc ttgccggggg ttgcccgggg cctctggggc atggctacag 1380
ctgtggcaga cagtgatgtt catgttctta aaatgccaca cacacatttc ctcctcggat 1440
aatgtgaacc actaaggggg ttgtgactgg gctgtgtgag ggtggggtgg gaggggggcc 1500
agcaaccccc caccctcccc atgcctctct cttctctgct ttcttctca cttccgagtc 1560 catgtgcagt gcttgataga atcacccccca cctggagggg ctggctcctg ccctcccgga 1620
gcctatgggt tgagccgtcc ctcaagggcc cctgcccagc tgggctcgtg ctgtgcttca 1680
ttcacctctc catcgtctct aaatcttcct ctttttttcct aaagacagaa ggtttttggt 1740 ctgtttttttc agtcggatct tctcttctct gggaggcttt ggaatgatga aagcatgtac 1800
cctccaccct tttcctggcc ccctaatggg gcctgggccc tttcccaacc cctcctagga 1860
tgtgcgggca gtgtgctggc gcctcacagc cagccgggct gcccattcac gcagagctct 1920
ctgagcggga ggtggaagaa aggatggctc tggttgccac agagctggga cttcatgttc 1980
ttctagagag ggccacaaga gggccacagg ggtggccggg agttgtcagc tgatgcctgc 2040
tgagaggcag gaattgtgcc agtgagtgac agtcatgagg gagtgtctct tcttggggag 2100
gaaagaaggt agagcctttc tgtctgaatg aaaggccaag gctacagtac agggccccac 2160
cccagccagg gtgttaatgc ccacgtagtg gaggcctctg gcagatcctg cattccaagg 2220
tcactggact gtacgttttt atggttgtgg gaagggtggg tggctttaga attaagggcc 2280
ttgtaggctt tggcaggtaa gagggcccaa ggtaagaacg agagccaacg ggcacaagca 2340
ttctatatat aagtggctca ttaggtgttt attttgttct atttaagaat ttgttttatt 2400
aaattaatat aaaaatcttt gtaaatctct aaaaaaaaaa aaaaaaaa 2448

<210> SEQ ID NO 14
<211> LENGTH: 5948
<212> TYPE: DNA
<213> ORGANISM: Homo sapiens

<400> SEQUENCE: 14

-continued

```
ggagcgggcc gagccgccac cgcggccgga gctgtccctt agccagaccc ggcgagacac     60
gagcggcggg agggaggcgg tggcgcgccc ggccccgccc gcccgaccaa gcgtcggacg    120
cggcccggcg ccgagccatg gagcctgagc cagtggagga ctgtgtgcag agcactctcg    180
ccgccctgta tccacccttt gaggcaacag cccccaccct gttgggccag gtgttccagg    240
tggtggagag gacttatcgg gaggacgcac tgaggtacac gctggacttc ctggtaccag    300
ccaagcacct gcttgccaag gtccagcagg aagcctgtgc ccaatacagt ggattcctct    360
tcttccatga ggggtggccg ctctgcctgc atgaacaggt ggtggtgcag ctagcagccc    420
taccctggca actgctgcgc ccaggagact tctatctgca ggtggtgccc tcagctgccc    480
aagcaccccg actagcactc aagtgtctgg cccctggggg tgggcgggtg caggaggttc    540
ctgtgcccaa tgaggcttgt gcctacctat tcacacctga gtggctacaa ggcatcaaca    600
aggaccggcc aacaggtcgc ctcagtacct gcctactgtc tgcgccctct gggattcagc    660
ggctgccctg ggctgagctc atctgtccac gatttgtgca caaagagggc ctcatggttg    720
gacatcagcc aagtacactg cccccagaac tgccctctgg acctccaggg cttcccagcc    780
ctccacttcc tgaggaggcg ctgggtaccc ggagtcctgg ggatgggcac aatgcccctg    840
tggaaggacc tgagggcgag tatgtggagc tgttagaggt gacgctgccc gtgaggggga    900
gcccaacaga tgctgaaggc tccccaggcc tctccagagt ccggacggta cccacccgca    960
agggcgctgg agggaagggc cgccaccgga gacaccgggc gtggatgcac cagaagggcc   1020
tggggcctcg gggccaggat ggagcacgcc cacccggcga ggggagcagc accggagcct   1080
cccctgagtc tcccccagga gctgaggctg tcccagaggc agcagtcttg gaggtgtctg   1140
agcccccagc agaggctgtg ggagaagcct ccggatcttg ccccctgagg ccaggggagc   1200
ttagaggagg aggaggagga ggccaggggg ctgaaggacc acctggtacc cctcggagaa   1260
caggcaaagg aaacagaaga aagaagcgag ctgcaggtcg aggggctctt agccgaggag   1320
gggacagtgc cccactgagc cctggggaca aggaagatgc cagccaccaa gaagcccttg   1380
gcaatctgcc ctcaccaagt gagcacaagc ttccagaatg ccacctggtt aaggaggaat   1440
atgaaggctc agggaagcca gaatctgagc caaaagagct caaaacagca ggcgagaaag   1500
agcctcagct ctctgaagcc tgtgggccta cagaagaggg ggccggagag agagagctgg   1560
aggggccagg cctgctgtgt atggcaggac acacaggccc agaaggcccc ctgtctgaca   1620
ctccaacacc tccgctggag actgtgcagg aaggaaaagg ggacaacatt ccagaagagg   1680
cccttgcagt ctccgtctct gatcaccctg atgtagcttg ggacttgatg gcatctggat   1740
tcctcatcct gacgggaggg gtggaccaga gtgggcgagc tctgctgacc attaccccac   1800
cgtgccctcc tgaggagccc ccaccctccc gagacacgct gaacacaact cttcattacc   1860
tccactcact gctcaggcct gatctacaga cactggggct gtccgtcctg ctggaccttc   1920
gtcaggcacc tccactgcct ccagcactca ttcctgcctt gagccaactt caggactcag   1980
gagatcctcc ccttgttcag cggctgctga ttctcattca tgatgacctt ccaactgaac   2040
tctgtggatt tcagggtgct gaggtgctgt cagagaatga tctgaaaaga gtggccaagc   2100
cagaggagct gcagtgggag ttaggaggtc acagggaccc ctctcccagt cactgggtag   2160
agatacacca ggaagtggta aggctatgtc gcctgtgcca aggtgtgctg ggctcggtac   2220
ggcaggccat tgaggagctg gagggagcag cagagccaga ggaagaggag gcagtgggaa   2280
tgcccaagcc actgcagaag gtgctggcag atccccggct gacggcactg cagagggatg   2340
```

-continued

```
gggggccat cctgatgagg ctgcgctcca ctcccagcag caagctggag ggccaaggcc   2400
cagctacact gtatcaggaa gtggacgagg ccattcacca gcttgtgcgc ctctccaacc   2460
tgcacgtgca gcagcaagag cagcggcagt gcctgcggcg actccagcag gtgttgcagt   2520
ggctctcggg cccaggggag gagcagctgg caagctttgc tatgcctggg gacaccttgt   2580
ctgccctgca ggagacagag ctgcgattcc gtgctttcag cgctgaggtc caggagcgcc   2640
tggcccaggc acgggaggcc ctggctctgg aggagaatgc cacctcccag aaggtgctgg   2700
atatctttga acagcggctg gagcaggttg agagtggcct ccatcgggcc ctgcggctac   2760
agcgcttctt ccagcaggca catgaatggg tggatgaggg ctttgctcgg ctggcaggag   2820
ctgggccggg tcgggaggct gtgctggctg cactggccct gcggcgggcc ccagagccca   2880
gtgccggcac cttccaggag atgcgggccc tggccctgga cctgggcagc ccagcagccc   2940
tgcgagaatg ggccgctgc caggcccgct gccaagagct agagaggagg atccagcaac   3000
acgtgggaga ggaggcgagc ccacggggct accgacgacg gcgggcagac ggtgccagca   3060
gtggagggc ccagtggggg ccccgcagcc cctcgcccag cctcagctcc ttgctgctcc   3120
ccagcagccc tgggccacgg ccagccccat cccattgctc cctggcccca tgtggagagg   3180
actatgagga agagggccct gagctggctc cagaagcaga gggcaggccc ccaagagctg   3240
tgctgatccg aggcctggag gtcaccagca ctgaggtggt agacaggacg tgctcaccac   3300
gggaacacgt gctgctgggc cgggctaggg ggccagacgg accctgggga gtaggcaccc   3360
cccggatgga gcgcaagcga agcatcagtg cccagcagcg gctggtgtct gagctgattg   3420
cctgtgaaca agattacgtg gccaccttga gtgagccagt gccacccct gggcctgagc   3480
tgacgcctga acttcggggc acctgggctg ctgccctgag tgcccgggaa aggcttcgca   3540
gcttccaccg gacacacttt ctgcgggagc ttcagggctg cgccacccac cccctacgca   3600
ttggggcctg cttccttcgc cacggggacc agttcagcct ttatgcacag tacgtgaagc   3660
accgacacaa actggagaat ggtctggctg cgctcagtcc cttaagcaag ggctccatgg   3720
aggctggccc ttacctgccc cgagccctgc agcagcctct ggaacagctg actcggtatg   3780
ggcggctcct ggaggagctc ctgagggaag ctgggcctga gctcagttct gagtgccggg   3840
cccttggggc tgctgtacag ctgctccggg aacaagaggc ccgtggcaga gacctgctgg   3900
ccgtggaggc ggtgcgtggc tgtgagatag atctgaagga gcagggacag ctcttgcatc   3960
gagacccctt cactgtcatc tgtggccgaa agaagtgcct tcgccatgtc tttctcttcg   4020
agcatctcct cctgttcagc aagctcaagg gccctgaagg ggggtcagag atgtttgttt   4080
acaagcaggc ctttaagact gctgatatgg ggctgacaga aaacatcggg gacagcggac   4140
tctgctttga gttgtggttt cggcggcggc gtgcacgaga ggcatacact ctgcaggcaa   4200
cctcaccaga gatcaaactc aagtggacaa gttctattgc ccagctgctg tggagacagg   4260
cagcccacaa caaggagctc cgagtgcagc agatggtgtc catgggcatt gggaataaac   4320
ccttcctgga catcaaagcc cttggggagc ggacgctgag tgccctgctc actggaagag   4380
ccgcccgcac ccgggcctcc gtggccgtgt catcctttga gcatgccggc ccctcccttc   4440
ccggcctttc gccgggagcc tgctccctgc ctgcccgcgt cgaggaggag gcctgggatc   4500
tggacgtcaa gcaaatttcc ctggccccag aaacacttga ctcttctgga gatgtgtccc   4560
caggaccaag aaacagcccc agcctgcaac ccccccaccc tgggagcagc actcccaccc   4620
tggccagtcg agggatctta gggctatccc gacagagtca tgctcgagcc ctgagtgacc   4680
ccaccacgcc tctgtgacct ggagaagatc cagaacttgc gtgcagcttc tcctctcagc   4740
```

acactttggg ctgggatggc agtggggcat aatggagccc tgggcgatcg ctgaatttct 4800
tccctctgct tcctggacac agaggaggtc taacgaccag agtattgccc tgccaccact 4860
atctctagtc tccctagctt ggtgccttct cctgcaggag tcagagcagc cacattgctt 4920
gccttcatac cctggaggtg gggaagttat ccctcttccg gtgctttccc atcctgggcc 4980
actgtatcca ggacatcact cccatgccag ccctccctgg cagcccatgt tctcctcttt 5040
tctcaccccc tgactttccc tgagaagaat catctctgcc aggtcaactg gagtccctgg 5100
tgactccatt ctgaggtgtc acaagcaatg aagctatgca aacaatagga gggtgtgaca 5160
ggggaaccgt agactttata tatgtaatta ctgttattat aatactattg ttatattaaa 5220
tgtatttact cacactttgc ctctaaggag ctagagtagt cctctggatt aaggtgataa 5280
ataacttgag cactttccct caaccagccc ttaactagaa cacagaaaat aaaaccaaga 5340
ctggaaggtc ccctctaccc ctcccaggcc cagagctagc tgactgtgta tgagcctggg 5400
agaatgtgtc tcctccacag tggctcccag aggttccaca cactctctga agctccttct 5460
cccacactgc acctactcct tgaggctgaa ctggtcacag acaaactggg atccagcaca 5520
gtccagcagt tctcaaaatg aggtcctcag gccacagtgc gtgagaactt gcttggctgt 5580
ttgttaaatg ctaattcttg ggccccatca gagctactgc atcgaaacct gggggtaaaa 5640
cccaatattc tgcatttctt atcaaactct ttgggtgata actaagtgtc tgaagaggtg 5700
actatttcct gacagaagga cccaaagagg gaagcaggac ataggtaggc agacagacac 5760
agggccctgt gcctcaagac acctgtttat tggggacacg actctgcaat agggatgaca 5820
ggaatcgtac caaaaatagc gacgtctaca gggcccctga tggggctaga agggtacagt 5880
gccccccacc ctcacccctt gtacaaaaat aaactctcac gcctatggac cagcaaaaaa 5940
aaaaaaaa 5948

<210> SEQ ID NO 15
<211> LENGTH: 3851
<212> TYPE: DNA
<213> ORGANISM: Homo sapiens

<400> SEQUENCE: 15
ctctcccaac cgcctcgtcg cactcctcag gctgagagca ccgctgcact cgcggccggc 60
gatgcgggac cccggcgcgg ccgctccgct ttcgtccctg ggcctctgtg ccctggtgct 120
ggcgctgctg ggcgcactgt ccgcgggcgc cggggcgcag ccgtaccacg gagagaaggg 180
catctccgtg ccggaccacg gcttctgcca gcccatctcc atcccgctgt gcacggacat 240
cgcctacaac cagaccatcc tgcccaacct gctgggccac acgaaccaag aggacgcggg 300
cctcgaggtg caccagttct acccgctggt gaaggtgcag tgttctcccg aactccgctt 360
tttcttatgc tccatgtatg cgcccgtgtg caccgtgctc gatcaggcca tcccgccgtg 420
tcgttctctg tgcgagcgcg cccgccaggg ctgcgaggcg ctcatgaaca agttcggctt 480
ccagtggccc gagcggctgc gctgcgagaa cttcccggtg cacggtgcgg gcgagatctg 540
cgtgggccag aacacgtcgg acggctccgg gggcccaggc ggcggcccca ctgcctaccc 600
taccgcgccc tacctgccgg acctgccctt caccgcgctg cccccggggg cctcagatgg 660
cagggggcgt cccgccttcc ccttctcatg cccccgtcag ctcaaggtgc ccccgtacct 720
gggctaccgc ttcctgggtg agcgcgattg tggcgccccg tgcgaaccgg gccgtgccaa 780
cggcctgatg tactttaagg aggaggagag gcgcttcgcc cgcctctggg tgggcgtgtg 840

-continued

```
gtccgtgctg tgctgcgcct cgacgctctt taccgttctc acctacctgg tggacatgcg    900
gcgcttcagc tacccagagc ggcccatcat cttcctgtcg ggctgctact tcatggtggc    960
cgtggcgcac gtggccggct tccttctaga ggaccgcgcc gtgtgcgtgg agcgcttctc   1020
ggacgatggc taccgcacgg tggcgcaggg caccaagaag gagggctgca ccatcctctt   1080
catggtgctc tacttcttcg gcatggccag ctccatctgg tgggtcattc tgtctctcac   1140
ttggttcctg gcggccggca tgaagtgggg ccacgaggcc atcgaggcca actcgcagta   1200
cttccacctg gccgcgtggg ccgtgcccgc cgtcaagacc atcactatcc tggccatggg   1260
ccaggtagac ggggacctgc tgagcggggt gtgctacgtt ggcctctcca gtgtggacgc   1320
gctgcggggc ttcgtgctgg cgcctctgtt cgtctacctc ttcataggca cgtccttctt   1380
gctggccggc ttcgtgtccc tcttccgtat ccgcaccatc atgaaacacg acggcaccaa   1440
gaccgagaag ctggagaagc tcatggtgcg catcggcgtc ttcagcgtgc tctacacagt   1500
gcccgccacc atcgtcctgg cctgctactt ctacgagcag gccttccgcg agcactggga   1560
gcgcacctgg ctcctgcaga cgtgcaagag ctatgccgtg ccctgcccgc ccggccactt   1620
cccgcccatg agccccgact tcaccgtctt catgatcaag tacctgatga ccatgatcgt   1680
cggcatcacc actggcttct ggatctggtc gggcaagacc ctgcagtcgt ggcgccgctt   1740
ctaccacaga cttagccaca gcagcaaggg ggagactgcg gtatgagccc cggcccctcc   1800
ccacctttcc caccccagcc ctcttgcaag aggagaggca cggtagggaa aagaactgct   1860
gggtgggggc ctgtttctgt aactttctcc ccctctactg agaagtgacc tggaagtgag   1920
aagttctttg cagatttggg gcgaggggtg atttggaaaa gaagacctgg gtggaaagcg   1980
gtttggatga aaagatttca ggcaaagact tgcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccgggaaagg tacagccctg tctgcggtgg   2220
ctgctttgtt ggaaagaggg agggcctcct gcggtgtgct tgtcaagcag tggtcaaacc   2280
ataatctctt ttcactgggg ccaaactgga gcccagatgg gttaatttcc agggtcagac   2340
attacggtct ctcctcccct gccccctccc gcctgttttt cctcccgtac tgctttcagg   2400
tcttgtaaaa taagcatttg gaagtcttgg gaggcctgcc tgctagaatc ctaatgtgag   2460
gatgcaaaag aaatgatgat aacattttga gataaggcca aggagacgtg gagtaggtat   2520
ttttgctact ttttcatttt ctggggaagg caggaggcag aaagacgggt gttttatttg   2580
gtctaatacc ctgaaaagaa gtgatgactt gttgcttttc aaaacaggaa tgcatttttc   2640
cccttgtctt tgttgtaaga gacaaaagag gaaacaaaag tgtctccctg tggaaaggca   2700
taactgtgac gaaagcaact tttataggca aagcagcgca aatctgaggt ttcccgttgg   2760
ttgttaattt ggttgagata aacattcctt tttaaggaaa agtgaagagc agtgtgctgt   2820
cacacaccgt taagccagag gttctgactt cgctaaagga aatgtaagag gttttgttgt   2880
ctgttttaaa taaatttaat tcggaacaca tgatccaaca gactatgtta aaatattcag   2940
ggaaatctct cccttcattt actttttctt gctataagcc tatatttagg tttcttttct   3000
atttttttct cccatttgga tcctttgagg taaaaaaaca taatgtcttc agcctcataa   3060
taaaggaaag ttaattaaaa aaaaaaagca aagagccatt ttgtcctgtt ttcttggttc   3120
catcaatctg tttattaaac atcatccata tgctgaccct gtctctgtgt ggttgggttg   3180
ggaggcgatc agcagatacc atagtgaacg aagaggaagg tttgaaccat gggccccatc   3240
```

tttaaagaaa gtcattaaaa gaaggtaaac ttcaaagtga ttctggagtt ctttgaaatg 3300
tgctggaaga cttaaattta ttaatcttaa atcatgtact ttttttctgt aatagaactc 3360
ggattctttt gcatgatggg gtaaagctta gcagagaatc atgggagcta acctttatcc 3420
cacctttgac actaccctcc aatcttgcaa cactatcctg tttctcagaa cagtttttaa 3480
atgccaatca tagagggtac tgtaaagtgt acaagttact ttatatatgt aatgttcact 3540
tgagtggaac tgctttttac attaaagtta aaatcgatct tgtgtttctt caaccttcaa 3600
aactatctca tctgtcagat ttttaaaact ccaacacagg ttttggcatc ttttgtgctg 3660
tatcttttaa gtgcatgtga aatttgtaaa atagagataa gtacagtatg tatattttgt 3720
aaatctccca tttttgtaag aaaatatata ttgtatttat acatttttac tttggatttt 3780
tgttttgttg gctttaaagg tctaccccac tttatcacat gtacagatca caaataaatt 3840
tttttaaata c 3851

<210> SEQ ID NO 16
<211> LENGTH: 2394
<212> TYPE: DNA
<213> ORGANISM: Homo sapiens

<400> SEQUENCE: 16
gacgggccgg tacagcccgt gtccccgccc cgcgccatcg ctaggcgacg tgcgcttttg 60
ccgcgccgtg ctgcccgcga gggcagctga ggtggtggtg gcggccgcct tgtcgaggca 120
tcgcgcgccc gtgaagtgtt cgccgtcagt gctgttgggt gcctggagcc gcgtccccccg 180 tcccgaaaac tgtccttgac agtacttgcg cggcccaacg gccgccggcg cccccgcgtc 240
tccatggcga cggccttttt ccctgcgagg accccggcgg cagggctgcc ccgcggcgcc 300
tgcttggcgc gacgctctag cggttaccgc tgcgggctgg ctgggcgtag tggggctgcg 360
cggctgccac ggagctagag ggcaagtgtg ctcggcccag cgtgcaggga acgcgggcgg 420
ccagacaacg ggctgggctc cggggcctgc ggcgcgggcg ctgagctggc agggcgggtc 480
ggggcgcggg ctgcatccgc atctcctcca tcgcctgcag taagggcggc cgcggcgagc 540
ctttgagggg aacgacttgt cggagcccta accaggggta tctctgagcc tggtgggatc 600
cccggagcgt cacatcactt tccgatcact tcaaagtaca gcagaccgag gacacggttg 660
ttaccaagac caggctgttg ccttggaaga gcccagagcg tgtcaaggga gacagccaca 720
tcacgccaga aatacatgac agctggatta gccctgggag agggaggccc agatgtggga 780
gctcagggga ggtgcagctc aacgtggagt ttggaggagg ctaccttgac ctttgaatgc 840
caagtgggag ccagccagat gaaaggggtt aaaaactaat atttatatga cagaagaaaa 900
agatgtcatt ccgtaaagta aacatcatca tcttggtcct ggctgttgct ctcttcttac 960
tggttttgca ccataacttc ctcagcttga gcagtttgtt aaggaatgag gttacagatt 1020
caggaattgt agggcctcaa cctatagact ttgtcccaaa tgctctccga catgcagtag 1080
atgggagaca agaggagatt cctgtggtca tcgctgcatc tgaagacagg cttggggggg 1140
ccattgcagc tataaacagc attcagcaca acactcgctc caatgtgatt ttctacattg 1200
ttactctcaa caatacagca gaccatctcc ggtcctggct caacagtgat tccctgaaaa 1260
gcatcagata caaaattgtc aattttgacc ctaaactttt ggaaggaaaa gtaaaggagg 1320
atcctgacca gggggaatcc atgaaacctt taacctttgc aaggttctac ttgccaattc 1380
tggttcccag cgcaaagaag gccatataca tggatgatga tgtaattgtg caaggtgata 1440

```
ttcttgccct ttacaataca gcactgaagc caggacatgc agctgcattt tcagaagatt   1500

gtgattcagc ctctactaaa gttgtcatcc gtggagcagg aaaccagtac aattacattg   1560

gctatcttga ctataaaaag gaaagaattc gtaagctttc catgaaagcc agcacttgct   1620

catttaatcc tggagttttt gttgcaaacc tgacggaatg gaaacgacag aatataacta   1680

accaactgga aaaatggatg aaactcaatg tagaagaggg actgtatagc agaaccctgg   1740

ctggtagcat cacaacacct cctctgctta tcgtatttta tcaacagcac tctaccatcg   1800

atcctatgtg gaatgtccgc caccttggtt ccagtgctgg aaaacgatat tcacctcagt   1860

ttgtaaaggc tgccaagtta ctccattgga atggacattt gaagccatgg ggaaggactg   1920

cttcatatac tgatgtttgg gaaaaatggt atattccaga cccaacaggc aaattcaacc   1980

taatccgaag atataccgag atctcaaaca taaagtgaaa cagaatttga actgtaagca   2040

agcatttctc aggaagtcct ggaagatagc atgcgtggga agtaacagtt gctaggcttc   2100

aatgcctatc ggtagcaagc catggaaaaa gatgtgtcag ctaggtaaag atgacaaact   2160

gccctgtctg gcagtcagct tcccagacag actatagact ataaatatgt ctccatctgc   2220

cttaccaagt gttttcttac tacaatgctg aatgactgga aagaagaact gatatggcta   2280

gttcagctag ctggtacaga taattcaaaa ctgctgttgg ttttaatttt gtaacctgtg   2340

gcctgatctg taaataaaac ttacattttt caataggtaa aaaaaaaaaa aaaa         2394
```

<210> SEQ ID NO 17
<211> LENGTH: 4463
<212> TYPE: DNA
<213> ORGANISM: Homo sapiens

<400> SEQUENCE: 17

```
gcagcgcgca ccgagccggc cgcgccgcgc ccgccgctct cgccgctttc gccgcggtct     60

cctcctctag cgcccgccgc ggccggtaaa tctcggctgg aggagcagcg gcggcccccg    120

agtcaacttt cattcccttt ttgcttctgc ctcaccattc tcttctcctc ctcgaaagat    180

ggctgtttgg agaaggggga gaagttaaga ggtcgccagc gcggagcgaa ggagggcgcg    240

atagcctcag caggagcggg cggaggtttc tcctctgcca acccctcctg gaccattgtc    300

agcagttgaa cgacaaaggc tgtgaatctg catcctagtc ttagcagtcc ctctgattct    360

catgatgagc tcacctgcac agcctgacct catgtggaac cttgtaccat gggtgctatt    420

ctgtggctgc tgtaggatct tcccagatgg ggtggctgga cgagagcagc tcttggctca    480

gcaaagaatg cacagtatga tcagctcagt ggatgtgaag tcagaagttc ctgtgggcct    540

ggagcccatc tcacctttag acctaaggac agacctcagg atgatgatgc ccgtggtgga    600

ccctgttgtc cgtgagaagc aattgcagca ggaattactt cttatccagc agcagcaaca    660

aatccagaag cagcttctga tagcagagtt tcagaaacag catgagaact tgacacggca    720

gcaccaggct cagcttcagg agcatatcaa ggaacttcta gccataaaac agcaacaaga    780

actcctagaa aaggagcaga aactggagca gcagaggcaa gaacaggaag tagagaggca    840

tcgcagagaa cagcagcttc ctcctctcag aggcaaagat agaggacgag aaagggcagt    900

ggcaagtaca gaagtaaagc agaagcttca agagttccta ctgagtaaat cagcaacgaa    960

agacactcca actaatggaa aaaatcattc cgtgagccgc catcccaagc tctggtacac   1020

ggctgcccac cacacatcat tggatcaaag ctctccaccc cttagtggaa catctccatc   1080

ctacaagtac acattaccag gagcacaaga tgcaaaggat gatttccccc ttcgaaaaac   1140

tgaatcctca gtcagtagca gttctccagg ctctggtccc agttcaccaa acaatgggcc   1200
```

```
aactggaagt gttactgaaa atgagacttc ggttttgccc cctacccctc atgccgagca   1260
aatggtttca cagcaacgca ttctaattca tgaagattcc atgaacctgc taagtcttta   1320
tacctctcct tctttgccca acattacctt ggggcttccc gcagtgccat cccagctcaa   1380
tgcttcgaat tcactcaaag aaaagcagaa gtgtgagacg cagacgctta ggcaaggtgt   1440
tcctctgcct gggcagtatg gaggcagcat cccggcatct tccagccacc ctcatgttac   1500
tttagaggga aagccaccca acagcagcca ccaggctctc ctgcagcatt tattattgaa   1560
agaacaaatg cgacagcaaa agcttcttgt agctggtgga gttcccttac atcctcagtc   1620
tcccttggca acaaaagaga gaatttcacc tggcattaga ggtacccaca aattgccccg   1680
tcacagaccc ctgaaccgaa cccagtctgc acctttgcct cagagcacgt tggctcagct   1740
ggtcattcaa cagcaacacc agcaattctt ggagaagcag aagcaatacc agcagcagat   1800
ccacatgaac aaactgcttt cgaaatctat tgaacaactg aagcaaccag gcagtcacct   1860
tgaggaagca gaggaagagc ttcaggggga ccaggcgatg caggaagaca gagcgccctc   1920
tagtggcaac agcactagga gcgacagcag tgcttgtgtg gatgacacac tgggacaagt   1980
tggggctgtg aaggtcaagg aggaaccagt ggacagtgat gaagatgctc agatccagga   2040
aatggaatct ggggagcagg ctgcttttat gcaacaggta ataggcaaag atttagctcc   2100
aggatttgta attaaagtca ttatctgaac atgaaatgca ttgcaggttt ggtaaatgga   2160
tatgatttcc tatcagttta tatttctcta tgatttgagt tcagtgttta aggattctac   2220
ctaatgcaga tatatgtata tatctatata gaggtctttc tatatactga tctctatata   2280
gatatcaatg tttcattgaa aatccactgg taaggaaata cctgttatac taaaattatg   2340
atacataata tctgagcagt taataggctt taaatttatc ccaaagcctg ctacaccaat   2400
tacttctaaa gaaaacaaat tcactgttat tttgagttta tgtgttgaga tcagtgactg   2460
ctggatagtc tcccagtctg atcaatgaag cattcgatta gtttttgatt ttttgcaaca   2520
tctagaattt aattttcaca tcactgtaca taatgtatca tactatagtc ttgaacactg   2580
ttaaaggtag tctgcccctt ccttcctctc tcttttttta gttaagtaga aatgttctgg   2640
tcaccatgcc agtagtccta ggttattgtg taggttgcaa ttgaacatat taggaataca   2700
ggtggtttta aatatataga tgcaaattgc agcactactt taaatattag attatgtctc   2760
acatagcact gctcatttta cttttatttt gtgtaatttg atgacactgt ctatcaaaaa   2820
agagcaaatg aagcagatgc aaatgttagt gagaagtaat gtgcagcatt atggtccaat   2880
cagatacaat attgtgtcta caattgcaaa aaacacagta acaggatgaa tattatctga   2940
tatcaagtca aaatcagttt gaaaagaagg tgtatcatat tttatattgt cactagaatc   3000
tcttaagtat aattccataa tgacatgggc atataccgta acattctggc aaataacaat   3060
tagaaaagat aggtttaaca aaaaaattta cttgtatata atgcaccttc aggaggacta   3120
tgtcctttga tgctataaaa tacaaacaac tttgaaggca acagaagaca ctgtttattc   3180
aagtcagttc tttgtcaggt tcctgctgtt ctcctacaga aaagtgattc tgtgagggtg   3240
aacaggaaat gccttgtgga aacaggaagt ccaagtgatt catgtactga ggaatgtagg   3300
aaaaaaaatc tgaggatagt gctttactct ttctgttttt aaagggcact ctatgaattg   3360
atttattgtc taagaaaata acaccacaag tagggaaatt gttacggaag cttttcactg   3420
gaacatttcc ttcatattcc cttttgatat gtttaccttg ttttataggt ttacttttgt   3480
taagctagtt aaaggttcgt tgtattaaga ccccttttaat atggataatc caaattgacc   3540
```

tagaatcttt gtgaggtttt ttctattaaa atatttatat ttctaaatcc gaggtatttc 3600
aaggtgtagt atcctatttc aaaggagata tagcagtttt gccaaatgta gacattgttc 3660
aactgtatgt tattggcacg tgttgtttac attttgctgt gacatttaaa aatatttctt 3720
taaaaatgtt actgctaaag atacattatc ctttttttaaa aagtctccat tcaaattaaa 3780
ttaacataac tagaagttag aaagtttaaa agttttccac ataatgaaag tccttctgat 3840
aatttgacaa atagctataa taggaacact ccctatcacc aacatatttt ggttagtata 3900
ttccttcata ttaaaatgac tttttgtcag ttgttttgca ttaaaaatat ggcatgccta 3960
agataaaatt gtatattttt tccatctcat aaatattcat tttcttcaaa gtctttttttc 4020 aatctcataa aaaagggata gtgcatcttt taaaatacat tttatttggg gaggaacatg 4080
tggctgagca gacttttgta taatattact tcaaagatat gtaatcacaa acaaaaaaaa 4140
ctatttttta taatgtcatt tgagagagtt tcatcagtac agttggtgga cgttaattgt 4200
ttgaatttga tagtctttga atttaatcaa gaaactacct ggaaccagtg aaaaggaaag 4260
ctggacttaa ataatcttag aattaattga taaatgtctc ttttaaaatc tactgtattt 4320
attataattt acacccttga aggtgatctc ttgttttgtg ttgtaaatat attgtttgta 4380
tgtttccctt cttgccttct gttataagtc tcttcctttc tcaaataaag tttttttttaa 4440 aagaaaaaaa aaaaaaaaaa aaa 4463

<210> SEQ ID NO 18
<211> LENGTH: 2697
<212> TYPE: DNA
<213> ORGANISM: Homo sapiens

<400> SEQUENCE: 18
acttgtccgt cacgtgcggc cgcccggcct ctcggccttg ccgcgcgcct ggcggggttg 60
ggggggcggg gaccaagatc tgctgcgcct gcgttgtggg cgttctcggg gagctgctgc 120
cgtagctgcc gccgccgcta ccaccgcgtt cgggtgtaga atttggaatc cctgcgccgc 180
gttaacaatg aagcagagtt cgaacgtgcc ggctttcctc agcaagctgt ggacgcttgt 240
ggaggaaacc cacactaacg agttcatcac ctggagccag aatggccaaa gttttctggt 300
cttggatgag caacgatttg caaaagaaat tcttcccaaa tatttcaagc acaataatat 360
ggcaagcttt gtgaggcaac tgaatatgta tggtttccgt aaagtagtac atatcgactc 420
tggaattgta aagcaagaaa gagatggtcc tgtagaattt cagcatcctt acttcaaaca 480
aggacaggat gacttgttgg agaacattaa aaggaaggtt tcatcttcaa aaccagaaga 540
aaataaaatt cgtcaggaag atttaacaaa aattataagt agtgctcaga aggttcagat 600
aaaacaggaa actattgagt ccaggctttc tgaattaaaa agtgagaatg agtccctttg 660
gaaggaggtg tcagaattac gagcaaagca tgcacaacag caacaagtta ttcgaaagat 720
tgtccagttt attgttacat tggttcaaaa taaccaactt gtgagtttaa aacgtaaaag 780
gcctctactt ctaaacacta atggagccca aaagaagaac ctgtttcagc acatagtcaa 840
agaaccaact gataatcatc atcataaagt tccacacagt aggactgaag gtttaaagcc 900
aagggagagg atttcagatg acatcattat ttatgatgtt actgatgata atgcagatga 960
agaaaatatc ccagttattc cagaaactaa tgaggatgtt atatctgatc cctccaactg 1020
tagccagtac cctgatattg tcatcgttga agatgacaat gaagatgagt atgcacctgt 1080
cattcagagt ggagagcaga atgaaccagc cagagaatcc ctaagttcag gcagtgatgg 1140
cagcagccct ctcatgtcta gtgctgtcca gctaaatggc tcatccagtc tgacctcaga 1200
agatccagtg accatgatgg attccatttt gaatgataac atcaatcttt tgggaaaggt 1260
tgagctgttg gattatcttg acagtattga ctgcagttta gaggacttcc aggccatgct 1320
atcaggaaga caatttagca tagacccaga tctcctggtt gatcttttca ctagttctgt 1380
gcagatgaat cccacagatt acatcaataa tacaaaatct gagaataaag gattagaaac 1440
taccaagaac aatgtagttc agccagtttc ggaagaggga agaaaatcta aatccaaacc 1500
agataagcag cttatccagt ataccgcctt tccacttctt gcattcctcg atgggaaccc 1560
tgcttcttct gttgaacagg cgagtacaac agcatcatca gaagttttgt cctctgtaga 1620
taaacccata gaagttgatg agcttctgga tagcagccta gacccagaac caacccaaag 1680
taagcttgtt cgcctggagc cattgactga agctgaagct agtgaagcta cactgtttta 1740
tttatgtgaa cttgctcctg cacctctgga tagtgatatg ccacttttag atagctaaat 1800
ccccaggaag tggactttac atgtatatat tcatcaaaat gatgaactat ttattttaaa 1860
gtatcatttg gtactttttt tgtaaattgc tttgttttgt ttaatcagat actgtggaat 1920
aaaagcacct tttgcttttc tcactaacca cacactcttg cagagctttc aggtgttact 1980
cagctgcata gttacgcaga tgtaatgcac attattggcg tatctttaag ttggattcaa 2040
atggccattt ttctccaatt ttggtaaatt ggatatcttt tttttacaaa tacgaccatt 2100
aacctcagtt aaatttttgt ttgttttcct gtttgatgct gtctatttgc attgagtgta 2160
agtcatttga actaatggta taactcctaa agctttctct gctccagtta tttttattaa 2220
atatttttca cttggcttat ttttaaaact gggaacataa agtgcctgta tcttgtaaaa 2280
cttcatttgt ttcttttggt tcagagaagt tcatttatgt tcaaagacgt ttattcatgt 2340
tcaacaggaa agacaaagtg tacgtgaatg ctcgctgtct gatagggttc cagctccata 2400
tatatagaaa gatcgggggt gggatgggat ggagtgagcc ccatccagtt agttggacta 2460
gttttaaata aaggttttcc ggtttgtgtt tttttgaacc atactgttta gtaaaataaa 2520
tacaatgaat gttgagtact agtgtctgtt atgtgtcttc tttagaggtg acactcacat 2580
gaaacaattt tttcttctca taggaagcag tagctttaaa ctgtctgtgg ttcattattc 2640
tcaatatgaa tcataccaag atatttgtgc ctcatctcga aaatatattg tatattg 2697

<210> SEQ ID NO 19
<211> LENGTH: 11427
<212> TYPE: DNA
<213> ORGANISM: Homo sapiens

<400> SEQUENCE: 19
taccgggcgg aggtgagcgc ggcgccggct cctcctgcgg cggactttgg gtgcgacttg 60
acgagcggtg gttcgacaag tggccttgcg ggccggatcg tcccagtgga agagttgtaa 120
atttgcttct ggccttcccc tacggattat acctggcctt cccctacgga ttatactcaa 180
cttactgttt agaaaatgtg gcccacgaga cgcctggtta ctatcaaaag gagcggggtc 240
gacggtcccc actttcccct gagcctcagc acctgcttgt ttggaagggg tattgaatgt 300
gacatccgta tccagcttcc tgttgtgtca aaacaacatt gcaaaattga aatccatgag 360
caggaggcaa tattacataa tttcagttcc acaaatccaa cacaagtaaa tgggtctgtt 420
attgatgagc ctgtacggct aaaacatgga gatgtaataa ctattattga tcgttccttc 480
aggtatgaaa atgaaagtct tcagaatgga aggaagtcaa ctgaatttcc aagaaaaata 540
cgtgaacagg agccagcacg tcgtgtctca agatctagct tctcttctga ccctgatgag 600

-continued

```
agtgagggaa tacctttgaa aagaaggcgt gtgtcctttg gtgggcacct aagacctgaa    660
ctatttgatg aaaacttgcc tcctaatacg cctctcaaaa ggggagaagc cccaaccaaa    720
agaaagtctc tggtaatgca cactccacct gtcctgaaga aaatcatcaa ggaacagcct    780
caaccatcag gaaaacaaga gtcaggttca gaaatccatg tggaagtgaa ggcacaaagc    840
ttggttataa gccctccagc tcctagtcct aggaaaactc cagttgccag tgatcaacgc    900
cgtaggtcct gcaaaacagc cctgcttcc agcagcaaat ctcagacaga ggttcctaag    960
agaggaggga gaaagagtgg caacctgcct tcaaagagag tgtctatcag ccgaagtcaa   1020
catgatattt tacagatgat atgttccaaa agaagaagtg gtgcttcgga agcaaatctg   1080
attgttgcaa aatcatgggc agatgtagta aaacttggtg caaaacaaac acaaactaaa   1140
gtcataaaac atggtcctca aaggtcaatg aacaaaaggc aaagaagacc tgctactcca   1200
aagaagcctg tgggcgaagt tcacagtcaa tttagtacag gccacgcaaa ctctccttgt   1260
accataataa tagggaaagc tcatactgaa aaagtacatg tgcctgctcg accctacaga   1320
gtgctcaaca acttcatttc caaccaaaaa atggacttta aggaagatct ttcaggaata   1380
gctgaaatgt tcaagacccc agtgaaggag caaccgcagt tgacaagcac atgtcacatc   1440
gctatttcaa attcagagaa tttgcttgga aaacagtttc aaggaactga ttcaggagaa   1500
gaacctctgc tccccacctc agagagtttt ggaggaaatg tgttcttcag tgcacagaat   1560
gcagcaaaac agccatctga taaatgctct gcaagccctc ccttaagacg gcagtgtatt   1620
agagaaaatg gaaacgtagc aaaaacgccc aggaacacct acaaaatgac ttctctggag   1680
acaaaaactt cagatactga gacagagcct tcaaaaacag tatccactgc aaacaggtca   1740
ggaaggtcta cagagttcag gaatatacag aagctacctg tggaaagtaa gagtgaagaa   1800
acaaatacag aaattgttga gtgcatccta aaaagaggtc agaaggcaac actactacaa   1860
caaaggagag aaggagagat gaaggaaata gaaagacctt ttgagacata taaggaaaat   1920
attgaattaa aagaaaacga tgaaaagatg aaagcaatga agagatcaag aacttggggg   1980
cagaaatgtg caccaatgtc tgacctgaca gacctcaaga gcttgcctga tacagaactc   2040
atgaaagaca cggcacgtgg ccagaatctc ctccaaaccc aagatcatgc caaggcacca   2100
aagagtgaga aaggcaaaat cactaaaatg ccctgccagt cattacaacc agaaccaata   2160
aacaccccaa cacacacaaa acaacagttg aaggcatccc tggggaaagt aggtgtgaaa   2220
gaagagctcc tagcagtcgg caagttcaca cggacgtcag gggagaccac gcacacgcac   2280
agagagccag caggagatgg caagagcatc agaacgttta aggagtctcc aaagcagatc   2340
ctggacccag cagcccgtgt aactggaatg aagaagtggc caagaacgcc taaggaagag   2400
gcccagtcac tagaagacct ggctggcttc aaagagctct tccagacacc aggtccctct   2460
gaggaatcaa tgactgatga gaaaactacc aaaatagcct gcaaatctcc accaccagaa   2520
tcagtggaca ctccaacaag cacaaagcaa tggcctaaga gaagtctcag gaaagcagat   2580
gtagaggaag aattcttagc actcaggaaa ctaacaccat cagcagggaa agccatgctt   2640
acgcccaaac cagcaggagg tgatgagaaa gacattaaag catttatggg aactccagtg   2700
cagaaactgg acctggcagg aactttacct ggcagcaaaa gacagctaca gactcctaag   2760
gaaaaggccc aggctctaga agacctggct ggctttaaag agctcttcca gactcctggt   2820
cacaccgagg aattagtggc tgctggtaaa accactaaaa taccctgcga ctctccacag   2880
tcagacccag tggacacccc aacaagcaca aagcaacgac ccaagagaag tatcaggaaa   2940
gcagatgtag agggagaact cttagcgtgc aggaatctaa tgccatcagc aggcaaagcc   3000
```

-continued

```
atgcacacgc ctaaaccatc agtaggtgaa gagaaagaca tcatcatatt tgtgggaact   3060
ccagtgcaga aactggacct gacagagaac ttaaccggca gcaagagacg gccacaaact   3120
cctaaggaag aggcccaggc tctggaagac ctgactggct ttaaagagct cttccagacc   3180
cctggtcata ctgaagaagc agtggctgct ggcaaaacta ctaaaatgcc ctgcgaatct   3240
tctccaccag aatcagcaga caccccaaca agcacaagaa ggcagcccaa gacacctttg   3300
gagaaaaggg acgtacagaa ggagctctca gccctgaaga agctcacaca gacatcaggg   3360
gaaaccacac acacagataa agtaccagga ggtgaggata aaagcatcaa cgcgtttagg   3420
gaaactgcaa aacagaaact ggacccagca gcaagtgtaa ctggtagcaa gaggcaccca   3480
aaaactaagg aaaaggccca accccctagaa gacctggctg gcttgaaaga gctcttccag   3540
acaccagtat gcactgacaa gcccacgact cacgagaaaa ctaccaaaat agcctgcaga   3600
tcacaaccag acccagtgga cacaccaaca agctccaagc cacagtccaa gagaagtctc   3660
aggaaagtgg acgtagaaga agaattcttc gcactcagga aacgaacacc atcagcaggc   3720
aaagccatgc acacacccaa accagcagta agtggtgaga aaaacatcta cgcatttatg   3780
ggaactccag tgcagaaact ggacctgaca gagaacttaa ctggcagcaa gagacggcta   3840
caaactccta aggaaaaggc ccaggctcta gaagacctgg ctggctttaa agagctcttc   3900
cagacacgag gtcacactga ggaatcaatg actaacgata aaactgccaa agtagcctgc   3960
aaatcttcac aaccagaccc agacaaaaac ccagcaagct ccaagcgacg gctcaagaca   4020
tccctgggga aagtgggcgt gaaagaagag ctcctagcag ttggcaagct cacacagaca   4080
tcaggagaga ctacacacac acacacagag ccaacaggag atggtaagag catgaaagca   4140
tttatggagt ctccaaagca gatcttagac tcagcagcaa gtctaactgg cagcaagagg   4200
cagctgagaa ctcctaaggg aaagtctgaa gtccctgaag acctggccgg cttcatcgag   4260
ctcttccaga caccaagtca cactaaggaa tcaatgacta acgaaaaaac taccaaagta   4320
tcctacagag cttcacagcc agacctagtg gacaccccaa caagctccaa gccacagccc   4380
aagagaagtc tcaggaaagc agacactgaa gaagaatttt tagcatttag gaaacaaacg   4440
ccatcagcag gcaaagccat gcacacaccc aaaccagcag taggtgaaga gaaagacatc   4500
aacacgtttt tgggaactcc agtgcagaaa ctggaccagc caggaaattt acctggcagc   4560
aatagacggc tacaaactcg taaggaaaag gcccaggctc tagaagaact gactggcttc   4620
agagagcttt tccagacacc atgcactgat aaccccacga ctgatgagaa aactaccaaa   4680
aaaatactct gcaaatctcc gcaatcagac ccagcggaca ccccaacaaa cacaaagcaa   4740
cggcccaaga gaagcctcaa gaaagcagac gtagaggaag aatttttagc attcaggaaa   4800
ctaacaccat cagcaggcaa agccatgcac acgcctaaag cagcagtagg tgaagagaaa   4860
gacatcaaca catttgtggg gactccagtg gagaaactgg acctgctagg aaatttacct   4920
ggcagcaaga gacggccaca aactcctaaa gaaaaggcca aggctctaga agatctggct   4980
ggcttcaaag agctcttcca gacaccaggt cacactgagg aatcaatgac cgatgacaaa   5040
atcacagaag tatcctgcaa atctccacaa ccagacccag tcaaaacccc aacaagctcc   5100
aagcaacgac tcaagatatc cttggggaaa gtaggtgtga aagaagaggt cctaccagtc   5160
ggcaagctca cacagacgtc agggaagacc acacagacac acagagagac agcaggagat   5220
ggaaagagca tcaaagcgtt taaggaatct gcaaagcaga tgctggaccc agcaaactat   5280
ggaactggga tggagaggtg gccaagaaca cctaaggaag aggcccaatc actagaagac   5340
```

```
ctggccggct tcaaagagct cttccagaca ccagaccaca ctgaggaatc aacaactgat   5400
gacaaaacta ccaaaatagc ctgcaaatct ccaccaccag aatcaatgga cactccaaca   5460
agcacaagga ggcggcccaa aacacctttg ggaaaaggg atatagtgga agagctctca   5520
gccctgaagc agctcacaca gaccacacac acagacaaag taccaggaga tgaggataaa   5580
ggcatcaacg tgttcaggga aactgcaaaa cagaaactgg acccagcagc aagtgtaact   5640
ggtagcaaga ggcagccaag aactcctaag ggaaaagccc aacccctaga agacttggct   5700
ggcttgaaag agctcttcca gacaccaata tgcactgaca agcccacgac tcatgagaaa   5760
actaccaaaa tagcctgcag atctccacaa ccagacccag tgggtacccc aacaatcttc   5820
aagccacagt ccaagagaag tctcaggaaa gcagacgtag aggaagaatc cttagcactc   5880
aggaaacgaa caccatcagt agggaaagct atggacacac ccaaaccagc aggaggtgat   5940
gagaaagaca tgaaagcatt tatgggaact ccagtgcaga aattggacct gccaggaaat   6000
ttacctggca gcaaaagatg gccacaaact cctaaggaaa aggcccaggc tctagaagac   6060
ctggctggct tcaaagagct cttccagaca ccaggcactg acaagcccac gactgatgag   6120
aaaactacca aaatagcctg caaatctcca caaccagacc cagtggacac cccagcaagc   6180
acaaagcaac ggcccaagag aaacctcagg aaagcagacg tagaggaaga atttttagca   6240
ctcaggaaac gaacaccatc agcaggcaaa gccatggaca caccaaaacc agcagtaagt   6300
gatgagaaaa atatcaacac atttgtggaa actccagtgc agaaactgga cctgctagga   6360
aatttacctg gcagcaagag acagccacag actcctaagg aaaaggctga ggctctagag   6420
gacctggttg gcttcaaaga actcttccag acaccaggtc acactgagga atcaatgact   6480
gatgacaaaa tcacagaagt atcctgtaaa tctccacagc cagagtcatt caaaacctca   6540
agaagctcca agcaaaggct caagataccc ctggtgaaag tggacatgaa agaagagccc   6600
ctagcagtca gcaagctcac acggacatca ggggagacta cgcaaacaca cacagagcca   6660
acaggagata gtaagagcat caaagcgttt aaggagtctc caaagcagat cctggaccca   6720
gcagcaagtg taactggtag caggaggcag ctgagaactc gtaaggaaaa ggcccgtgct   6780
ctagaagacc tggttgactt caaagagctc ttctcagcac caggtcacac tgaagagtca   6840
atgactattg acaaaaacac aaaaattccc tgcaaatctc ccccaccaga actaacagac   6900
actgccacga gcacaaagag atgccccaag acacgtccca ggaaagaagt aaaagaggag   6960
ctctcagcag ttgagaggct cacgcaaaca tcagggcaaa gcacacacac acacaaagaa   7020
ccagcaagcg gtgatgaggg catcaaagta ttgaagcaac gtgcaaagaa gaaaccaaac   7080
ccagtagaag aggaacccag caggagaagg ccaagagcac ctaaggaaaa ggcccaaccc   7140
ctggaagacc tggccggctt cacagagctc tctgaaacat caggtcacac tcaggaatca   7200
ctgactgctg gcaaagccac taaaataccc tgcgaatctc ccccactaga agtggtagac   7260
accacagcaa gcacaaagag gcatctcagg acacgtgtgc agaaggtaca agtaaaagaa   7320
gagccttcag cagtcaagtt cacacaaaca tcaggggaaa ccacggatgc agacaaagaa   7380
ccagcaggtg aagataaagg catcaaagca ttgaaggaat ctgcaaaaca gacaccggct   7440
ccagcagcaa gtgtaactgg cagcaggaga cggccaagag cacccaggga aagtgcccaa   7500
gccatagaag acctagctgg cttcaaagac ccagcagcag gtcacactga agaatcaatg   7560
actgatgaca aaaccactaa aataccctgc aaatcatcac cagaactaga agacaccgca   7620
acaagctcaa agagacggcc caggacacgt gcccagaaag tagaagtgaa ggaggagctg   7680
ttagcagttg gcaagctcac acaaacctca ggggagacca cgcacaccga caaagagccg   7740
```

```
gtaggtgagg gcaaaggcac gaaagcattt aagcaacctg caaagcggaa gctggacgca   7800
gaagatgtaa ttggcagcag gagacagcca agagcaccta aggaaaaggc ccaacccctg   7860
gaagatctgg ccagcttcca agagctctct caaacaccag gccacactga ggaactggca   7920
aatggtgctg ctgatagctt tacaagcgct ccaaagcaaa cacctgacag tggaaaacct   7980
ctaaaaatat ccagaagagt tcttcgggcc cctaaagtag aacccgtggg agacgtggta   8040
agcaccagag accctgtaaa atcacaaagc aaaagcaaca cttccctgcc cccactgccc   8100
ttcaagaggg gaggtggcaa agatggaagc gtcacgggaa ccaagaggct gcgctgcatg   8160
ccagcaccag aggaaattgt ggaggagctg ccagccagca agaagcagag ggttgctccc   8220
agggcaagag gcaaatcatc cgaacccgtg gtcatcatga agagaagttt gaggacttct   8280
gcaaaaagaa ttgaacctgc ggaagagctg aacagcaacg acatgaaaac caacaaagag   8340
gaacacaaat tacaagactc ggtccctgaa aataagggaa tatccctgcg ctccagacgc   8400
caaaataaga ctgaggcaga acagcaaata actgaggtct ttgtattagc agaaagaata   8460
gaaataaaca gaaatgaaaa gaagcccatg aagacctccc cagagatgga cattcagaat   8520
ccagatgatg gagcccggaa acccatacct agagacaaag tcactgagaa caaaaggtgc   8580
ttgaggtctg ctagacagaa tgagagctcc cagcctaagg tggcagagga gagcggaggg   8640
cagaagagtg cgaaggttct catgcagaat cagaaaggga aaggagaagc aggaaattca   8700
gactccatgt gcctgagatc aagaaagaca aaaagccagc ctgcagcaag cactttggag   8760
agcaaatctg tgcagagagt aacgcggagt gtcaagaggt gtgcagaaaa tccaaagaag   8820
gctgaggaca atgtgtgtgt caagaaaata agaaccagaa gtcataggga cagtgaagat   8880
atttgacaga aaaatcgaac tgggaaaaat ataataaagt tagttttgtg ataagttcta   8940
gtgcagtttt tgtcataaat tacaagtgaa ttctgtaagt aaggctgtca gtctgcttaa   9000
gggaagaaaa ctttggattt gctgggtctg aatcggcttc ataaactcca ctgggagcac   9060
tgctgggctc ctggactgag aatagttgaa caccgggggc tttgtgaagg agtctgggcc   9120
aaggtttgcc ctcagctttg cagaatgaag ccttgaggtc tgtcaccacc cacagccacc   9180
ctacagcagc cttaactgtg acacttgcca cactgtgtcg tcgtttgttt gcctatgtcc   9240
tccagggcac ggtggcagga acaactatcc tcgtctgtcc caacactgag caggcactcg   9300
gtaaacacga atgaatggat gagcgcacgg atgaatggag cttacaagat ctgtctttcc   9360
aatggccggg ggcatttggt ccccaaatta aggctattgg acatctgcac aggacagtcc   9420
tatttttgat gtcctttcct ttctgaaaat aaagttttgt gctttggaga atgactcgtg   9480
agcacatctt tagggaccaa gagtgacttt ctgtaaggag tgactcgtgg cttgccttgg   9540
tctcttggga atactttct aactagggtt gctctcacct gagacattct ccacccgcgg   9600
aatctcaggg tcccaggctg tgggccatca cgacctcaaa ctggctccta atctccagct   9660
ttcctgtcat tgaaagcttc ggaagtttac tggctctgct cccgcctgtt ttctttctga   9720
ctctatctgg cagcccgatg ccacccagta caggaagtga caccagtact ctgtaaagca   9780
tcatcatcct tggagagact gagcactcag caccttcagc cacgatttca ggatcgcttc   9840
cttgtgagcc gctgcctccg aaatctcctt tgaagcccag acatctttct ccagcttcag   9900
acttgtagat ataactcgtt catcttcatt tactttccac tttgcccct gtcctctctg   9960
tgttccccaa atcagagaat agcccgccat cccccaggtc acctgtctgg attcctcccc  10020
attcacccac cttgccaggt gcaggtgagg atggtgcacc agacagggta gctgtccccc  10080
```

aaaatgtgcc ctgtgcgggc agtgccctgt ctccacgttt gtttccccag tgtctggcgg 10140
ggagccaggt gacatcataa atacttgctg aatgaatgca gaaatcagcg gtactgactt 10200
gtactatatt ggctgccatg atagggttct cacagcgtca tccatgatcg taagggagaa 10260
tgacattctg cttgagggag ggaatagaaa ggggcaggga ggggacatct gagggcttca 10320
cagggctgca aagggtacag ggattgcacc agggcagaac aggggagggt gttcaaggaa 10380
gagtggctct tagcagaggc actttggaag gtgtgaggca taaatgcttc cttctacgta 10440
ggccaacctc aaaactttca gtaggaatgt tgctatgatc aagttgttct aacactttag 10500
acttagtagt aattatgaac ctcacataga aaaatttcat ccagccatat gcctgtggag 10560
tggaatattc tgtttagtag aaaaatcctt tagagttcag ctctaaccag aaatcttgct 10620
gaagtatgtc agcacctttt ctcaccctgg taagtacagt atttcaagag cacgctaagg 10680
gtggttttca ttttacaggg ctgttgatga tgggttaaaa atgttcattt aagggctacc 10740
cccgtgttta atagatgaac accacttcta cacaaccctc cttggtactg ggggagggag 10800
agatctgaca aatactgccc attcccctag gctgactgga tttgagaaca aatacccacc 10860
catttccacc atggtatggt aacttctctg agcttcagtt tccaagtgaa tttccatgta 10920
ataggacatt cccattaaat acaagctgtt tttacttttt cgcctcccag ggcctgtggg 10980
atctggtccc ccagcctctc ttgggctttc ttacactaac tctgtaccta ccatctcctg 11040
cctcccttag gcaggcacct ccaaccacca cacactccct gctgttttcc ctgcctggaa 11100
ctttccctcc tgccccacca agatcatttc atccagtcct gagctcagct taagggaggc 11160
ttcttgcctg tgggttccct cacccccatg cctgtcctcc aggctggggc aggttcttag 11220
tttgcctgga attgttctgt acctctttgt agcacgtagt gttgtggaaa ctaagccact 11280
aattgagttt ctggctcccc tcctggggtt gtaagttttg ttcattcatg agggccgact 11340
gcatttcctg gttactctat cccagtgacc agccacagga gatgtccaat aaagtatgtg 11400
atgaaatggt cttaaaaaaa aaaaaaa 11427

<210> SEQ ID NO 20
<211> LENGTH: 5765
<212> TYPE: DNA
<213> ORGANISM: Homo sapiens

<400> SEQUENCE: 20
tcctaggcgg cggccgcggc ggcggaggca gcagcggcgg cggcagtggc ggcggcgaag 60
gtggcggcgg ctcggccagt actcccggcc cccgccattt cggactggga gcgagcgcgg 120
cgcaggcact gaaggcggcg gcggggccag aggctcagcg gctcccaggt gcgggagaga 180
ggcctgctga aaatgactga atataaactt gtggtagttg gagctggtgg cgtaggcaag 240
agtgccttga cgatacagct aattcagaat cattttgtgg acgaatatga tccaacaata 300
gaggattcct acaggaagca agtagtaatt gatggagaaa cctgtctctt ggatattctc 360
gacacagcag gtcaagagga gtacagtgca atgagggacc agtacatgag gactggggag 420
ggctttcttt gtgtatttgc cataaataat actaaatcat ttgaagatat tcaccattat 480
agagaacaaa ttaaaagagt taaggactct gaagatgtac ctatggtcct agtaggaaat 540
aaatgtgatt tgccttctag aacagtagac acaaaacagg ctcaggactt agcaagaagt 600
tatggaattc cttttattga aacatcagca aagacaagac agggtgttga tgatgccttc 660
tatacattag ttcgagaaat tcgaaaacat aaagaaaaga tgagcaaaga tggtaaaaag 720
aagaaaaaga agtcaaagac aaagtgtgta attatgtaaa tacaatttgt actttttttct 780

-continued

```
taaggcatac tagtacaagt ggtaattttt gtacattaca ctaaattatt agcatttgtt    840
ttagcattac ctaatttttt tcctgctcca tgcagactgt tagcttttac cttaaatgct    900
tattttaaaa tgacagtgga agtttttttt tcctctaagt gccagtattc ccagagtttt    960
ggtttttgaa ctagcaatgc ctgtgaaaaa gaaactgaat acctaagatt tctgtcttgg   1020
ggtttttggt gcatgcagtt gattacttct tatttttctt accaattgtg aatgttggtg   1080
tgaaacaaat taatgaagct tttgaatcat ccctattctg tgttttatct agtcacataa   1140
atggattaat tactaatttc agttgagacc ttctaattgg tttttactga aacattgagg   1200
gaacacaaat ttatgggctt cctgatgatg attcttctag gcatcatgtc ctatagtttg   1260
tcatccctga tgaatgtaaa gttacactgt tcacaaaggt tttgtctcct ttccactgct   1320
attagtcatg gtcactctcc ccaaaatatt atatttttc tataaaaaga aaaaaatgga    1380
aaaaaattac aaggcaatgg aaactattat aaggccattt ccttttcaca ttagataaat   1440
tactataaag actcctaata gcttttcctg ttaaggcaga cccagtatga aatggggatt   1500
attatagcaa ccattttggg gctatattta catgctacta aatttttata ataattgaaa   1560
agattttaac aagtataaaa aattctcata ggaattaaat gtagtctccc tgtgtcagac   1620
tgctctttca tagtataact ttaaatcttt tcttcaactt gagtctttga agatagtttt   1680
aattctgctt gtgacattaa aagattattt gggccagtta tagcttatta ggtgttgaag   1740
agaccaaggt tgcaaggcca ggccctgtgt gaacctttga gctttcatag agagtttcac   1800
agcatggact gtgtccccac ggtcatccag tgttgtcatg cattggttag tcaaaatggg   1860
gagggactag ggcagtttgg atagctcaac aagatacaat ctcactctgt ggtggtcctg   1920
ctgacaaatc aagagcattg cttttgtttc ttaagaaaac aaactctttt ttaaaaatta   1980
cttttaaata ttaactcaaa agttgagatt ttggggtggt ggtgtgccaa gacattaatt   2040
tttttttaa acaatgaagt gaaaaagttt tacaatctct aggtttggct agttctctta    2100
acactggtta aattaacatt gcataaacac ttttcaagtc tgatccatat ttaataatgc   2160
tttaaaataa aaataaaaac aatccttttg ataaatttaa aatgttactt attttaaaat   2220
aaatgaagtg agatggcatg gtgaggtgaa agtatcactg gactaggaag aaggtgactt   2280
aggttctaga taggtgtctt ttaggactct gattttgagg acatcactta ctatccattt   2340
cttcatgtta aaagaagtca tctcaaactc ttagtttttt ttttttacaa ctatgtaatt   2400
tatattccat ttacataagg atacacttat ttgtcaagct cagcacaatc tgtaaatttt   2460
taacctatgt tacaccatct tcagtgccag tcttgggcaa aattgtgcaa gaggtgaagt   2520
ttatatttga atatccattc tcgttttagg actcttcttc catattagtg tcatcttgcc   2580
tccctacctt ccacatgccc catgacttga tgcagtttta atacttgtaa ttcccctaac   2640
cataagattt actgctgctg tggatatctc catgaagttt tcccactgag tcacatcaga   2700
aatgccctac atcttatttc ctcagggctc aagagaatct gacagatacc ataaagggat   2760
ttgacctaat cactaatttt caggtggtgg ctgatgcttt gaacatctct ttgctgccca   2820
atccattagc gacagtagga tttttcaaac ctggtatgaa tagacagaac cctatccagt   2880
ggaaggagaa tttaataaag atagtgctga aagaattcct taggtaatct ataactagga   2940
ctactcctgg taacagtaat acattccatt gttttagtaa ccagaaatct tcatgcaatg   3000
aaaaatactt taattcatga agcttacttt tttttttgg tgtcagagtc tcgctcttgt    3060
cacccaggct ggaatgcagt ggcgccatct cagctcactg caacctccat ctcccaggtt   3120
```

caagcgattc tcgtgcctcg gcctcctgag tagctgggat tacaggcgtg tgccactaca 3180
ctcaactaat ttttgtattt ttaggagaga cggggtttca ccctgttggc caggctggtc 3240
tcgaactcct gacctcaagt gattcaccca ccttggcctc ataaacctgt tttgcagaac 3300
tcatttattc agcaaatatt tattgagtgc ctaccagatg ccagtcaccg cacaaggcac 3360
tgggtatatg gtatccccaa acaagagaca taatcccggt ccttaggtag tgctagtgtg 3420
gtctgtaata tcttactaag gcctttggta tacgacccag agataacacg atgcgtattt 3480
tagttttgca aagaaggggt ttggtctctg tgccagctct ataattgttt tgctacgatt 3540
ccactgaaac tcttcgatca agctacttta tgtaaatcac ttcattgttt taaaggaata 3600
aacttgatta tattgttttt ttatttggca taactgtgat tcttttagga caattactgt 3660
acacattaag gtgtatgtca gatattcata ttgacccaaa tgtgtaatat tccagttttc 3720
tctgcataag taattaaaat atacttaaaa attaatagtt ttatctgggt acaaataaac 3780
aggtgcctga actagttcac agacaaggaa acttctatgt aaaaatcact atgatttctg 3840
aattgctatg tgaaactaca gatctttgga acactgttta ggtagggtgt taagacttac 3900
acagtacctc gtttctacac agagaaagaa atggccatac ttcaggaact gcagtgctta 3960
tgaggggata tttaggcctc ttgaattttt gatgtagatg ggcatttttt taaggtagtg 4020
gttaattacc tttatgtgaa ctttgaatgg tttaacaaaa gatttgtttt tgtagagatt 4080
ttaaaggggg agaattctag aaataaatgt tacctaatta ttacagcctt aaagacaaaa 4140
atccttgttg aagttttttt aaaaaaagct aaattacata gacttaggca ttaacatgtt 4200
tgtggaagaa tatagcagac gtatattgta tcatttgagt gaatgttccc aagtaggcat 4260
tctaggctct atttaactga gtcacactgc ataggaattt agaacctaac ttttataggt 4320
tatcaaaact gttgtcacca ttgcacaatt ttgtcctaat atatacatag aaactttgtg 4380
gggcatgtta agttacagtt tgcacaagtt catctcattt gtattccatt gatttttttt 4440
ttcttctaaa cattttttct tcaaacagta tataactttt tttaggggat tttttttag 4500
acagcaaaaa ctatctgaag atttccattt gtcaaaaagt aatgatttct tgataattgt 4560
gtagtaatgt tttttagaac ccagcagtta ccttaaagct gaatttatat ttagtaactt 4620
ctgtgttaat actggatagc atgaattctg cattgagaaa ctgaatagct gtcataaaat 4680
gaaactttct ttctaaagaa agatactcac atgagttctt gaagaatagt cataactaga 4740
ttaagatctg tgttttagtt taatagtttg aagtgcctgt ttgggataat gataggtaat 4800
ttagatgaat ttaggggaaa aaaaagttat ctgcagatat gttgagggcc catctctccc 4860
cccacacccc cacagagcta actgggttac agtgttttat ccgaaagttt ccaattccac 4920
tgtcttgtgt tttcatgttg aaaatacttt tgcatttttc ctttgagtgc caatttctta 4980
ctagtactat ttcttaatgt aacatgttta cctggaatgt attttaacta tttttgtata 5040
gtgtaaactg aaacatgcac attttgtaca ttgtgctttc ttttgtggga catatgcagt 5100
gtgatccagt tgttttccat catttggttg cgctgaccta ggaatgttgg tcatatcaaa 5160
cattaaaaat gaccactctt ttaattgaaa ttaactttta aatgtttata ggagtatgtg 5220
ctgtgaagtg atctaaaatt tgtaatattt ttgtcatgaa ctgtactact cctaattatt 5280
gtaatgtaat aaaaatagtt acagtgacta tgagtgtgta tttattcatg aaatttgaac 5340
tgtttgcccc gaaatggata tggaatactt tataagccat agacactata gtataccagt 5400
gaatctttta tgcagcttgt tagaagtatc ctttatttct aaaaggtgct gtggatatta 5460
tgtaaaggcg tgtttgctta aacttaaaac catatttaga agtagatgca aaacaaatct 5520
gcctttatga caaaaaaata ggataacatt atttatttat ttccttttat caaagaaggt 5580
aattgataca caacaggtga cttggtttta ggcccaaagg tagcagcagc aacattaata 5640
atggaaataa ttgaatagtt agttatgtat gttaatgcca gtcaccagca ggctatttca 5700
aggtcagaag taatgactcc atacatatta tttatttcta taactacatt taaatcatta 5760
ccagg 5765

<210> SEQ ID NO 21
<211> LENGTH: 2202
<212> TYPE: DNA
<213> ORGANISM: Homo sapiens

<400> SEQUENCE: 21
cgtaaagaga ggccgggagc tgcccctaac cgaggcagca gcggacgtga gcgataatgg 60
cggatatgga ggatctcttc gggagcgacg ccgacagcga agctgagcgt aaagattctg 120
attctggatc tgactcagat tctgatcaag agaatgctgc ctctggcagt aatgcctctg 180
gaagtgaaag tgatcaggat gaaagaggtg attcaggaca accaagtaat aaggaactgt 240
ttggagatga cagtgaggac gagggagctt cacatcatag tggtagtgat aatcactctg 300
aaagatcaga caatagatca gaagcttctg agcgttctga ccatgaggac aatgacccct 360
cagatgtaga tcagcacagt ggatcagaag cccctaatga tgatgaagac gaaggtcata 420
gatcggatgg agggagccat cattcagaag cagaaggttc tgaaaaagca cattcagatg 480
atgaaaaatg gggcagagaa gataaaagtg accagtcaga tgatgaaaag atacaaaatt 540
ctgatgatga ggagagggca caaggatctg atgaagataa gctgcagaat tctgacgatg 600
atgagaaaat gcagaacaca gatgatgagg agaggcctca gctttccgat gatgagagac 660
aacagctatc tgaggaggaa aaggctaatt ctgatgatga acggccggta gcttctgata 720
atgatgatga gaaacagaat tctgatgatg aagaacaacc acagctgtct gatgaagaga 780
aaatgcaaaa ttctgatgat gaaaggccac aggcctcaga tgaagaacac aggcattcag 840
atgatgaaga ggaacaggat cataaatcag aatctgcaag aggcagtgat agtgaagatg 900
aagttttacg aatgaaacgc aagaatgcga ttgcatctga ttcagaagcg gatagtgaca 960
ctgaggtgcc aaaagataat agtggaacca tggatttatt tggaggtgca gatgatatct 1020
cttcagggag tgatggagaa gacaaaccac ctactccagg acagcctgtt gatgaaaatg 1080
gattgcctca ggatcaacag gaagaggagc caattcctga gaccagaata gaagtagaaa 1140
tacccaaagt aaacactgat ttaggaaacg acttatattt tgttaaactg cccaactttc 1200
tcagtgtaga gcccagacct tttgatcctc agtattatga agatgaattt gaagatgaag 1260
aaatgctgga tgaagaaggt agaaccaggt taaaattaaa ggtagaaaat actataagat 1320
ggaggatacg ccgagatgaa gaaggaaatg aaattaaaga aagcaatgct cggatagtca 1380
agtggtcaga tggaagcatg tccctgcatt taggcaatga agtgtttgat gtgtacaaag 1440
ccccactgca gggcgaccac aatcatcttt ttataagaca aggtactggt ctacagggac 1500
aagcagtctt taaaacgaaa ctcaccttca gacctcactc tacggacagt gccacacata 1560
gaaagatgac tctgtcactt gcagataggt gttcaaagac acagaagatt agaatcttgc 1620
caatggctgg tcgtgatcct gaatgccaac gcacagaaat gattaagaaa gaagaagaac 1680
gtttgagggc ttccatacgt agggaatctc agcagcgccg aatgagagag aaacagcacc 1740
agcgggggct gagcgccagt tacctggaac ctgatcgata cgatgaggag gaggaaggcg 1800

```
aggagtccat cagcttggct gccattaaaa accgatataa agggggcatt cgagaggaac   1860

gagccagaat ctattcatca gacagtgatg agggatcaga agaagataaa gctcaaagat   1920

tactcaaagc aaagaaactt accagtgatg aggaaggtga accttccgga aagagaaaag   1980

cagaagatga tgataaagca aataaaaagc ataagaagta tgtgatcagc gatgaagagg   2040

aagaagatga tgattgaagt atgaaatatg aaaacatttt atatatttta ttgtacagtt   2100

ataaatatgt aaacatgagt tattttgatt gaaatgaatc gatttgcttt tgtgtaattt   2160

taattgtaat aaaacaattt aaaagcaaaa aaaaaaaaaa aa                      2202
```

<210> SEQ ID NO 22
<211> LENGTH: 2047
<212> TYPE: DNA
<213> ORGANISM: Homo sapiens

<400> SEQUENCE: 22

```
ttgattatgg aacattctaa aacttagaca agacgattgt gattggctga agggcatacg     60

ccctcctcca gggtgacgtg tctgcctatg gatatcagtt gccagagaaa cctggcttta    120

ctatggcggt tggaggaacg gcagtgatca cacgtcggct gctgggaaga tctggattct    180

cgtttcaggt caccatcaga aaagctaagt ttgctgtata gtgaggatca ggagatctga    240

tcctgattgc agaaccttcc ctgattacag aatcttggga ttgttgagag gattacatgt    300

aaagtaccag gacagtgcat ggcacatatg atttcacaaa agttcatctt cattgcagat    360

acctgccttt ctttctaggt tgtatctccc acttcaccct tctagaccat cccagaagat    420

ctataagatt tcatctggga aatcactagg agttcttgga agggaaagaa ggaagattgt    480

tggttggaat aaaaacaggg ttgaatgagt tccagaaagc agggttctca acctcgtgga    540

cagcaatctg cagaagaaga gaacttcaaa aaaccaacta gaagcaacat gcagagaagt    600

aaaatgagag gggcctcctc aggaaagaag acagctggtc cacagcagaa aaatcttgaa    660

ccagctctcc caggaagatg gggtggtcgc tctgcagaga acccccccttc aggatccgtg    720

aggaagacca gaaagaacaa gcagaagact cctggaaacg gagatggtgg cagtaccagc    780

gaagcacctc agccccctcg gaagaaaagg gcccgggcag accccactgt tgaaagtgag    840

gaggcgttta agaatagaat ggaggttaaa gtgaagattc ctgaagaatt aaaaccatgg    900

cttgttgagg actgggactt agttaccagg cagaagcagc tgtttcaact ccctgccaag    960

aaaaatgtag atgcaattct ggaggagtat gcaaattgca agaaatcgca gggaaatgtt   1020

gataataagg aatatgcggt taatgaagtt gtggcaggaa taaaagaata tttcaatgtg   1080

atgttgggca ctcagctgct ctacaaattt gagaggcccc agtatgctga aatcctcttg   1140

gctcaccctg atgctccaat gtcccaggtt tatggagcac cacacctact gagattattt   1200

gtaagaattg gagcaatgtt ggcctatacg cccccttgatg agaaaagcct tgcattattg   1260

ttgggctatt tgcatgattt cctaaaatat ctggcaaaga attctgcatc tctctttact   1320

gccagtgatt acaaagtggc ttctgctgag taccaccgca aagccctgtg agcgtctaca   1380

gacagctcac catttttgtc ctgtatctgt aaacactttt tgttcttagt ctttttcttg   1440

taaaattgat gttctttaaa atcgttaatg tataacaggg cttatgtttc agtttgtttt   1500

ccgttctgtt ttaaacagaa aataaaagga gtgtaagctc cttttctcat ttcaaagttg   1560

ctaccagtgt atgcagtaat tagaacaaag aagaaacatt cagtagaaca ttttattgcc   1620

tagttgacaa cattgcttga atgctggtgg ttcctatccc tttgacacta cacaattttc   1680

taatatgtgt taatgctatg tgacaaaacg ccctgattcc tagtgccaaa ggttcaactt   1740
```

aatgtatata cctgaaaacc catgcatttg tgctcttttt ttttttttat ggtgcttgaa 1800
gtaaaacagc ccatcctctg caagtccatc tatgttgttc ttaggcattc tatctttgct 1860
caaattgttg aaggatggtg atttgtttca tggtttttgt atttgagtct aatgcacgtt 1920
ctaacatgat agaggcaatg cattattgtg tagccacggt tttctggaaa agttgatatt 1980
ttaggaattg tatttcagat cttaaataaa atttgtttct aaatttcaaa gcaaaaaaaa 2040
aaaaaaa 2047

<210> SEQ ID NO 23
<211> LENGTH: 4451
<212> TYPE: DNA
<213> ORGANISM: Homo sapiens

<400> SEQUENCE: 23
aaaagatatg gtggggtgct taacagagga ggttagacac cggcgggaac cagaggagcc 60
caagcgcggc gcctgggcct cggggctgca ggagtcctcg gtgggggtat ggaggtcgcc 120
ggggaaggag gacggttcag ttgctaggca acccggcctg gacccgcctc tcgctcgcgt 180
tgctgggaga ctacaaggcc gggaggaggg cggcgaaagg gccctacgtg ctgacgctaa 240
ttgtatatga gcgcgagcgg cgggctcttg ggtctttttt agcgccatct gctcgcggcg 300
ccgcctcctg ctcctcccgc tgctgctgcc gctgccgccc tgagtcactg cctgcgcagc 360
tccggccgcc tggctcccca tactagtcgc cgatatttgg agttcttaca acatggcaga 420
cattgacaac aaagaacagt ctgaacttga tcaagatttg gatgatgttg aagaagtaga 480
agaagaggaa actggtgaag aaacaaaact caaagcacgt cagctaactg ttcagatgat 540
gcaaaatcct cagattcttg cagcccttca agaaagactt gatggtctgg tagaaacacc 600
aacaggatac attgaaagcc tgcctagggt agttaaaaga cgagtgaatg ctctcaaaaa 660
cctgcaagtt aaatgtgcac agatagaagc caaattctat gaggaagttc acgatcttga 720
aaggaagtat gctgttctct atcagcctct atttgataag cgatttgaaa ttattaatgc 780
aatttatgaa cctacggaag aagaatgtga atggaaacca gatgaagaag atgagatttc 840
ggaggaattg aaagaaaagg ccaagattga agatgagaaa aaagatgaag aaaaagaaga 900
ccccaaagga attcctgaat tttggttaac tgtttttaag aatgttgact tgctcagtga 960
tatggttcag gaacacgatg aacctattct gaagcacttg aaagatatta aagtgaagtt 1020
ctcagatgct ggccagccta tgagttttgt cttagaattt cactttgaac ccaatgaata 1080
ttttacaaat gaagtgctga caaagacata caggatgagg tcagaaccag atgattctga 1140
tccctttctt tttgatggac cagaaattat gggttgtaca gggtgccaga tagattggaa 1200
aaaaggaaag aatgtcactt tgaaaactat taagaagaag cagaaacaca agggacgtgg 1260
gacagttcgt actgtgacta aaacagtttc caatgactct ttctttaact tttttgcccc 1320
tcctgaagtt cctgagagtg gagatctgga tgatgatgct gaagctatcc ttgctgcaga 1380
cttcgaaatt ggtcactttt tacgtgagcg tataatccca agatcagtgt tatattttac 1440
tggagaagct attgaagatg atgatgatga ttatgatgaa gaaggtgaag aagcggatga 1500
ggaaggggaa gaagaaggag atgaggaaaa tgatccagac tatgacccaa agaaggatca 1560
aaacccagca gagtgcaagc agcagtgaag caggatgtat gtggccttga ggataacctg 1620
cactggtcta ccttctgctt ccctggaaag gatgaattta catcatttga caagcctatt 1680
ttcaagttat ttgttgtttg tttgcttgtt tttgtttttg cagctaaaat aaaaatttca 1740

-continued

```
aatacaattt tagttcttac aagataatgt cttaattttg taccaattca ggtagaagta   1800
gaggcctacc ttgaattaag ggttatactc agtttttaac acattgttga agaaaaggta   1860
ccagctttgg aacgagatgc tatactaata agcaagtgta aaaaaaaaaa aaaaagagga   1920
agaaaatctt aagtgattga tgctgttttc ttttaaaaaa aaaaaaaaaa attcattttc   1980
tttgggttag agctagagag aaggccccaa gcttctatgg tttcttctaa ttcttattgc   2040
ttaaagtatg agtatgtcac ttacccgtgc ttctgtttac tgtgtaatta aaatgggtag   2100
tactgtttac ctaactacct catggatgtg ttaaggcata ttgagttaaa tctcatataa   2160
tgtttctcaa tcttgttaaa agctcaaaat tttgggccta tttgtaatgc cagtgtgaca   2220
ctaagcattt tgttcacacc acgctttgat aactaaactg gaaaacaaag gtgttaagta   2280
cctctgttct ggatctgggc agtcagcact ctttttagat ctttgtgtgg ctcctatttt   2340
tatagaagtg gagggatgca ctatttcaca aggtccaaga tttgttttca gatatttttg   2400
atgactgtat tgtaaatact acagggatag cactatagta ttgtagtcat gagacttaaa   2460
gtggaaataa gactattttt gacaaaagat gccattaaat ttcagactgt agagccacat   2520
ttacaatacc tcaggctaat tactgttaat tttggggttg aacttttttt tgacagtgag   2580
ggtggattat tggattgtca ttagaggaag gtctagattt cctgctctta ataaaattac   2640
attgaattga tttttagagg taatgaaaac ttcctttctg agaagttagt gttaaggtct   2700
tggaatgtga acacattgtt tgtagtgcta tccattcctc tcctgagatt ttaacttact   2760
actggaaatc cttaaccaat tataatagct tttttttcttt attttcaaaa tgatttcctt   2820
tgctttgatt agacactatg tgcttttttt ttttaaccat agttcatcga aatgcagctt   2880
tttctgaact tcaaagatag aatcccattt ttaatgaact gaagtagcaa aatcatcttt   2940
ttcattcttt aggaaatagc tattgccaaa gtgaaggtgt agataatacc tagtcttgtt   3000
acataaaggg gatgtggttt gcagaagaat tttctttata aaattgaagt tttaagggac   3060
gtcagtgttt atgccatttt tccagttcca aaatgattcc attccattct agaaatttga   3120
agtatgtaac ctgaaatcct taataaaatt tggatttaat tttataaaat gtactggtga   3180
tattttgggt gttttttttt aaatgaatgt atatactttt tttttgaaga gtggagagta   3240
gtgatgtcta gagggagcta ttttgtgctg aggccactat gttctgtaaa tatataattt   3300
taagagcaac ctcacaatcc ctgctaagtg gagtttatta tttgaagact aaaatggaat   3360
tccatagttc ctgataggtt atattctggg ttattattct gagttatcta caaacatttt   3420
tgagatttgt ctttacactc tgattgtagt ttccagcagc ccatgcacac tgccaagtaa   3480
gtctcatttt ttcctgttag aaatggtgaa atatcatata atcacttata aagaaaactg   3540
atatgaaaaa attttagagt tgtttgcttt atggtcactc aagtagggta agtgttccac   3600
aaattccaca agttgatagt ttaacatgga tgtctgaaag ccacatatat aatttcttag   3660
gattcttaaa ttagtaaatc tagcttactg aagcagtatt agcatcacta ttttagattg   3720
caaaaatacc ttaattgtgt ggaactggct tgtagagtgg tacttaagaa aaatgggatt   3780
ctacctctat ttctgtttta gcacacttaa tcaggaaagg atatattaac tttcataaaa   3840
atatttttgt tgtgtgaata ggttaatgat atggtaaggc ccctaaaata actgaattaa   3900
ttgtttattg taattgtagg ccattcccat tattaaaaat aaagacaaaa cttgaagtaa   3960
ctgaaaatct tatcgtgcta tgtagaaata ttgaactaat attcaaatat ttgaatgctt   4020
tggtttcagg gattggttta aaattggagt ccttttttat gggttagtct tacaaaaatt   4080
taagccttta tatttttgac tttaaatcaa aacaaatgtt attttaaatg tacagaatag   4140
```

attggtagtg cagaagagtg taagttcttc ataggagctt tagaaaagag aaatatgtgc 4200
taattcagtt ttttttaat ctgcactgta catatatact tggtaattat gagcttgatt 4260
ttgtttttgg aaatatgtgt tcataattta ggtaatttgc tacttaaagc actaagtctc 4320
tgatacctga aaagtacatg taaatggtga tggtgaaata atactgcagt taacttaata 4380
gatgtatact ggtgattttt gtatgctgga ttaaaactcc agatattaaa atataacctg 4440
gataaaaagc c 4451

<210> SEQ ID NO 24
<211> LENGTH: 1530
<212> TYPE: DNA
<213> ORGANISM: Homo sapiens

<400> SEQUENCE: 24
ggcattcaga gagtagatgc cagtcctggg aaaggcaggg gaggagagga gagccacggc 60
tgacgcttgg ggacagaagg aggagcctga ggaggagaca ggacagagcg tctggagagg 120
caggaggaca ccgagttccc cgtgttggcc tccaggtcct gtgcttgcgg agccgtccgg 180
cggctgggat cgagccccga caatgggcaa cgcgcaggag cggccgtcag agactatcga 240
ccgcgagcgg aaacgcctgg tcgagacgct gcaggcggac tcgggactgc tgttggacgc 300
gctgctggcg cggggcgtgc tcaccgggcc agagtacgag gcattggatg cactgcctga 360
tgccgagcgc agggtgcgcc gcctactgct gctggtgcag ggcaagggcg aggccgcctg 420
ccaggagctg ctacgctgtg cccagcgtac cgcgggcgcg ccggaccccg cttgggactg 480
gcagcacgct accgggaccg cagctatgac cctccatgcc caggccactg gacgccggag 540
gcacccggct cggggaccac atgccccggg ttgcccagag cttcagaccc tgacgaggcc 600
gggggccctg agggctccga ggcggtgcaa tccgggaccc cggaggagcc agagccagag 660
ctggaagctg aggcctctaa agaggctgaa ccggagccgg agccagagcc agagctggaa 720
cccgaggctg aagcagaacc agagccggaa ctggagccag aaccggaccc agagcccgag 780
cccgacttcg aggaaaggga cgagtccgaa gattcctgaa ggccagagct ctgacaggcg 840
gtgccccgcc catgctggat aggacctggg atgctgctgg agctgaatcg gatgccacca 900
aggctcggtc cagcccagta ccgctggaag tgaataaact ccggagggtc ggacgggacc 960
tgggctctct ccacgattct ggctgtttgc ccaggaactt agggtgggta cctctgagtc 1020
ccagggacct gggcaggccc aagcccacca cgagcatcat ccagtcctca gccctaatct 1080
gcccttagga gtccaggctg caccctggag atcccaaacc tagcccccta gtgggacaag 1140
gacctgaccc tcctgcccgc atacacaacc catttcccct ggtgagccac ttggcagcat 1200
atgtaggtac cagctcaacc ccacgcaagt tcctgagctg aacatggagc aaggggaggg 1260
tgacttctct ccacataggg agggcttaga gctcacagcc ttgggaagtg agactagaag 1320
aggggagcag aaagggacct tgagtagaca aaggccacac acatcattgt cattactgtt 1380
ttaattgtct ggcttctctc tggactggga gctcagtgag gattctgacc agtgacttac 1440
acaaaaggcg ctctatacat attataatat attcgcttac taaatgaata aggactttcc 1500
aaaaaaaaaa aaaaaaaaaa aaaaaaaaaa 1530

<210> SEQ ID NO 25
<211> LENGTH: 2410
<212> TYPE: DNA
<213> ORGANISM: Homo sapiens

<400> SEQUENCE: 25

```
ggtgcagcct tacgccgctg acgcatcgcg cccaagatgg cggcgcggtc gtcgtcgggg     60
gtggcggcgg cagagggggc ggcggccctg gcggcagcgg agacggcagc cgtgacggtg    120
gcagcggcgg cgcgggacct gggcctgggg gaatgaggcg gccgcggcgg gccagcggcg    180
gagccgtgta gcggagaagc tccccctccc tgcttccctt ggccgagccg ggggcgcgcg    240
cgcacgcggc cgtccagagc gggctcccca cccctcgact cctgcgaccc gcaccgcacc    300
cccacccggg cccggaggat gatgaagctc aagtcgaacc agacccgcac ctacgacggc    360
gacggctaca agaagcgggc cgcatgcctg tgtttccgca gcgagagcga ggaggaggtg    420
ctactcgtga gcagtagtcg ccatccagac agatggattg tccctggagg aggcatggag    480
cccgaggagg agccaagtgt ggcagcagtt cgtgaagtct gtgaggaggc tggagtaaaa    540
gggacattgg gaagattagt tggaattttt gagaaccagg agaggaagca caggacgtat    600
gtctatgtgc tcattgtcac tgaagtgctg gaagactggg aagattcagt taacattgga    660
aggaagaggg aatggtttaa aatagaagac gccataaaag tgctgcagta tcacaaaccc    720
gtgcaggcat catattttga aacattgagg caaggctact cagccaacaa tggcacccca    780
gtcgtggcca ccacatactc ggtttctgct cagagctcga tgtcaggcat cagatgactg    840
aagacttcct gtaagagaaa tggaaattgg aaactagact gaagtgcaaa tcttccctct    900
caccctggct ctttccactt ctcacaggcc tcctctttca aataaggcat ggtgggcagc    960
aaagaaaggg tgtattgata atgttgctgt ttggtgttaa gtgatggggc tttttcttct   1020
gtttttattg agggtggggg ttgggtgtgt aatttgtaag tacttttgtg catgatctgt   1080
ccctccctct tcccacccct gcagtcctct gaagagaggc caacagcctt cccctgcctt   1140
ggattctgaa gtgttcctgt ttgtcttatc ctggccctgg ccagacgttt tctttgattt   1200
ttaatttttt ttttttatta aaagatacca gtatgagatg aaaacttcca ataatttgtc   1260
ctataatgtg ctgtacagtt cagtagagtg gtcactttca ctgcagtata catttatcta   1320
cacattatat atcggacata taatatgtaa ataaatgact tctagaaaga gaaatttgtt   1380
taatttttca aggttttttt ctcttttaat ttgggcattt ctagaattga gagcctcaca   1440
attaacatac ctttttgttt tcgatgctag tggctgggca ggttgccctg tcctttctct   1500
atttcccagt cattgactgt agatatggga agagtttagc taccttcata gtgctcccag   1560
gactcatggc ctttccttct ttaagctgta tttccctgcc cagaaagaaa caggaagaaa   1620
ccttttttta tttttttatt ttttttaac caagcaagga gcaaatggcc tcagcccaga    1680
tctgtaaaaa caatgataga aattgaattc tgccccacat gttgacagta gagttggaac   1740
tggattcttg ggattactta tctaaaaaac tggagcatca ggtccatttc tgttctgctg   1800
gtttggaatc ttttccgtaa tgctatttat tgccaacaat ggcctctctt tgtgtccata   1860
tatgccttac accgtgctga cctgggtatc atccatgtgc tctgaagcat ccaactttac   1920
tttgcaggtg catcaatgta gtcctgtccc tgaactgagt aaccgtgttc ctgaaaagta   1980
cactagggaa attcacctgc ttgcttgtct ttgtattggc atggcacttg tgattgcacc   2040
atggagcatg ctcagagcta ttaaattggt ctcccatctc ccaccaggat atgaaaggtc   2100
catatgggag gccacgtaat cacttattac agtggttaca taatacactg gctcactgca   2160
gactctcttg ttttttgata cagtttcgtg ctggcttcat ttgccaattg tgttgtttag   2220
ttcggaagta agagggtctt gagattgagg ggtagggagg gctacactga ctgatccgtg   2280
gcttaagaca ggagattatc tctgtactcc agtggcatct ccttagccaa gatgtgaaat   2340
```

taaaatcata gttcgcctca tttaaaaatt ctaataaagc actcaaactt tgaaaaaaaa 2400
aaaaaaaaaa 2410

<210> SEQ ID NO 26
<211> LENGTH: 1947
<212> TYPE: DNA
<213> ORGANISM: Homo sapiens

<400> SEQUENCE: 26
atgcagatga ggcactcggg ggcggggcgg cggcggcggc ggcggcggtg gcggccgggg 60
agggtcagtt ggaggcaggc gctcgctgag gcaaaaggag gcgctcggcc cgcggcctga 120
cagggactta gcccgcagag atcgaccccg cgcgcgtgac cccacaccca cccactcatc 180
catctatcca ctccctgcgc cgcctcctcc caccctgagc agagccgccg aggatgataa 240
acacccagga cagtagtatt ttgcctttga gtaactgtcc ccagctccag tgctgcaggc 300
acattgttcc agggcctctg tggtgctcct gatgcccctc acccactgtc gaagatcccc 360
ggtgggcgag gggcggcag ggatccttct ctctcagctc taatatataa ggacgagaag 420
ctcactgtga cccaggacct ccctgtgaat gatggaaaac ctcacatcgt ccacttccag 480
tatgaggtca ccgaggtgaa ggtctcttct tgggatgcag tcctgtccag ccagagcctg 540
tttgtagaaa tcccagatgg attattagct gatgggagca aagaaggatt gttagcactg 600
ctagagtttg ctgaagagaa gatgaaagtg aactatgtct tcatctgctt caggaagggc 660
cgagaagaca gagctccact cctgaagacc ttcagcttct tgggctttga gattgtacgt 720
ccaggccatc cctgtgtccc ctctcggcca gatgtgatgt tcatggttta tcccctggac 780
cagaacttgt ccgatgagga ctaatagtca tagaggatgc tttacccaag agccacagtg 840
ggggaagagg ggaagttagg cagccctggg acagacgaga gggctcctcg ctgtctaggg 900
aaggacactg aggggctcag ggtgagggtt gcctattgtg ttctcggagt tgactcgttg 960
aaattgtttt ccataaagaa cagtataaac atattattca catgtaatca ccaatagtaa 1020
atgaagatgt ttatgaactg gcattagaag ctttctaaac tgcgctgtgt gatgtgttct 1080
atctagccta ggggaggaca ttgcctagag gggagggac tgtctgggtt caggggcatg 1140
gcctggaggg ctggtgggca gcactgtcag gctcaggttt ccctgctgtt ggctttctgt 1200
tttggttatt aagacttgtg tattttcttt ctttgcttcc tgtcacccca ggggctcctg 1260
agtataggct tttcagtccc tgggcagtgt ccttgagttg ttttttgaca ctcttacctg 1320
ggcttctctg tgtgcatttg cgtctggcct ggagtaagca ggtccgaccc ctccttcttt 1380
acagcttagt gttattctgg catttggtta agctggctta atctgtttaa tgttatcagt 1440
acattttaaa taggggcatt gaaatttact cccaccacca gggctttttt gggggatgcc 1500
tgggccttta aaacactagc caaactctaa ttaattctca aatcactgcc aggagttctt 1560
gctcctggct gcaggcccag gccccaaggt ctccttcttg ggtcacaaa cagcagtaag 1620 gaagaggaat atatagcaac tcagggcctg ggaattgtgg ggcaatccgt tcttagggac 1680
tggatacttc tggctggctg agtatagtac tagctgcctc cccaccaggt tccgagtagt 1740
gtctgagact ctgctctgca gggcctaggg tagcgctggg agtgtagaag tggcctgccc 1800
ttaactgttt tcactaaaca gctttttcta aggggagagc aagggggaga gatctagatt 1860
gggtgagggg gacggggatg tcagggaggc aagtgtgttg tgttactgtg tcaataaact 1920
gatttaaagt tgtgaaaaaa aaaaaaa 1947

<210> SEQ ID NO 27
<211> LENGTH: 1712
<212> TYPE: DNA
<213> ORGANISM: Homo sapiens

<400> SEQUENCE: 27
atgctggggg aggggctggc ggcctcgacg gcagctgcgg aactaggccg agggacaaag 60
gctaagtttt tccatggttt ggactggata tcggtggaac tctggtcaag ctggtatatt 120
ttgaacccaa agacatcact gctgaagaag aagaggaaga agtggaaagt cttaaaagca 180
ttcggaagta cctgacctcc aatgtggctt atgggtctac aggcattcgg gacgtgcacc 240
tcgagctgaa ggacctgact ctgtgtggac gcaaaggcaa tctgcacttt atacgctttc 300
ccactcatga catgcctgct tttattcaaa tgggcagaga taaaaacttc tcgagtctcc 360
acactgtctt ttgtgccact ggaggtggag cgtacaaatt tgagcaggat tttctcacaa 420
taggtgatct tcagctttgc aaactggatg aactagattg cttgatcaaa ggaattttat 480
acattgactc agtcggattc aatggacggt cacagtgcta ttactttgaa aaccctgctg 540
attctgaaaa gtgtcagaag ttaccatttg atttgaaaaa tccgtatcct ctgcttctgg 600
tgaacattgg ctcaggggtt agcatcttag cagtatattc caaagataat tacaaacggg 660
tcacaggtac tagtcttgga ggaggaactt tttttggtct ctgctgtctt cttactggct 720
gtaccacttt tgaagaagct cttgaaatgg catctcgtgg agatagcacc aaagtggata 780
aactagtacg agatatttat ggaggggact atgagaggtt tggactgcca ggctgggctg 840
tggcttcaag ctttggaaac atgatgagca aggagaagcg agaggctgtc agtaaagagg 900
acctggccag agcgactttg atcaccatca ccaacaacat tggctcaata gcaagaatgt 960
gtgcccttaa tgaaaacatt aaccaggtgg tatttgttgg aaatttcttg agaattaata 1020
cgatcgccat gcggcttttg gcatatgctt tggattattg gtccaagggg cagttgaaag 1080
cactttttct ggaacacgag ggttattttg gagctgttgg agcactcctt gagctgttga 1140
agatcccgtg atcattacct ggggaggggt tcctgaaacc ttccacaatg ggatctgtgg 1200
actttcattt ttttaagaga cttactcaat ttcatgactg tactacctga aacaaagtga 1260
gaaaggacag gtgtattttt ctaagtcatc aagataaatc cttaagaatt cagtctaaat 1320
tagcaaccag gaaggaaaaa tatattaaaa acaacaaaaa agtggcacat gtccaggcag 1380
tgtgaggatt tgctgtatat aagttgcctg ctttgtattt ttgaaatctc tgcatcactc 1440
attggaagtg cttctgaaga gagctgctct gtgttcagtt gactggtttt gtgtcctgtt 1500
tgaacttgct gaatgtaagg caggctacta tgcgttataa tctaatcaca atttgtcaat 1560
atggtcttgg caatcatctg tgcattactc tggtttgcat taagcctgtg tgtgaactta 1620
ctgtaaaaca tgttttattt caaggttctg caaaattaat tgggcaggtt aattgtgtac 1680
ctgaaactta acaagcagtt tttggaaggg ca 1712

<210> SEQ ID NO 28
<211> LENGTH: 7332
<212> TYPE: DNA
<213> ORGANISM: Homo sapiens

<400> SEQUENCE: 28
ggtgaatggg ctggtggtgc tcgctgctgc tgctgagagg aggaggagga tgaagagttg 60
ggcttgtttg tctcctacag tttctctcct gctgctctga ttcccccctc ccgattccgg 120
cccggggcct gtgtgtgtcc ctcctggagg aggaggagga tccagttcct ccccccaacc 180

```
ccctcctccc caccccccct tgcctgggga agaggaggaa agaaacagcc cagagagaga    240
gagagagaga gagtgagtga gagagagagg agaggagagg aggaggagga ggagggagaa    300
gggaacaacc taccatctta acacactaat atctaaaaag tgcgagaggc ccagagcagc    360
agcagaagca gcagcagcag ctccagcttc ttccctccct ccccatgaag aagagttccc    420
tcctcctcct cctcctgctt ctcctgctca gagttcctgc ctccagctgc cagggggggac   480
agccagccag cagcaggagg ggggctagag agctgaagga gagccagttt ccccaaaatt    540
gctgcagtga gaagaggagt ttgttacttt aaacagaggc tgaagaaact atagaattag    600
cagagaaagt ggagaaggta gaggatggag ttgcagactc tacaggaggc tcttaaagtg    660
gaaattcagg ttcaccagaa actggttgct caaatgaagc aggatccaca gaatgctgac    720
ttaaagaaac agcttcatga actccaagcc aaaatcacag ctttgagtga gaaacagaaa    780
agagtagttg aacagctacg gaagaacctg atagtaaagc aagaacaacc ggacaagttc    840
caaatacagc cattgccaca atctgaaaac aaactacaaa cagcacagca gcaaccacta    900
cagcaactac aacaacagca gcagtaccac caccaccacg cccagcagtc agctgcagcc    960
tctcccaacc tgactgcttc acagaagact gtaactacag cttctatgat taccacaaag   1020
acactacctc tcgtcttgaa agcagcaact gcgaccatgc ctgcctctgt ggtgggccag   1080
agacctacca ttgctatggt gaccgccatc aacagtcaga aggctgtgct cagcactgat   1140
gtgcagaaca caccagtcaa cctccagacg tctagtaagg tcactgggcc tggggcagag   1200
gctgtccaaa ttgtggcaaa aaacacagtc actctggttc aggcaacacc tcctcagccc   1260
atcaaagtac cacagtttat ccccccctcct agactcactc cacgtccaaa ctttcttcca   1320
caggttcgac ccaagcctgt ggcccagaat aacattccta ttgccccagc accacctccc   1380
atgctcgcag ctcctcagct tatccagagg cccgtcatgc tgaccaagtt cacccccaca   1440
acccttccca catcccagaa ttccatccac cccgtccgtg tcgtcaatgg gcagactgca   1500
accatagcca aaacgttccc catggcccag ctcaccagca ttgtgatagc tactccaggg   1560
accagactcg ctggacctca aactgtacag cttagcaagc caagtcttga aaaacagaca   1620
gttaaatctc acacagaaac agatgagaaa caaacagaga gccgcaccat caccccacct   1680
gctgcaccca aaccaaaacg ggaggagaac cctcagaaac ttgccttcat ggtgtctcta   1740
gggttggtaa cacatgacca tctagaagaa atccaaagca agaggcaaga gcgaaaaaga   1800
agaacaacag caaatccggt ctacagtgga gcagtctttg agccagagcg taagaagagt   1860
gcagtgacat acctaaacag cacaatgcac cctgggaccc ggaagagagg tcgtcctcca   1920
aaatacaatg cagtgctggg gtttggagcc cttaccccaa catcccccca atccagtcat   1980
cctgactccc ctgaaaatga aaagacagag accacattca ctttccctgc acctgttcag   2040
cctgtgtccc tgcccagccc cacctccaca gacggtgata ttcatgagga tttttgcagc   2100
gtttgcagaa aaagtggcca gttactgatg tgcgacacat gttcccgtgt atatcatttg   2160
gactgcttag accccccctct gaaaacaatt cccaagggca tgtggatctg tcccagatgt   2220
caggaccaga tgctgaagaa ggaagaagca attccatggc ctggaacttt agcaattgtt   2280
cattcctata ttgcctacaa agcagcaaaa gaagaagaga aacagaagtt acttaaatgg   2340
agttcagatt taaaacaaga acgagaacaa ctagagcaaa aggtgaaaca gctcagcaat   2400
tccataagta aatgcatgga aatgaagaac accatcctgg cccggcagaa ggagatgcac   2460
agctccctgg agaaggtaaa acagctgatt cgcctcatcc acggcatcga cctctccaaa   2520
```

-continued

```
cctgtagact ctgaggccac tgtgggggcc atctccaatg gcccggactg caccccccct   2580
gccaatgccg ccacctccac gccggcccct tcccccctcct cccagagctg cacagcgaac   2640
tgtaaccagg gggaagagac taaataacag agcccctcta ggagaagcca cgggatcccg   2700
gcggcaagga gaacagaaca ctgaagactc tagaaaagca aagccggatt tctggaaagt   2760
gcagaattct tttggttctt tggttccaga gagagagaag atgcttgtgc caggtggcac   2820
cagagtttgc caattgatcc ttcttattct gtgtgtacat gcaaagattg gaccatgtta   2880
catgaaatag tgccagctgg aggttctttg ccagcaccat gccaagtgaa ataatatatt   2940
tactctctct attatacacc agtgtgtgcc tgcagcagcc tccacagcca cgatgggttt   3000
gtttctgttt tcttgggtgg ggagcaggga cgggcggagg gaggagagca ggtttcagat   3060
ccttacttgc cgagccgttt gtttaggtag agaagacaag tccaaagagt gtgtgggctt   3120
tcctgtttct aaactttcgc tactataaaa ccaaaaaaag gaattgagat ttcaccaacc   3180
ccagtgccca gaagagggaa ggggagtggc tggagggagc agggggtggg acagtgtatc   3240
aaataagcag tatttaatca cctctggcgg gggcctcgtg caaggggaga ctgacaccaa   3300
gaacagccag taggttcttc tcccctgcac tctgctccct gcgcggtaac cccaccactc   3360
ctgaagcctg cccagtctcc ttccttccct gcttggtgag tcgcgcatct ccgtggttat   3420
cccgctgtct cctctccaag aacaagcaga gcccgggcca ctggcccttg cccaaggcag   3480
ggaagaagga tgtgtgtgtc caggaaggaa aaaaaggtgg atcagtgatt ttacttgaaa   3540
acaagctcca tccctttctt atatttataa gaagagaaga tcttgagtga agcagcacgc   3600
gacccaggtg tgtgtgaatt gaatggagac gtttcttttc tctttcttta atttttgttt   3660
ttgttctttt tttctttaag gaaagtttta ttttactgtt cattttactt tcttggtaac   3720
aaaaactaaa ataaggaata gaaaagctgt ttttcaggct gacagtccaa ttaagggtag   3780
ccaagacctt gcatggtaga gtaggaatca tagtgtcagt gaggtcccgt gagtctttgt   3840
gagtccttgt gtcatcgttc gggcactgtt tttttatgca agggcaaaaa tctttgtatc   3900
tggggaaaaa aaactttttt ttaaattaaa aaggaaaata aaagatattg aggtcttcct   3960
agtgttactt aaattaagat caaggtaaga aacattgtaa aaaaaaatta caaaagtgct   4020
atttgtttcc taaaaacagt gatttctatt aaaaaggtgt cagaactgga gaaaatgccg   4080
tgtagttata atttttagc acagaccctg ctgatcacga tgacattttg ccgtgtgtgt   4140
gtctctagac tggtgggcca gtctccttga aggacagagg cggagctccc cacccttctc   4200
tctcctcaga aaagaccgtg ctctcttctt ggtgcaggga tcttgtctcc tgttgtgaag   4260
cccaaatgga agcgtggatg gtatcagggc cctacccgtg gtcttctcag attctgctag   4320
agcaaaaggc tggtgcctaa ataagatccc ttcctttggt gctgcttttg gtctttcagc   4380
caccagcatt atgagtgcct gggggacacc tccgagggaa ctggccagcg gagctctgtg   4440
gtgcgcacgc accctggccg tgacaggagg gtgcgggagt acaggctggc tgcatcagcc   4500
cttggtgctt agaacagagg aggagtgaca tgttttgagg gtacgtctct gagacagagc   4560
cccagcgtgg ccttcgctct gtcttgcctt tggggagagg tctgaagctc ccactccttt   4620
ctctgcctgt tggctccagg caccagaaat ttactccact ccacccaccc acaagcctcc   4680
tgggtgaccc tgggctagaa ttgctgcgct tgcctcggct tggccggttg tggcctctcc   4740
ttgagaaaac cagggttgtg aaagactcag accattctct catcttgcct tgtcagaagt   4800
aaattgtgtc agatttgtgc tctcgctgga gacctttgcc ccttgcgtgc ccctggccga   4860
tgggagggcg gtggaggctc tgtaccctgg ccctgctgga gcatctcccc caagcccact   4920
```

```
ccaggccctg ggaatggcca gagtctagga gaggtagaaa cgatcctatc agcttctctc   4980
ccacccaatt aggcccagag agacaaagac agatctgaaa gcaaatgcaa cagagaagag   5040
acacttctta gagtaaaatg tgtctcatct ctatcagcca tcgcctttca tcttcccagg   5100
ggcctcagaa gaaggaatta agttaggctg aacaggcctc agagttaggc cctggctgct   5160
tgattggctg agggggaaag agttcccttt tctcattcag aaaccaaggt gctgtgtcta   5220
gtcagggagc cttggagatg cctggactag ttggaggaat cgttggcaga ggatcagaga   5280
ccagcagcag gctgtctgcc ctgtctagag ctcttcccct caacttgtct gggcccatct   5340
gggggttgcc acacaacacc taacttacct tttcctgaaa gaagttggga aaccatcatc   5400
actagaggcc tttgctcaga gaggagctgc cttaggagtc ttgggtcgga ggacggggct   5460
aggaattgac cagggctttg cctgccgccc tcagcagtgt cgggtacatt ctgacctcgc   5520
ctgcagctgg gctgtggatt cttcctgaca ttcagatgtg agctgttttg ggagtcagct   5580
agtatggagt acgagatgca acccagcccc caaacctaca ttctgcactc aaattccaaa   5640
acactgcttt actgtaaaga agaggcccct ggcacccaat ctccctgtcc ttcactgtcc   5700
cctcagacct gggcggggag gggggggggc ctgtgaccac ctgagacata cgctcgtgac   5760
actgccccac cccagccacc tccacttgct tcctcctcct tccctccgct gctctttccc   5820
cacggcccag aatttagctg ctctgacagc cacttttgag accagctggc tttgtagtca   5880
cttcagagag ctggagcggc tgcccactgg gccctgactg ggagtcccct gccagctcct   5940
gatcaggcgc tgcgccctgg tggcagtgat gactgggagt cccctgccag ctcctgtcca   6000
ggcgctgcat cctggtaaca gtgaggccat gttgctgtca tctccacctc tgcattcttg   6060
ctgcctgtgg gtccttttc tttcatggag cctgctgggt cttgtctcac ctgtgctgag    6120
ctcctctggg gttttgattt cttccttcct tatcaggccc tttggggtaa gcctgctggt   6180
tgtacctgac atagggaggc agttaggggc agtccctggt ggggccgccc tggcagcctc   6240
cagctggcac catcgtgtgc ctggtttccc tgcaacacct gcctctctgt ccctgctgct   6300
gcttggctca ggcccaacag gcagcgtgca tggaggtggt tacacacagc tgtttccgtg   6360
agggtgaccg tgtctgcagc acgcttccgt ctccgcatgc acggctgcct ctccagccac   6420
ctctgatact tctctcttgg ggccatcaga gcctcccttg ggctgtcacc tcccagctca   6480
cacacactct tcagtggttt cctctcttca ttctcttata gggcgtggtc cttcttattt   6540
atctaaaggg ctgaatttag gagacttttt acccaggggc aaaaggctct tagggtaatg   6600
agatggatgg tggcccaggt gcattttcca gggcctgggt tctccagatc ccgtggcttc   6660
tgttgagtgg aggcaacttt gctctgtgtg aacctcgccc ctgtccctct gccgggcacc   6720
cctggcagga agcaggactc ccatcctcac cctgacttag actgtcctct gagtcagctc   6780
ctctccaaga caggagtggg cagccctggg cagtcttctg gccccttgct aaagtgaggg   6840
gcaggaagct ggggctgccc tccagaaagc cggggtagga actctgaaaa atacctcctc   6900
taaacggaag cagggctctc cagttccact tggcgccccc tcccacaagg cccttcctcc   6960
ctgaggaccc cacccccta ccccttcccc agcagccttt ggaccctcac ctctctccgg    7020
tgtccgtggg tcctcagccc agggtgagct gcagtcaggc gggatgggac gggcaggcca   7080
gaggtcagcc agctcctagc agagaagagc cagccagacc ccaaccctgt ctcttgtcca   7140
tgccctttgt gatttcagtc ttggtagact tgtatttgga gttttgtgct tcaaagtttt   7200
tgtttttgtt tgtttggttt ttgttttgag ggggtggggg gggatacaga gcagctgatc   7260
```

aatttgtatt tatttatttt aacattttac taaataaagc caaataaagc ctctcaaaaa 7320
aaaaaaaaaa aa 7332

<210> SEQ ID NO 29
<211> LENGTH: 14135
<212> TYPE: DNA
<213> ORGANISM: Homo sapiens

<400> SEQUENCE: 29
gcactgcagc gccagcgtcc gagcgggcgg ccgagctccc ggagcggcct ggccccgagc 60
cccgagcggg cgtcgctcag cagcaggtcg cggccgcagc cccatccagc cccgcgcccg 120
ccatgccgtc cgcgggcccc gcctgagctg cggcctccgc gcgcgggcgg gcctggggac 180
ggcggggcca tgcgcgcgct gccctaacga tgccgcccgc cgcgcccgcc cgcctggcgc 240
tggccctggg cctgggcctg tggctcgggg cgctggcggg gggccccggg cgcggctgcg 300
ggccctgcga gccccccctgc ctctgcggcc cagcgcccgg cgccgcctgc cgcgtcaact 360
gctcgggccg cgggctgcgg acgctcggtc ccgcgctgcg catccccgcg gacgccacag 420
cgctagacgt ctcccacaac ctgctccggg cgctggacgt tgggctcctg gcgaacctct 480
cggcgctggc agagctggat ataagcaaca acaagatttc tacgttagaa gaaggaatat 540
ttgctaattt atttaattta agtgaaataa acctgagtgg gaacccgttt gagtgtgact 600
gtggcctggc gtggctgccg cgatgggcgg aggagcagca ggtgcgggtg gtgcagcccg 660
aggcagccac gtgtgctggg cctggctccc tggctggcca gcctctgctt ggcatcccct 720
tgctggacag tggctgtggt gaggagtatg tcgcctgcct ccctgacaac agctcaggca 780
ccgtggcagc agtgtccttt tcagctgccc acgaaggcct gcttcagcca gaggcctgca 840
gcgccttctg cttctccacc ggccagggcc tcgcagccct ctcggagcag ggctggtgcc 900
tgtgtggggc ggcccagccc tccagtgcct cctttgcctg cctgtccctc tgctccggcc 960
ccccgccacc tcctgccccc acctgtaggg gccccaccct cctccagcac gtcttccctg 1020
cctccccagg ggccaccctg gtggggcccc acggacctct ggcctctggc cagctagcag 1080
ccttccacat cgctgccccg ctccctgtca ctgccacacg ctgggacttc ggagacggct 1140
ccgccgaggt ggatgccgct gggccggctg cctcgcatcg ctatgtgctg cctgggcgct 1200
atcacgtgac ggccgtgctg gccctggggg ccggctcagc cctgctgggg acagacgtgc 1260
aggtggaagc ggcacctgcc gccctggagc tcgtgtgccc gtcctcggtg cagagtgacg 1320
agagccttga cctcagcatc cagaaccgcg gtggttcagg cctggaggcc gcctacagca 1380
tcgtggccct gggcgaggag ccggcccgag cggtgcaccc gctctgcccc tcggacacgg 1440
agatcttccc tggcaacggg cactgctacc gcctggtggt ggagaaggcg gcctggctgc 1500
aggcgcagga gcagtgtcag gcctgggccg gggccgccct ggcaatggtg gacagtcccg 1560
ccgtgcagcg cttcctggtc tcccgggtca ccaggagcct agacgtgtgg atcggcttct 1620
cgactgtgca gggggtggag gtgggcccag cgccgcaggg cgaggccttc agcctggaga 1680
gctgccagaa ctggctgccc ggggagccac acccagccac agccgagcac tgcgtccggc 1740
tcgggcccac cgggtggtgt aacaccgacc tgtgctcagc gccgcacagc tacgtctgcg 1800
agctgcagcc cggaggccca gtgcaggatg ccgagaacct cctcgtggga gcgcccagtg 1860
gggacctgca gggacccctg acgcctctgg cacagcagga cggcctctca gccccgcacg 1920
agcccgtgga ggtcatggta ttcccgggcc tgcgtctgag ccgtgaagcc ttcctcacca 1980
cggccgaatt tgggacccag gagctccggc ggcccgccca gctgcggctg caggtgtacc 2040

```
ggctcctcag cacagcaggg accccggaga acggcagcga gcctgagagc aggtccccgg   2100
acaacaggac ccagctggcc cccgcgtgca tgccaggggg acgctggtgc cctggagcca   2160
acatctgctt gccgctggac gcctcctgcc acccccaggc ctgcgccaat ggctgcacgt   2220
cagggccagg gctacccggg gcccccctatg cgctatggag agagttcctc ttctccgttc   2280
ccgcggggcc ccccgcgcag tactcggtca ccctccacgg ccaggatgtc ctcatgctcc   2340
ctggtgacct cgttggcttg cagcacgacg ctggccctgg cgccctcctg cactgctcgc   2400
cggctcccgg ccaccctggt ccccaggccc cgtacctctc cgccaacgcc tcgtcatggc   2460
tgccccactt gccagcccag ctggagggca cttgggcctg ccctgcctgt gccctgcggc   2520
tgcttgcagc cacggaacag ctcaccgtgc tgctgggctt gaggcccaac cctggactgc   2580
ggctgcctgg gcgctatgag gtccgggcag aggtgggcaa tggcgtgtcc aggcacaacc   2640
tctcctgcag ctttgacgtg gtctccccag tggctgggct gcgggtcatc taccctgccc   2700
cccgcgacgg ccgcctctac gtgcccacca acggctcagc cttggtgctc caggtggact   2760
ctggtgccaa cgccacggcc acggctcgct ggcctggggg cagtgtcagc gcccgctttg   2820
agaatgtctg ccctgccctg gtggccacct tcgtgcccgg ctgcccctgg gagaccaacg   2880
ataccctgtt ctcagtggta gcactgccgt ggctcagtga gggggagcac gtggtggacg   2940
tggtggtgga aaacagcgcc agccgggcca acctcagcct gcgggtgacg gcggaggagc   3000
ccatctgtgg cctccgcgcc acgcccagcc ccgaggcccg tgtactgcag ggagtcctag   3060
tgaggtacag ccccgtggtg gaggccggct cggacatggt cttccggtgg accatcaacg   3120
acaagcagtc cctgaccttc cagaacgtgg tcttcaatgt catttatcag agcgcggcgg   3180
tcttcaagct ctcactgacg gcctccaacc acgtgagcaa cgtcaccgtg aactacaacg   3240
taaccgtgga gcggatgaac aggatgcagg gtctgcaggt ctccacagtg ccggccgtgc   3300
tgtcccccaa tgccacgcta gcactgacgg cgggcgtgct ggtggactcg gccgtggagg   3360
tggccttcct gtggaccttt ggggatgggg agcaggccct ccaccagttc cagcctccgt   3420
acaacgagtc cttcccggtt ccagacccct cggtggccca ggtgctggtg gagcacaatg   3480
tcatgcacac ctacgctgcc ccaggtgagt acctcctgac cgtgctggca tctaatgcct   3540
tcgagaacct gacgcagcag gtgcctgtga gcgtgcgcgc ctccctgccc tccgtggctg   3600
tgggtgtgag tgacggcgtc ctggtggccg gccggcccgt caccttctac ccgcacccgc   3660
tgccctcgcc tgggggtgtt ctttacacgt gggacttcgg ggacggctcc cctgtcctga   3720
cccagagcca gccggctgcc aaccacacct atgcctcgag gggcacctac cacgtgcgcc   3780
tggaggtcaa caacacggtg agcggtgcgg cggcccaggc ggatgtgcgc gtctttgagg   3840
agctccgcgg actcagcgtg gacatgagcc tggccgtgga gcagggcgcc cccgtggtgg   3900
tcagcgccgc ggtgcagacg ggcgacaaca tcacgtggac cttcgacatg gggacggca   3960
ccgtgctgtc gggcccggag gcaacagtgg agcatgtgta cctgcgggca cagaactgca   4020
cagtgaccgt gggtgcggcc agccccgccg gccacctggc ccggagcctg cacgtgctgg   4080
tcttcgtcct ggaggtgctg cgcgttgaac ccgccgcctg catccccacg cagcctgacg   4140
cgcggctcac ggcctacgtc accgggaacc cggcccacta cctcttcgac tggaccttcg   4200
gggatggctc ctccaacacg accgtgcggg ggtgcccgac ggtgacacac aacttcacgc   4260
ggagcggcac gttccccctg gcgctggtgc tgtccagccg cgtgaacagg gcgcattact   4320
tcaccagcat ctgcgtggag ccagaggtgg gcaacgtcac cctgcagcca gagaggcagt   4380
```

```
ttgtgcagct cggggacgag gcctggctgg tggcatgtgc ctggcccccg ttcccctacc   4440
gctacacctg ggactttggc accgaggaag ccgcccccac ccgtgccagg ggccctgagg   4500
tgacgttcat ctaccgagac ccaggctcct atcttgtgac agtcaccgcg tccaacaaca   4560
tctctgctgc caatgactca gccctggtgg aggtgcagga gcccgtgctg gtcaccagca   4620
tcaaggtcaa tggctccctt gggctggagc tgcagcagcc gtacctgttc tctgctgtgg   4680
gccgtgggcg ccccgccagc tacctgtggg atctggggga cggtgggtgg ctcgagggtc   4740
cggaggtcac ccacgcttac aacagcacag gtgacttcac cgttagggtg gccggctgga   4800
atgaggtgag ccgcagcgag gcctggctca atgtgacggt gaagcggcgc gtgcgggggc   4860
tcgtcgtcaa tgcaagccgc acggtggtgc ccctgaatgg gagcgtgagc ttcagcacgt   4920
cgctggaggc cggcagtgat gtgcgctatt cctgggtgct ctgtgaccgc tgcacgccca   4980
tccctggggg tcctaccatc tcttacacct tccgctccgt gggcaccttc aatatcatcg   5040
tcacggctga gaacgaggtg ggctccgccc aggacagcat cttcgtctat gtcctgcagc   5100
tcatagaggg gctgcaggtg gtgggcggtg gccgctactt ccccaccaac cacacggtac   5160
agctgcaggc cgtggttagg gatggcacca acgtctccta cagctggact gcctggaggg   5220
acaggggccc ggccctggcc ggcagcggca aaggcttctc gctcaccgtg ctcgaggccg   5280
gcacctacca tgtgcagctg cgggccacca acatgctggg cagcgcctgg gccgactgca   5340
ccatggactt cgtggagcct gtggggtggc tgatggtggc cgcctccccg aacccagctg   5400
ccgtcaacac aagcgtcacc ctcagtgccg agctggctgg tggcagtggt gtcgtataca   5460
cttggtcctt ggaggagggg ctgagctggg agacctccga gccatttacc acccatagct   5520
tccccacacc cggcctgcac ttggtcacca tgacggcagg gaacccgctg ggctcagcca   5580
acgccaccgt ggaagtggat gtgcaggtgc ctgtgagtgg cctcagcatc agggccagcg   5640
agcccggagg cagcttcgtg gcggccgggt cctctgtgcc cttttggggg cagctggcca   5700
cgggcaccaa tgtgagctgg tgctgggctg tgcccggcgg cagcagcaag cgtggccctc   5760
atgtcaccat ggtcttcccg gatgctggca ccttctccat ccggctcaat gcctccaacg   5820
cagtcagctg ggtctcagcc acgtacaacc tcacggcgga ggagcccatc gtgggcctgg   5880
tgctgtgggc cagcagcaag gtggtggcgc ccgggcagct ggtccatttt cagatcctgc   5940
tggctgccgg ctcagctgtc accttccgcc tgcaggtcgg cggggccaac cccgaggtgc   6000
tccccgggcc ccgtttctcc cacagcttcc cccgcgtcgg agaccacgtg gtgagcgtgc   6060
ggggcaaaaa ccacgtgagc tgggcccagg cgcaggtgcg catcgtggtg ctggaggccg   6120
tgagtgggct gcaggtgccc aactgctgcg agcctggcat cgccacgggc actgagagga   6180
acttcacagc ccgcgtgcag cgcggctctc gggtcgccta cgcctggtac ttctcgctgc   6240
agaaggtcca gggcgactcg ctggtcatcc tgtcgggccg cgacgtcacc tacacgcccg   6300
tggccgcggg gctgttggag atccaggtgc gcgccttcaa cgccctgggc agtgagaacc   6360
gcacgctggt gctggaggtt caggacgccg tccagtatgt ggccctgcag agcggcccct   6420
gcttcaccaa ccgctcggcg cagtttgagg ccgccaccag ccccagcccc cggcgtgtgg   6480
cctaccactg ggactttggg gatgggtcgc cagggcagga cacagatgag cccagggccg   6540
agcactccta cctgaggcct ggggactacc gcgtgcaggt gaacgcctcc aacctggtga   6600
gcttcttcgt ggcgcaggcc acggtgaccg tccaggtgct ggcctgccgg gagccggagg   6660
tggacgtggt cctgcccctg caggtgctga tgcggcgatc acagcgcaac tacttggagg   6720
cccacgttga cctgcgcgac tgcgtcacct accagactga gtaccgctgg gaggtgtatc   6780
```

gcaccgccag ctgccagcgg ccggggcgcc cagcgcgtgt ggccctgccc ggcgtggacg 6840
tgagccggcc tcggctggtg ctgccgcggc tggcgctgcc tgtggggcac tactgctttg 6900
tgtttgtcgt gtcatttggg gacacgccac tgacacagag catccaggcc aatgtgacgg 6960
tggcccccga gcgcctggtg cccatcattg agggtggctc ataccgcgtg tggtcagaca 7020
cacgggacct ggtgctggat gggagcgagt cctacgaccc caacctggag gacggcgacc 7080
agacgccgct cagtttccac tgggcctgtg tggcttcgac acagagggag gctggcgggt 7140
gtgcgctgaa ctttgggccc cgcgggagca gcacggtcac cattccacgg gagcggctgg 7200
cggctggcgt ggagtacacc ttcagcctga ccgtgtggaa ggccggccgc aaggaggagg 7260
ccaccaacca gacggtgctg atccggagtg gccgggtgcc cattgtgtcc ttggagtgtg 7320
tgtcctgcaa ggcacaggcc gtgtacgaag tgagccgcag ctcctacgtg tacttggagg 7380
gccgctgcct caattgcagc agcggctcca agcgagggcg gtgggctgca cgtacgttca 7440
gcaacaagac gctggtgctg gatgagacca ccacatccac gggcagtgca ggcatgcgac 7500
tggtgctgcg gcggggcgtg ctgcgggacg gcgagggata caccttcacg ctcacggtgc 7560
tgggccgctc tggcgaggag gagggctgcg cctccatccg cctgtccccc aaccgcccgc 7620
cgctgggggg ctcttgccgc ctcttcccac tgggcgctgt gcacgccctc accaccaagg 7680
tgcacttcga atgcacgggc tggcatgacg cggaggatgc tggcgccccg ctggtgtacg 7740
ccctgctgct gcggcgctgt cgccagggcc actgcgagga gttctgtgtc tacaagggca 7800
gcctctccag ctacggagcc gtgctgcccc cgggtttcag gccacacttc gaggtgggcc 7860
tggccgtggt ggtgcaggac cagctgggag ccgctgtggt cgccctcaac aggtctttgg 7920
ccatcaccct cccagagccc aacggcagcg caacggggct cacagtctgg ctgcacgggc 7980
tcaccgctag tgtgctccca gggctgctgc ggcaggccga tccccagcac gtcatcgagt 8040
actcgttggc cctggtcacc gtgctgaacg agtacgagcg ggccctggac gtggcggcag 8100
agcccaagca cgagcggcag caccgagccc agatacgcaa gaacatcacg gagactctgg 8160
tgtccctgag ggtccacact gtggatgaca tccagcagat cgctgctgcg ctggcccagt 8220
gcatggggcc cagcagggag ctcgtatgcc gctcgtgcct gaagcagacg ctgcacaagc 8280
tggaggccat gatgctcatc ctgcaggcag agaccaccgc gggcaccgtg acgcccaccg 8340
ccatcggaga cagcatcctc aacatcacag gagacctcat ccacctggcc agctcggacg 8400
tgcgggcacc acagccctca gagctgggag ccgagtcacc atctcggatg gtggcgtccc 8460
aggcctacaa cctgacctct gccctcatgc gcatcctcat gcgctcccgc gtgctcaacg 8520
aggagcccct gacgctggcg ggcgaggaga tcgtggccca gggcaagcgc tcggacccgc 8580
ggagcctgct gtgctatggc ggcgccccag ggcctggctg ccacttctcc atccccgagg 8640
ctttcagcgg ggccctggcc aacctcagtg acgtggtgca gctcatcttt ctggtggact 8700
ccaatccctt tccctttggc tatatcagca actacaccgt ctccaccaag gtggcctcga 8760
tggcattcca gacacaggcc ggcgcccaga tccccatcga gcggctggcc tcagagcgcg 8820
ccatcaccgt gaaggtgccc aacaactcgg actgggctgc ccggggccac cgcagctccg 8880
ccaactccgc caactccgtt gtggtccagc cccaggcctc cgtcggtgct gtggtcaccc 8940
tggacagcag caaccctgcg gccgggctgc atctgcagct caactatacg ctgctggacg 9000
gccactacct gtctgaggaa cctgagccct acctggcagt ctacctacac tcggagcccc 9060
ggcccaatga gcacaactgc tcggctagca ggaggatccg cccagagtca ctccagggtg 9120

-continued

```
ctgaccaccg gccctacacc ttcttcattt ccccggggag cagagaccca gcggggagtt   9180
accatctgaa cctctccagc cacttccgct ggtcggcgct gcaggtgtcc gtgggcctgt   9240
acacgtccct gtgccagtac ttcagcgagg aggacatggt gtggcggaca gaggggctgc   9300
tgcccctgga ggagacctcg ccccgccagg ccgtctgcct cacccgccac ctcaccgcct   9360
tcggcgccag cctcttcgtg cccccaagcc atgtccgctt tgtgtttcct gagccgacag   9420
cggatgtaaa ctacatcgtc atgctgacat gtgctgtgtg cctggtgacc tacatggtca   9480
tggccgccat cctgcacaag ctggaccagt tggatgccag ccggggccgc gccatccctt   9540
tctgtgggca gcggggccgc ttcaagtacg agatcctcgt caagacaggc tggggccggg   9600
gctcaggtac cacggcccac gtgggcatca tgctgtatgg ggtggacagc cggagcggcc   9660
accggcacct ggacggcgac agagccttcc accgcaacag cctggacatc ttccggatcg   9720
ccaccccgca cagcctgggt agcgtgtgga agatccgagt gtggcacgac aacaaagggc   9780
tcagccctgc ctggttcctg cagcacgtca tcgtcaggga cctgcagacg gcacgcagcg   9840
ccttcttcct ggtcaatgac tggctttcgg tggagacgga ggccaacggg ggcctggtgg   9900
agaaggaggt gctggccgcg agcgacgcag cccttttgcg cttccggcgc ctgctggtgg   9960
ctgagctgca gcgtggcttc tttgacaagc acatctggct ctccatatgg gaccggccgc  10020
ctcgtagccg tttcactcgc atccagaggg ccacctgctg cgttctcctc atctgcctct  10080
tcctgggcgc caacgccgtg tggtacgggg ctgttggcga ctctgcctac agcacggggc  10140
atgtgtccag gctgagcccg ctgagcgtcg acacagtcgc tgttggcctg gtgtccagcg  10200
tggttgtcta tcccgtctac ctggccatcc tttttctctt ccggatgtcc cggagcaagg  10260
tggctgggag cccgagcccc acacctgccg ggcagcaggt gctggacatc gacagctgcc  10320
tggactcgtc cgtgctggac agctccttcc tcacgttctc aggcctccac gctgaggcct  10380
ttgttggaca gatgaagagt gacttgtttc tggatgattc taagagtctg gtgtgctggc  10440
cctccggcga gggaacgctc agttggccgg acctgctcag tgacccgtcc attgtgggta  10500
gcaatctgcg gcagctggca cggggccagg cgggccatgg gctgggccca gaggaggacg  10560
gcttctccct ggccagcccc tactcgcctg ccaaatcctt ctcagcatca gatgaagacc  10620
tgatccagca ggtccttgcc gagggggtca gcagcccagc ccctacccaa gacacccaca  10680
tggaaacgga cctgctcagc agcctgtcca gcactcctgg ggagaagaca gagacgctgg  10740
cgctgcagag gctgggggag ctggggccac ccagcccagg cctgaactgg gaacagcccc  10800
aggcagcgag gctgtccagg acaggactgg tggagggtct gcggaagcgc ctgctgccgg  10860
cctggtgtgc ctccctggcc cacgggctca gcctgctcct ggtggctgtg gctgtggctg  10920
tctcagggtg ggtgggtgcg agcttccccc cgggcgtgag tgttgcgtgg ctcctgtcca  10980
gcagcgccag cttcctggcc tcattcctcg gctgggagcc actgaaggtc ttgctggaag  11040
ccctgtactt ctcactggtg gccaagcggc tgcacccgga tgaagatgac accctggtag  11100
agagcccggc tgtgacgcct gtgagcgcac gtgtgccccg cgtacggcca ccccacggct  11160
ttgcactctt cctggccaag gaagaagccc gcaaggtcaa gaggctacat ggcatgctgc  11220
ggagcctcct ggtgtacatg ctttttctgc tggtgaccct gctggccagc tatggggatg  11280
cctcatgcca tgggcacgcc taccgtctgc aaagcgccat caagcaggag ctgcacagcc  11340
gggccttcct ggccatcacg cggtctgagg agctctggcc atggatggcc cacgtgctgc  11400
tgccctacgt ccacgggaac cagtccagcc cagagctggg gcccccacgg ctgcggcagg  11460
tgcggctgca ggaagcactc tacccagacc ctcccggccc cagggtccac acgtgctcgg  11520
```

-continued

```
ccgcaggagg cttcagcacc agcgattacg acgttggctg ggagagtcct cacaatggct  11580
cggggacgtg ggcctattca gcgccggatc tgctgggggc atggtcctgg ggctcctgtg  11640
ccgtgtatga cagcgggggc tacgtgcagg agctgggcct gagcctggag gagagccgcg  11700
accggctgcg cttcctgcag ctgcacaact ggctggacaa caggagccgc gctgtgttcc  11760
tggagctcac gcgctacagc ccggccgtgg ggctgcacgc cgccgtcacg ctgcgcctcg  11820
agttcccggc ggccggccgc gccctggccg ccctcagcgt ccgccccttt gcgctgcgcc  11880
gcctcagcgc gggcctctcg ctgcctctgc tcacctcggt gtgcctgctg ctgttcgccg  11940
tgcacttcgc cgtggccgag gcccgtactt ggcacaggga agggcgctgg cgcgtgctgc  12000
ggctcggagc ctgggcgcgg tggctgctgg tggcgctgac ggcggccacg gcactggtac  12060
gcctcgccca gctgggtgcc gctgaccgcc agtggacccg tttcgtgcgc ggccgcccgc  12120
gccgcttcac tagcttcgac caggtggcgc agctgagctc cgcagcccgt ggcctggcgg  12180
cctcgctgct cttcctgctt ttggtcaagg ctgcccagca gctacgcttc gtgcgccagt  12240
ggtccgtctt tggcaagaca ttatgccgag ctctgccaga gctcctgggg gtcaccttgg  12300
gcctggtggt gctcggggta gcctacgccc agctggccat cctgctcgtg tcttcctgtg  12360
tggactccct ctggagcgtg gcccaggccc tgttggtgct gtgccctggg actgggctct  12420
ctaccctgtg tcctgccgag tcctggcacc tgtcacccct gctgtgtgtg gggctctggg  12480
cactgcggct gtggggcgcc ctacggctgg gggctgttat tctccgctgg cgctaccacg  12540
ccttgcgtgg agagctgtac cggccggcct gggagcccca ggactacgag atggtggagt  12600
tgttcctgcg caggctgcgc ctctggatgg gcctcagcaa ggtcaaggag ttccgccaca  12660
aagtccgctt tgaagggatg gagccgctgc cctctcgctc ctccaggggc tccaaggtat  12720
ccccggatgt gcccccaccc agcgctggct ccgatgcctc gcacccctcc acctcctcca  12780
gccagctgga tgggctgagc gtgagcctgg gccggctggg gacaaggtgt gagcctgagc  12840
cctcccgcct ccaagccgtg ttcgaggccc tgctcaccca gtttgaccga ctcaaccagg  12900
ccacagagga cgtctaccag ctggagcagc agctgcacag cctgcaaggc cgcaggagca  12960
gccgggcgcc cgccggatct tcccgtggcc catccccggg cctgcggcca gcactgccca  13020
gccgccttgc ccgggccagt cggggtgtgg acctggccac tggccccagc aggacacccc  13080
ttcgggccaa gaacaaggtc caccccagca gcacttagtc ctccttcctg gcgggggtgg  13140
gccgtggagt cggagtggac accgctcagt attactttct gccgctgtca aggccgaggg  13200
ccaggcagaa tggctgcacg taggttcccc agagagcagg caggggcatc tgtctgtctg  13260
tgggcttcag cactttaaag aggctgtgtg gccaaccagg acccagggtc ccctccccag  13320
ctcccttggg aaggacacag cagtattgga cggtttctag cctctgagat gctaatttat  13380
ttccccgagt cctcaggtac agcgggctgt gcccggcccc accccctggg cagatgtccc  13440
ccactgctaa ggctgctggc ttcagggagg gttagcctgc accgccgcca ccctgcccct  13500
aagttattac ctctccagtt cctaccgtac tccctgcacc gtctcactgt gtgtctcgtg  13560
tcagtaattt atatggtgtt aaaatgtgta tatttttgta tgtcactatt ttcactaggg  13620
ctgaggggcc tgcgcccaga gctggcctcc cccaacacct gctgcgcttg gtaggtgtgg  13680
tggcgttatg gcagcccggc tgctgcttgg atgcgagctt ggccttgggc cggtgctggg  13740
ggcacagctg tctgccaggc actctcatca ccccagaggc cttgtcatcc tcccttgccc  13800
caggccaggt agcaagagag cagcgcccag gcctgctggc atcaggtctg ggcaagtagc  13860
```

aggactaggc atgtcagagg accccagggt ggttagagga aaagactcct cctgggggct 13920
ggctcccagg gtggaggaag gtgactgtgt gtgtgtgtgt gtgcgcgcgc gcacgcgcga 13980
gtgtgctgta tggcccaggc agcctcaagg ccctcggagc tggctgtgcc tgcttctgtg 14040
taccacttct gtgggcatgg ccgcttctag agcctcgaca cccccccaac ccccgcacca 14100
agcagacaaa gtcaataaaa gagctgtctg actgc 14135

<210> SEQ ID NO 30
<211> LENGTH: 2207
<212> TYPE: DNA
<213> ORGANISM: Homo sapiens

<400> SEQUENCE: 30
gcatcctctc accgccggaa gctgaactga ctcgtccgcg gccgctctac cccaacaggc 60
cgccaccagc gagagtgcgg ccataaccat cacgtgaccg cccaccgaca ccagcgagag 120
tgcagtcgta accgtcacgt gaccgcccac cgtcggcccg gcgctcccct ccgccccgaag 180 ctagcaagcg gcgcggccaa tgagaaaggc gcatgcctgg cccccgccgg cctgcagtct 240
agccgtagtg cgcctgcgcg cggctaggag gggccgtcag gcggggatac agcctggaag 300
gtaatgcatg tccatggtac acaaattcac aagtttggag accctgacac acccaccttc 360
tcacctgggc tctgcgtatc ccccagcctt gagggaagat gaagcctaaa ctgatgtacc 420
aggagctgaa ggtgcctgca gaggagcccg ccaatgagct gcccatgaat gagattgagg 480
cgtggaaggc tgcggaaaag aaagcccgct gggtcctgct ggtcctcatt ctggcggttg 540
tgggcttcgg agccctgatg actcagctgt ttctatggga atacggcgac ttgcatctct 600
ttgggcccaa ccagcgccca gcccccctgct atgacccttg cgaagcagtg ctggtggaaa 660
gcattcctga gggcctggac ttccccaatg cctccacggg gaacccttcc accagccagg 720
cctggctggg cctgctcgcc ggtgcgcaca gcagcctgga catcgcctcc ttctactgga 780
ccctcaccaa caatgacacc cacacgcagg agccctctgc ccagcagggt gaggaggtcc 840
tccggcagct gcagaccctg gcaccaaagg gcgtgaacgt ccgcatcgct gtgagcaagc 900
ccagcgggcc ccagccacag gcggacctgc aggctctgct gcagagcggt gcccaggtcc 960
gcatggtgga catgcagaag ctgacccatg gcgtcctgca taccaagttc tgggtggtgg 1020
accagaccca cttctacctg ggcagtgcca acatggactg gcgttcactg acccaggtca 1080
aggagctggg cgtggtcatg tacaactgca gctgcctggc tcgagacctg accaagatct 1140
ttgaggccta ctggttcctg ggccaggcag gcagctccat cccatcaact tggccccggt 1200
tctatgacac ccgctacaac caagagacac caatggagat ctgcctcaat ggaacccctg 1260
ctctggccta cctggcgagt gcgcccccac ccctgtgtcc aagtggccgc actccagacc 1320
tgaaggctct actcaacgtg gtggacaatg cccggagttt catctacgtc gctgtcatga 1380
actacctgcc cactctggag ttctcccacc ctcacaggtt ctggcctgcc attgacgatg 1440
ggctgcggcg ggccacctac gagcgtggcg tcaaggtgcg cctgctcatc agctgctggg 1500
gacactcgga gccatccatg cgggccttcc tgctctctct ggctgccctg cgtgacaacc 1560
atacccactc tgacatccag gtgaaactct ttgtggtccc cgcggatgag gcccaggctc 1620
gaatcccata tgcccgtgtc aaccacaaca agtacatggt gactgaacgc gccacctaca 1680
tcggaacctc caactggtct ggcaactact tcacggagac ggcgggcacc tcgctgctgg 1740
tgacgcagaa tgggaggggc ggcctgcgga gccagctgga ggccattttc ctgagggact 1800
gggactcccc ttacagccat gaccttgaca cctcagctga cagcgtgggc aacgcctgcc 1860
gcctgctctg aggcccgatc cagtgggcag gccaaggcct gctgggcccc cgcggaccca 1920
ggtgctctgg gtcacggtcc ctgtccccgc gcccccgctt ctgtctgccc cattgtggct 1980
cctcaggctc tctcccctgc tctcccacct ctacctccac ccccaccggc ctgacgctgt 2040
ggccccggga cccagcagag ctgggggagg gatcagcccc caaagaaatg gggtgcatg 2100 ctgggcctgg ccccctggcc cacccccact ttccagggca aaaagggccc agggttataa 2160
taagtaaata acttgtctgt acagcctgaa aaaaaaaaaa aaaaaaa 2207

<210> SEQ ID NO 31
<211> LENGTH: 4846
<212> TYPE: DNA
<213> ORGANISM: Homo sapiens

<400> SEQUENCE: 31
gagcggtgct caggggaggg ctggagggga gggaaggaga gagagagggg agggcggcac 60
cgcccctagc cccgcgctcc ggaagtgaag cggccagacc accagctaat ggatgcggag 120
cggagggccc gctgaccgct ctccgcgcct ggagcagctt ggcttggctg gagctaagag 180
ccagacacac cactgtgtgg aggtgggtga tgtcttcctg tgctaaaagg tgaataaata 240
agctcctcac ctctcgcgga acactcggga acacatcaac aggggtccaa gccgccctgc 300
tgggaggctt ctcttcaaga gttctgggtc ccagagtgga aggcattttc ccatcaactg 360
gagagagacg aaacatcaga gaccaggagg ctgtggagaa agcagctgtc ccaggtgcct 420
caactatcag agaagggtca gcgtcacgtg gctgccagca tctttgagaa aatcactggc 480
aatcggactt cagagctgcg ggcacaggtg tggttagaac tgagatacga cctgcccacc 540
tgggtcaggc ctaaagacaa gaagtcctga gttcttgcca ctgagtaggc cagggtcatt 600
tgtccagaaa actttgtgac tgtctttgag tgacctagtc tgggacccat tcattggtgg 660
gttctaaggt tagaagctca tccaggatat tttcaatatt aagtcagtgc atagctgcac 720
cactaacaaa ttggtgcctg tagagtcaga gtgggtcaat tcttaggaca atggcgctgg 780
cactgttaga ggactggtgc aggataatga gtgtggatga gcagaagtca ctgatggtta 840
cggggatacc ggcggacttt gaggaggctg agattcagga ggtccttcag gagactttaa 900
agtctctggg caggtataga ctgcttggca agatattccg gaagcaggag aatgccaatg 960
ctgtcttact agagcttctg gaagatactg atgtctcggc cattcccagt gaggtccagg 1020
gaaagggggg tgtctggaag gtgatcttta agacccctaa tcaggacact gagtttcttg 1080
aaagattgaa cctgtttcta gaaaaagagg ggcagacggt ctcgggtatg tttcgagccc 1140
tggggcagga gggcgtgtct ccagccacag tgccctgcat ctcaccagaa ttactggccc 1200
atttgttggg acaggcaatg gcacatgcgc ctcagcccct gctacccatg agataccgga 1260
aactgcgagt attctcaggg agtgctgtcc cagccccaga ggaagagtcc tttgaggtct 1320
ggttggaaca ggccacggag atagtcaaag agtggccagt aacagaggca gaaaagaaaa 1380
ggtggctggc ggaaagcctg cggggccctg ccctggacct catgcacata gtgcaggcag 1440
acaacccgtc catcagtgta gaagagtgtt tggaggcctt taagcaagtg tttgggagcc 1500
tagagagccg caggacagcc caggtgaggt atctgaagac ctatcaggag gaaggagaga 1560
aggtctcagc ctatgtgtta cggctagaaa ccctgctccg gagagcggtg gagaaacgcg 1620
ccatccctcg gcgtattgcg gaccaggtcc gcctggagca ggtcatggct ggggccactc 1680
ttaaccagat gctgtggtgc cggcttaggg agctgaagga tcagggcccg ccccccagct 1740

-continued

```
tccttgagct aatgaaggta atacgggaag aagaggagga agaggcctcc tttgagaatg   1800
agagtatcga agagccagag gaacgagatg gctatggccg ctggaatcat gagggagacg   1860
actgaaaacc acctgggggc aggacccaca gccagtgggc taagaccttt aaaaaatttt   1920
tttctttaat gtatgggact gaaatcaaac catgaaagcc aattattgac cttccttcct   1980
tccttccttc cctcccttcc tccttctctc cttctctcct cctctctcct ctcctctcct   2040
ctctttcctt ccttccttcc ttttttcttt ttctctttct tctttatttc ttgggtctca   2100
ctctcatcac ccaggctaga gtgcagtggc acaaaaatct cggctcactg cagccttgac   2160
ttcccaggct caggctcagg tgatcctcac accttagcct cccaagtacc tgggactaca   2220
ggcacgcacc accatgccta gctattcttt tgtatttttg gtagagacag ggttttgctg   2280
tgttgctcag gctggtctgg aacccctagg ctcaaatgat gtgcccaact cggcctccca   2340
aagtgctggg attacaggca tgaaccgcca tgcctggccc ttgatttttc tttttaagaa   2400
aaaaatatct aggagtttct tagaccctat gtagattatt aatgaacaaa agattaaact   2460
ccaaatatta aatagtaagc ctgaaggaat ctgaaacact tgtacttcca attttcttta   2520
aataatccca aatagaccag aattggccca taccatagaa gaaagaattg gcagtcaaaa   2580
aaaaaaatac cttttgtaat gtttgaaaaa taaagctgtt tgacttgtca ggtgttttcc   2640
tttctcaaat cagcaaattc tctctgagtg cctggctttg tgagacactg tacaaggagt   2700
tacaagacta cagctataac ctgcagttga gcagttataa acctacaaaa tgggccctgc   2760
cctcagagag gttccagtct agatgaggag ctgatctaga caggtaaaag gctaactaac   2820
cctttgtgta aataagttca tcaccccagt aaaagtgtca tcacccagtg aataggacca   2880
cctctgcctg cagatttttg ttgttgttgt tgtcattgtt gttgttgttt taacctggga   2940
agtgttcttc ctgcctttct gctaggtgtc agatagatgg tcccagagct aggtgctgtg   3000
tcaggccctg aagacacaga tgactcaacc taagctttac tttccagagg tccacagcct   3060
gagaggtgtc cccaaagaaa gggggacatg aggggactgc atgcttgaga gcagggttgt   3120
ttagggcagg tttggattta gtgagcaggc tggtttgctt agagaaggct tttagtggca   3180
acaaaggatg aagaggagag aaaaggaact cacatttatt gagggcctac tgtgtgcaaa   3240
gtgtttcatg tatatctcat tgaatgtata cagccaccct gttgtggtat aattttgctc   3300
tttataaaga gaaagaccga agctcagatg agttaagtgg tctcctcaac accaaaatgc   3360
caagaagtga tggagcctag acagaagccc agaactttct gactcacact agtccatcct   3420
ctaccatcac gatgactttc aaattgtgct ctgcagttct gcagattttc tagcagtgcc   3480
atctccaaaa tgtgttttaa actctttatt tttttaatta ttattagtat tattttgaga   3540
ctgagtcttg ctctatcacc caggctggag tgcagtggtg caatctcagc tcactgcaac   3600
ctccgcctcc caggttcaag cgatttcgtg cctcagcctc ccgagtagct gggattacag   3660
gcacccacca ccacgcccag ctaatttttg tatttttagt agaaatgggg tttcaccatg   3720
ttggccaggc tggtctcgaa ctcctgacct caagtgatcc actcacctcg gcctcccaaa   3780
gtgctgggat tacaggtgtg agccaccatg cctgggctaa actctttaag tctctagtaa   3840
atgcagctag attcaaatgg gctgataacc aaattttaac acatcagcat tcaccaccag   3900
gtttactttt attttcagat tggctcattt tgtgcagacc ttagagcaaa gtttccttta   3960
tggtatctgt gtacgtatcc aaacttcttt taattgttca cagattttaa aagcggtagc   4020
accacatggt tgtgtagatc agacctgtgt atttagatca gacctgtgta tcacgtaagt   4080
gtgtgagtgc agtgcagatg agcaccattt agttatatgt gctaggcaaa tctccaacac   4140
```

agttgatgtg tagtcttgtg gtagatttgt gcatactgta agcaaattgc ttagcttctc 4200
tagacatcag tttccacatc tgaaaaataa gaagatgaga gtacacggtt gttatgaaca 4260
aatgacttaa tgctttttaa gcacgttgca tgacatctgg aacacagaaa gccctcaata 4320
cattgaagct cttaggattt tcacgatgtt cctgtctgct caatgcatgc tttctttatt 4380
gttctgacag ttgtgtggta acaagctaat atgcttccag ttgacttcca gtctaccctg 4440
gtgttagaaa ccgtttcatc tcttattgta aatttgagtg cttgttgttt tttatatttg 4500
tgatgactct tccagcagtt gttgacaatt gttagaggtt tgacttttaa ataattactt 4560
attttttctg attgtggttc agtttaactg aagaatatcc tgagattgta agaaaagcat 4620
tttttaaaag gtatcacttg tgatcattta tctttctaaa ttctattttt aatactgttc 4680
caccaaagtg atgcagtggt taccatgaca ccctaatttc atgtgttttt gtatttatga 4740
aaatagtttc attgtcattt attggcggta tacaaagtaa aatgttataa atgtgaagtt 4800
ataaaataaa tatatgctaa taaaatcctg agtttttctg tttcct 4846

<210> SEQ ID NO 32
<211> LENGTH: 1014
<212> TYPE: DNA
<213> ORGANISM: Homo sapiens

<400> SEQUENCE: 32
tgcctcctga gcgtagtcca gttactttca ggctcgggga gtgaaggcct cgttgagaga 60
aggtctcatt cggtgttttg ggaagagagt cgtgtgggcc caggtctgtc tgctatcagc 120
tatgccgctg cccgttgcgc tgcagacccg cttggccaag agaggcatcc tcaaacatct 180
ggagcctgaa ccagaggaag agatcattgc cgaggactat gacgatgatc ctgtggacta 240
cgaggccacc aggttggagg gcctaccacc aagctggtac aaggtgttcg acccttcctg 300
cgggctccct tactactgga atgcagacac agaccttgta tcctggctct ccccacatga 360
ccccaactcc gtggttacca aatcggccaa gaagctcaga agcagtaatg cagatgctga 420
agaaaagttg gaccggagcc atgacaagtc ggacaggggc catgacaagt cggaccgcag 480
ccatgagaaa ctagacaggg gccacgacaa gtcagaccgg ggccacgaca agtctgacag 540
ggatcgagag cgtggctatg acaaggtaga cagagagaga gagcgagaca gggaacggga 600
tcgggaccgc gggtatgaca aggcagaccg ggaagagggc aaagaacggc gccaccatcg 660
ccgggaggag ctggctccct atcccaagag caagaaggca gtaagccgaa aggatgaaga 720
gttagacccc atggacccta gctcatactc agacgccccc cggggcacgt ggtcaacagg 780
actccccaag cggaatgagg ccaagactgg cgctgacacc acagcagctg ggcccctctt 840
ccagcagcgg ccgtatccat ccccaggggc tgtgctccgg gccaatgcag aggcctcccg 900
aaccaagcag caggattgaa gcttcggcct ccctggccct gggttaaaat aaaagctttc 960
tggtgatcct gcccaccaaa aaaaaaaaaa aaaaaaaaaa aaaaaaaaaa aaaa 1014

<210> SEQ ID NO 33
<211> LENGTH: 3291
<212> TYPE: DNA
<213> ORGANISM: Homo sapiens

<400> SEQUENCE: 33
agaatcggag agccggtggc gtcgcaggtc gggaggacga gcaccgagtc gagggctcgc 60
tcgtctgggc cgcccgagag tcttaatcgc gggcgcttgg gccgccatct tagatggcgg 120

```
gagtaagagg aaaacgattg tgaggcggga acggctttct gctgcctttt ttgggccccg    180
aaaagggtca gctggccggg ctttggggcg cgtgccctga ggcgcggagc gcgtttgcta    240
cgatgcgggg gctgctcggg gctccgtccc ctgggctggg gacgcgccga atgtgaccgc    300
ctcccgctcc ctcacccgcc gcggggagga ggagcgggcg agaagctgcc gccgaacgac    360
aggacgttgg ggcggcctgg ctccctcagg tttaagaatt gtttaagctg catcaatgga    420
gcacatacag ggagcttgga agacgatcag caatggtttt ggattcaaag atgccgtgtt    480
tgatggctcc agctgcatct ctcctacaat agttcagcag tttggctatc agcgccgggc    540
atcagatgat ggcaaactca cagatccttc taagacaagc aacactatcc gtgttttctt    600
gccgaacaag caaagaacag tggtcaatgt gcgaaatgga atgagcttgc atgactgcct    660
tatgaaagca ctcaaggtga ggggcctgca accagagtgc tgtgcagtgt tcagacttct    720
ccacgaacac aaaggtaaaa aagcacgctt agattggaat actgatgctg cgtctttgat    780
tggagaagaa cttcaagtag atttcctgga tcatgttccc ctcacaacac acaactttgc    840
tcggaagacg ttcctgaagc ttgccttctg tgacatctgt cagaaattcc tgctcaatgg    900
atttcgatgt cagacttgtg gctacaaatt tcatgagcac tgtagcacca aagtacctac    960
tatgtgtgtg gactggagta acatcagaca actcttattg tttccaaatt ccactattgg   1020
tgatagtgga gtcccagcac taccttcttt gactatgcgt cgtatgcgag agtctgtttc   1080
caggatgcct gttagttctc agcacagata ttctacacct cacgccttca cctttaacac   1140
ctccagtccc tcatctgaag gttccctctc ccagaggcag aggtcgacat ccacacctaa   1200
tgtccacatg gtcagcacca ccctgcctgt ggacagcagg atgattgagg atgcaattcg   1260
aagtcacagc gaatcagcct caccttcagc cctgtccagt agccccaaca atctgagccc   1320
aacaggctgg tcacagccga aaacccccgt gccagcacaa agagagcggg caccagtatc   1380
tgggacccag gagaaaaaca aaattaggcc tcgtggacag agagattcaa gctattattg   1440
ggaaatagaa gccagtgaag tgatgctgtc cactcggatt gggtcaggct cttttggaac   1500
tgtttataag ggtaaatggc acggagatgt tgcagtaaag atcctaaagg ttgtcgaccc   1560
aaccccagag caattccagg ccttcaggaa tgaggtggct gttctgcgca aaacacggca   1620
tgtgaacatt ctgcttttca tggggtacat gacaaaggac aacctggcaa ttgtgaccca   1680
gtggtgcgag ggcagcagcc tctacaaaca cctgcatgtc caggagacca agtttcagat   1740
gttccagcta attgacattg cccggcagac ggctcaggga atggactatt tgcatgcaaa   1800
gaacatcatc catagagaca tgaaatccaa caatatattt ctccatgaag gcttaacagt   1860
gaaaattgga gattttggtt tggcaacagt aaagtcacgc tggagtggtt ctcagcaggt   1920
tgaacaacct actggctctg tcctctggat ggccccagag gtgatccgaa tgcaggataa   1980
caacccattc agtttccagt cggatgtcta ctcctatggc atcgtattgt atgaactgat   2040
gacgggggag cttccttatt ctcacatcaa caaccgagat cagatcatct tcatggtggg   2100
ccgaggatat gcctccccag atcttagtaa gctatataag aactgcccca aagcaatgaa   2160
gaggctggta gctgactgtg tgaagaaagt aaaggaagag aggcctcttt ttccccagat   2220
cctgtcttcc attgagctgc tccaacactc tctaccgaag atcaaccgga gcgcttccga   2280
gccatccttg catcgggcag cccacactga ggatatcaat gcttgcacgc tgaccacgtc   2340
cccgaggctg cctgtcttct agttgacttt gcacctgtct tcaggctgcc aggggaggag   2400
gagaagccag caggcaccac ttttctgctc cctttctcca gaggcagaac acatgttttc   2460
agagaagctg ctgctaagga ccttctagac tgctcacagg gccttaactt catgttgcct   2520
```

-continued

```
tcttttctat ccctttgggc cctgggagaa ggaagccatt tgcagtgctg gtgtgtcctg   2580

ctccctcccc acattcccca tgctcaaggc ccagccttct gtagatgcgc aagtggatgt   2640

tgatggtagt acaaaaagca ggggcccagc cccagctgtt ggctacatga gtatttagag   2700

gaagtaaggt agcaggcagt ccagccctga tgtggagaca catgggattt tggaaatcag   2760

cttctggagg aatgcatgtc acaggcggga ctttcttcag agagtggtgc agcgccagac   2820

attttgcaca taaggcacca aacagcccag gactgccgag actctggccg cccgaaggag   2880

cctgctttgg tactatggaa cttttcttag gggacacgtc ctcctttcac agcttctaag   2940

gtgtccagtg cattgggatg gttttccagg caaggcactc ggccaatccg catctcagcc   3000

ctctcaggga gcagtcttcc atcatgctga attttgtctt ccaggagctg cccctatggg   3060

gcggggccgc agggccagcc ttgtttctct aacaaacaaa caaacaaaca gccttgtttc   3120

tctagtcaca tcatgtgtat acaaggaagc caggaataca ggttttcttg atgatttggg   3180

ttttaatttt gtttttattg cacctgacaa aatacagtta tctgatggtc cctcaattat   3240

gttattttaa taaaataaat taaatttagg tgtaaaaaaa aaaaaaaaaa a            3291
```

<210> SEQ ID NO 34
<211> LENGTH: 5216
<212> TYPE: DNA
<213> ORGANISM: Homo sapiens

<400> SEQUENCE: 34

```
gatgtcccag gggtattggg gcggggggtt gaaataactg gggttcagga ggagggatgg     60

tggtagagat aaaaatgtga gaagggagca gcactggcga ggagtcggga gagtactcct    120

gattgtgaca tcacattcat cccctgggcg atggagcttg tcactgggaa ggaatactca    180

gtcggagaat agccaacaag atgggttact gggagaatct cttcagtggc actgagtgga    240

ggcatcaggg ggttggagcc ttgtgaacag ggaacctgcc ccccaacact tggaaggacc    300

tgggtttcag tgatgagaca tggggtatga tgtaacccgt ttccaggggg atgttgacga    360

agatcttatc tgccctattt gcagtggagt cttggaggag ccagtacagg cacctcattg    420

tgaacatgct ttctgcaacg cctgcatcac ccagtggttc tctcagcaac agacatgtcc    480

agtggaccgt agtgttgtga cggtcgccca tctgcgccca gtacctcgga tcatgcggaa    540

catgttgtca aagctgcaga ttgcctgtga caacgctgtg ttcggctgta gtgccgttgt    600

ccggcttgac aacctcatgt ctcacctcag cgactgtgag cacaaccoga agcggcctgt    660

gacctgtgaa cagggctgtg gcctggagat gcccaaagat gagctgccca accataactg    720

cattaagcac ctgcgctcag tggtacagca gcagcagaca cgcatcgcag agctggagaa    780

gacgtcagct gaacacaaac accagctggc ggagcagaag cgagacatcc agctgctaaa    840

ggcatacatg cgtgcaatcc gcagtgtcaa ccccaacctt cagaacctgg aggagacaat    900

tgaatacaac gagatcctag agtgggtgaa ctcccttcag ccagcaagag tgacccgctg    960

gggagggatg atctcgactc ctgatgctgt gctccaggct gtaatcaagc gctccctggt   1020

ggagagtggc tgtcctgctt ctattgtcaa cgagctgatt gaaaatgccc acgagcgtag   1080

ctggccccag ggtctggcca cactagagac tagacagatg aaccgacgct actatgagaa   1140

ctacgtggcc aagcgcatcc ctggcaagca ggctgttgtc gtgatggcct gtgagaacca   1200

gcacatgggg gatgacatgg tgcaagagcc aggccttgtc atgatatttg cgcatggcgt   1260

ggaagagata taagagaact cgactggcta tcaggaagag atggaaatca gaaaatccca   1320
```

```
tcactccagc agctgggacc tgagtcctac ccaccattct taatactgtg gcttatacct   1380
gagccacaca tctccctgcc cttctggcac tgaagggcct tggggtagtt tgctcagcct   1440
ttcaggtggg aaacccagat ttcctccctt tgccatattc ccctaaaatg tctataaatt   1500
atcagtctgg gtgggaaagc ccccacctcc atccattttc ctgcttaggg tccctggttc   1560
cagttatttt cagaaagcac aaagagattc aatttccctg gaggatcagg acagaggaag   1620
gaatctctaa tcgtccctct cctccaaaac cagggaatca gagcagtcag gcctgttgac   1680
tctaagcagc agacatcctg aagaaatggt aagggtggag ccaaatctct agaaataagt   1740
agtgaggccg ttaattggcc atcactgatg gcccttaggg aaagactgga cctctgtgcc   1800
aagcagtatc cctgttcagc ccaccttaaa ggtgtaggca cccactgggt ctaccagtat   1860
gcaggttggg atactgaaaa tttccagatg agctcttctt tcctacaagt tttcataatt   1920
agggaatgcc agggtttagg gtaggggtta atctgttggg ggttgatgtg tttagcaaga   1980
agctactcct agcttttgct aaaatatggt tggcactgcc tcttgtggca caggccataa   2040
ttgttccata gacccctctc tagccctgtg actgtagtta gttactttga taattttctt   2100
tggccattgt ttgtttatat ttcacaaact ccacctactg cccccccccc tctttttttt   2160
aagaatggcc tgatcatggc tatctcagcc acattgttgg caatttaatt tatttacttc   2220
cttttttttt ttttaagaaa ggaaaaaaga aaaaaaaatc aaacttgaaa cttttctttt   2280
gatgttccta ttgtgggggt tctggatagg gtgggacagg gatgggggtg tgttttatat   2340
tttttccttt tcagcacaac ctttggcttt aatataggaa gagccaaggg agtcctcggc   2400
tgaacttacg atatctgccc caaacctctg taaccccaac tgaaatgagg agcttcctct   2460
cttcctgtga aggatatgac agtccagcat cgatgcctgt gccctctgga aaaatttcct   2520
cctagccctt ccagggcctt atcataaaac tctggattta gagtattcat tttgaaggca   2580
actcccccctt ccccaagttt ccttggagct gtatagctgg gttctaagct tcaccatgca   2640
aatcagaaat tttatctcta agtacaggct gtgccgtgtc tcacccacac ccccctgggg   2700
acttcagttc catttcaggt tacctggggt ataccttgat ccctagagtg actggcagag   2760
taagagaagg ggagagataa taggtgtgat tattttaata tggaggtggg agtgtggttg   2820
gagatagaaa ggctcctccc caccatgtaa tggcttcctc tcagaatttt attccaggct   2880
agcttgctgc aggtctgggt agttggatca tggctccact gggattgggg tggaaagctt   2940
gaggggagta gggttccagc tctgggacat tgtgctcagg aatttgaaaa cgctgctata   3000
cttactctgg ttactacatt tcttccactc ccctttcccc tacctgcctt aaccaaggct   3060
catactgtcc tgtccttacc ctcagatgga gccaggaagc tcagtgaaag gcttccctac   3120
cctttgcact agtgtctctg caggttgctg gttgtgttgt atgtgctgtt ccatggtgtt   3180
gactgcacta ataataaacc ttttactcaa ctctctaaat tcttcagcat tactcccttt   3240
cttgagaagg tttcccctct gcttttgcct ttctctcacc ttaattccct ttcttcctta   3300
ctttgttacc taccctttatc ttagtgctaa cttctctttc aggaggatgt ctgggagtag   3360
tgtgcacttc acagctgctt tcccatgtac cctcctgcat tcttccctcc tatctcctgt   3420
tctgtagcag ccaaagctct ctagtgatct gaactgtgtg cttcccaggg tctgccttta   3480
tcctaaattc catgtcttcc ctgagtggtc ctgagttttt gggataattt ctacagaaga   3540
tatgtatata tctttttcct ttgtcccaca agcaactttg ctttagaatc tagaattcct   3600
ttgcaggcag agaagtctct acctcccagt gtttcctagc taagaacgta aatgtgagga   3660
gggaaatgta cttgcagagg tttcataatt atttacttat aaaaatagtc ttcatagccg   3720
```

```
ggcgcggtgg ctcacgcctg taatcccagc actttgggag gccgaggtgg gtggatcaca   3780

aggtcaggag ttcgagacca tcctggctaa cacagtgaaa ccccgtctct actaaaaata   3840

caaaaaatta gccgggcgtg gtggcaggca cctgtagtcc cagctactta ggaggctgag   3900

gcaggagaat ggcgtgaacc cgggaggcag agcttgcagt gagcagagat tgggccactg   3960

cattccagcc tgggcgacag agcaaggctc cgtctaaaaa aaaaaaaaaa aaaaaaagtc   4020

ttcataggcc gggcacggtg gctcacgtct gtaatcccag cactttggga ggccaaggtg   4080

ggtggatcac aacgtcagga gatcgagacc atcctggcta acatggtgaa accctgtctc   4140

tactaaaaat ataaataaat tagccggaca ggcgcctgtc ctcccagcta ctcaggaggc   4200

tgaggcagga gaatggtgtg aacctgggag gcggagcttg cagtgagctg agatcacgcc   4260

actgcactcc agcctgggca acagagcaag actccgtctc aaaaaaaaaa aaaaaaaaac   4320

cagtcttcat aagtatttgc tgctaccttt ccctgtcata agaaaaagga tagccagaca   4380

tggtgggacg ccactatgat cccagctcct tggaaggcta aggcacaaga atcgcttgaa   4440

cctgggaggt ggaggttgca gtgagctgag atcatgccac tgcactccag cctggtgaca   4500

gagcaagagc ctgtctcaaa aaaaaaaaag aaaagaaaag aaaaagggat atcttttcct   4560

cctcccagaa gtttgtttta aatttgagca tttatcatgc acctgatgta aacctaatag   4620

tactcttgat actctagtgg cttgaaaaaa aaaaaaaagg catttctgtg ctgagtctgc   4680

gcttctatgc acacaaggta tgtttataaa atactgataa gcatgtcaca gtatagagca   4740

taagaggcaa tgtatgtatc ctagtgacat tagcagtgct tttccccccct taaactcctt   4800

taaaattact tttagaactt gctgctcatt cttgtgaatg ttatgaatgg tgtcatattg   4860

tccttttaca gaagatacga tttttagaaa caaatattca ttgaatgtct gccctgtgag   4920

atactcacta gagtgaacat gaggaggctt atgtagcaaa atggcaccta cctgcaaaga   4980

acttagtccc taatggagat gaatatataa taagggatca taaatgtgct aagtggattt   5040

actagtaata tgtgagccaa ggacgataaa gctcctgatt ctgatgggta tcaggaaagg   5100

cttttcagga agtgttactt gttataggtc agaggtcagc aaactacagg ttacaacccc   5160

actgcctgct tttgtaaaaa actttattgg aatacagtta tgcccacttg tttata       5216
```

<210> SEQ ID NO 35
<211> LENGTH: 5138
<212> TYPE: DNA
<213> ORGANISM: Homo sapiens

<400> SEQUENCE: 35

```
gatccgcaga ggagcccact tgagagcgcc tcctgtcgtc tgtaaggttg ccttgccatc     60

cctcggcacc ccaacttccc ccgccccccc atcgcctcct cctccatcct ccagttcaaa    120

atggcgacgg cggcggcagc ggcggcggtg atggctcctc cgggctgccc gggttcgtgc    180

cccaacttcg ccgtagtctg ctccttcttg gagcgctacg ggccgctgct agacctgcct    240

gagttgccgt tccctgagct ggagcgggtg ctgcaggcgc cgccgccgga cgtcggcaac    300

ggagaagtac caaaagaatt ggtggagctc catttgaagc tgatgaggaa aattggcaaa    360

tctgttactg cagacagatg ggaaaaatat ttgatcaaga tatgccaaga gtttaacagt    420

acctgggcat gggagatgga gaagaagggc tatcttgaaa tgagtgttga atgcaaacta    480

gcactcttaa agtacctctg tgagtgtcag tttgatgaca atctcaaatt caagaatatt    540

attaatgagg aggatgccga tactatgcgt ctccagccaa ttggtcgaga caaagatggc    600
```

-continued

```
ctcatgtact ggtaccaatt ggatcaagat cacaatgtca gaatgtacat agaagaacaa    660
gatgatcaag atggctcttc atggaaatgc attgtcagaa atcgaaacga gttggctgag    720
actcttgcac tcctgaaagc acaaattgat cctgtactat tgaaaaactc tagccaacaa    780
gacaactctt ctcgggaaag tcccagctta gaggatgagg agactaaaaa agaggaagaa    840
acacctaaac aagaggaaca gaaagaaagt gaaaagatga aaagtgagga gcagcctatg    900
gatttagaaa accgttctac agccaatgtt ctagaagaga ctactgtgaa aaaagaaaaa    960
gaagatgaaa aggaacttgt gaaactgcca gtcatagtga agctagaaaa acctttgcca   1020
gaaaatgaag aaaaaaagat tatcaaagaa gaaagtgatt ccttcaagga aaatgtcaaa   1080
cccattaaag ttgaggtgaa ggaatgtaga gcagatccta aagataccaa aagtagcatg   1140
gagaagccag tggcacagga gcctgaaagg atcgaatttg gtggcaatat taaatcttct   1200
cacgaaatta ctgagaaatc tactgaagaa actgagaaac ttaaaaatga ccagcaggcc   1260
aagataccac taaaaaaacg agaaattaaa ctgagtgatg attttgacag tccagtcaag   1320
ggacctttgt gtaaatcagt tactccaaca aaagagtttt tgaaagatga aataaaacaa   1380
gaggaagaga cttgtaaaag gatctctaca atcactgctt tgggtcatga agggaaacag   1440
ctggtaaatg gagaagttag tgatgaaagg gtagctccaa attttaagac agaaccaata   1500
gagacaaagt tttatgagac aaaggaagag agctatagcc cctctaagga cagaaatatc   1560
atcacggagg gaaatggaac agagtcctta aattctgtca taacaagtat gaaaacaggt   1620
gagcttgaga aagaaacagc ccctttgagg aaagatgcag atagttcaat atcagtctta   1680
gagatccata gtcaaaaagc acaaatagag gaacccgatc ctccagaaat ggaaacttct   1740
cttgattctt ctgagatggc aaaagatctc tcttcaaaaa ctgctttatc ttccaccgag   1800
tcgtgtacca tgaaaggtga agagaagtct cccaaaacta agaaggataa gcgcccacca   1860
atcctagaat gtcttgaaaa gttagagaag tccaaaaaga cttttcttga taaggacgca   1920
caaagattga gtccaatacc agaagaagtt ccaaagagta ctctagagtc agaaaagcct   1980
ggctctcctg aggcagctga aacttctcca ccatctaata tcattgacca ctgtgagaaa   2040
ctagcctcag aaaaagaagt ggtagaatgc cagagtacaa gtactgttgg tggccagtct   2100
gtgaaaaaag tagacctaga aaccctaaaa gaggattctg agttcacaaa ggtagaaatg   2160
gataatctgg acaatgccca gacctctggc atagaggagc cttctgagac aaagggttct   2220
atgcaaaaaa gcaaattcaa atataagttg gttcctgaag aagaaaccac tgcctcagaa   2280
aatacagaga taacctctga aaggcagaaa gagggcatca aattaacaat caggatatca   2340
agtcggaaaa agaagcccga ttctcccccc aaagttctag aaccagaaaa caagcaagag   2400
aagacagaaa aggaagagga gaaaacaaat gtgggtcgta ctttaagaag atctccaaga   2460
atatctagac ccactgcaaa agtggctgag atcagagatc agaaagctga taaaaaaaga   2520
ggggaaggag aagatgaggt ggaagaagag tcaacagctt tgcaaaaaac tgacaaaaag   2580
gaaattttga aaaaatcaga gaaagataca aattctaaag taagcaaggt aaaacccaaa   2640
ggcaaagttc gatggactgg ttctcggaca cgtggcagat ggaaatattc cagcaatgat   2700
gaaagtgaag ggtctggcag tgaaaaatca tctgcagctt cagaagagga ggaagaaaag   2760
gaaagtgaag aagccatcct agcagatgat gatgaaccat gcaaaaaatg tggccttcca   2820
aaccatcctg agctaattct tctgtgtgac tcttgcgata gtggatacca tactgcctgc   2880
cttcgccctc ctctgatgat catcccagat ggagaatggt tctgcccacc ttgccaacat   2940
aaactgctct gtgaaaaatt agaggaacag ttgcaggatt tggatgttgc cttaaagaag   3000
```

```
aaagagcgtg ccgaacgaag aaaagaacgc ttggtgtatg ttggtatcag tattgaaaac   3060
atcattcctc cacaagagcc agacttttct gaagatcaag aagaaaagaa aaaagattca   3120
aaaaaatcca aagcaaactt gcttgaaagg aggtcaacaa gaacaaggaa atgtataagc   3180
tacagatttg atgagtttga tgaagcaatt gatgaagcta ttgaagatga catcaaagaa   3240
gccgatggag gaggagttgg ccgaggaaaa gatatctcca ccatcacagg tcatcgtggg   3300
aaagacatct ctactatttt ggatgaagaa agaaaagaaa ataaacgacc ccagagggca   3360
gctgctgctc gaaggaagaa acgccggcga ttaaatgatc tggacagtga tagcaacctg   3420
gatgaagaag agagcgagga tgaattcaag atcagtgatg gatctcaaga tgagtttgtt   3480
gtgtctgatg aaaacccaga tgaaagtgaa gaagatccgc catctaatga tgacagtgac   3540
actgactttt gtagccgtag actgaggcga cacccctctc ggccaatgag gcagagcagg   3600
cgtttgcgaa gaaagacccc aaagaaaaaa tattccgatg atgatgaaga ggaggaatct   3660
gaggagaata gtagagactc tgaaagtgac ttcagtgatg attttagtga tgattttgta   3720
gaaactcggc gaaggcggtc aaggagaaat cagaaaagac aaattaacta caaagaagac   3780
tcagaaagtg acggttccca gaagagtttg cgacgtggta aagaaataag gcgagtacac   3840
aagcgaagac tttccagctc agagagtgaa gagagctatt tgtccaagaa ctctgaagat   3900
gatgagctag ctaaagaatc aaagcggtca gttcgaaagc ggggccgaag cacagacgag   3960
tattcagaag cagatgagga ggaggaggaa gaggaaggca aaccatcccg caaacggcta   4020
caccggattg agacggatga ggaggagagt tgtgacaatg ctcatggaga tgcaaatcag   4080
cctgcccgtg acagccagcc tagggtcctg ccctcagaac aagagagcac caagaagccc   4140
taccggatag aaagtgatga ggaagaggac tttgaaaatg taggcaaagt ggggagccca   4200
ttggactata gcttagtgga cttaccttca accaatggac agagccctgg caaagccatt   4260
gagaacttga ttggcaagcc tactgagaag tctcagaccc ccaaggacaa cagcacagcc   4320
agtgcaagcc tagcctccaa tgggacaagt ggtgggcagg aggcaggagc accagaagag   4380
gaggaagatg agcttttgag agtgactgac cttgttgatt atgtctgtaa cagtgaacag   4440
ttataagact ttttttccat ttttgtgcta atttattcca cggtagctct cacaccagcg   4500
ggccagttat taaaagctgt ttaatttttc ctagaaaact ccactacaga atgactttta   4560
gaagaaaaat ttcaacaaat cctgaagtct ttctgtgaag tgaccagttc tgaactttga   4620
agataaataa ttgctgtaaa ttccttttga ttttcttttt ccaggttcat ggtccttggt   4680
aatttcattc atggaaaaaa atcttattat aataacaaca aagatttgta tatttttgac   4740
tttatatttc ctgagctctc ctgactttgt gaaaaagggt ggatgaaaat gcattccgaa   4800
tctgtgaggg cccaaaacag aatttagggg tgggtgaaag cacttgtgct ttagcttttt   4860
catattaaat atatattata tttaaacatt catggcatag atgatgattt acagacaatt   4920
taaaagttca agtctgtact gttacagttt gagaattgta gataacatca tacataagtc   4980
atttagtaac agcctttgtg aaatgaactt gtttactatt ggagataacc acacttaata   5040
aagaagagac agtgaaagta ccatcataat taacctaaat ttttgttata gcagagtttc   5100
ttgtttaaaa aaaaataaaa tcatctgaaa agcaaaaa                           5138
```

<210> SEQ ID NO 36
<211> LENGTH: 2288
<212> TYPE: DNA
<213> ORGANISM: Homo sapiens

<400> SEQUENCE: 36

```
cgcgcgctgc agtgccttcc ccacctcggc cccgcccgcc cccgccgagc cgagcaccag     60
ggcggcggcg gcggcggcgg cggcggcggc ggctggagca gcccgggagg aggaggcggc    120
gagaatggca gcggcgtcgt gggcgcggcg gagatgagcg cccgcgaccc cgggcccagg    180
gcggcacagc cggagtgggc gggggtcccg atgcaggccc gagggggggcc atggggcagg    240
tcctgccggt cttcgcccac tgcaaagaag ctccgtctac agcctcctca actcctgatt    300
ccacagaagg agggaacgac gactctgatt ttcgagagct gcacacagcc cgggaattct    360
cagaggagga cgaggaggag accacgtcgc aggactgggg cacccccccgg gagctgacct    420
tctcctacat cgcctttgat ggtgtagtgg gctccggggg ccgcagggat tcaactgccc    480
gccgcccccg cccccagggc cgctcagtct cggaaccacg agaccagcac cctcagccca    540
gcctgggcga cagcttggag agcatcccca gcctgagcca atccccggag cctggacgac    600
ggggtgatcc tgacaccgcg cctccatccg agcgccctct ggaagacctg aggcttcggt    660
tggaccatct gggctgggtg gcccggggaa cgggatccgg ggaggactct tccaccagca    720
gctccacccc gctggaagac gaagaacccc aagaacccaa cagattggag acaggagaag    780
ctggggaaga actggaccta cgactccgac ttgctcagcc ctcatcgccc gaggtcttga    840
ctccccagct cagtccgggc tctgggacac cccaggccgg tactccgtcc ccatcccgat    900
cgcgagattc gaactctggg cccgaagagc cattgctgga agaggaagaa aagcagtggg    960
ggccactgga gcgagagcca gtaaggggac agtgcctcga tagcacggac caattagaat   1020
tcacggtgga gccacgcctt ctaggaacag ctatggaatg gttaaagaca tcattgcttt   1080
tggctgttta caagacggtt ccaattttgg aattgtcccc acctctgtgg acagccattg   1140
gctgggtcca aaggggcccc acccccccta ctcctgtcct ccgggttcta ctgaagtggg   1200
caaaatcccc gagaagcagc ggtgtcccca gcctctcact cggagccgat atggggagta   1260
aagtggcgga cctgctgtac tggaaggaca cgaggacgtc aggagtggtc ttcacaggcc   1320
tgatggtctc cctcctctgc ctcctgcact ttagcatcgt gtccgtggcc gcgcacttgg   1380
ctctgttgct gctctgcggc accatctctc tcagggttta ccgcaaagtg ctgcaggccg   1440
tgcaccgggg ggatggagcc aaccctttcc aggcctacct ggatgtggac ctcaccctga   1500
ctcgggagca gacggaacgt ttgtcccacc agatcacctc ccgcgtggtc tcggcggcca   1560
cgcagctgcg gcacttcttc ctggtagaag acctcgtgga ttccctcaag ctggccctcc   1620
tcttctacat cttgaccttc gtgggtgcca tcttcaatgg tttgactctt ctcattctgg   1680
gagtgattgg tctattcacc atccccctgc tgtaccggca gcaccaggct cagatcgacc   1740
aatatgtggg gttggtgacc aatcagttga gccacatcaa agctaagatc cgagctaaaa   1800
tcccagggac cggagccctg gcctctgcag cagccgcagt ctccggatcc aaagccaaag   1860
ccgaatgaga acggtgtctc tgcccgcagg acgcctgccc ccagcccccg cagccctctg   1920
gccccctcca tctcttgtcc gttcccaccc accccccctcc tcggcccgag ccttttcccg   1980
gtgggtgtca ggatcactcc cactagggac tctgcgctaa ttacctgagc gaccaggact   2040
acatttccca agaggctctg ctccaggagt ccaggaaaga cgaggcacct tggccgcggg   2100
gcctgctggg acttgtagtt gcctagacag ggcaccaccc tgcacttccg gacccgccgc   2160
tggaggcgcc gtgaggcgtt ggtgtctcct ggatgctact agccccaacg ccggggcttt   2220
gcatggggcc caggggaggc ctgagcttgg atttacactg taataaagac tcctgtggaa   2280
aacccgag                                                            2288
```

<210> SEQ ID NO 37
<211> LENGTH: 1700
<212> TYPE: DNA
<213> ORGANISM: Homo sapiens

<400> SEQUENCE: 37
agcaggactc agaggggaga gttggaggaa aaaaaaaggc agaaaaggga aagaaagagg 60
aagagagaga gagagtgaga ggagccgctg agcccacccc gatggccgcg gacgaagttg 120
ccggaggggc gcgcaaagcc acgaaaagca aactttttga gtttctggtc catggggtgc 180
gccccgggat gccgtctgga gcccggatgc cccaccaggg ggcgcccatg ggcccccccgg 240 gctccccgta catgggcagc cccgccgtgc gacccggcct ggcccccgcg ggcatggagc 300
ccgcccgcaa gcgagcagcg cccccgcccg ggcagagcca ggcacagagc cagggccagc 360
cggtgcccac cgcccccgcg cggagccgca gtgccaagag gaggaagatg gctgacaaaa 420
tcctccctca aaggattcgg gagctggtcc ccgagtccca ggcttacatg gacctcttgg 480
catttgagag gaaactggat caaaccatca tgcggaagcg ggtggacatc caggaggctc 540
tgaagaggcc catgaagcaa aagcggaagc tgcgactcta tatctccaac acttttaacc 600
ctgcgaagcc tgatgctgag gattccgacg gcagcattgc ctcctgggag ctacgggtgg 660
aggggaagct cctggatgat cccagcaaac agaagcggaa gttctcttct ttcttcaaga 720
gtttggtcat cgagctggac aaagatcttt atggccctga caaccacctc gttgagtggc 780
atcggacacc cacgacccag gagacggacg gcttccaggt gaaacggcct ggggacctga 840
gtgtgcgctg cacgctgctc ctcatgctgg actaccagcc tccccagttc aaactggatc 900
cccgcctagc ccggctgctg gggctgcaca cacagagccg ctcagccatt gtccaggccc 960
tgtggcagta tgtgaagacc aacaggctgc aggactccca tgacaaggaa tacatcaatg 1020
gggacaagta tttccagcag atttttgatt gtccccggct gaagttttct gagattcccc 1080
agcgcctcac agccctgcta ttgccccctg acccaattgt catcaaccat gtcatcagcg 1140
tggacccttc agaccagaag aagacggcgt gctatgacat tgacgtggag gtggaggagc 1200
cattaaaggg gcagatgagc agcttcctcc tatccacggc caaccagcag gagatcagtg 1260
ctctggacag taagatccat gagacgattg agtccataaa ccagctcaag atccagaggg 1320
acttcatgct aagcttctcc agagacccca aaggctatgt ccaagacctg ctccgctccc 1380
agagccggga cctcaaggtg atgacagatg tagccggcaa ccctgaagag gagcgccggg 1440
ctgagttcta ccaccagccc tggtcccagg aggccgtcag tcgctacttc tactgcaaga 1500
tccagcagcg caggcaggag ctggagcagt cgctggttgt gcgcaacacc taggagccca 1560
aaaataagca gcacgacgga actttcagcc gtgtcccggg ccccagcatt ttgccccggg 1620
ctccagcatc actcctctgc caccttgggg tgtggggctg gattaaaagt cattcatctg 1680
acaaaaaaaa aaaaaaaaaa 1700

<210> SEQ ID NO 38
<211> LENGTH: 1935
<212> TYPE: DNA
<213> ORGANISM: Homo sapiens

<400> SEQUENCE: 38
acaatagcga ctcactggac ccagccctta gcaacggcct ggcgacggtt tccctgctgc 60
tgcagccccc gtcggctcct cttttccagt cctccactgc cggggctggg cccggccgcg 120
ggaaggaccg aaggggatac agcgtgtccc tgcggcggct gcaagaggac taagcatgga 180
tggcagccgg agagtcagag caacctctgt ccttcccaga tatggtccac cgtgcctatt 240
taaaggacac ttgagcacca aaagtaatgc tgcagtagac tgctcggttc cagtaagcgt 300
gagtaccagc ataaagtatg cagaccaaca acgaagagag aaactcaaaa aggaattagc 360
acaatgtgaa aaagagttca aattaactaa aactgcaatg cgagccaatt ataaaaataa 420
ttccaagtca ctttttaata ccttacaaaa gccctcaggc gaaccgcaaa ttgaggatga 480
catgttaaaa gaagaaatga atggattttc atcctttgca aggtcactag taccctcttc 540
agagagacta cacctaagtc tacataaatc cagtaaagtc atcacaaatg gtcctgagaa 600
gaactccagt tcctccccgt ccagtgtgga ttatgcagcc tccgggcccc ggaaactgag 660
ctctggagcc ctgtatggca gaaggcccag aagcacattc ccaaattccc accggtttca 720
gttagtcatt tcgaaagcac ccagtgggga tcttttggat aaacattctg aactcttttc 780
taacaaacaa ttgccattca ctcctcgcac tttaaaaaca gaagcaaaat ctttcctgtc 840
acagtatcgc tattatacac ctgccaaaag aaaaaaggat tttacagatc aacggataga 900
agctgaaacc cagactgaat taagctttaa atctgagttg ggacagctg agactaaaaa 960 catgacagat tcagaaatga acataaagca ggcatctaat tgtgtgacat atgatgccaa 1020
agaaaaaata gctcctttac ctttagaagg gcatgactca acatgggatg agattaagga 1080
tgatgctctt cagcattcct caccaagggc aatgtgtcag tattccctga agccccccttc 1140 aactcgtaaa atctactctg atgaagaaga actgttgtat ctgagtttca ttgaagatgt 1200
aacagatgaa attttgaaac ttggtttatt ttcaaacagg tttttagaac gactgttcga 1260
gcgacatata aaacaaaata aacatttgga ggaggaaaaa atgcgccacc tgctgcatgt 1320
cctgaaagta gacttaggct gcacatcgga ggaaaactcg gtaaagcaaa atgatgttga 1380
tatgttgaat gtatttgatt ttgaaaaggc tgggaattca gaaccaaatg aattaaaaaa 1440
tgaaagtgaa gtaacaattc agcaggaacg tcaacaatac caaaaggctt tggatatgtt 1500
attgtcggca ccaaaggatg agaacgagat attcccttca ccaactgaat tttcatgcc 1560 tatttataaa tcaaagcatt cagaaggggt tataattcaa caggtgaatg atgaaacaaa 1620
tcttgaaact tcaactttgg atgaaaatca tccaagtatt tcagacagtt taacagatcg 1680
ggaaacttct gtgaatgtca ttgaaggtga tagtgaccct gaaaaggttg agatttcaaa 1740
tggattatgt ggtcttaaca catcaccctc ccaatctgtt cagttctcca gtgtcaaagg 1800
cgacaataat catgacatgg agttatcaac tcttaaaatc atggaaatga gcattgagga 1860
ctgccctttg gatgtttaat cttcattaat aaatacctca aatggccagt aactcaaaaa 1920
aaaaaaaaaa aaaaa 1935

<210> SEQ ID NO 39
<211> LENGTH: 4343
<212> TYPE: DNA
<213> ORGANISM: Homo sapiens

<400> SEQUENCE: 39
tggtcatcgc acggcggcag ctcctcacct ggatttagaa gagctggcgt ccccgcccgc 60
ccaagccttt aaactctcgt ctgccagaac ccgccaactc tccaggctta gggccagttt 120
ccgcgattct aagagtaatt gcgtgggcac ctgtgctggg gccaggcgca aagaagggag 180
ttggtctgcg cgaagatcgt caacctgcta acagaccgca catgcacttt gcaccgacca 240
tctacgtctc agtctggagg ttgcgcactt tggctgctga cgcgctggtg gtgcctatta 300

-continued

```
atcatttacc agtccagagc cgcgccagtt aatggctgtg ccgtgcggtg ctcccacatc    360
ctggcctctc ctctccacgg tcgcctgtgc ccgggcaccc cggagctgca aactgcagag    420
cccaggcaac cgctgggctg tgcgccccgc cggcgccggt aggagccgcg ctccccgcag    480
cggttgcgct ctacccggag gcgctgggcg gctgtgggct gcaggcaagc ggtcgggtgg    540
ggagggaggg cgcaggcggc gggtgcgcga ggagaaagcc ccagccctgg cagccccact    600
ggcccccctc agctgggatg ttccccaatg gcaccgcctc ctctccttcc tcctctccta    660
gccccagccc gggcagctgc ggcgaaggcg gcggcagcag gggccccggg gccggcgctg    720
cggacggcat ggaggagcca gggcgaaatg cgtcccagaa cgggaccttg agcgagggcc    780
agggcagcgc catcctgatc tctttcatct actccgtggt gtgcctggtg gggctgtgtg    840
ggaactctat ggtcatctac gtgatcctgc gctatgccaa gatgaagacg gccaccaaca    900
tctacatcct aaatctggcc attgctgatg agctgctcat gctcagcgtg cccttcctag    960
tcacctccac gttgttgcgc cactggccct tcggtgcgct gctctgccgc ctcgtgctca   1020
gcgtggacgc ggtcaacatg ttcaccagca tctactgtct gactgtgctc agcgtggacc   1080
gctacgtggc cgtggtgcat cccatcaagg cggcccgcta ccgccggccc accgtggcca   1140
aggtagtaaa cctgggcgtg tgggtgctat cgctgctcgt catcctgccc atcgtggtct   1200
tctctcgcac cgcggccaac agcgacggca cggtggcttg caacatgctc atgccagagc   1260
ccgctcaacg ctggctggtg ggcttcgtgt tgtacacatt tctcatgggc ttcctgctgc   1320
ccgtgggggc tatctgcctg tgctacgtgc tcatcattgc taagatgcgc atggtggccc   1380
tcaaggccgg ctggcagcag cgcaagcgct cggagcgcaa gatcacctta atggtgatga   1440
tggtggtgat ggtgtttgtc atctgctgga tgcctttcta cgtggtgcag ctggtcaacg   1500
tgtttgctga gcaggacgac gccacggtga gtcagctgtc ggtcatcctc ggctatgcca   1560
acagctgcgc caaccccatc ctctatggct ttctctcaga caacttcaag cgctctttcc   1620
aacgcatcct atgcctcagc tggatggaca acgccgcgga ggagccggtt gactattacg   1680
ccaccgcgct caagagccgt gcctacagtg tggaagactt ccaacctgag aacctggagt   1740
ccggcggcgt cttccgtaat ggcacctgca cgtcccggat cacgacgctc tgagcccggg   1800
ccacgcaggg gctctgagcc cgggccacgc aggggccctg agccaaaaga gggggagaat   1860
gagaagggaa ggccgggtgc gaaagggacg gtatccaggg cgccagggtg ctgtcgggat   1920
aacgtggggc taggacactg acagcctttg atggaggaac ccaagaaagg cgcgcgacaa   1980
tggtagaagt gagagctttg cttataaact gggaaggctt tcaggctacc tttttctggg   2040
tctcccactt tctgttcctt cctccactgc gcttactcct ctgaccctcc ttctattttc   2100
cctaccctgc aacttctatc ctttcttccg caccgtcccg ccagtgcaga tcacgaactc   2160
attaacaact cattctgatc ctcagcccct ccagtcgtta tttctgtttg tttaagctga   2220
gccacggata ccgccacggg tttccctcgg cgttagtccc tagccgcgcg gggccgctgt   2280
ccaggttctg tctggtgccc ctactggagt cccgggaatg accgctctcc ctttgcgcag   2340
ccctacctta aggaaagttg gacttgagaa agatctaagc agctggtctt ttctcctact   2400
cttgggtgaa ggtgcatctt tccctgccct cccctgtccc cctctcgccg cccgcccgcc   2460
accaccactc tcactccacc cagagtagag ccaggtgctt agtaaaatag gtcccgcgct   2520
tcgaactcca ggctttctgg agttcccacc caagccctcc tttggagcaa agaaggagct   2580
gagaacaagc cgaatgagga gtttttataa gattgcgggg tcggagtgtg ggcgcgtaat   2640
```

-continued

```
aggaatcacc ctcctactgc gcgttttcaa agaccaagcg ctgggcgctc ccgggccgcg   2700
cgtctgcgtt aggcagggca gggtagtgca gggcacacct tccccggggt tcggggttcg   2760
gggttcggtt gcagggctgc agcccgcctt ggctttctcc ctcacccaag tttccggagg   2820
agccgaccta aaagtaacaa tagataaggt ttcctgctcc agtgtatctc aaaagaccgg   2880
gcgccagggg cgggggacct agggcgacgt cttcagagtc cgccagtgtt ggcggtgtcg   2940
ccgcaacctg caggctcccg agtggggcct gcctggtctc tagagggttg ctgcctttca   3000
agcggtgcct aagaagttat tttcttgttt aacatatata tttattaatt tatttgtcgt   3060
gttggaaaat gtgtctctgc tttccttttc tctgcttgcc tagccccagg tcttttcttt   3120
gggaccctgg gggcgggcat ggaagtggaa gtaggggcaa gctcttgccc cactccctgg   3180
ccatctcaac gcctctcctc aatgctgggc cctcttatct catcctttcc tctagctttt   3240
ctatttttga ttgtgttgag tgaagtttgg agatttttca tacttttctt actatagtct   3300
cttgtttgtc ttattaggat aatacataaa tgataatgtg ggttatcctc ctctccatgc   3360
acagtggaaa gtcctgaact cctggctttc caggagacat atatagggga acatcaccct   3420
atatataatt tgagtgtata tatatttata tatatgatgt ggacatatgt atacttatct   3480
tgctccattg tcatgagtcc atgagtctaa gtatagccac tgatggtgac aggtgtgagt   3540
ctggctggaa cactttcagt ttcaggagtg caagcagcac tcaaacctgg agctgaggaa   3600
tctaattcag acagagactt taatcactgc tgaagatgcc cctgctccct ctgggttcca   3660
gcagaggtga ttcttacata tgatccagtt aacatcatca cttttttga ggacattgaa    3720
agtgaaataa tttgtgtctg tgtttaatat taccaactac attggaagcc tgagcagggc   3780
gaggaccaat aattttaatt atttatattt cctgtattgc tttagtatgc tggcttgtac   3840
atagtaggca ctaaatacat gtttgttggt tgattgttta agccagagtg tattacaaca   3900
atctggagat actaaatctg gggttctcag gttcactcat tgacatgata tacaatggtt   3960
aaaatcacta ttgaaaaata cgttttgtgt atatttgctt caacaacttt gtgctttcct   4020
gaaagcagta accaagagtt aagatatccc taatgttttg cttaaactaa tgaacaaata   4080
tgctttgggt cataaatcag aaagtttaga tctgtccctt aataaaaata tatattacta   4140
ctcctttgga aaatagattt ttaatggtta agaactgtga aatttacaaa tcaaaatctt   4200
aatcattatc cttctaagag gatacaaatt tagtgctctt aacttgttac cattgtaata   4260
ttaactaaat aaacagatgt attatgctgt taaaaaaaaa aaaaaaaaaa aaaaaaaaaa   4320
aaaaaaaaaa aaaaaaaaaa aaa                                           4343
```

<210> SEQ ID NO 40
<211> LENGTH: 4171
<212> TYPE: DNA
<213> ORGANISM: Homo sapiens

<400> SEQUENCE: 40

```
ctgcatctct ccctctcacc cgtgtctcct ctcctctctt tccttctcgt cttctccctg     60
tcacgcatct ctcatcactc cccctcattc tgcctttcct cctactcacg gtctcctctc    120
cctctccctc tctctctctc cccctccctc tttctctctc tctctctttc tccacctcct    180
cccgaccccc tttcccctct atttctattg gcttctgtgt cccttgctcc cctcttctct    240
tcctcaccct gggaagcttc tccccccctat ccttgcccct gcccccccag gatgtgtcct    300
ggagatgggg ggtgacgtac caggctctgg ttgggaagtc agggccggag accagatggg    360
agaggctctg tggacagccg tggccgaggg cctgggaggg aacctgagcc cgcaagcggt    420
```

-continued

```
ctagaagtgg gtgccttgtg gggaccctag ttaggagtgc cctgggggca cctggggact    480
gggcagggag aggggacagc agaatgataa ccagcctggc ggcaaggagg gaagccctca    540
ccccatgggc aggcaaatag ctgactgctg accaccctcc cctcagccat ggacatgctt    600
catccatcat cggtgtccac gacctcagaa cctgagaatg cctcctcggc ctggccccca    660
gatgccaccc tgggcaacgt gtcggcgggc ccaagcccgg cagggctggc cgtcagtggc    720
gttctgatcc ccctggtcta cctggtggtg tgcgtggtgg gcctgctggg taactcgctg    780
gtcatctatg tggtcctgcg gcacacggcc agcccttcag tcaccaacgt ctacatcctc    840
aacctggcgc tggccgacga gctcttcatg ctggggctgc ccttcctggc cgcccagaac    900
gccctgtcct actggccctt cggctccctc atgtgccgcc tggtcatggc ggtggatggc    960
atcaaccagt tcaccagcat attctgcctg actgtcatga gcgtggaccg ctacctggcc   1020
gtggtacatc ccacccgctc ggcccgctgg cgcacagctc cggtggcccg cacggtcagc   1080
gcggctgtgt gggtggcctc agccgtggtg gtgctgcccg tggtggtctt ctcgggagtg   1140
ccccgcggca tgagcacctg ccacatgcag tggcccgagc cggcggcggc ctggcgagcc   1200
ggcttcatca tctacacggc cgcactgggc ttcttcgggc cgctgctggt catctgcctc   1260
tgctacctgc tcatcgtggt gaaggtgcgc tcagctgggc gccgggtgtg ggcaccctcg   1320
tgccagcggc ggcggcgctc cgaacgcagg gtcacgcgca tggtggtggc cgtggtggcg   1380
ctcttcgtgc tctgctggat gcccttctac gtgctcaaca tcgtcaacgt ggtgtgccca   1440
ctgcccgagg agcctgcctt ctttgggctc tacttcctgg tggtggcgct gccctatgcc   1500
aacagctgtg ccaaccccat cctttatggc ttcctctcct accgcttcaa gcagggcttc   1560
cgcagggtcc tgctgcggcc ctcccgccgt gtgcgcagcc aggagcccac tgtggggccc   1620
ccggagaaga ctgaggagga ggatgaggag gaggaggatg gggaggagag cagggagggg   1680
ggcaagggga aggagatgaa cggccgggtc agccagatca cgcagcctgg caccagcggg   1740
caggagcggc cgcccagcag agtggccagc aaggagcagc agctcctacc ccaagaggct   1800
tccactgggg agaagtccag cacgatgcgc atcagctacc tgtaggggcc tggggaaagc   1860
caggatggcc cgaggaagag gcagaagccg tgggtgtgcc tagggcctac ttcccaaggt   1920
gccacaggcc catgatggga tgttgagggg cctggacttt gatgctattg ctgccaggtc   1980
ttgctgtgtg accttgggta ggttgcttct actctctggg ccttgttttc tcctctgtga   2040
ctcagggata ggagtcatca gcctggatga gctatgtcag atgagaggtt tggagggcac   2100
tgttgctggg ctgacctggc tgagcaggca aaaggtgggt gcagactggc ctccccccag   2160
ggatggagtg tcttggggca tcaactagaa tcttggccct cagagggata aaccaaggcc   2220
aggatttctt gggctcagag tcaggaacac aggagctgct gggggctggg ctggaaacct   2280
aaacagaaga aagcctaacc cggtgggagg agtggggcag aaatggtcag gccccagatc   2340
agctccctcc cctcgactgt gaggccttgg accagctctg ctcctctcta ggcctcaggc   2400
ttcacctggg taaaacccaa caacctctac acccttttgg cccaggcagt caatgctgga   2460
ggtcctgtgc tcctggacgg gaagagcagg tgaatttcct gctcatggaa gcgaatgaag   2520
tccagcttca gggtctctca ctgcctgggc ttttgcaagg ccctgcatct acttttgtac   2580
ttgtcatttt gtattcgttt tcttaaagag ggacctcgaa ctgcataagc ttaggccacc   2640
caaagcctgg ctctgcccct gctgaggtca gccacccaat ccccaaggaa gctcatgttg   2700
ggtcttatgg ctggagtagg ggcccccggg ggttcccagg tcttttgagg gcttccaggc   2760
```

acctccttgt aggaagggcc atccctgttc ctctccttgt gacccatatt ctcccttcct 2820
ggagaccgag acagggaccc agcccatgag gactggcatg gaaaggcaga gtgtctgaag 2880
agcgctgtga ggagaaggaa gaggaaggga gaagaggaag aggaaggaga aggaagagga 2940
agacaagggg gaaaggggag gatgaggagg gggaaggaga agtacagatc tgtttcctgg 3000
agccgtcttt ggcccccctg ggctgagctc agtggtagca tctgtgaacc tgagttgccg 3060
acaacagccc cacccaacca gtactgaggg aaggacacga tcagggtgga acagccaggg 3120
tgcaatggca aatgcacaga gtacagacag gcacagggcc tgcgtccctg aggggcctca 3180
gagtgctgcc aagagggctc aggccttaat aaagccctag ggtggagctg gctaccaggg 3240
acattgggag gactggggag ctccctcccc atgctctatc atcctggaga ctacaggtcg 3300
ggaggcccag ggaagacaag aagaggctga agtgggactg tggaggggga ccatggggag 3360
cagccaccat ccaaggctgg gcctagactc cctcccagag atggtccctc agagctgtgg 3420
tgaggctggc cctgggaggg tgagaccccc ggtgaaatcc ttccgcttcc ccaccccttg 3480
cagagggcag gggtcctcag ggaaagcaca ggaaccagac ttttggagac ttggatcttc 3540
agcacacctc agggtcctgg gctggcattg gccttccggg cctcaatttc cccatcaaca 3600
aatggagatg aatcccagct tggctgcctc ctgggatcta acgagaaaat gagtcatgtg 3660
aggtaacttc caggctcact gcaatgggta cggtggggtg tatcagatta taaagtgggg 3720
gtgccctcct cacccccagg cttggcctat accccccctct ccatcaagtg gcctctctgt 3780
gtctgtcctt tggggtgagg acactgtagg ccatgagaaa tgggcagttg gggggtcaga 3840
ggccaagggt tagggaggca gggcttgggg agagtgtggg accatcagaa gagaaggaag 3900
tttacaaaac cacattttgt gtggagatgg aggctggagg cccggccctg ggacttggtc 3960
tggggtttct tgaggaagat ctgagggtcc aagggaggaa ggatgccctg gccttctggc 4020
cttctctggc tgatcctgcc ttcttgctgc ctaggacagg agagtaatgt cctagaatgg 4080
tccctgggag gccagttagg aaaccctttg ctgcttctgt ctctagctct tgtcaataaa 4140
gacggtgaca cctgaaaaaa aaaaaaaaaa a 4171

<210> SEQ ID NO 41
<211> LENGTH: 1258
<212> TYPE: DNA
<213> ORGANISM: Homo sapiens

<400> SEQUENCE: 41
ccgagctctc tggcgcagcg ctagctccgc cgcgctcagc tgccctgcgc cggcacccct 60
ggtcatgagc gccccctcga cgctgccccc cgggggcgag gaagggctgg ggacggcctg 120
gccctctgca gccaatgcca gtagcgctcc ggcggaggcg gaggaggcgg tggcggggcc 180
cggggacgcg cgggcggcgg gcatggtcgc tatccagtgc atctacgcgc tggtgtgcct 240
ggtggggctg gtgggcaacg ccctggtcat cttcgtgatc cttcgctacg ccaagatgaa 300
gacggctacc aacatctacc tgctcaacct ggccgtagcc gacgagctct tcatgctgag 360
cgtgcccttc gtggcctcgt cggccgccct gcgccactgg cccttcggct ccgtgctgtg 420
ccgcgcggtg ctcagcgtcg acggcctcaa catgttcacc agcgtcttct gtctcaccgt 480
gctcagcgtg gaccgctacg tggccgtggt gcaccctctg cgcgcggcga cctaccggcg 540
gcccagcgtg gccaagctca tcaacctggg cgtgtggctg gcatccctgt tggtcactct 600
ccccatcgcc atcttcgcag acaccagacc ggctcgcggc ggccaggccg tggcctgcaa 660
cctgcagtgg ccacacccgg cctggtcggc agtcttcgtg gtctacactt tcctgctggg 720
cttcctgctg cccgtgctgg ccattggcct gtgctacctg ctcatcgtgg gcaagatgcg 780
cgccgtggcc ctgcgcgctg gctggcagca gcgcaggcgc tcggagaaga aaatcaccag 840
gctggtgctg atggtcgtgg tcgtctttgt gctctgctgg atgcctttct acgtggtgca 900
gctgctgaac ctcttcgtga ccagccttga tgccaccgtc aaccacgtgt cccttatcct 960
tagctatgcc aacagctgcg ccaaccccat tctctatggc ttcctctccg acaacttccg 1020
ccgattcttc cagcgggttc tctgcctgcg ctgctgcctc ctggaaggtg ctggaggtgc 1080
tgaggaggag cccctggact actatgccac tgctctcaag agcaaaggtg gggcagggtg 1140
catgtgcccc ccactcccct gccagcagga agccctgcaa ccagaacccg gccgcaagcg 1200
catccccctc accaggacca ccaccttctg aggagccctt cccctaccca ccctgcgt 1258

<210> SEQ ID NO 42
<211> LENGTH: 2674
<212> TYPE: DNA
<213> ORGANISM: Homo sapiens

<400> SEQUENCE: 42
atgcctgcat gtgctggttc agggactcac caccctggcg tcctcccttc ttctcttgca 60
gagcctgacg caccccaggg ctgccgccat ggagcccctg ttcccagcct ccacgcccag 120
ctggaacgcc tcctccccgg gggctgcctc tggaggcggt gacaacagga cgctggtggg 180
gccggcgccc tcggcagggg cccgggcggt gctggtgccc gtgctgtacc tgctggtgtg 240
tgcggccggg ctgggcggga acacgctggt catctacgtg gtgctgcgct tcgccaagat 300
gaagaccgtc accaacatct acattctcaa cctggcagtg gccgacgtcc tgtacatgct 360
ggggctgcct ttcctggcca cgcagaacgc cgcgtccttc tggcccttcg gccccgtcct 420
gtgccgcctg gtcatgacgc tggacggcgt caaccagttc accagtgtct tctgcctgac 480
agtcatgagc gtggaccgct acctggcagt ggtgcacccg ctgagctcgg cccgctggcg 540
ccgcccgcgt gtggccaagc tggcgagcgc cgcggcctgg gtcctgtctc tgtgcatgtc 600
gctgccgctc ctggtgttcg cggacgtgca ggagggcggt acctgcaacg ccagctggcc 660
ggagcccgtg gggctgtggg gcgccgtctt catcatctac acggccgtgc tgggcttctt 720
cgcgccgctg ctggtcatct gcctgtgcta cctgctcatc gtggtgaagg tgagggcggc 780
gggcgtgcgc gtgggctgcg tgcggcggcg ctcggagcgg aaggtgacgc gcatggtgtt 840
ggtggtggtg ctggtgtttg cgggatgttg gctgcccttc ttcaccgtca acatcgtcaa 900
cctggccgtg gcgctgcccc aggagcccgc ctccgccggc ctctacttct tcgtggtcat 960
cctctcctac gccaacagct gtgccaaccc cgtcctctac ggcttcctct ctgacaactt 1020
ccgccagagc ttccagaagg ttctgtgcct ccgcaagggc tctggtgcca aggacgctga 1080
cgccacggag ccgcgtccag acaggatccg gcagcagcag gaggccacgc cacccgcgca 1140
ccgcgccgca gccaacgggc ttatgcagac cagcaagctg tgagagtgca ggcggggggt 1200
gggcggcccc gtgtcacccc caggagcgga ggttgcactg cggtgacccc cacccatgac 1260
ctgccagtca ggatgctccc cggcggtggt gtgaggacag agctggctga agccaggctg 1320
gggtagacac agggcagtag gttccccacc gtgaccgacc atcccctcta accgtctgcc 1380
acacagcggg ggctcccggg aggtagggga ggtggccaga ccggtggggg gctccgccat 1440
gccgtgcaag tgctcagggc cgcctcaccc tccatctggc cccagcccat gccggccttc 1500
cctctgggga gcgacttttc cagaaggccg gccaggcgag agggtcttcc tgacggcgga 1560
gctgacctgc ccggcccacc agctgcatgt cagctccgag ccaccgggtc cccgtccaag 1620
gctgctctgc taagttaaag acacccgaaa gcgcttgact caggtccccg gagtccctgg 1680
ccagggcccc agcccctcgc ttgccctgca ctgtgtggac tctggggatg caggtgtaag 1740
gggagtgtgg ctgggcagcc cctggtcagc cagggtcacg cctgtcctgg gggccccacc 1800
ctgctgcccg acacccccca tgggaggctg cgggcggcag ttgctgtctc agagagggga 1860
gtgtgggggc ttgggcgctg gcctagccag gggcgaggtg gggaggcggc tggtgcagag 1920
gagagctggg ggctgaggtt ggggtgaagg ctgcagccct ccaggctgct gggggtgcag 1980
atggctgtgc cgtgctgaga ttggctctgt ctggaggggt ccagtgtggg gtgcctgagg 2040
gcactaggga gaggtgctcc tgctgcagga ggacctgagg gtcagggctt ggagaggaca 2100
gggaacctgc ggccgtctct tctgctttgg ggcaggggct ctggcccggg agagggaacg 2160
gggacaggag cagaggacgg tcatccaggc gcagcgggga gctgctcccc aggccacagc 2220
agacagcact gctgagaggc agcggccgcg cgggtgacgc aaatggcagg ccctgggaat 2280
cccgccgcct cccacctaga attgtcctac ctccccccacc ccaaacacca gcttttcctg 2340
gcgccccagg cccagaacgt gggcccagag agccttgctg ggtctctgg ggcaccttgg 2400 ccttgctctg aggctggaag gagaaggacc agggtgcggc atcactcggc ctcagggacc 2460
cctctgccct gcccagcact ggccccgacc cgtgctcccg ccgtctgccc agagcaggac 2520
ctcaacctcc tggagggcac agggagcggc tgagtgggca caaatcctgg caggagaaag 2580
gcccaggctg aggccaggcc tgggaaacat ccaagcagtg aggacacgcg tgtttgacaa 2640
ctgctcccct gaataaatgc gaggataaat gttt 2674

<210> SEQ ID NO 43
<211> LENGTH: 4427
<212> TYPE: DNA
<213> ORGANISM: Homo sapiens

<400> SEQUENCE: 43
cccccggcgg agccagctgc tgctcttcgg tgctggcccc ggtgccggcc ccgttgccca 60
gggaacaggc tcccggcagc ccccgcggcc cggagtccat cccgcctcct ccggcccggc 120
ggggccgacg agtccggagg ggctgccgcg ggagccccca ggtttcccta gatgacaaat 180
aaacattcct tttcctgcgt gaagatagtc tgtggaaacc ttggccatgg catcgatatc 240
agagcctgtt acattcagag agttctgccc gttgtactat ctcctcaatg ccattccgac 300
aaagatccag aagggtttcc gctctatcgt ggtctatctc acggccctcg acaccaacgg 360
ggactacatc gcggtgggca gcagcatcgg catgctctat ctgtactgcc ggcacctcaa 420
ccagatgagg aagtacaact ttgaggggaa gacggaatct atcactgtgg tgaagctgct 480
gagctgcttt gatgacctgg tggcagcagg cacagcctct ggcagggttg cagtttttca 540
acttgtatct tcattgccag ggagaaataa acagcttcgg agatttgatg tcactggtat 600
tcacaaaaat agcattacag ctctggcttg gagccccaat ggaatgaaat tgttctctgg 660
agatgacaaa ggcaaaattg tttattcttc tctggatcta gaccaggggc tctgtaactc 720
ccagctggtg ttggaggagc catcttccat tgtgcagctg gattatagcc agaaagtgct 780
gctggtctct actctgcaaa gaagtctgct cttttacact gaagaaaagt ctgtaaggca 840
aattggaaca caaccaagga aaagtactgg gaaatttggt gcttgtttta taccaggact 900
ctgtaagcaa agtgatctaa ccttgtatgc gtcacggccc gggctccggc tatggaaggc 960
tgatgtccac gggactgttc aagccacgtt tatcttaaaa gatgcttttg ccgggggagt 1020

```
caagcctttt gaactgcacc cgcgtctgga atcccccaac agtggaagtt gcagcttacc   1080
tgagaggcac ctggggcttg tttcatgttt ctttcaagaa ggctgggtgc tgagttggaa   1140
tgaatatagt atctatctcc tagacacagt caaccaggcc acagttgctg gtttggaagg   1200
atccggtgat attgtgtctg tttcgtgcac agaaaatgaa atatttttct tgaaaggaga   1260
taggaacatt ataagaattt caagcaggcc tgaaggatta acatcaacag tgagagatgg   1320
tctggagatg tctggatgct cagagcgtgt ccacgtgcag caagcggaga agctgccagg   1380
ggccacagtt tctgagacga ggctcagagg ctcttccatg gccagctccg tggccagcga   1440
gccaaggagc aggagcagct cgctcaactc caccgacagc ggctccgggc tcctgccccc   1500
tgggctccag gccacccctg agctgggcaa gggcagccag cccctgtcac agagattcaa   1560
cgccatcagc tcagaggact ttgaccagga gcttgtcgtg aagcctatca aagtgaaaag   1620
gaagaagaag aagaagaaga cagaaggtgg aagcaggagc acctgtcaca gctccctgga   1680
atcgacaccc tgctccgaat ttcctgggga cagtccccag tccttgaaca cagacttgct   1740
gtcgatgacc tcaagtgtcc tgggcagtag cgtggatcag ttaagtgcag agtctccaga   1800
ccaggaaagc agcttcaatg gtgaagtgaa cggtgtccca caggaaaata ctgaccccga   1860
aacgtttaat gtcctggagg tgtcaggatc aatgcctgat tctctggctg aggaagatga   1920
cattagaact gaaatgccac actgtcacca tgcacatggg cgggagctgc tcaatggagc   1980
gagggaagat gtgggaggca gtgatgtcac gggactcgga gatgagccgt gtcctgcaga   2040
tgatggacca aatagcacac agttaccctt ccaagaacag gacagctctc ctggggcgca   2100
tgatggggaa gacatccaac ccattggccc ccaaagcact tttgtgaag tccccctcct    2160
gaactcactc actgtgcctt ccagcctcag ctgggcccca agtgctgaac agtggctgcc   2220
tgggaccaga gctgatgaag gcagccccgt ggagcccagc caagagcagg acatcctaac   2280
cagcatggag gcctctggcc acctcagcac aaatctctgg catgctgtca ctgatgatga   2340
cacaggtcag aaagaaatac ccatttctga acgtgtcttg gggagtgtgg gaggacagct   2400
gactccggtc tctgccttgg cagccagcac tcacaagccc tggcttgagc agcctccacg   2460
ggatcagaca ttgacgtcca gcgatgagga ggacatctat gcccacgggc ttccttcttc   2520
atcctcagag acgagtgtga cagagctcgg acctagttgc tcccagcagg acctgagccg   2580
gctgggtgca gaggacgccg ggctgctcaa gccagatcag tttgcagaaa gctggatggg   2640
ctactcgggt cccggctatg gcatcctcag cttggtggtc tccgagaagt atatctggtg   2700
cctggactac aaaggcggcc tgttctgcag cgcgttgccg ggcgccgggc tgcgctggca   2760
gaagtttgaa gatgctgtcc agcaggtggc agtctcgccc tcaggagccc ttctctggaa   2820
gattgaacag aaatctaacc gggcttttgc ttgtgggaaa gtcaccatca aggggaagcg   2880
gcactggtac gaagccctgc cccaggcagt gtttgtggcc ctgagcgatg acacggcctg   2940
gatcatcagg accagtgggg acctatactt gcagacaggt ctgagcgtgg atcgcccttg   3000
tgccagagcc gtaaaggtgg actgtcccta cccgctgtcc cagatcacag cccggaacaa   3060
tgtggtgtgg gcgctgacag agcagagggc cctcctgtac cgggagggcg tgagcagctt   3120
ctgtccggaa ggcgagcagt ggaagtgtga cattgtcagc gaaaggcaag ctttagaacc   3180
cgtctgcata acgctcgggg atcagcagac tctctgggcc ctggacatcc atgggaacct   3240
gtggttcaga actggcatta tttccaagaa gccccaagga gatgacgacc attggtggca   3300
agtgagcatc acggactatg tggtgtttga ccagtgcagc ttatttcaga cgataatcca   3360
```

tgccactcac tcggtggcca cagcagccca agccccgta gaaaaggtgg cagataagct 3420
gcgcatggcg ttttggtccc agcagcttca gtgccagcca agccttctcg gggtcaataa 3480
cagcggtgtc tggatctcct cgggcaagaa tgaattccac gtcgctaagg gaagtctcat 3540
aggcacctac tggaatcatg tggttccccg tgggacagct tctgctacaa aatgggcctt 3600
tgtgttggct tctgcagctc ccacgaagga aggaagcttc ctgtggctgt gccagagcag 3660
caaggacctg tgcagcgtca gcgcccagag cgcacagtcg cggccctcca cggtgcagct 3720
gcctcccgaa gccgagatgc gcgcctatgc cgcctgccag gatgcgctgt gggcgctgga 3780
cagcctcggc caggtgttca tcaggacgct ctccaagagc tgccccacgg gcatgcactg 3840
gaccaggctg gacctctccc agctaggagc tgtaaaattg acaagcttgg catgtggaaa 3900
tcagcacatc tgggcctgtg attccagggg tggagtttac ttccgtgtag ggactcagcc 3960
tctcaatccc agtctcatgc ttccagcctg gataatgatt gagccacctg tccaggtaag 4020
cagaagttag ctggtggaac tcactcttca gtaagacaga aactgtgagg atgctggtac 4080
tgggaaaaag gatctgcaca gcctctagag gcctcccagc aaatgcgggg agccatgccc 4140
ccagggtcta cacactctcg ttcatcaaca tcacaactgg aattcgggat ttgtgaagtt 4200
tagagctgaa cagactgtta cagattatga gtcaacacgt atattttctc tttcaaaata 4260
ataatatttc gtttttgact ttttactaag tgaatattat tttttaaatc tgcctatata 4320
ttggaacctc tattttataa taataatgat aataaatcag tacccagaag tataaagaag 4380
gtaaaagtta ctttgaaaaa aaaaaaaaaa aaaaaaaaaa aaaaaaa 4427

<210> SEQ ID NO 44
<211> LENGTH: 1815
<212> TYPE: DNA
<213> ORGANISM: Homo sapiens

<400> SEQUENCE: 44
ttttagagaa ttactccaaa ttcatcatga ttgaagacaa taaggagaac aaagaccatt 60
ccttagaaag gggaagagca agtctcattt tttccttaaa gaatgaagtt ggaggactta 120
taaaagccct gaaaatcttt caggagaagc atgtgaatct gttacatatc gagtcccgaa 180
aatcaaaaag aagaaactca gaatttgaga tttttgttga ctgtgacatc aacagagaac 240
aattgaatga tatttttcat ctgctgaagt ctcataccaa tgttctctct gtgaatctac 300
cagataattt tactttgaag gaagatggta tggaaactgt tccttggttt ccaaagaaga 360
tttctgacct ggaccattgt gccaacagag ttctgatgta tggatctgaa ctagatgcag 420
accatcctgg cttcaaagac aatgtctacc gtaaacgtcg aaagtatttt gcggacttgg 480
ctatgaacta taaacatgga gaccccattc caaaggttga attcactgaa gaggagatta 540
agacctgggg aaccgtattc caagagctca acaaactcta cccaacccat gcttgcagag 600
agtatctcaa aaacttacct ttgctttcta aatattgtgg atatcgggag gataatatcc 660
cacaattgga agatgtctcc aactttttaa aagagcgtac aggtttttcc atccgtcctg 720
tggctggtta cttatcacca agagatttct tatcaggttt agcctttcga gtttttcact 780
gcactcaata tgtgagacac agttcagatc ccttctatac cccagagcca gatacctgcc 840
atgaactctt aggtcatgtc ccgcttttgg ctgaacctag ttttgcccaa ttctcccaag 900
aaattggctt ggcttctctt ggcgcttcag aggaggctgt tcaaaaactg gcaacgtgct 960
actttttcac tgtggagttt ggtctatgta aacaagatgg acagctaaga gtctttggtg 1020
ctggcttact ttcttctatc agtgaactca aacatgcact ttctggacat gccaaagtaa 1080
agccctttga tcccaagatt acctgcaaac aggaatgtct tatcacaact tttcaagatg 1140
tctactttgt atctgaaagt tttgaagatg caaaggagaa gatgagagaa tttaccaaaa 1200
caattaagcg tccatttgga gtgaagtata atccatatac acggagtatt cagatcctga 1260
aagacaccaa gagcataacc agtgccatga atgagctgca gcatgatctc gatgttgtca 1320
gtgatgccct tgctaaggtc agcaggaagc cgagtatcta acagtagcca gtcatccagg 1380
aacatttgag catcaattcg gaggtctggg ccatctcttg ctttccttga acacctgatc 1440
ctggagggac agcatcttct ggccaaacaa tattatcgaa ttccactact taaggaatca 1500
ctagtctttg aaaatttgta cctggatatt ctatttacca cttatttttt tgtttagttt 1560
tatttctttt tttttttggt agcagcttta atgagacaat ttatatacca tacaagccac 1620
tgaccaccca tttttaatag agaagttgtt tgacccaata gatagatcta atctcagcct 1680
aactctattt tccccaatcc tccttgagta aaatgaccct ttaggatcgc ttagaataac 1740
ttgaggagta ttatggcgct gactcatatt gttacctaag atccccttat ttctaaagta 1800
tctgttactt attgc 1815

<210> SEQ ID NO 45
<211> LENGTH: 1305
<212> TYPE: DNA
<213> ORGANISM: Homo sapiens

<400> SEQUENCE: 45
ggccacccgc agaacagagc ttccgggacc cacgcctcgt ttgcactggg tgctggacag 60
ccgacgcaac tacaaatggg gcggagcttt cggcactgga gcagctaatt tgcatatagg 120
aatgaggtgc ggctcggctt ccatgggcct aatttacaga tagggcggta tttctgcccc 180
ttaaccgaaa gtgggataca gaggacgacg gtgttaggcg cctgtgtagg agtaaaatgt 240
gtttattttg cattcaacga gagctcctgc attgcagcta ttttgcatat gatttgcatc 300
ttacgaagaa tttgtggcaa aaaaaagctg ggcgtgcgcc gtaggaacct cctgctgaga 360
cgcttccggt agcggcgcgt gacccgacag gtctttcacc tacctacctc agctcccaca 420
aacacgagaa gttccagcaa gttcgccact tccggttctc ctggctatcc aatagcatcg 480
agaggagcat ccccggaagt gaggcagcgg aggacgacct ttttccggtt ccggcctggc 540
gagagtttgt gcggcgacat gaaactgctt acccacaatc tgctgagctc gcatgtgcgg 600
ggggtggggt cccgtggctt ccccctgcgc ctccaggcca ccgaggtccg tatctgccct 660
gtggaattca accccaactt cgtggcgcgt atgataccta aagtggagtg gtcggcgttc 720
ctggaggcgg ccgataactt gcgtctgatc caggtgccga aagggccggt tgagggatat 780
gaggagaatg aggagtttct gaggaccatg caccacctgc tgctggaggt ggaagtgata 840
gagggcaccc tgcagtgccc ggaatctgga cgtatgttcc ccatcagccg cgggatcccc 900
aacatgctgc tgagtgaaga ggaaactgag agttgattgt gccaggcgcc agtttttctt 960
gttatgactg tgtattttttg ttgatctata ccctgtttcc gaattctgcc gtgtgtatcc 1020
ccaacccttg acccaatgac accaaacaca gtgtttttga gctcggtatt atatattttt 1080
ttctcattaa aggtttaaaa ccaaaagcgg tttctctttg cagcaaatat acattaaaat 1140
agagtctctg tacagccaag ggctctgggc cctggcttgc cccatgtccc tgcgcctccc 1200
tggccaaacc caaaaataaa tatagtgtta ttgctctgca gggcatagag gcagtgctct 1260 cctacccccct gaggaggctc gttgggagct gatggggaag ccctg 1305

<210> SEQ ID NO 46
<211> LENGTH: 2770
<212> TYPE: DNA
<213> ORGANISM: Homo sapiens

<400> SEQUENCE: 46
cacacacaca catacacaga atcctcagat aacaggaggc aataaatcca acagcacatc 60
cacgttcaga gaacagtgtc cctgctgtct tgctaacagc tgccaatacc tcactgagtg 120
cctcacacca acatgggctc caagtgagtt tccttcgtct gggcagactc cctcccctct 180
tccataaagg ctgcaggaga cctgtagctg tcacaggacc ttccctaaga gcccgcaggg 240
gaagactgcc ccagtccggc catcaccatg ctccggacca ttctggatgc tccccagcgg 300
ttgctgaagg aggggagagc gtcccggcag ctggtgctgg tggtggtatt cgtcgctttg 360
ctcctggaca acatgctgtt tactgtggtg gtgccaattg tgcccacctt cctatatgac 420
atggagttca aagaagtcaa ctcttctctg cacctcggcc atgccggaag ttccccacat 480
gccctcgcct ctcctgcctt ttccaccatc ttctccttct tcaacaacaa caccgtggct 540
gttgaagaaa gcgtacctag tggaatagca tggatgaatg acactgccag caccatccca 600
cctccagcca ctgaagccat ctcagctcat aaaaacaact gcttgcaagg cacaggtttc 660
ttggaggaag agattacccg ggtcggggtt ctgtttgctt caaaggctgt gatgcaactt 720
ctggtcaacc cattcgtggg ccctctcacc aacaggattg gatatcatat ccccatgttt 780
gctggctttg ttatcatgtt tctctccaca gttatgtttg ctttttctgg gacctatact 840
ctactctttg tggcccgaac ccttcaaggc attggatctt cattttcatc tgttgcaggt 900
cttggaatgc tggccagtgt ctacactgat gaccatgaga gaggacgagc catgggaact 960
gctctggggg gcctggcctt ggggttgctg gtgggagctc cctttggaag tgtaatgtac 1020
gagtttgttg ggaagtctgc acccttcctc atcctggcct tcctggcact actggatgga 1080
gcactccagc tttgcatcct acagccttcc aaagtctctc ctgagagtgc caaggggact 1140
cccctcttta tgcttctcaa agacccttac atcctggtgg ctgcagggtc catctgcttt 1200
gccaacatgg gggtggccat cctggagccc acactgccca tctggatgat gcagaccatg 1260
tgctccccca agtggcagct gggtctagct ttcttgcctg ccagtgtgtc ctacctcatt 1320
ggcaccaacc tctttggtgt gttggccaac aagatgggtc ggtggctgtg ttccctaatc 1380
gggatgctgg tagtaggtac cagcttgctc tgtgttcctc tggctcacaa tatttttggt 1440
ctcattggcc ccaatgcagg gcttggcctt gccataggca tggtggattc ttctatgatg 1500
cccatcatgg ggcacctggt ggatctacgc cacacctcgg tgtatgggag tgtctacgcc 1560
atcgctgatg tggctttttg catgggcttt gctataggtc catccaccgg tggtgccatt 1620
gtaaaggcca tcggttttcc ctggctcatg gtcatcactg ggtcatcaa catcgtctat 1680 gctccactct gctactacct gcggagcccc ccggcaaagg aagagaagct tgctattctg 1740
agtcaggact gccccatgga gacccggatg tatgcaaccc agaagcccac gaaggaattt 1800
cctctggggg aggacagtga tgaggagcct gaccatgagg agtagcagca gaaggtgctc 1860
cttgaattca tgatgcctca gtgaccacct ctttccctgg gaccagatca ccatggctga 1920
gcccacggct cagtgggctt cacatacctc tgcctgggaa tcttctttcc tcccctccca 1980
tggacactgt ccctgatact cttctcacct gtgtaacttg tagctcttcc tctatgcctt 2040
ggtgccgcag tggcccatct tttatgggaa gacagagtga tgcaccttcc cgctgctgtg 2100
aggttgatta aacttgagct gtgacgggtt ctgcaagggg tgactcattg catagaggtg 2160
gtagtgagta atgtgcccct gaaaccagtg gggtgactga caagcctctt taatctgttg 2220
cctgattttc tctggcatag tcccaacaga tcggaagagt gttaccctct tttcctcaac 2280
gtgttctttc ccgggttttc ccagccgagt tgagaaaatg ttctcagcat tgtcttgctg 2340
ccaaatgcca gcttgaagag ttttgttttg ttttttttca tttatttttt tttttaataa 2400
agtgagtgat ttttctgtgg ctaaatctag agctgctaaa agggctttac cctcagtgaa 2460
aagtgtcttc tattttcatt atctttcaga aacaggagcc catttctctt ctgctggagt 2520
tattgacatt ctcctgacct cccctgtgtg ttcctacctt ttctgaacct cttagactct 2580
tagaaataaa agtagaagaa agacagaaaa aataactgat tagacccaag atttcatggg 2640
aagaagttaa aagaaactgc cttgaaatcc ctcctgattg tagatttcct aacaggaggg 2700
gtgtaatgtg acattgttca tacttgctaa taaatacatt attgcctaat tcaaaaaaaa 2760
aaaaaaaaaa 2770

<210> SEQ ID NO 47
<211> LENGTH: 3885
<212> TYPE: DNA
<213> ORGANISM: Homo sapiens

<400> SEQUENCE: 47
agagccggac ggggtaaact gagcggcggc ggcggggcgc tggggcggag actgcgaccc 60
ggagccgccc ggactgacgg agcccactgc ggtgcgggcg ttggcgcggg cacggaggac 120
ccgggcaggc atcgcaagcg accccgagcg gagccccgga gccatggccc tgagcgagct 180
ggcgctggtc cgctggctgc aggagagccg ccgctcgcgg aagctcatcc tgttcatcgt 240
gttcctggcg ctgctgctgg acaacatgct gctcactgtc gtggtcccca tcatcccaag 300
ttatctgtac agcattaagc atgagaagaa tgctacagaa atccagacgg ccaggccagt 360
gcacactgcc tccatctcag acagcttcca gagcatcttc tcctattatg ataactcgac 420
tatggtcacc gggaatgcta ccagagacct gacacttcat cagaccgcca cacagcacat 480
ggtgaccaac gcgtccgctg ttccttccga ctgtcccagt gaagacaaag acctcctgaa 540
tgaaaacgtg caagttggtc tgttgtttgc ctcgaaagcc accgtccagc tcatcaccaa 600
ccctttcata ggactactga ccaacagaat tggctatcca attcccatat ttgcgggatt 660
ctgcatcatg tttgtctcaa caattatgtt tgccttctcc agcagctatg ccttcctgct 720
gattgccagg tcgctgcagg gcatcggctc gtcctgctcc tctgtggctg ggatgggcat 780
gcttgccagt gtctacacag atgatgaaga gagaggcaac gtcatgggaa tcgccttggg 840
aggcctggcc atgggggtct tagtgggccc cccctcggg agtgtgctct atgagtttgt 900
ggggaagacg gctccgttcc tggtgctggc cgccctggta ctcttggatg gagctattca 960
gctctttgtg ctccagccgt cccgggtgca gccagagagt cagaagggga cacccctaac 1020
cacgctgctg aaggacccgt acatcctcat tgctgcaggc tccatctgct ttgcaaacat 1080
gggcatcgcc atgctggagc cagccctgcc catctggatg atggagacca tgtgttcccg 1140
aaagtggcag ctgggcgttg ccttcttgcc agctagtatc tcttatctca ttggaaccaa 1200
tatttttggg atacttgcac acaaaatggg gaggtggctt tgtgctcttc tgggaatgat 1260
aattgttgga gtcagcattt tatgtattcc atttgcaaaa aacatttatg gactcatagc 1320
tccgaacttt ggagttggtt ttgcaattgg aatggtggat tcgtcaatga tgcctatcat 1380
gggctacctc gtagacctgc ggcacgtgtc cgtctatggg agtgtgtacg ccattgcgga 1440

-continued

```
tgtggcattt tgtatggggt atgctatagg tccttctgct ggtggtgcta ttgcaaaggc   1500
aattggattt ccatggctca tgacaattat tgggataatt gatattcttt ttgcccctct   1560
ctgctttttt cttcgaagtc cacctgccaa agaagaaaaa atggctattc tcatggatca   1620
caactgccct attaaaacaa aaatgtacac tcagaataat atccagtcat atccgatagg   1680
tgaagatgaa gaatctgaaa gtgactgaga tgagatcctc aaaaatcatc aaagtgttta   1740
attgtataaa acagtgtttc cagtgacaca actcatccag aactgtctta gtcataccat   1800
ccatccctgg tgaaagagta aaaccaaagg ttattatttc ctttccatgg ttatggtcga   1860
ttgccaacag ccttataaag aaaaagaagc ttttctaggg gtttgtataa atagtgttga   1920
aactttattt tatgtattta attttattaa atatcataca atatattttg atgaaatagg   1980
tattgtgtaa atctataaat atttgaatcc aaaccaaata taattttta acttacatta   2040
acaaacattt gggcaaaaat catattggta atgagtgttt aaaattaaag cacacattat   2100
ctctgagact cttccaacaa agagaaacta gaatgaagtc tgaaaaacag aatcaagtaa   2160
gacagcatgt tatatagtga cactgaatgt tatttaactt gtagttacta tcaatatatt   2220
tatgcgttaa acagctagtt ctctcaagtg tagaggacaa gaacttgtgt cagttatctt   2280
ttgaatccat aaatcttagc tggcattagt tttctatgta atcacctacc tagagagagt   2340
tgtaaattat atgttaacat gttatctggt tggcagcaaa cactaaagcc aataaaggaa   2400
aaacagtaaa tgttccgaaa gcagagaaaa gcaaccaaac atattgttat gaactaaaag   2460
ctttcccttt aagatgcata cttgtcttac tggatgaaga aaattgaggg tacatgtacc   2520
ttatactgtc aaggttgttt aaacatgata aggttaatcg ccatctactt caagttttag   2580
aaaaggaaac aagaagctga aaacagctgc tctgacttta atatctgact atatctttga   2640
tctgtttgca ggtcatccaa gtgttttcta ggaatatatt tattttaggt tgtctgaaac   2700
tactattttt tagactcctg aaagttgttc acatcaatgt gaagacaaat tttaaatgaa   2760
aatgaagaat gaaattatgt cttgaatcat atattaagaa gtaaaaataa tagtgatcag   2820
gcagaaaaga aaaatggaac atctaaaaat gtatgtgcta actatatcat ccagtgtgca   2880
gtgttgtgta tttttctaag catgacaaca ttgatgtgcc ttttcagtgt aacagcaaat   2940
actgttagtg aacattgtca atttatgtca ttttgttaag agatatgact ggagtgtgca   3000
gtgtggaatg tctctaatac tacttgtgaa tcctgcagtt ctataatcat aaacaaaaat   3060
tacttagttt cgttaagcta agattgtgtt tgtgttaact tcgacatcaa ggagcaaaga   3120
actttagaac agactcctca atcttgtgac tttcttattc tctaggaaag taacacttcg   3180
tttcatgaag cttttctgtg gggcttcgat tatttcaagt ctggtttcta agtgcagtgt   3240
gtttgaagca aacgaacttc caactcactt atttggcatt gggcaacttg gccaagtctg   3300
ccactttgga agatggctct ggaggaaact ctcatatggc taaaaaggca ggctagtttc   3360
ttacttctac aggggtagag ccttaaaaaa gaacgtgcta caaattggtt ctctttgagg   3420
gtttctggtt ctccctgccc ccaataccat atactttatt gcaattttat ttttgccttt   3480
acggctctgt gtctttctgc aagaaggcct ggcaaaggta tgcctgctgt tggtccctcg   3540
ggataagata aaatataaat aaaaccttca gaactgtttt ggagcaaaag atagcttgta   3600
cttggggaaa aaaattctaa gttcttttat atgactaata ttcttggtta gcaagactgg   3660
aaagaggtgt ttttttaaaa tgtacatacc agaacaaaga acatacagct ctctgaacat   3720
ttattttttg aacagaggtg gtttttatgt ttggacctgg taatacagat acaaaaactt   3780
taatgaggta gcaatgaata ttcaactgtt tgactgctaa gtgtatctgt ccatatttta   3840
```

gcaagtttac ttaataaatc ttctgaacca tgaaaaaaaa aaaaa 3885

<210> SEQ ID NO 48
<211> LENGTH: 14607
<212> TYPE: DNA
<213> ORGANISM: Homo sapiens

<400> SEQUENCE: 48
ccggaggggc tgtcatttgc agcgctggtc gcagccctca gctgcgccgg gcggttccgg 60
ctcctccctc tccttgtgcc tcagcgccac catggtgctg gagtcggtgg tcgcggactt 120
gctgaaccgc ttcctggggg actatgtgga gaacctgaac aagtcccagc tgaagctggg 180
catctggggc ggaaatgtgg ctttagataa tctacagata aaagaaaatg ccctgagtga 240
attggatgtt ccttttaaag tcaaggctgg ccaaattgat aaattaactt tgaagattcc 300
ttggaagaac ctttatggag aagcagttgt tgcgaccctg gaaggattat acctgcttgt 360
tgtccctgga gcaagtatta agtatgatgc tgtaaaagaa gaaaaatcct tgcaggatgt 420
taaacagaaa gagctatccc gaattgaaga agcccttcaa aaagcagcag aaaaaggcac 480
acattcaggg gagttcatat atggcttgga gaactttgtt tacaaggaca tcaagcctgg 540
acgtaaacgt aaaaagcaca aaaaacattt taagaaacct tttaaaggtc ttgatcgttc 600
aaaagataag ccaaaagaag ccaaaaagga tacatttgtg gaaaaattgg caactcaagt 660
aataaaaaat gtacaagtaa aaatcacaga tattcacatt aaatatgaag atgatgtcac 720
tgatccaaag cggcctcttt catttggtgt cacactggga gagcttagtc tactgactgc 780
aaatgaacac tggactccat gcatattaaa tgaagcagac aaaattatat acaagcttat 840
acgacttgat agtcttagcg cctactggaa tgtaaattgc agcatgtctt accagagatc 900
aagggaacag attttggatc agctgaaaaa tgaaattctt acaagtggaa atatacccc 960 aaattatcaa tacattttcc agccaatatc agcctctgca aaactctaca tgaatcctta 1020
tgcagaatca gagctcaaaa cgcccaaact ggattgcaac atagaaatac aaaatattgc 1080
cattgaactg accaaacctc agtacttaag tatgattgac cttttggagt cagtggatta 1140
tatggttagg aatgcgcctt ataggaaata caagccttat ttaccacttc ataccaatgg 1200
tcgacgatgg tggaaatatg caattgattc tgttcttgaa gttcatataa gaaggtatac 1260
acagatgtgg tcatggagta acataaaaaa gcacaggcag ttactcaaga gttataaaat 1320
tgcctacaaa aacaagttaa cacagtctaa agtctcagaa gaaatacaga aagaaattca 1380
ggacttggag aagactctag atgtttttaa cataatttta gcaaggcaac aagcacaagt 1440
tgaggtgatt cggtctgggc aaaaattaag gaaaaagtct gctgacacag gcgagaaacg 1500
tggaggctgg tttagtgggt tgtggggtaa gaaagagtct aagaaaaagg acgaagaatc 1560
attgattcct gaaactattg atgaccttat gactccagag gaaaaagata aactcttcac 1620
tgccattggt tatagtgaga gtacccacaa cctaacttta cctaagcagt atgttgccca 1680
tattatgacc ctgaagttag taagcacctc tgttacgata agagaaaaca agaatattcc 1740
agaaatacta aaaattcaga taattggcct gggcactcaa gtatctcagc gaccaggagc 1800
acaagcactt aaggtagaag cgaaattaga acactggtat ataacaggtt tgagacagca 1860
ggatattgtg ccatcacttg tggcttcaat tggtgacact acatcatcct tgcttaaaat 1920
taaatttgaa accaatccgg aggatagtcc tgctgaccag actctgattg ttcagtccca 1980
gcctgtggag gtcatctatg atgctaaaac tgtcaatgca gtggttgaat tctttcaatc 2040

```
aaataaggga ttggatcttg agcaaataac atcagcaaca ttgatgaagc tggaagaaat   2100
taaggagaga acagctacag gacttacaca tattattgaa actcgaaaag tccttgattt   2160
aaggataaat ctgaagcctt cttatctagt agttccacag acgggtttcc accatgaaaa   2220
gtcagatctt ctgattttag attttggtac atttcagctc aacagtaaag atcaaggttt   2280
acagaagact actaattcat ctctggaaga aataatggat aaggcatatg acaagtttga   2340
tgttgaaata aaaaatgtac aactactttt tgcaagagca gaggaaacct ggaaaaagtg   2400
tcgatttcag catccatcaa ctatgcatat attgcaaccc atggatattc atgttgagtt   2460
ggctaaggcc atggtagaaa aagacattag aatggccaga tttaaagtgt caggaggact   2520
tcctttgatg catgtgagaa tttctgacca gaagatgaaa gatgtgctat atttgatgaa   2580
cagtatacct ttgccacaga aatcatcagc ccagtctcca gagagacagg tatcctcaat   2640
tcctattatt tcaggtggta caaaaggtct acttggtact tcactattgc tagacactgt   2700
ggaatcagag tctgatgatg agtattttga tgctgaagat ggagaaccac agacttgtaa   2760
aagtatgaaa ggatcagaac ttaaaaaagc tgcagaggtc ccaaatgagg agctcatcaa   2820
tcttctactc aagtttgaaa ttaaagaagt gattttggaa tttactaaac agcagaaaga   2880
agaagataca attctagtat ttaatgttac tcagttagga acagaggcca caatgagaac   2940
atttgactta actgtggtat cttatttaaa gaaaatcagc ttggattatc atgaaattga   3000
aggatccaaa aggaagcccc ttcacttgat tagctcttct gacaaacctg gattagatct   3060
tttgaaagtg gagtatatta aggctgataa gaatggacct agttttcaaa ctgcttttgg   3120
aaaaactgaa caaacagtta aggtggcctt ttcatcttta aatctgttgc tgcaaacaca   3180
agctcttgtc gcttctatta attacctcac aaccattatt ccatctgatg atcaaagcat   3240
aagtgttgct aaggaggtac aaatttcaac tgaaaaacaa caaaaaaatt caactctgcc   3300
aaaagcgatt gtatcctcca gagatagtga cattattgat ttcaggctat ttgccaagtt   3360
gaatgctttc tgtgtcattg tttgcaacga aaagaacaat atcgccgaaa tcaagattca   3420
aggactggat tcctcccttt ctctccagtc aagaaagcag tcactttttg cccgactaga   3480
aaatattatt gtcacagatg ttgatccaaa gacagttcat aagaaagctg tgtcaataat   3540
gggaaatgaa gttttccgtt ttaatttgga tttgtatcca gatgctactg agggggattt   3600
gtatactgac atgtccaaag tggatggtgt gctgtctctg aatgttggct gtattcagat   3660
tgtctatctt cataaattcc ttatgtcact tctgaacttc ctgaataatt tccagacagc   3720
caaagagtct ctgagtgctg ccactgccca ggctgcagaa agggctgcca caagtgtgaa   3780
agatcttgcc cagaggagtt ttcgtgtttc catcaatatt gatttgaaag caccggttat   3840
agtcatccca cagtcttcta tttccaccaa tgcagtagtg gtagatcttg ggttaatcag   3900
agttcataat cagttcagtc tggtgtctga tgaagactac ttaaatcctc cagtaattga   3960
tagaatggat gtgcagctaa caaagcttac actttatagg acagtgatcc agccaggcat   4020
ctaccatcct gatattcagc tgttgcaccc aattaacttg gaatttcttg taaatcggaa   4080
tctagctgca tcttggtacc acaaggtgcc tgttgtggaa attaaaggac atcttgattc   4140
aatgaatgtt agtctaaatc aagaagatct taatctttta tttaggatac taacagaaaa   4200
tctctgtgag ggtactgaag acttggataa agtgaaacca agagtacaag agacaggtga   4260
aattaaagag ccccttgaaa tctctatatc acaagatgta catgattcaa aaaatacttt   4320
aacaactgga gtggaagaaa ttaggtctgt agacatcatt aatatgctgc tgaattttga   4380
aattaaagag gttgtggtta ctttgatgaa aaaatcagaa aagaaaggaa ggcctttaca   4440
```

-continued

```
tgagctaaat gtcctgcaac ttggaatgga agctaaagtt aaaacctatg acatgactgc   4500
taaagcttat ctaaaaaaaa ttagtatgca gtgctttgat ttcactgact ctaaagggga   4560
acctcttcac attattaact cttctaatgt gactgacgaa ccccttctga aaatgttact   4620
gacaaaggca gacagtgatg gaccagaatt taaaactatt catgacagta ccaaacagag   4680
actgaaggtt tcatttgcat ccttagactt agtacttcat ttggaagctt tactttcctt   4740
catggatttt ttatcatctg ctgctccatt ctctgagcct tcctcttctg agaaggaatc   4800
cgagctgaaa ccacttgtgg gggagtccag aagtatcgct gtcaaagctg tatccagcaa   4860
catttcccaa aaggatgtgt ttgatttaaa gatcacagct gaattaaatg catttaatgt   4920
ctttgtctgt gatcagaagt gtaacattgc agatattaaa atacatggaa tggatgcctc   4980
tatttctgtg aagcctaagc agactgatgt gtttgccaga cttaaagata ttatagttat   5040
gaatgtagat ttgcagtcca ttcacaaaaa ggctgtctct attttgggag atgaagtctt   5100
taggttccaa ctgactcttt atccagatgc cacagaagga gaggcctatg ctgatatgtc   5160
caaagtagac ggcaaactta gttttaaagt gggttgtatt cagattgttt atgttcataa   5220
attcttcatg tctcttttga acttcctcaa caatttccaa actgctaaag aagctttgag   5280
tacagccaca gtccaggctg cagaaagagc tgcttccagc atgaaagact tggctcaaaa   5340
gagtttccgc cttttgatgg atattaattt gaaagcacca gttattatta ttcctcagtc   5400
ttcagtatca cctaatgctg ttatagcaga tctgggttta atcagagttg aaaacaagtt   5460
tagcttggtt cctatggaac attattctct tcctccagtc attgataaaa tgaacatcga   5520
actcactcag ttgaagctgt caagaactat tttgcaggct agcttgccac aaaatgacat   5580
tgaaatttta aaaccagtca acatgctttt gtccatacag cgaaacttag cagcagcatg   5640
gtatgtgcaa attccagga tggagataaa aggaaaacta aaacctatgc aggttgctct   5700
cagtgaagat gacttgacag ttttaatgaa aattttgcta gaaaatcttg gagaagcttc   5760
ctcacaacca agccctacac agtctgtgca ggagactgta agagtgagaa aagttgatgt   5820
ttcaagtgta cctgaccatc tcaaagaaca agaagattgg acagactcaa agctctctat   5880
gaaccagatt gtcagtctcc aatttgactt tcactttgaa tctctttcca ttatccttta   5940
taacaatgat atcaaccagg aatctggagt tgcatttcat aatgacagtt tccaacttgg   6000
tgaactcaga ctacatctta tggcctcctc agggaagatg tttaaggatg gctcaatgaa   6060
tgtcagcgtt aaacttaaga catgcaccct tgatgatctc agagaaggaa ttgagagagc   6120
aacatcgaga atgattgaca gaaagaatga ccaagataac aacagttcta tgattgatat   6180
aagttacaaa caagacaaaa atggaagtca aattgatgct gttcttgaca agctgtatgt   6240
atgtgccagt gtggaatttc tgatgactgt ggcagatttc tttatcaaag ctgtgcctca   6300
gagtccagaa aatgtggcaa aagaaacaca gattttacca agacagactg ccacagggaa   6360
ggtcaagata gagaaagatg actctgttag accaaatatg actttaaagg ccatgatcac   6420
agatccagaa gtggtatttg ttgccagcct gacaaaggct gatgctcctg ctctgacagc   6480
ctcgtttcag tgcaaccttt ctctgtcaac atccaaactc gaacagatga tggaagcttc   6540
tgtgagagat ctgaaagtgc tcgcttgccc ttttctcaga gaaaagagag ggaaaaacat   6600
taccacagtc ttgcagccct gttctttatt tatggaaaaa tgtacgtggg cttcaggaaa   6660
gcaaaatata aatattatgg ttaaagaatt tataattaag atttcaccca taattcttaa   6720
tactgtgttg acaatcatgg ctgcattgtc tccaaaaaca aaagaagatg gatccaaaga   6780
```

```
tacgtctaag gaaatggaaa atctttgggg tatcaaatcg attaatgatt ataacacttg   6840
gtttcttggt gttgacacgg caacagaaat aacggaaagc ttcaaaggca ttgaacattc   6900
actgatagag gaaaattgtg gtgttgttgt agaatccatt caagttacct tagaatgtgg   6960
ccttggacat cgaactgtac ctttattatt ggcagagtct aagttttcag gaaatattaa   7020
aaattggact tctctaatgg ctgctgttgc tgacgtgaca ctacaggtgc actattacaa   7080
tgagatccat gctgtctggg agccactgat tgagagagtg gaggggaaga gacaatggaa   7140
tttaaggctt gatgtaaaga agaacccagt tcaggataaa agtttgctgc caggagatga   7200
ttttattcct gagccacaaa tggcaattca tatttcttca ggaaatacaa tgaatataac   7260
aatatccaaa agttgtctta atgttttcaa caatttagca aaaggttttt cagagggcac   7320
tgcttctact tttgactact ctttaaagga cagagctcct tttacggtaa aaaatgctgt   7380
aggtgttccc attaaggtga agcccaattg taatctcaga gtaatgggct tccctgagaa   7440
aagtgatatt tttgatgttg atgctggcca gaatttggaa ctggagtatg ccagcatggt   7500
accttcaagt caagggaacc tatctatatt gagccgtcaa gaaagctcct tcttcactct   7560
gaccattgta cctcatggat atacagaagt tgcaaatatc cctgtggcca gacctggacg   7620
gcgattgtat aatgtacgga atcccaatgc cagtcattct gactctgtct tggtacaaat   7680
tgatgcaact gaagggaata aagtaattac ccttcgctct cctctacaga tcaaaaacca   7740
tttctccatt gcatttatca tctataaatt tgttaagaat gttaagctat tggagcgcat   7800
tgggatagcc agacctgaag aggagttcca tgttccttta gattcatata gatgtcaatt   7860
gtttatccag ccagctggaa tcttagagca tcagtacaaa gaatctacca cttatatttc   7920
ctggaaggaa gaacttcata ggagcaggga agtcagatgc atgttgcagt gtccatcagt   7980
agaagtcagc ttcttacctc tcatagtgaa tacagttgct ctgcctgatg aattgagcta   8040
catatgtaca catggggaag actgggatgt agcttacatt attcatcttt atccttctct   8100
cactttgcgg aatcttctcc catattccct aagatattta cttgagggaa cagcagaaac   8160
tcatgagctg gcagaaggca gtactgctga tgttctgcat tcgagaatca gtggtgaaat   8220
aatggaatta gtcctggtga aataccaggg caaaaactgg aatggacatt tccgcatacg   8280
tgatacacta ccagaattct ttcctgtgtg tttttcttct gactccacag aagtgacgac   8340
agtcgacctg tcagtccacg tcaggagaat tggcagccgg atggtgctgt ctgtctttag   8400
tccctattgg ttaatcaaca agactacccg ggttctccag tatcgttcag aagatattca   8460
tgtgaaacat ccagctgatt tcagggatat tattttattt tctttcaaga agaagaacat   8520
ttttactaaa aataaggtac aattaaaaat ttcaaccagt gcctggtcca gtagtttctc   8580
attggataca gtgggaagtt atgggtgtgt gaagtgtcct gccaacaata tggagtacct   8640
ggttggtgtt agcatcaaaa tgagcagttt caacctttca cgaatagtta ccctgactcc   8700
cttttgtacc attgcaaaca agtcatcatt agaactagaa gttggcgaga ttgcatctga   8760
tggctcaatg ccaactaata aatggaacta tattgcttct tcagagtgcc ttccattttg   8820
gccagaaagt ttgtcaggca aactttgtgt gagagtggtg ggctgtgaag gatcttccaa   8880
accattcttt tataaccgac aggataatgg cactttattg agcttagaag atctgaatgg   8940
gggtatcttg gtggatgtaa acactgccga acattcaact gtcataactt ttctgatta    9000
ccatgaggga tctgcacctg ccttgataat gaaccataca ccatgggaca tcctcacata   9060
caaacagagt gggtcaccag aagaaatggt cttgctgcca agacaggctc gactttttgc   9120
ctgggcagat cctactggta ccagaaaact tacatggaca tatgcagcaa atgttgggga   9180
```

```
acatgatctg ttaaaggatg gatgtggaca gtttccatat gatgcaaaca tccagataca   9240
ctgggtatca tttctggatg ggcgccagag agttttgctt ttcaccgatg atgttgcctt   9300
ggtttccaaa gcactgcagg cagaagaaat ggaacaggct gattatgaaa taaccttgtc   9360
tctccacagt cttgggcttt cactggttaa caatgaaagc aagcaggaag tttcctatat   9420
tgggataacc agttctggtg ttgtttggga ggtgaaacca aagcagaaat ggaagccatt   9480
tagtcaaaag cagataatct tattggaaca atcctatcag aaacatcaaa tatcaagaga   9540
ccatggctgg attaagctag ataataattt tgaggtcaat tttgataaag atccaatgga   9600
aatgcgcctc cctattcgta gccctattaa acgagacttt ttatcaggaa ttcagattga   9660
atttaagcag tcttctcacc agagaagttt aagggccagg ttgtactggc ttcaggttga   9720
taatcagtta ccaggtgcaa tgttccctgt tgtatttcat cctgttgccc ctccaaaatc   9780
tattgcttta gattcagagc ccaagccttt cattgatgtg agtgtcatca caagatttaa   9840
tgagtacagt aaagtcttac agttcaagta ttttatggtc ctcattcagg aaatggcctt   9900
aaaaattgat caagggtttc taggagctat tattgcactg tttaccccaa caacagaccc   9960
tgaagctgaa agaagacgga caaagttaat ccaacaagat attgatgctc taaatgcaga  10020
attaatggag acttcaatga ctgatatgtc aattcttagt ttctttgaac atttccatat  10080
ttctcctgtg aagttgcatt tgagtttgtc tttgggttcc ggaggtgaag aatcagacaa  10140
agaaaaacag gaaatgtttg cagttcattc tgtcaacttg ctgttgaaaa gcataggtgc  10200
tactctgact gatgtggatg accttatatt caaacttgct tattatgaaa ttcgatatca  10260
gttctacaag agagatcagc ttatatggag tgttgttagg cattacagtg aacagttctt  10320
gaaacagatg tatgtccttg tattggggtt agatgtactt ggaaacccat ttggattaat  10380
tagaggtctg tctgaaggag ttgaagcttt attctatgaa cccttccagg gtgctgttca  10440
aggccctgaa gaatttgcag aggggttagt gattggagtg agaagcctct ttggacacac  10500
agtaggtggt gcagcaggag ttgtatctcg aatcaccggt tctgttggga aaggtttggc  10560
agcaattaca atggacaagg aatatcagca aaaaagaaga gaagagttga gtcgacagcc  10620
cagagatttt ggagacagcc tggccagagg aggaaagggc tttctgcgag gagttgttgg  10680
tggagtgact ggaataataa caaaacctgt ggaaggtgcc aaaaaggaag gagctgctgg  10740
attctttaaa ggaattggaa aagggcttgt gggtgctgtg gcccgtccaa ctggtggaat  10800
cgtagatatg gccagtagta ccttccaagg cattcagagg gcagcagaat caactgagga  10860
agtatctagc ctccgtcccc ctcgcctgat ccatgaagat ggcatcattc gtccttatga  10920
cagacaggaa tctgagggct ctgacttact tgagcaagaa ctggaaatac aggaataaat  10980
gtttcctaaa ctactacttg atttcatcct taaaaatcaa aacaaactgt ggtgttaatt  11040
gactgtgtgt gaattccatt gtcaatttta atgaaatttt ctttaaaact ctcacctcca  11100
tctgaacttt tcatagtagt gggattgact acaaataaaa acttgtggta ttcctggtaa  11160
tactgtccag aaataagaga ttagtataaa atattaaagg atgcagagaa tcagctctct  11220
tctgcgttta atagatgaaa gcctttattg agctcagaag cagatactgt tactatcatt  11280
tcgaaaattt tatcttatgg tgttcatgtg catttcaggt aaaattgaaa aacaggacaa  11340
ttattatgtc caattaatat gtttatgttt gtgagtcttg atgatggaat tacatagctt  11400
tctgtttcac aaatggctct aaatttgctt aagttacggg actattacct ggagcatctg  11460
ctttaataat tgaattgtca gttgctctga gcctgccctt agacctcaag taataaatag  11520
```

ttggcacatg aattttgagg atatgtttcc tcttccctct ttttcctatt taaccccttg 11580
gtactgttgc taaataaatg atagccattt tataattatg ttatatacat tttcagcctt 11640
tagcatttct gcttttcaaa aattgaatct ccttgttggt tatgcttatt tcataattat 11700
tagttttaat taatgtagat agaagttgaa catgtaatta ggcaaattgc tgtgtggcac 11760
ttgaatacat agatttcttt attttcaaaa accaaccttt tgcttttaaa tccttagaga 11820
gggtttatta tcttagagaa aaaataatta taatcattat ttttgaaatt agtatcctct 11880
taattctcaa cataagttat gtttcaattt cttttttttg taataaatga tggaaatgtt 11940
taacaatgtc ttatctagca actttcatgc ttctcctcag aaatgaagcc aaagtataaa 12000
cttagattta atgtgttgta tatttgaaga gaatgaaact attaacatat aattgttcag 12060
ttggattatg tattttaagg attgcagtta tcaaaataat aaattgaatg ttttatgttt 12120
aaccacttta aagaagaaag actgacatcc aaaaaccagc gtgtgctaga tatacaaagg 12180
aaattacttc tgtccttaag ggaccaagta taacaaaaca tgtaactgtt aaaagtagct 12240
gacaaacctt tcttgtgcct agataattta gcattggcaa aaatgtcacc acatgcagtt 12300
ttctaggaga gtcaagcaca aataactaat tcaagatgct gacttaaatc atctccaata 12360
gttacccttc ctgagattct aaagtaacaa tttttaattt tactggttat attgctgttt 12420
tactgagact tacttttaag aacccctgta acttaagatt ttttcttaat tgttttgttt 12480
agctctgtta ttaatttttt ccttgtgata tctttttata actctctgtc aaaaagcaca 12540
aaacttcaag aaacttttaa ttattttgtc tgaacatata atcttgtctg atttcttagt 12600
ttttattaag atatcagaca acttttaaaa ctttagtgca ttattataat tactggaaga 12660
aaaagaatga ttatacacta atgagaggac ttggtagttt ttgtcgtgga tgtcaagtgt 12720
gggcatggat aattgaaata tttaggctat ttcattcttt gcccatcttg ctgtgatcag 12780
ttagttgggt aaaaatattt attgattatt tagactgtac tggatataca aaagaagcct 12840
tctgtcctta agggaccgag taaaacaaaa catggaaata ttaaagagta ttagagtata 12900
aaagtatatc tttttagccc tttgtaatat ggccaaattc taaataattt atttggggat 12960
cttttgatcc tcatgttcct ttttctccta agtactactt tgtattcttt aatatgcagc 13020
tttgagagtt actgaatcat atattatatt tccatgagat gtactattct acttatcctc 13080
taatcttcat atatatatac acacacacat atatatacac atacatatat acacacgtac 13140
atatatgtac acatacagat atacatacac acaaacacat atatacacac atacatatac 13200
acacatatat atacacatac aaatatacac atatatacac atacatatat atacacacat 13260
acaaatatac ccatatgtac acatacatat atacacatac atatatacac acacatatac 13320
acacatatat acgcaaacat acacatattt acacatacat atatacatac attatatgta 13380
tgtatatata gtcatttaat actcattttg gttcacatac ttatgatcat gcaacgttta 13440
aaacagcatt tcttgctttt tagttttagt tatatttttc catgttctta gaaatgcctc 13500
attaacattt ttaattcttg tattgccatc tattgaggtg acattacatt gtgtttttat 13560
ctcgtcttaa ttcatgacat taaattattc tactaacagt aataatgctg taataaacat 13620
cattatagat tttgcttttt tatatcttgt ttgctttttc atatttcctt agaatttact 13680
tgaaaaaatt gaattactgg gtaaagggct tttgcaaagt attgttaaat tcctcgagtt 13740
gcatttttgg aaaggggacg tgaatatttt atcaactaat ttggtctccc tgctgccatt 13800
agtgactgaa tatcttaatc tgaatctcag agtgtagtgg gtttttagta gtgctgaaga 13860
caagttttct aaagtgtatt atggtgataa attatatttt aaaaactgtc aatggcttga 13920
agcacaatag cctaataact aacgaaaata catacaagat agaaagtggg tagtatttct 13980
tgtacttgca tttcagatct aaatatttta acatatttaa atttcaagct gcagataaat 14040
gcattacatt attaaattca tttcccattt tctctttgaa gaaattaagg caaaagtgtt 14100
aaaagatttt aactaattcg cacaagtgaa ttgtgaaaca agtagctatt gctgtgaaat 14160
ctgcactcct ctctgagact cattctgaag atgagatccc agttctttgt ggattcctct 14220
tccttattca tggctttttg caattgtcaa ggaatgacta ggtaccaagc aactttaaaa 14280
aatgtatatt taagcattga aataatatca aatgtgattt ctctgcttgt ggttatattg 14340
attatattat ccttttaata atattggcat tatattcttg gtcgtaaaat gtcaaggtct 14400
tatttattca gtatatttat gttctgtatt ttcatatata ttatctattt tcagccatgc 14460
attatatata atgtcagtaa tagtatttca ttagcattca ttataaaaaa actcgttttt 14520
aatatttgac taattcaagt cacagtactt ttgagatagc tgaaaaggaa aataaatgtg 14580
ttttaatgtg ctactaaaaa aaaaaaa 14607

<210> SEQ ID NO 49
<211> LENGTH: 14329
<212> TYPE: DNA
<213> ORGANISM: Homo sapiens

<400> SEQUENCE: 49
gcggccgcag aatcgagctc gggccccggc ccccggcccg cggcgcgggg ctcccgggcc 60
ccgccgcgga cgtcgcgccg gtcgcccctt ccccgtagcc cgtgcgccct cggcgcggag 120
ccccggcccg ccgcggtccc gtctcctggg cctgtcccgc ccgcgccctc cgccggccct 180
caggtataat acttctccac gtctgcttca ggaagaaagt gcctgccatt cttatcattt 240
ctaagcaggt tcatgccagc ccagaacaga gaatcagctg gagcccagat ttcaagtttt 300
gagtaaaata ccttcaagcg aatgggccct attgtgctca cacattcaga acctgttacc 360
caaggaattc cctaaagaat tagaagtgcg tctcaccaac cagccaagat gaacatggtg 420
aagaggatca tggggcggcc gaggcaggag gagtgcagcc cacaagacaa cgccttagga 480
ctgatgcacc tccgccggct cttcacggag ttgtgccatc ctccccggca catgactcag 540
aaggaacaag aagagaaact gtatatgatg ctgccagtgt ttaacagggt ttttggaaat 600
gctccgccga atacaatgac agaaaaattt tctgatcttc tgcagttcac aacacaagtc 660
tcacgactaa tggtgacaga aattcgaagg agagcatcaa acaaatccac agaggctgca 720
agtcgggcca tagttcagtt cctagagatt aatcagagtg aagaagccag tagaggctgg 780
atgcttctaa cgacaattaa tttgttagct tcctctggtc agaaaaccgt ggactgcatg 840
acaacaatgt cagtgccttc caccctggtt aaatgtttat atctgttttt tgaccttcca 900
catgtgcctg aggcagttgg aggtgcacag aatgagctac ctctagcaga acgtcgagga 960
ctactccaga aagtttttgt acagatctta gtgaaactgt gcagttttgt ttcccctgcg 1020
gaggagctgg ctcagaaaga tgatctccag cttctattca gtgcaataac ctcttggtgc 1080
cctccctata acctgccttg gagaaagagt gctggagaag tcctcatgac catatctcgt 1140
catggtctta gtgtcaatgt agtgaagtat attcatgaga aagagtgttt atctacatgt 1200
gttcagaata tgcagcaatc agatgacctg tctcccctag aaattgtcga aatgtttgct 1260
gggctttctt gtttcctcaa agattccagc gatgtttccc aaacacttct ggatgatttt 1320
cggatatggc aaggatataa ttttctttgt gatctcttgc ttagattgga acaagcaaaa 1380

-continued

```
gaggcagaat ccaaagatgc cttgaaagat ctggttaatc tgataacttc cctaacaaca   1440
tatggtgtca gtgaactaaa accagctggt attaccacag gggcaccctt tttattgcct   1500
ggatttgcag tacctcagcc tgcaggcaaa ggtcacagtg tgagaaacgt ccaggccttt   1560
gcagttcttc agaatgcatt tttaaaagca aaaaccagct tccttgccca aatcatcctt   1620
gatgctatca caaatattta catggctgac aatgccaatt acttcatcct agagtcacag   1680
cacacattgt cacagtttgc agagaagatt tctaaactcc cagaagtaca aaacaaatac   1740
tttgagatgc tggagtttgt tgtttttagc ttaaattata taccttgtaa agaacttatt   1800
agtgtcagta tcctcttaaa atctagctct tcttatcact gtagcattat tgcaatgaaa   1860
acacttctta agtttacaag acatgactac atatttaaag acgtgttcag ggaggttggc   1920
cttttggagg tcatggtaaa ccttttgcat aaatatgctg ccctgttgaa ggatccaact   1980
caggcactaa atgaacaagg ggactcaaga aataatagtt cagttgaaga ccaaaaacac   2040
ctggctttat tggttatgga gaccttgaca gtgcttcttc aaggatcaaa cacaaatgca   2100
ggaatttttc gagaatttgg aggtgcaaga tgtgcacata atatagtaaa gtaccctcaa   2160
tgccggcagc atgccttgat gactatccaa cagctggtgc tctccccaaa tggggacgat   2220
gacatgggca ctctcctggg gctaatgcat tcagccccac cgacggaatt gcagttgaag   2280
actgatattt taagggccct cctgtcggtc cttcgagaaa gccatcgttc aagaacagtt   2340
tttaggaaag ttggaggatt tgtgtacatt acatccttgc tcgttgctat ggaaagatct   2400
ttgagctgtc cacccaagaa tggctgggag aaagtgaacc agaatcaagt gtttgaactt   2460
cttcacactg tgttctgcac gttgactgca gcaatgcgct atgagccagc caactctcat   2520
ttcttcaaaa cagagattca gtatgagaag ttggcagatg ctgttcgatt tcttggctgc   2580
ttctcagacc taagaaaaat aagcgccatg aatgtcttcc cctcaaatac acagccattt   2640
caaagacttt tagaggaaga tgtaatctca atagaatcag tgtcacccac gttacggcac   2700
tgcagtaaac tttttattta tctttacaaa gtagccacag attcttttga cagtcgtgca   2760
gaacagatcc ctccttgcct gacaagtgag tcttctctcc cctctccttg ggtacacca   2820
gctttgtcca ggaaaaggca tgcatatcat tctgtttcaa ctccccctgt ttaccctcct   2880
aaaaatgttg ccgacctgaa actacatgtg acaacttcat ctctgcagag ttctgatgca   2940
gtcatcattc atcctggagc catgcttgcc atgctggacc tactggcctc tgttgggtca   3000
gtgacacagc cagaacatgc tttggatctt caacttgccg tggcaaatat tttacaatcc   3060
ctggtgcaca cagaaaggaa ccagcaagtc atgtgtgaag ctggtcttca tgcacgactg   3120
ctgcagaggt gcagtgctgc attggctgat gaggaccact cactgcaccc gcccctgcag   3180
cggatgtttg aacgattagc ctctcaggct ctggaaccca tggtgttgag ggagtttta   3240
cgtttggcaa gtcctttaaa ttgtggtgcc tgggacaaaa aactgctaaa acaatatagg   3300
gtccacaaac caagttcact gagttatgaa ccagaaatga gaagtagtat gatcacatct   3360
ctggaaggtc tgggtactga taatgttttt agcttacatg aagataacca ttaccggata   3420
agcaagagcc tggtaaaatc tgcggaagga agtactgtac ccctgaccag ggtgaagtgt   3480
ctggtctcca tgacaacccc acatgacatc agacttcatg ggtcatcagt tactccagct   3540
tttgttgaat ttgacacatc acttgaaggg tttggatgtc ttttttgcc cagtttggcc   3600
cctcataatg ctcctacaaa taataccgtc acaacaggtc ttattgatgg ggctgtggtc   3660
agtggcattg gttctggtga aagattcttc cctcctccct ccggcttaag ttactctagc   3720
tggttttgta ttgaacattt tagttctcct ccaaataacc accctgtcag acttcttact   3780
```

gttgtgcgcc gagcaaattc ttctgagcaa cattacgtgt gccttgcaat agttctatca 3840
gcaaaagacc gatctctgat tgtttccacc aaagaggaac tcctccaaaa ttatgttgat 3900
gattttagtg aagagtcctc attttatgaa attctcccat gctgtgctcg ctttcgatgt 3960
ggagagctta tcattgaggg acagtggcat catttggtcc tggtaatgag caaaggcatg 4020
ttgaaaaaca gtactgcagc cctttatatt gatggacagc ttgttaacac tgtaaagctt 4080
cattatgtcc acagtactcc aggggggttca ggttcggcaa atccaccagt ggtgagcacg 4140
gtctatgcct acattggtac tccacctgcc caacgccaaa ttgcctcatt ggtttggcgc 4200
ctgggaccca cacattttct agaagaagtt ttaccttctt caaatgttac taccatttat 4260
gaacttggac caaattatgt tggaagcttt caggctgtat gtatgccatg taaagatgca 4320
aaatccgaag ggtggtgcc atcccctgtg tcattagtac cagaggagaa agtgtcattt 4380
ggcctctatg cactctctgt gtcgtctcta acagtggcaa gaatccggaa agtgtataac 4440
aaattggata gcaaagccat tgctaagcag ttaggcattt cctcacatga gaatgccact 4500
cctgtgaagt tgatacacaa ttcagcagga catcttaatg gatctgcacg gacaattggg 4560
gccgctctga ttggatactt gggagtaaga acatttgtcc ctaagcctgt tgccactact 4620
ttgcagtacg ttggtggagc tgcagccatc ctgggcctgg tggccatggc ctctgatgtg 4680
gaagggttat atgcagcagt caaggccctg gtttgtgtgg tcaagagtaa cccactagcc 4740
agcaaagaaa tggaaagaat caagggctac cagttgctgg caatgttgct taagaagaaa 4800
cgttcccttc ttaacagcca catcctccat ctaacttttt ctttggtggg aactgttgat 4860
agtggacatg agacctccat tattccaaat tcaactgctt tccaggacct cctctgtgat 4920
tttgaagtct ggctccatgc accatatgaa cttcatcttt ccttatttga acactttatt 4980
gaactgctca cagagtccag tgaagcctca aagaatgcca aattaatgag agaattccag 5040
ttaatcccaa agctgctcct gactcttcga gatatgtctt tatcccagcc tactattgct 5100
gctattagta atgtcctgag cttcttactg caaggttttc ctagcagcaa tgatctgctc 5160
agatttgggc agtttatttc ttctactttg ccaacctttg cggtttgtga gaaatttgta 5220
gtaatggaaa taaataatga agagaagctt gacactggaa ctgaagagga gtttggaggt 5280
cttgtatcag ctaatcttat acttttgagg aacagacttc tggatatctt gctaaaacta 5340
atttatacat ctaaagaaaa gacaagcatt aatttgcaag cttgtgaaga actggtgaag 5400
acactgggtt ttgactggat catgatgttt atggaggaac acttacattc caccacagtt 5460
acagcagcca tgaggattct tgttgtccta ctaagtaatc agtctattct catcaagttt 5520
aaagaaggac tcagtggtgg aggatggctt gaacagacag attctgtctt aactaataag 5580
attggaactg tattaggatt caacgtgggc agaagtgctg gtgggagatc gacggtcagg 5640
gagattaacc gagatgcttg tcattttcct ggttttccag tccttcagtc attccttcct 5700
aaacacacta atgtccctgc cctctatttt ctcctcatgg ccttgtttct gcagcagcca 5760
gttagtgagc tgcctgagaa cctgcaggtc agtgtgcctg tcatcagctg ccggagtaag 5820
cagggttgcc agtttgattt ggattccatt tggacattca tctttggagt tcctgcctcc 5880
agcggaactg tggtctcttc tatccataac gtatgcacag aagctgtttt tttattattg 5940
ggaatgctcc gcagcatgct gacttcacct tggcaatcag aagaagaggg atcttggctc 6000
cgagaatatc ctgtgaccct gatgcagttc ttcagatatt tgtatcacaa cgtgccagac 6060
cttgcctcca tgtggatgag ccctgacttc ctgtgtgcat tagcagccac cgtcttcccc 6120

-continued

```
ttcaatattc gcccttactc agagatggtg actgaccttg atgatgaagt tggatctcca   6180
gcagaagagt ttaaagcgtt tgcagcagac acagggatga acaggagcca atcagagtac   6240
tgcaatgtgg gcaccaagac atatctgacc aatcacccgg ctaaaaagtt cgtttttgac   6300
ttcatgcggg tcttaatcat agacaacctc tgtctcactc ctgccagcaa gcaaactcca   6360
ctaattgatc ttttgttgga ggcttcccct gaaaggtcta caagaactca gcaaaaagaa   6420
tttcaaactt acattttgga tagcgtgatg gaccatttgc ttgcagctga tgtgttatta   6480
ggggaagatg catctctgcc tattaccagt ggaggaagct accaggtatt ggtgaacaat   6540
gtgttttatt tcacacagcg tgtggtggac aagctttggc aaggcatgtt caacaaagaa   6600
tctaaacttc ttatagattt tataattcaa ctaattgcac agtcaaagag aagatcacag   6660
ggattgtcac tggatgcagt gtatcattgc ctcaatagga ccatcttgta ccagttctca   6720
cgggcacaca aaaccgttcc tcagcaagta gctctgcttg attcactcag ggtcctcact   6780
gtaaacagaa acttgatcct gggacctggg aaccatgacc aagaattcat tagctgtctg   6840
gcccactgct tgataaatct acatgttgga agcaacgtgg atggatttgg actggaagca   6900
gaagcccgca tgaccacatg gcacattatg atcccctcgg acattgaacc agatggtagt   6960
tacagccaag atattagtga agggcgtcag cttctcataa aagctgtcaa cagagtttgg   7020
actgaactga tacatagtaa gaaacaagtc ttagaggaac ttttcaaagt aactctacct   7080
gtgaatgaaa ggggccacgt ggacatagct acagcaaggc cactcattga agaagctgcc   7140
ctgaagtgct ggcagaatca tttggcccat gaaaagaaat gcataagtcg aggagaagct   7200
ttagcgccca ccacacagtc caaattatcc cgtgtcagca gtggctttgg tctttccaag   7260
ttaacaggat caagaaggaa tcgaaaagaa agtggtctta ataaacacag tctttccacc   7320
caggagattt cgcagtggat gtttactcac attgctgttg ttcgtgactt agtagataca   7380
caatataaag aatatcagga gcgtcagcag aatgccctga agtacgtgac agaagagtgg   7440
tgtcagatcg agtgcgagct gttgagggag cgggggctgt ggggccctcc catcggctcc   7500
cacctcgaca agtggatgct ggagatgaca gaagggccct gcaggatgag gaaaaagatg   7560
gtgcgaaatg atatgtttta taaccattac ccttacgtgc cagaaactga gcaagagaca   7620
aatgtggcgt ctgagatccc aagtaaacag cctgagacac ccgatgatat tcctcaaaag   7680
aaacctgctc gatatagaag agccgtaagt tatgacagta aagagtacta catgcgactg   7740
gcctctggca atcccgccat tgtccaagac gccattgtgg agagttcaga aggtgaagct   7800
gctcagcaag aaccagagca tggggaagac actattgcta aagtcaaagg tttggtcaag   7860
cctcctctaa aacgctcccg atctgcacct gatggaggag atgaggagaa ccaggagcag   7920
ctacaagacc agattgctga gggcagctcc atagaagagg aggagaaaac agataatgct   7980
accttactgc gcctgttaga ggaaggagaa aagatccaac acatgtaccg ctgtgctcga   8040
gtccagggcc tagataccag tgaggggctc cttctttttg gtaaagagca tttttatgtg   8100
attgatggat ttaccatgac agcaaccagg gaaataagag atattgaaac cttacctcca   8160
aatatgcatg agcctattat tcctagagga gccaggcaag gccctagtca actcaagaga   8220
acatgcagca tttttgcata tgaagatatc aaggaagttc ataaaaggag atatctcctg   8280
cagcctattg ctgtggaagt ttctctggga gatggacgga attacctcct tgcttttcag   8340
aaaggaatca gaaacaaagt ctatcaaagg tttttggctg tagtgccatc tctaacggac   8400
agttcagaat ctgtatctgg gcaacgacca aacacgagtg tggagcaggg atctgggtta   8460
cttagcactt tggttggaga gaagtctgtg actcagagat gggagagagg tgaaatcagc   8520
```

aacttccaat atttgatgca tttgaacact ttggctggca gatcatataa tgatctcatg 8580
cagtatcctg tcttcccctg gatccttgca gattatgact cagaggaggt ggatcttact 8640
aatcccaaga cgtttagaaa cctggctaag ccaatgggag cacaaacaga tgaacgatta 8700
gctcagtata agaagcggta taaagactgg gaggatccta atggagaaac tcctgcatac 8760
cactatggga cccactattc atctgcaatg attgtggcct cataccttgt aaggatggag 8820
cctttcacac agatattctt aaggctacag ggtggccact ttgacctggc tgaccggatg 8880
tttcacagtg tgcgcgaggc ctggtattca gcgtcaaagc acaatatggc agatgtaaaa 8940
gaacttatcc cagagttctt ttatttacca gaattcctgt tcaattccaa caactttgat 9000
ctaggctgta aacaaaatgg caccaagctt ggagatgtta tccttccacc ctgggcaaaa 9060
ggggacccac gagaattcat cagagtccat cgtgaggctt tggagtgtga ttacgtgagt 9120
gcccatctac atgagtggat tgacttaatc ttcggttata aacagcaagg ccctgctgca 9180
gtagaagctg taaatgtctt ccatcatctt ttttatgagg gtcaagtgga tatctacaac 9240
atcaatgacc cactaaagga gacagccaca attgggttca ttaataactt cggtcagatc 9300
cctaaacagt tatttaaaaa acctcatcca ccaaagcgag tgagaagtcg actcaatgga 9360
gacaatgcag gaatctctgt cctaccagga tctacaagtg acaagatctt ttttcatcat 9420
ctagacaact tgaggccttc tctaacacct gtaaaagaac tcaaagaacc tgtaggacaa 9480
atcgtatgta cagataaagg tattcttgcg gtggaacaga ataaggttct tatcccacca 9540
acctggaata aaacttttgc ttggggctat gcagacctca gttgcagact gggaacctat 9600
gagtcagaca aggccatgac tgtttatgaa tgcttgtctg agtggggcca gattctctgt 9660
gcaatctgcc ccaaccccaa gctggtcatc acgggtggaa caagcacggt tgtgtgtgtg 9720
tgggagatgg gcacctccaa agaaaaggcc aagaccgtca ccctcaaaca ggccttactg 9780
ggccacactg ataccgtcac ctgcgccaca gcatcattag cctatcacat aattgtcagt 9840
gggtcccgtg atcgaacctg tatcatttgg gatttgaaca aactgtcatt tctaacccag 9900
cttcgagggc atcgagctcc agtttctgct ctttgtatca atgaattaac aggggacatt 9960
gtgtcctgcg ctggcacata tatccatgtg tggagcatca atgggaaccc tatcgtgagt 10020
gtcaacacgt tcacaggtag gagccagcag atcatctgct gctgcatgtc ggagatgaac 10080
gaatgggaca cgcagaacgt catagtgaca ggacactcag atggagtggt tcggttttgg 10140
agaatggaat ttttgcaagt tcctgaaaca ccagctcctg agcctgctga agtcctagaa 10200
atgcaggaag actgtccaga agcacaaata gggcaggaag cccaagacga ggacagcagt 10260
gattcagaag cagatgagca gagcatcagc caggacccta aggacactcc aagccaaccc 10320
agcagcacca gccacaggcc ccgggcagcc tcctgccgcg caacagccgc ctggtgtact 10380
gacagtggct ctgacgactc cagacgctgg tccgaccagc tcagtctaga tgagaaagac 10440
ggcttcatat ttgtgaacta ttcagagggc cagaccagag cccatctgca gggccccctt 10500
agccaccccc accccaatcc cattgaggtg cggaattaca gcagattgaa acctgggtac 10560
cgatgggaac ggcagctggt gttcaggagt aagctgacta tgcacacagc ctttgatcga 10620
aaggacaatg cacacccagc tgaggtcact gccttgggca tctccaagga tcacagtagg 10680
atcctcgttg gtgacagtcg aggccgagtt ttcagctggt ctgtgagtga ccagccaggc 10740
cgttctgctg ctgatcactg ggtgaaggat gaaggtggtg acagctgctc aggctgctcg 10800
gtgaggtttt cactcacaga aagacgacac cattgcagga actgtggtca gctcttctgc 10860

```
cagaagtgca gtcgctttca atctgaaatc aaacgcttga aaatctcatc cccggtgcgt  10920
gtttgtcaga actgttatta taacttacag catgagagag gttcagaaga tgggcctcga  10980
aattgttgaa gattcaacaa gctgagtgga gaccatggtc tgtagacccc ttcccgattc  11040
tcctgtccca gcttggaagg cattgaaaac agtctccgtt tacacatctc ttcataccac  11100
gtgtttgaag tgttaaaatt caaagggatc attgaataaa acgggtgtag agtacaggaa  11160
tggggcagac gcgattcagg tgaacagcac aagaagaata tgaggtggtt cctaggagca  11220
acactttcga cctccagttc tccctgatga cagtagctgt ctccaagaga aaaatcctca  11280
cttattaact ctcttttctt gcatctcatt tttatagagc tactcatcct tatttggaaa  11340
aaccaacaac aaaaaaggct tttagaaaat ggttgtaaat ctgacttctt tgcaagtaac  11400
tatgtatatt gtaaatagat ataaaaggcc ttttttctaa ataaggactt aactgcctgt  11460
aacatgaaac ttcaaactaa accactaact caatgaacta cttatggttt gtctgacatc  11520
cctcacttac caattaatta taaatatgtt tttttaaatc cccaaagaca ttatctgtgg  11580
tcttttttc ctttcaagct cagcctgtgt gcctgatgtc atttctttca agttgcccac  11640
agtatctcca cttaaactag gctagtaacc aaaataatgt ggaccttctt taggaaacag  11700
tgtgggagaa taggagtcca gccgtaagat aaactggaaa tatttgggcg tcttgtacct  11760
ggctacgcac cacctcagtg ttgttcctac ataaacaggg ccccttttaa acttgtatgt  11820
ggactgctgt ttggtcaaag aataccttct tagcattgca gaaaggtggt cagatgacca  11880
gtgtagtgca ggaaacagcc ctgtctcaac taatggaaat atatttgcat gtaacccaaa  11940
attagcttat cttgcataga acataataag tatgtgtctt tggtgacact aatgttctac  12000
tatagcttat tttcaaacaa ggggtaaaaa aaggaaagaa agaagtgtac agaattaaca  12060
tataaacttt gttgtaaaac tgaatcatgt cagaactgct taaaattaac ctttaccatt  12120
taatgtcatc tacctgaaaa cagtgagatt tatactgtat caatgtctat ttttttgttt  12180
ttgctatgaa tataattaca gtattttaat atttagttat ttaatttgtt ctactagttg  12240
gatacagaac acacaaatcc agggggatta aagctggaag gggctaagag attagtttac  12300
agagaaaagg cttggtggtg ggattttttt aaatgtgtgt tatgtacata tatatatata  12360
tataatatat attaaaaatg aaacaattaa tctagatttt aacattttca gaaacttagt  12420
gataacatta tgaacaattc taaaagccct gtgatttgaa aaatatagaa tcattaatgg  12480
cccaagatag gccttcacac cttcacaggt gcgaaaggaa aggccttcac accctcacag  12540
aggcatcatg caaaggacag cggctttggc ttttccaatt ttccatcttt aggccctggt  12600
gagaggcaca cttatgcact aaaatgcaca tatatgcaca tgcattcaaa aataggcatt  12660
tggtacaatg gtgatcttgt acctgatggg ctgaaaccag cttaagaaca aatttgttct  12720
tcctgatatg ataactaggt ctccaagaga aaatagaaag gctgctttag tgccttacgc  12780
ttactaaatt taaatcttta tttacctggg tttgagccta cagtctattt atgattacat  12840
atcaaaattg attaaaacac ttccatttct aaaagttcaa atatacttgt taataaaagg  12900
attatcggca ttaatacttt aatttaaaga aaagttgtgt tctgttttcc tttctgtgtc  12960
ttactccccc cacactctcc ctcccccatc accatcttca attctaataa ataatgctga  13020
tgttcaacag ttgcagaaat tgtgctatta tgtaactgtg ggccttgccc ctgtctggcc  13080
ctctagatga tttgtagcag tgttattcta cactttttaa aagaagcgtc ctccttttgt  13140
ccatgaatca tgtttacccc atacccagtg gcagaggtgt tctttaaaga cttgaatata  13200
tgaatgtgtg tgtgtagtta cttaaaggtt attcctcttt gtaataggaa actatatggg  13260
```

atgaacactt ttaaactttc cgacacaact tccattacta actttctaac agaacttcca 13320
taactagaag gtggaaacca aaaccctcat ggtagtattt cctctggcag ctggtgctgt 13380
gggcaactgt tttgttcaat cgggtttctt ttctttttgc ctctaatgca gaaatcaaca 13440
gaatcactca cacatacaag tacactcaca tacataaact aattatttct ctggatatct 13500
ttctgtgttc catgtaaatt tatttaccaa catctattgt caacatgtac atctacctta 13560
gtatggtctg cattcttttt ctgagagtac ctcatagggc tcctgcctga tctttgtagt 13620
ttgttcattc atccatccac ctgttcattt gttcatccat gtattctaac atttctatgt 13680
agtgtgcaac tctaatgtca tgcttttgaa gaagagaata gctgcccata gcagccatcc 13740
gtctggataa tagcaaaaca ctctagataa gttattttgc actttcttat gtataaagtt 13800
ggtagaaact tatttttgct ttgtatcatt taaatacatt ttgttttggt aaatgaactg 13860
tgtataaaat atttatgccg ttaaaactgt ttttagaaag tatttttaat ttcagcaagt 13920
ttggttactt gttgcatgac tcttaacaca gctgactttt tgtgtcagtg caatgtatat 13980
tttttgtcct gttattaact tgtaagccct agtaatggcc aattatttgt acagcaacag 14040
aagtaaattg aagatactgg ctaagactgg attgattgtg gacttttata ctatattgca 14100
gaaaccaata tctgtttctt ggtggttatg taaaagacct gaagaattac tatctagtgt 14160
gcagtctgtg atatctgaat gttcattgta tatttgtctc tgatgcaaaa aggtagagta 14220
acacaattac aatacatgat taaatgcaat agtccaggta cttaagtaat tttttttca 14280 tttcaaataa atacctattt accaccaaaa gaaagaaaaa aaaaaaaaa 14329

<210> SEQ ID NO 50
<211> LENGTH: 12778
<212> TYPE: DNA
<213> ORGANISM: Homo sapiens

<400> SEQUENCE: 50
cgcggcccga gcgcctcttt tcgggattaa aagcgccgcc agctcccgcc gccgccgccg 60
tcgccagcag cgccgctgca gccgccgccg ccggagaagc aaccgctggg cggtgagatc 120
cccctagaca tgcggctcgg gggcgggcag ctggtgtcag aggagctgat gaacctgggc 180
gagagcttca tccagaccaa cgacccgtcg ctgaagctct tccagtgcgc cgtctgcaac 240
aagttcacga cggacaacct ggacatgctg ggcctgcaca tgaacgtgga gcgcagcctg 300
tcggaggacg agtggaaggc ggtgatgggg gactcatacc agtgcaagct ctgccgctac 360
aacacccagc tcaaggccaa cttccagctg cactgcaaga cagacaagca cgtgcagaag 420
taccagctgg tggcccacat caaggagggc ggcaaggcca acgagtggag gctcaagtgt 480
gtggccatcg gcaaccccgt gcacctcaag tgcaacgcct gtgactacta caccaacagc 540
ctggagaagc tgcggctgca cacggtcaac tccaggcacg aggccagcct gaagttgtac 600
aagcacctgc agcagcatga gagtggtgta gaaggtgaga gctgctacta ccactgcgtt 660
ctgtgcaact actccaccaa ggccaagctc aacctcatcc agcatgtgcg ctccatgaag 720
caccagcgaa gcgagagcct gcgaaagctg cagcggctgc agaagggcct tccagaggag 780
gacgaggacc tggggcagat cttcaccatc cgcaggtgcc cctccacgga cccagaagaa 840
gccattgaag atgttgaagg acccagtgaa acagctgctg atccagagga gcttgctaag 900
gaccaagagg gcggagcatc gtccagccaa gcagagaagg agctgacaga ttctcctgca 960
acctccaaac gcatctcctt cccaggtagc tcagagtctc cctctcttc gaagcgacca 1020

-continued

```
aaaacagctg aggagatcaa accggagcag atgtaccagt gtccctactg caagtacagt   1080
aatgccgatg tcaaccggct ccgggtgcat gccatgacgc agcactcggt gcaacccatg   1140
cttcgctgcc ccctgtgcca ggacatgctc aacaacaaga tccacctcca gctgcacctc   1200
acccacctcc acagcgtggc acctgactgc gtggagaagc tcattatgac ggtgaccacc   1260
cctgagatgg tgatgccaag cagcatgttc ctcccagcag ctgttccaga tcgagatggg   1320
aattccaatt tggaagaggc aggaaagcag cctgaaacct cagaggatct gggaaagaac   1380
atcttgccat ccgcaagcac agagcaaagc ggagatttga aaccatcccc tgctgaccca   1440
ggctctgtga gagaagactc aggcttcatc tgctggaaga aggggtgcaa ccaggttttc   1500
aaaacttctg ctgcccttca gacgcatttt aatgaagtgc atgccaagag gcctcagctg   1560
ccggtgtcag atcgccatgt gtacaagtac cgctgtaatc agtgtagcct ggccttcaag   1620
accattgaaa agttgcagct ccattctcag taccatgtga tcagagctgc caccatgtgc   1680
tgtctttgtc agcgcagttt ccgaactttc caggctctga agaagcacct tgagacaagc   1740
cacctggagc tgagtgaggc tgacatccaa cagctttatg gtggcctgct ggccaatggg   1800
gacctcctgg caatgggaga ccccactctg gcagaggacc ataccataat tgttgaggaa   1860
gacaaggagg aagagagtga cttggaagat aaacagagcc caacgggcag tgactctggg   1920
tcagtacaag aagactcggg ctcagagcca aagagagctc tgcctttcag aaaaggtccc   1980
aattttacta tggaaaagtt cctagaccct tctcgccctt acaagtgtac cgtctgcaag   2040
gaatctttca ctcaaaagaa tatcctgcta gtacactaca attctgtctc ccacctgcat   2100
aagttaaaga gagcccttca agaatcagca accggtcagc cagaacccac cagcagccca   2160
gacaacaaac cttttaagtg taacacttgt aatgtggcct acagccagag ttccactctg   2220
gagatccata tgaggtctgt gttacatcaa accaaggccc gggcagccaa gctggaggct   2280
gcaagtggca gcagcaatgg gactgggaac agcagcagta tttccttgag ctcctccacg   2340
ccaagtcctg tgagcaccag tggcagtaac acctttacca cctccaatcc aagcagtgct   2400
ggcattgctc caagctctaa cttactaagc caagtgccca ctgagagtgt agggatgcca   2460
cccctgggga atcctattgg tgccaacatt gcttcccctt cagagcccaa agaggccaat   2520
cggaagaaac tggcagatat gattgcatcc aggcagcagc aacaacagca gcagcaacag   2580
caacaacaac aacaacaaca acaacaacaa gcacaaacgc tggcccaggc ccaggctcaa   2640
gttcaagctc acctgcagca ggagctgcag caacaggctg ccctgatcca gtctcagctg   2700
tttaacccca ccctccttcc tcacttcccc atgacaactg agaccctgct gcaactacag   2760
cagcagcagc acctcctctt ccctttctac atccccagtg ctgagttcca gcttaacccc   2820
gaggtgagct tgccagtgac cagtggggca ctgacactga ctgggacagg cccaggcctg   2880
ctggaagatc tgaaggctca ggttcaggtc ccacagcaga gccatcagca gatcttgccg   2940
cagcagcagc agaaccaact ctctatagcc cagagtcact ctgccctcct tcagccaagc   3000
cagcaccccg aaaagaagaa caaattggtc atcaaagaaa aggaaaaaga aagccagaga   3060
gagagggaca gcgccgaggg gggagagggc aacaccggtc cgaaggaaac actgccagat   3120
gccttgaagg ccaaagagaa gaaagagttg gcaccagggg gtggttctga gccttccatg   3180
ctccctccac gcattgcttc agatgccaga gggaacgcca ccaaggccct gctggagaac   3240
tttggctttg agttggtcat ccagtataat gagaacaagc agaaggtgca gaaaaagaat   3300
gggaagactg accagggaga gaacctggaa aagctcgagt gtgactcctg cggcaagttg   3360
ttttccaaca tcttgatttt aaagagtcat caagagcacg ttcatcagaa ttactttcct   3420
```

-continued

```
ttcaaacagc tcgagaggtt tgccaaacag tacagagacc actacgataa actgtaccca   3480
ctgaggcccc agaccccaga gccaccacca cctccccctc cacccccctcc acccccactt   3540
ccggcagcgc cgcctcagcc ggcgtccaca ccagccatcc ccgcatcagc cccacccatc   3600
acctcaccta caattgcacc ggcccagcca tcagtgccgc tcacccagct ctccatgccg   3660
atggagctgc ccatcttctc gccgctgatg atgcagacga tgccgctgca gaccttgccg   3720
gctcagctac ccccgcagct gggacctgtg gagcctctgc ctgcggacct ggcccaactc   3780
taccagcatc agctcaatcc aaccctgctc cagcagcaga acaagaggcc tcgcaccagg   3840
atcacagatg atcagctccg agtcttgcgg caatattttg acattaacaa ctcccccagt   3900
gaagagcaaa taaaagagat ggcagacaag tccgggttgc cccagaaagt gatcaagcac   3960
tggttcagga acactctctt caaagagagg cagcgtaaca aggactcccc ttacaacttc   4020
agtaatcctc ctatcaccag cctggaggag ctcaagattg actcccggcc cccttcgccg   4080
gaacctccaa agcaggagta ctggggaagc aagaggtctt caagaacaag gtttacggac   4140
taccagctga gggtcttaca ggacttcttc gatgccaatg cttacccaaa ggatgatgaa   4200
tttgagcaac tctctaattt actgaacctt ccaacccgag tgatagtggt gtggtttcag   4260
aatgcccgac agaaggccag gaagaattat gagaatcagg gagagggcaa agatggagag   4320
cggcgtgagc ttacaaatga tagatacatt cgaacaagca acttgaacta ccagtgcaaa   4380
aaatgtagcc tggtgtttca gcgcatcttt gatctcatca agcaccagaa gaagctgtgt   4440
tacaaggatg aggatgagga ggggcaggac gacagccaaa atgaggattc catggatgcc   4500
atggaaatcc tgacgcctac cagctcatcc tgcagtaccc cgatgccctc acaggcttac   4560
agcgccccag caccatcagc caataataca gcttcctccg ctttcttgca gcttacagcg   4620
gaggctgagg aactggccac cttcaattca aaaacagagg caggcgatga gaaaccaaag   4680
ctggcggaag ctcccagtgc acagccaaac caaacccaag aaaagcaagg acaaccaaag   4740
ccagagctgc agcagcaaga gcagcccgag cagaagacca acactcccca gcagaagctc   4800
ccccagctgg tgtccctgcc ttcgttgcca cagcctcctc cacaagcgcc ccctccacag   4860
tgccccttac cccagtcgag ccccagtcct tcccagctct cccacctgcc cctcaagccc   4920
ctccacacat caactcctca acagctcgca aacctacctc ctcagctaat cccctaccag   4980
tgtgaccagt gtaagttggc atttccgtca tttgagcact ggcaggagca tcagcagctc   5040
cacttcctga gcgcgcagaa ccagttcatc cacccccagt tttggacag gtccctggat   5100
atgcctttca tgctctttga tcccagtaac ccactcctgg ccagccagct gctctctggg   5160
gccatacctc agattccagc aagctcagcc acttctcctt caactccaac ctccacaatg   5220
aacactctca agaggaagct ggaggaaaag gccagtgcaa gccctggcga aaacgacagt   5280
gggacaggag gagaagagcc tcagagagac aagcgtttga gaacaaccat cacaccggaa   5340
caactagaaa ttctctacca gaagtatcta ctggattcca atccgactcg aaagatgttg   5400
gatcacattg cacacgaggt gggcttgaag aaacgtgtgg tacaagtctg gtttcagaac   5460
acccgagctc gggaaaggaa aggacagttc cgggctgtag gcccagcgca ggcccacagg   5520
agatgccctt tttgcagagc gctcttcaaa gccaagactg ctcttgaggc tcatatccgg   5580
tcccgtcact ggcatgaagc caagagagct ggctacaacc taactctgtc tgcgatgctc   5640
ttagactgtg atgggggact ccagatgaaa ggagatattt ttgacggaac tagcttttcc   5700
cacctacccc caagcagtag tgatggtcag ggtgtccccc tctcacctgt gagtaaaacc   5760
```

-continued

```
atggaattgt cacccagaac tcttctaagc ccttcctcca ttaaggtgga agggattgaa   5820
gactttgaaa gcccctccat gtcctcagtt aatctaaact ttgaccaaac taagctggac   5880
aacgatgact gttcctctgt caacacagca atcacagata ccacaactgg agacgagggc   5940
aacgcagata acgacagtgc aacgggaata gcaactgaaa ccaaatcctc ttctgcaccc   6000
aacgaagggt tgaccaaagc ggccatgatg gcaatgtctg agtatgaaga tcggttgtca   6060
tctggtctgg tcagcccggc cccgagcttt tatagcaagg aatatgacaa tgaaggtaca   6120
gtggactaca gtgaaacctc aagccttgca gatccctgct ccccgagtcc tggtgcgagt   6180
ggatctgcag gcaaatctgg tgacagcgga gatcggcctg ggcagaaacg ttttcgcact   6240
caaatgacca atctgcagct gaaggtcctc aagtcatgct ttaatgacta caggacaccc   6300
actatgctag aatgtgaggt cctgggcaat gacattggac tgccaaagag agtcgttcag   6360
gtctggttcc agaatgcccg ggcaaaagaa aagaagtcca agttaagcat ggccaagcat   6420
tttggtataa accaaacgag ttatgaggga cccaaaacag agtgcacttt gtgtggcatc   6480
aagtacagcg ctcggctgtc tgtacgtgac catatctttt cccaacagca tatctccaaa   6540
gttaaagaca ccattggaag ccagctggac aaggagaaag aatactttga cccagccacc   6600
gtacgtcagt tgatggctca acaagagttg gaccggatta aaaaggccaa cgaggtcctt   6660
ggactggcag ctcagcagca agggatgttt gacaacaccc ctcttcaggc ccttaacctt   6720
cctacagcat atccagcgct ccagggcatt cctcctgtgt tgctcccggg cctcaacagc   6780
ccctccttgc caggctttac tccatccaac acagctttaa cgtctcctaa gccgaacttg   6840
atgggtctgc ccagcacaac tgttccttcc cctggcctcc ccacttctgg attaccaaat   6900
aaaccgtcct cagcgtcgct gagctcccca accccagcac aagccacgat ggcgatgggc   6960
cctcagcaac ccccccagca gcagcagcag cagcagcaac cacaggtgca gcagcctccc   7020
ccgccgccag cagcccagcc gccacccaca ccacagctcc cactgcaaca gcagcagcaa   7080
cgcaaggaca aagacagtga gaaagtaaag gagaaggaaa aggcacacaa agggaaaggg   7140
gaacccctgc ctgtccccaa gaaggagaaa ggagaggccc ccacggcaac tgcagccacg   7200
atctcagccc cgctgcccac catggagtat gcggtagacc ctgcacagct gcaggccctg   7260
caggccgcgt tgacttcgga ccccacagca ttgctcacaa gccagttcct tccttacttt   7320
gtaccaggct tttctcctta ttatgctccc cagatccctg gcgccctgca gagcgggtac   7380
ctgcagccta tgtatggcat ggaaggcctg ttcccctaca gccctgcact gtcgcaggcc   7440
ctgatggggc tgtccccagg ctccctactg cagcagtacc agcaatacca gcagagtctg   7500
caggaggcaa ttcagcagca gcagcagcgg caactacagc agcagcagca gcaaaaagtg   7560
cagcagcagc agcccaaagc aagccaaacc ccagtccccc ccggggctcc ttccccagac   7620
aaagaccctg ccaaagaatc ccccaaacca gaagaacaga aaaacacccc ccgtgaggtg   7680
tccccccctcc tgccgaaact ccctgaagag ccagaagcag aaagcaaaag tgcggactcc   7740
ctctacgacc ccttcattgt tccaaaggtg cagtacaagt tggtctgccg caagtgccag   7800
gcgggcttca gcgacgagga ggcagcgagg agccacctga agtccctctg cttcttcggc   7860
cagtctgtgg tgaacctgca agagatggtg cttcacgtcc ccaccggcgg cggcggcggt   7920
ggcagtggcg gcggcggcgg cggtggcggc ggcggcggcg gcggcggctc gtaccactgc   7980
ctggcgtgcg agagcgcgct ctgtggggag gaagctctga gtcaacatct cgagtcggcc   8040
ttgcacaaac acagaacaat cacgagagca gcaagaaacg ccaaagagca ccctagttta   8100
ttacctcact ctgcctgctt ccccgatcct agcaccgcat ctacctcgca gtctgccgct   8160
```

```
cactcaaacg acagcccccc tcccccgtcg gccgccgccc cctcctccgc ttccccccac   8220
gcctccagga agtcttggcc gcaagtggtc tcccgggctt cggcagcgaa gccccccttct   8280
tttcctcctc tctcctcatc ttcaacggtt acctcaagtt catgcagcac ctcaggggtt   8340
cagccctcga tgccaacaga cgactattcg gaggagtctg acacggatct cagccaaaag   8400
tccgacggac cggcgagccc ggtggagggt cccaaagacc ccagctgccc caaggacagt   8460
ggtctgacca gtgtaggaac ggacaccttc agattgtaag ctttgaagat gaacaataca   8520
aacaaatgaa tttaaataca aaaattaata acaaaccaat ttcaaaaata gactaactgc   8580
aattccaaag cttctaacca aaaaacaaaa aaaaaaaaaa aaagaaaaaa aagaaaaagc   8640
gtgggttgtt ttcccatata cctatctatg ccggtgattt tacattcttg tctttttctt   8700
ttcttttaat attaaaaaaa aaaaaaaagc cctaaccctg ttacattgtg tccttttgaa   8760
ggtactattg gtctgggaaa cagaagtccg cagggcctcc ctaatgtctt tggagcttaa   8820
acccccttgta tatttgcccc ttttcaataa acgccccacg ctgatagcac agaggagccc   8880
ggcatgcact gtatgggaaa gcagtccacc ttgttacagt tttaaatttc ttgctatctt   8940
agcattcaga taccaatggc ttgctaaaag aaaaaaagaa atgtaatgtc tttttattct   9000
caggtcaatc gctcacactt tgttttcaga atcattgttt tatatattat tgtttttttca   9060
gttttttttt tttttttgt tccagaaaag atttttttgtt ttgttaactt aaaaatgggc   9120
agaaagtatt caagaaaaac aatgtgaact gctttagctt tctggggatt tttaaggata   9180
gcttttctgc tgaagccaat ttcaagggga aaagttaagc actcccactt tcaaaaaaaa   9240
aaaaaaataa taacccacac acacaaagag tgttgaggac ttgtagctta aaaaaaataa   9300
gttttaaaaa ctgactttct gtatttatga tagatatgac catttttggt gttgagtaga   9360
ttgttgcatt ggaaatgaac tgaagcagta tggtagattt aaaaggaaaa aaaaaaaaaa   9420
accttttgtg tacatttagc tttttgtatg gtccagctga cagctcctca tttgatgttg   9480
tcttgttcat tcctagcaga tgatagattg caatccgttg attcgcctaa gcttttctcc   9540
ccttgtccct taattccact ttctctttct tgtcccttaa ttccactttc tctttccttc   9600
tcccacctcc cgtcctataa tctcccactt aaggtagctg ccttcatttc ttagagggag   9660
ctgcagaatt attttataaa actaaagaaa gaatttcaag ggattctagg ggtcattagg   9720
atcctcacag attatttttg gttggggagt tgaaactttt taaaggcata taattctagt   9780
tacctgtgtc tgttagcttt gtgcatttat tttttattta tccttctttt ggcttttttt   9840
tctttgtacc ccttctttc ctccttgttt ggtaggagct tcaaatattc tttttttttc   9900
tatactaaag gatttgtttc catttgtgta attggctgtg tacttttctt ttctaaaaaa   9960
agtttttggt tagggatttg gtttttggtt ttgtgtttgt tttttctttc ctctctcaga  10020
aaaaaaaatt tcatgcttta aataaaatcc aaagacacac cctttcactg ctgatgcaga  10080
aaaaagggaa agggttcttg ttacttgaga atttgtttct gatttaaaca aacaagactt  10140
agtttaataa aagaaagaga aaaacaaaag attcccaggt tgttatgtgc ttcttctgca  10200
agcagagagg caaatgttaa tgacaattcc atataccaaa agacacattt tttacttcaa  10260
agttttgtcc ttgtgttagg cagtctgagc agcgagtgat ccagagcgca gccaacaaag  10320
cagcagatag cagtgtacag aaagcaaaaa aggaactgta tgtgaggcac ttgtttctgt  10380
taatatccat attcctgtta acacacaccc tttctcatgt aaaaagaaaa ataaataaat  10440
ggtctgaact ttgaaaactt tgtgctgcta aaacatagat tttggagaca aataaataga  10500
```

```
tgctttgctg tttcactttc atagctaaac atcaacagaa accatctccc cttgccccca  10560
aagtgtgaaa tccttcttcc cttcgttttc ttccttatgt ttcaaaaggg aactttgaag  10620
actgtgaata caggttccat tggtcacctt tcgggcttct ttccccagtg ctgaagccac  10680
tcatcgactt tgcaaaagac tggagcattc caagatctga aaatggattt tttttctttt  10740
tttctttttt agccgggact attttatttt tatgaatttg tttttagttt aatgaaatag  10800
tagatcctga aatgttgtac atatttctaa ctaggctgat gcacagtgca aattcctttt  10860
ttaattgttt tttttaagta gaaatactaa agaaagaata ccatctaact attcatacca  10920
gtatccagtt gtagcataag gtgtcaaaag caagtacgca aaacatttac tgttttaaca  10980
agctatttcc ttttaacaag aaatcttgta tttcttcctg tgtttgagat gaacattttt  11040
aaattttaaa gttgtacagt tttttgtttt ccattatttt atcttgtttg taactctatg  11100
aaatatatat atatatattt tttgccattt aactgttgta tgttactctg tgtctgtacc  11160
atatagaaaa aaaattgttt ttgtttttgg ttctctatgt gatatcagtt aacaatgtaa  11220
cactagcttt acctgtcaaa ttctgctagg tcttctctga aaacgttgtt tttaaaaatg  11280
atattgcttg gtaatagtgc aatttctatc cttttccctc cccccctcaac ttttaagttc  11340
ttttctttat aattttgctg ccccctccct gatggtttgg gtttttgttt ttgtttttgt  11400
tttttttttt catggagcta ctatgccatc ctccctctgt gaggcagagt gactgtcagt  11460
gttttgttat gccatgcctt gagctgtggg tgtttggcga caataaggtg gttgaataga  11520
ttggctgagc acacttccac ccacctagtg ttctcagagg ggttatgtga ttgtttcaac  11580
ctggagtggg ttgcaccctt aatgctttcc tctgcaacta aaccgcccac atatatgttc  11640
attgaaaaaa gtaagaataa ttctcagcac taacccagaa gtagcaaagc agtcagtgat  11700
ggtgaacatt agaggtcaaa catgagttag atgtttgtgg gctgacagcc atcgtggcta  11760
tgaccagtac tatttacaaa gcatgaattc actacaatgc tcaactgttt gtttagcttt  11820
atctcacttg gggaatttat tcctgtctgc tgcattgtag gtagctgggt aggatatatt  11880
tccacttgct ttttaaatta gttcttcacc tccattgaca ctcgtttttt ggttttctcc  11940
ctatagtgtg ggttggtgct agacaccagt ctgacccaca gaatgggagt tatttcatcc  12000
atctttcctc catccttcca aaaaccacat atctacacaa ggaaaaaattt aatacatcta  12060
ggaatttttt ttttaattac aagctattta aagagatgaa tgtggccaaa gttttacaca  12120
attgaaaata aagtaaaaca gacggcatgt gtttaaacct gagtttatca ggcatggcag  12180
gaagttgcag gagagagagg cagtgaccca agccagtgca cttgatgttc atggacatat  12240
atttttttta aataataaat taaaacattt taaatagaag cataaattga gttgtttgtt  12300
ggcgctgaga tactgcccac tgtgaaacaa agctttgact agtttttttgt ttgtttactt  12360
tcttcagggg ggagggggc aagtttgggt aggaaagaaa gcataaatga acgtgaccct  12420
gaggtgaaga ggtatatgaa cagcctttgc aatgtacaaa aagaaaaaaa aacaaaaaac  12480
aacaaaaaaa atagagcaag tgaaaccaaa aatgatgttc ttggtgtttt tctataatgt  12540
agtcttgtta gcttttttgt tactgtaaca atgctgatct cgaactgtac caaaatacat  12600
ggagactaac aaacagaacc acatggaact ttcaaactga aaaaaaaatt tgtcacaaaa  12660
actttgttgt catagttaag ttgattgtag atggtaattg aatatactcc tttgaaaata  12720
tttcatcaag tatgtttcct gctcattgtg atacattaaa aaaaaaatat gagcaaaa    12778
```

<210> SEQ ID NO 51
<211> LENGTH: 4826

<212> TYPE: DNA
<213> ORGANISM: Homo sapiens

<400> SEQUENCE: 51
gggcgcgggc agctctgcgt ccgaagctgc tccgacgccg tcgctgggac caagatggac 60
ctcccggcgc tgctccccgc cccgactgcg cgcggagggc aacatggcgg cggccccggc 120
ccgctccgcc gagccccagc gccgctcggc gcgagccccg cgcgccgccg cctgctactg 180
gtgcggggcc ctgaagatgg cgggcccggg gcgcggcccg gggaggcctc cgggccaagc 240
ccgccgcccg ccgaggacga cagcgacggc gactctttct tggtgctgct ggaagtgccg 300
cacggcggcg ctgccgccga ggctgccgga tcacaggagg ccgagcctgg ctcccgtgtc 360
aacctggcga gccgccccga gcagggcccc agcggcccgg ccgccccccc cggccctggc 420
gtagccccgg cgggcgccgt caccatcagc agccaggacc tgctggtgcg tctcgaccgc 480
ggcgtcctcg cgctgtctgc gccgcccggc cccgcaaccg cgggcgccgc cgctccccgc 540
cgcgcgcccc aggcctccgg ccccagcacg cccggctacc gctgccccga gccgcagtgc 600
gcgctggcct tcgccaagaa gcaccagctc aaggtgcacc tgctcacgca cggcggcggt 660
cagggccggc ggcccttcaa gtgcccactg gagggctgtg gttgggcctt cacaacgtcc 720
tacaagctca agcggcacct gcagtcgcac gacaagctgc ggcccttcgg ctgtccagtg 780
ggcggctgtg gcaagaagtt cactacggtc tataacctca aggcgcacat gaagggccac 840
gagcaggaga gcctgttcaa gtgcgaggtg tgcgccgagc gcttccccac gcacgccaag 900
ctcagctccc accagcgcag ccacttcgag cccgagcgcc cttacaagtg tgactttccc 960
ggctgtgaga agacatttat cacagtgagt gccctgtttt cccataaccg agcccacttc 1020
agggaacaag agctcttttc ctgctccttt cctgggtgca gcaagcagta tgataaagcc 1080
tgtcggctga aaattcacct gcggagccat acaggtgaaa gaccatttat ttgtgactct 1140
gacagctgtg gctggacctt caccagcatg tccaaacttc taaggcacag aaggaaacat 1200
gacgatgacc ggaggtttac ctgccctgtc gagggctgtg ggaaatcatt caccagagca 1260
gagcatctga aaggccacag cataacccac ctaggcacaa agccgttcga gtgtcctgtg 1320
gaaggatgtt gcgcgaggtt ctccgctcgt agcagtctgt acattcactc taagaaacac 1380
gtgcaggatg tgggtgctcc gaaaagccgt tgcccagttt ctacctgcaa cagactcttc 1440
acctccaagc acagcatgaa ggcgcacatg gtcagacagc acagccggcg ccaagatctc 1500
ttacctcagc tagaagctcc gagttctctt actcccagca gtgaactcag cagcccaggc 1560
caaagtgagc tcactaacat ggatcttgct gcactcttct ctgacacacc tgccaatgct 1620
agtggttctg caggtgggtc ggatgaggct ctgaactccg gaatcctgac tattgacgtc 1680
acttctgtga gctcctctct gggagggaac ctccctgcta ataatagctc cctagggccg 1740
atggaacccc tggtcctggt ggcccacagt gatattcccc caagcctgga cagccctctg 1800
gttctcggga cagcagccac ggttctgcag cagggcagct tcagtgtgga tgacgtgcag 1860
actgtgagtg caggagcatt aggctgtctg gtggctctgc ccatgaagaa cttgagtgac 1920
gacccactgg ctttgacctc caatagtaac ttagcagcac atatcaccac accgacctct 1980
tcgagcaccc cccgagaaaa tgccagtgtc ccggaactgc tggctccaat caaggtggag 2040
ccggactcgc cttctcgccc aggagcagtt gggcagcagg aaggaagcca tgggctgccc 2100
cagtccacgt tgcccagtcc agcagagcag cacggtgccc aggacacaga gctcagtgca 2160
ggcactggca acttctattt ggtatgaagc actctattca gtcaccacca tataggtcac 2220

```
ttctctcata ctcggtcttg aggatattct ggattaatcc tttctatgca gacgtttctg   2280

gtttacaaaa ggacgcagcc ctggactaca agtctggaac tgacaagttc ttatgacctt   2340

gacaaatcac cttaacccat ctgagcctta aattctcatt tatttcctgc ataaggagat   2400

ttggctaaat gctttctgag gtcctttgga gtcctgtggc tccatggtaa tgtgctcctt   2460

tccttgaaga ttgggggttt tgtaatgttg agatactttg cctctatgct tgtcagctca   2520

tgaccagtcc tagaagagga gtcgagacat aagccacctt cagaggttca atggaaactt   2580

taaaaccata ccaaactctt ttttaaaatt agaattaaca agaaaaaaaa aaagggtggg   2640

gtttatgagc cttagttctt ggaggattat aagagtactt ccccagtttt gaggctggac   2700

agttaatata ctttatatca attatacatt taatataatt taatttaaaa taatttaaag   2760

attcttagga gatagtctga ctttcctgac ctagatggga atgatcagat agggattttt   2820

tttgtggcac aggctaaatt tgatggtgac atttatattg ttgagaatgt tacatcttat   2880

tttaccacaa cttttaaaaa atgttacatc ttttgcagta ggatcagttg tgaggcacat   2940

agtagctgag gctccatgga gccacctttc atttctttca gtcagagagg aggacagtct   3000

ctgtctctgc atttctggtg tcttgcttgt cggtggcaga gccatgcttg ccggcatttg   3060

cttaggcggc catagtagtt gctaagtgta caggtgactg ggcagggatg ggaggtggcc   3120

acaggtcaga gacaagtgct cagtcagtcc ctggtgccag gactgtgtgc ctcggtgcct   3180

tgggaaatgg aagctccctg gtgcagctgc agctgtgggt ggaggtagag aagccagcaa   3240

gaccttggtc ttaaccccgt gttcattttc ttgctagctg tgtgacgttg ggctacctcg   3300

cttctctgag tacaaatggt gtgtggtgaa tgggtcccag gtatgctacg agctttgagg   3360

gctgctcttt ttctcttcat agcgataagt gttaaactgt ctttcttagg aaacgttcac   3420

agacttgcaa cagctgatgt cctctgagta ctgtctgact ccctcaggca agttcctgaa   3480

ttcagtacca tcattattat ttttgtgtaa gactttgaca aagtatagcc cctgccacca   3540

gagcagcctg tacagtgggt ctctaaggtg ggacctgccc cgggcctgcc atgcacgtgt   3600

gtgaaacagc gtgaaaagtg tcgcggtaag gtgaccctgg gttacccagg caaggctcgg   3660

tgtttgtttc agaaagcaga gaagtatgta attgatttta aaagtttctg tttaaaatat   3720

ttggctatgt tttagactat gaaggaatga actttgcttc tctggataag aaagtcacat   3780

acattgttcc agctccaagt ttgttcggcc ctcgccacaa gtggatgtag cgtttggccc   3840

tttgtgtgcc ttgctggtga ctctggtttt gggagctcgg atatgtccca gaagcaggct   3900

tatggcactt ctgtagctcc cttgctaccc ttcctttgtg tctagataag tgactgacat   3960

gcttttcttt ggtctcagga aagtgggggc tcagcaagaa ctgattaccg agccattcaa   4020

ctagccaagg aaaaaaagca gagaggagcg gggagcaatg caggtgaggc cgtgtgtgct   4080

gcagccggac gagcaagggc ctgagggttc tctgtcactg ttactggcag aagaaacaca   4140

gcaggtgttt ctgtgctctt ggttttactt ttctgttcag aataccottt tatcaactcc   4200

ttagttttat ttgaacttaa gggaaaaaat tagtaacaaa attcccagca tcagtatgaa   4260

catattttat ttgcctaaac aagctttgtg aaagttaagc gttcaaacac cagtgtcagt   4320

tacctggaag gctactaagg taaataagca aagcaggcca gttgtcagga aagcagagat   4380

tgtgcctggt gctgaatggc cttggggcct gatcttggca tggcagagac ctggggactg   4440

ccactgtccc caggtacgtg tacatggagc caaactgtgt gtcctgtggc attgtcagag   4500

ttatgttgaa atcttatttg aaaatgttag caacttactt gcatttttaa agaccaaaca   4560

agagctggta acctatggcc tcaagcatct gtccttccta aaaatggaat agtgggatgt   4620
```

agtgcttaat ggaaactgct aaatcttttt ctaaaaacta acagtggatt tttaaaatat 4680
attgtttttt gtgtatttca tttgtccttt gtatttatct aaaagggttg atatgatttt 4740
atatcttgct ctctattcct aatagtatta tgacttctta tttaaaataa ataacaattg 4800
ccggttttct gttaaaaaaa aaaaaa 4826

<210> SEQ ID NO 52
<211> LENGTH: 4344
<212> TYPE: DNA
<213> ORGANISM: Homo sapiens

<400> SEQUENCE: 52
gttggcagag cagttgtcct ggatggcgga gccttgggtt ccgggggcct gggacctgca 60
actctttcta caagatatca agttattcta gtacaaccat ataaataaat aatacctgaa 120
gtctcagtgt aacatggaca attaacagtg atgacagata aatacagacg catggggatc 180
aaatactagg caaaacgctt tttaaaagtg tatcaggctt ttaagaaaca ctgcaggatc 240
ctgtctatct taatgctgat agagctcagc taaaaattta ggaggttcta gtattcttca 300
tggctgaagc tgagagagtc tgaaaccctg atgcttaagc tccattctag atcatagctc 360
caactccttc aggatataag gaaaagagat tatatttcca caatgataga tctttggttg 420
tacaggtttc ccaatgagtg gatcatgatg accgtattgt agggacttgc catagtatgg 480
ctgcttcccg atctactcgt gttacaagat caacagtggg gttaaacggc ttggatgaat 540
ctttttgtgg tagaacttta aggaatcgta gcattgcgca tcctgaagaa atctcttcta 600
attctcaagt acgatcaaga tcaccaaaga agagaccaga gcctgtgcca attcagaaag 660
gaaataataa tgggagaacc actgatttaa aacagcagag tacccgagaa tcatgggtaa 720
gccctaggaa aagaggactt tcttcttcag aaaaggataa catagaaagg caggctatag 780
aaaattgtga gagaaggcaa acagaacctg tttcaccagt tttaaaaaga attaagcgtt 840
gtcttagatc tgaagcacca aacagttcag aagaagattc tcctataaaa tcagacaagg 900
agtcagtaga acagaggagt acagtagtgg acaatgatgc agattttcaa gggactaaac 960
gagcttgtcg atgtcttata ctggatgatt gtgagaaaag ggaaattaaa aaggtgaatg 1020
tcagtgagga agggccactt aattctgcag tagttgaaga aatcacaggc tatttggctg 1080
tcaatggtgt tgatgacagt gattcagctg ttataaactg tgatgactgt cagcctgatg 1140
ggaacactaa acaaaatagc attggttcct atgtgttaca ggaaaaatca gtagctgaaa 1200
atggggatac ggatacccaa acttcaatgt tccttgatag taggaaggag gacagttata 1260
tagaccataa ggtgccttgc acagattcac aagtgcaggt caagttggag gaccacaaaa 1320
tagtaactgc ctgcttgcct gtggaacatg ttaatcagct gactactgag ccagctacag 1380 ggccctttc tgaaactcag tcatctttaa gggattctga ggaggaagta gatgtggtgg 1440
gagatagcag tgcctcaaaa gagcagtgta aagaaaacac caataacgaa ctggacacaa 1500
gtcttgagag tatgccagcc tccggagaac ctgaaccatc tcctgttcta gactgtgttt 1560
cagctcaaat gatgtcttta tcagaacctc aagaacatcg ttatactctg agaacctcac 1620
cacgaagggc agcccctacc agaggtagtc ccactaaaaa cagttctcct tacagagaaa 1680
atggacaatt tgaggagaat aatcttagtc ctaatgaaac aaatgcaact gttagtgata 1740
atgtaagtca atctcctaca aatcctggtg aaatttctca aaatgaaaaa gggatatgtt 1800
gtgactctca aaataatgga agtgaaggag taagtaaacc accctcagag gcaagactca 1860

-continued

```
atattggaca tttgccatct gccaaagaga gtgccagtca gcacattaca gaagaggaag   1920
atgatgatcc tgatgtttat tactttgaat cagatcatgt ggcactgaaa cacaacaaag   1980
attatcagag actattacag acgattgctg tactcgaggc tcagcgttct caagcagtcc   2040
aagaccttga aagtttaggc aggcaccaga gagaagcact gaaaaatccc attggatttg   2100
tggaaaaact ccagaagaag gctgatattg ggcttccata tccacagaga gttgttcaat   2160
tgcctgagat cgtatgggac caatataccc atagccttgg gaattttgaa agagaattta   2220
aaaatcgtaa aagacatact agaagagtta agctagtttt tgataaagta ggtttacctg   2280
ctagaccaaa aagtccttta gatcctaaga aggatggaga gtccctttca tattctatgt   2340
tgcctttgag tgatggtcca gaaggctcaa gcagtcgtcc tcagatgata agaggacgct   2400
tgtgtgatga taccaaacct gaaacattta accagttgtg gactgttgaa gaacagaaaa   2460
agctggaaca gctactcatc aaataccctc ctgaagaagt agaatctcga cgctggcaga   2520
agatagcaga tgaattgggc aacaggacag caaaacaggt tgccagccga gtacagaagt   2580
atttcataaa gctaactaaa gctggcattc cagtaccagg cagaacacca aacttatata   2640
tatactccaa aaagtcttca acaagcagac gacagcaccc tcttaataag catctcttta   2700
agccttccac tttcatgact tcacatgaac cgccagtgta tatggatgaa gatgatgacc   2760
gatcttgttt tcatagccac atgaacactg ctgttgaaga tgcatcagat gacgaaagta   2820
ttcctatcat gtataggaat ttacctgaat ataaagaact attacagttt aaaaagttaa   2880
agaagcagaa acttcagcaa atgcaagctg aaagtggatt tgtgcaacat gtgggcttta   2940
agtgtgataa ctgtggcata gaacccatcc agggtgttcg gtggcattgc caggattgtc   3000
ctccagaaat gtctttggat ttctgtgatt cttgttcaga ctgtctacat gaaacagata   3060
ttcacaagga agatcaccaa ttagaaccta tttataggtc agagacattc ttagacagag   3120
actactgtgt gtctcagggc accagttaca attaccttga cccaaactac tttccagcaa   3180
acagatgaca tggaagagaa catcatttac tagtcctctt caacacatag caatggtatc   3240
attgttaatt atgtgcacag tttggaaaga ttctctgctt tcccagaaat gacactcaca   3300
gcatgagagc ttcctgagtg ttctcgtcaa gtacagctct gcaccgttgt ggctctagat   3360
cactgttcag cagctgaaca ttcctggtga gcaaaggttt ccctggtgaa tttttcacca   3420
ctgcgtttta ggtggtgatc ttaaatgggt gagatggaac gagagcacac attaaagaga   3480
gagtaaattc caaaggtttc aaagaacttg gtcataaata tgataatgag aagacaaagt   3540
atttatatta aaacagttta gtagccttca gttttgtgaa aatagttttc agcacagaaa   3600
ctgacttctt tagacaaagt tttaaccaat gatggtgttt gcttctagga tatacacttt   3660
aaaagaactc actgtcccag tggtggtcat tgatggcctt tagtaaattg gagctgctta   3720
atcatattga tatctaattt cttttaacca caatgaattg tccttaatta ccaacagtga   3780
agcactacag gaggcaactg tggcattgct tccttaacca gctcatggtg tgtgaatgtt   3840
ataaaattgt cactcagata tattttttaa atgtaatgtt atataagatg atcatgtgat   3900
gtgtacaaac tatggtgaaa agtgccagtg gtagtaactg tgtaaagttt ctaattcaca   3960
acattaattc ctttaaaata cacagccttc tgcctctgta tttggagttg tcagtacaac   4020
tcatcaaaga aaactgccta atataaaaat catatatatg gtaataattt ccctcttttg   4080
```

-continued

| | |
|---|---|
| tagtctgcac aagatccata aaagattgta tttttattac tatttaaaca agtgattaaa | 4140 |
| tttagtctgc acagtgagca agggttcaca tgcattcttt tatactgctg gattttgttg | 4200 |
| tgcatcattt aaaacatttt gtatgtttct tcttatctgt gtatacagta tgttcttgaa | 4260 |
| tgatgttcat ttgtcaggag aactgtgaga aataaactat gtggatactg tctgtttata | 4320 |
| ttaaaagaaa aaaaaaaaaa aaaa | 4344 |